US012563966B2

(12) United States Patent
Kim et al.

(10) Patent No.: US 12,563,966 B2
(45) Date of Patent: Feb. 24, 2026

(54) HETEROCYCLIC COMPOUND AND ORGANIC LIGHT EMITTING DEVICE COMPRISING SAME

(71) Applicant: LG CHEM, LTD., Seoul (KR)

(72) Inventors: Kyunghee Kim, Daejeon (KR); Wanpyo Hong, Daejeon (KR); Sujeong Geum, Daejeon (KR); Moung Gon Kim, Daejeon (KR); Seonwoo Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 1114 days.

(21) Appl. No.: 17/610,283

(22) PCT Filed: Nov. 13, 2020

(86) PCT No.: PCT/KR2020/015941
§ 371 (c)(1),
(2) Date: Nov. 10, 2021

(87) PCT Pub. No.: WO2021/096273
PCT Pub. Date: May 20, 2021

(65) Prior Publication Data

US 2022/0255012 A1 Aug. 11, 2022

(30) Foreign Application Priority Data

Nov. 15, 2019 (KR) ........................ 10-2019-0146438

(51) Int. Cl.
*H10K 85/60* (2023.01)
*C07D 487/06* (2006.01)
(Continued)

(52) U.S. Cl.
CPC ......... *H10K 85/636* (2023.02); *C07D 487/06* (2013.01); *C07D 491/16* (2013.01);
(Continued)

(58) Field of Classification Search
CPC .. H10K 85/622; H10K 85/623; H10K 85/633; H10K 85/636; H10K 85/657; C07D 487/06; C07D 491/16; C07D 495/16
See application file for complete search history.

(56) References Cited

U.S. PATENT DOCUMENTS

2017/0324045 A1* 11/2017 Takahashi .............. C09K 11/06
2019/0341556 A1 11/2019 Takahashi et al.
(Continued)

FOREIGN PATENT DOCUMENTS

CN 106977520 A * 7/2017 ........... C07D 487/06
CN 108047233 5/2018
(Continued)

OTHER PUBLICATIONS

Office Action of Korean Patent Office in Appl'n No. 10-2020-0151815, dated Jun. 28, 2022.

*Primary Examiner* — Michael M Dollinger
(74) *Attorney, Agent, or Firm* — Bryan Cave Leighton Paisner LLP

(57) ABSTRACT

Provided is a heterocyclic compound of Chemical Formula 1:
(Continued)

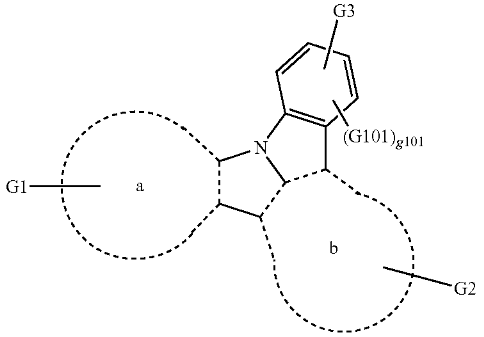

a is a substituted or unsubstituted tetracyclic or higher aromatic or heteroaromatic ring, and b is a benzene or naphthalene ring;

at least two of G1 to G3 are a group of Chemical Formula A, and any remaining group, and G101, is hydrogen, deuterium, halogen, cyano, nitro, or a substituted or unsubstituted: silyl, boron, alkyl, alkoxy, cycloalkyl, aryl, or heteroaryl group;

<Chemical Formula A>

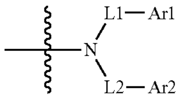

L1 and L2 are a direct bond, or a substituted or unsubstituted arylene or heteroarylene group;

Ar1 and Ar2 are hydrogen, deuterium, halogen, cyano, nitro, or a substituted or unsubstituted: silyl, boron, alkyl, alkoxy, cycloalkyl, aryl, or a heteroaryl group, or a fused ring group of an aromatic hydrocarbon ring and aliphatic hydrocarbon ring, or bond to each other to form a substituted or unsubstituted heteroring;

and an organic light emitting device including the same.

14 Claims, 3 Drawing Sheets

(51) Int. Cl.

| | |
|---|---|
| ***C07D 491/16*** | (2006.01) |
| ***C07D 495/16*** | (2006.01) |
| ***C07F 7/08*** | (2006.01) |
| ***C09K 11/06*** | (2006.01) |
| ***H10K 85/40*** | (2023.01) |
| *H10K 50/11* | (2023.01) |
| *H10K 101/30* | (2023.01) |

(52) U.S. Cl.

CPC .......... *C07D 495/16* (2013.01); *C07F 7/0812* (2013.01); *C09K 11/06* (2013.01); *H10K 85/40* (2023.02); *H10K 85/633* (2023.02); *C07B 2200/05* (2013.01); *C09K 2211/1018* (2013.01); *H10K 50/11* (2023.02); *H10K 85/626* (2023.02); *H10K 85/654* (2023.02); *H10K 85/657* (2023.02); *H10K 85/6572* (2023.02); *H10K 85/6574* (2023.02); *H10K 85/6576* (2023.02); *H10K 2101/30* (2023.02)

(56) References Cited

U.S. PATENT DOCUMENTS

2021/0005825 A1* 1/2021 Tasaki .................. C07D 487/06
2021/0057650 A1 2/2021 Kim et al.

FOREIGN PATENT DOCUMENTS

| | | | |
|---|---|---|---|
| CN | 108084198 | | 5/2018 |
| CN | 109020979 | | 12/2018 |
| KR | 10-2017-0092129 | | 8/2017 |
| KR | 10-2018-0000322 | | 1/2018 |
| KR | 10-2018-0041480 | A | 4/2018 |
| KR | 10-2019-0082752 | | 7/2019 |
| KR | 10-2019-0116947 | | 10/2019 |
| WO | 2018/034443 | A1 | 2/2018 |
| WO | 2018/070824 | A1 | 4/2018 |
| WO | 2019/194617 | A1 | 10/2019 |

* cited by examiner

[FIG. 1]
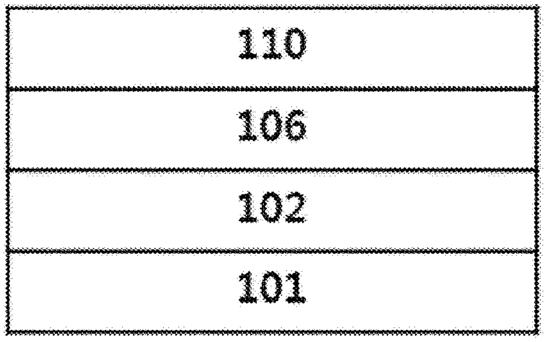
[FIG. 2]
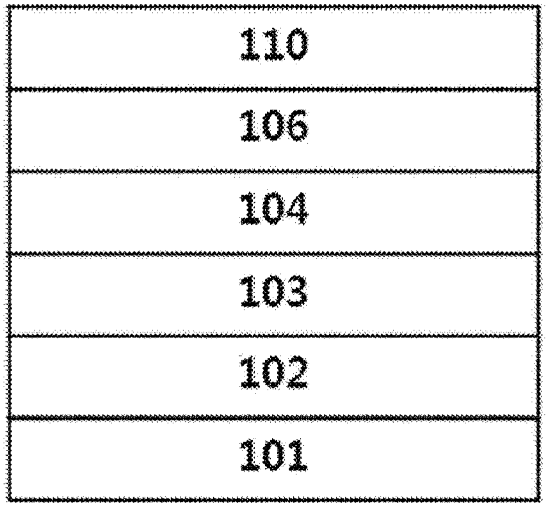

[FIG. 3]
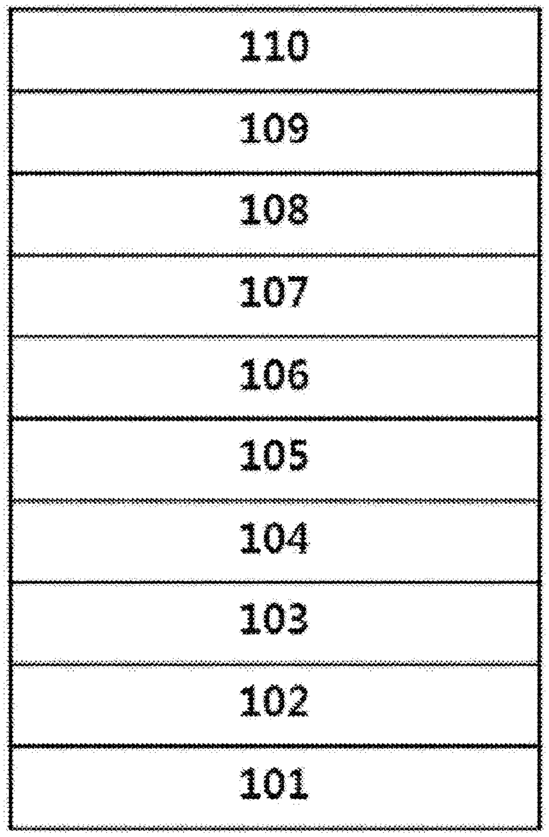

[FIG. 4]
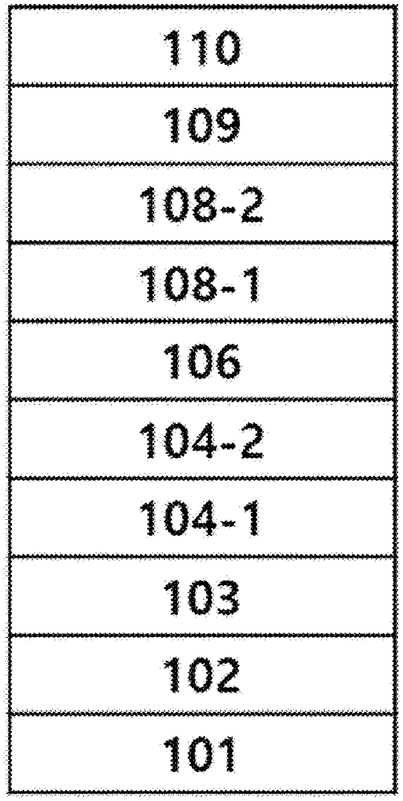

HETEROCYCLIC COMPOUND AND ORGANIC LIGHT EMITTING DEVICE COMPRISING SAME

CROSS-REFERENCE TO RELATED APPLICATION

This application is a National Stage Application of International Application No. PCT/KR2020/015941 filed on Nov. 13, 2020, which claims priority to and the benefits of Korean Patent Application No. 10-2019-0146438, filed with the Korean Intellectual Property Office on Nov. 15, 2019, the entire contents of which are incorporated herein by reference.

TECHNICAL FIELD

The present specification relates to a heterocyclic compound, and an organic light emitting device including the same.

BACKGROUND

An organic light emission phenomenon generally refers to a phenomenon converting electrical energy to light energy using an organic material. An organic light emitting device using an organic light emission phenomenon normally has a structure including an anode, a cathode, and an organic material layer therebetween. Herein, the organic material layer is often formed in a multilayer structure formed with different materials in order to increase efficiency and stability of the organic light emitting device, and for example, may be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state.

Development of new materials for such an organic light emitting device has been continuously required.

BRIEF DESCRIPTION

Technical Problem

The present specification is directed to providing a heterocyclic compound, and an organic light emitting device including the same.

Technical Solution

One embodiment of the present specification provides a heterocyclic compound of the following Chemical Formula 1:

<Chemical Formula 1>

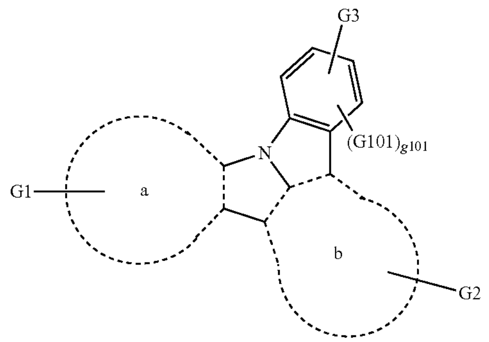

wherein in Chemical Formula 1:

a is a substituted or unsubstituted tetracyclic or higher aromatic or heteroaromatic ring, and b is a benzene ring or a naphthalene ring;

at least two of G1 to G3 are a group of the following Chemical Formula A, and any remaining group of G1 to G3 that is not the following Chemical Formula A, and G101, are the same as or different from each other, and each independently is hydrogen, deuterium, a halogen group, a cyano group, a nitro group, a substituted or unsubstituted silyl group, a substituted or unsubstituted boron group, a substituted or unsubstituted alkyl group, a substituted or unsubstituted alkoxy group, a substituted or unsubstituted cycloalkyl group, a substituted or unsubstituted aryl group, or a substituted or unsubstituted heteroaryl group, g101 is an integer of 1 to 3; and when g101 is 2 or greater, the two or more G101s are the same as or different from each other;

<Chemical Formula A>

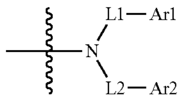

wherein in Chemical Formula A:

L1 and L2 are the same as or different from each other, and each independently is a direct bond, a substituted or unsubstituted arylene group, or a substituted or unsubstituted heteroarylene group;

Ar1 and Ar2 are the same as or different from each other, and each independently is hydrogen, deuterium, a halogen group, a cyano group, a nitro group, a substituted or unsubstituted silyl group, a substituted or unsubstituted boron group, a substituted or unsubstituted alkyl group, a substituted or unsubstituted alkoxy group, a substituted or unsubstituted cycloalkyl group, a substituted or unsubstituted aryl group, a substituted or unsubstituted fused ring group of aromatic hydrocarbon ring and aliphatic hydrocarbon ring, or a substituted or unsubstituted heteroaryl group, or bond to each other to form a substituted or unsubstituted heteroring; and

means a site bonding to Chemical Formula 1.

Another embodiment of the present specification provides an organic light emitting device including a first electrode; a second electrode provided opposite to the first electrode; and one or more organic material layers provided between the first electrode and the second electrode, wherein one or more layers of the organic material layers include the heterocyclic compound.

Advantageous Effects

Using a heterocyclic compound according to one embodiment of the present specification in an organic light emitting device is capable of lowering a driving voltage and enhancing light efficiency of the organic light emitting device. In addition, lifetime properties of the device can be enhanced by thermal stability of the heterocyclic compound.

DESCRIPTION OF THE DRAWINGS

FIG. 1 to FIG. 4 each illustrate an example of an organic light emitting device according to one embodiment of the present specification.

REFERENCE NUMERALS

101: Substrate
102: Anode
103: Hole Injection Layer
104: Hole Transfer Layer
104-1: First Hole Transfer Layer
104-2: Second Hole Transfer Layer
105: Electron Blocking Layer
106: Light Emitting Layer
107: Hole Blocking Layer
108: Electron Transfer Layer
108-1: First Electron Transfer Layer
108-2: Second Electron Transfer Layer
109: Electron Injection Layer
110: Cathode

DETAILED DESCRIPTION

Hereinafter, the present specification will be described in more detail.

A heterocyclic compound according to one embodiment of the present specification has a structure in which a substituted or unsubstituted tetracyclic or higher aromatic or heteroaromatic ring is fused to an indolocarbazole structure as a core structure. Accordingly, an overlap of HOMO and LUMO orbitals increases by the core structure of Chemical Formula 1 of the present specification, which increases oscillator strength, and as a result, light emission efficiency of an organic light emitting device including the same may be enhanced.

Examples of substituents in the present specification are described below, however, the substituents are not limited thereto.

In the present specification,

means a linking site.

The term "substitution" means a hydrogen atom bonding to a carbon atom of a compound being changed to another substituent, and the position of substitution is not limited as long as it is a position at which the hydrogen atom is substituted, that is, a position at which a substituent can substitute, and when two or more substituents substitute, the two or more substituents can be the same as or different from each other.

In the present specification, the term "substituted or unsubstituted" means being substituted with one or more substituents selected from the group consisting of deuterium, a halogen group, a cyano group, a nitro group, an alkyl group, a cycloalkyl group, an alkoxy group, a haloalkyl group, a silyl group, a boron group, an amine group, an aryl group, a fused ring group of aromatic hydrocarbon and aliphatic hydrocarbon, and a heteroaryl group, or being substituted with a substituent linking two or more substituents among the substituents illustrated above, or having no substituents.

In the present specification, linking two or more substituents refers to linking hydrogen of any one substituent to another substituent. For example, linking two substituents can include a phenyl group and a naphthyl group being linked to become a substituent of

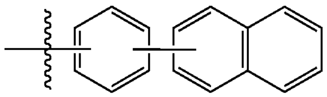

or

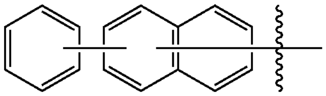

.

In addition, linking three substituents includes not only continuously linking (substituent 1)-(substituent 2)-(substituent 3), but also linking (substituent 2) and (substituent 3) to (substituent 1). For example, a phenyl group, a naphthyl group and an isopropyl group can be linked to become a substituent of

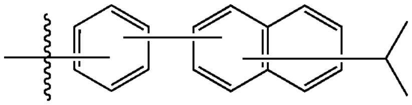

,

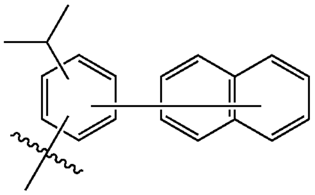

or

-continued

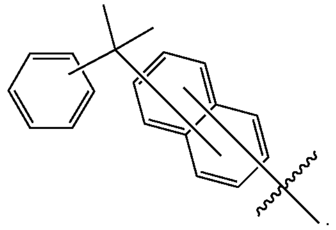

The same rule described above applies to cases of linking four or more substituents.

In the present specification, examples of the halogen group can include fluorine, chlorine, bromine or iodine.

In the present specification, the alkyl group can be linear or branched, and although not particularly limited thereto, the number of carbon atoms is preferably from 1 to 30. Specific examples thereof can include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl and the like, but are not limited thereto.

In the present specification, the cycloalkyl group is not particularly limited, but preferably has 3 to 30 carbon atoms. Specific examples thereof can include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the alkoxy group can be linear, branched or cyclic. The number of carbon atoms of the alkoxy group is not particularly limited, but is preferably from 1 to 30. Specific examples thereof can include methoxy, ethoxy, n-propoxy, isopropoxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the haloalkyl group means, in the definition of the alkyl group, hydrogen of the alkyl group being substituted with at least one halogen group.

In the present specification, the aryl group is not particularly limited, but preferably has 6 to 30 carbon atoms, and the aryl group can be monocyclic or polycyclic.

When the aryl group is a monocyclic aryl group, the number of carbon atoms is not particularly limited, but is preferably from 6 to 30. Specific examples of the monocyclic aryl group can include a phenyl group, a biphenyl group, a terphenyl group and the like, but are not limited thereto.

When the aryl group is a polycyclic aryl group, the number of carbon atoms is not particularly limited, but is preferably from 10 to 30. Specific examples of the polycyclic aryl group can include a naphthyl group, an anthracene group, a phenanthrene group, a triphenylene group, a pyrene group, a phenalene group, a perylene group, a chrysene group, a fluorene group and the like, but are not limited thereto.

In the present specification, the fluorene group can be substituted, and adjacent groups can bond to each other to form a ring.

When the fluorene group is substituted,

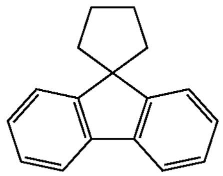,
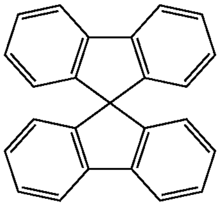,
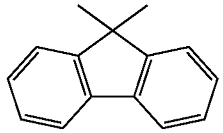,
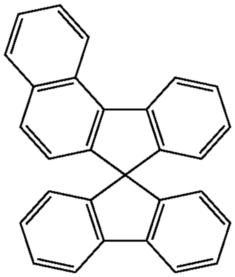,
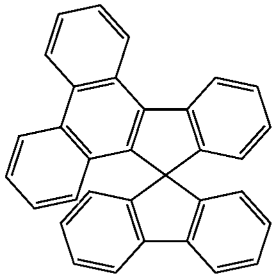,
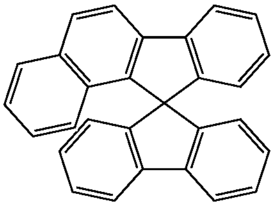,
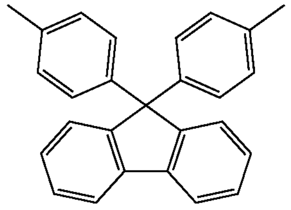
and
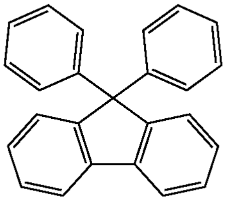

and the like can be included, however, the structure is not limited thereto.

In the present specification, an "adjacent" group can mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring can be interpreted as groups "adjacent" to each other.

In the present specification, the heteroaryl group is a group including one or more atoms that are not carbon, that is, heteroatoms, and specifically, the heteroatom can include one or more atoms selected from the group consisting of O, N, Se, S and the like. The number of carbon atoms is not particularly limited, but is preferably from 2 to 30, and the heteroaryl group can be monocyclic or polycyclic. Examples of the heterocyclic group can include a thiophene group, a furan group, a pyrrole group, an imidazole group, a thiazole group, an oxazole group, an oxadiazole group, a pyridine group, a bipyridine group, a pyrimidine group, a triazine group, a triazole group, an acridine group, a pyridazine group, a pyrazine group, a quinoline group, a quinazoline group, a quinoxaline group, a phthalazine group, a pyridopyrimidine group, a pyridopyrazine group, a pyrazinopyrazine group, an isoquinoline group, an indole group, a carbazole group, a benzoxazole group, a benzimidazole group, a benzothiazole group, a benzocarbazole group, a benzothiophene group, a dibenzothiophene group, a benzofuran group, a phenanthridine group, a phenanthroline group, an isoxazole group, a thiadiazole group, a dibenzofuran group, dibenzosilole group, a phenoxanthine group, a phenoxazine group, a phenothiazine group, a dihydroindenocarbazole group, a spirofluorenexanthene group, a spirofluorenethioxanthene group and the like, but are not limited thereto.

In the present specification, the silyl group can be an alkylsilyl group, an arylsilyl group, a heteroarylsilyl group or the like. As the alkyl group in the alkylsilyl group, the examples of the alkyl group described above can be applied, and as the aryl group in the arylsilyl group, the examples of the aryl group described above can be applied. As the heteroaryl group in the heteroarylsilyl group, the examples of the heteroaryl group can be applied.

In the present specification, the boron group can be $-BR_{100}R_{101}$. $R_{100}$ and $R_{101}$ are the same as or different from each other, and can be each independently selected from the group consisting of hydrogen, deuterium, halogen, a nitrile group, a substituted or unsubstituted monocyclic or polycyclic cycloalkyl group having 3 to 30 carbon atoms, a substituted or unsubstituted linear or branched alkyl group having 1 to 30 carbon atoms, a substituted or unsubstituted monocyclic or polycyclic aryl group having 6 to 30 carbon atoms, and a substituted or unsubstituted monocyclic or polycyclic heteroaryl group having 2 to 30 carbon atoms. Specific examples of the boron group can include a trimethylboron group, a triethylboron group, a t-butyldimethylboron group, a triphenylboron group, a phenylboron group and the like, but are not limited thereto.

In the present specification, the amine group can be selected from the group consisting of $-NH_2$, an alkylamine group, an N-alkylarylamine group, an arylamine group, an N-arylheteroarylamine group, an N-alkylheteroarylamine group and a heteroarylamine group, and although not particularly limited thereto, the number of carbon atoms is preferably from 1 to 30. Specific examples of the amine group can include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a ditolylamine group, an N-phenyltolylamine group, a triphenylamine group, an N-phenylbiphenylamine group, an N-phenylnaphthylamine group, an N-biphenylnaphthylamine group, an N-naphthylfluorenylamine group, an N-phenylphenanthrenylamine group, an N-biphenylphenanthrenylamine group, an N-phenylfluorenylamine group, an N-phenylterphenylamine group, an N-phenanthrenylfluorenylamine group, an N-biphenylfluorenylamine group and the like, but are not limited thereto.

In the present specification, the N-alkylarylamine group means an amine group in which N of the amine group is substituted with an alkyl group and an aryl group. The alkyl group and the aryl group in the N-alkylarylamine group are the same as the examples of the alkyl group and the aryl group described above.

In the present specification, the N-arylheteroarylamine group means an amine group in which N of the amine group is substituted with an aryl group and a heteroaryl group. The aryl group and the heteroaryl group in the N-arylheteroarylamine group are the same as the examples of the aryl group and the heteroaryl group described above.

In the present specification, the N-alkylheteroarylamine group means an amine group in which N of the amine group is substituted with an alkyl group and a heteroaryl group. The alkyl group and the heteroaryl group in the N-alkylheteroarylamine group are the same as the examples of the alkyl group and the heteroaryl group described above.

In the present specification, examples of the alkylamine group include a substituted or unsubstituted monoalkylamine group, or a substituted or unsubstituted dialkylamine group. The alkyl group in the alkylamine group can be a linear or branched alkyl group. The alkylamine group including two or more alkyl groups can include linear alkyl groups, branched alkyl groups, or both linear alkyl groups and branched alkyl groups. For example, the alkyl group in the alkylamine group can be selected from among the examples of the alkyl group described above.

In the present specification, examples of the heteroarylamine group include a substituted or unsubstituted monoheteroarylamine group, or a substituted or unsubstituted diheteroarylamine group. The heteroarylamine group including two or more heteroaryl groups can include monocyclic heteroaryl groups, polycyclic heteroaryl groups, or both monocyclic heteroaryl groups and polycyclic heteroaryl groups. For example, the heteroaryl group in the heteroarylamine group can be selected from among the examples of the heteroaryl group described above.

In the present specification, the hydrocarbon ring group can be an aromatic hydrocarbon ring, an aliphatic hydrocarbon ring, or a fused ring group of aromatic hydrocarbon and aliphatic hydrocarbon, and can be selected from among the examples of the cycloalkyl group, the aryl group, and a combination thereof. Examples of the hydrocarbon ring group can include a phenyl group, a cyclohexyl group, an adamantyl group, a tetrahydronaphthalene group, a tetrahydroanthracene group and the like, but are not limited thereto.

In the present specification, the meaning of "adjacent two of the substituents bonding to each other to form a ring" is adjacent groups bonding to each other to forma substituted or unsubstituted hydrocarbon ring or a substituted or unsubstituted heteroring.

In the present specification, the "ring" in the substituted or unsubstituted ring formed by bonding to each other means a substituted or unsubstituted hydrocarbon ring or a substituted or unsubstituted heteroring.

In the present specification, the hydrocarbon ring can be an aromatic hydrocarbon ring, an aliphatic hydrocarbon ring, or a fused ring group of aromatic hydrocarbon and aliphatic hydrocarbon, and can be selected from among the examples of the cycloalkyl group and the aryl group except for those that are not monovalent. Examples of the hydrocarbon ring can include benzene, cyclohexane, adamantane, tetrahydronaphthalene, tetrahydroanthracene and the like, but are not limited thereto.

In the present specification, the heteroring includes one or more atoms that are not carbon, that is, heteroatoms, and specifically, the heteroatom can include one or more atoms selected from the group consisting of O, N, Se, S and the like. The heteroring can be monocyclic or polycyclic, can be aromatic, aliphatic, or a fused ring of aromatic and aliphatic, and can be selected from among the examples of the heteroaryl group or the heterocyclic group except for those that are not monovalent.

In the present specification, the aliphatic heteroring means an aliphatic ring including one or more of heteroatoms. Examples of the aliphatic heteroring can include oxirane, tetrahydrofuran, 1,4-dioxane, pyrrolidine, piperidine, morpholine, oxepane, azocane, thiocane, tetrahydronaphthothiophene, tetrahydronaphthofuran, tetrahydrobenzothiophene, tetrahydrobenzofuran and the like, but are not limited thereto.

In the present specification, the arylene group means the aryl group having two bonding sites, that is, a divalent group. The descriptions on the aryl group provided above can be applied thereto except for those that are each a divalent group.

In the present specification, the heteroarylene group means the heteroaryl group having two bonding sites, that is, a divalent group. The descriptions on the heteroaryl group provided above can be applied thereto except for those that are each a divalent group.

Hereinafter, the heterocyclic compound of Chemical Formula 1 will be described in detail.

According to one embodiment of the present specification, Chemical Formula 1 is any one of the following Chemical Formulae 1-1 to 1-3:

<Chemical Formula 1-1>

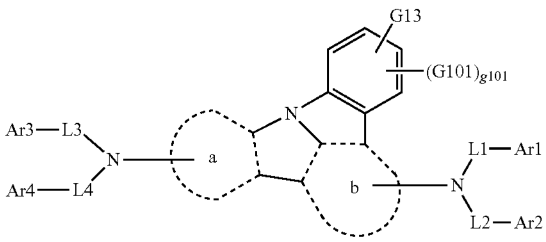

<Chemical Formula 1-2>

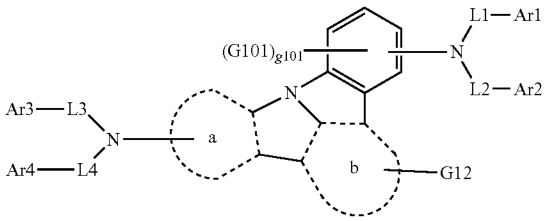

<Chemical Formula 1-3>

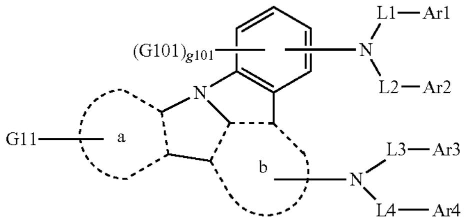

wherein in Chemical Formulae 1-1 to 1-3:

a, b, G101 and g101 have the same definitions as in Chemical Formula 1;

L1, L2, Ar1 and Ar2 have the same definitions as in Chemical Formula A;

G11 to G13 are the same as or different from each other, and each independently is hydrogen, deuterium, a halogen group, a cyano group, a nitro group, a substituted or unsubstituted silyl group, a substituted or unsubstituted boron group, a substituted or unsubstituted alkyl group, a substituted or unsubstituted alkoxy group, a substituted or unsubstituted cycloalkyl group, a substituted or unsubstituted aryl group, or a substituted or unsubstituted heteroaryl group;

L3 and L4 are the same as or different from each other, and each independently is a direct bond, a substituted or unsubstituted arylene group, or a substituted or unsubstituted heteroarylene group;

Ar3 and Ar4 are the same as or different from each other, and each independently is hydrogen, deuterium, a halogen group, a cyano group, a nitro group, a substituted or unsubstituted silyl group, a substituted or unsubstituted boron group, a substituted or unsubstituted alkyl group, a substituted or unsubstituted alkoxy group, a substituted or unsubstituted cycloalkyl group, a substituted or unsubstituted aryl group, a substituted or unsubstituted fused ring group of aromatic hydrocarbon ring and aliphatic hydrocarbon ring, or a substituted or unsubstituted heteroaryl group, or bond to each other to form a substituted or unsubstituted heteroring.

According to one embodiment of the present specification, two of G1 to G3 are the group of Chemical Formula A.

According to one embodiment of the present specification, two of G1 to G3 are the group of Chemical Formula A, and the two Chemical Formula A are the same as or different from each other.

According to one embodiment of the present specification, any two of G1 to G3 are Chemical Formula A, and the two Chemical Formula A are the same as each other.

According to one embodiment of the present specification, G1 and G2 are Chemical Formula A, and G1 and G2 are the same as each other.

According to one embodiment of the present specification, G1 and G3 are Chemical Formula A, and G1 and G3 are the same as each other.

According to one embodiment of the present specification, G2 and G3 are Chemical Formula A, and G2 and G3 are the same as each other.

According to one embodiment of the present specification, in Chemical Formula 1, the remaining group of G1 to G3 that is not Chemical Formula A, and G101, are the same as or different from each other, and each independently is hydrogen, deuterium, a substituted or unsubstituted linear or branched alkyl group having 1 to 30 carbon atoms, or a substituted or unsubstituted monocyclic or polycyclic aryl group having 6 to 30 carbon atoms.

According to one embodiment of the present specification, in Chemical Formula 1, the remaining group of G1 to G3 that is not Chemical Formula A, and G101, are the same as or different from each other, and each independently is hydrogen, deuterium, a substituted or unsubstituted linear or branched alkyl group having 1 to 20 carbon atoms, or a substituted or unsubstituted monocyclic or polycyclic aryl group having 6 to 20 carbon atoms.

According to one embodiment of the present specification, in Chemical Formula 1, the remaining group of G1 to G3 that is not Chemical Formula A, and G101, are the same as or different from each other, and each independently is hydrogen, deuterium, a substituted or unsubstituted linear or branched alkyl group having 1 to 10 carbon atoms, or a substituted or unsubstituted monocyclic or polycyclic aryl group having 6 to 10 carbon atoms.

According to one embodiment of the present specification, in Chemical Formula 1, the remaining group of G1 to G3 that is not Chemical Formula A, and G101, are the same as or different from each other, and each independently is hydrogen, deuterium, a linear or branched alkyl group having 1 to 30 carbon atoms, or a monocyclic or polycyclic aryl group having 6 to 30 carbon atoms unsubstituted or substituted with deuterium or a linear or branched alkyl group having 1 to 30 carbon atoms.

According to one embodiment of the present specification, in Chemical Formula 1, the remaining group of G1 to G3 that is not Chemical Formula A, and G101, are the same as or different from each other, and each independently is hydrogen, deuterium, a linear or branched alkyl group having 1 to 20 carbon atoms, or a monocyclic or polycyclic aryl group having 6 to 20 carbon atoms unsubstituted or substituted with deuterium or a linear or branched alkyl group having 1 to 20 carbon atoms.

According to one embodiment of the present specification, in Chemical Formula 1, the remaining group of G1 to G3 that is not Chemical Formula A, and G101, are the same as or different from each other, and each independently is hydrogen, deuterium, a linear or branched alkyl group having 1 to 10 carbon atoms, or a monocyclic or polycyclic aryl group having 6 to 10 carbon atoms unsubstituted or substituted with deuterium or a linear or branched alkyl group having 1 to 10 carbon atoms.

According to one embodiment of the present specification, in Chemical Formula 1, the remaining group of G1 to G3 that is not Chemical Formula A, and G101, are the same as or different from each other, and each independently is hydrogen, deuterium, a tert-butyl group, or a phenyl group.

According to one embodiment of the present specification, in Chemical Formula 1, the remaining group of G1 to G3 that is not Chemical Formula A, and G101, are the same as or different from each other, and each independently is hydrogen, an isopropyl group, a tert-butyl group, or a phenyl group unsubstituted or substituted with deuterium or a methyl group.

According to one embodiment of the present specification, in Chemical Formula 1, the substituted or unsubstituted tetracyclic or higher aromatic or heteroaromatic ring is of the following Chemical Formula a-1:

<Chemical Formula a-1>

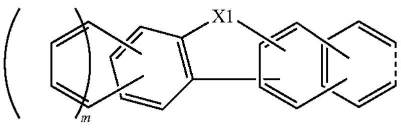

wherein in Chemical Formula a-1:

X1 is O, S or CRR';

m is 0 or 1;

R and R' are the same as or different from each other, and each independently is a substituted or unsubstituted alkyl group, or a substituted or unsubstituted aryl group, or bond to each other to form a substituted or unsubstituted ring; and is a site bonding to Chemical Formula 1.

According to one embodiment of the present specification, in Chemical Formula a-1, m is 1.

According to one embodiment of the present specification, in Chemical Formula a-1, m is 0.

According to one embodiment of the present specification, Chemical Formula a-1 is the following Chemical Formula a-2 or a-3:

<Chemical Formula a-2>

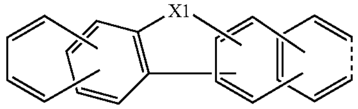

<Chemical Formula a-3>

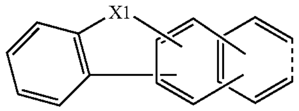

wherein in Chemical Formulae a-2 and a-3:

X1 is O, S or CRR';

R and R' are the same as or different from each other, and each independently is a substituted or unsubstituted alkyl group, or a substituted or unsubstituted aryl group, or can bond to each other to form a substituted or unsubstituted ring; and is a site bonding to Chemical Formula 1.

According to one embodiment of the present specification, in Chemical Formula a-1, X1 is 0.

According to one embodiment of the present specification, in Chemical Formula a-1, X1 is S.

According to one embodiment of the present specification, in Chemical Formula a-1, X1 is CRR'.

According to one embodiment of the present specification, Chemical Formula 1 is any one of the following Chemical Formulae 1-5 to 1-10:

<Chemical Formula 1-5>

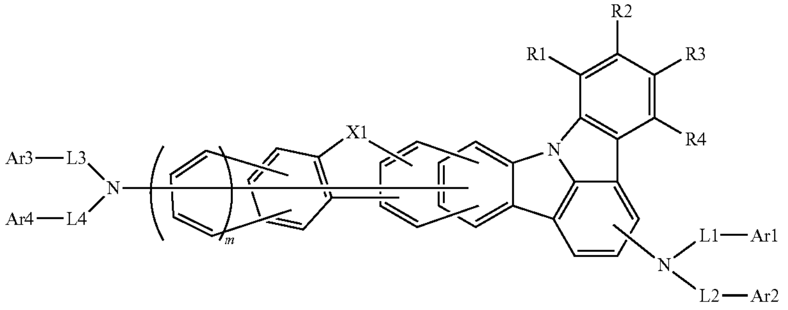

-continued

<Chemical Formula 1-6>

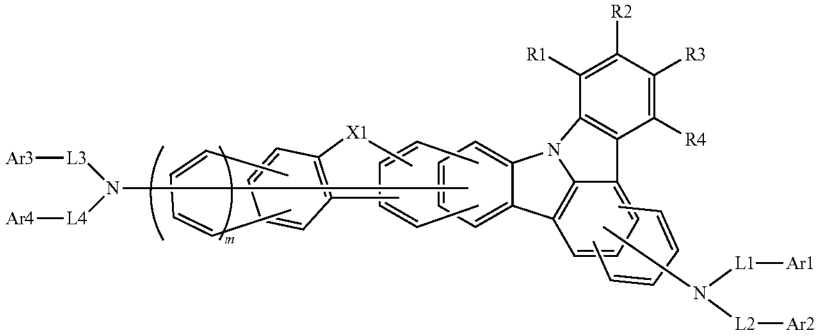

<Chemical Formula 1-7>

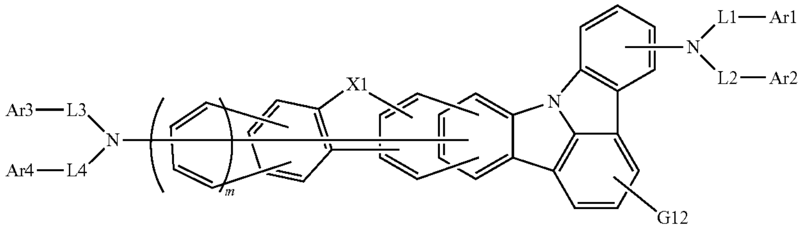

<Chemical Formula 1-8>

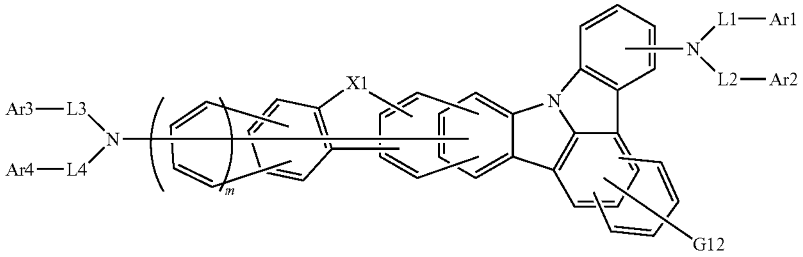

<Chemical Formula 1-9>

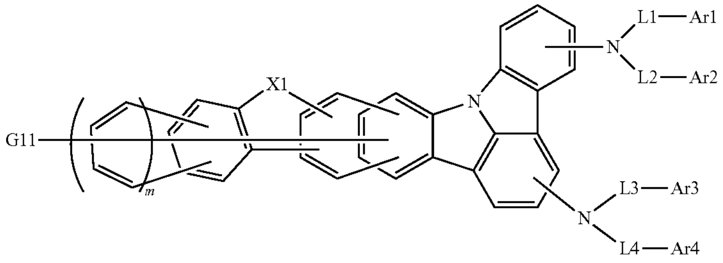

<Chemical Formula 1-10>

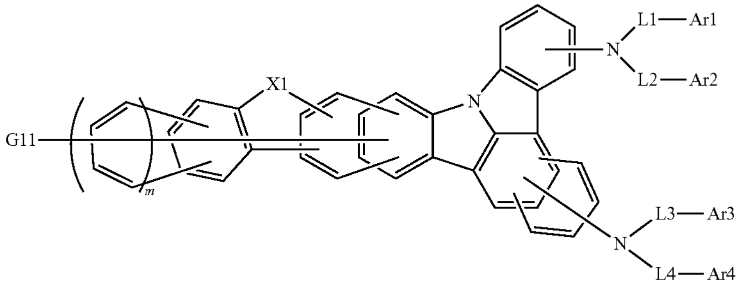

wherein in Chemical Formulae 1-5 to 1-10:

L1, L2, Ar1 and Ar2 have the same definitions as in Chemical Formula A;

R1 to R4, G11 and G12 are the same as or different from each other, and each independently is hydrogen, deuterium, a halogen group, a cyano group, a nitro group, a substituted or unsubstituted silyl group, a substituted or unsubstituted boron group, a substituted or unsubstituted alkyl group, a substituted or unsubstituted alkoxy group, a substituted or unsubstituted cycloalkyl group, a substituted or unsubstituted aryl group, or a substituted or unsubstituted heteroaryl group;

L3 and L4 are the same as or different from each other, and each independently is a direct bond, a substituted or unsubstituted arylene group, or a substituted or unsubstituted heteroarylene group;

Ar3 and Ar4 are the same as or different from each other, and each independently is hydrogen, deuterium, a halogen group, a cyano group, a nitro group, a substituted or unsubstituted silyl group, a substituted or unsubstituted boron group, a substituted or unsubstituted alkyl group, a substituted or unsubstituted alkoxy group, a substituted or unsubstituted cycloalkyl group, a substituted or unsubstituted aryl group, a substituted or unsubstituted fused ring group of aromatic hydrocarbon ring and aliphatic hydrocarbon ring, or a substituted or unsubstituted heteroaryl group, or bond to each other to form a substituted or unsubstituted heteroring;

X1 is O, S or CRR';

m is 0 or 1; and

R and R' are the same as or different from each other, and each independently is a substituted or unsubstituted alkyl group or a substituted or unsubstituted aryl group, or can bond to each other to form a substituted or unsubstituted ring.

According to one embodiment of the present specification, in Chemical Formula a-1, X1 is 0.

According to one embodiment of the present specification, in Chemical Formula a-1, X1 is S.

According to one embodiment of the present specification, in Chemical Formula a-1, X1 is CRR'.

According to one embodiment of the present specification, Chemical Formula 1 is any one of the following Chemical Formulae 1-5-1 to 1-5-6:

<Chemical Formula 1-5-1>

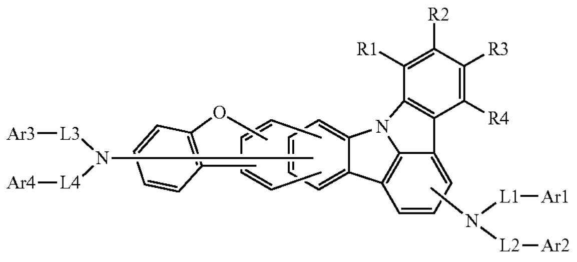

<Chemical Formula 1-5-2>

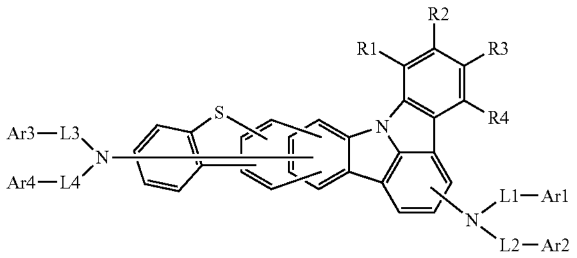

<Chemical Formula 1-5-3>

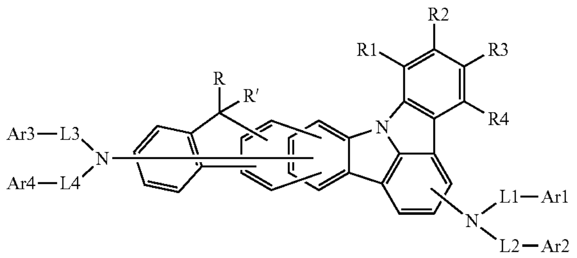

-continued

<Chemical Formula 1-5-4>

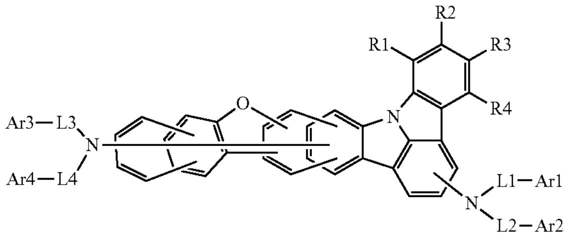

<Chemical Formula 1-5-5>

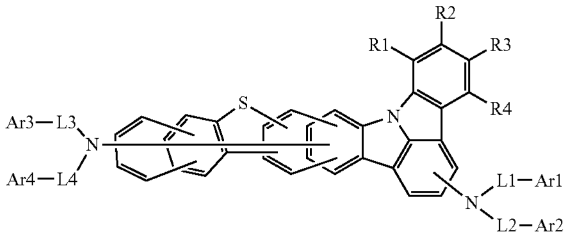

<Chemical Formula 1-5-6>

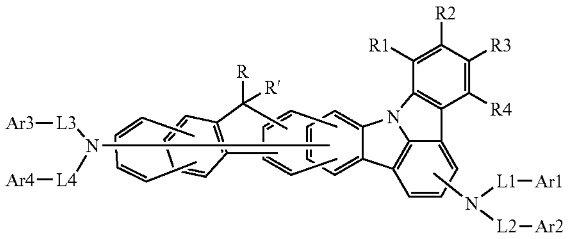

wherein in Chemical Formulae 1-5-1 to 1-5-6:

L1, L2, Ar1 and Ar2 have the same definitions as in Chemical Formula A;

R1 to R4 are the same as or different from each other, and each independently is hydrogen, deuterium, a halogen group, a cyano group, a nitro group, a substituted or unsubstituted silyl group, a substituted or unsubstituted boron group, a substituted or unsubstituted alkyl group, a substituted or unsubstituted alkoxy group, a substituted or unsubstituted cycloalkyl group, a substituted or unsubstituted aryl group, or a substituted or unsubstituted heteroaryl group;

L3 and L4 are the same as or different from each other, and each independently is a direct bond, a substituted or unsubstituted arylene group, or a substituted or unsubstituted heteroarylene group;

Ar3 and Ar4 are the same as or different from each other, and each independently is hydrogen, deuterium, a halogen group, a cyano group, a nitro group, a substituted or unsubstituted silyl group, a substituted or unsubstituted boron group, a substituted or unsubstituted alkyl group, a substituted or unsubstituted alkoxy group, a substituted or unsubstituted cycloalkyl group, a substituted or unsubstituted aryl group, a substituted or unsubstituted fused ring group of aromatic hydrocarbon ring and aliphatic hydrocarbon ring, or a substituted or unsubstituted heteroaryl group, or bond to each other to form a substituted or unsubstituted heteroring; and R and R' are the same as or different from each other, and each independently is a substituted or unsubstituted alkyl group, or a substituted or unsubstituted aryl group, or can bond to each other to form a substituted or unsubstituted ring.

According to one embodiment of the present specification, Chemical Formula 1 is any one of the following Chemical Formulae 1-6-1 to 1-6-6:
<Chemical Formula 1-6-1>
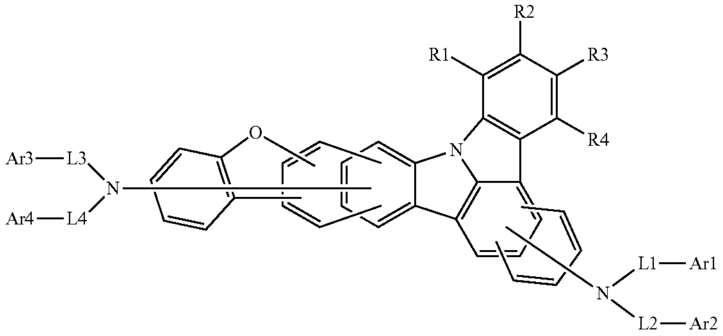
<Chemical Formula 1-6-2>
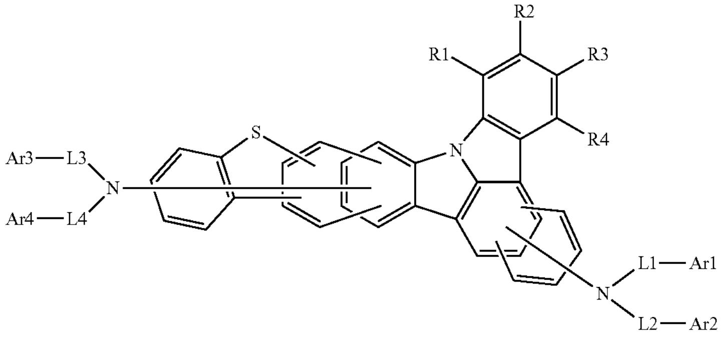
<Chemical Formula 1-6-3>
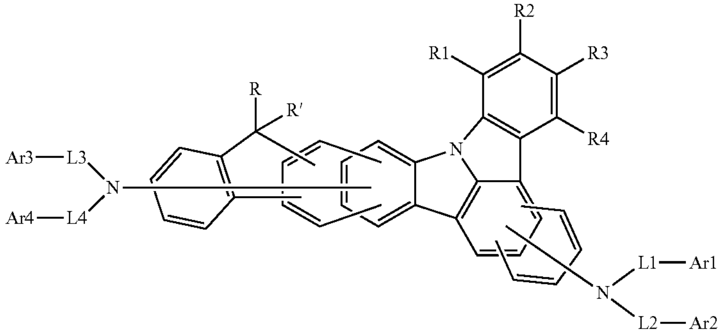
<Chemical Formula 1-6-4>
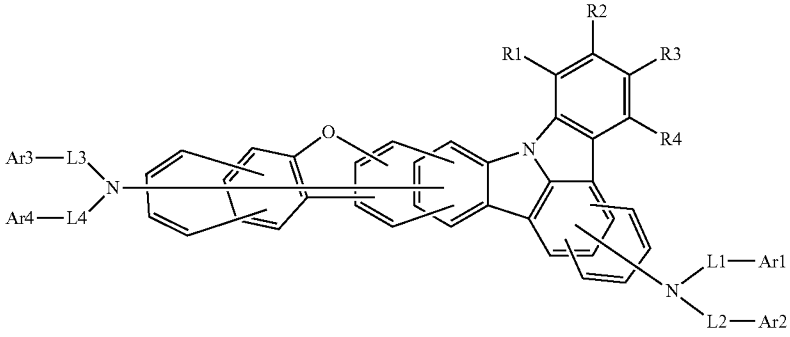

-continued

<Chemical Formula 1-6-5>

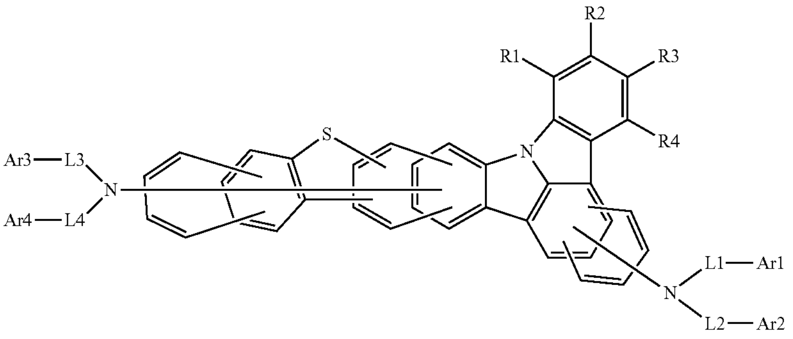

<Chemical Formula 1-6-6>

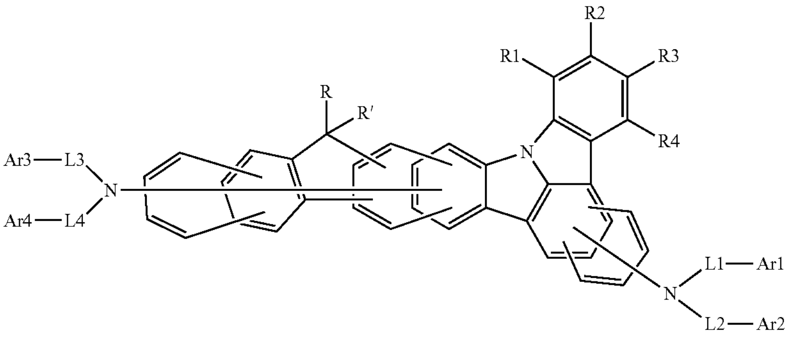

wherein in Chemical Formulae 1-6-1 to 1-6-6:

L1, L2, Ar1 and Ar2 have the same definitions as in Chemical Formula A;

R1 to R4 are the same as or different from each other, and each independently is hydrogen, deuterium, a halogen group, a cyano group, a nitro group, a substituted or unsubstituted silyl group, a substituted or unsubstituted boron group, a substituted or unsubstituted alkyl group, a substituted or unsubstituted alkoxy group, a substituted or unsubstituted cycloalkyl group, a substituted or unsubstituted aryl group, or a substituted or unsubstituted heteroaryl group;

L3 and L4 are the same as or different from each other, and each independently is a direct bond, a substituted or unsubstituted arylene group, or a substituted or unsubstituted heteroarylene group;

Ar3 and Ar4 are the same as or different from each other, and each independently is hydrogen, deuterium, a halogen group, a cyano group, a nitro group, a substituted or unsubstituted silyl group, a substituted or unsubstituted boron group, a substituted or unsubstituted alkyl group, a substituted or unsubstituted alkoxy group, a substituted or unsubstituted cycloalkyl group, a substituted or unsubstituted aryl group, a substituted or unsubstituted fused ring group of aromatic hydrocarbon ring and aliphatic hydrocarbon ring, or a substituted or unsubstituted heteroaryl group, or bond to each other to form a substituted or unsubstituted heteroring; and R and R' are the same as or different from each other, and each independently is a substituted or unsubstituted alkyl group or a substituted or unsubstituted aryl group, or can bond to each other to form a substituted or unsubstituted ring.

According to one embodiment of the present specification, Chemical Formula 1 is any one of the following Chemical Formulae 1-7-1 to 1-7-6:

<Chemical Formula 1-7-1>

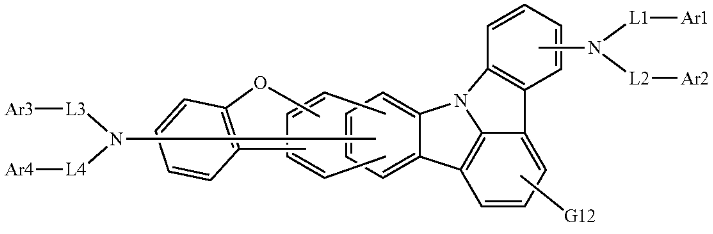

-continued

<Chemical Formula 1-7-2>

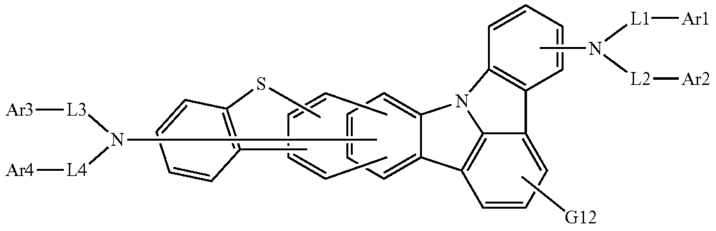

<Chemical Formula 1-7-3>

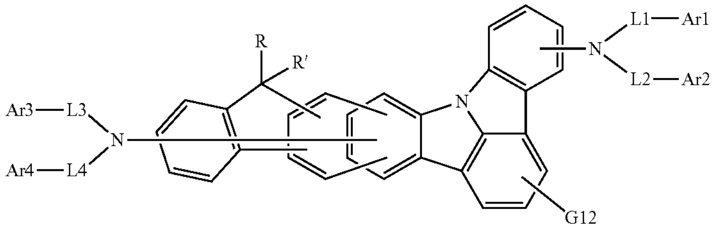

<Chemical Formula 1-7-4>

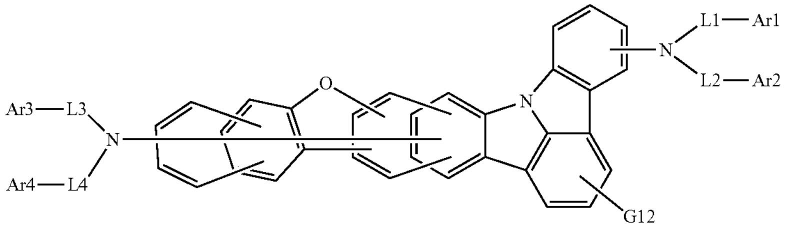

<Chemical Formula 1-7-5>

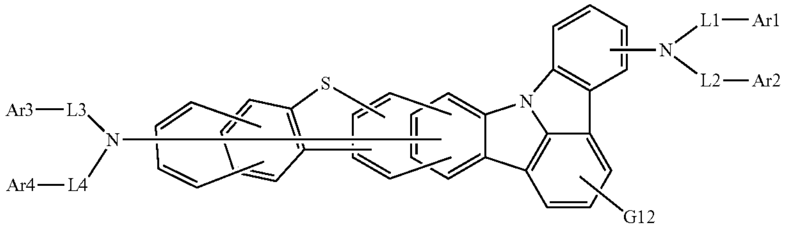

<Chemical Formula 1-7-6>

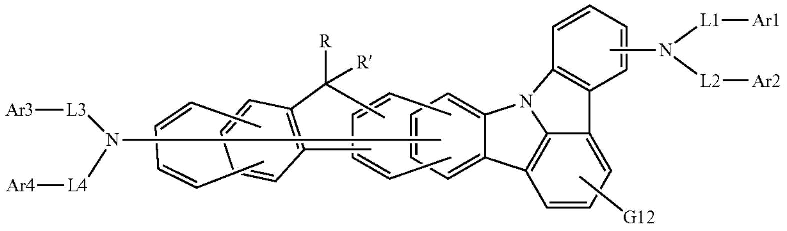

wherein in Chemical Formulae 1-7-1 to 1-7-6:

L1, L2, Ar1 and Ar2 have the same definitions as in Chemical Formula A;

G12 is hydrogen, deuterium, a halogen group, a cyano group, a nitro group, a substituted or unsubstituted silyl group, a substituted or unsubstituted boron group, a substituted or unsubstituted alkyl group, a substituted or unsubstituted alkoxy group, a substituted or unsubstituted cycloalkyl group, a substituted or unsubstituted aryl group, or a substituted or unsubstituted heteroaryl group, L3 and L4 are the same as or different from each other, and each independently a direct bond, a substituted or unsubstituted arylene group, or a substituted or unsubstituted heteroarylene group;

Ar3 and Ar4 are the same as or different from each other, and each independently is hydrogen, deuterium, a halogen group, a cyano group, a nitro group, a substituted or unsubstituted silyl group, a substituted or unsubstituted boron group, a substituted or unsubstituted alkyl group, a substituted or unsubstituted alkoxy group, a substituted or unsubstituted cycloalkyl group, a substituted or unsubstituted aryl group, a substituted or unsubstituted fused ring group of aromatic hydrocarbon ring and aliphatic hydrocarbon ring, or a substituted or unsubstituted heteroaryl group, or bond to each other to form a substituted or unsubstituted heteroring; and R and R' are the same as or different from each other, and each independently is a substituted or unsubstituted alkyl group or a substituted or unsubstituted aryl group, or can bond to each other to form a substituted or unsubstituted ring.

According to one embodiment of the present specification, Chemical Formula 1 is any one of the following Chemical Formulae 1-8-1 to 1-8-6:
<Chemical Formula 1-8-1>
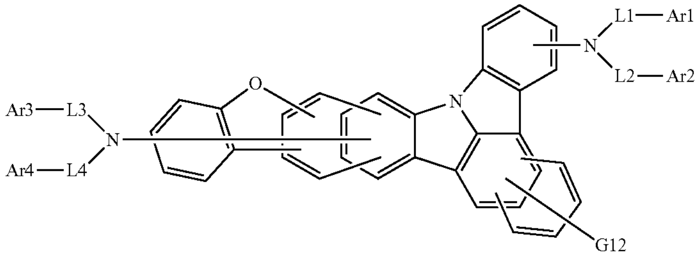
<Chemical Formula 1-8-2>
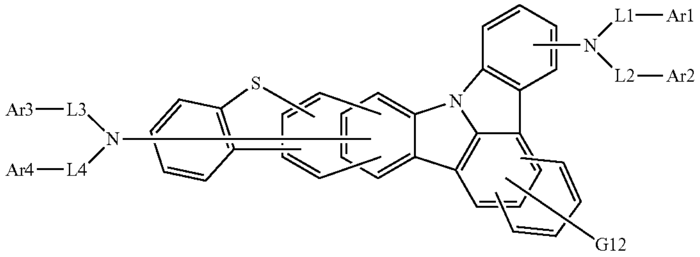
<Chemical Formula 1-8-3>
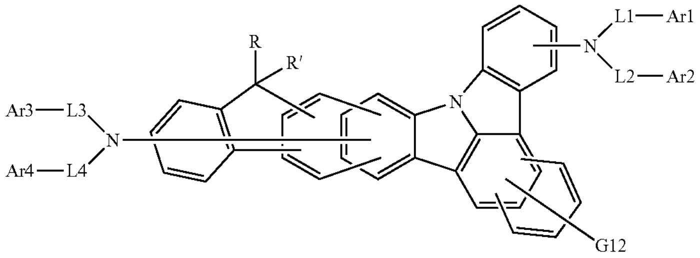
<Chemical Formula 1-8-4>
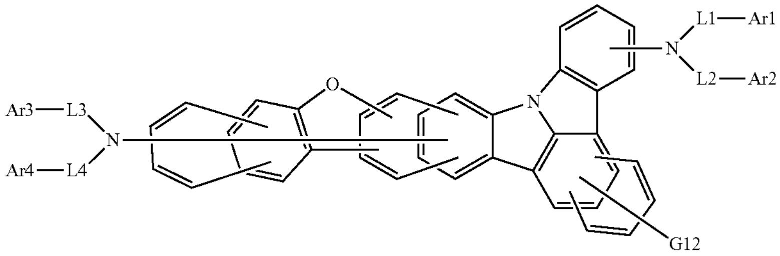
<Chemical Formula 1-8-5>
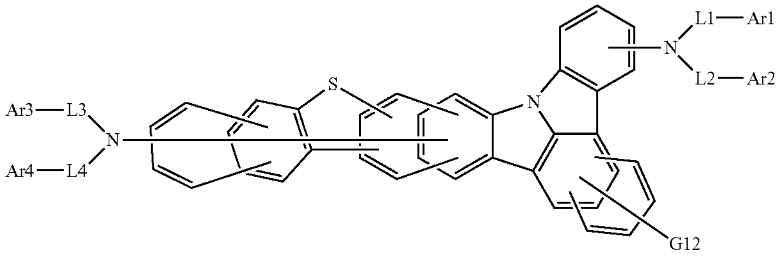

-continued

<Chemical Formula 1-8-6>

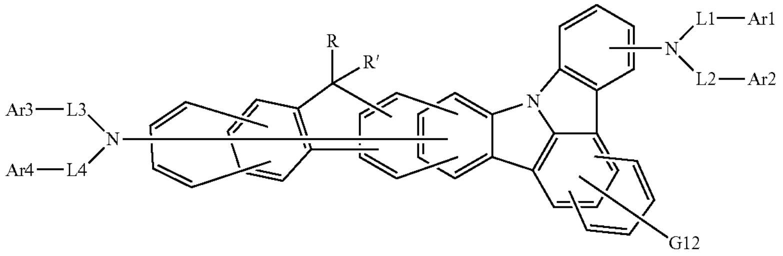

wherein in Chemical Formulae 1-8-1 to 1-8-6:

L1, L2, Ar1 and Ar2 have the same definitions as in Chemical Formula A;

G12 is hydrogen, deuterium, a halogen group, a cyano group, a nitro group, a substituted or unsubstituted silyl group, a substituted or unsubstituted boron group, a substituted or unsubstituted alkyl group, a substituted or unsubstituted alkoxy group, a substituted or unsubstituted cycloalkyl group, a substituted or unsubstituted aryl group, or a substituted or unsubstituted heteroaryl group;

L3 and L4 are the same as or different from each other, and each independently is a direct bond, a substituted or unsubstituted arylene group, or a substituted or unsubstituted heteroarylene group;

Ar3 and Ar4 are the same as or different from each other, and each independently is hydrogen, deuterium, a halogen group, a cyano group, a nitro group, a substituted or unsubstituted silyl group, a substituted or unsubstituted boron group, a substituted or unsubstituted alkyl group, a substituted or unsubstituted alkoxy group, a substituted or unsubstituted cycloalkyl group, a substituted or unsubstituted aryl group, a substituted or unsubstituted fused ring group of aromatic hydrocarbon ring and aliphatic hydrocarbon ring, or a substituted or unsubstituted heteroaryl group, or bond to each other to form a substituted or unsubstituted heteroring; and R and R' are the same as or different from each other, and each independently is a substituted or unsubstituted alkyl group or a substituted or unsubstituted aryl group, or can bond to each other to form a substituted or unsubstituted ring.

According to one embodiment of the present specification, Chemical Formula 1 is any one of the following Chemical Formulae 1-9-1 to 1-9-6:

<Chemical Formula 1-9-1>

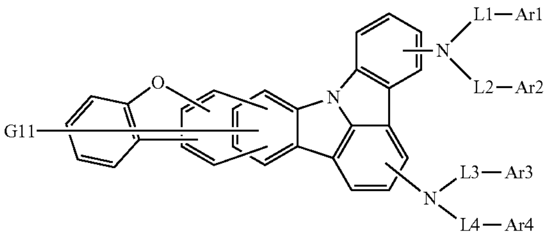

-continued

<Chemical Formula 1-9-2>

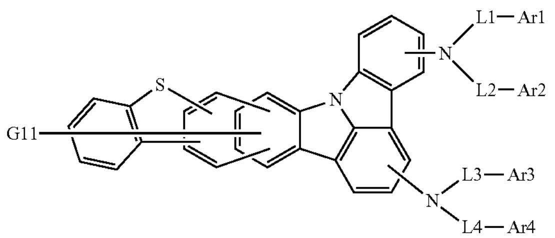

<Chemical Formula 1-9-3>

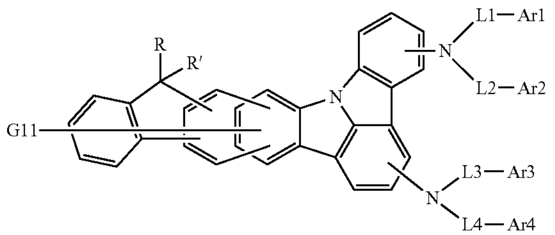

<Chemical Formula 1-9-4>

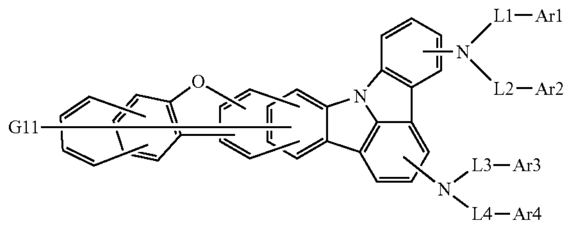

<Chemical Formula 1-9-5>

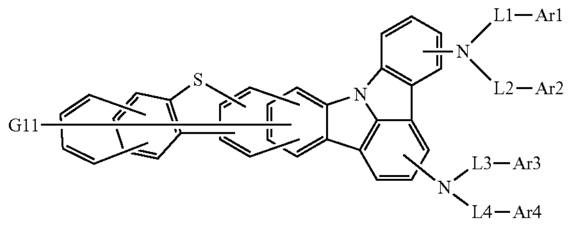

<Chemical Formula 1-9-6>

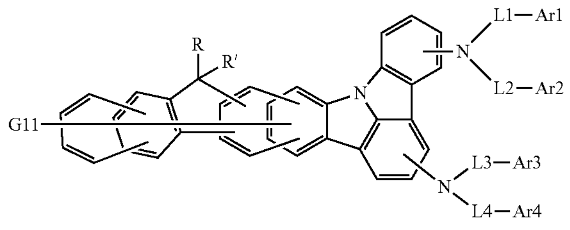

wherein in Chemical Formulae 1-9-1 to 1-9-6:

L1, L2, Ar1 and Ar2 have the same definitions as in Chemical Formula A;

G11 is hydrogen, deuterium, a halogen group, a cyano group, a nitro group, a substituted or unsubstituted silyl group, a substituted or unsubstituted boron group, a substituted or unsubstituted alkyl group, a substituted or unsubstituted alkoxy group, a substituted or unsubstituted cycloalkyl group, a substituted or unsubstituted aryl group, or a substituted or unsubstituted heteroaryl group;

L3 and L4 are the same as or different from each other, and each independently is a direct bond, a substituted or unsubstituted arylene group, or a substituted or unsubstituted heteroarylene group;

Ar3 and Ar4 are the same as or different from each other, and each independently is hydrogen, deuterium, a halogen group, a cyano group, a nitro group, a substituted or unsubstituted silyl group, a substituted or unsubstituted boron group, a substituted or unsubstituted alkyl group, a substituted or unsubstituted alkoxy group, a substituted or unsubstituted cycloalkyl group, a substituted or unsubstituted aryl group, a substituted or unsubstituted fused ring group of aromatic hydrocarbon ring and aliphatic hydrocarbon ring, or a substituted or unsubstituted heteroaryl group, or bond to each other to form a substituted or unsubstituted heteroring; and R and R' are the same as or different from each other, and each independently is a substituted or unsubstituted alkyl group or a substituted or unsubstituted aryl group, or can bond to each other to form a substituted or unsubstituted ring.

According to one embodiment of the present specification, Chemical Formula 1 is any one of the following Chemical Formulae 1-10-1 to 1-10-6:

<Chemical Formula 1-10-1>

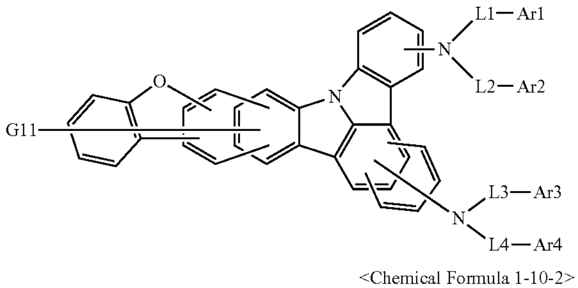

<Chemical Formula 1-10-2>

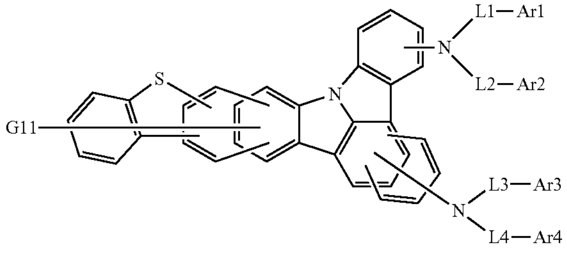

-continued

<Chemical Formula 1-10-3>

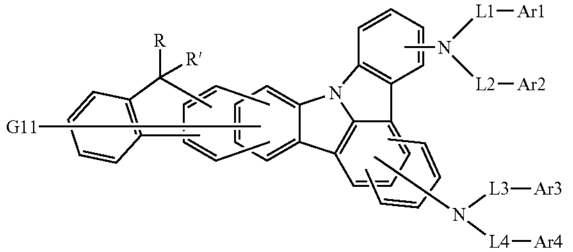

<Chemical Formula 1-10-4>

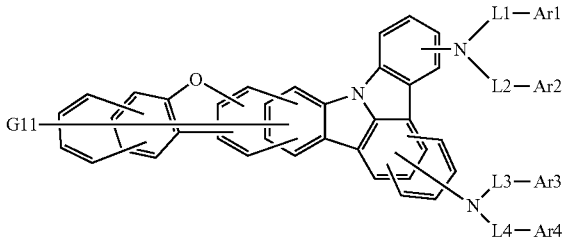

<Chemical Formula 1-10-5>

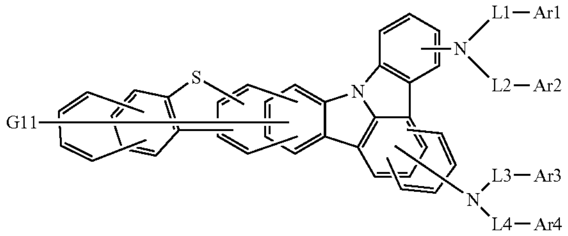

<Chemical Formula 1-10-6>

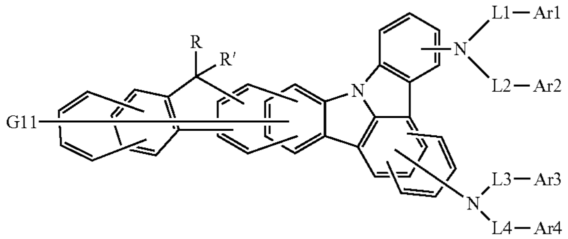

wherein in Chemical Formulae 1-10-1 to 1-10-6:

L1, L2, Ar1 and Ar2 have the same definitions as in Chemical Formula A;

G11 is hydrogen, deuterium, a halogen group, a cyano group, a nitro group, a substituted or unsubstituted silyl group, a substituted or unsubstituted boron group, a substituted or unsubstituted alkyl group, a substituted or unsubstituted alkoxy group, a substituted or unsubstituted cycloalkyl group, a substituted or unsubstituted aryl group, or a substituted or unsubstituted heteroaryl group, L3 and L4 are the same as or different from each other, and each independently a direct bond, a substituted or unsubstituted arylene group, or a substituted or unsubstituted heteroarylene group;

Ar3 and Ar4 are the same as or different from each other, and each independently is hydrogen, deuterium, a halogen group, a cyano group, a nitro group, a substituted or unsubstituted silyl group, a substituted or unsubstituted boron group, a substituted or unsubstituted alkyl group, a substituted or unsubstituted alkoxy group, a substituted or unsubstituted cycloalkyl group, a substituted or unsubstituted aryl group, a substituted or unsubstituted fused ring group of aromatic hydrocarbon ring and aliphatic hydrocarbon ring, or a substituted or unsubstituted heteroaryl group, or bond to each other to form a substituted or unsubstituted heteroring; and R and R' are the same as or different from each other, and each independently a substituted or unsubstituted alkyl group or a substituted or unsubstituted aryl group, or can bond to each other to form a substituted or unsubstituted ring.

According to another embodiment of the present specification, R and R' are the same as or different from each other, and each independently is a substituted or unsubstituted linear or branched alkyl group having 1 to 30 carbon atoms, or a substituted or unsubstituted monocyclic or polycyclic aryl group having 6 to 30 carbon atoms.

According to another embodiment of the present specification, R and R' are the same as or different from each other, and each independently is a substituted or unsubstituted linear or branched alkyl group having 1 to 20 carbon atoms, or a substituted or unsubstituted monocyclic or polycyclic aryl group having 6 to 20 carbon atoms.

According to another embodiment of the present specification, R and R' are the same as or different from each other, and each independently is a substituted or unsubstituted linear or branched alkyl group having 1 to 10 carbon atoms, or a substituted or unsubstituted monocyclic or polycyclic aryl group having 6 to 10 carbon atoms.

According to another embodiment of the present specification, R and R' are the same as or different from each other, and each independently is a linear or branched alkyl group having 1 to 30 carbon atoms, or a monocyclic or polycyclic aryl group having 6 to 30 carbon atoms.

According to another embodiment of the present specification, R and R' are the same as or different from each other, and each independently is a linear or branched alkyl group having 1 to 20 carbon atoms, or a monocyclic or polycyclic aryl group having 6 to 20 carbon atoms.

According to another embodiment of the present specification, R and R' are the same as or different from each other, and each independently is a linear or branched alkyl group having 1 to 10 carbon atoms, or a monocyclic or polycyclic aryl group having 6 to 10 carbon atoms.

According to another embodiment of the present specification, R and R' are the same as or different from each other, and each independently is a methyl group or a phenyl group.

According to another embodiment of the present specification, R and R' bond to each other to form a substituted or unsubstituted monocyclic or polycyclic hydrocarbon ring having 6 to 30 carbon atoms.

According to another embodiment of the present specification, R and R' bond to each other to form a substituted or unsubstituted monocyclic or polycyclic aromatic hydrocarbon ring having 6 to 30 carbon atoms.

According to another embodiment of the present specification, R and R' bond to each other to form a substituted or unsubstituted fluorene ring.

According to another embodiment of the present specification, R and R' bond to each other to form a monocyclic or polycyclic hydrocarbon ring having 6 to 30 carbon atoms.

According to another embodiment of the present specification, R and R' bond to each other to form a monocyclic or polycyclic aromatic hydrocarbon ring having 6 to 30 carbon atoms.

According to another embodiment of the present specification, R and R' bond to each other to form a fluorene ring.

According to another embodiment of the present specification, R and R' are a methyl group.

According to another embodiment of the present specification, R and R' are a phenyl group.

According to another embodiment of the present specification, R is a phenyl group, and R' is a methyl group.

According to another embodiment of the present specification, R' is a phenyl group, and R is a methyl group.

According to one embodiment of the present specification, R1 to R4 are the same as or different from each other, and each independently is hydrogen, deuterium, a substituted or unsubstituted linear or branched alkyl group having 1 to 30 carbon atoms, or a substituted or unsubstituted monocyclic or polycyclic aryl group having 6 to 30 carbon atoms.

According to one embodiment of the present specification, R1 to R4 are the same as or different from each other, and each independently is hydrogen, deuterium, a substituted or unsubstituted linear or branched alkyl group having 1 to 20 carbon atoms, or a substituted or unsubstituted monocyclic or polycyclic aryl group having 6 to 20 carbon atoms.

According to one embodiment of the present specification, R1 to R4 are the same as or different from each other, and each independently is hydrogen, deuterium, a substituted or unsubstituted linear or branched alkyl group having 1 to 10 carbon atoms, or a substituted or unsubstituted monocyclic or polycyclic aryl group having 6 to 10 carbon atoms.

According to one embodiment of the present specification, R1 to R4 are the same as or different from each other, and each independently is hydrogen, deuterium, a linear or branched alkyl group having 1 to 30 carbon atoms, or a monocyclic or polycyclic aryl group having 6 to 30 carbon atoms unsubstituted or substituted with deuterium or a linear or branched alkyl group having 1 to 30 carbon atoms.

According to one embodiment of the present specification, R1 to R4 are the same as or different from each other, and each independently is hydrogen, deuterium, a linear or branched alkyl group having 1 to 20 carbon atoms, or a monocyclic or polycyclic aryl group having 6 to 20 carbon atoms unsubstituted or substituted with deuterium or a linear or branched alkyl group having 1 to 20 carbon atoms.

According to one embodiment of the present specification, R1 to R4 are the same as or different from each other, and each independently is hydrogen, deuterium, a linear or branched alkyl group having 1 to 10 carbon atoms, or a monocyclic or polycyclic aryl group having 6 to 10 carbon atoms unsubstituted or substituted with deuterium or a linear or branched alkyl group having 1 to 10 carbon atoms.

According to one embodiment of the present specification, R1 to R4 are the same as or different from each other, and each independently is hydrogen, deuterium, an isopropyl group, a tert-butyl group, or a phenyl group unsubstituted or substituted with deuterium or a methyl group.

According to one embodiment of the present specification, R1 to R4 are the same as or different from each other, and each independently is hydrogen, an isopropyl group, a tert-butyl group, or a phenyl group unsubstituted or substituted with deuterium or a methyl group.

According to one embodiment of the present specification, L1 and L2 are the same as or different from each other, and each independently is a direct bond, a substituted or unsubstituted monocyclic or polycyclic arylene group having 6 to 30 carbon atoms, or a substituted or unsubstituted monocyclic or polycyclic heteroarylene group having 2 to 30 carbon atoms.

According to one embodiment of the present specification, L1 and L2 are the same as or different from each other, and each independently is a direct bond, a substituted or unsubstituted monocyclic or polycyclic arylene group having 6 to 20 carbon atoms, or a substituted or unsubstituted monocyclic or polycyclic heteroarylene group having 2 to 20 carbon atoms.

According to one embodiment of the present specification, L1 and L2 are the same as or different from each other, and each independently is a direct bond, a monocyclic or polycyclic arylene group having 6 to 30 carbon atoms, or a monocyclic or polycyclic heteroarylene group having 2 to 30 carbon atoms.

According to one embodiment of the present specification, L1 and L2 are the same as or different from each other, and each independently is a direct bond, a monocyclic or polycyclic arylene group having 6 to 20 carbon atoms, or a monocyclic or polycyclic heteroarylene group having 2 to 20 carbon atoms.

According to one embodiment of the present specification, L1 and L2 are the same as or different from each other, and each independently is a direct bond, a phenylene group, a biphenylylene group, a naphthylene group, a divalent carbazole group, a divalent dibenzofuran group, or a divalent dibenzothiophene group.

According to one embodiment of the present specification, L3 and L4 are the same as or different from each other, and each independently is a direct bond, a substituted or unsubstituted monocyclic or polycyclic arylene group having 6 to 30 carbon atoms, or a substituted or unsubstituted monocyclic or polycyclic heteroarylene group having 2 to 30 carbon atoms.

According to one embodiment of the present specification, L3 and L4 are the same as or different from each other, and each independently is a direct bond, a substituted or unsubstituted monocyclic or polycyclic arylene group having 6 to 20 carbon atoms, or a substituted or unsubstituted monocyclic or polycyclic heteroarylene group having 2 to 20 carbon atoms.

According to one embodiment of the present specification, L3 and L4 are the same as or different from each other, and each independently is a direct bond, a monocyclic or polycyclic arylene group having 6 to 30 carbon atoms, or a monocyclic or polycyclic heteroarylene group having 2 to 30 carbon atoms.

According to one embodiment of the present specification, L3 and L4 are the same as or different from each other, and each independently is a direct bond, a monocyclic or polycyclic arylene group having 6 to 20 carbon atoms, or a monocyclic or polycyclic heteroarylene group having 2 to 20 carbon atoms.

According to one embodiment of the present specification, L3 and L4 are the same as or different from each other, and each independently is a direct bond, a phenylene group, a biphenylylene group, a naphthylene group, a divalent carbazole group, a divalent dibenzofuran group, or a divalent dibenzothiophene group.

According to one embodiment of the present specification, Ar1 and Ar2 are the same as or different from each other, and each independently is hydrogen, deuterium, a cyano group, a halogen group, a substituted or unsubstituted silyl group, a substituted or unsubstituted linear or branched alkyl group having 1 to 30 carbon atoms, a substituted or unsubstituted linear or branched alkoxy group having 1 to 30 carbon atoms, a substituted or unsubstituted monocyclic or polycyclic cycloalkyl group having 3 to 30 carbon atoms, a substituted or unsubstituted monocyclic or polycyclic aryl group having 6 to 30 carbon atoms, a substituted or unsubstituted fused ring group of monocyclic or polycyclic aromatic hydrocarbon ring having 6 to 30 carbon atoms and monocyclic or polycyclic aliphatic hydrocarbon ring having 3 to 30 carbon atoms, or a substituted or unsubstituted monocyclic or polycyclic heteroaryl group having 2 to 30 carbon atoms.

According to one embodiment of the present specification, Ar1 and Ar2 are the same as or different from each other, and each independently is hydrogen, deuterium, a cyano group, a halogen group, a substituted or unsubstituted silyl group, a substituted or unsubstituted linear or branched alkyl group having 1 to 20 carbon atoms, a substituted or unsubstituted linear or branched alkoxy group having 1 to 20 carbon atoms, a substituted or unsubstituted monocyclic or polycyclic cycloalkyl group having 3 to 20 carbon atoms, a substituted or unsubstituted monocyclic or polycyclic aryl group having 6 to 20 carbon atoms, a substituted or unsubstituted fused ring group of monocyclic or polycyclic aromatic hydrocarbon ring having 6 to 20 carbon atoms and monocyclic or polycyclic aliphatic hydrocarbon ring having 3 to 20 carbon atoms, or a substituted or unsubstituted monocyclic or polycyclic heteroaryl group having 2 to 20 carbon atoms.

According to one embodiment of the present specification, Ar1 and Ar2 are the same as or different from each other, and each independently is hydrogen, deuterium, a cyano group, a halogen group, a silyl group substituted with a linear or branched alkyl group having 1 to 30 carbon atoms, a linear or branched alkyl group having 1 to 30 carbon atoms unsubstituted or substituted with deuterium, a halogen group, or a monocyclic or polycyclic aryl group having 6 to 30 carbon atoms, a linear or branched alkoxy group having 1 to 30 carbon atoms, a monocyclic or polycyclic cycloalkyl group having 3 to 30 carbon atoms, a monocyclic or polycyclic aryl group having 6 to 30 carbon atoms unsubstituted or substituted with deuterium, a halogen group, a linear or branched alkyl group having 1 to 30 carbon atoms substituted with a halogen group, a linear or branched alkyl group having 1 to 30 carbon atoms substituted with deuterium, or a linear or branched alkyl group having 1 to 30 carbon atoms, a fused ring group of monocyclic or polycyclic aromatic hydrocarbon ring having 6 to 30 carbon atoms and monocyclic or polycyclic aliphatic hydrocarbon ring having 3 to 30 carbon atoms unsubstituted or substituted with a linear or branched alkyl group having 1 to 30 carbon atoms, or a monocyclic or polycyclic heteroaryl group having 2 to 30 carbon atoms.

According to one embodiment of the present specification, Ar1 and Ar2 are the same as or different from each other, and each independently is hydrogen; deuterium; a cyano group; a halogen group; a silyl group substituted with a linear or branched alkyl group having 1 to 20 carbon atoms; a linear or branched alkyl group having 1 to 20 carbon atoms unsubstituted or substituted with deuterium, a halogen group, or a monocyclic or polycyclic aryl group having 6 to 20 carbon atoms; a linear or branched alkoxy group having 1 to 20 carbon atoms; a monocyclic or polycyclic cycloalkyl group having 3 to 20 carbon atoms; a monocyclic or polycyclic aryl group having 6 to 20 carbon atoms unsubstituted or substituted with deuterium, a halogen group, a linear or branched alkyl group having 1 to 20 carbon atoms substituted with a halogen group, a linear or branched alkyl group having 1 to 20 carbon atoms substituted with deuterium, or a linear or branched alkyl group having 1 to 20 carbon atoms; a fused ring group of monocyclic or polycyclic aromatic hydrocarbon ring having 6 to 20 carbon atoms and monocyclic or polycyclic aliphatic hydrocarbon ring having 3 to 20 carbon atoms unsubstituted or substituted with a linear or branched alkyl group having 1 to 20 carbon atoms; or a monocyclic or polycyclic heteroaryl group having 2 to 20 carbon atoms.

According to one embodiment of the present specification, Ar1 and Ar2 are the same as or different from each other, and each independently is hydrogen; deuterium; a cyano group; a halogen group; a linear or branched alkyl group having 1 to 30 carbon atoms unsubstituted or substituted with deuterium, or a monocyclic or polycyclic aryl group having 6 to 30 carbon atoms; a linear or branched alkylsilyl group having 1 to 30 carbon atoms; a linear or branched haloalkyl group having 1 to 30 carbon atoms; a linear or branched alkoxy group having 1 to 30 carbon atoms; a monocyclic or polycyclic cycloalkyl group having 3 to 30 carbon atoms; a monocyclic or polycyclic aryl group having 6 to 30 carbon atoms unsubstituted or substituted with deuterium, a halogen group, a linear or branched alkyl group having 1 to 30 carbon atoms unsubstituted or substituted with deuterium, or a linear or branched haloalkyl group having 1 to 30 carbon atoms; a fused ring group of monocyclic or polycyclic aromatic hydrocarbon ring having 6 to 30 carbon atoms and monocyclic or polycyclic aliphatic hydrocarbon ring having 3 to 30 carbon atoms unsubstituted or substituted with a linear or branched alkyl group having 1 to 30 carbon atoms; or a monocyclic or polycyclic heteroaryl group having 2 to 30 carbon atoms.

According to one embodiment of the present specification, Ar1 and Ar2 are the same as or different from each other, and each independently hydrogen; deuterium; a cyano group; a halogen group; a linear or branched alkyl group having 1 to 20 carbon atoms unsubstituted or substituted with deuterium, or a monocyclic or polycyclic aryl group having 6 to 20 carbon atoms; a linear or branched alkylsilyl group having 1 to 20 carbon atoms; a linear or branched haloalkyl group having 1 to 20 carbon atoms; a linear or branched alkoxy group having 1 to 20 carbon atoms; a monocyclic or polycyclic cycloalkyl group having 3 to 20 carbon atoms; a monocyclic or polycyclic aryl group having 6 to 20 carbon atoms unsubstituted or substituted with deuterium, a halogen group, a linear or branched alkyl group having 1 to 20 carbon atoms unsubstituted or substituted with deuterium, or a linear or branched haloalkyl group having 1 to 20 carbon atoms; a fused ring group of monocyclic or polycyclic aromatic hydrocarbon ring having 6 to 20 carbon atoms and monocyclic or polycyclic aliphatic hydrocarbon ring having 3 to 20 carbon atoms unsubstituted or substituted with a linear or branched alkyl group having 1 to 20 carbon atoms; or a monocyclic or polycyclic heteroaryl group having 2 to 20 carbon atoms.

According to one embodiment of the present specification, Ar1 and Ar2 are the same as or different from each other, and each independently hydrogen; deuterium; a cyano group; F; a methyl group; an isopropyl group; a tert-butyl group unsubstituted or substituted with a phenyl group; a trimethylsilyl group ($Si(CH_3)_3$); a methoxy group ($OCH_3$); a trifluoromethyl group ($CF_3$), a trideuteriummethyl group ($CD_3$); a cyclohexyl group; a phenyl group unsubstituted or substituted with deuterium, F, a methyl group, a tert-butyl group, a trifluoromethyl group ($CF_3$) or a trideuteriummethyl group ($CD_3$); a biphenyl group; a naphthyl group; a terphenyl group; a phenanthrene group; a fluorene group substituted with a methyl group; a dibenzofuran group; a dibenzothiophene group; a benzofluorene group substituted with a methyl group; a benzonaphthothiophene group; a benzonaphthofuran group; a tetrahydronaphthalene group unsubstituted or substituted with a methyl group; a pyridine group; or an isoquinoline group.

According to one embodiment of the present specification, Ar1 and Ar2 are the same as or different from each other, and each independently deuterium; a cyano group; F; a methyl group; an isopropyl group; a tert-butyl group unsubstituted or substituted with a phenyl group; a trimethylsilyl group ($Si(CH_3)_3$); a methoxy group ($OCH_3$); a trifluoromethyl group ($CF_3$), a trideuteriummethyl group ($CD_3$); a cyclohexyl group; a phenyl group unsubstituted or substituted with deuterium, F, a methyl group, a tert-butyl group, a trifluoromethyl group ($CF_3$) or a trideuteriummethyl group ($CD_3$); a biphenyl group; a naphthyl group; a terphenyl group; a phenanthrene group; a fluorene group substituted with a methyl group; a dibenzofuran group; a dibenzothiophene group; a benzofluorene group substituted with a methyl group; a benzonaphthothiophene group; a benzonaphthofuran group; a tetrahydronaphthalene group unsubstituted or substituted with a methyl group; a pyridine group; or an isoquinoline group.

According to one embodiment of the present specification, Ar3 and Ar4 are the same as or different from each other, and each independently hydrogen; deuterium; a cyano group; a halogen group; a substituted or unsubstituted silyl group; a substituted or unsubstituted linear or branched alkyl group having 1 to 30 carbon atoms; a substituted or unsubstituted linear or branched alkoxy group having 1 to 30 carbon atoms; a substituted or unsubstituted monocyclic or polycyclic cycloalkyl group having 3 to 30 carbon atoms; a substituted or unsubstituted monocyclic or polycyclic aryl group having 6 to 30 carbon atoms; a substituted or unsubstituted fused ring group of monocyclic or polycyclic aromatic hydrocarbon ring having 6 to 30 carbon atoms and monocyclic or polycyclic aliphatic hydrocarbon ring having 3 to 30 carbon atoms; or a substituted or unsubstituted monocyclic or polycyclic heteroaryl group having 2 to 30 carbon atoms.

According to one embodiment of the present specification, Ar3 and Ar4 are the same as or different from each other, and each independently hydrogen; deuterium; a cyano group; a halogen group; a substituted or unsubstituted silyl group; a substituted or unsubstituted linear or branched alkyl group having 1 to 20 carbon atoms; a substituted or unsubstituted linear or branched alkoxy group having 1 to 20 carbon atoms; a substituted or unsubstituted monocyclic or polycyclic cycloalkyl group having 3 to 20 carbon atoms; a substituted or unsubstituted monocyclic or polycyclic aryl group having 6 to 20 carbon atoms; a substituted or unsubstituted fused ring group of monocyclic or polycyclic aromatic hydrocarbon ring having 6 to 20 carbon atoms and monocyclic or polycyclic aliphatic hydrocarbon ring having 3 to 20 carbon atoms; or a substituted or unsubstituted monocyclic or polycyclic heteroaryl group having 2 to 20 carbon atoms.

According to one embodiment of the present specification, Ar3 and Ar4 are the same as or different from each other, and each independently hydrogen; deuterium; a cyano group; a halogen group; a silyl group substituted with a linear or branched alkyl group having 1 to 30 carbon atoms; a linear or branched alkyl group having 1 to 30 carbon atoms unsubstituted or substituted with deuterium, a halogen group, or a monocyclic or polycyclic aryl group having 6 to 30 carbon atoms; a linear or branched alkoxy group having 1 to 30 carbon atoms; a monocyclic or polycyclic cycloalkyl group having 3 to 30 carbon atoms; a monocyclic or polycyclic aryl group having 6 to 30 carbon atoms unsubstituted or substituted with deuterium, a halogen group, a linear or branched alkyl group having 1 to 30 carbon atoms substituted with a halogen group, a linear or branched alkyl group having 1 to 30 carbon atoms substituted with deuterium, or a linear or branched alkyl group having 1 to 30 carbon atoms; a fused ring group of monocyclic or polycyclic aromatic hydrocarbon ring having 6 to 30 carbon atoms and monocyclic or polycyclic aliphatic hydrocarbon ring having 3 to 30 carbon atoms unsubstituted or substituted with a linear or branched alkyl group having 1 to 30 carbon atoms; or a monocyclic or polycyclic heteroaryl group having 2 to 30 carbon atoms.

According to one embodiment of the present specification, Ar3 and Ar4 are the same as or different from each other, and each independently hydrogen; deuterium; a cyano group; a halogen group; a silyl group substituted with a linear or branched alkyl group having 1 to 20 carbon atoms; a linear or branched alkyl group having 1 to 20 carbon atoms unsubstituted or substituted with deuterium, a halogen group, or a monocyclic or polycyclic aryl group having 6 to 20 carbon atoms; a linear or branched alkoxy group having 1 to 20 carbon atoms; a monocyclic or polycyclic cycloalkyl group having 3 to 20 carbon atoms; a monocyclic or polycyclic aryl group having 6 to 20 carbon atoms unsubstituted or substituted with deuterium, a halogen group, a linear or branched alkyl group having 1 to 20 carbon atoms substituted with a halogen group, a linear or branched alkyl group having 1 to 20 carbon atoms substituted with deuterium, or a linear or branched alkyl group having 1 to 20 carbon atoms; a fused ring group of monocyclic or polycyclic aromatic hydrocarbon ring having 6 to 20 carbon atoms and monocyclic or polycyclic aliphatic hydrocarbon ring having 3 to 20 carbon atoms unsubstituted or substituted with a linear or branched alkyl group having 1 to 20 carbon atoms; or a monocyclic or polycyclic heteroaryl group having 2 to 20 carbon atoms.

According to one embodiment of the present specification, Ar3 and Ar4 are the same as or different from each other, and each independently hydrogen; deuterium; a cyano group; a halogen group; a linear or branched alkyl group having 1 to 30 carbon atoms unsubstituted or substituted with deuterium, or a monocyclic or polycyclic aryl group having 6 to 30 carbon atoms; a linear or branched alkylsilyl group having 1 to 30 carbon atoms; a linear or branched haloalkyl group having 1 to 30 carbon atoms; a linear or branched alkoxy group having 1 to 30 carbon atoms; a monocyclic or polycyclic cycloalkyl group having 3 to 30 carbon atoms; a monocyclic or polycyclic aryl group having 6 to 30 carbon atoms unsubstituted or substituted with deuterium, a halogen group, a linear or branched alkyl group having 1 to 30 carbon atoms unsubstituted or substituted with deuterium, or a linear or branched haloalkyl group having 1 to 30 carbon atoms; a fused ring group of monocyclic or polycyclic aromatic hydrocarbon ring having 6 to 30 carbon atoms and monocyclic or polycyclic aliphatic hydrocarbon ring having 3 to 30 carbon atoms unsubstituted or substituted with a linear or branched alkyl group having 1 to 30 carbon atoms; or a monocyclic or polycyclic heteroaryl group having 2 to 30 carbon atoms.

According to one embodiment of the present specification, Ar3 and Ar4 are the same as or different from each other, and each independently hydrogen; deuterium; a cyano group; a halogen group; a linear or branched alkyl group having 1 to 20 carbon atoms unsubstituted or substituted with deuterium, or a monocyclic or polycyclic aryl group having 6 to 20 carbon atoms; a linear or branched alkylsilyl group having 1 to 20 carbon atoms; a linear or branched haloalkyl group having 1 to 20 carbon atoms; a linear or branched alkoxy group having 1 to 20 carbon atoms; a monocyclic or polycyclic cycloalkyl group having 3 to 20 carbon atoms; a monocyclic or polycyclic aryl group having 6 to 20 carbon atoms unsubstituted or substituted with deuterium, a halogen group, a linear or branched alkyl group having 1 to 20 carbon atoms unsubstituted or substituted with deuterium, or a linear or branched haloalkyl group having 1 to 20 carbon atoms; a fused ring group of monocyclic or polycyclic aromatic hydrocarbon ring having 6 to 30 carbon atoms and monocyclic or polycyclic aliphatic hydrocarbon ring having 3 to 30 carbon atoms unsubstituted or substituted with a linear or branched alkyl group having 1 to 30 carbon atoms; or a monocyclic or polycyclic heteroaryl group having 2 to 20 carbon atoms.

According to one embodiment of the present specification, Ar3 and Ar4 are the same as or different from each other, and each independently hydrogen; deuterium; a cyano group; F; a methyl group; an isopropyl group; a tert-butyl group unsubstituted or substituted with a phenyl group; a trimethylsilyl group ($Si(CH_3)_3$); a methoxy group ($OCH_3$); a trifluoromethyl group ($CF_3$), a trideuteriummethyl group ($CD_3$); a cyclohexyl group; a phenyl group unsubstituted or substituted with deuterium, F, a methyl group, a tert-butyl group, a trifluoromethyl group ($CF_3$) or a trideuteriummethyl group ($CD_3$); a biphenyl group; a naphthyl group; a terphenyl group; a phenanthrene group; a fluorene group substituted with a methyl group; a dibenzofuran group; a dibenzothiophene group; a benzofluorene group substituted with a methyl group; a benzonaphthothiophene group; a benzonaphthofuran group; a tetrahydronaphthalene group unsubstituted or substituted with a methyl group; a pyridine group; or an isoquinoline group.

According to one embodiment of the present specification, Ar3 and Ar4 are the same as or different from each other, and each independently deuterium; a cyano group; F; a methyl group; an isopropyl group; a tert-butyl group unsubstituted or substituted with a phenyl group; a trimethylsilyl group ($Si(CH_3)_3$); a methoxy group ($OCH_3$); a trifluoromethyl group ($CF_3$), a trideuteriummethyl group ($CD_3$); a cyclohexyl group; a phenyl group unsubstituted or substituted with deuterium, F, a methyl group, a tert-butyl group, a trifluoromethyl group ($CF_3$) or a trideuteriummethyl group ($CD_3$); a biphenyl group; a naphthyl group; a terphenyl group; a phenanthrene group; a fluorene group substituted with a methyl group; a dibenzofuran group; a dibenzothiophene group; a benzofluorene group substituted with a methyl group; a benzonaphthothiophene group; a benzonaphthofuran group; a tetrahydronaphthalene group unsubstituted or substituted with a methyl group; a pyridine group; or an isoquinoline group.

According to one embodiment of the present specification, Chemical Formula 1 is any one compound selected from among the following compounds:

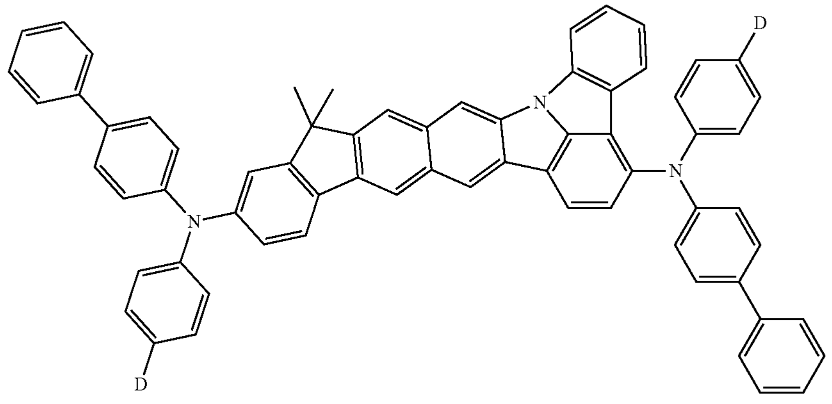
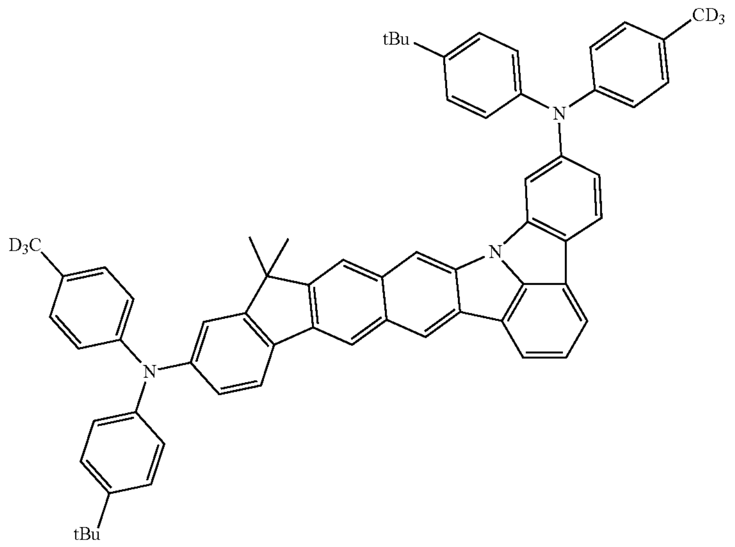
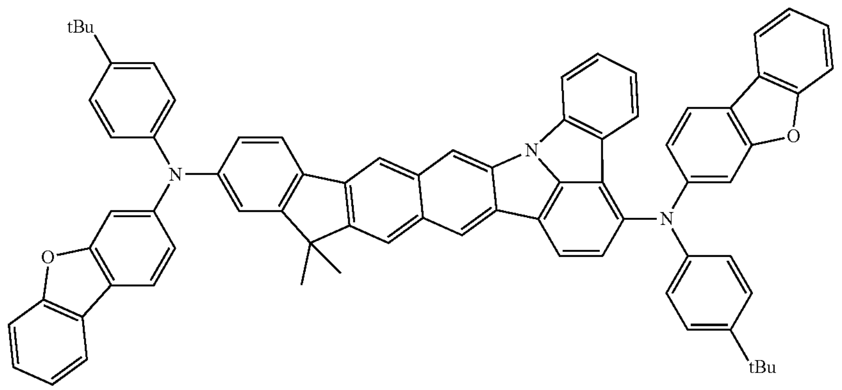

-continued
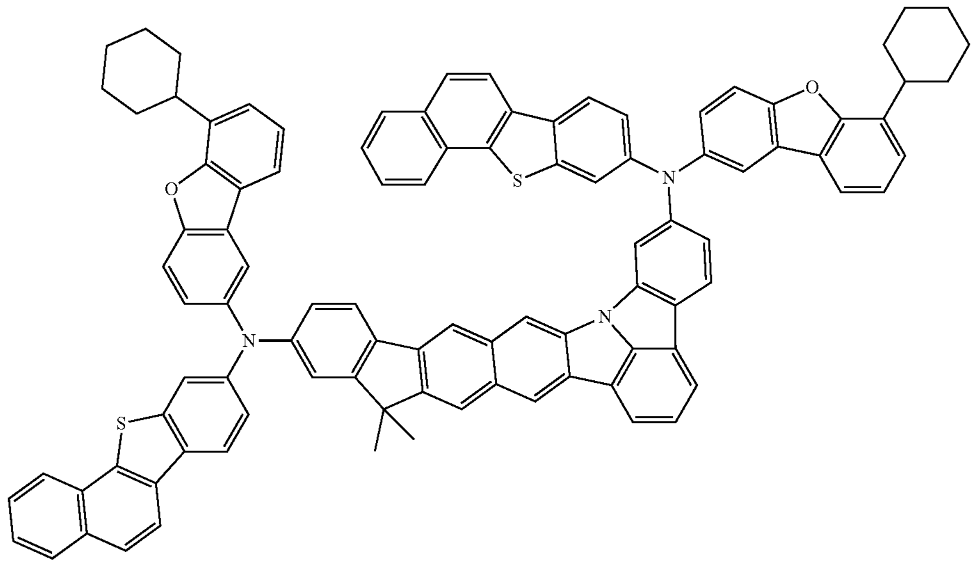
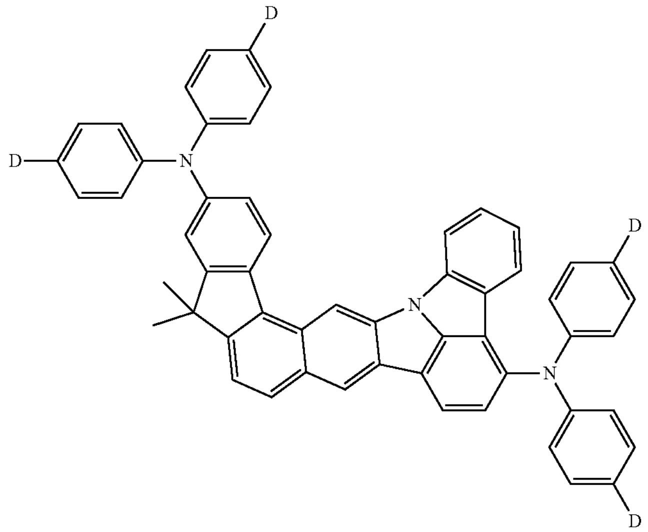
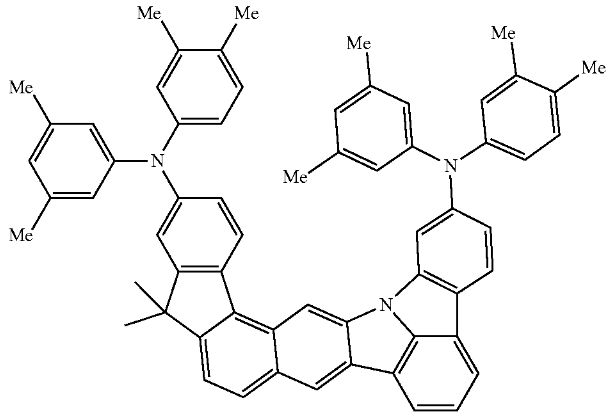

-continued
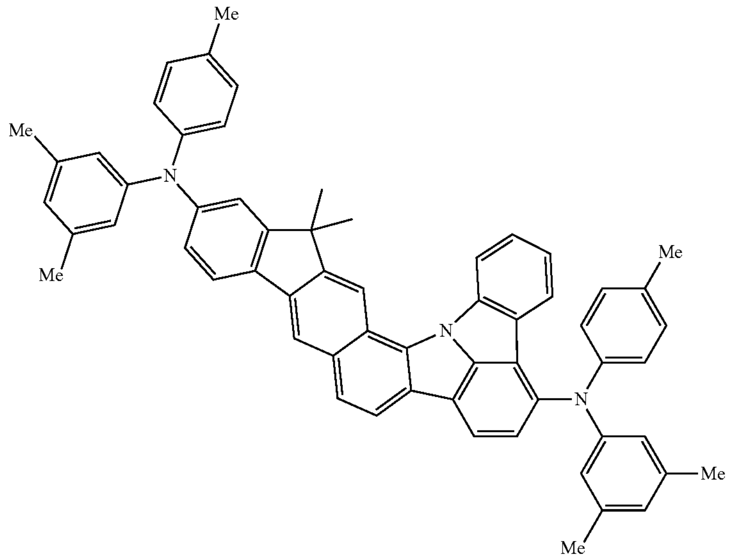
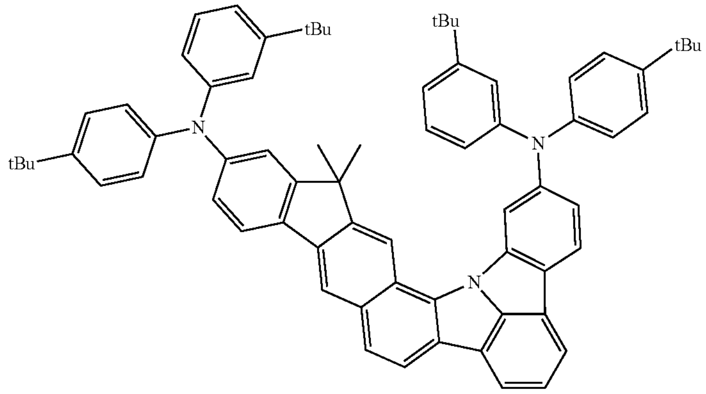
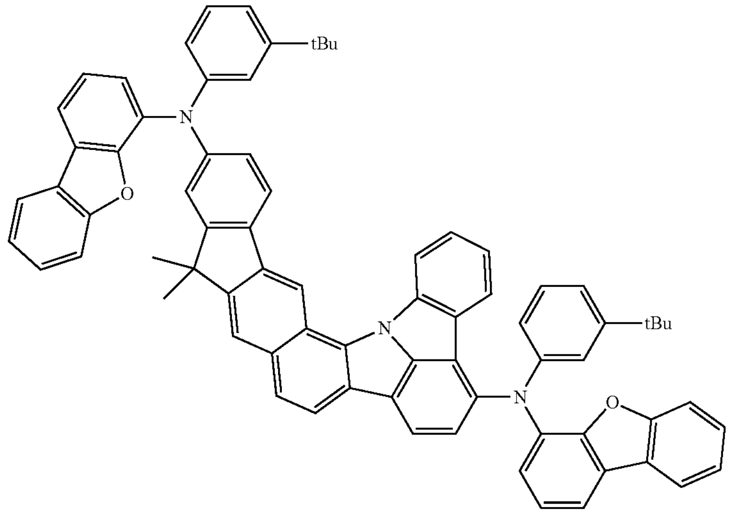

-continued
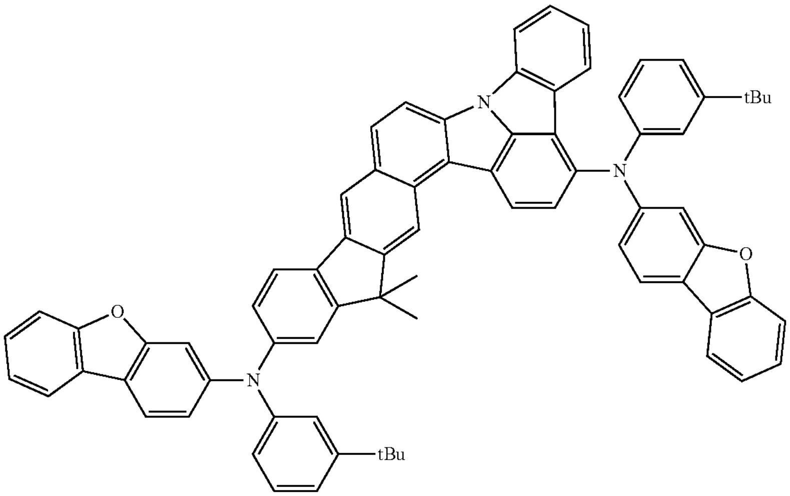
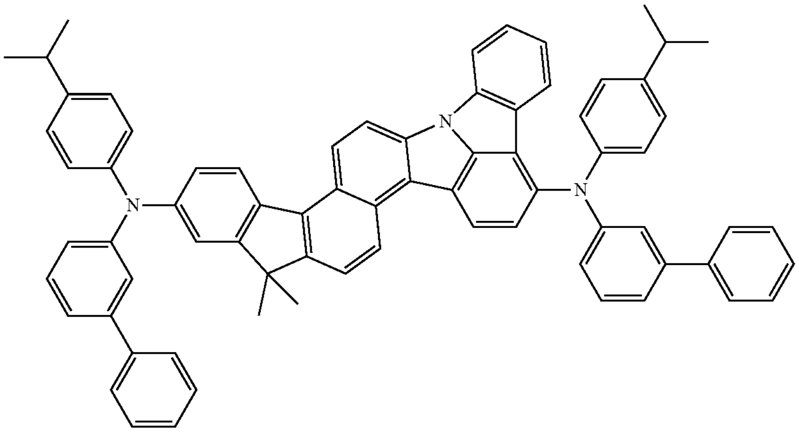
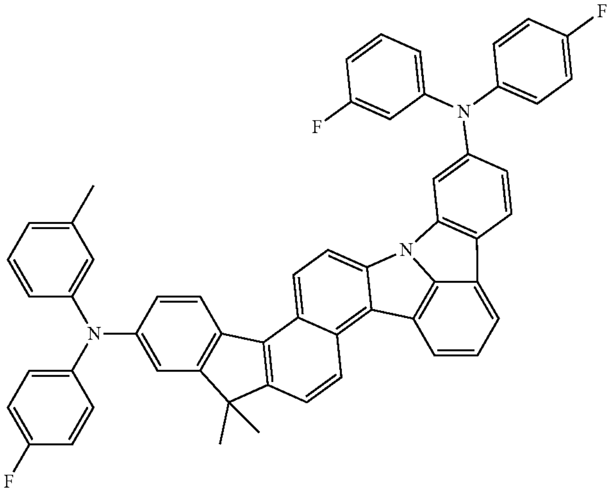

-continued
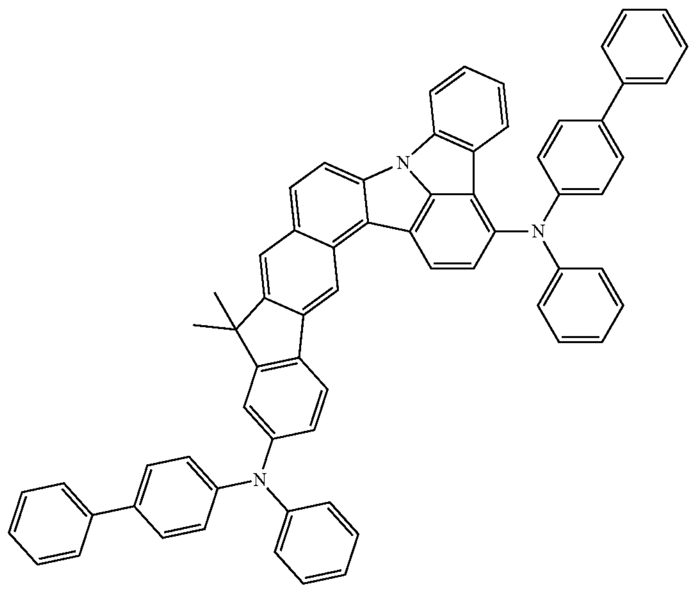
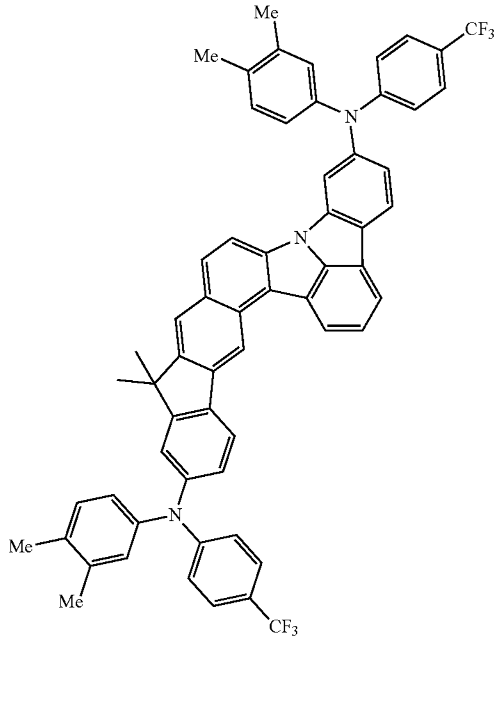

-continued
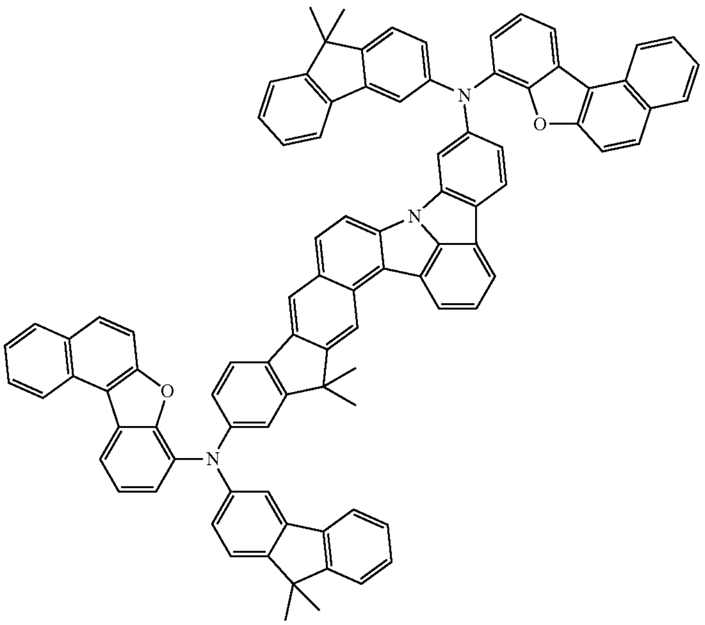
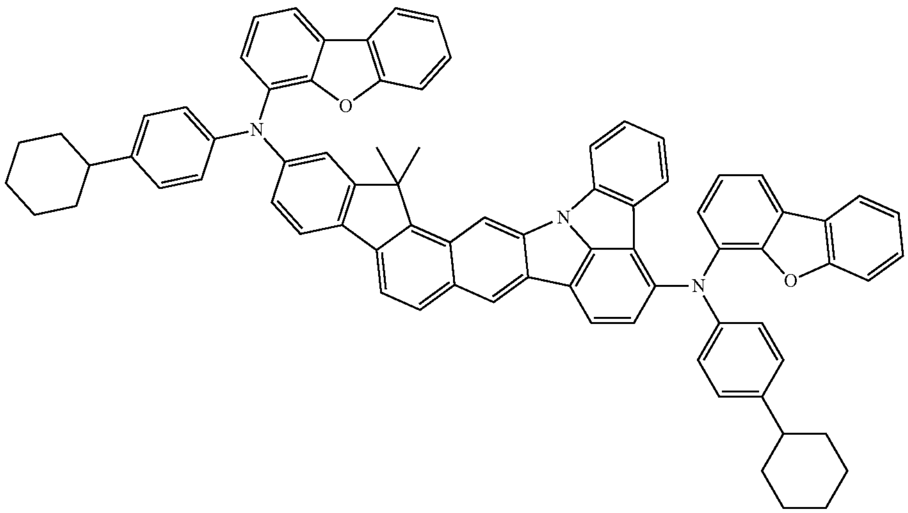
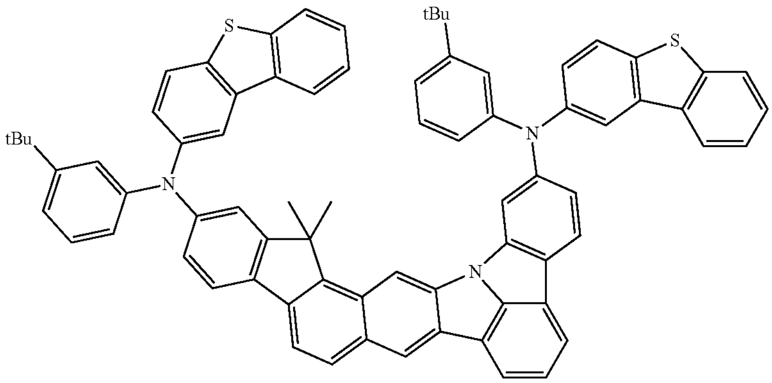

-continued
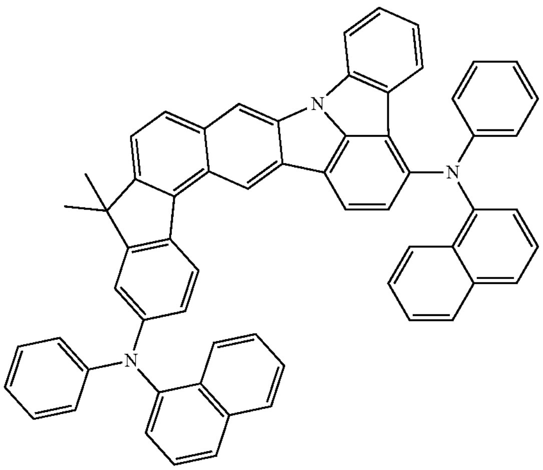
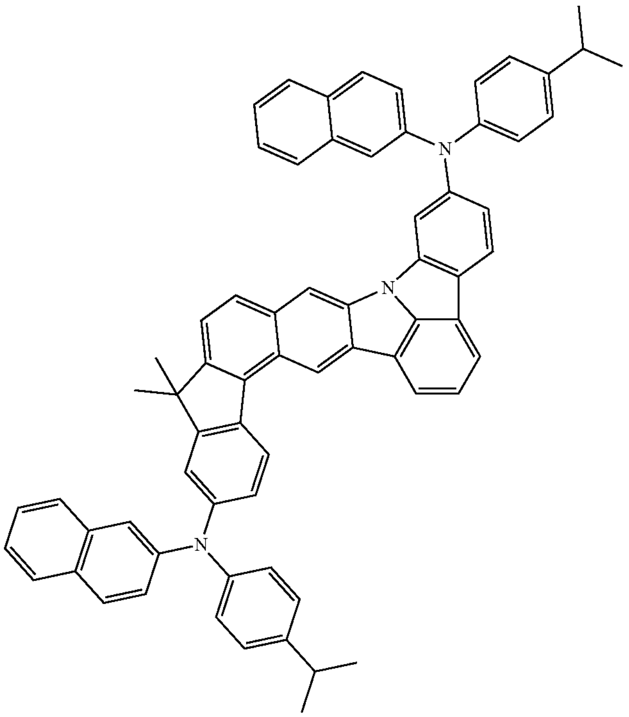
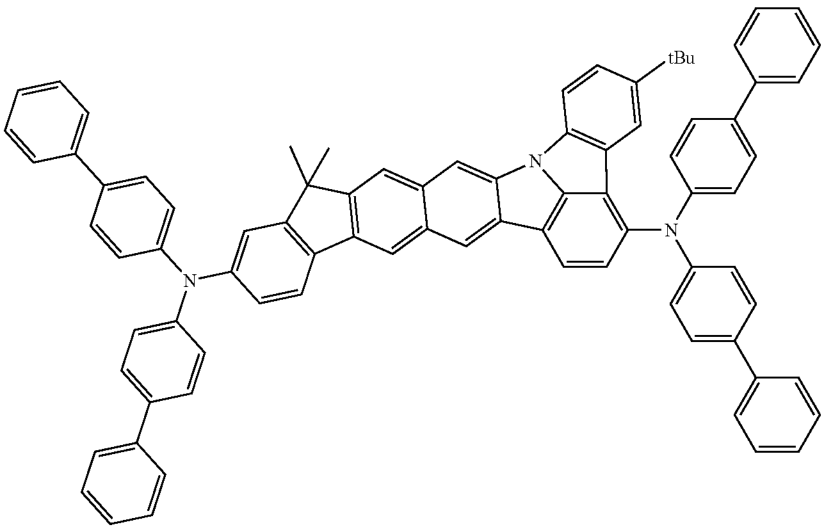

-continued
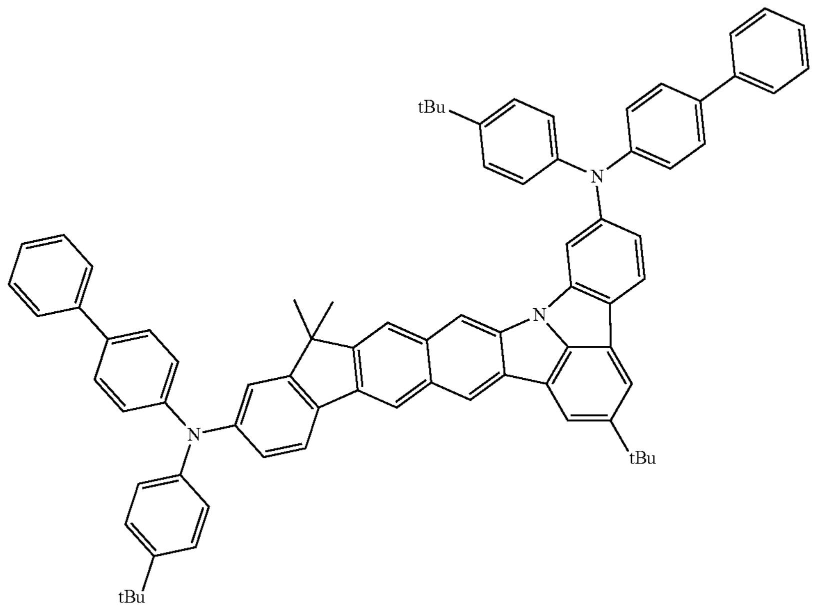
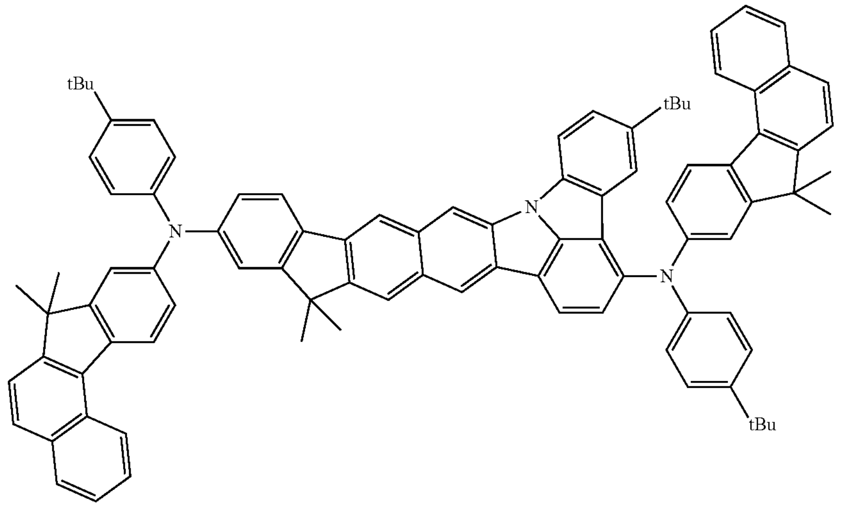
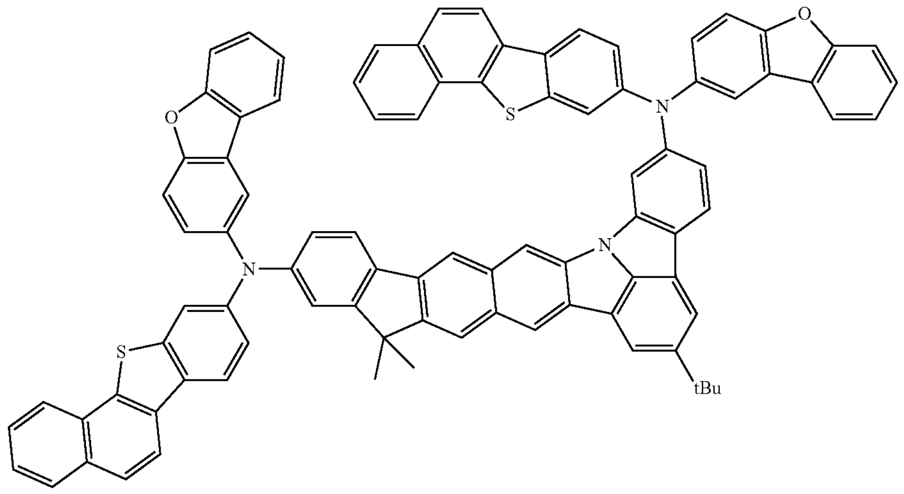

-continued
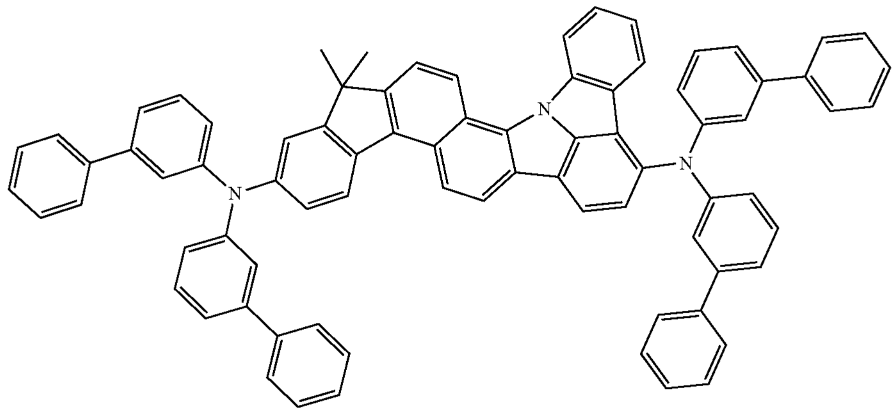
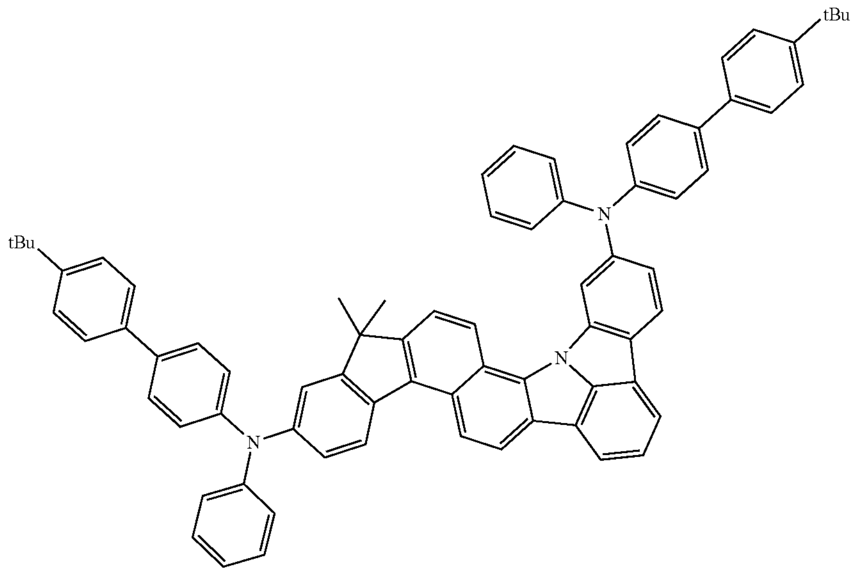
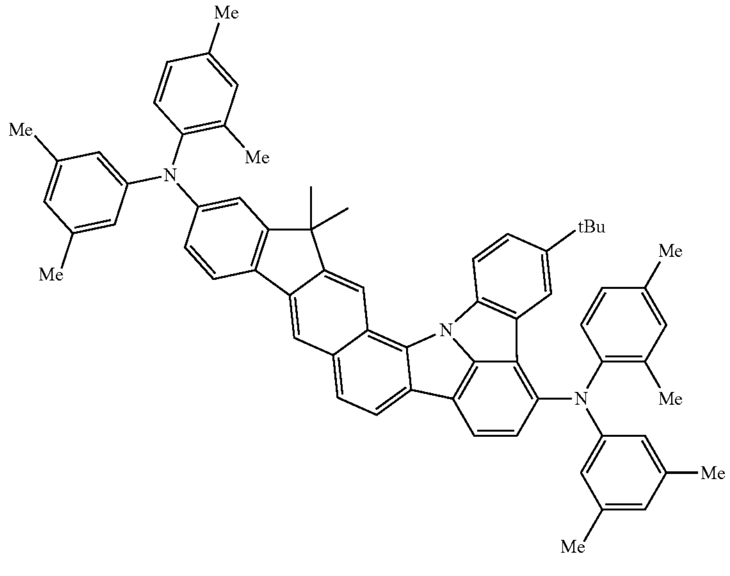

-continued
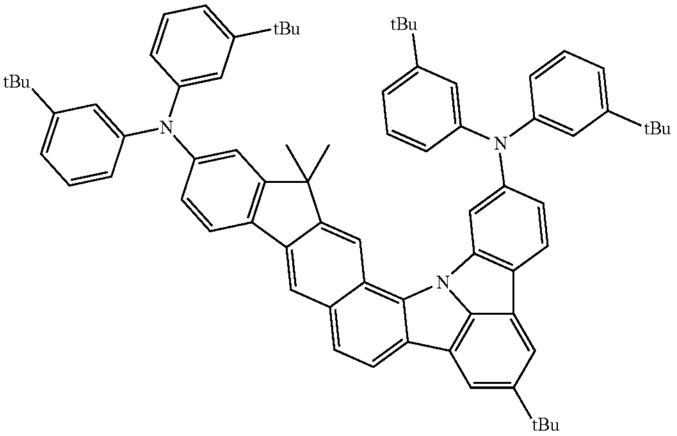
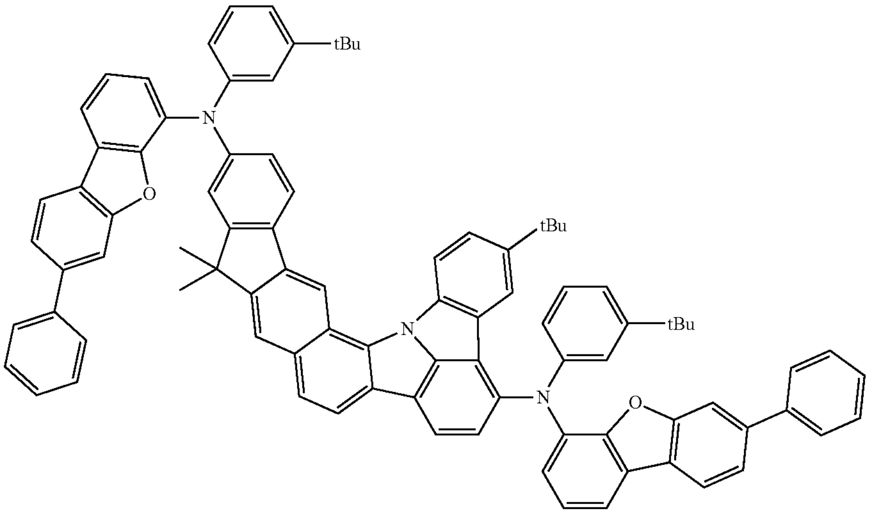
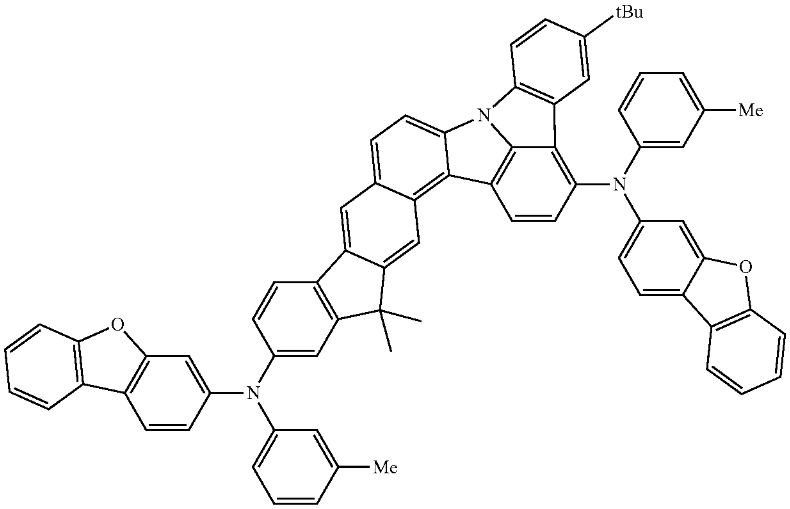

-continued
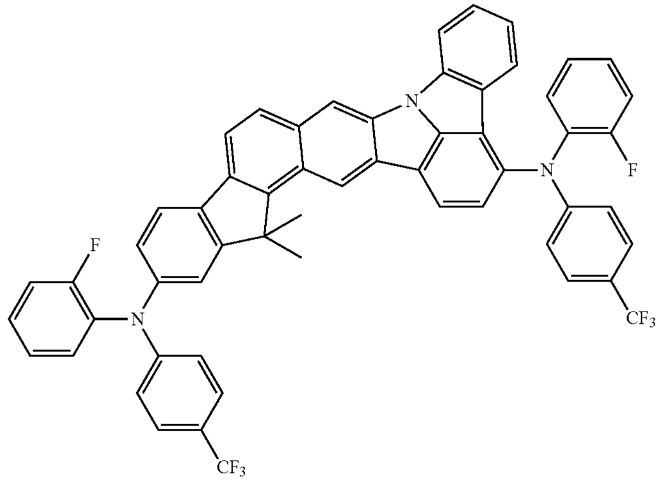
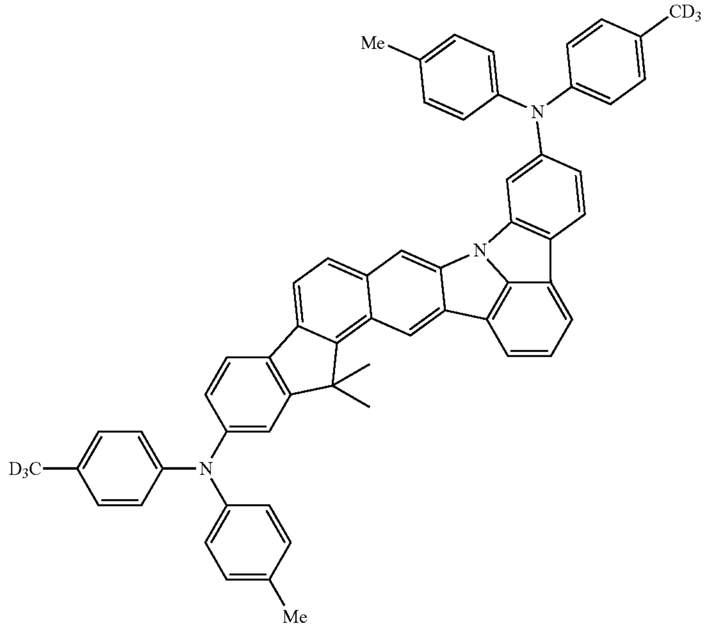
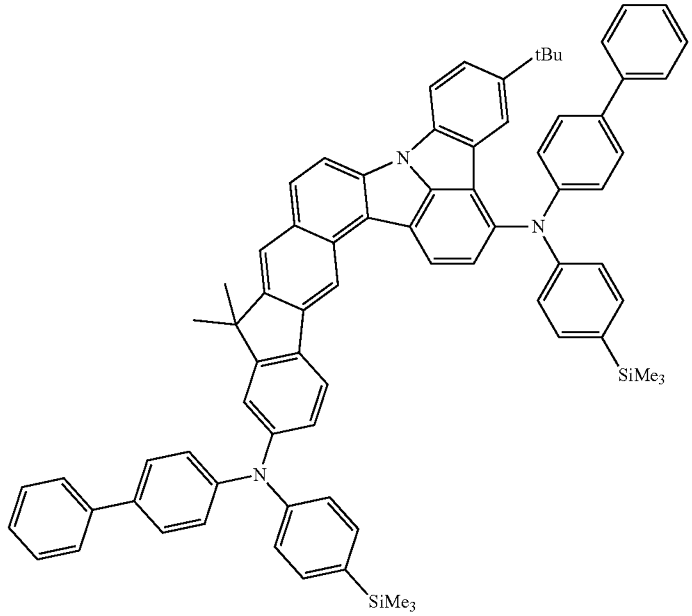

-continued
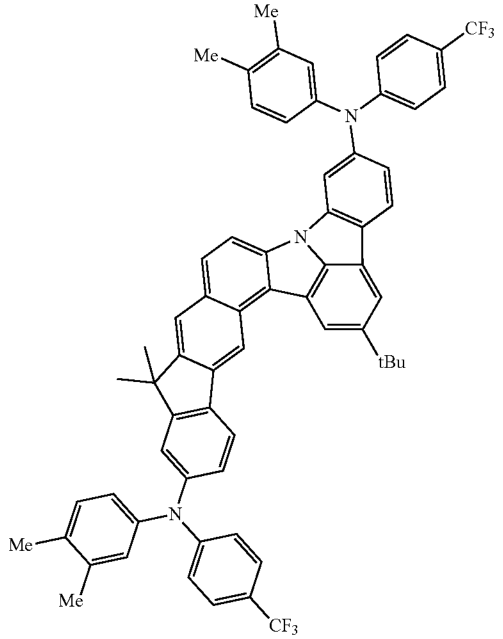
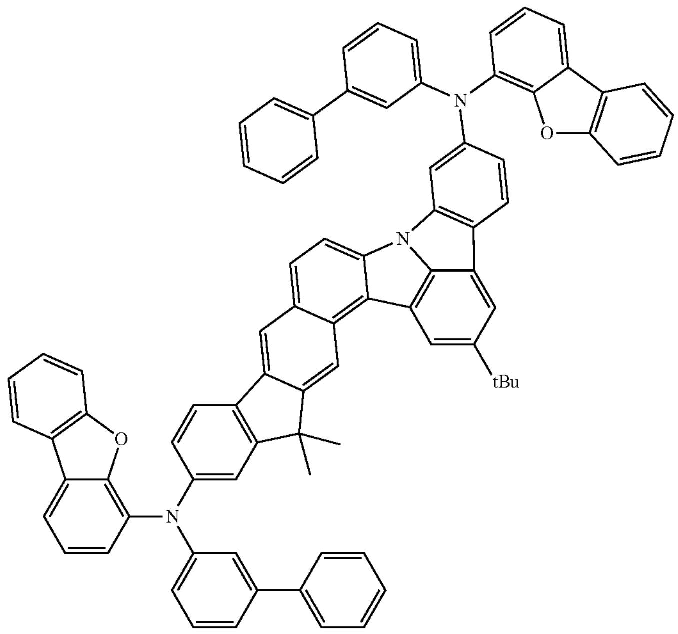

-continued
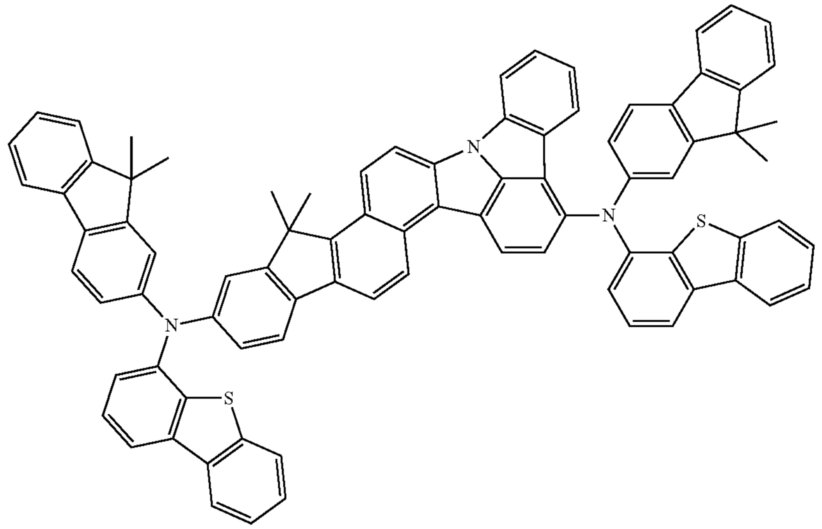
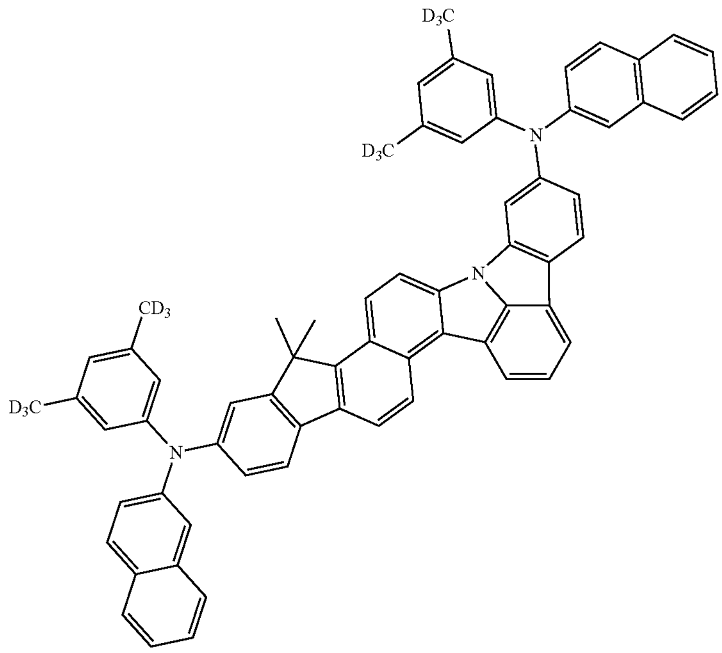
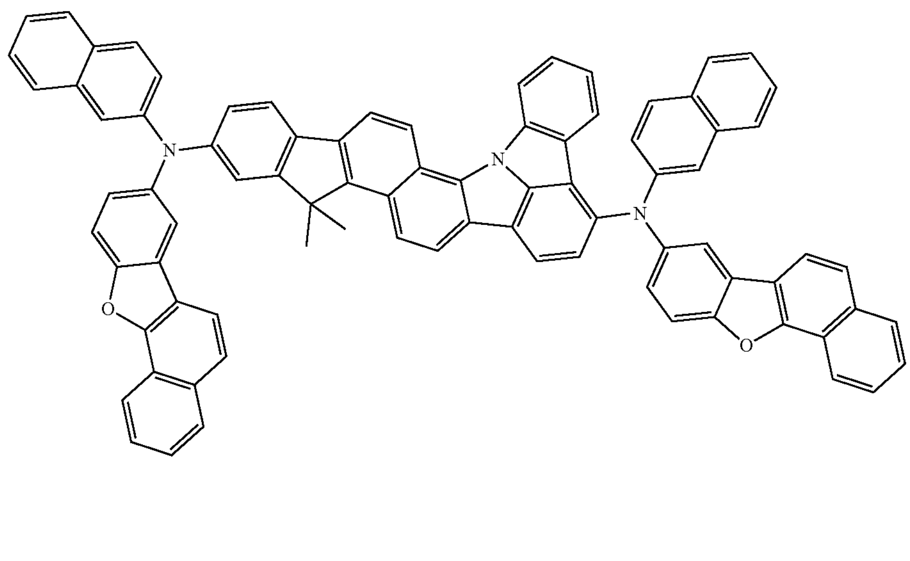

-continued
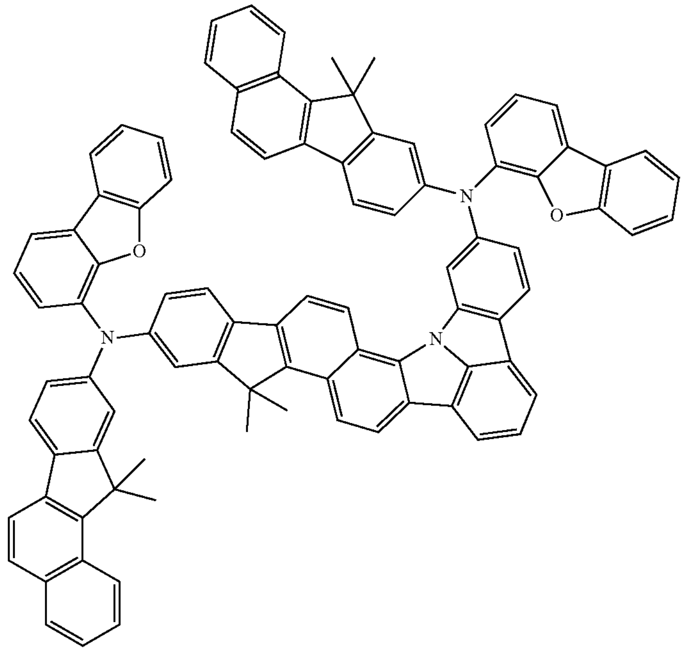
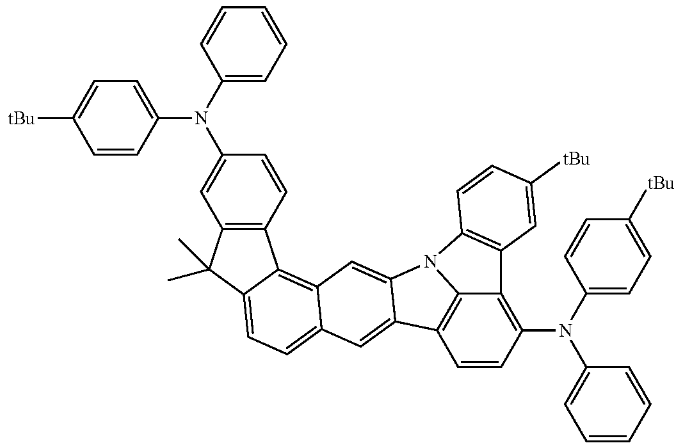
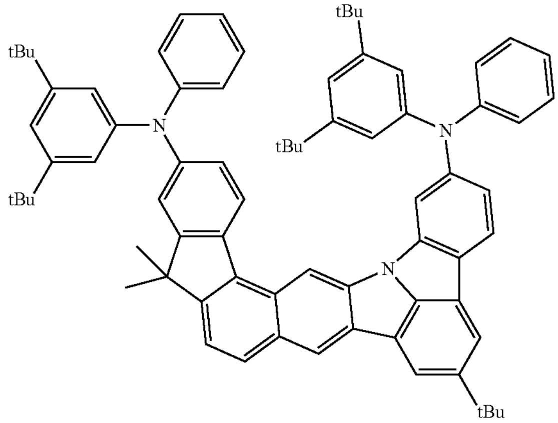

-continued
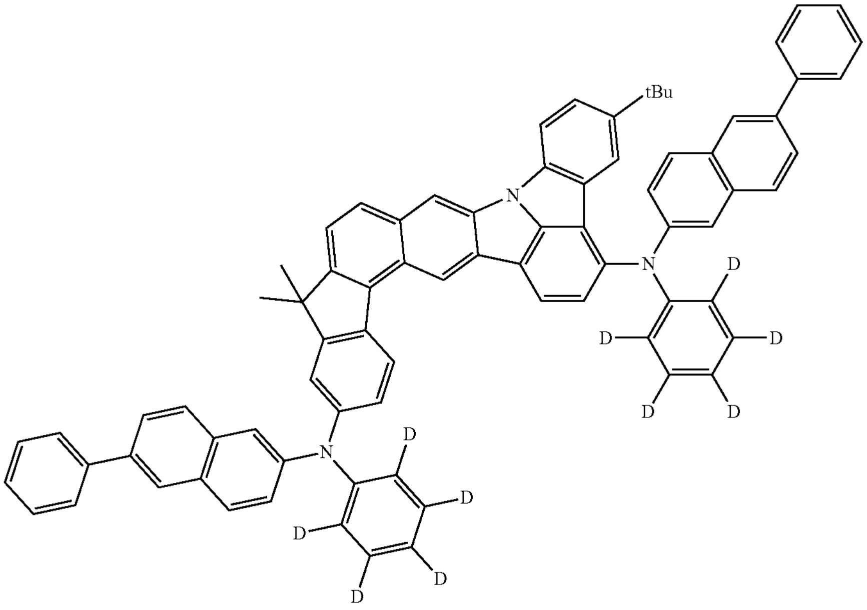
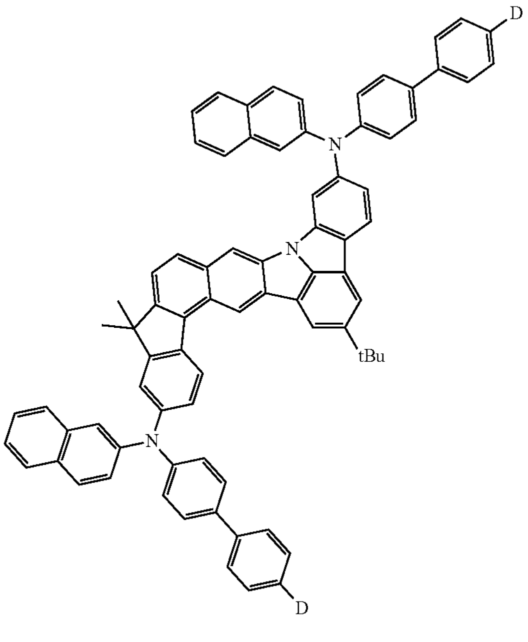

-continued
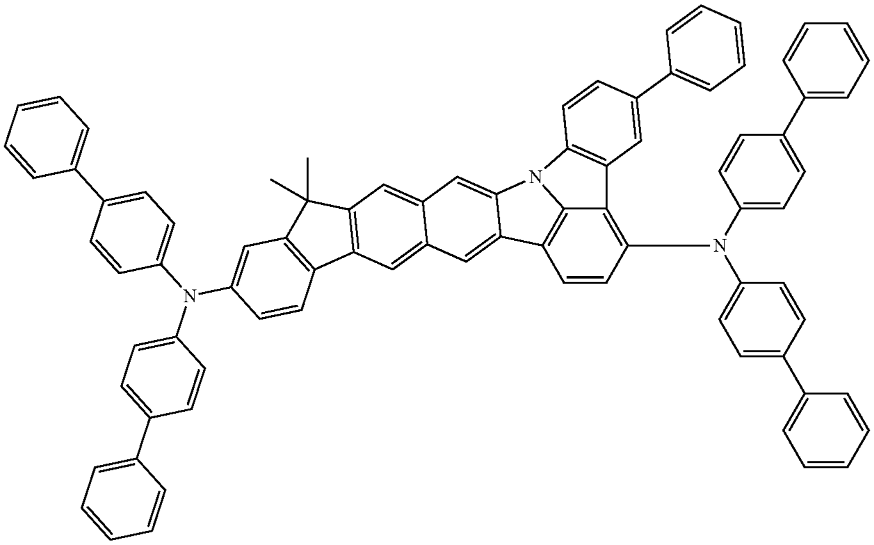
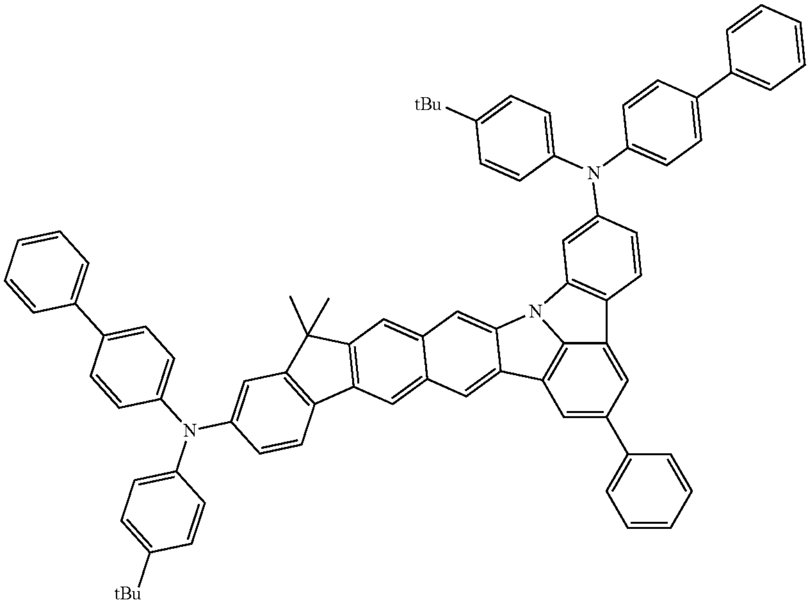
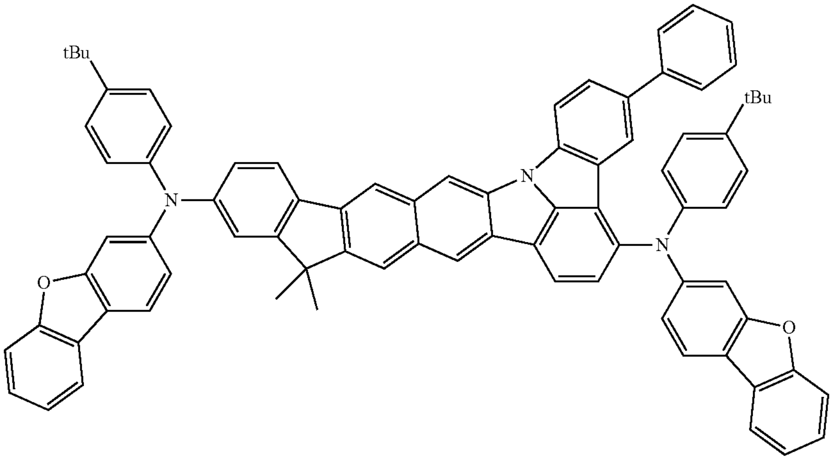

-continued
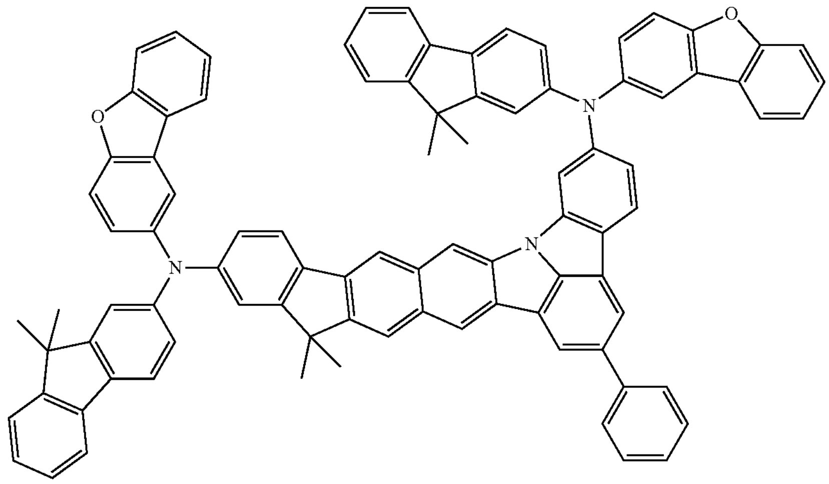
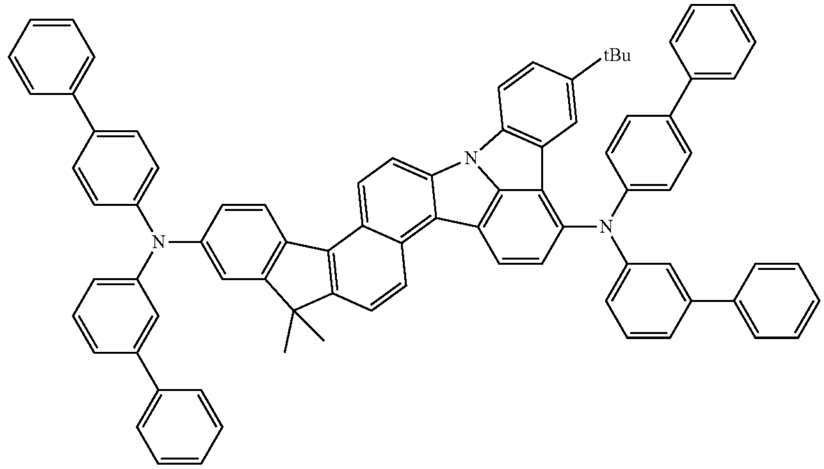
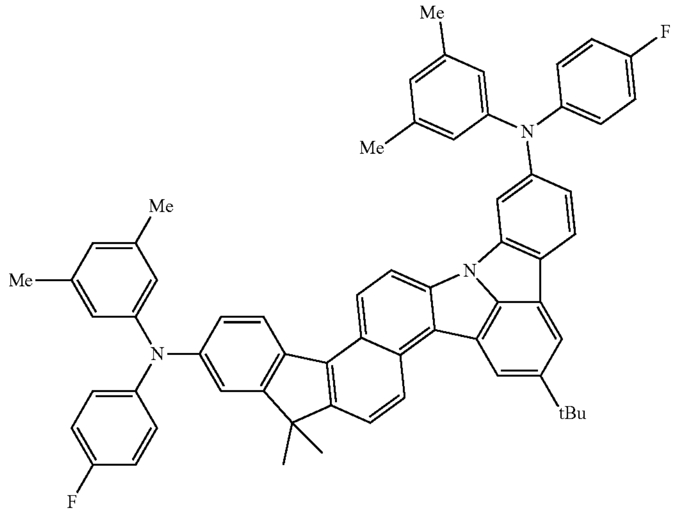

-continued
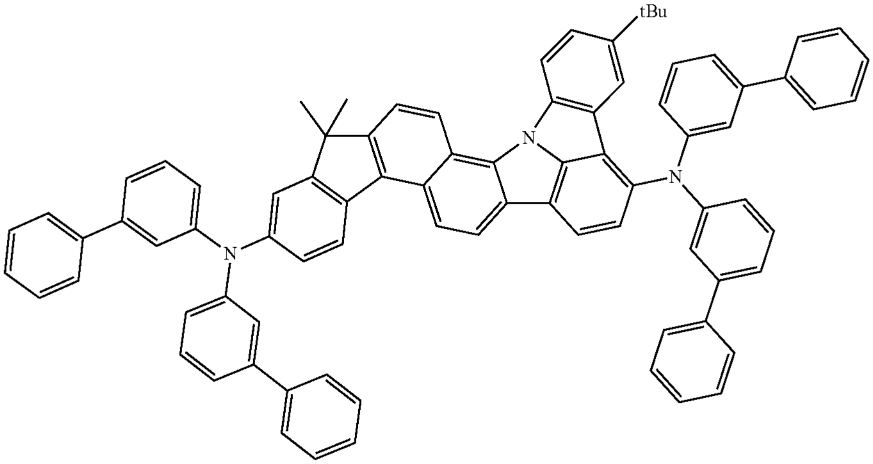
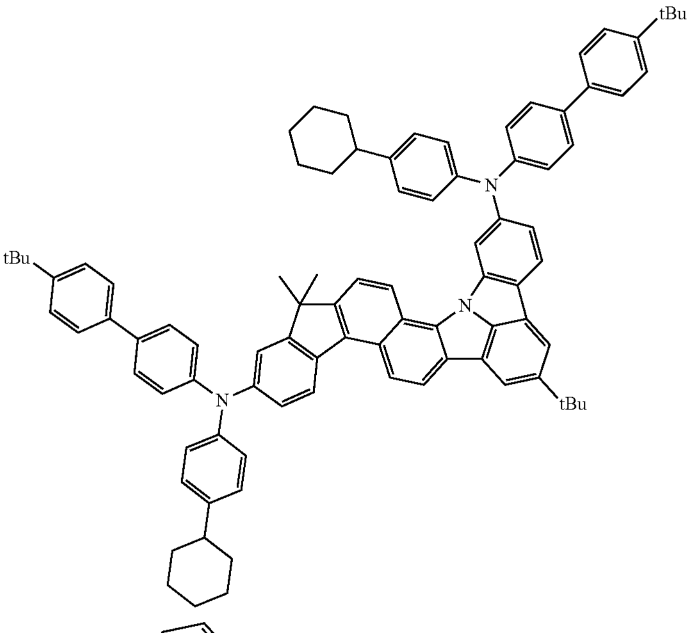
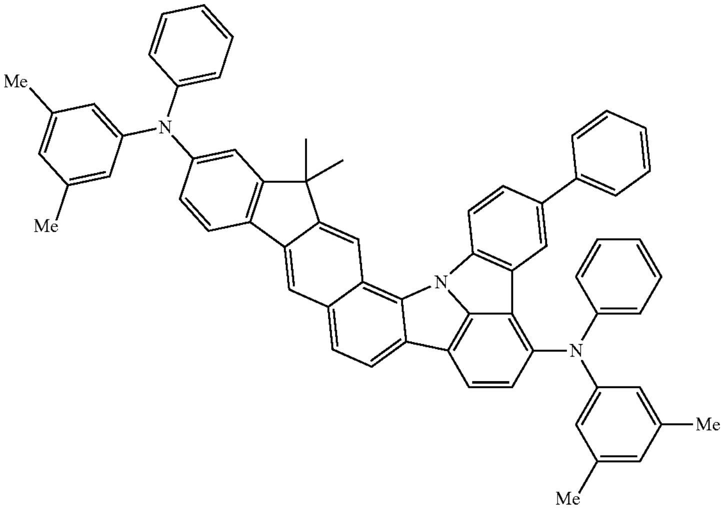

-continued
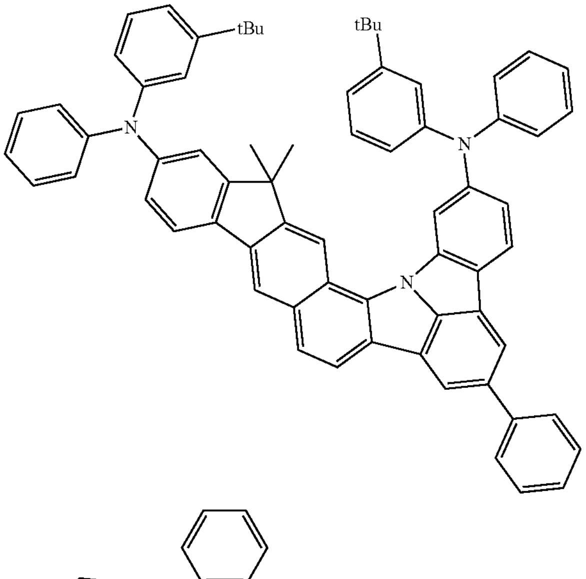
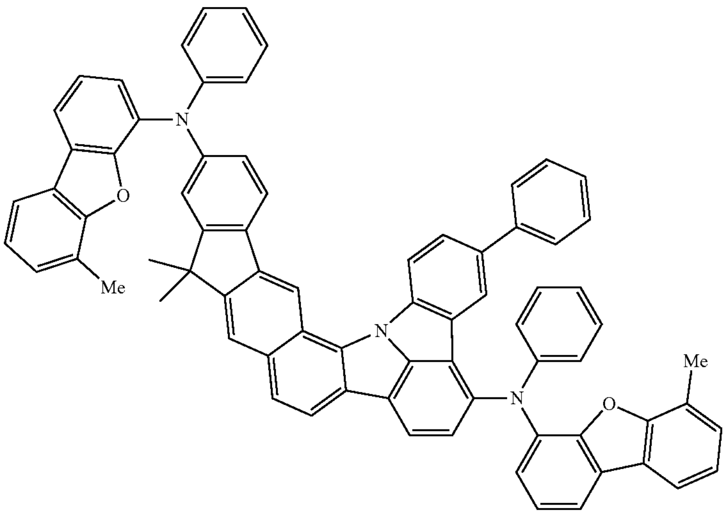
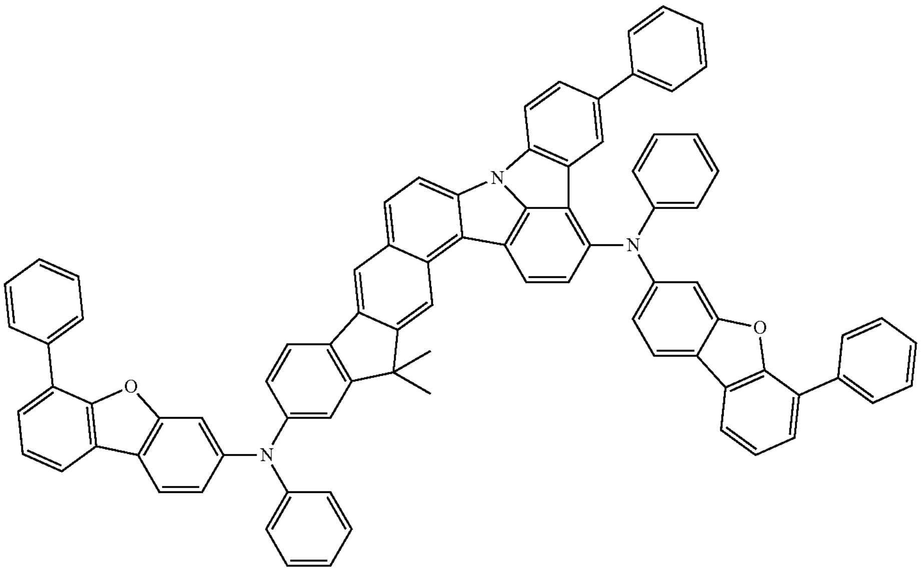

-continued
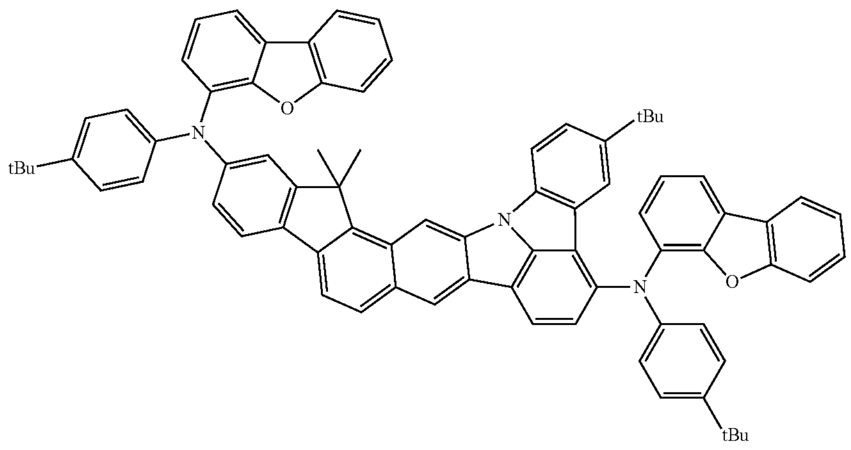
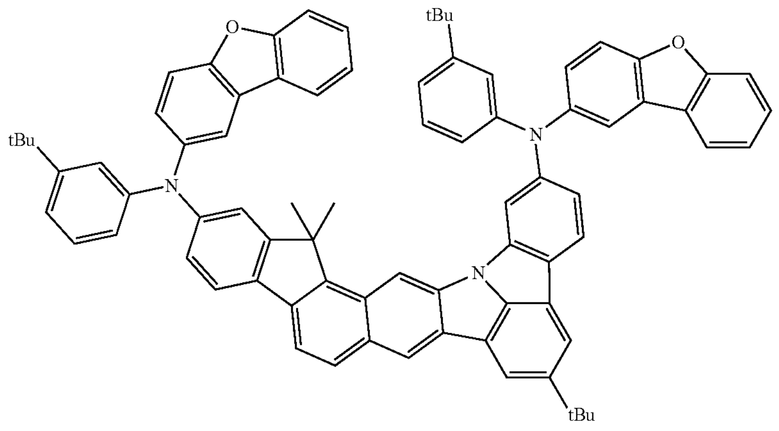
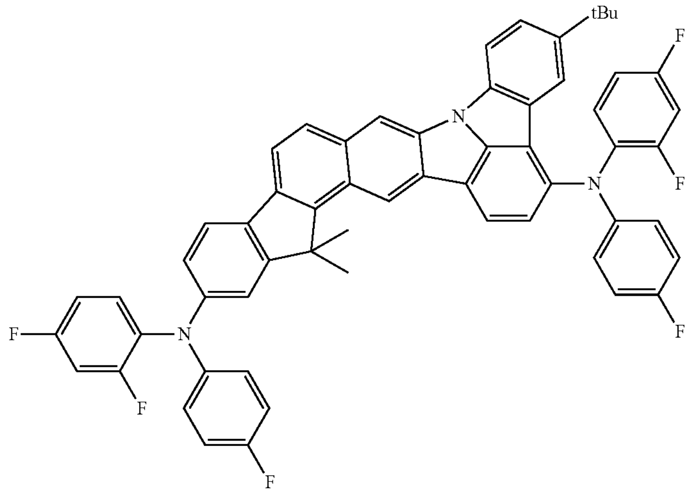

-continued
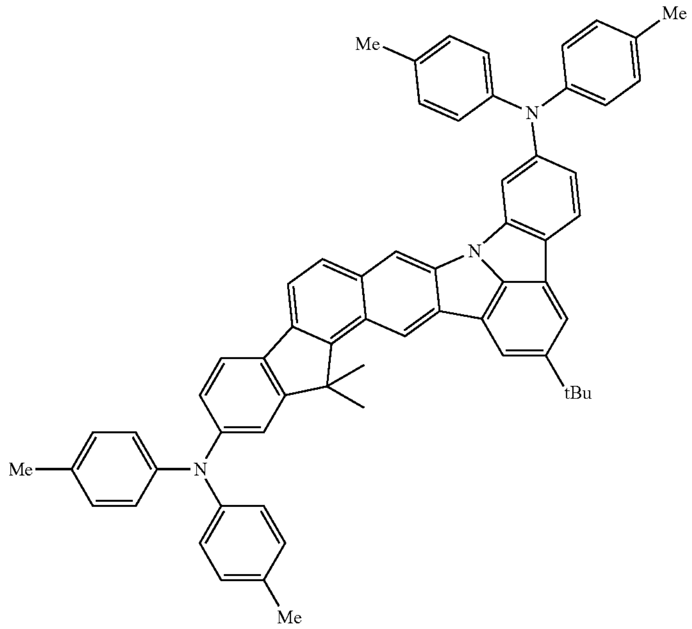
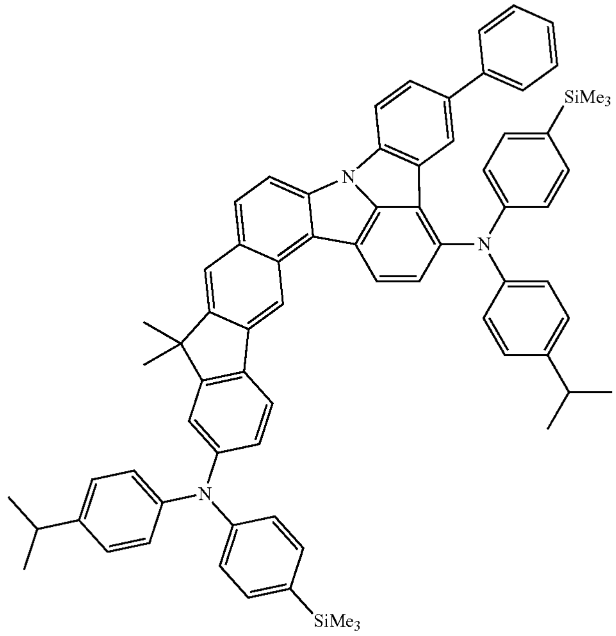

-continued
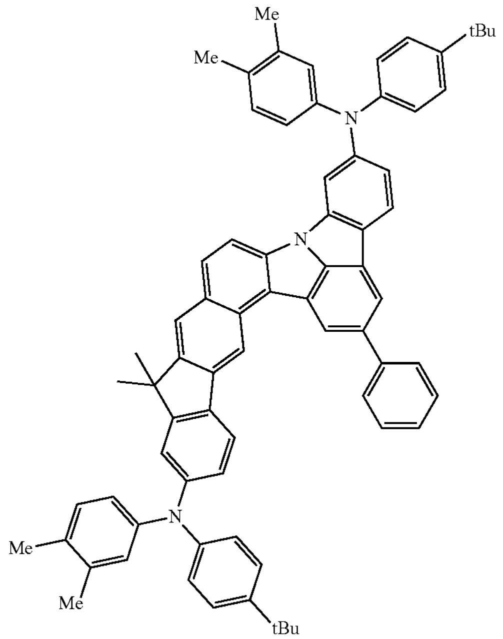
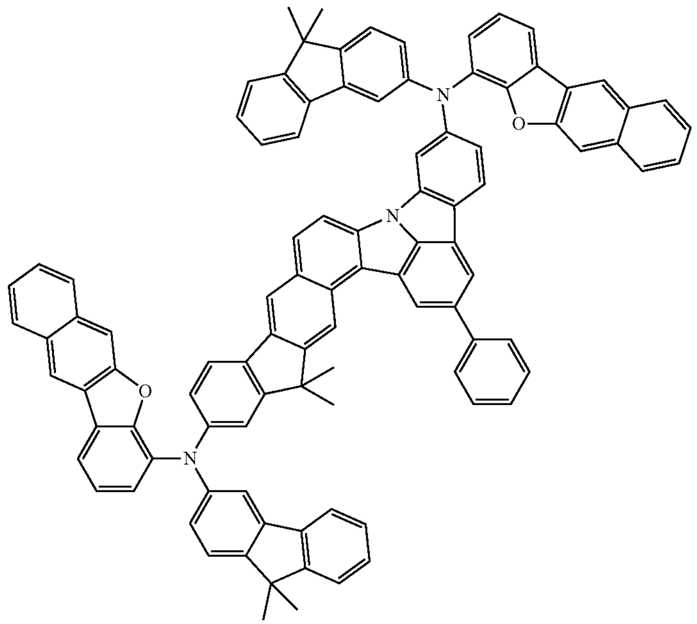

-continued
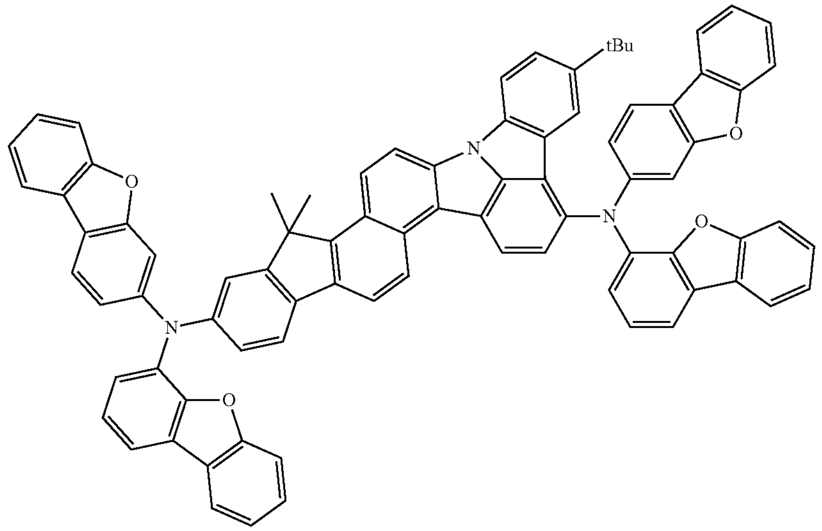
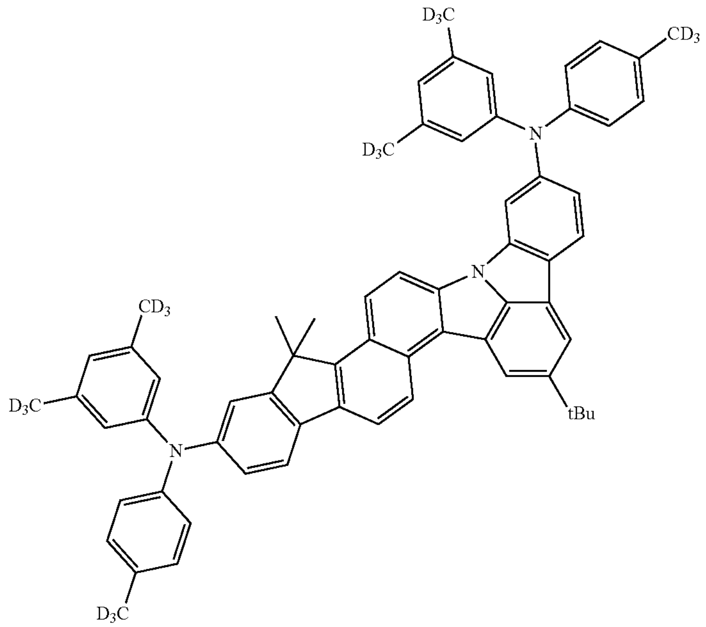
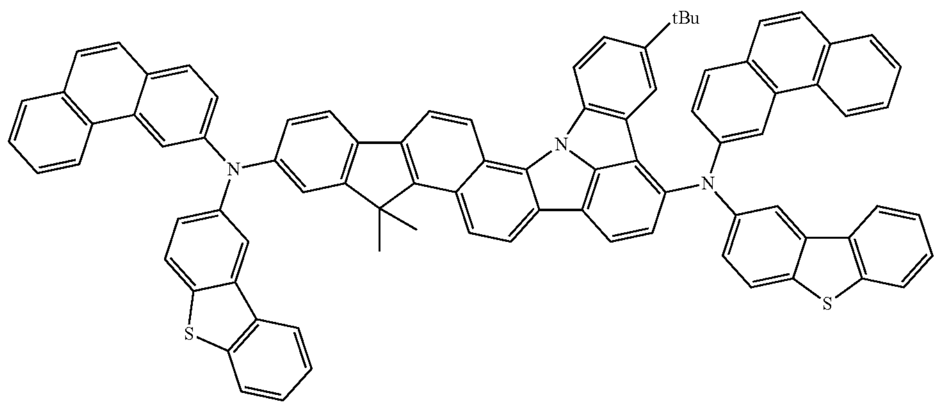

-continued
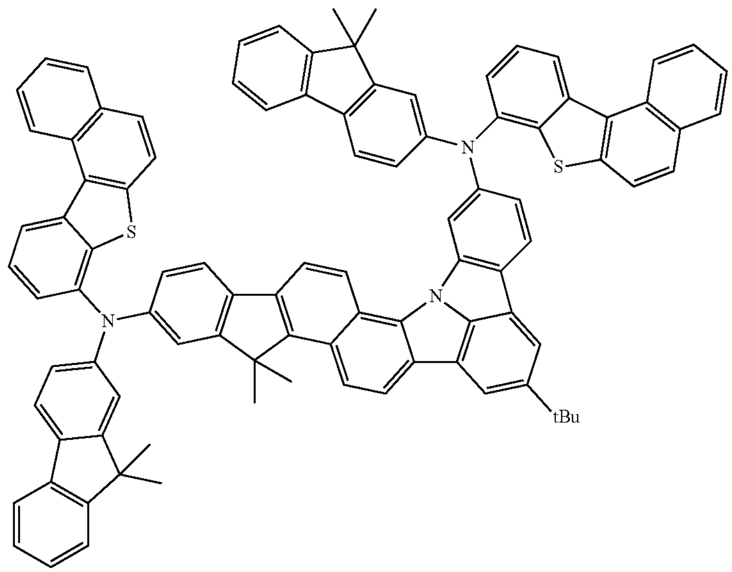
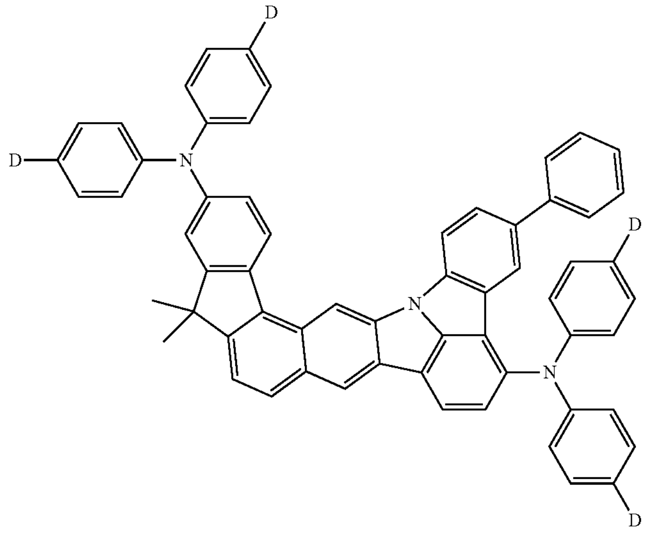
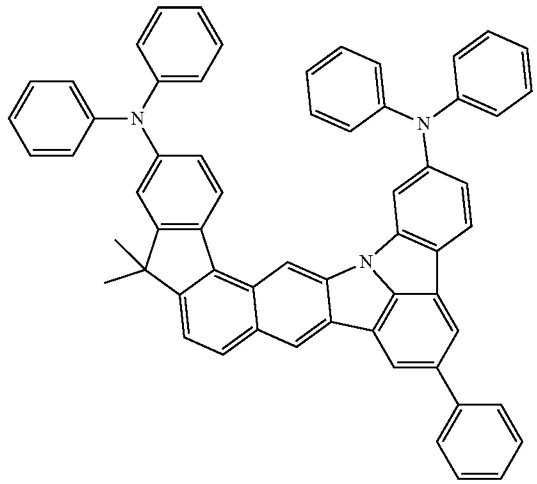

-continued
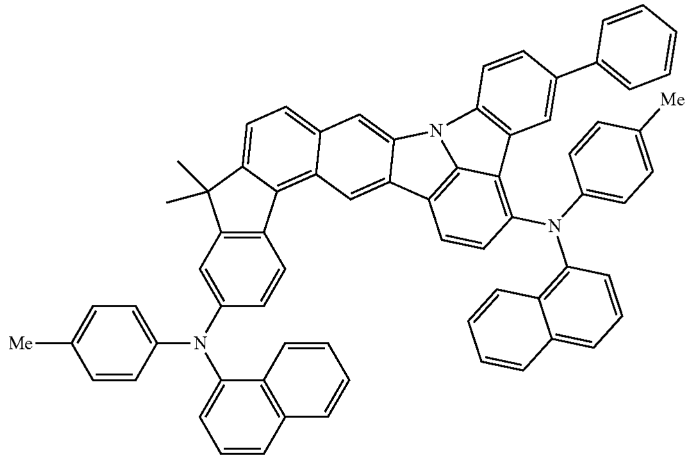
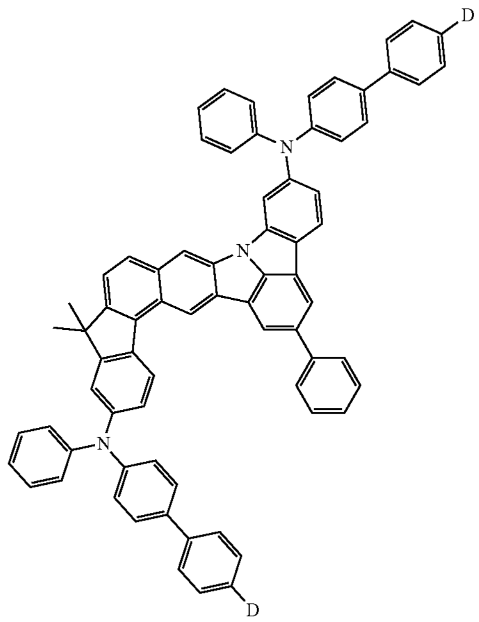
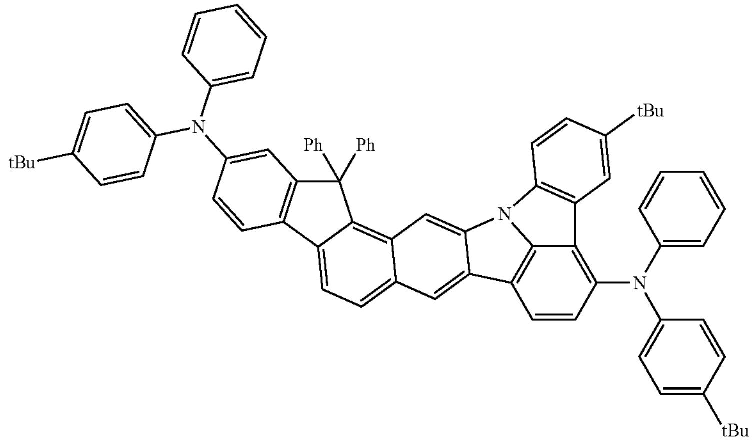

-continued
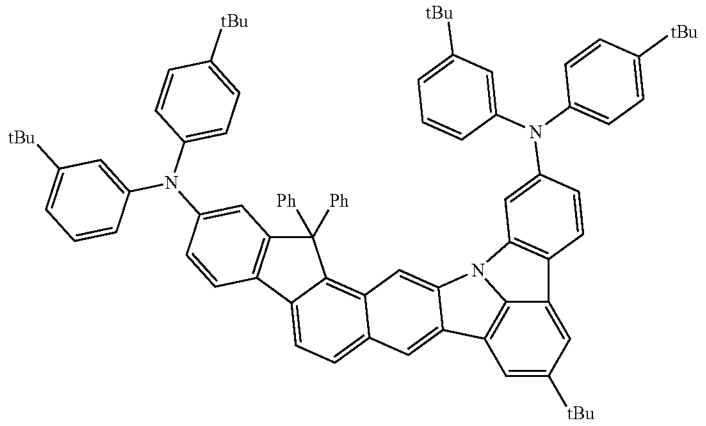
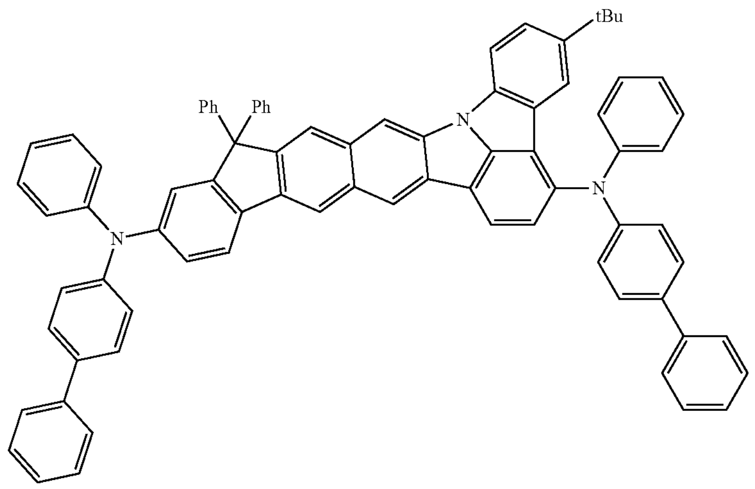
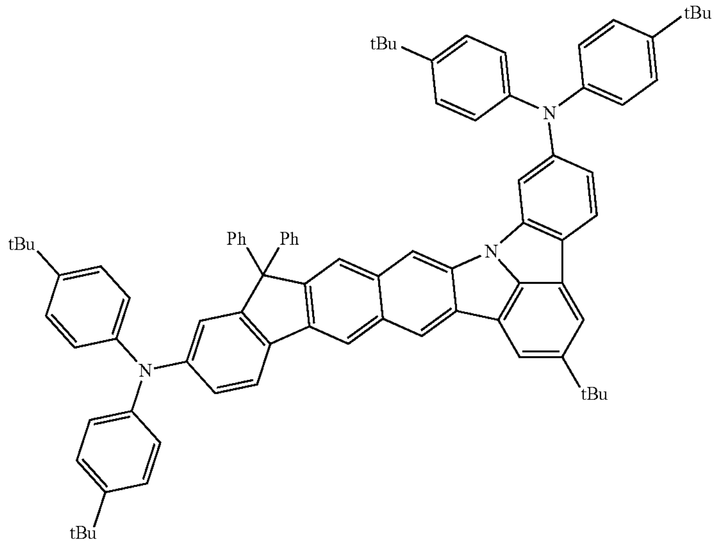

-continued
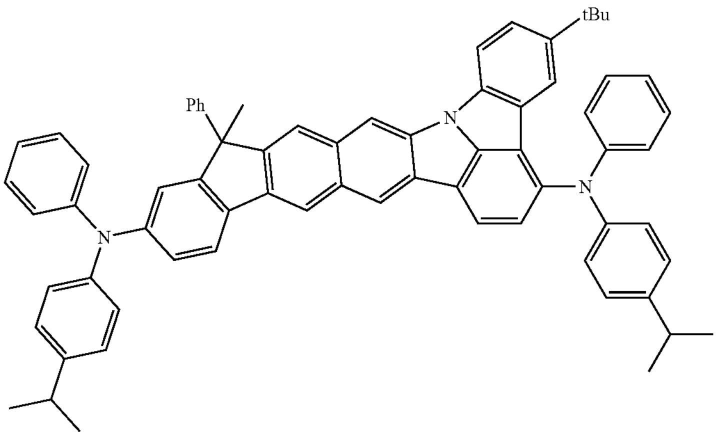
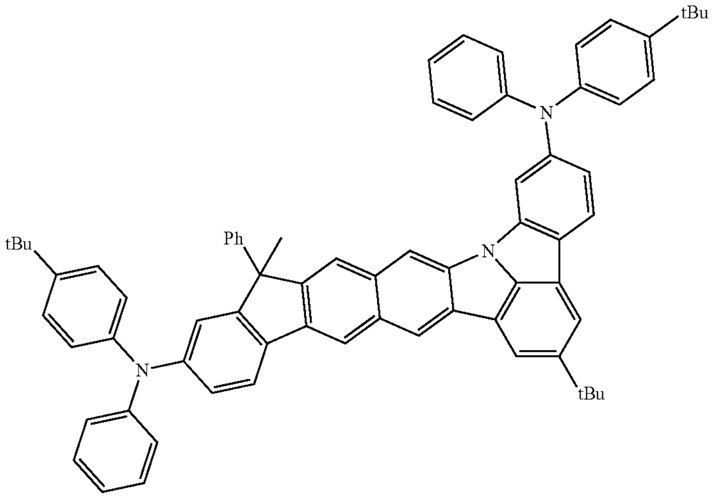
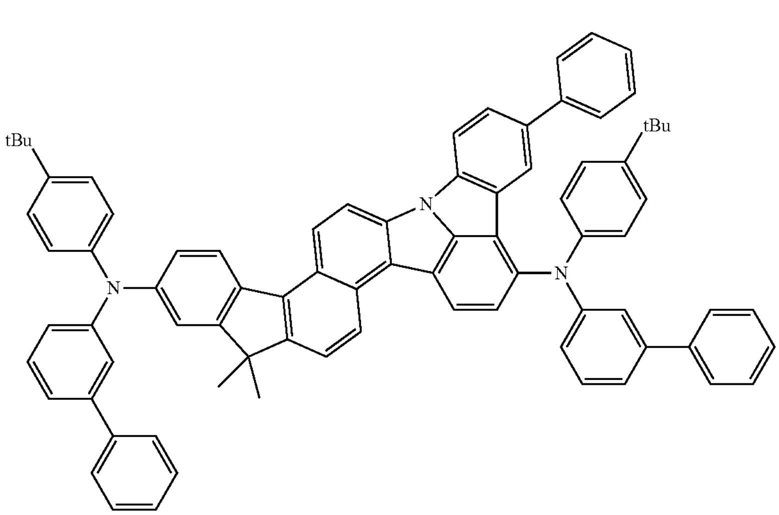

-continued
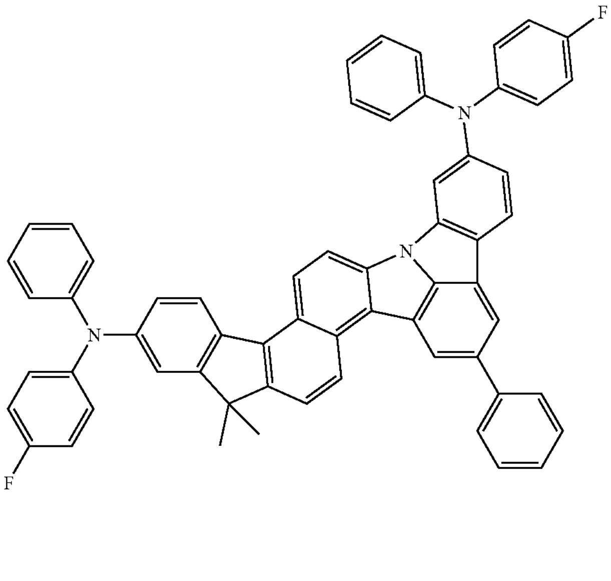
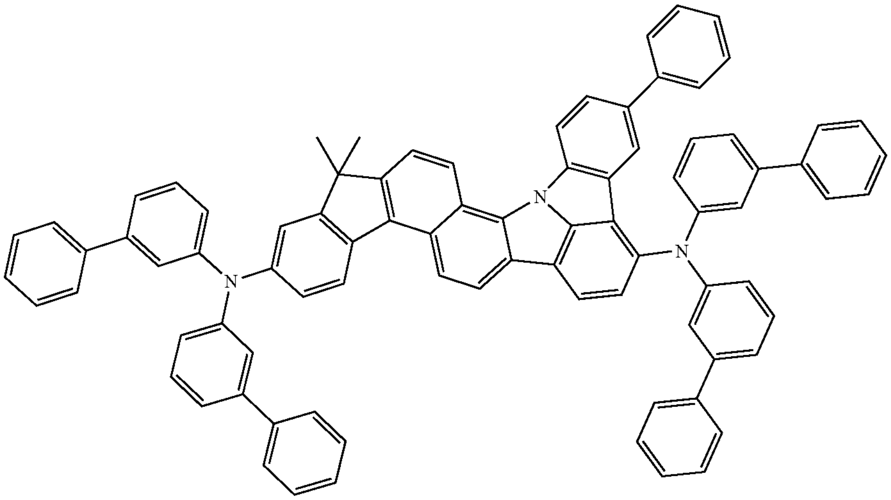
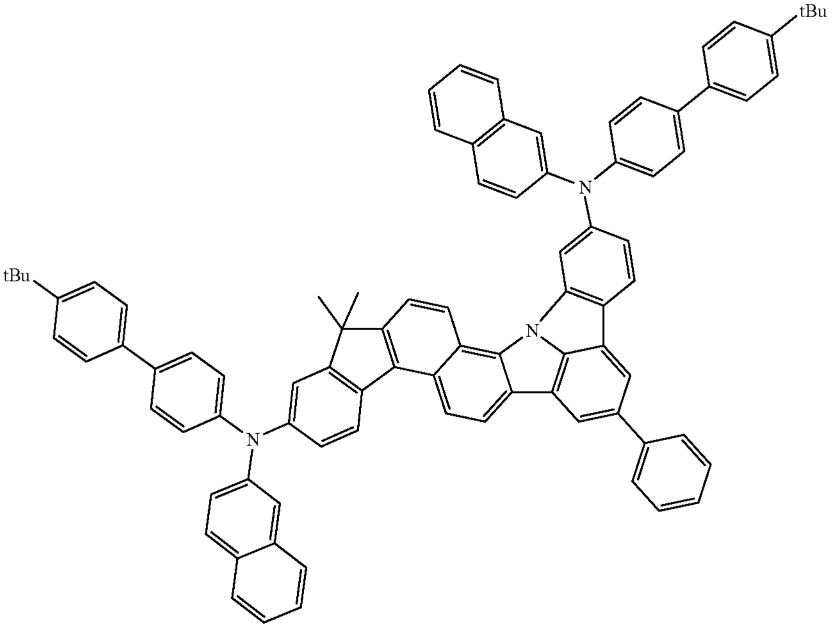

-continued
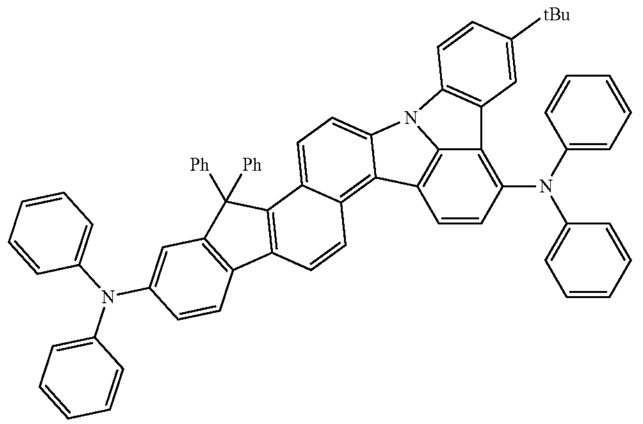
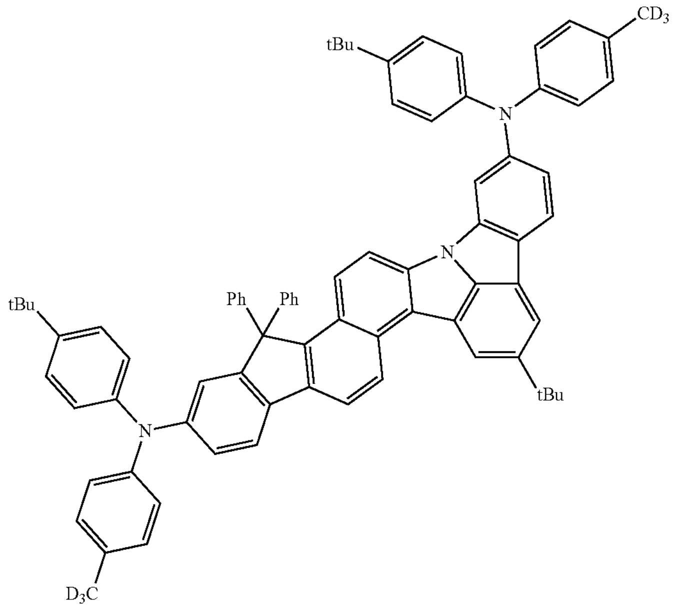
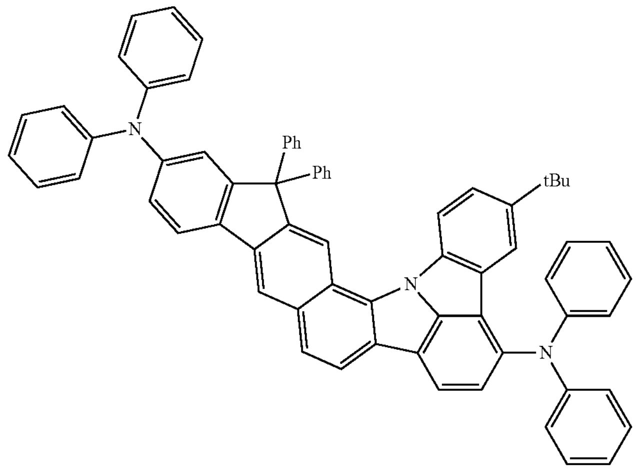

-continued
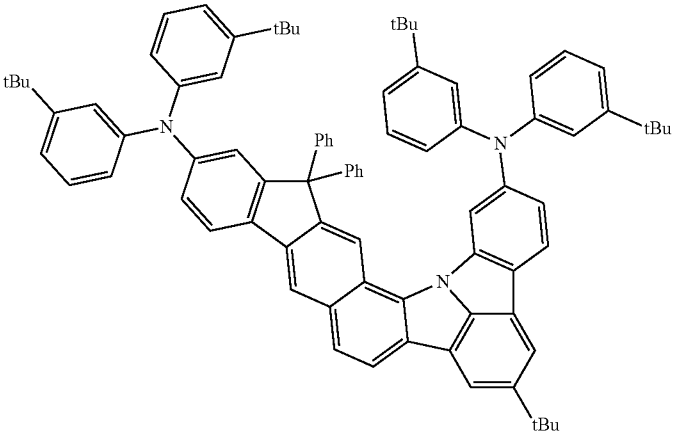
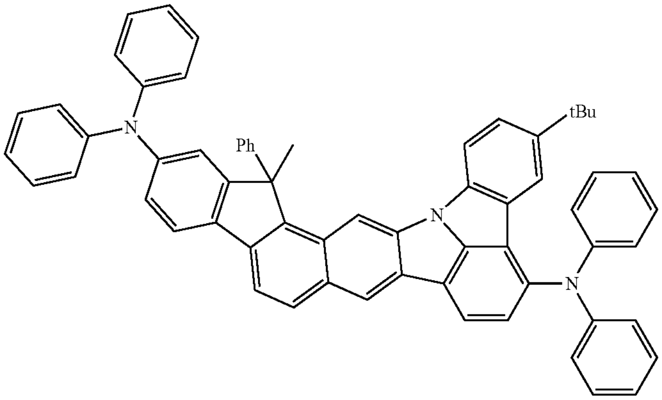
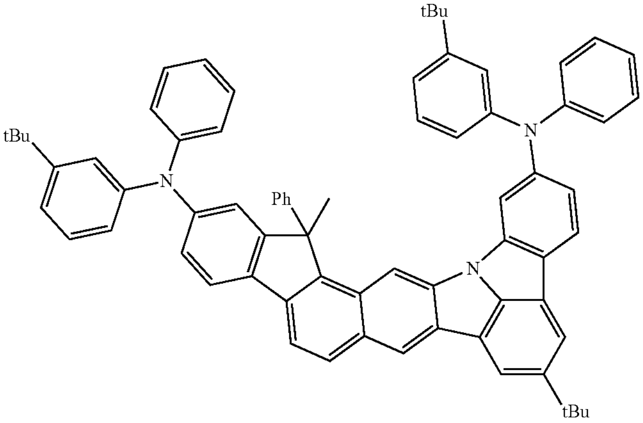
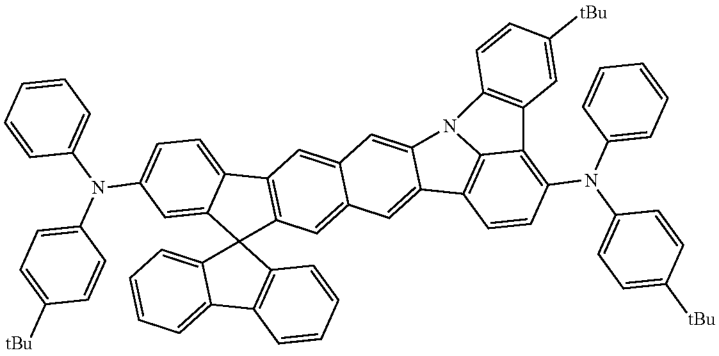

-continued
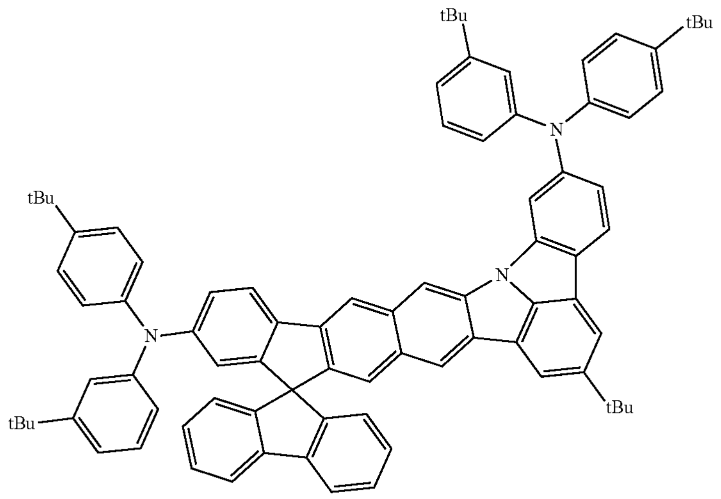
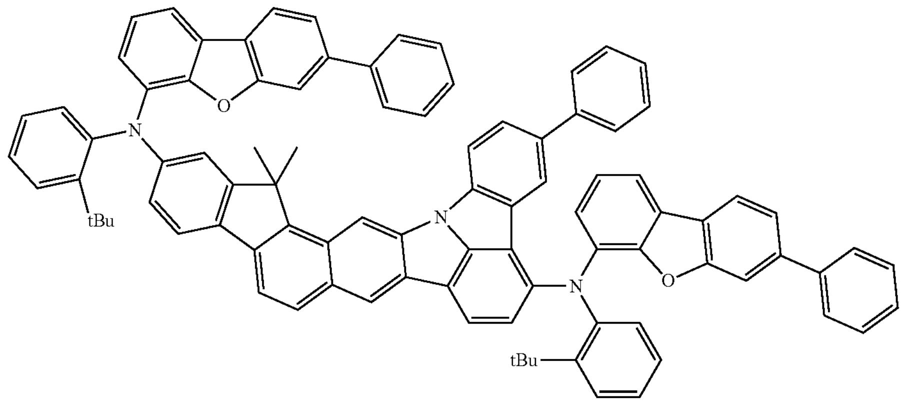
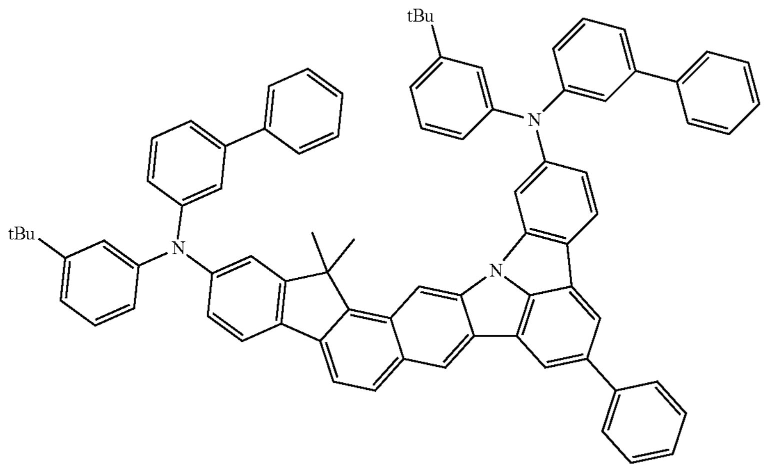

-continued
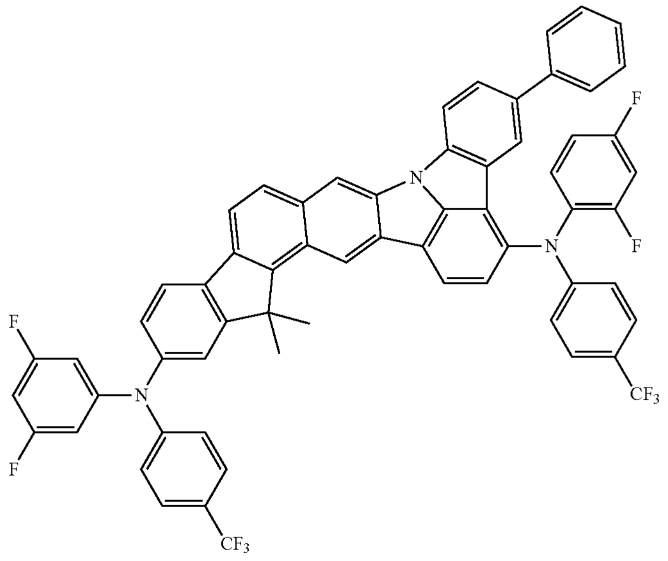
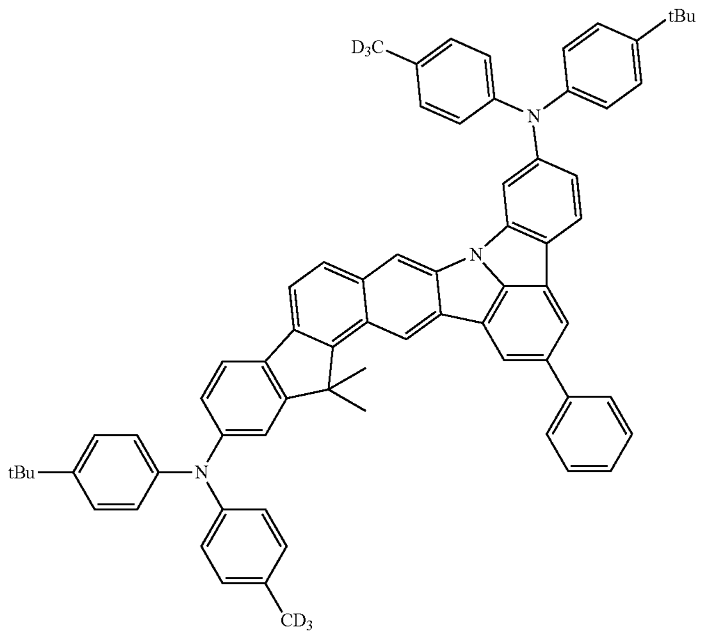

-continued
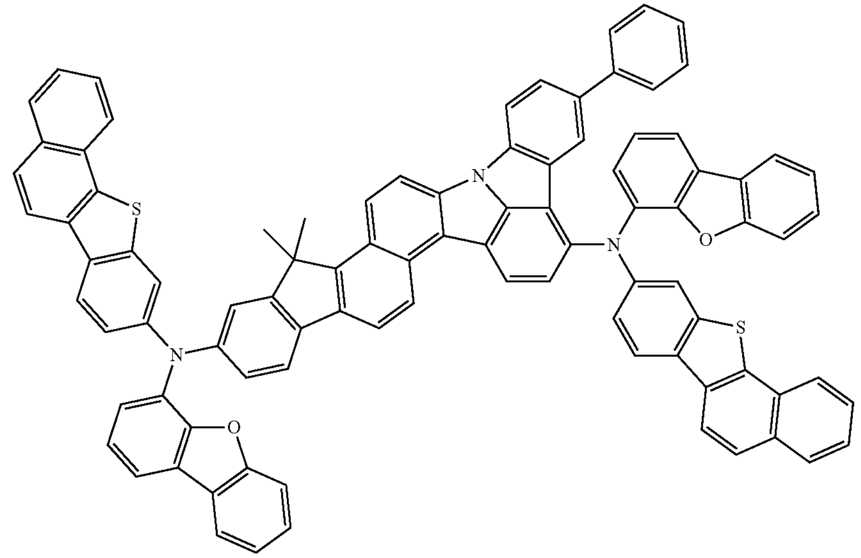
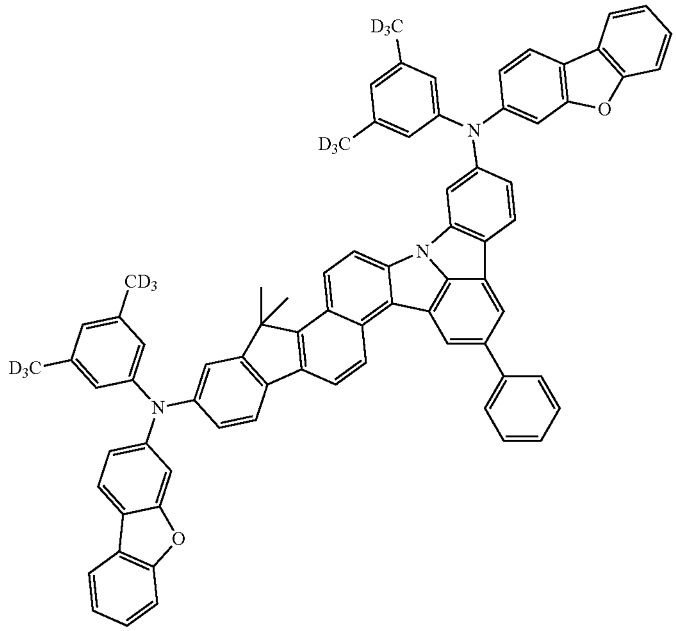
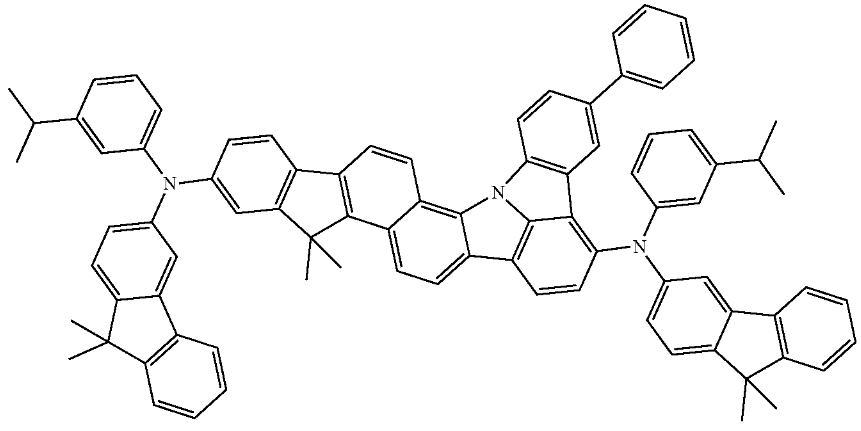

-continued
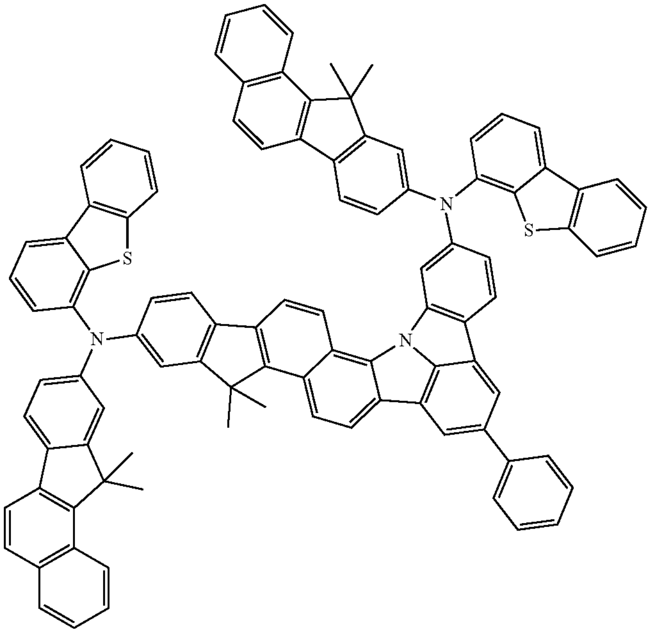
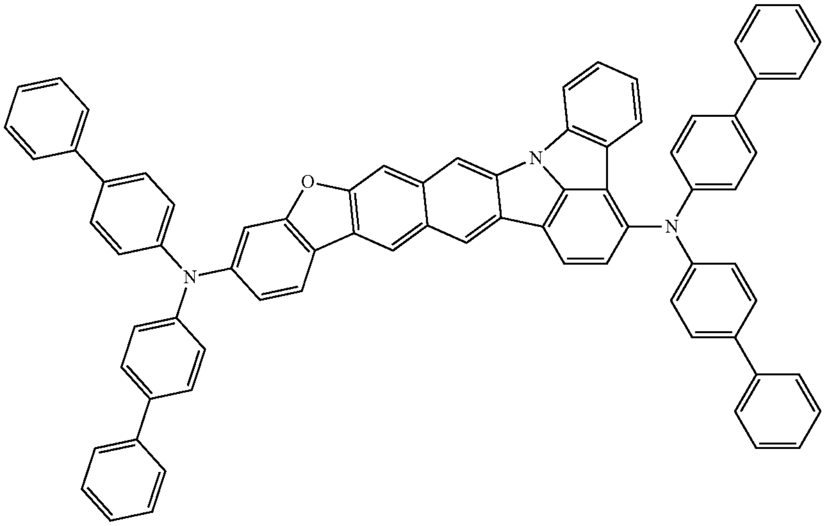

-continued
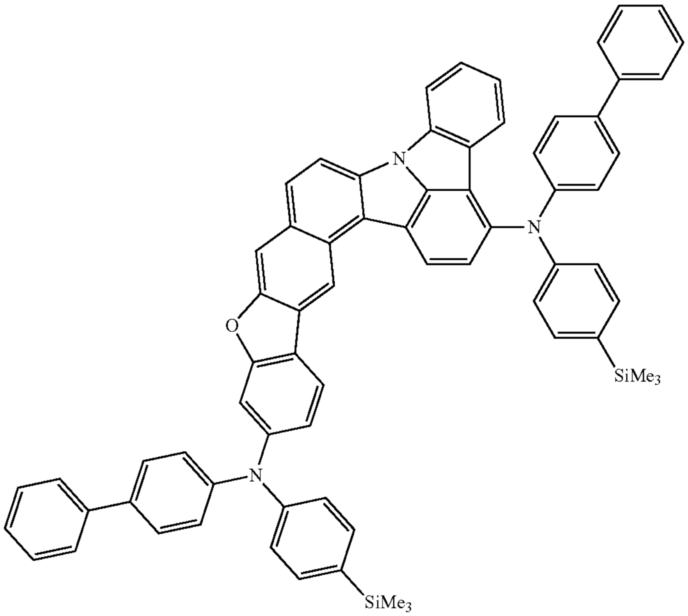
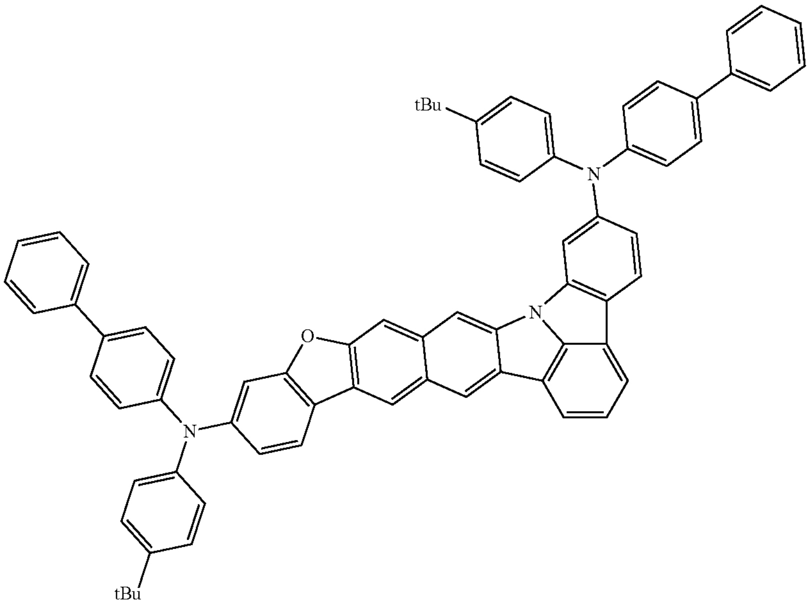
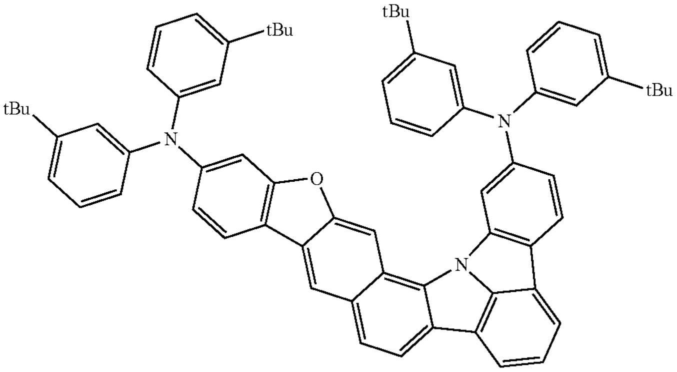

-continued
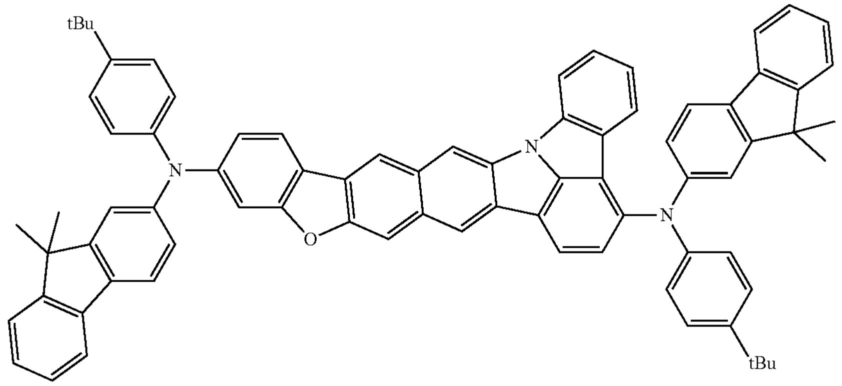
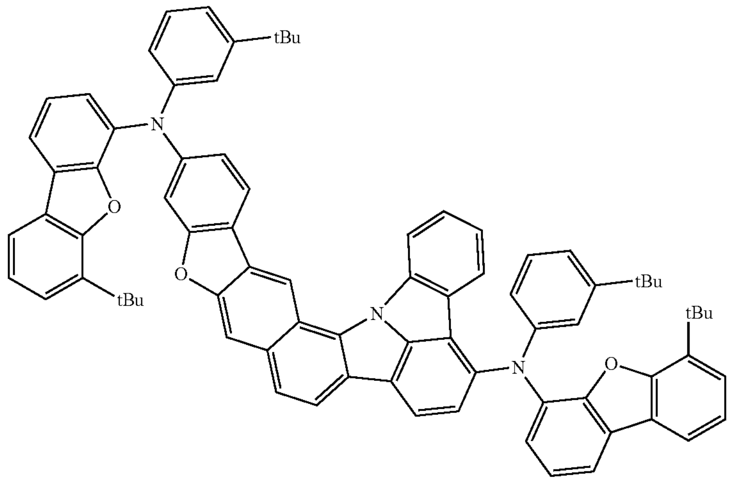
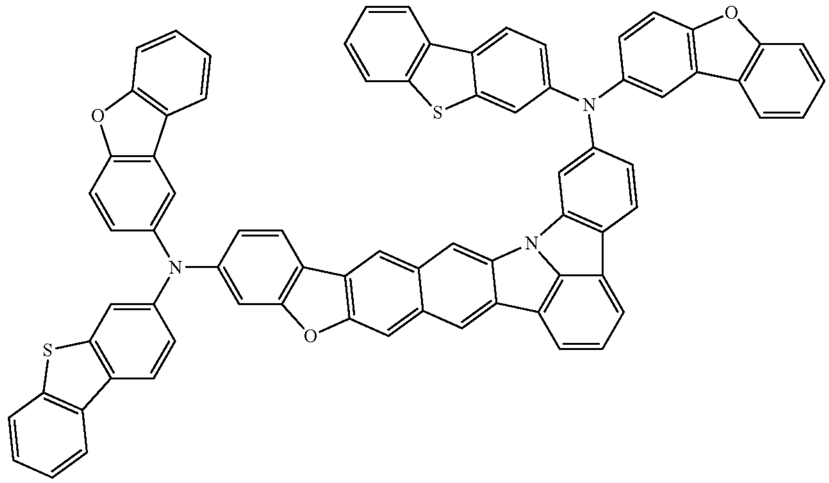

-continued
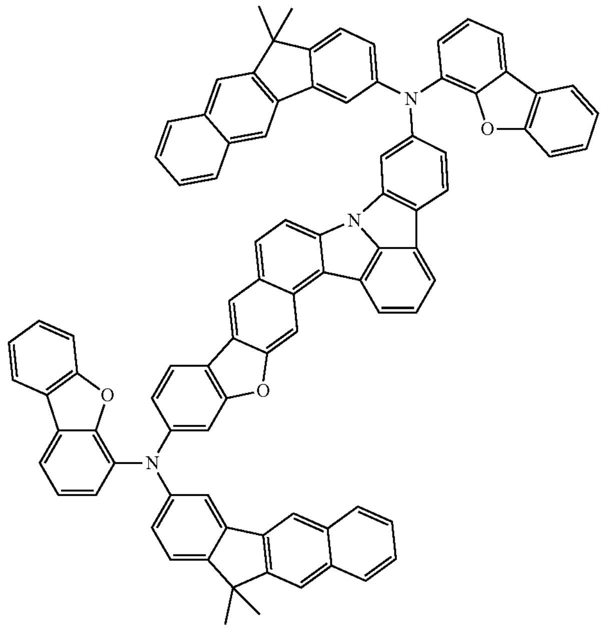
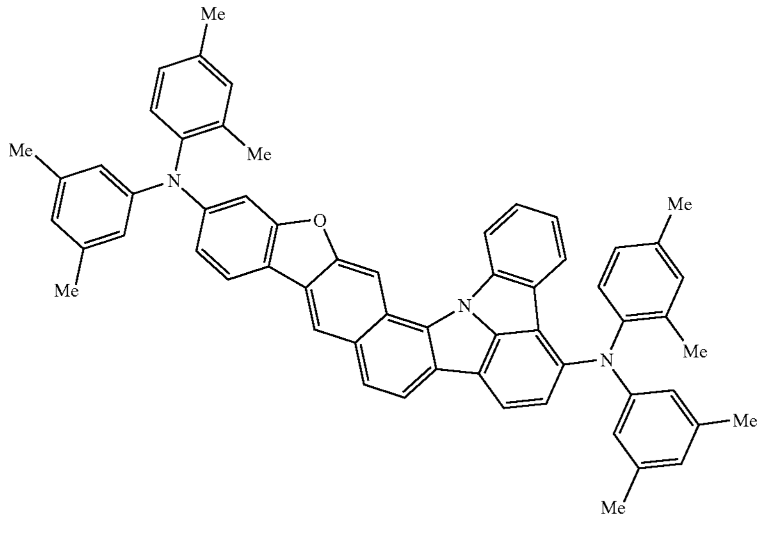

-continued
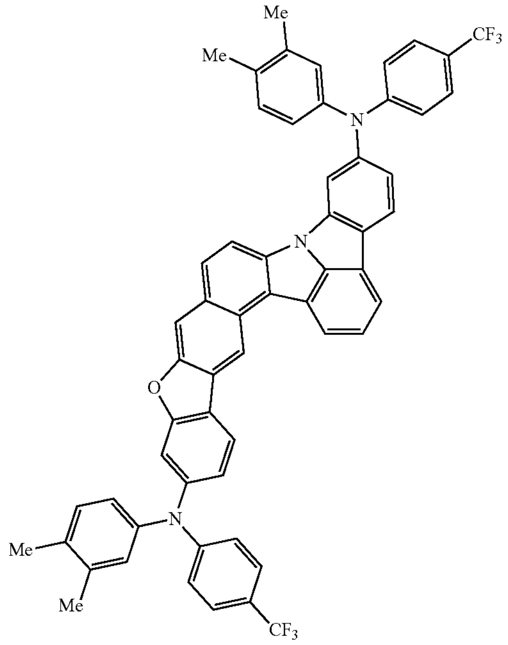
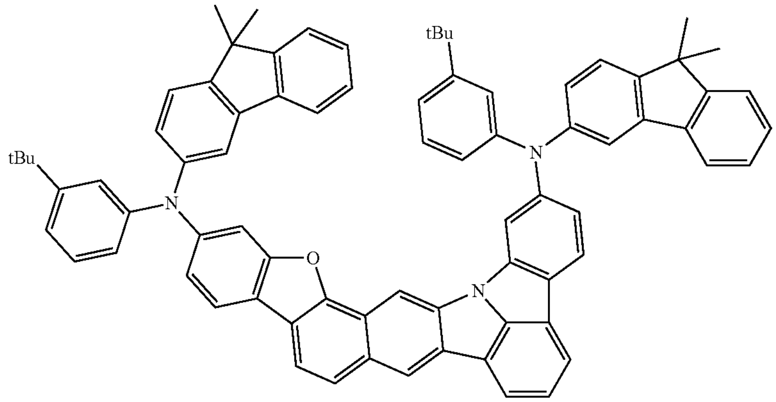
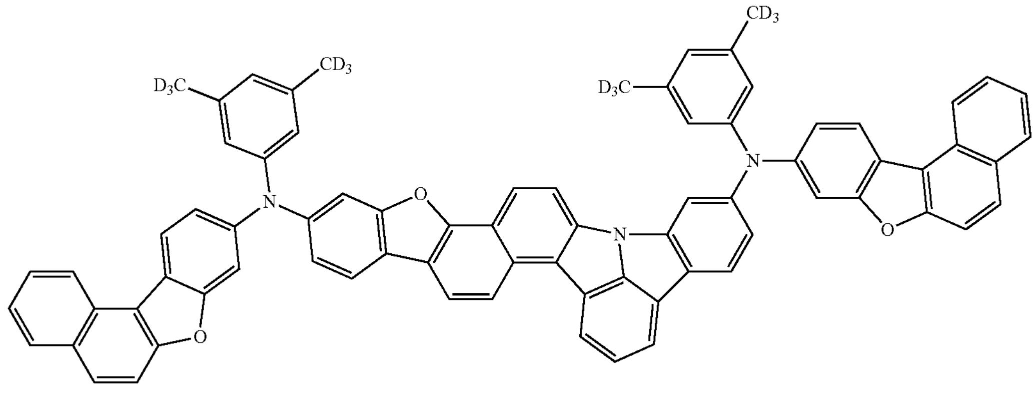

-continued
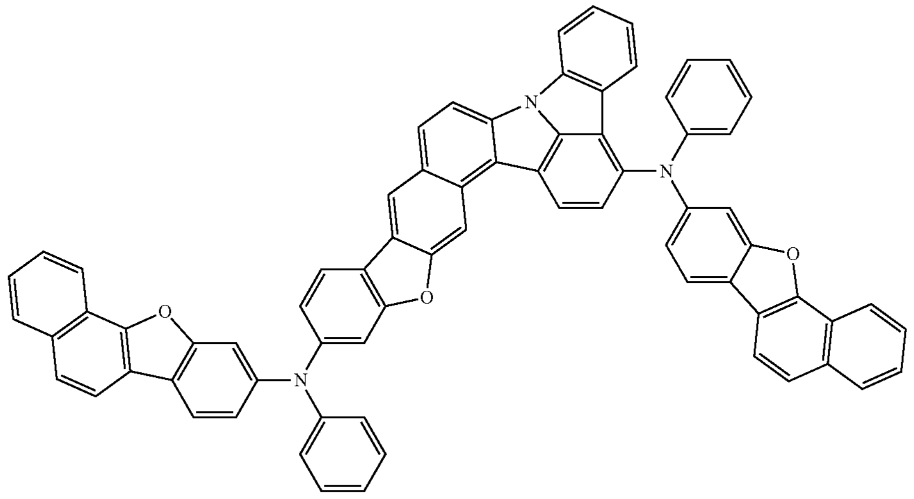
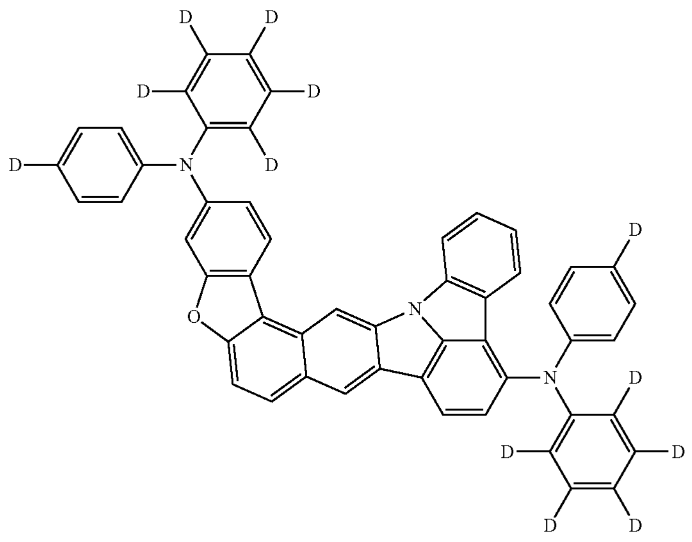
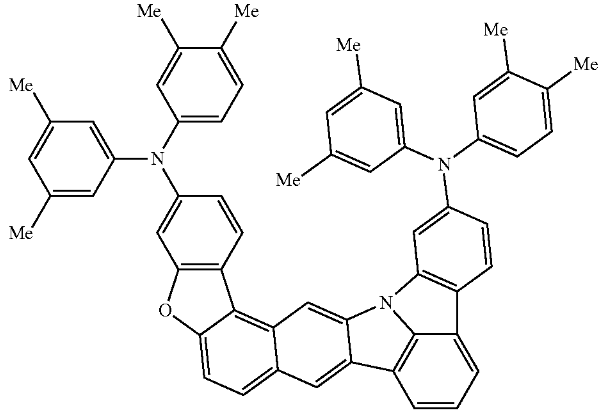

-continued
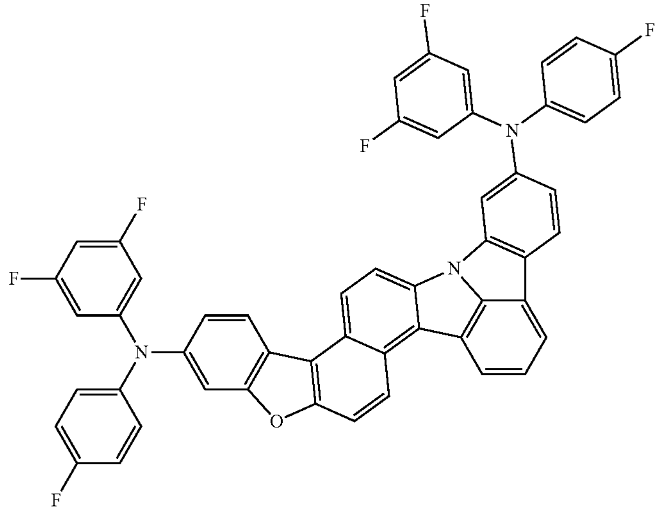
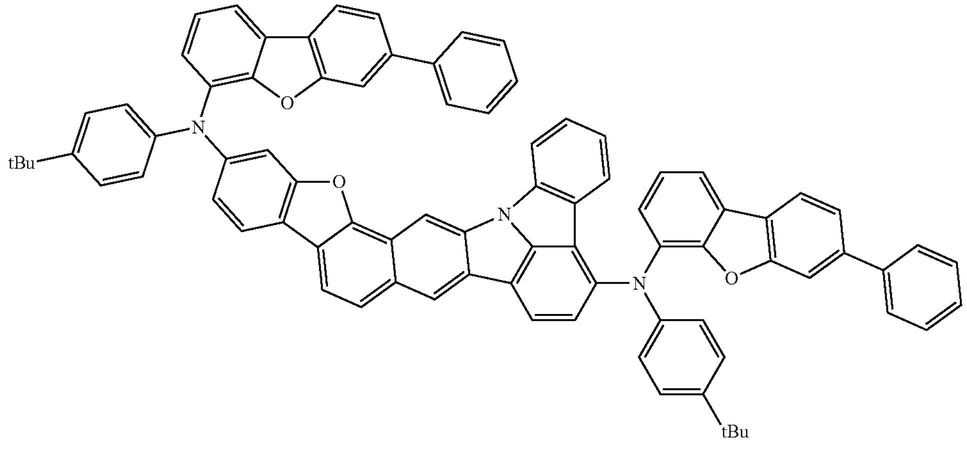
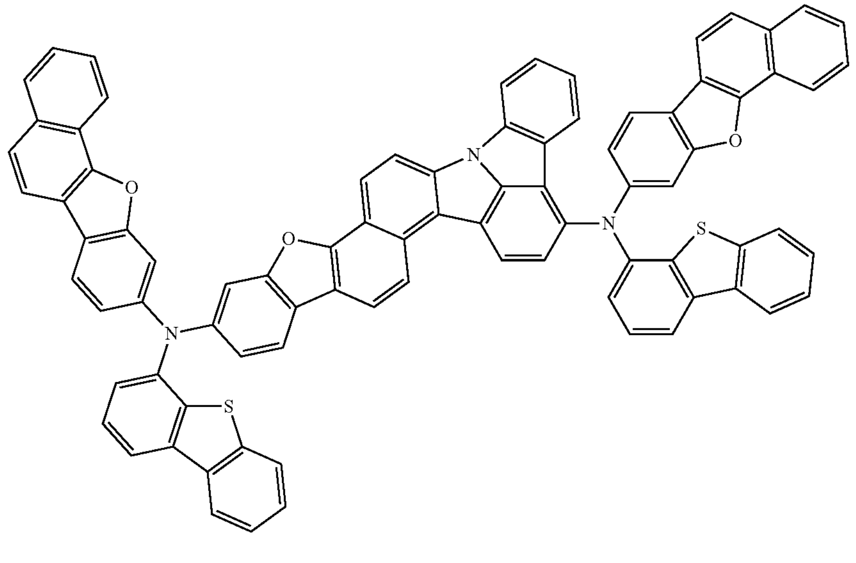

-continued
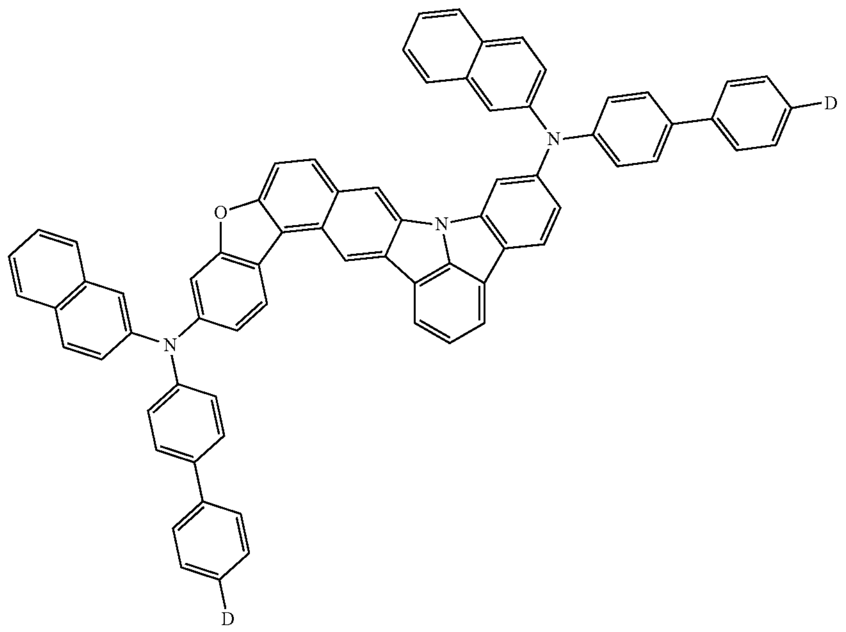
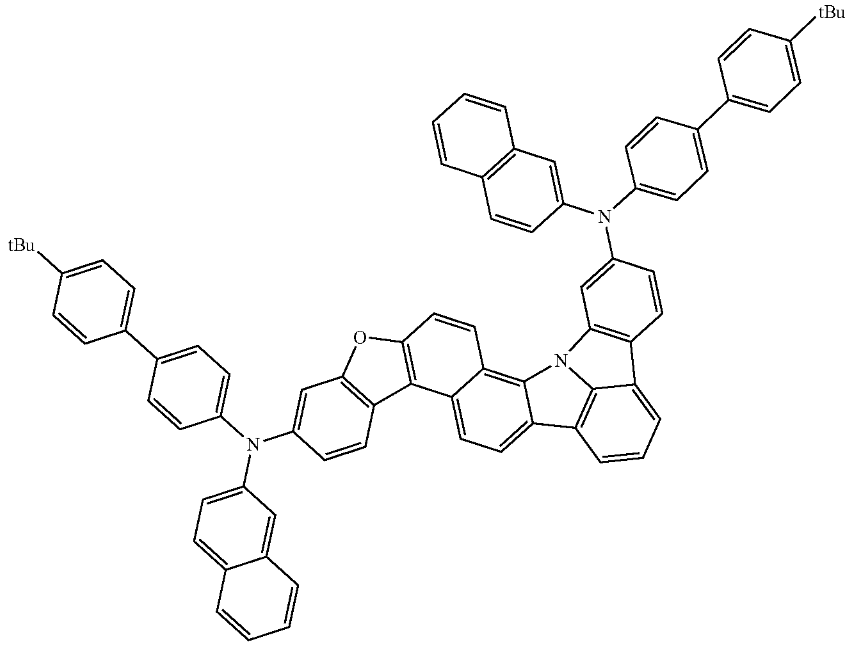

-continued
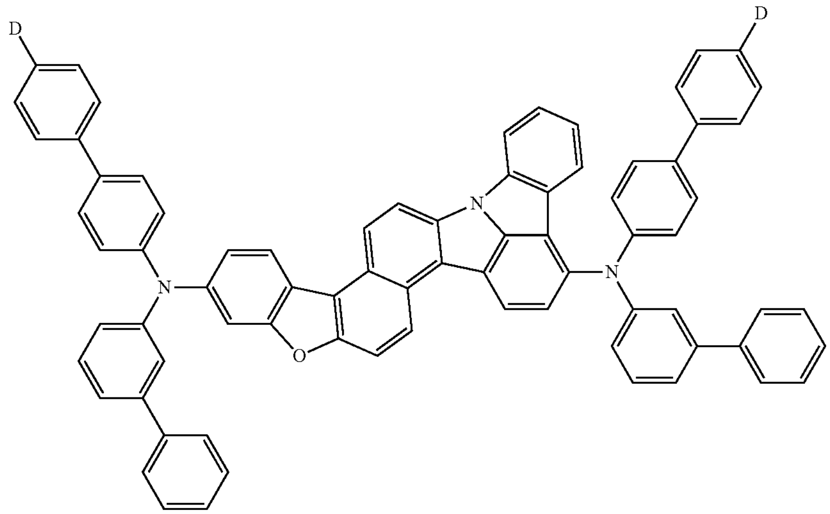
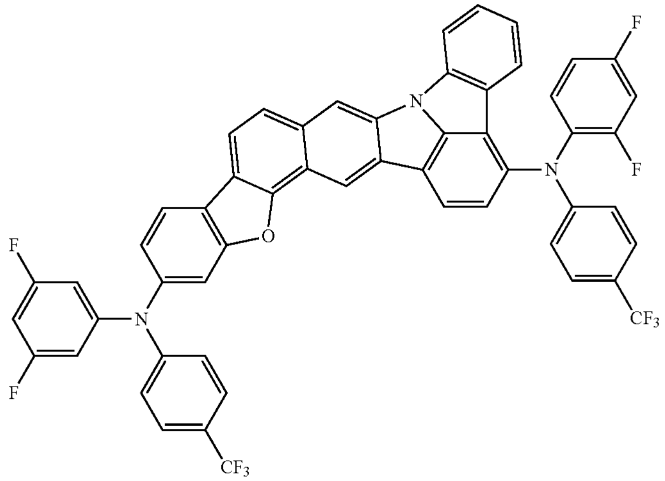
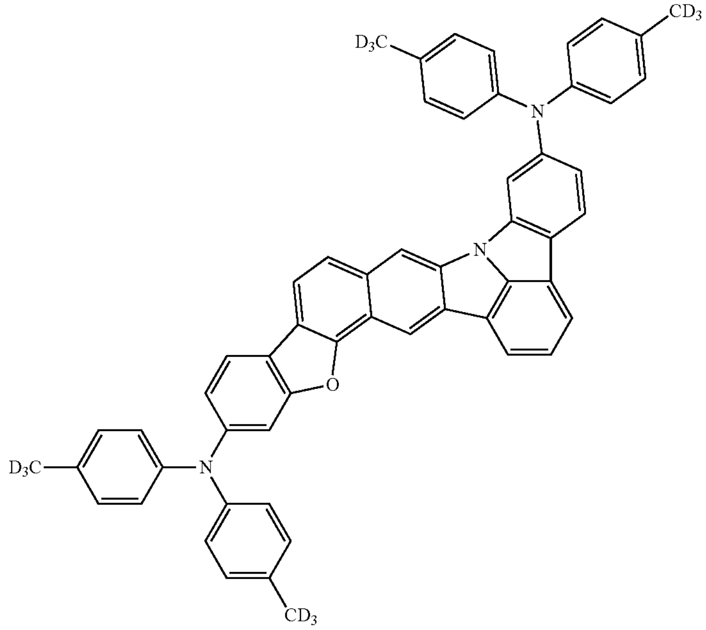

-continued
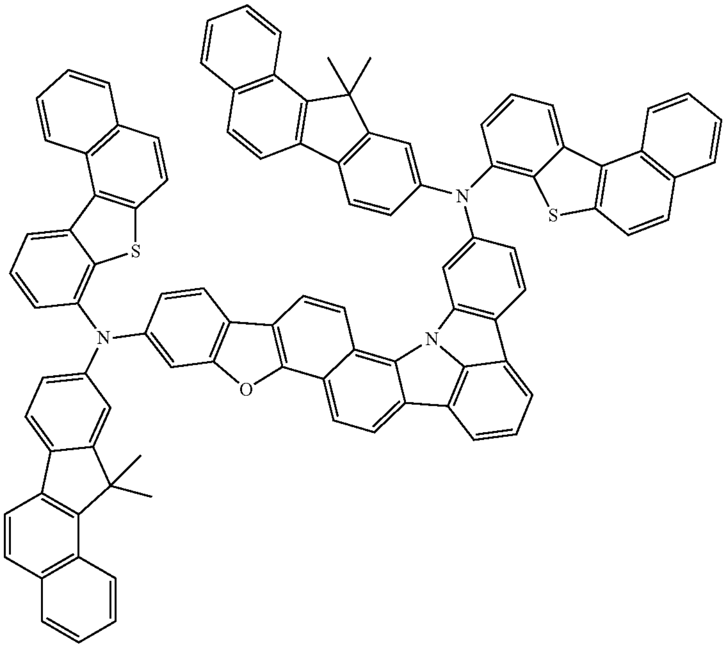
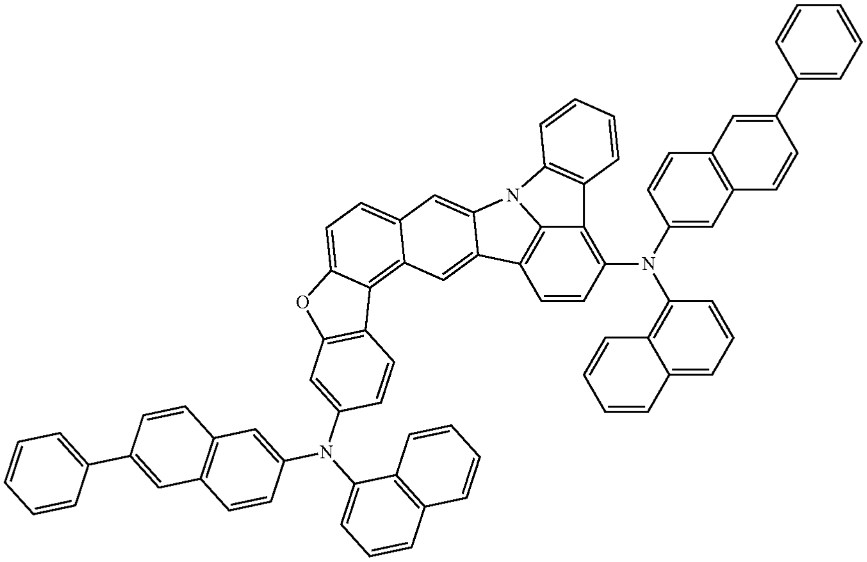
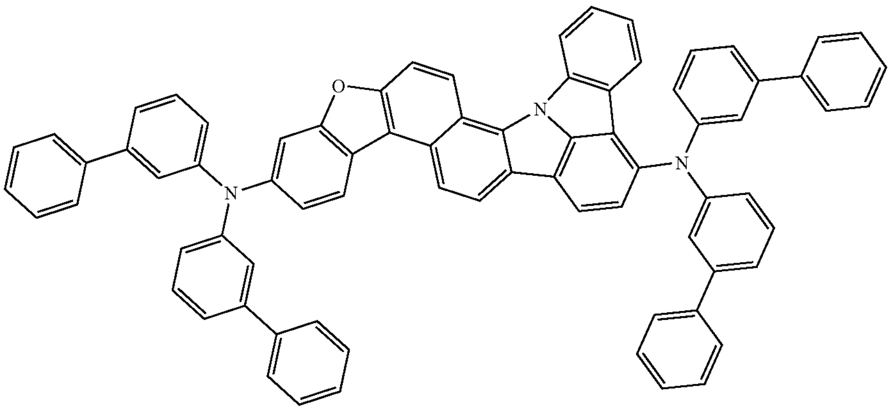

-continued
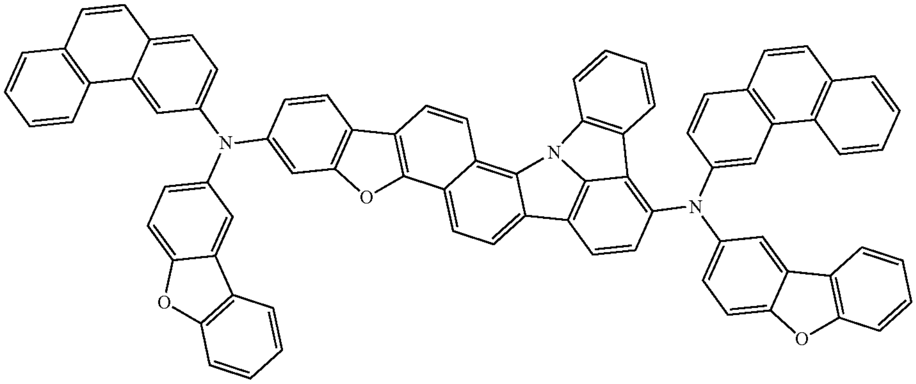
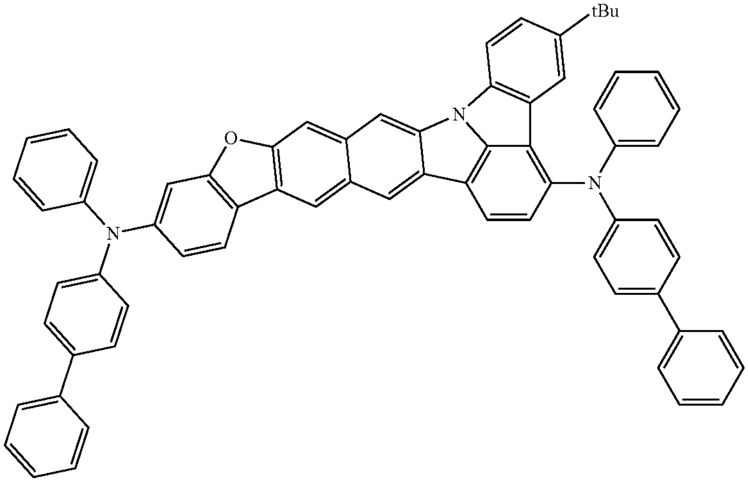
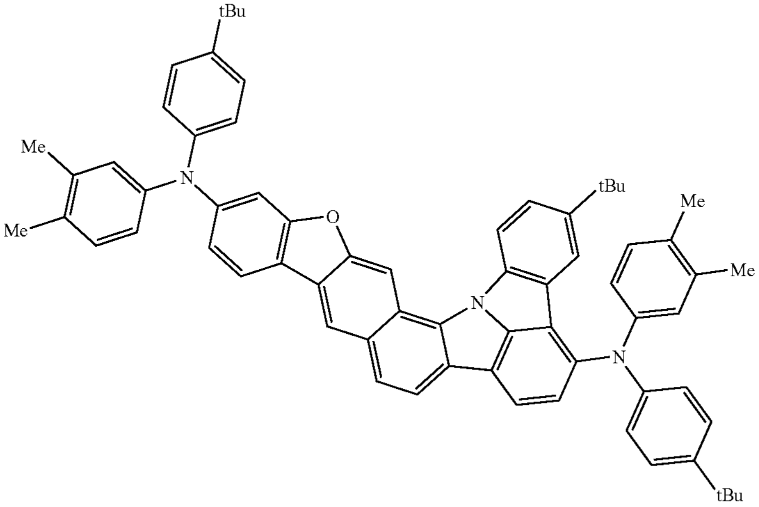

-continued
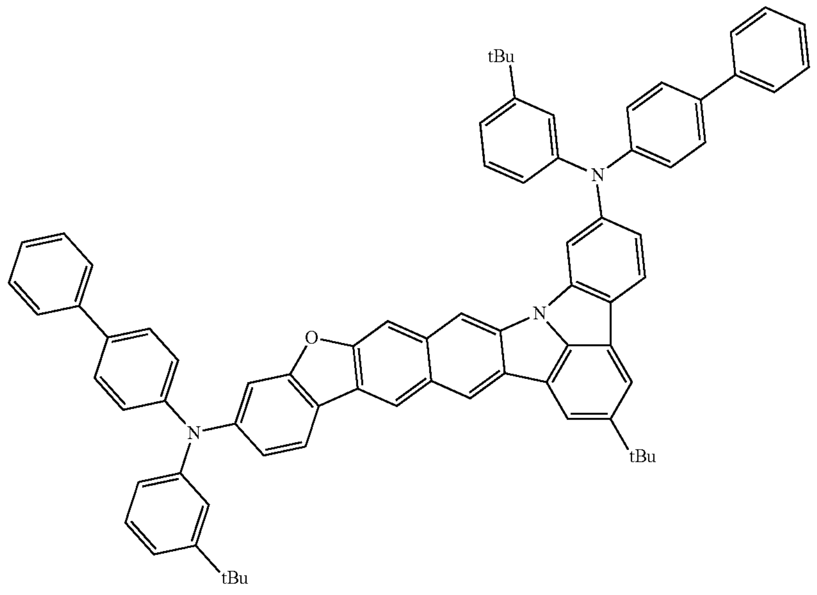
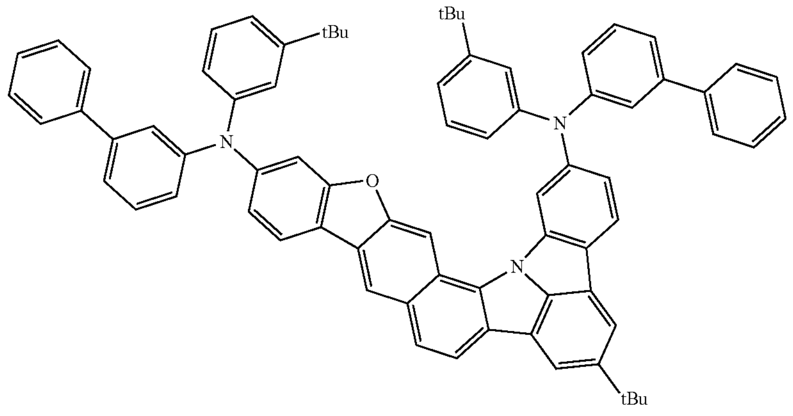
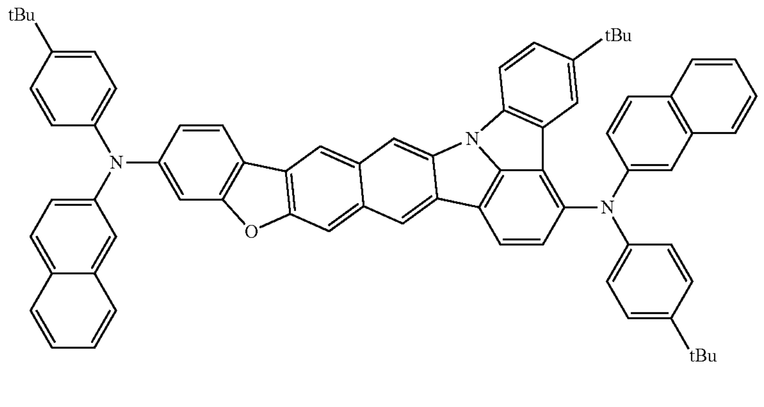

-continued
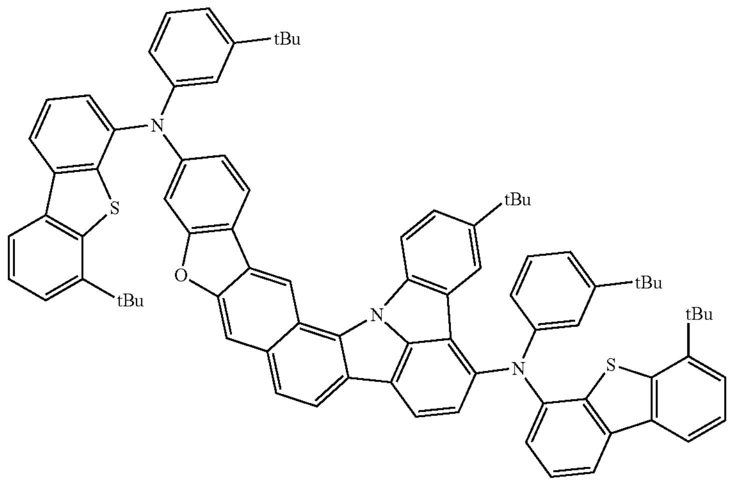
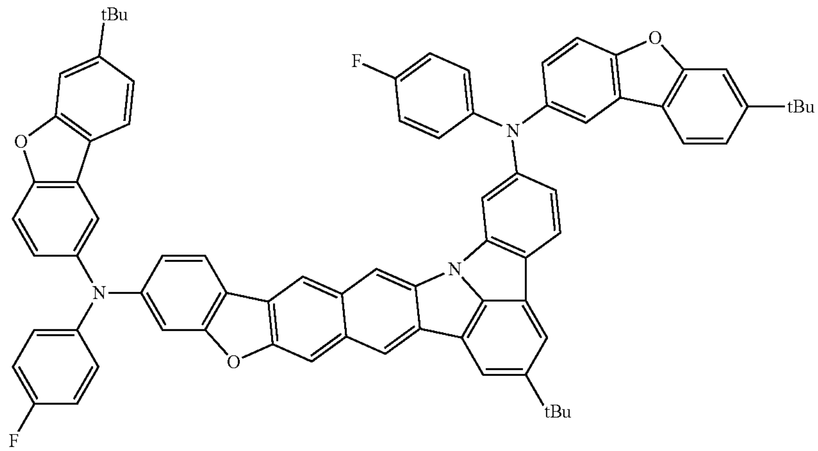
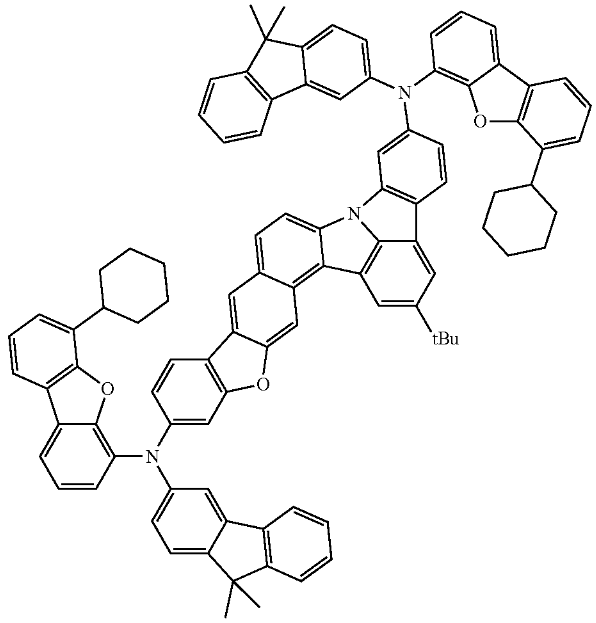

-continued
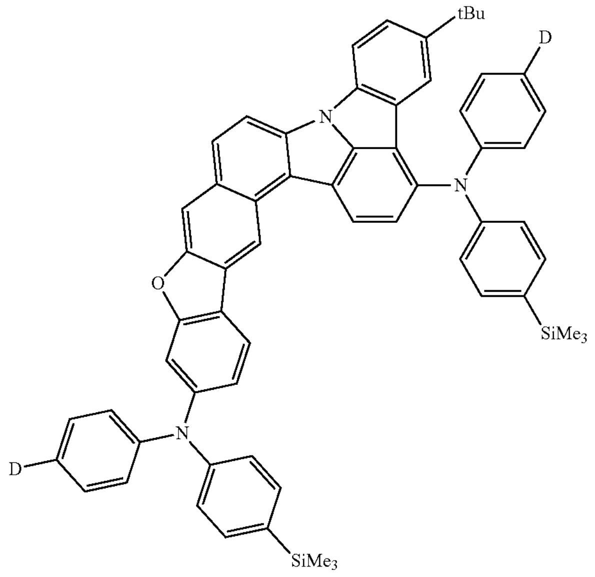
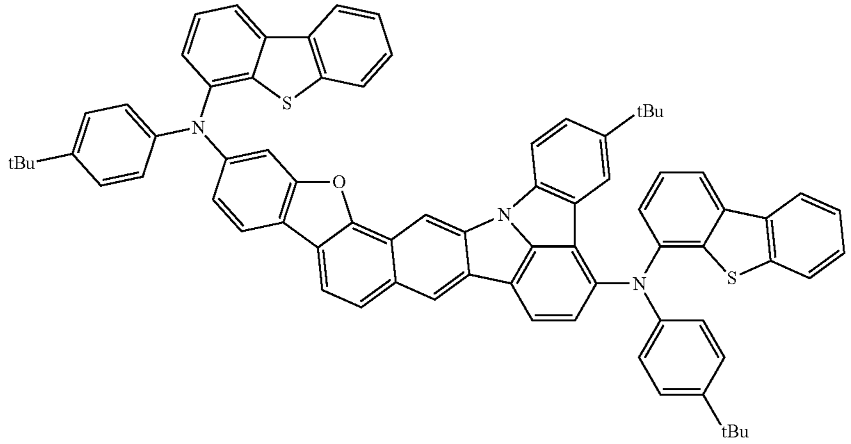
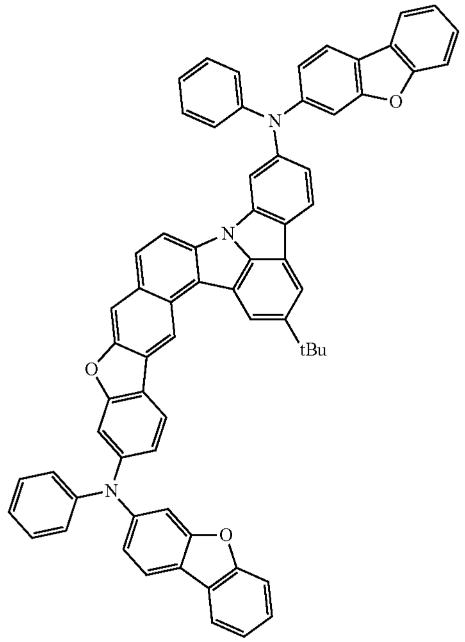

-continued
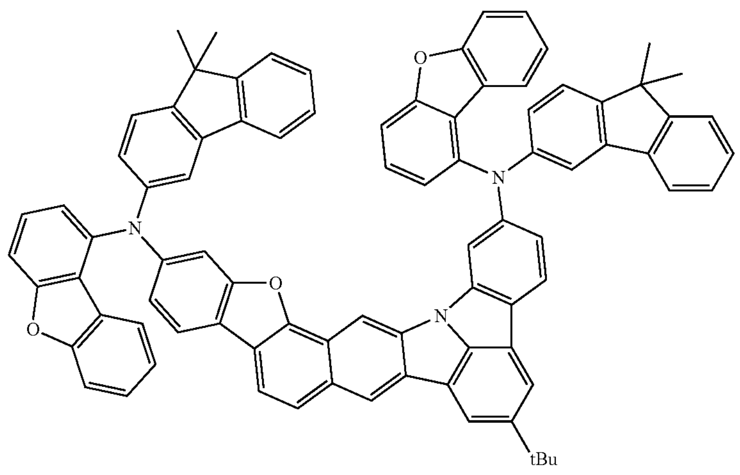
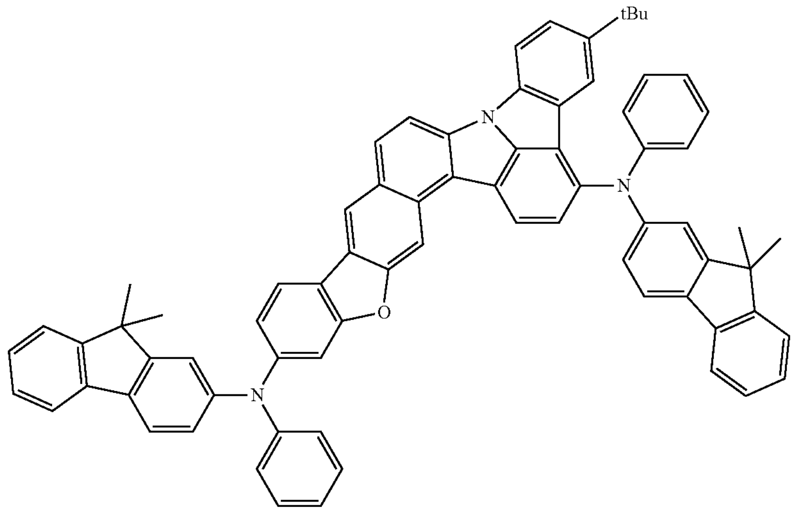
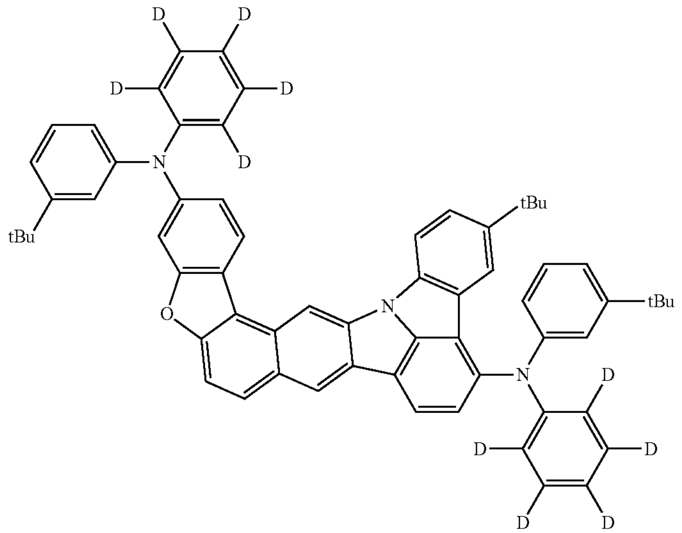

-continued
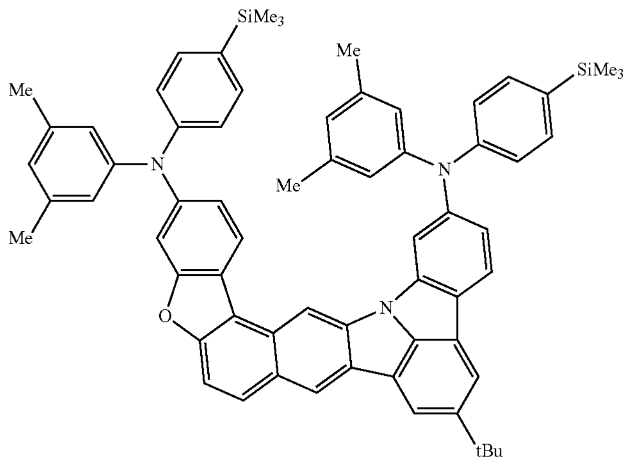
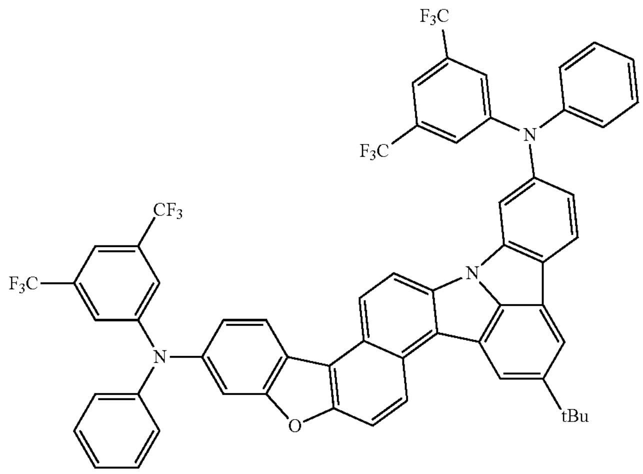
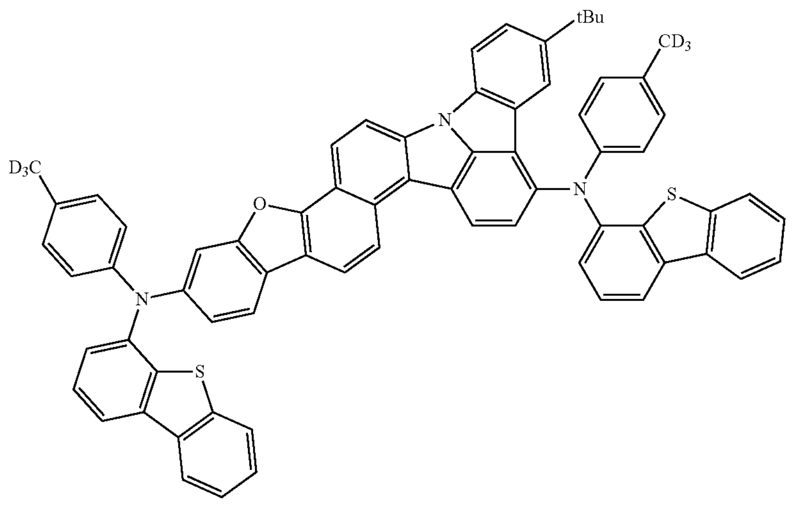

-continued
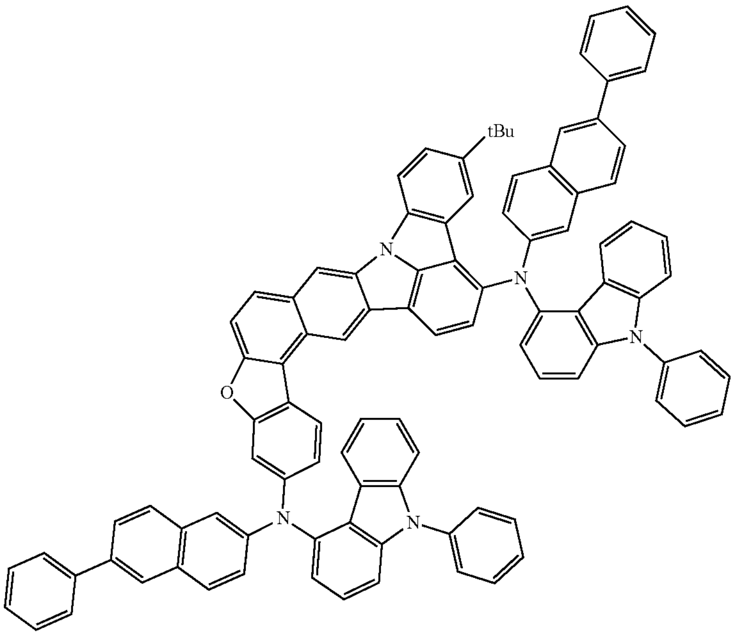
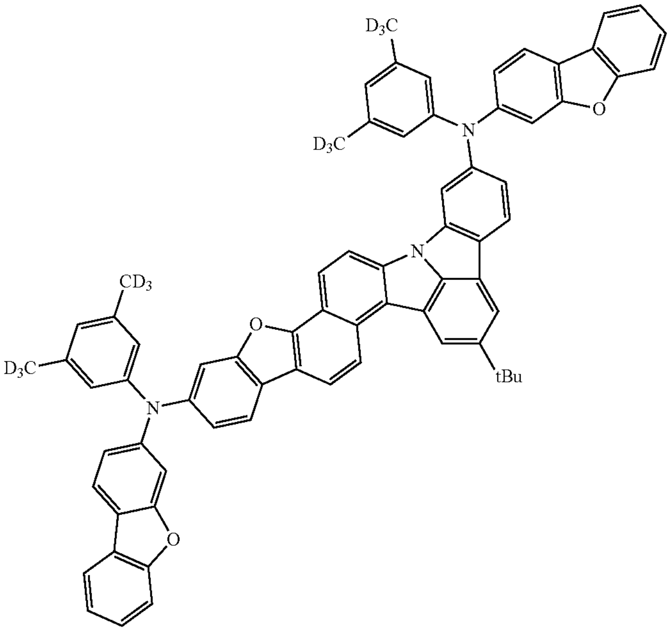

-continued
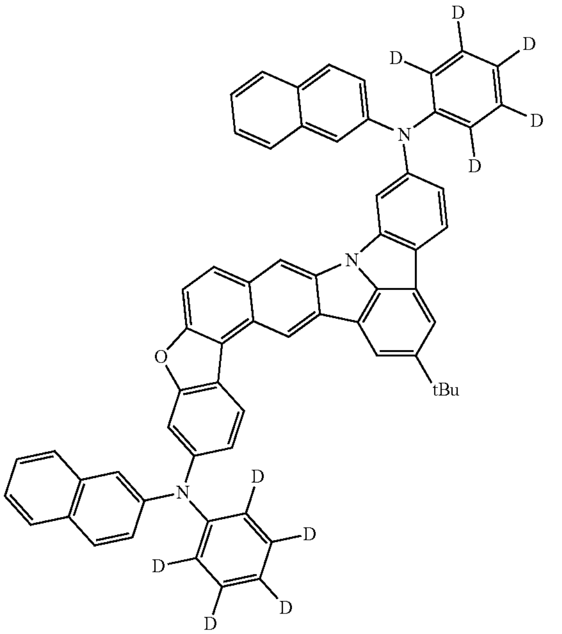
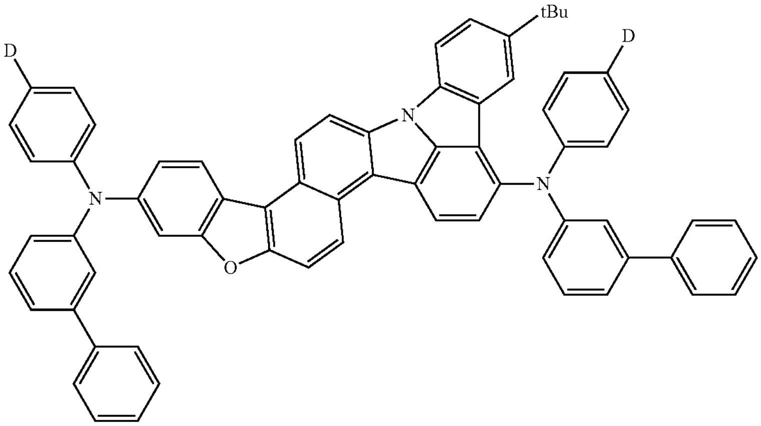
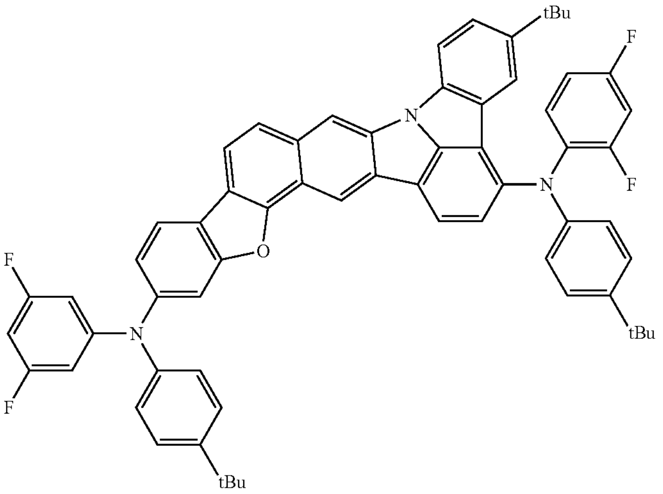

-continued
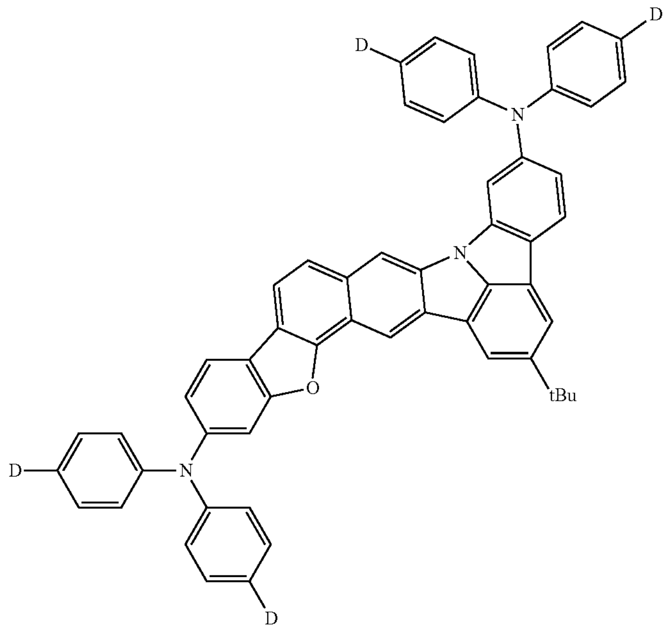
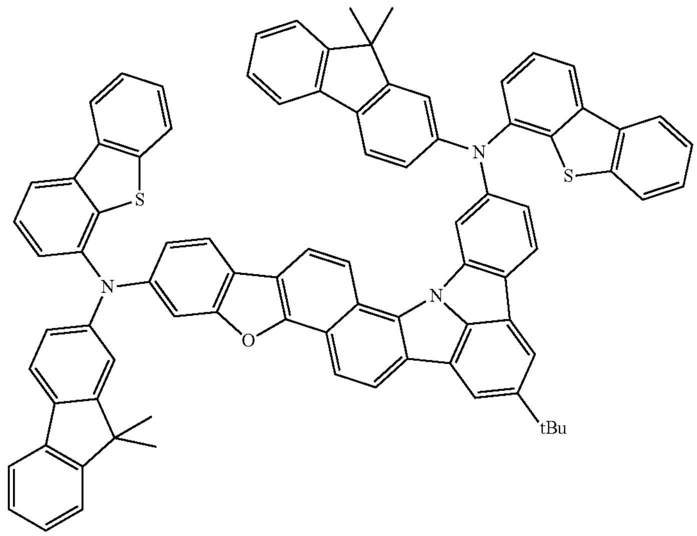
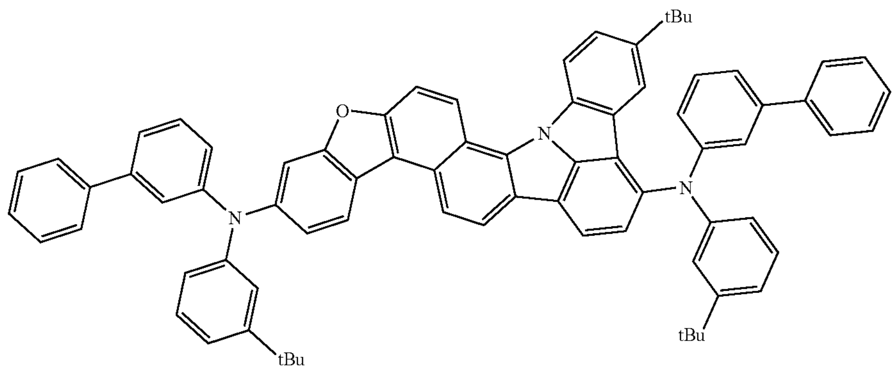

-continued
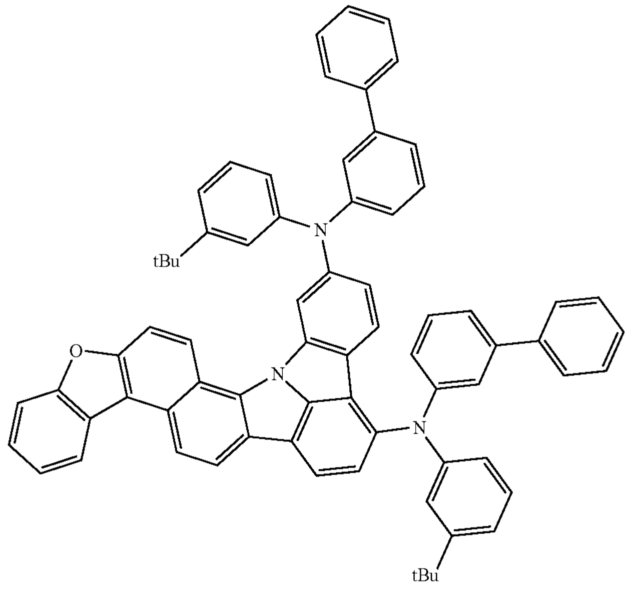
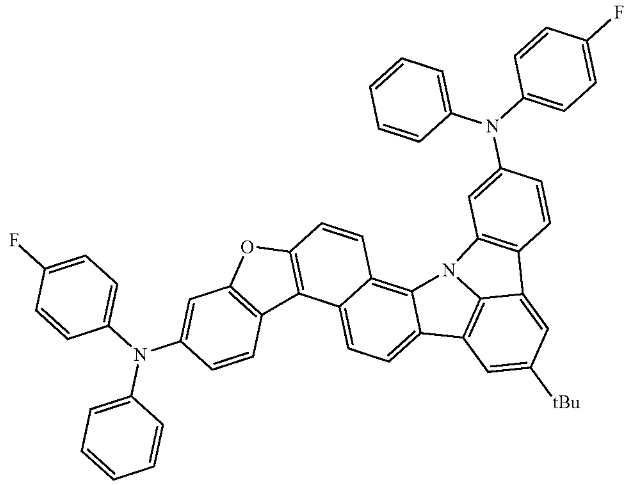
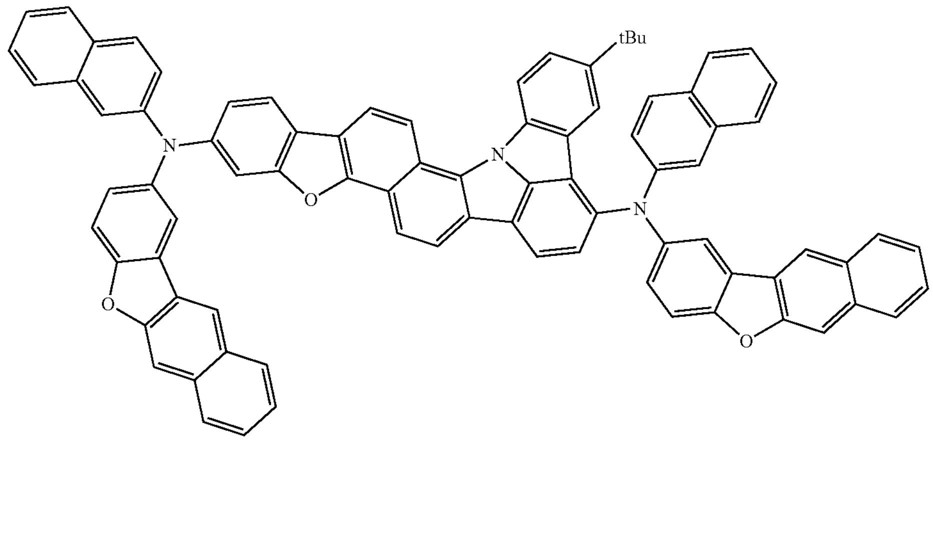

-continued
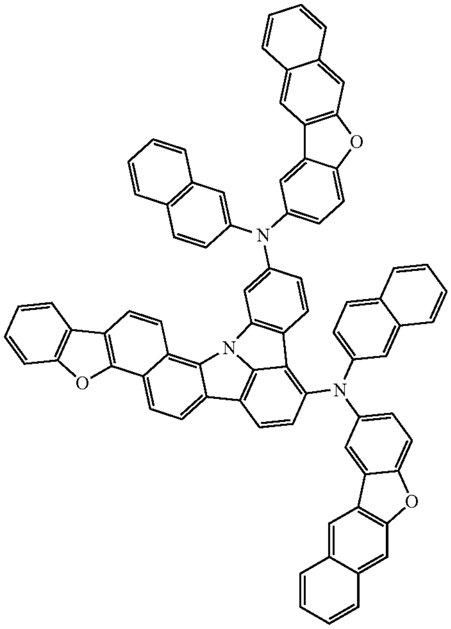
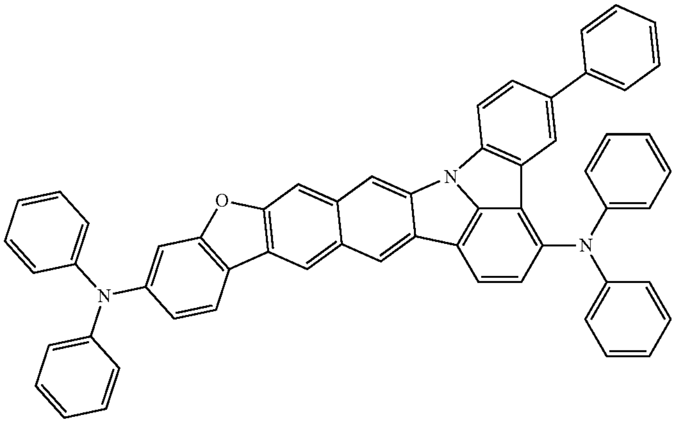
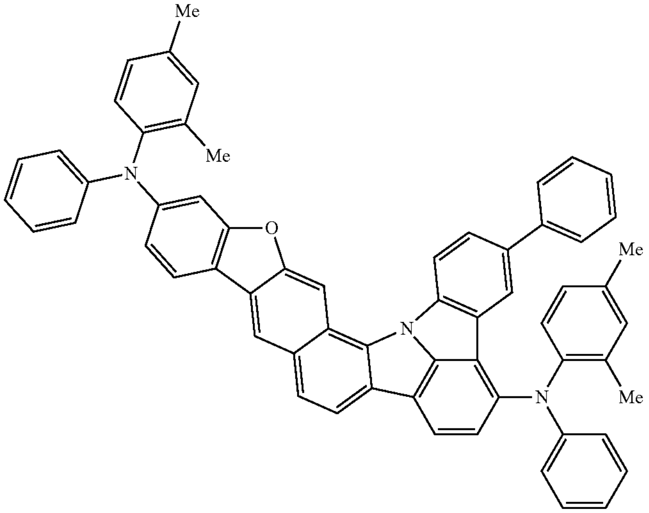

-continued
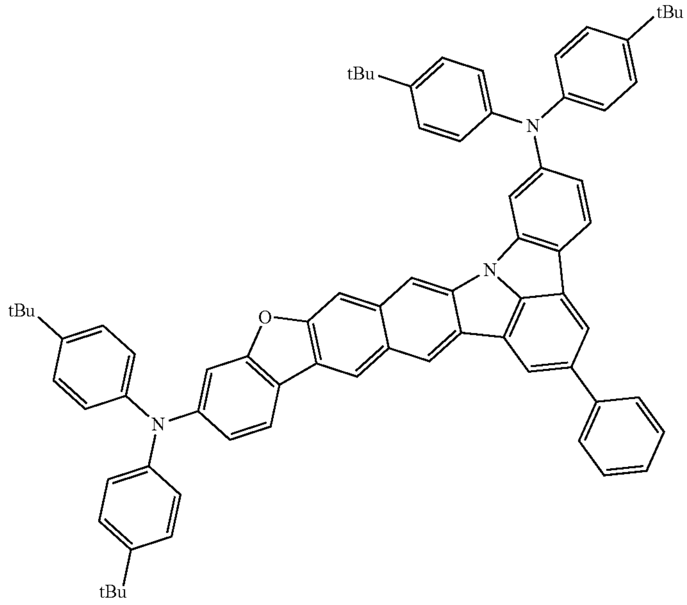
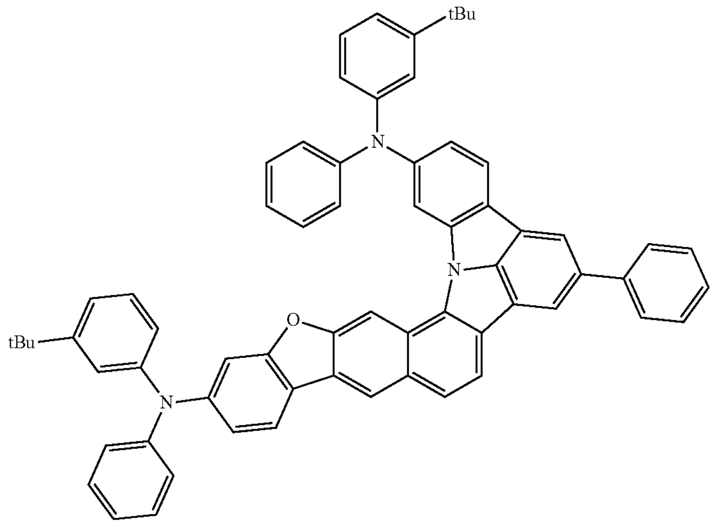
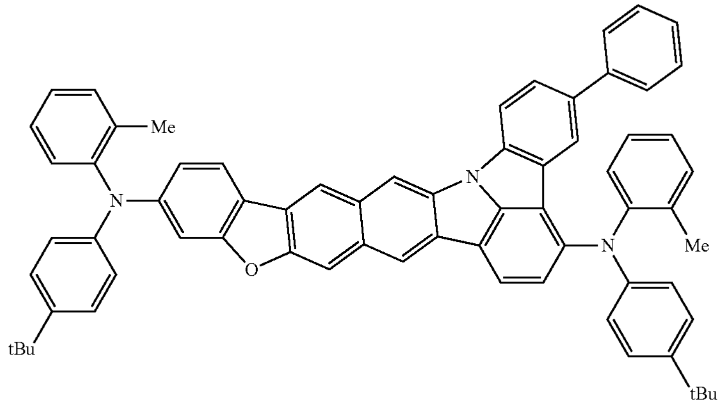

-continued
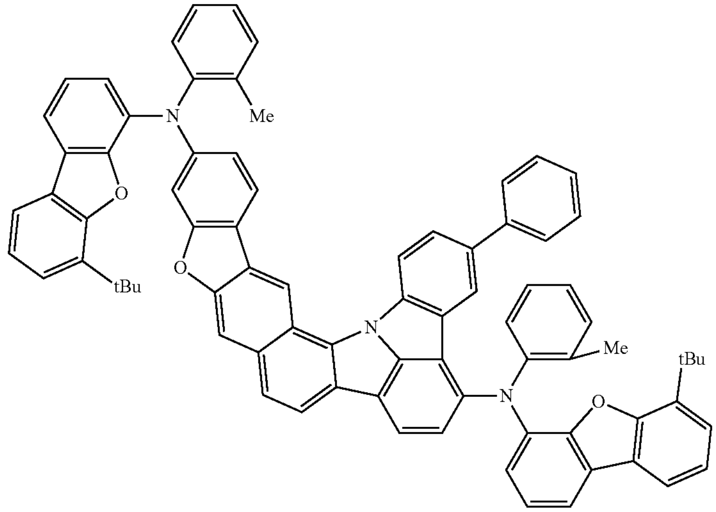
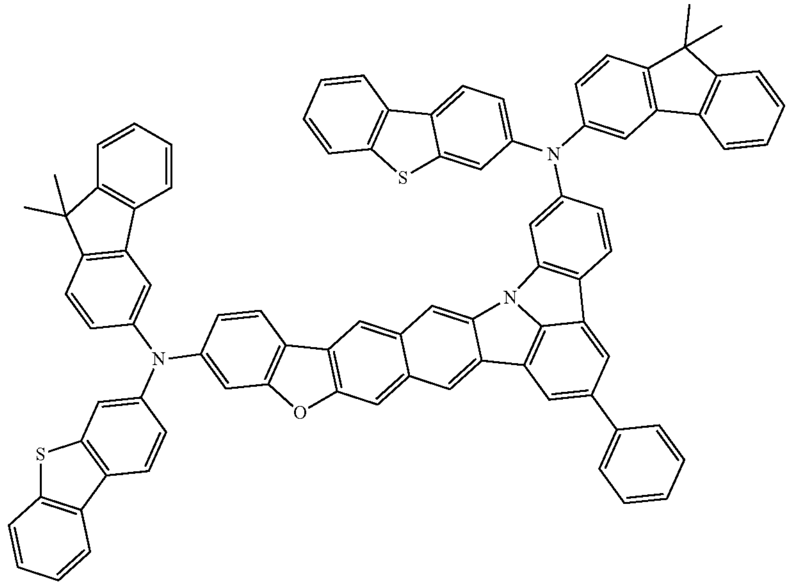
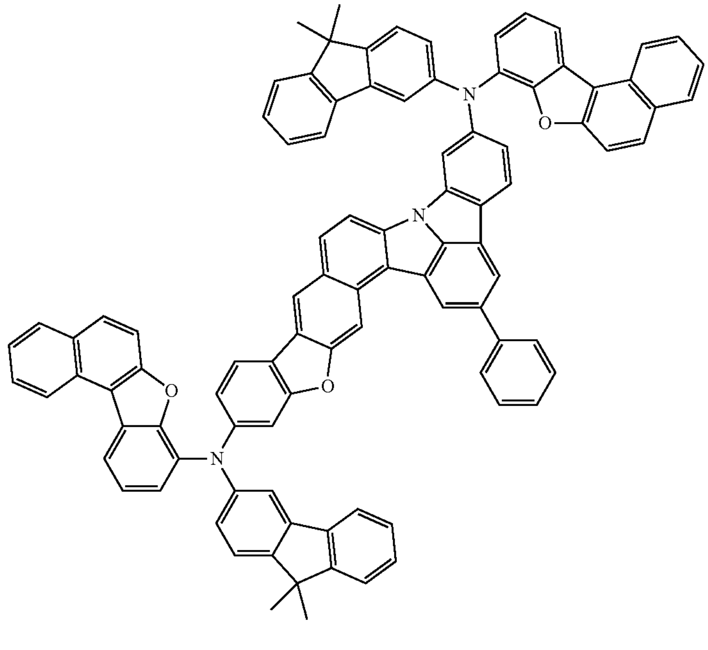

-continued
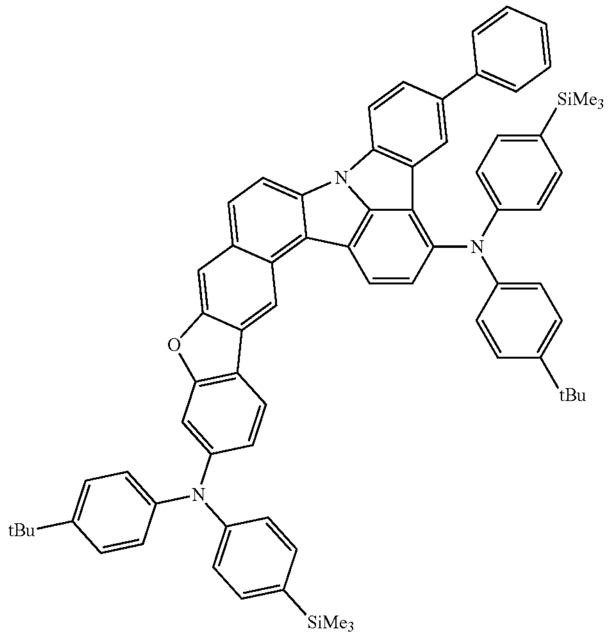
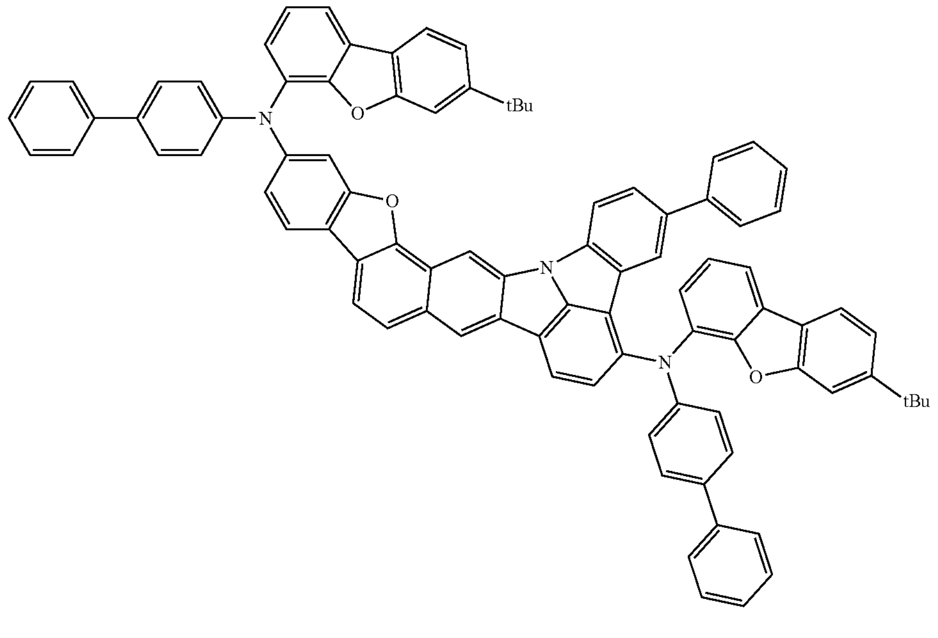

-continued
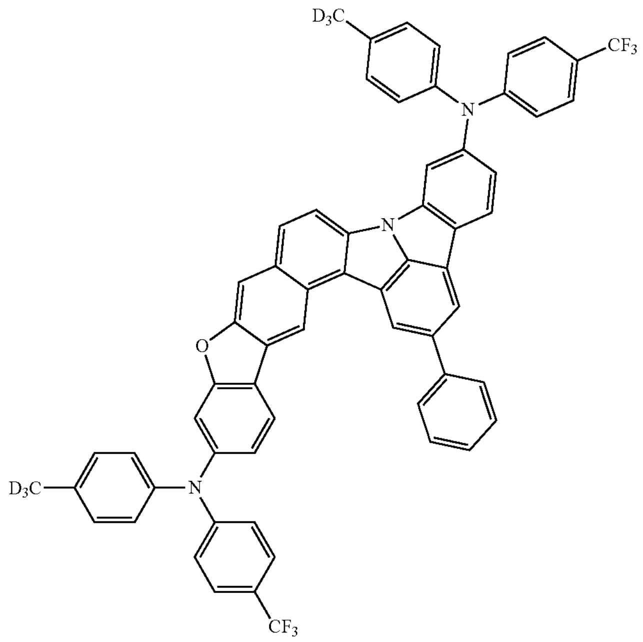
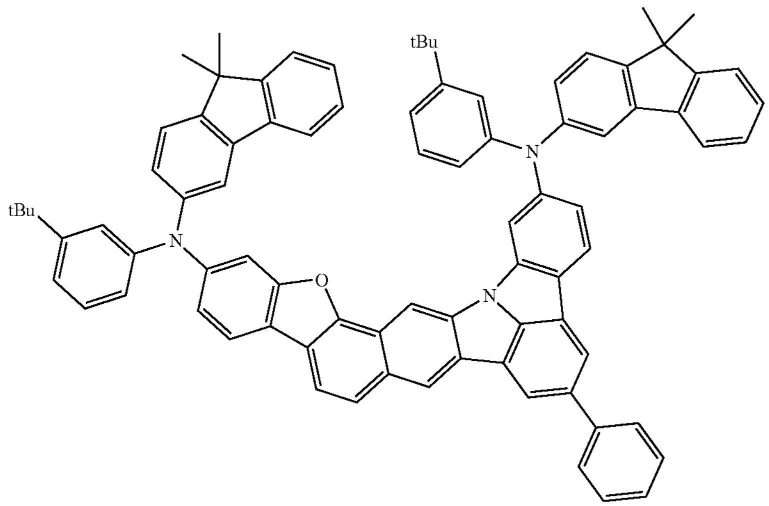
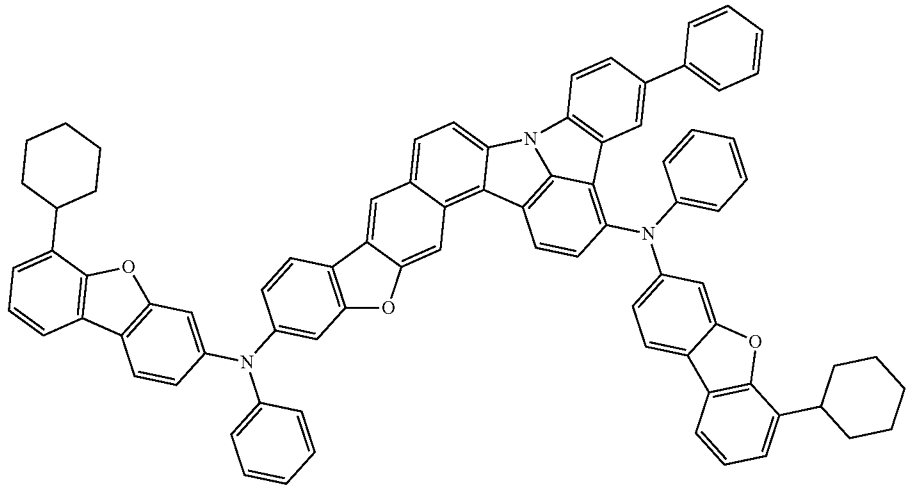

-continued
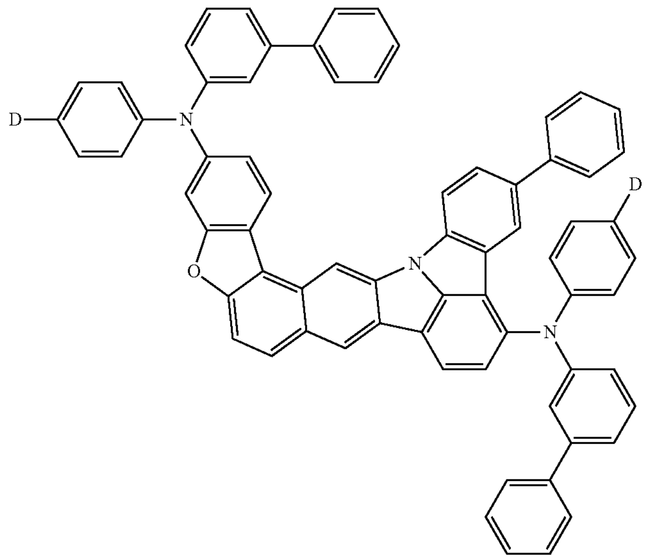
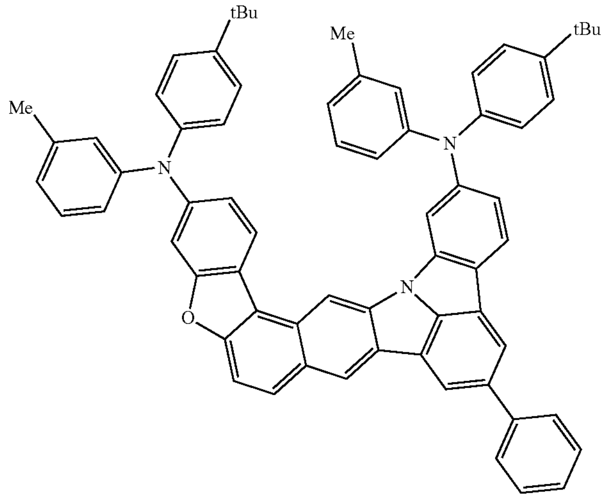
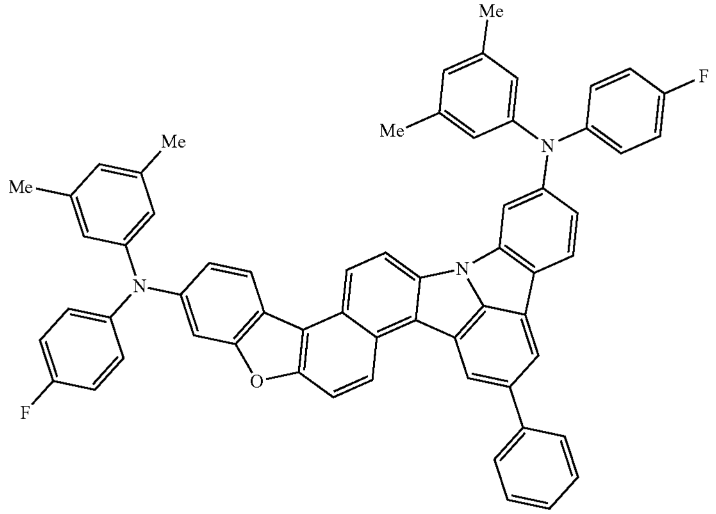

-continued
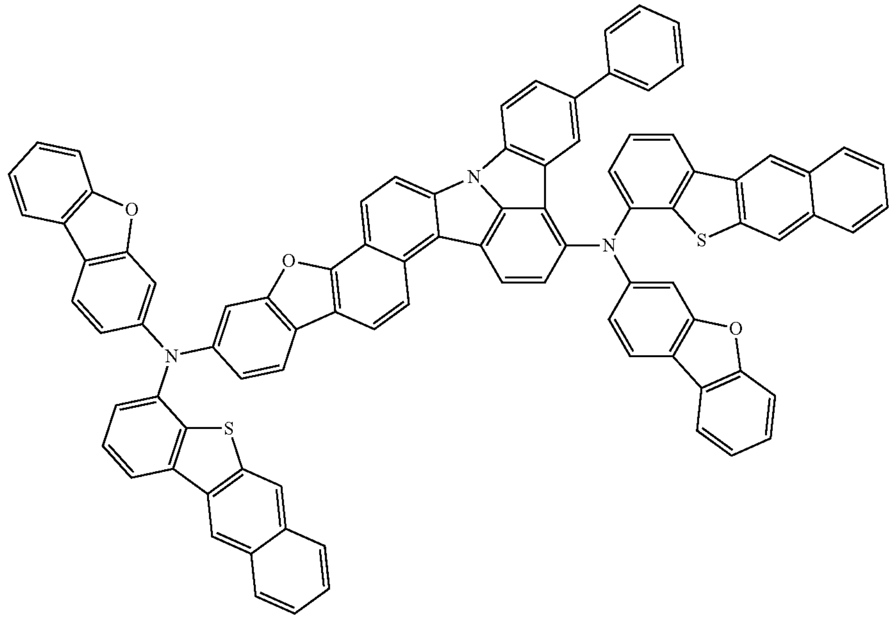
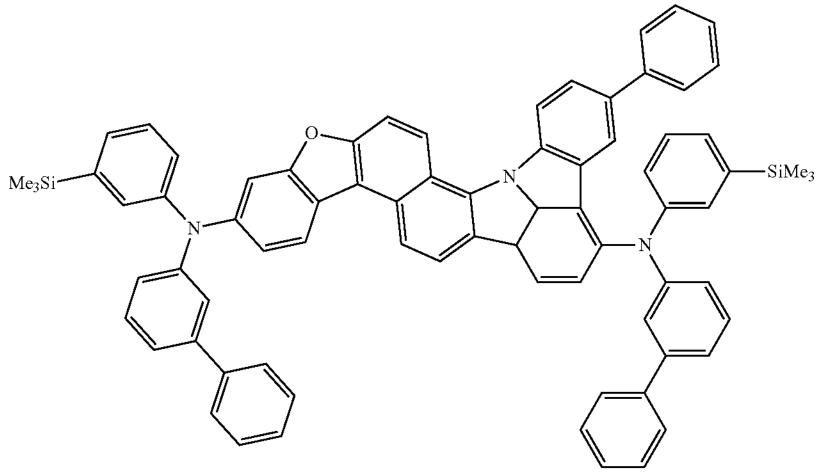
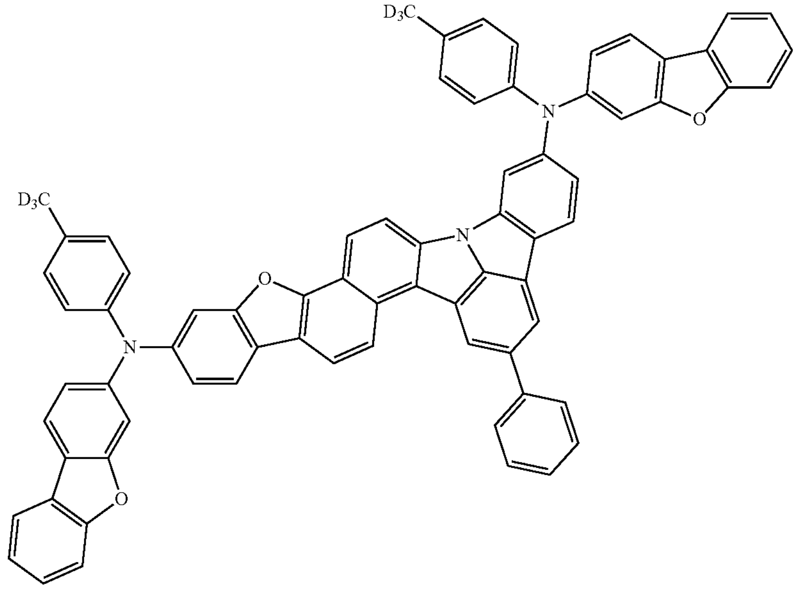

-continued
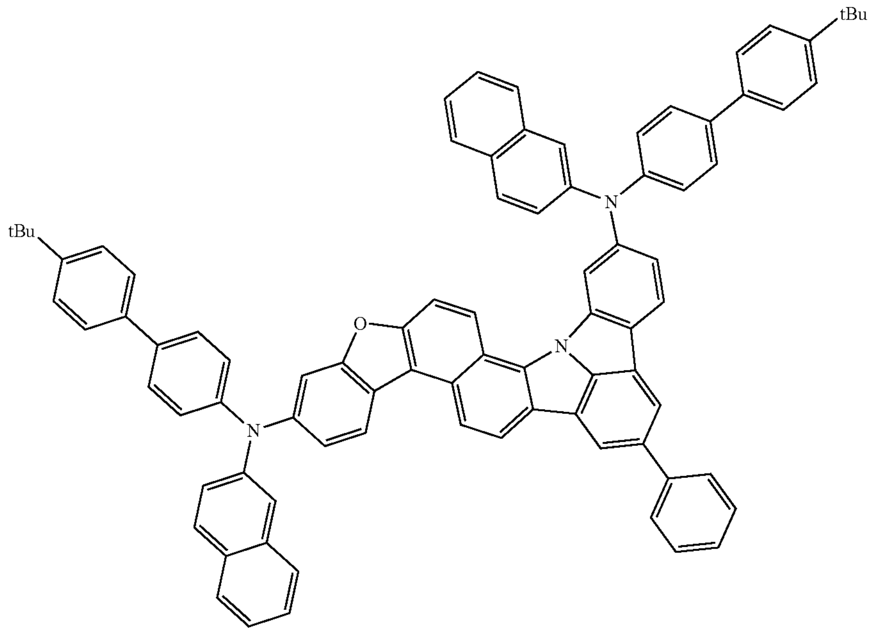
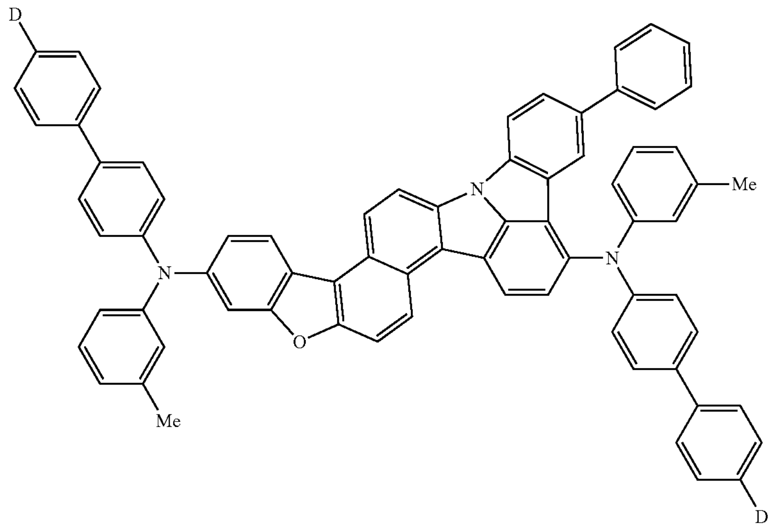
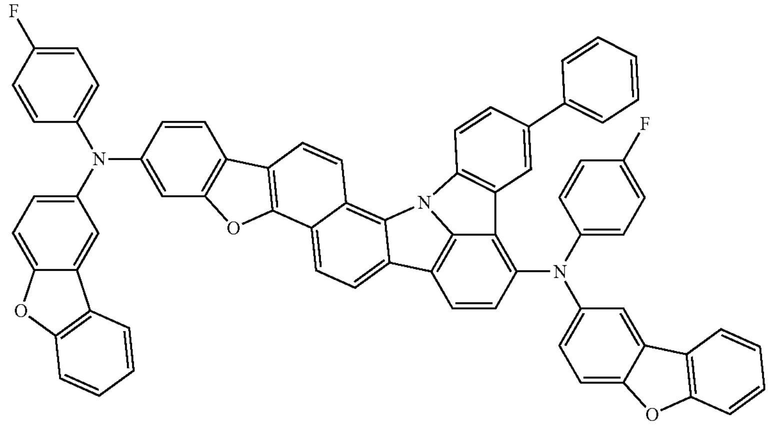

-continued
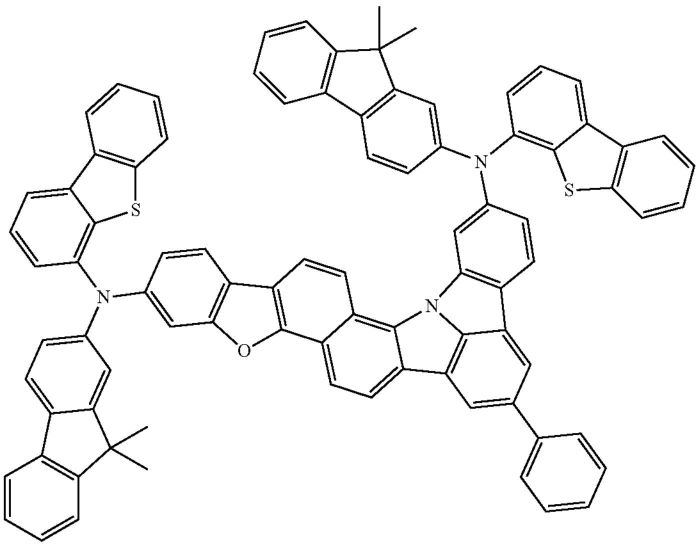
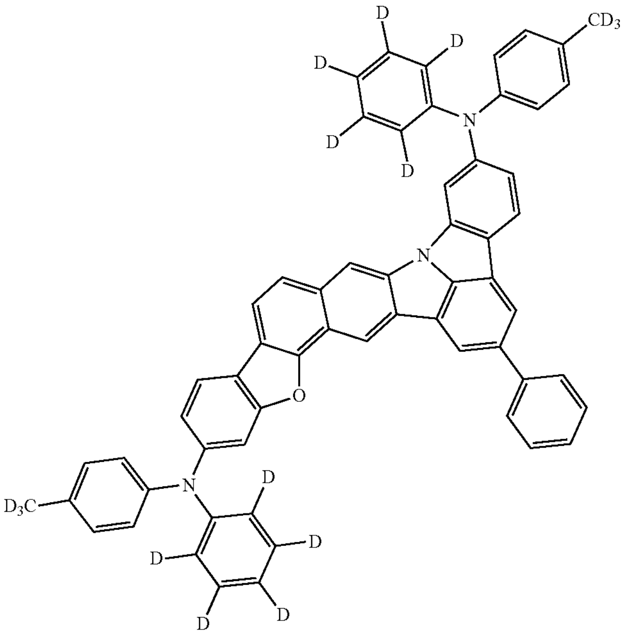
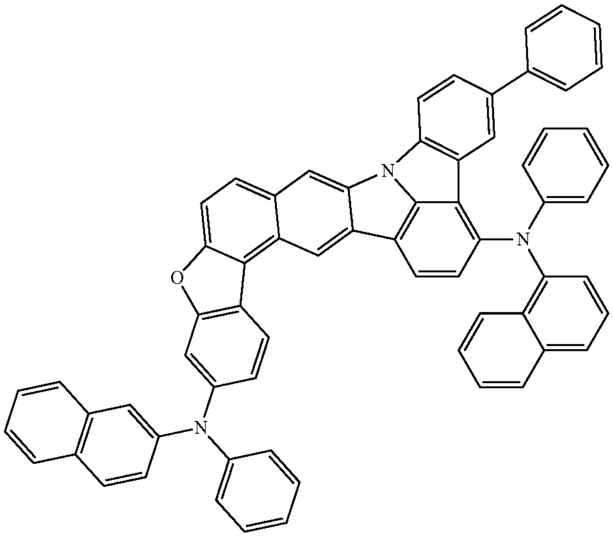

-continued
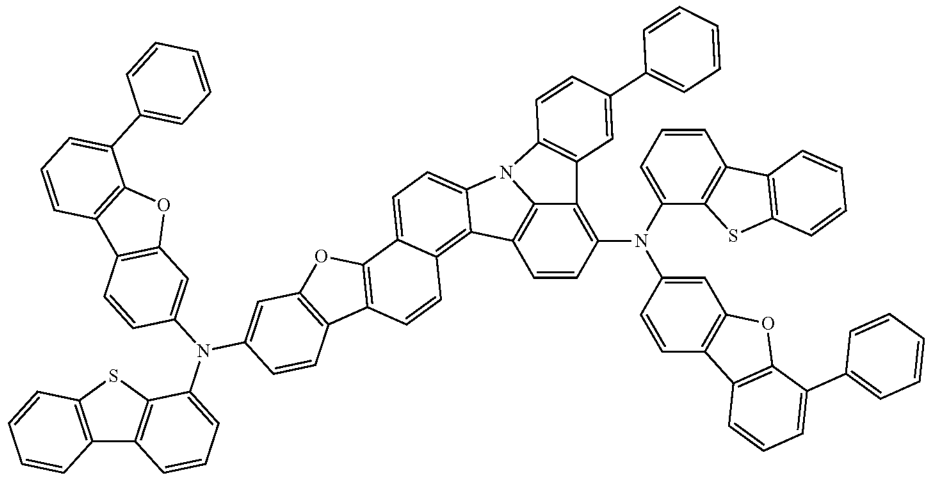
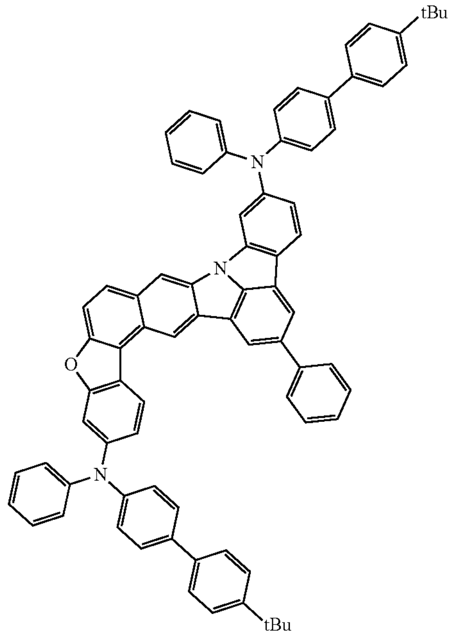
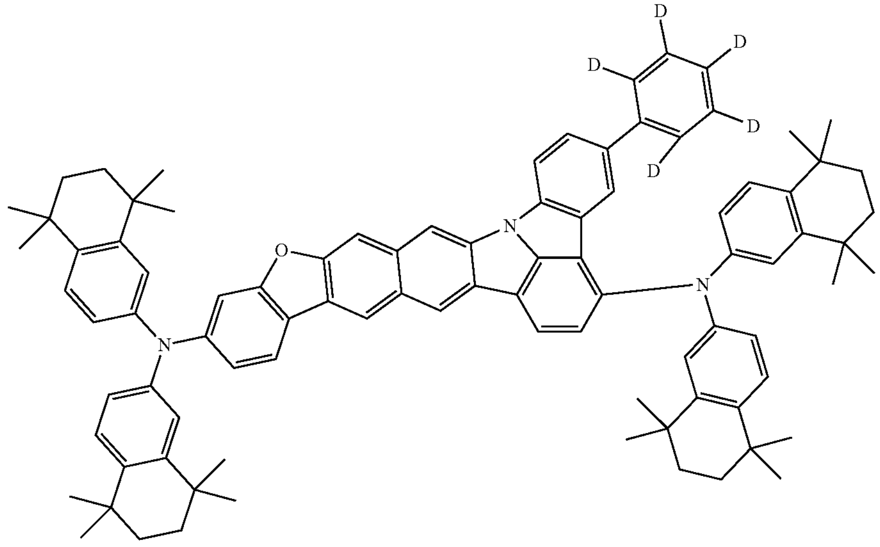

-continued
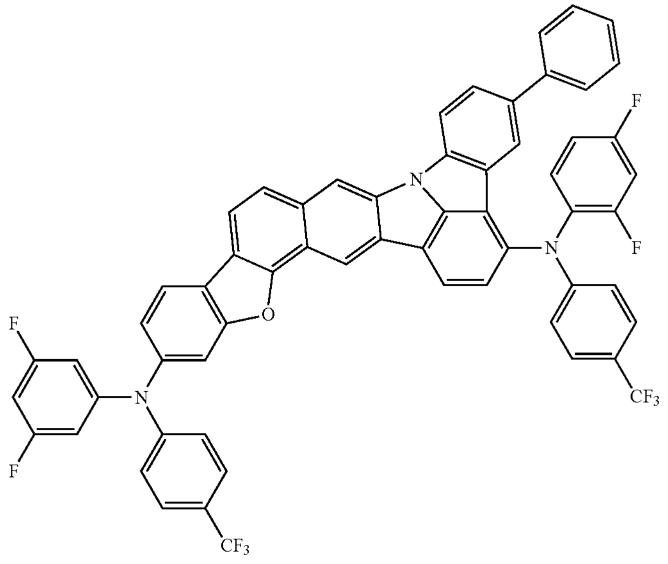
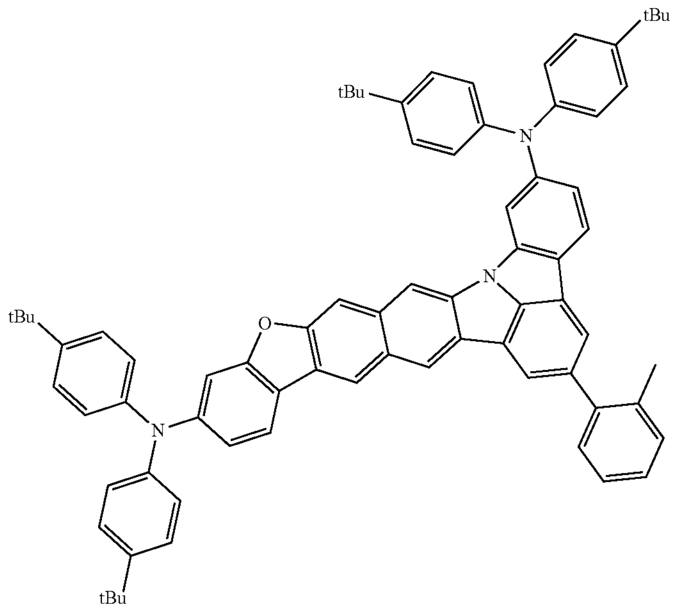

-continued
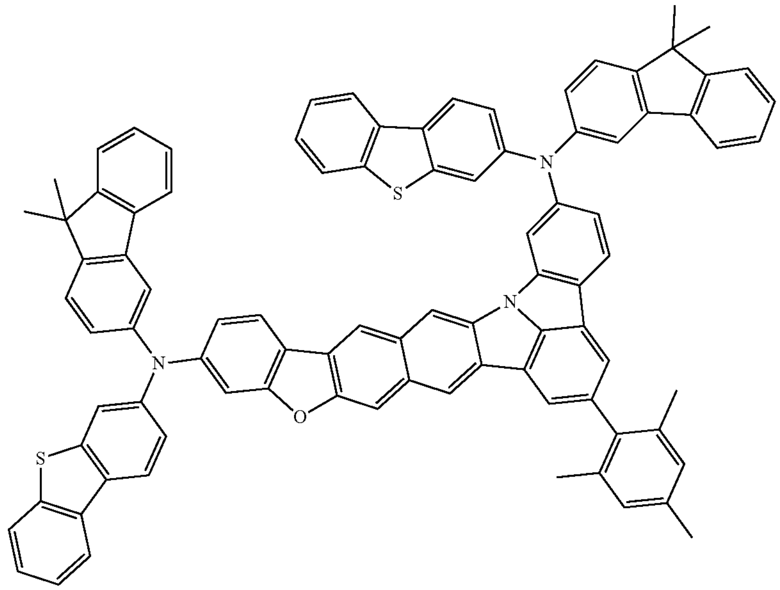
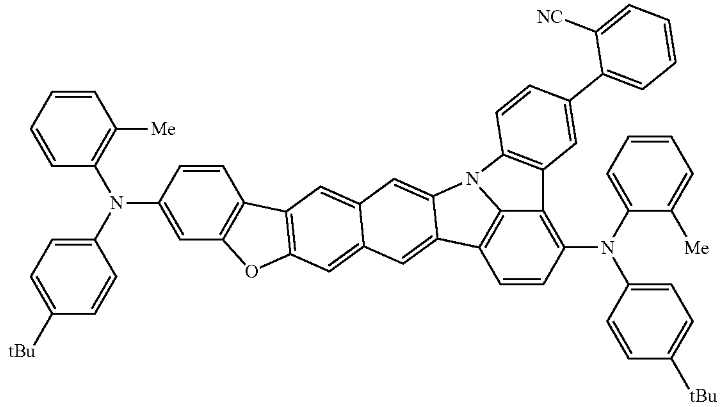
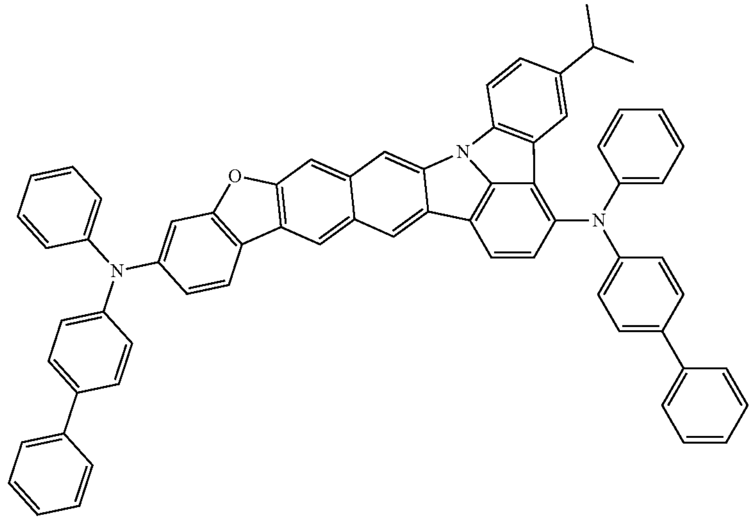

-continued
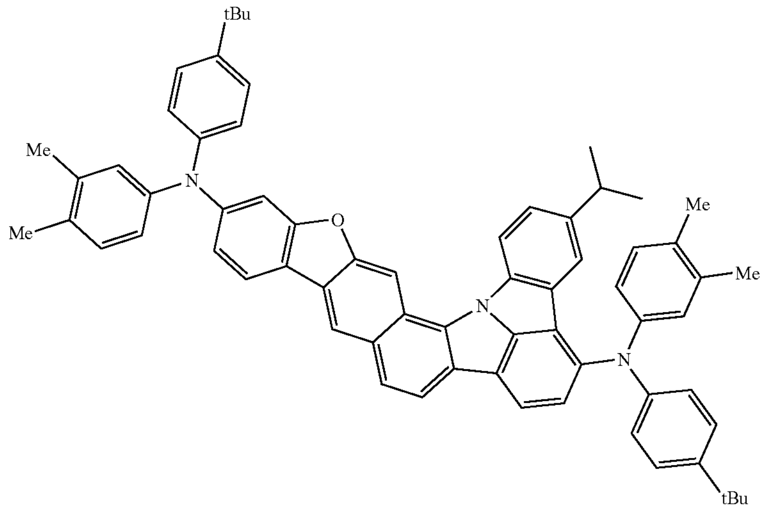
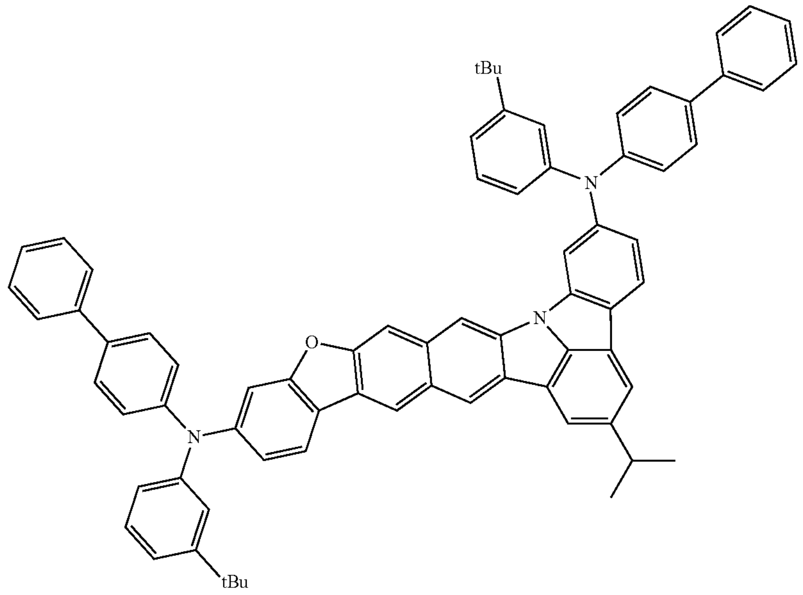
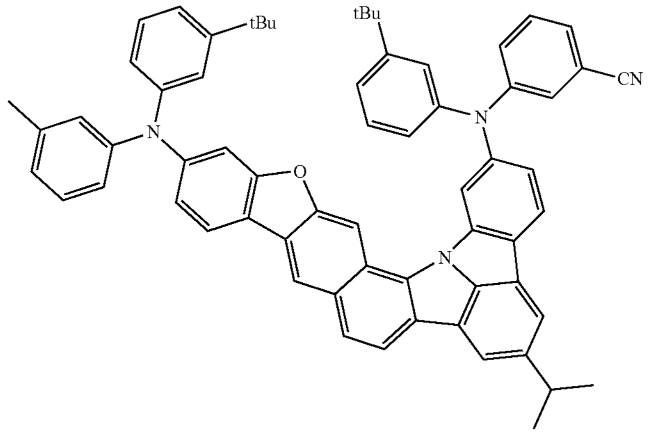

-continued
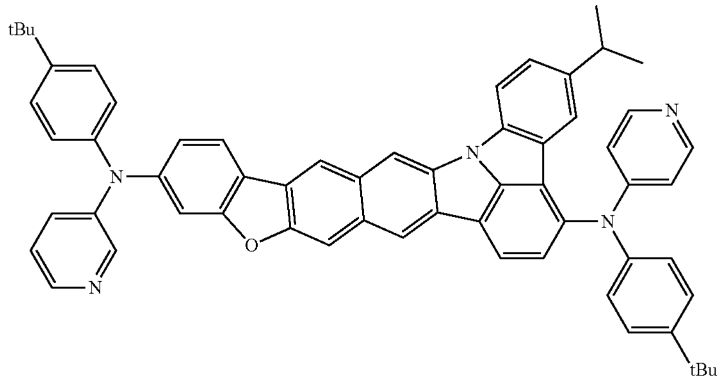
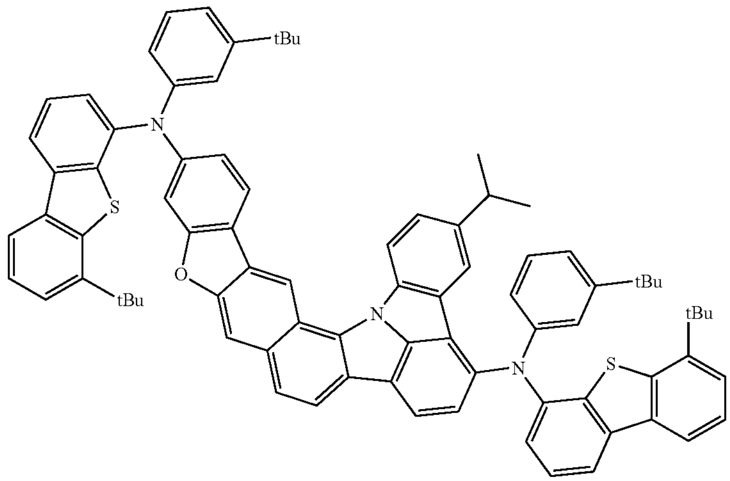
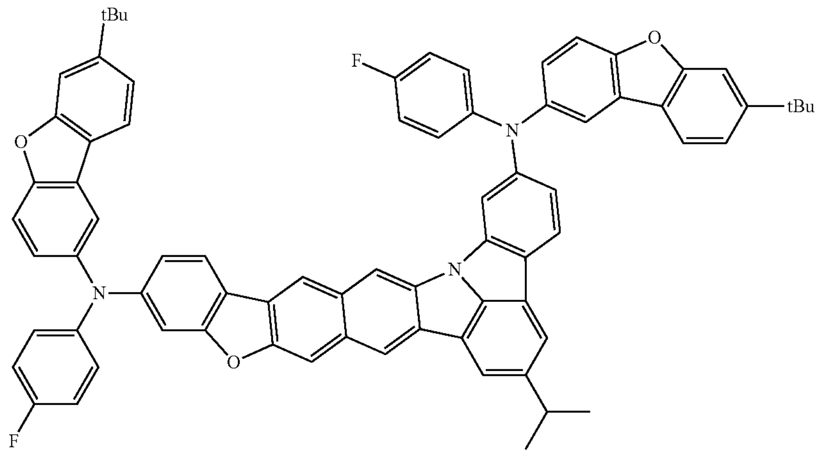

-continued
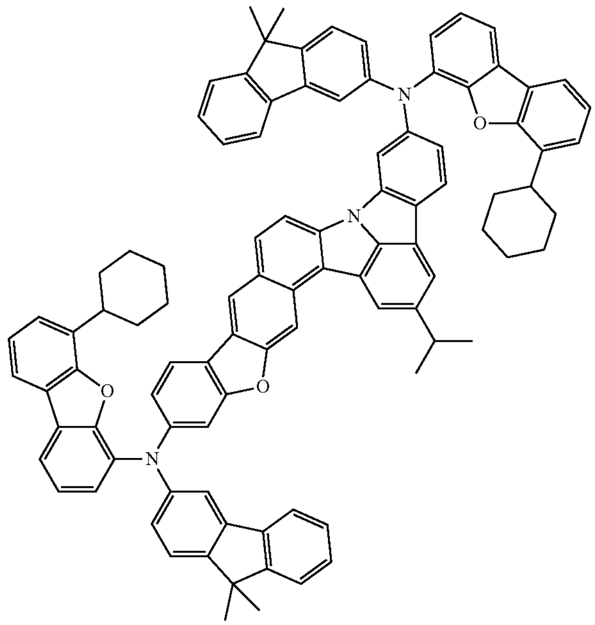
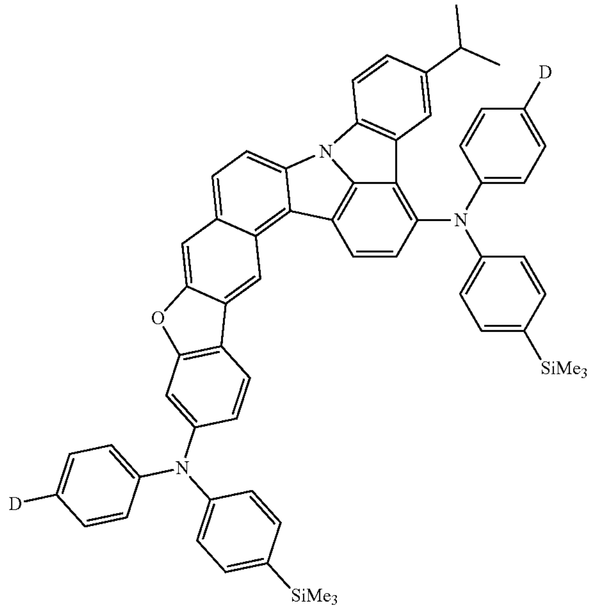
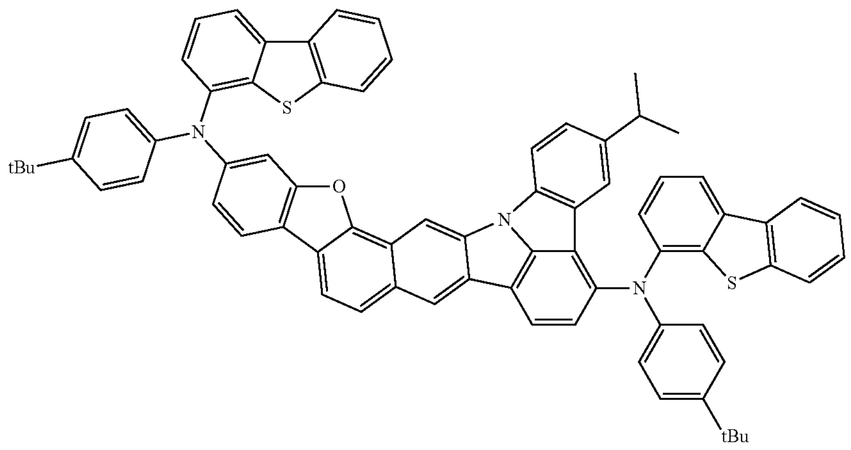

-continued
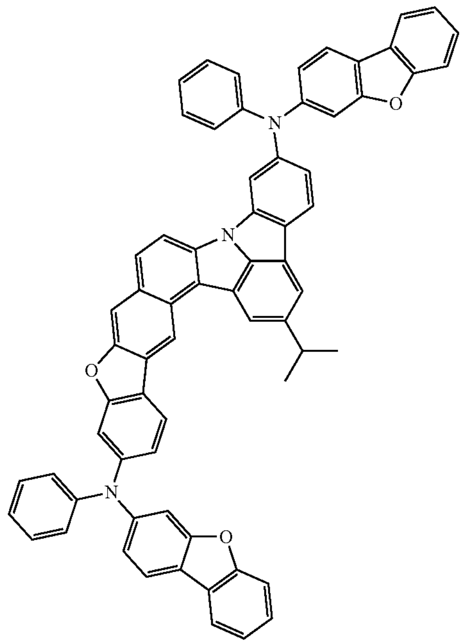
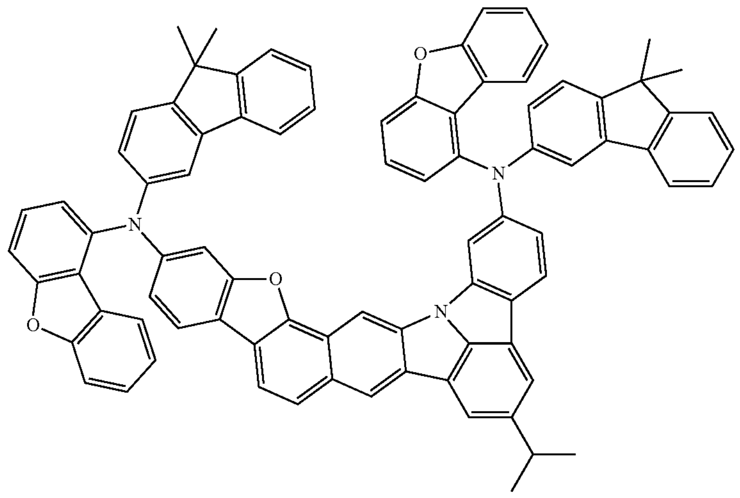
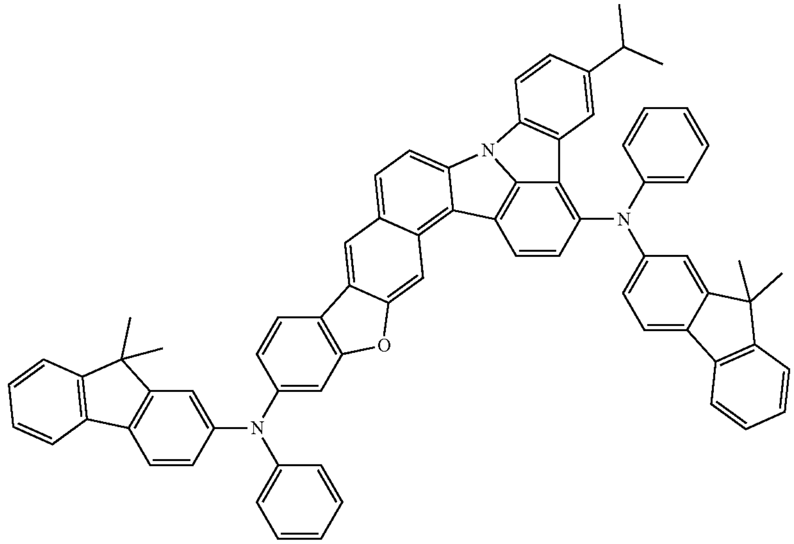

-continued
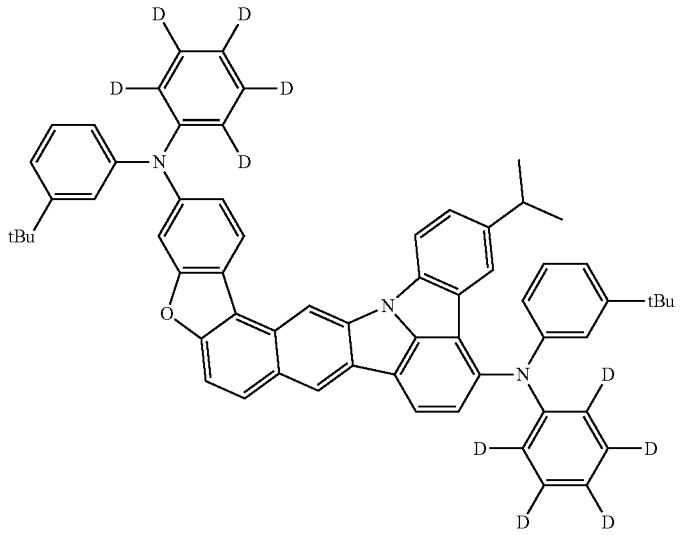
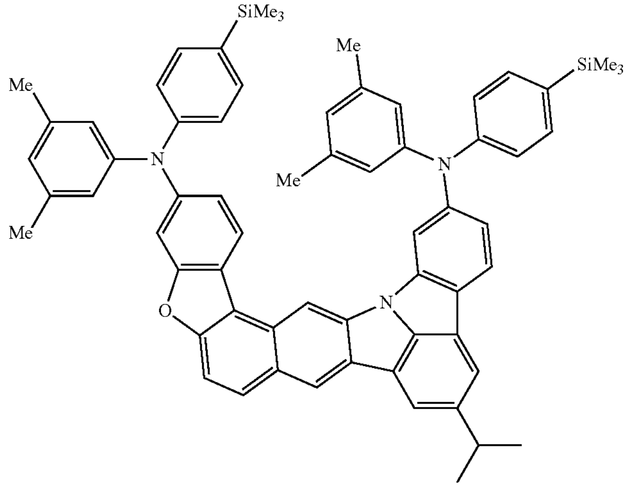
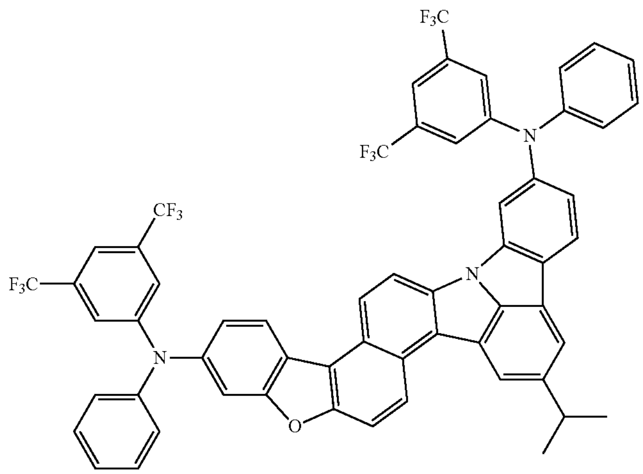

-continued
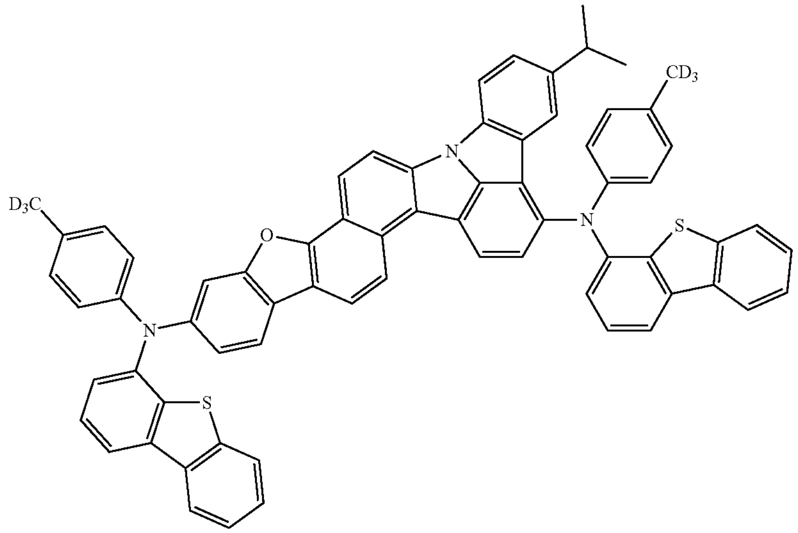
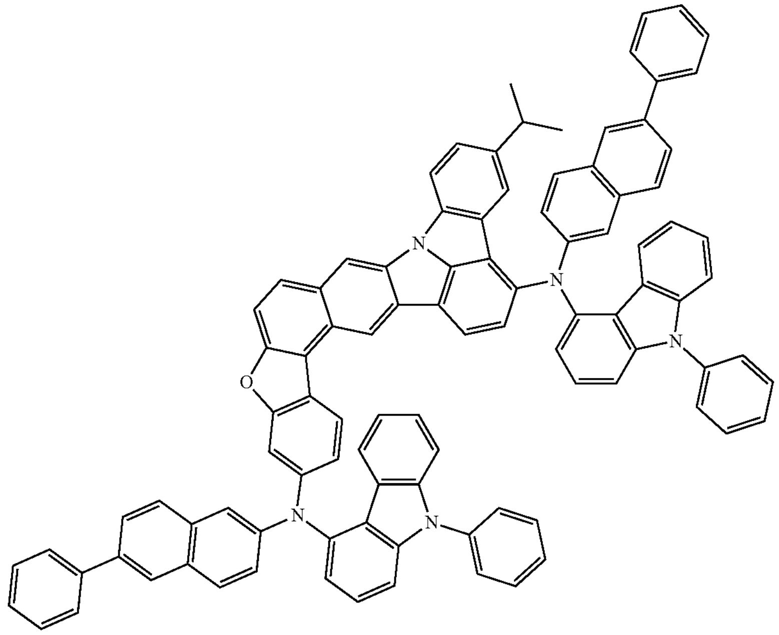

-continued
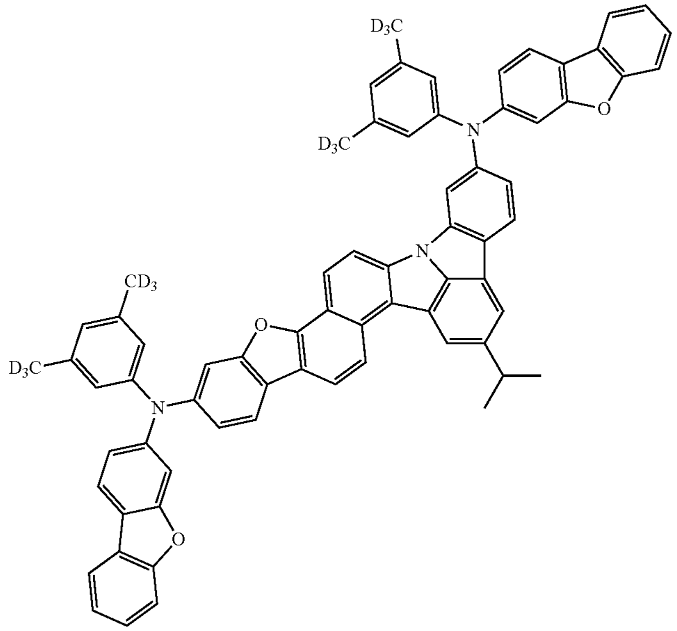
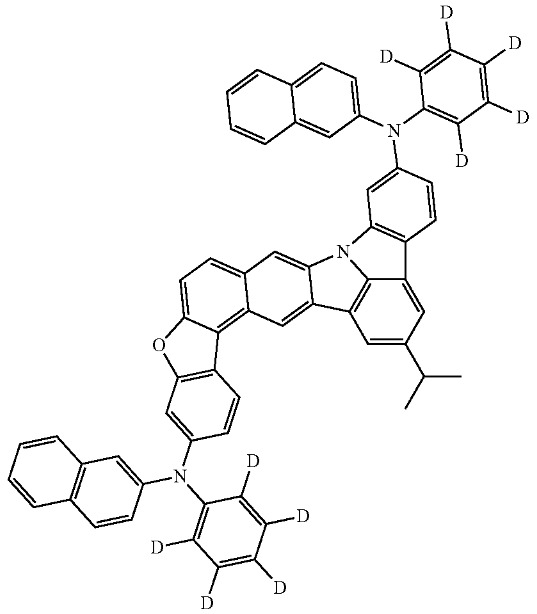
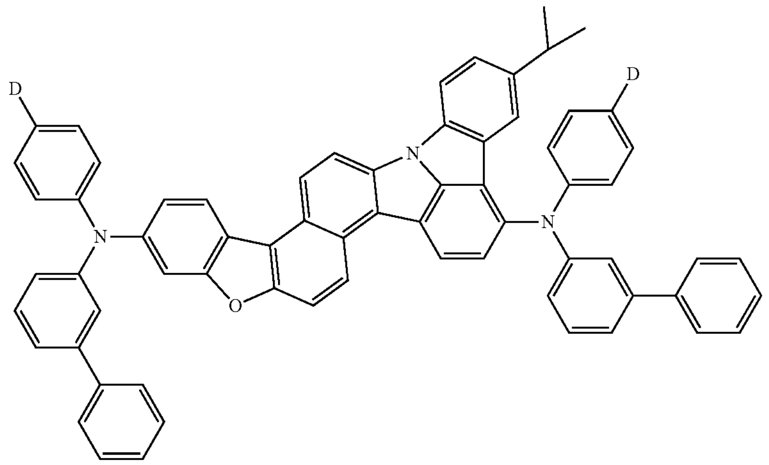

-continued
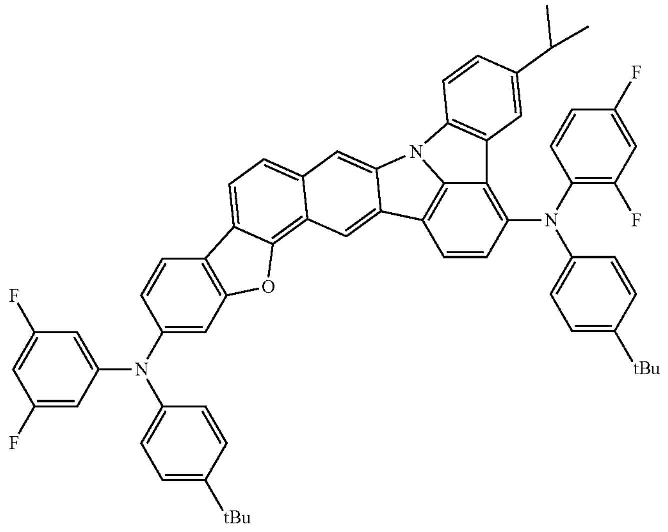
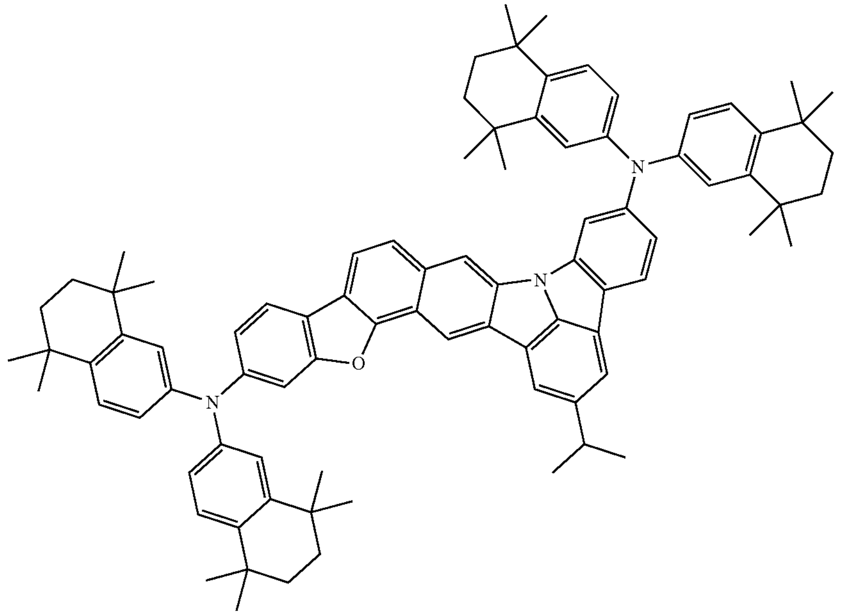
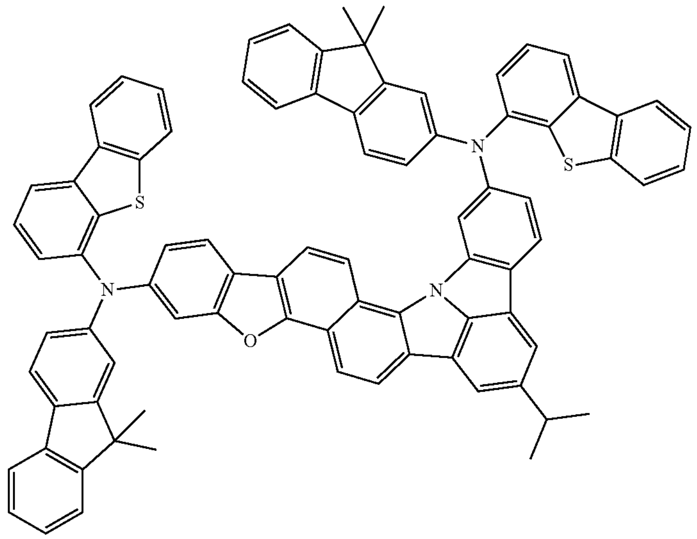

-continued
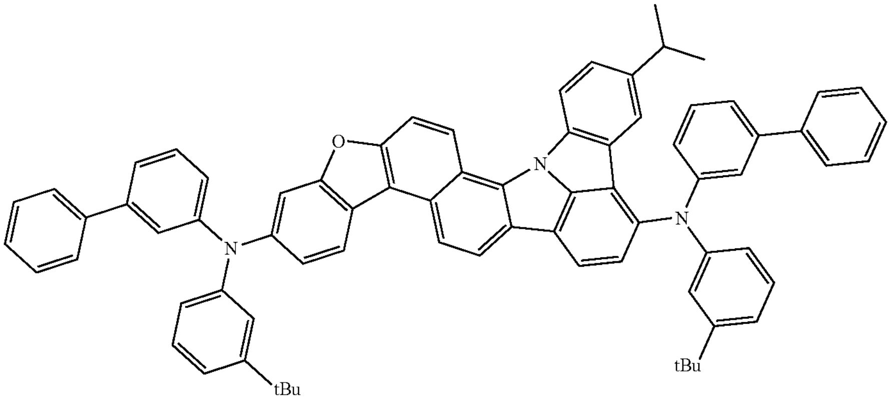
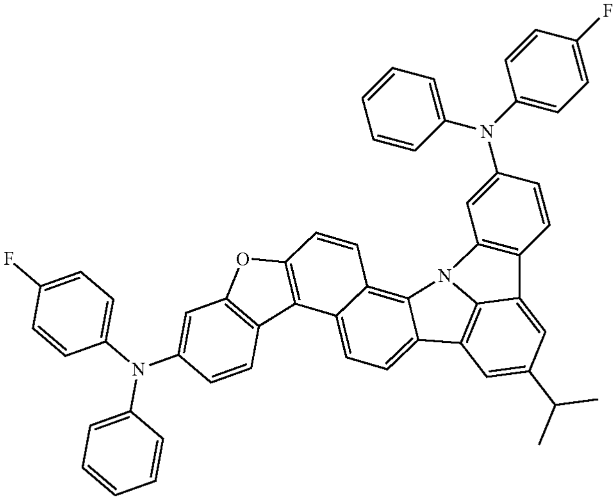
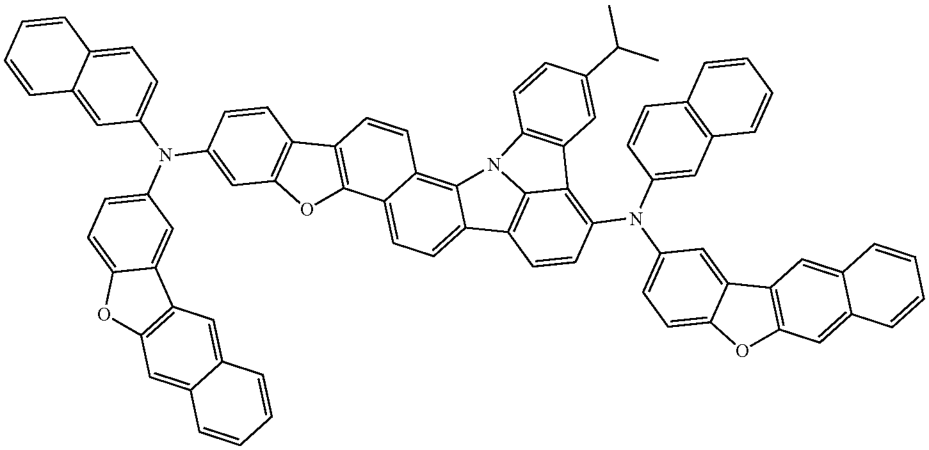

-continued
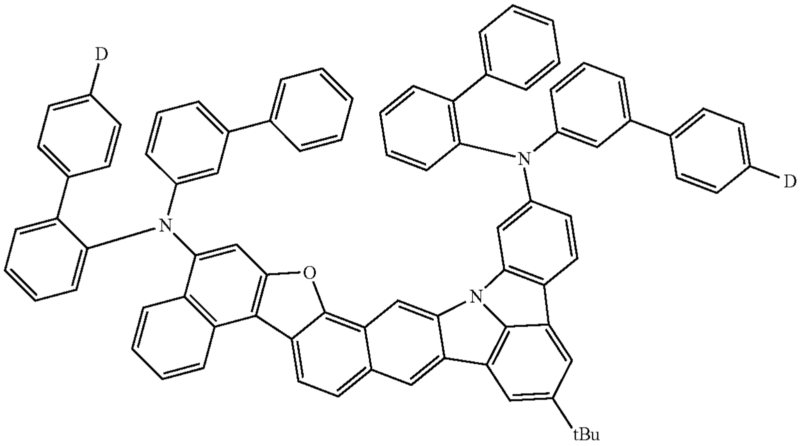
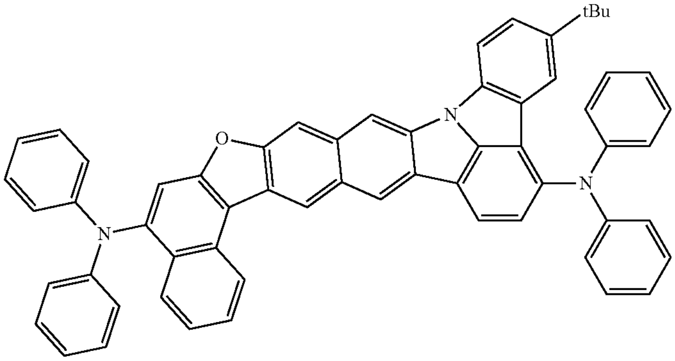
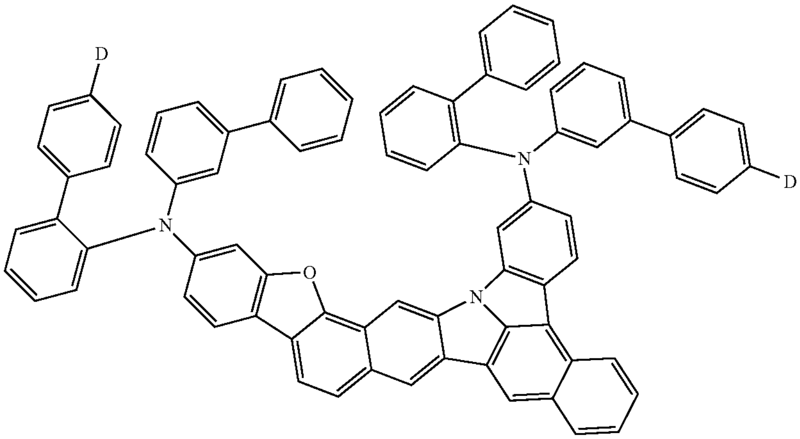
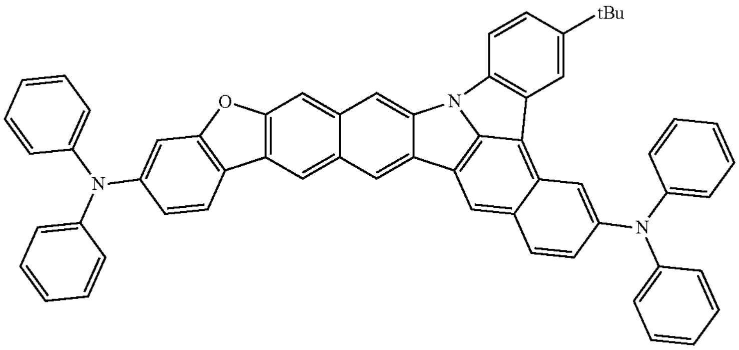

-continued
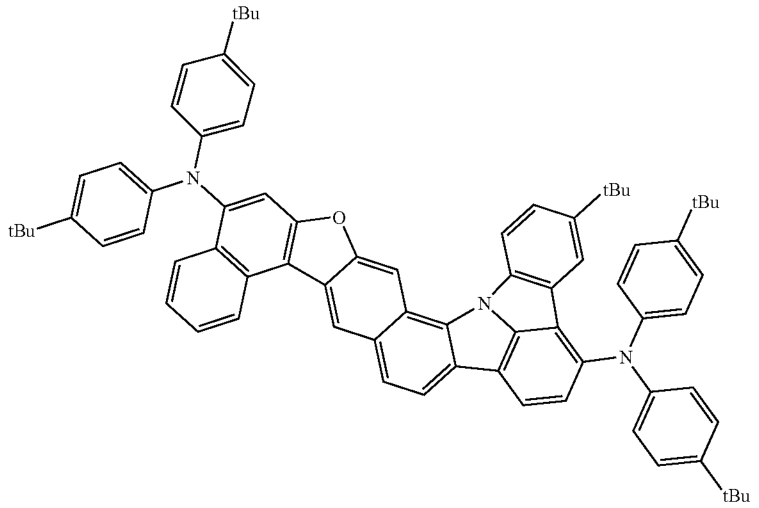
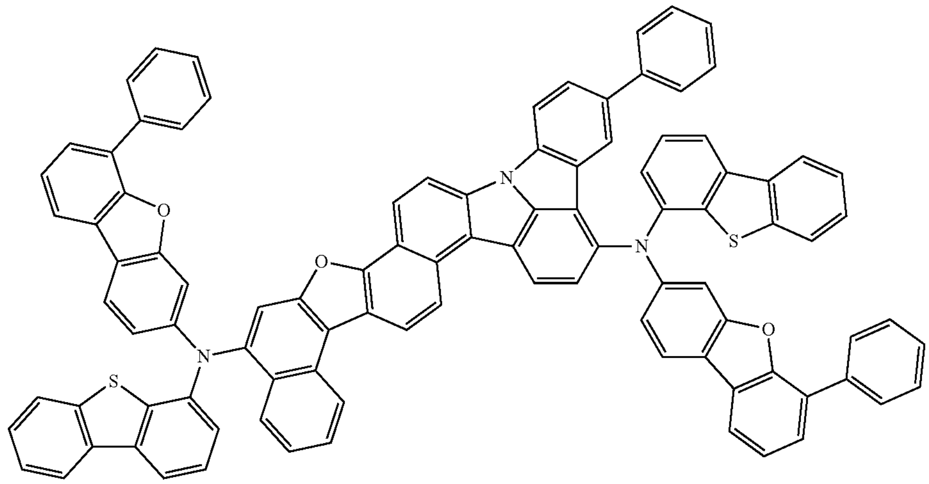
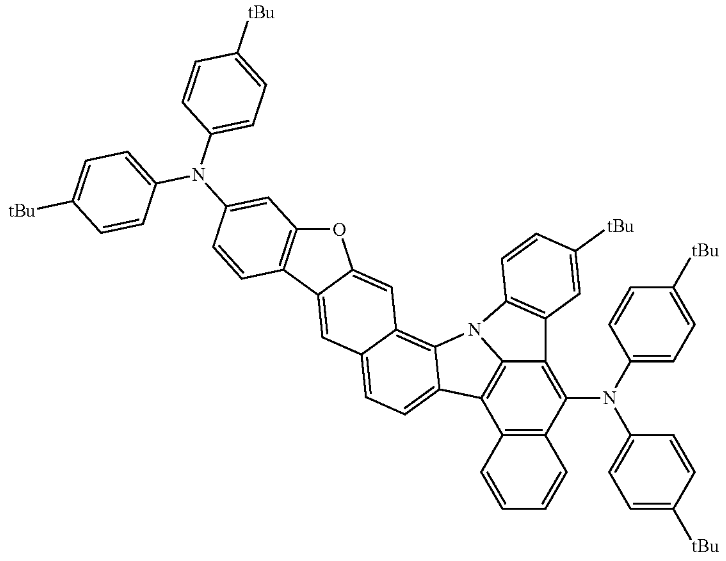

-continued
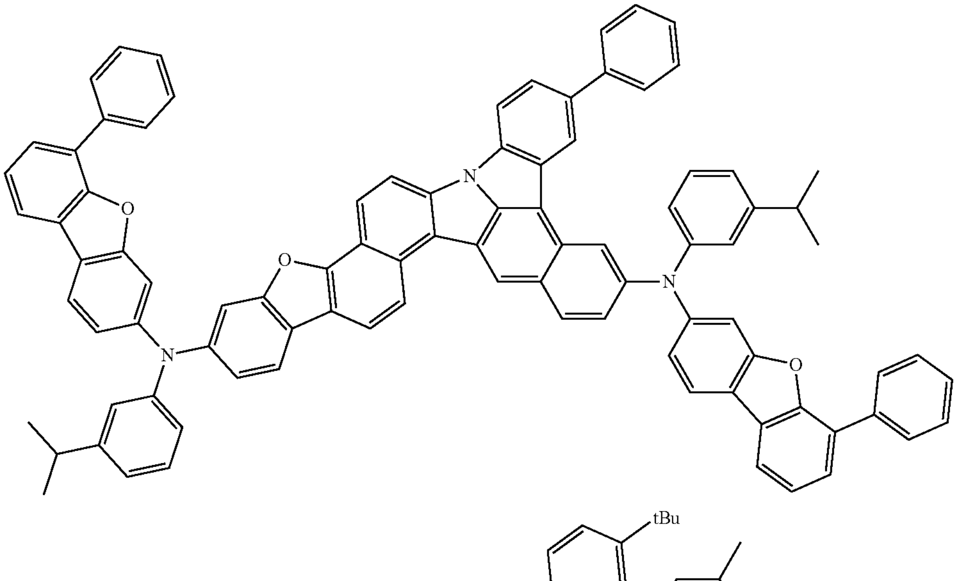
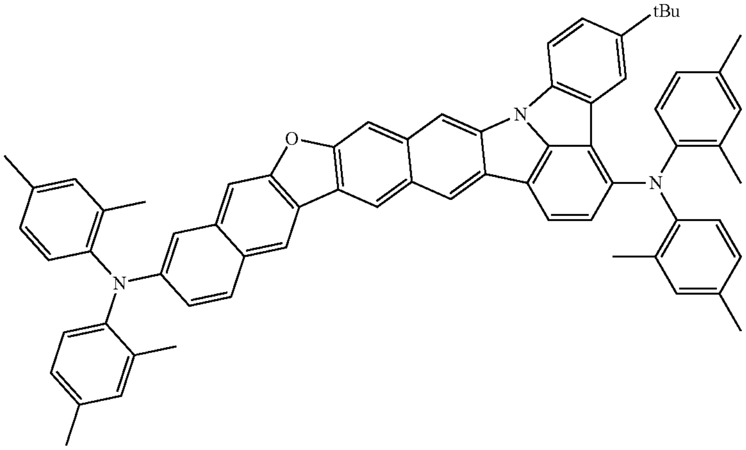
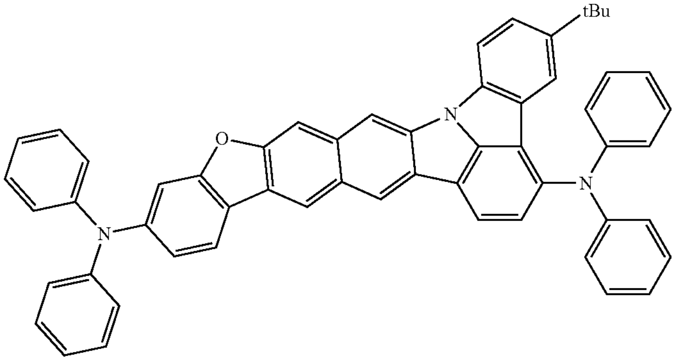
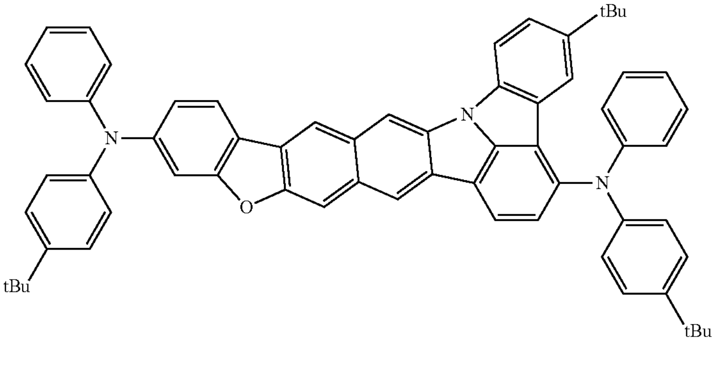

-continued
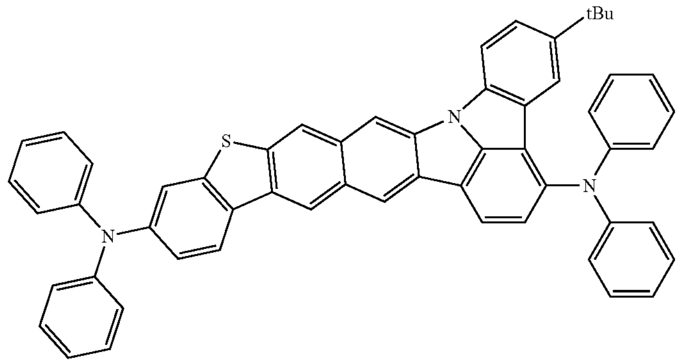
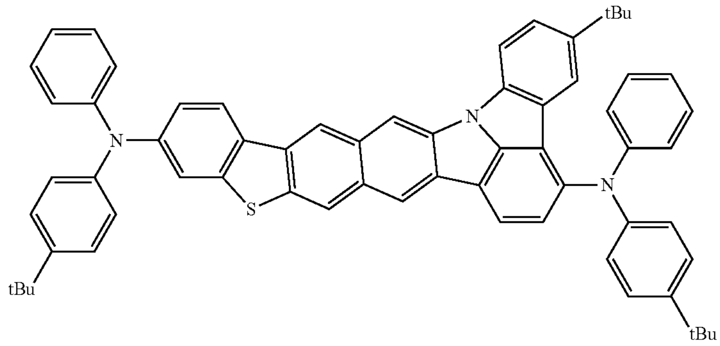
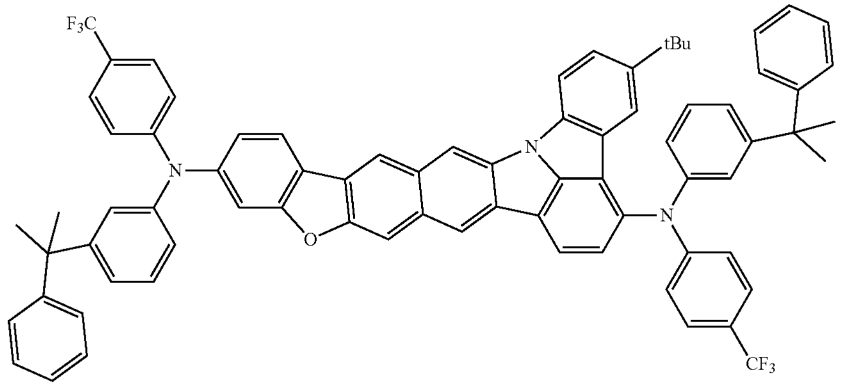
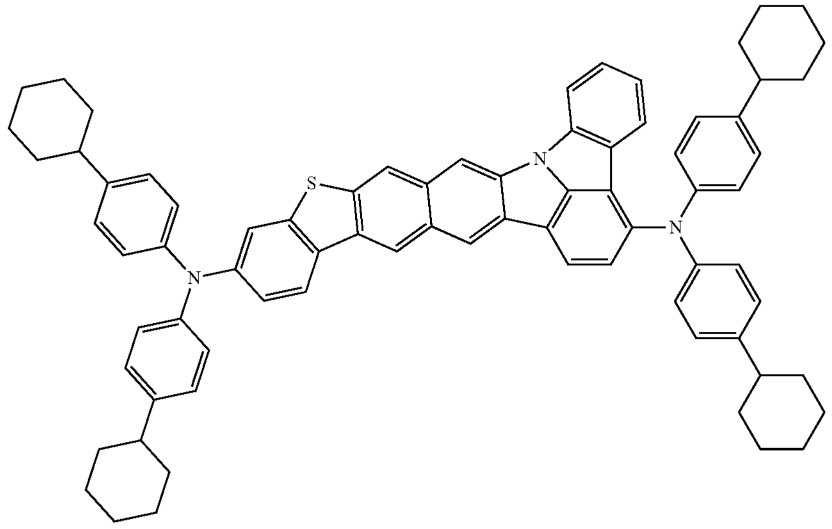

-continued
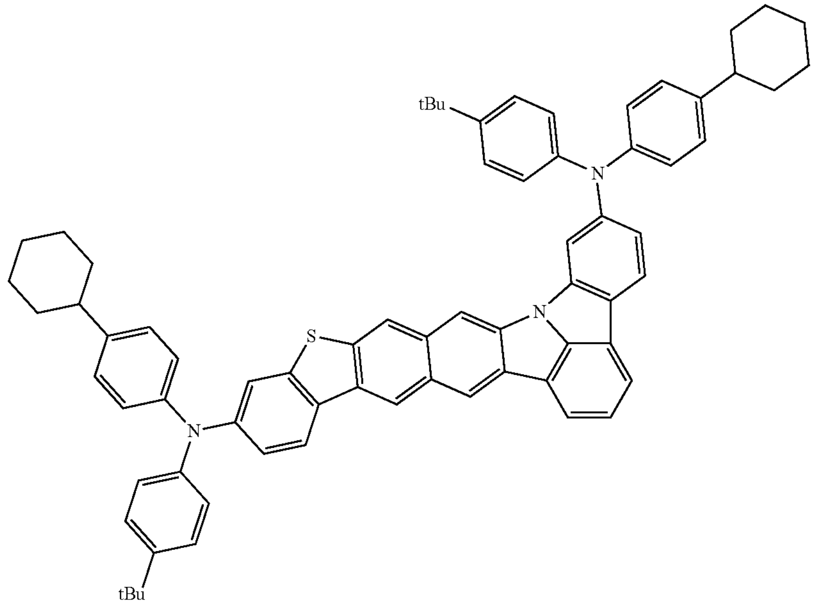
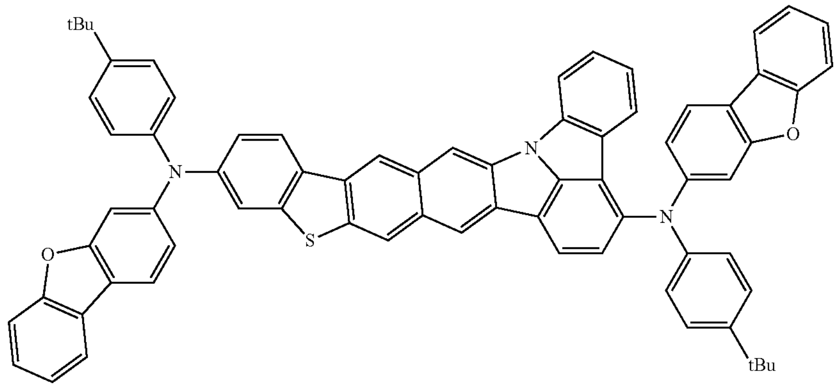
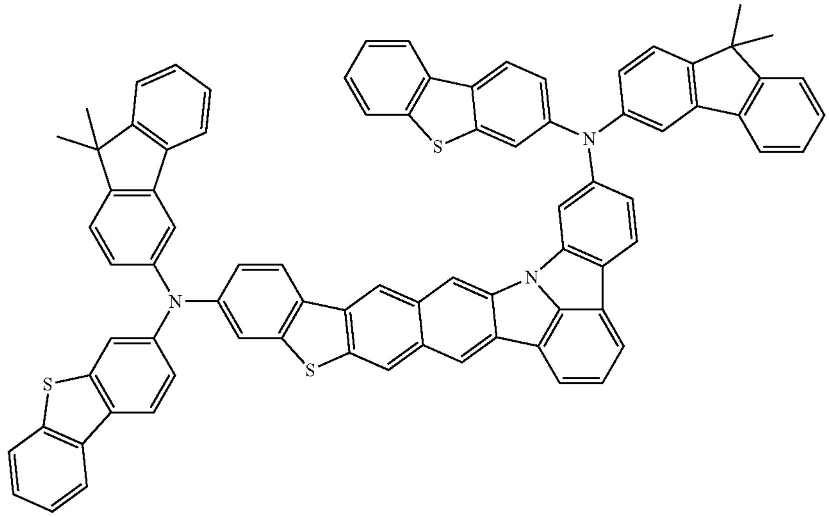

-continued
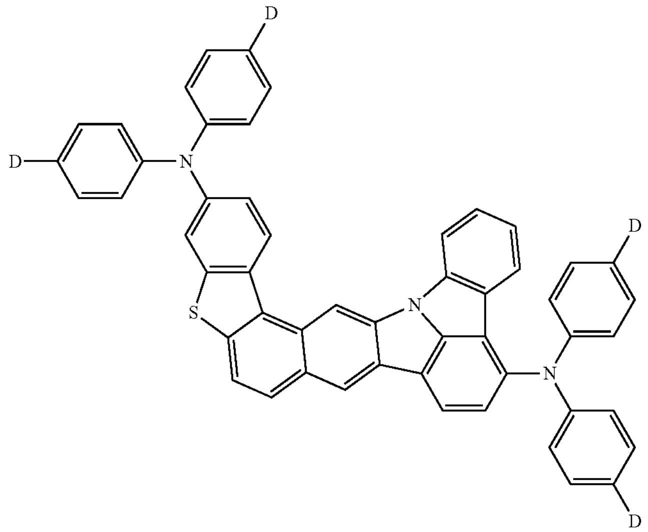
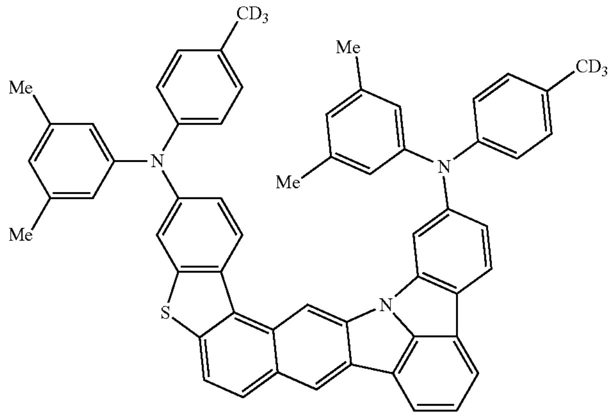
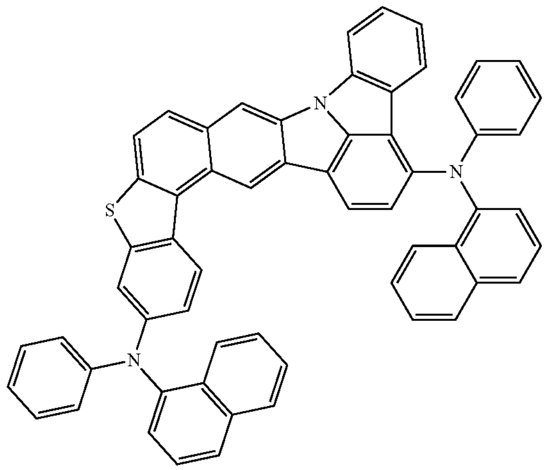
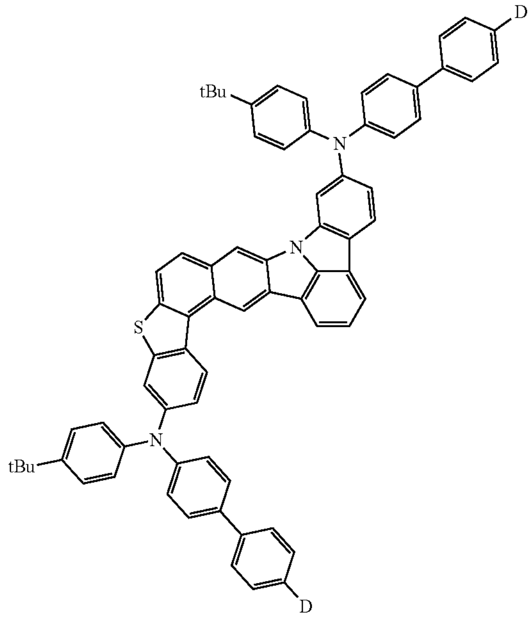

-continued
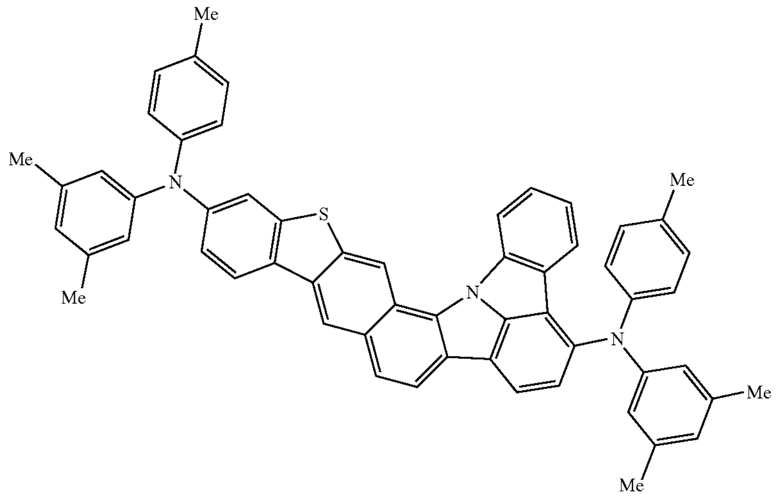
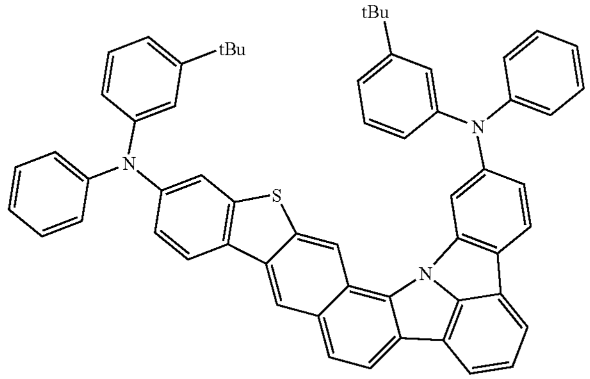
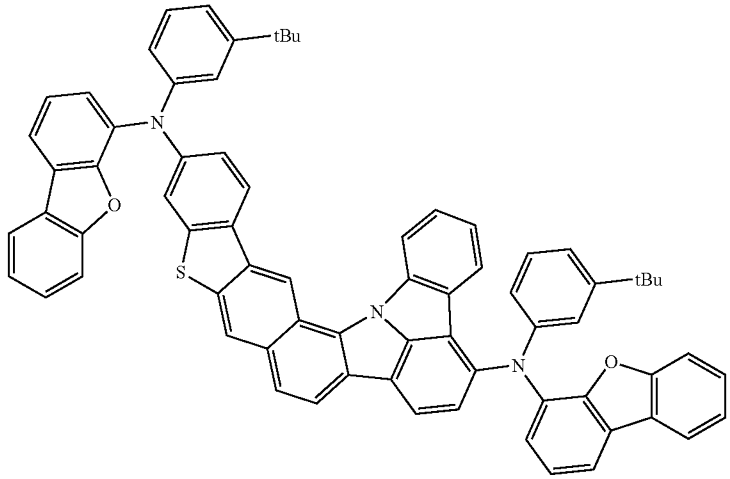

-continued
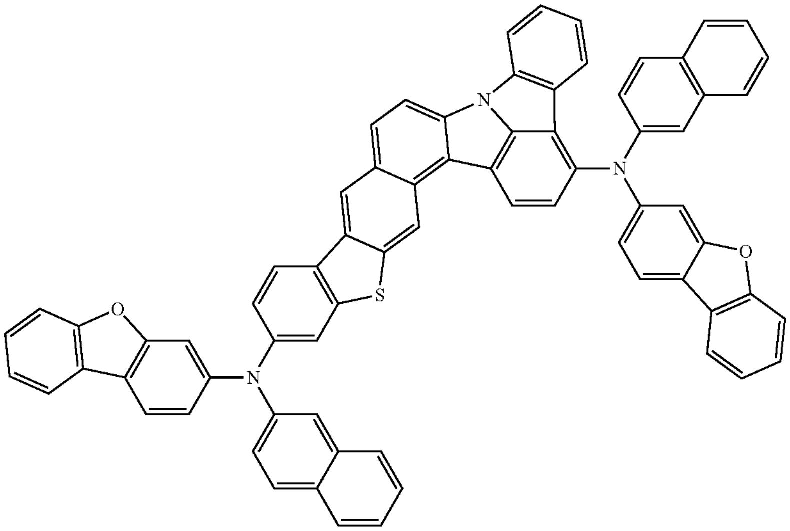
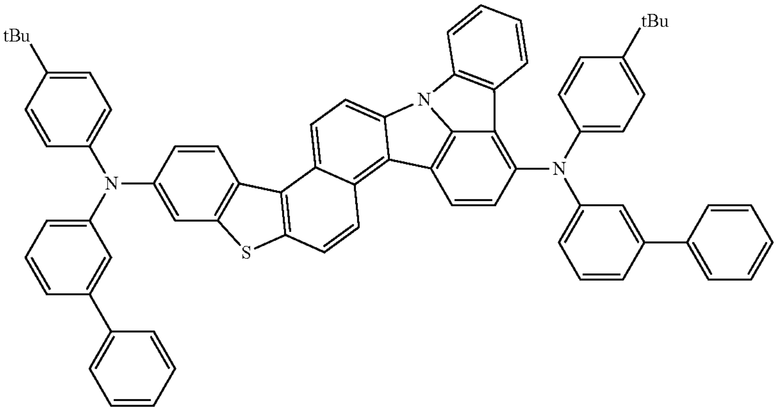
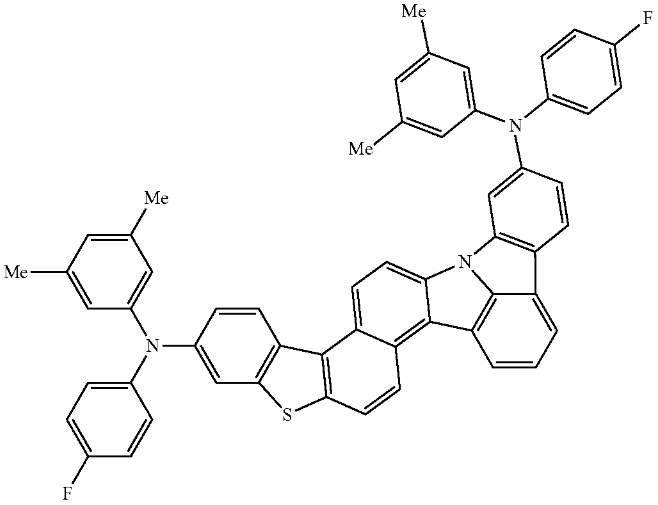

-continued
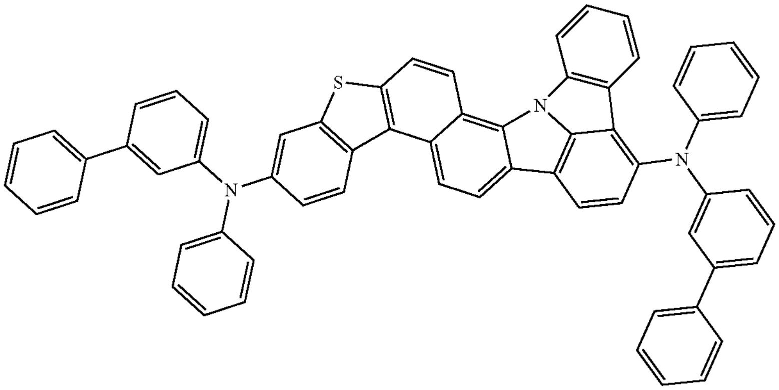
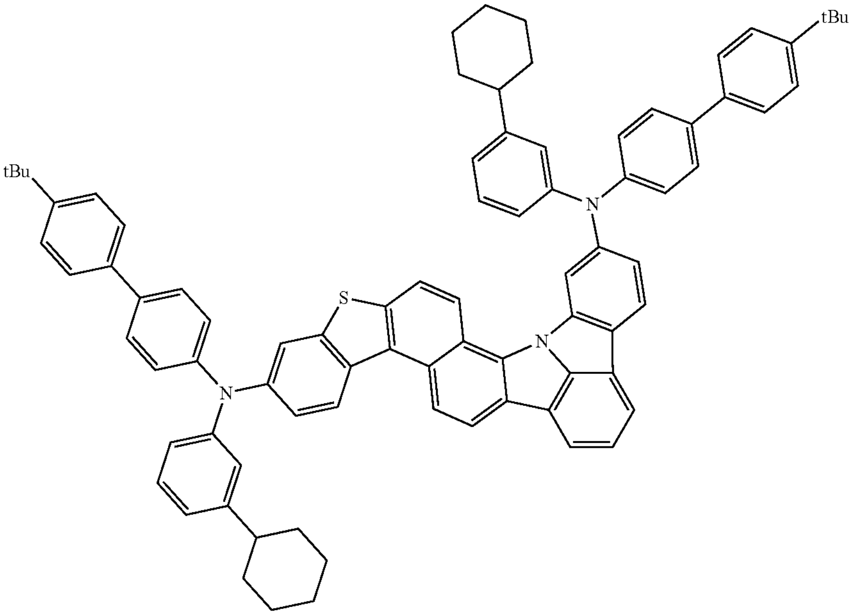
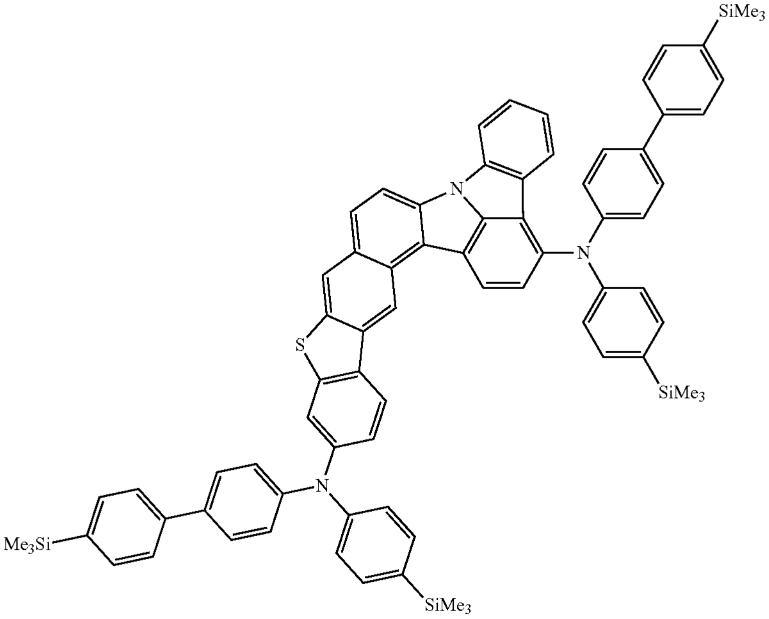

-continued
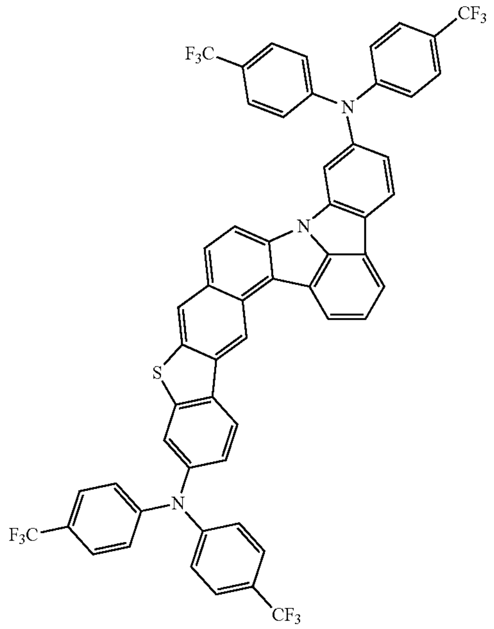
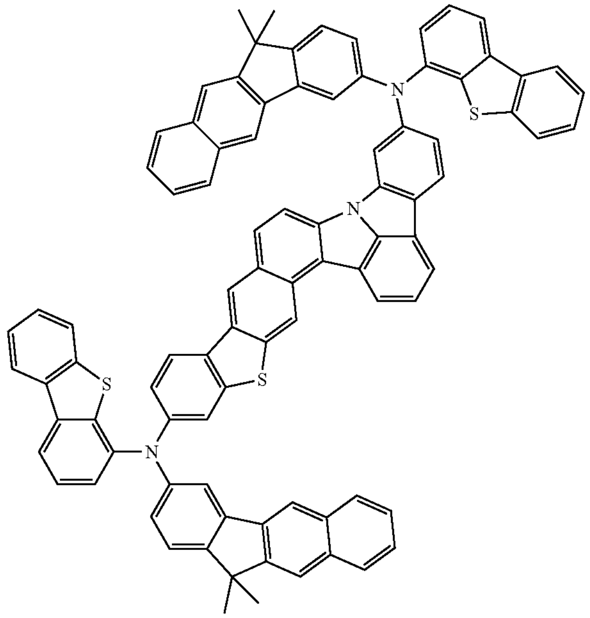
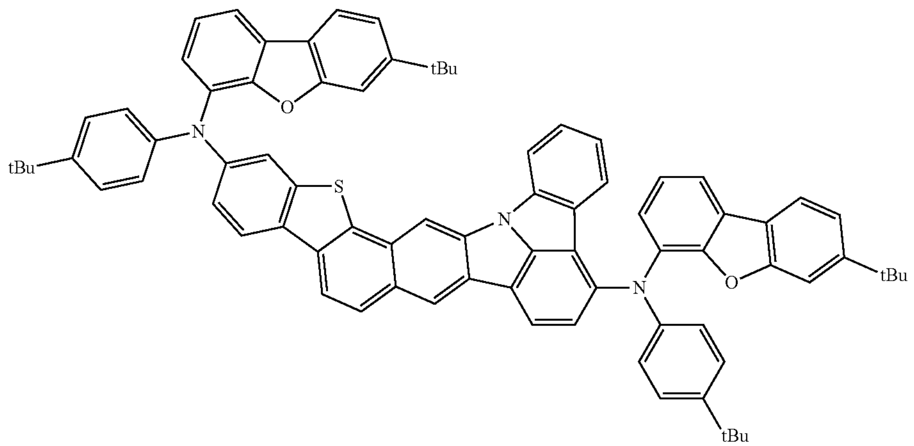
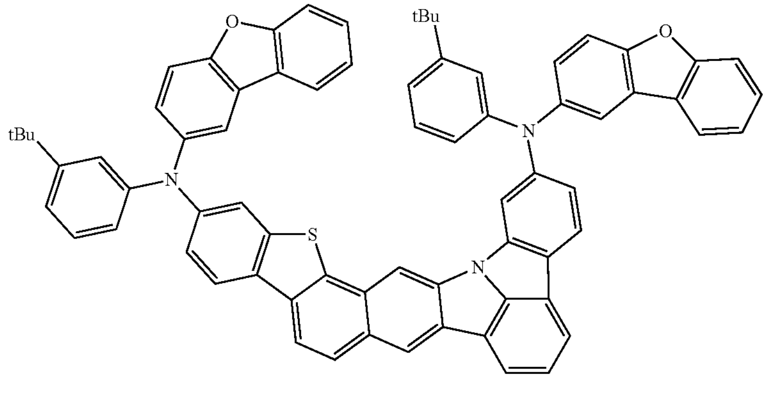

-continued
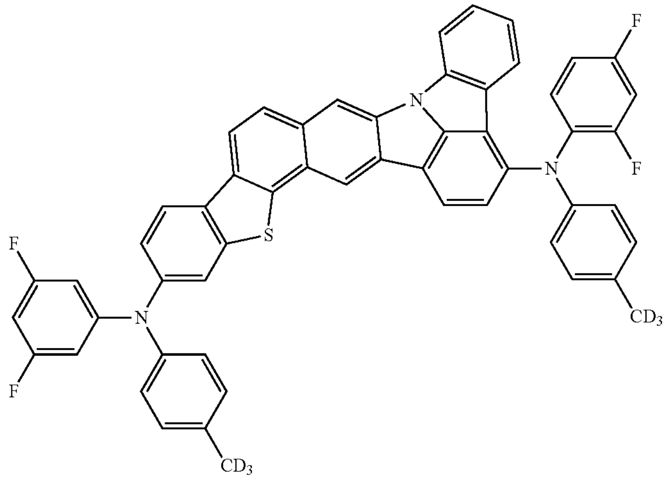
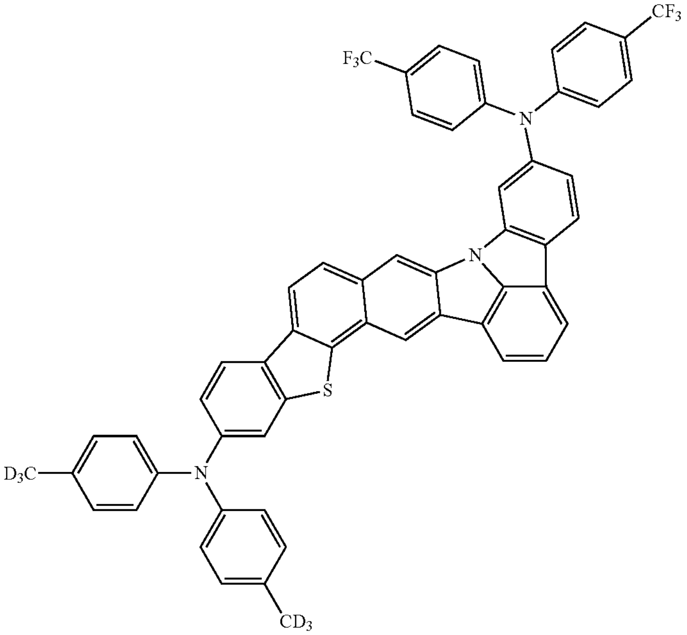
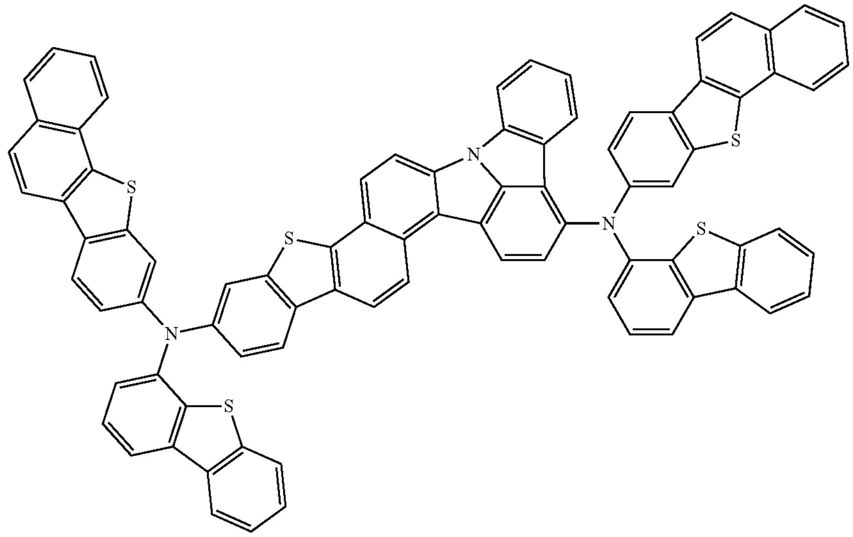

-continued
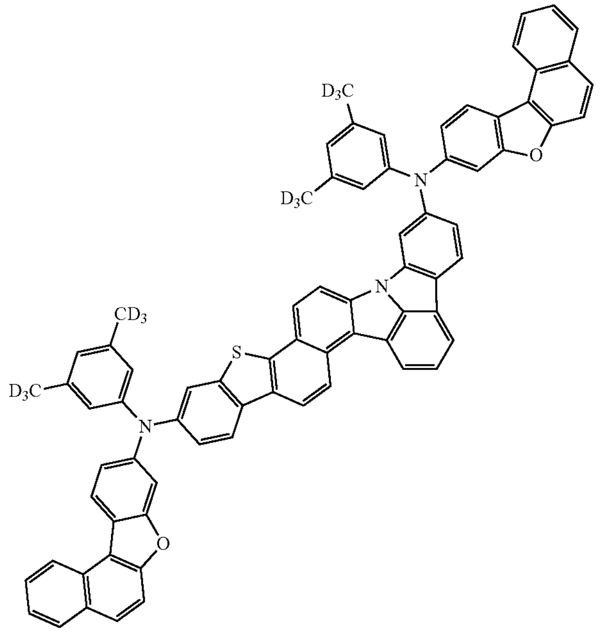
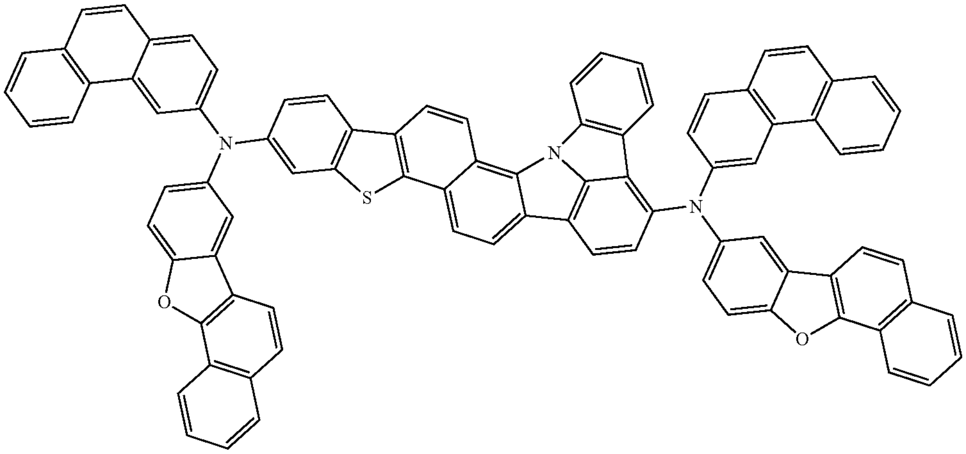
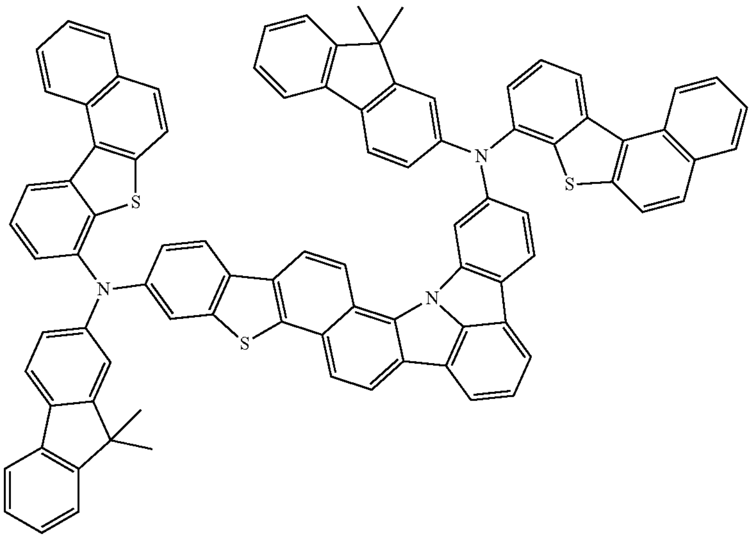

-continued
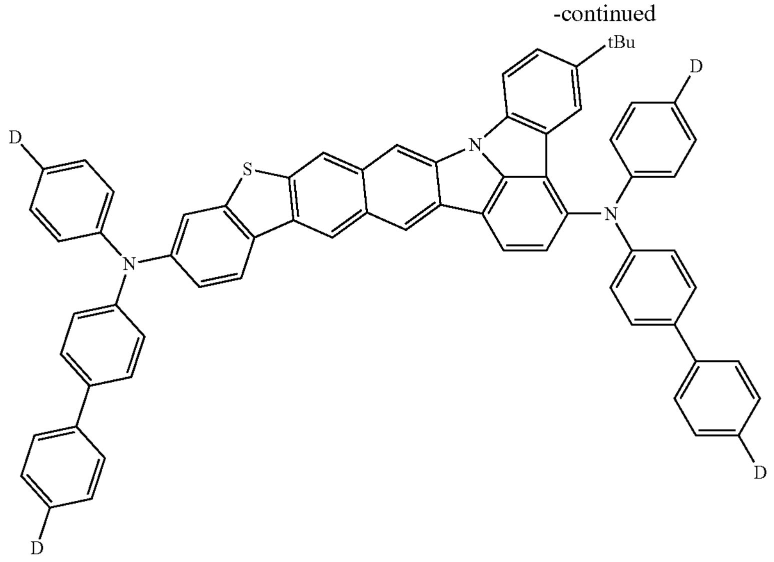
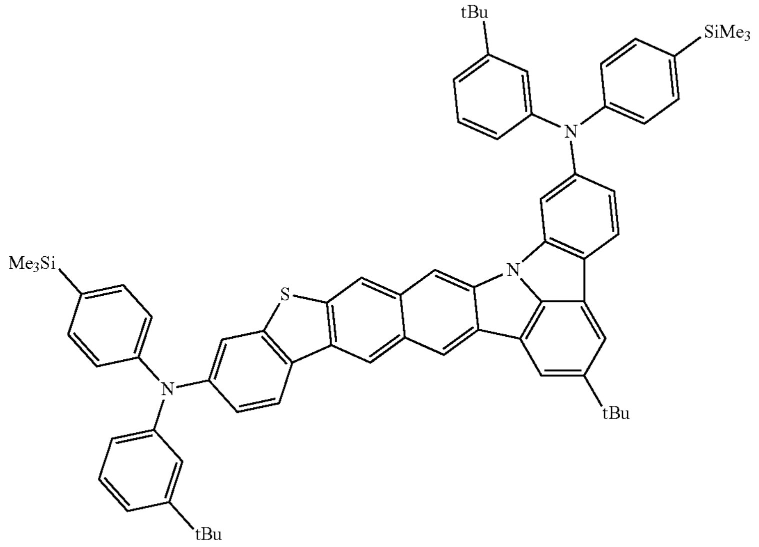
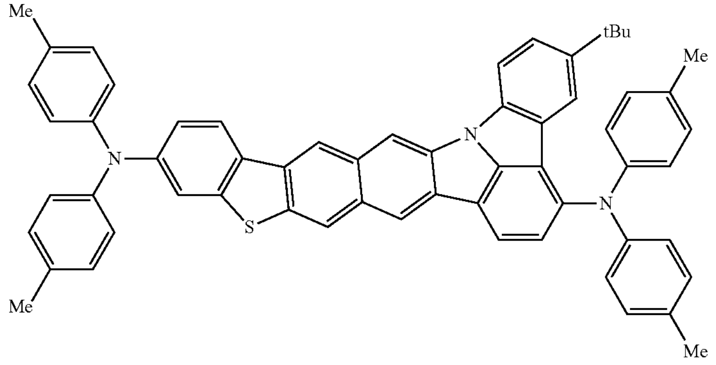

-continued
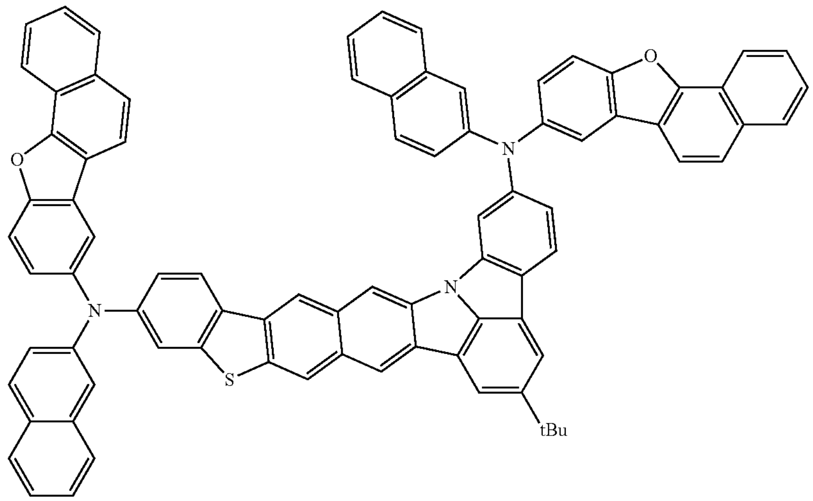
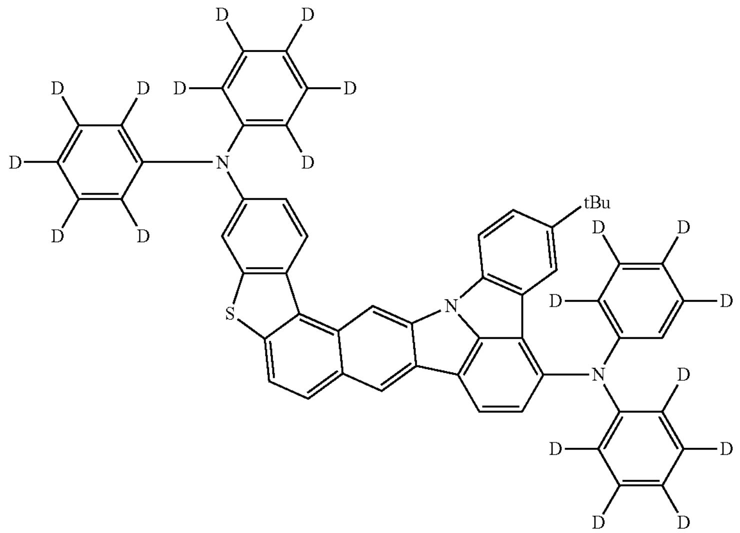
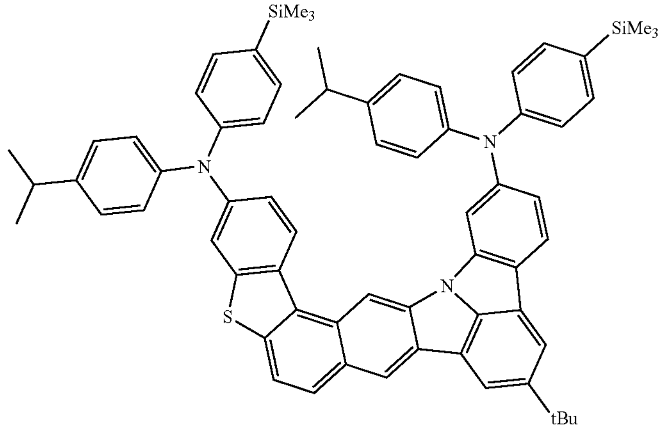

-continued
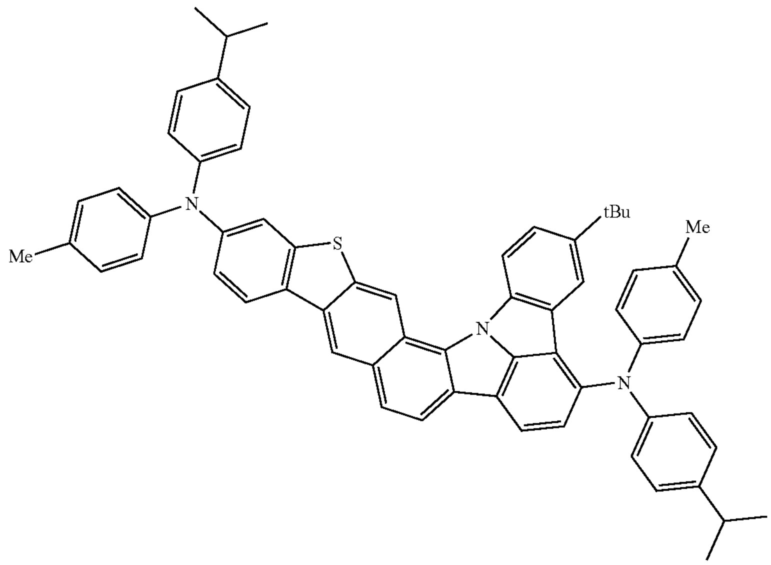
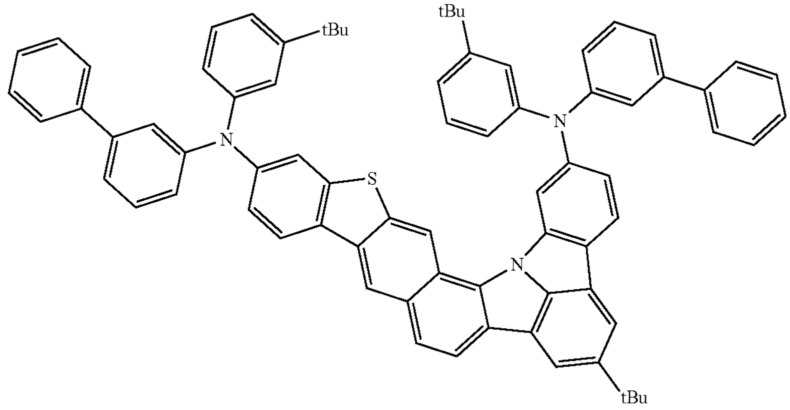
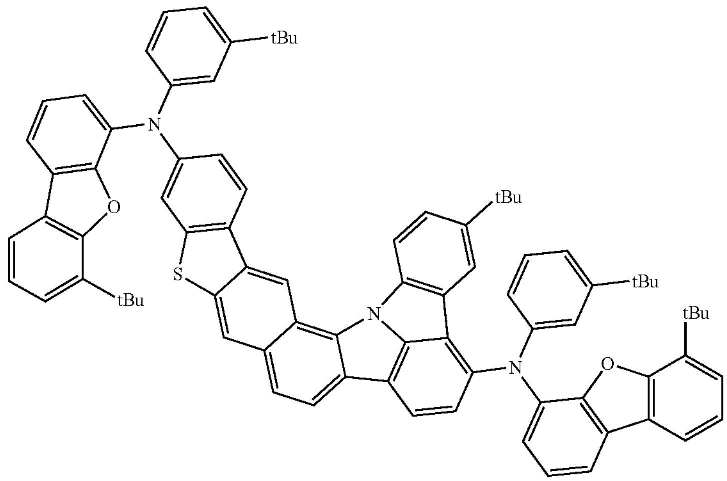

-continued
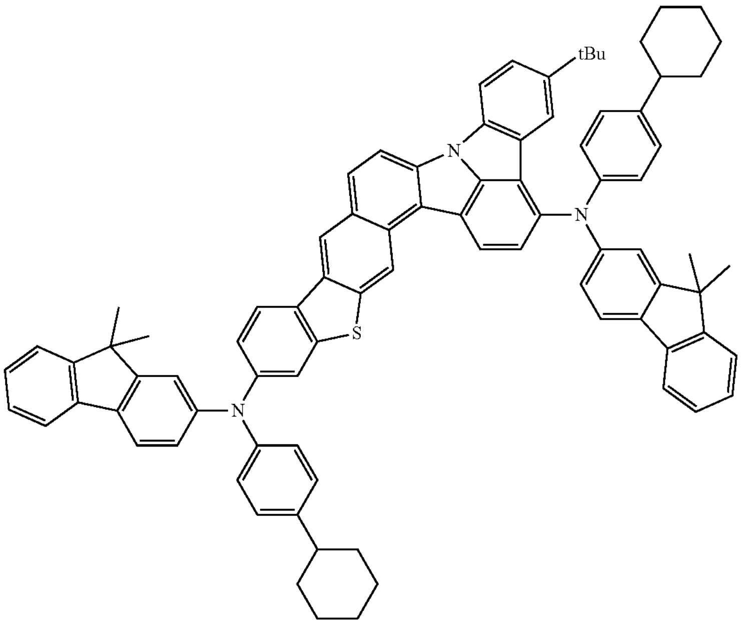
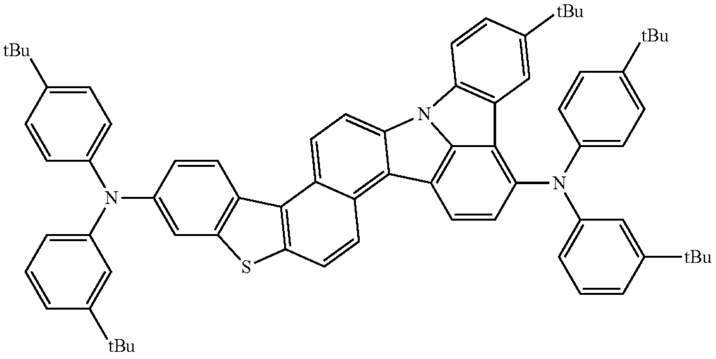
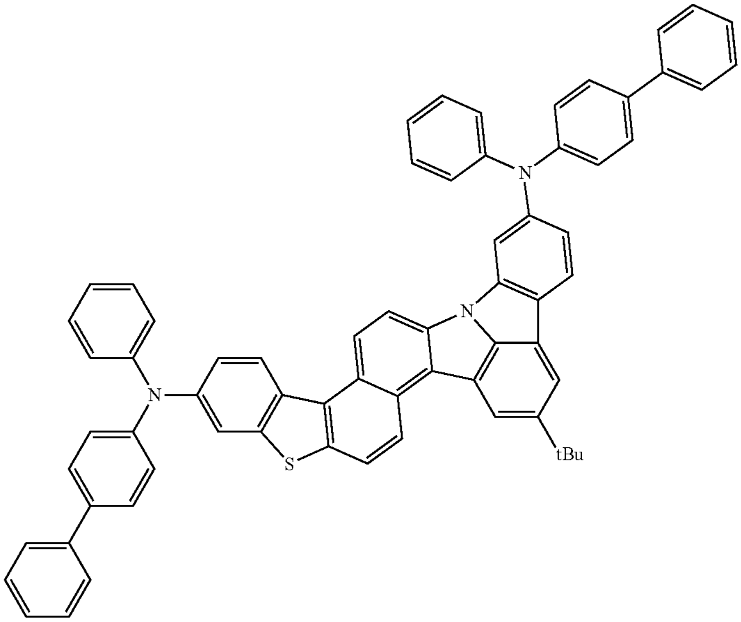

-continued
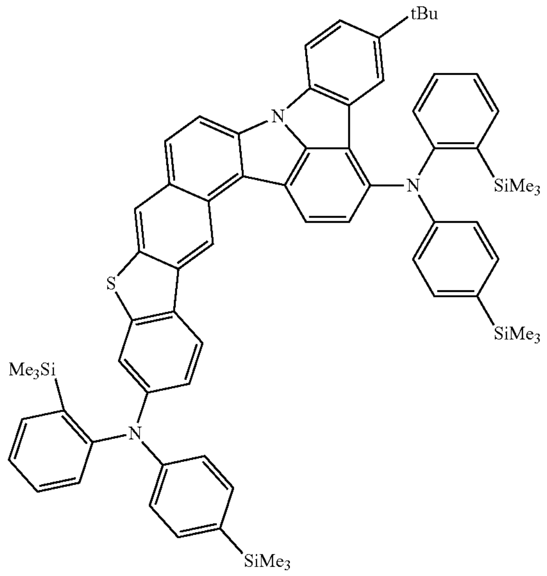
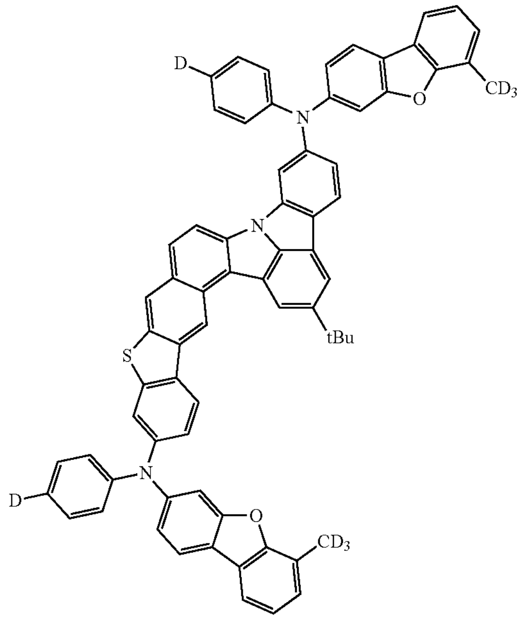

-continued
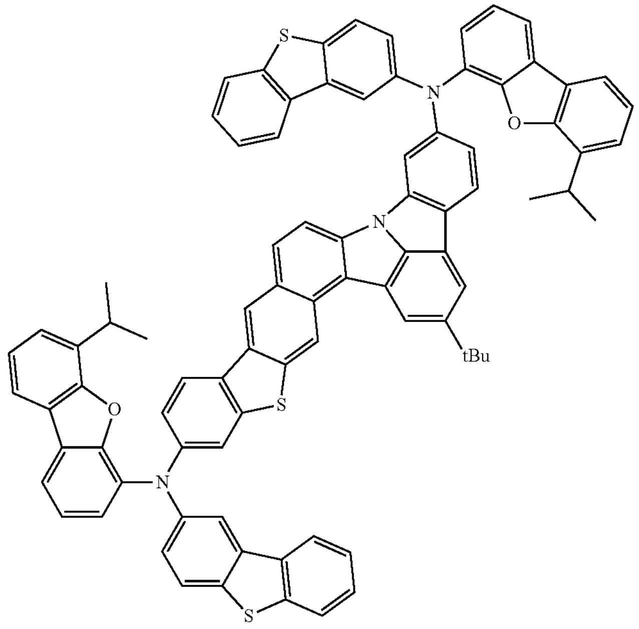
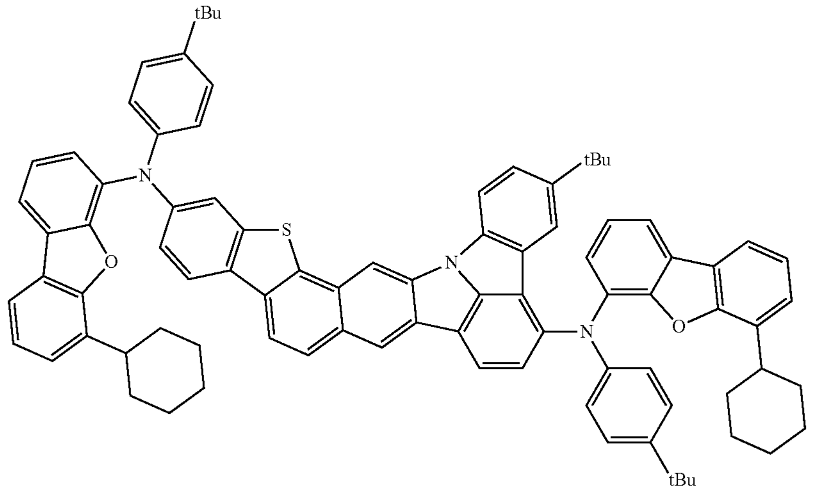
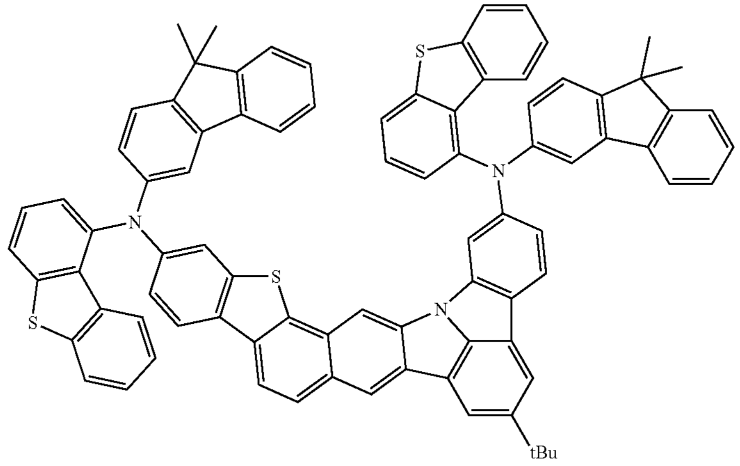

-continued
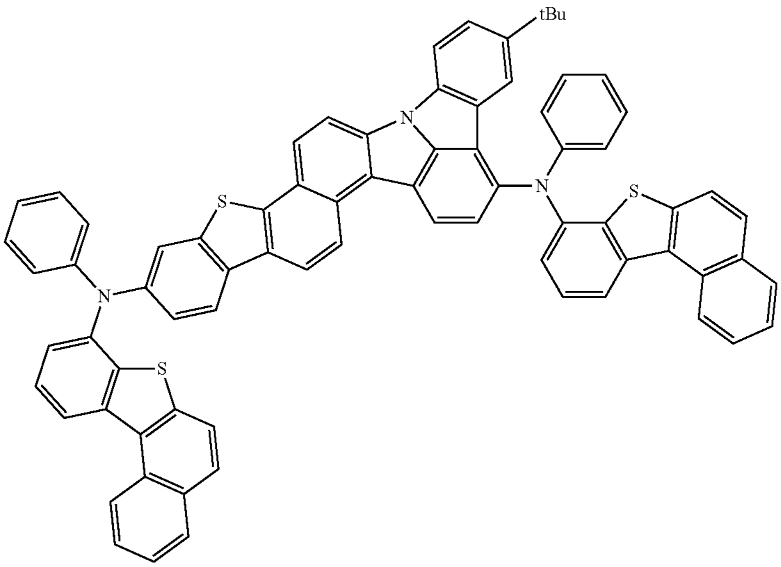
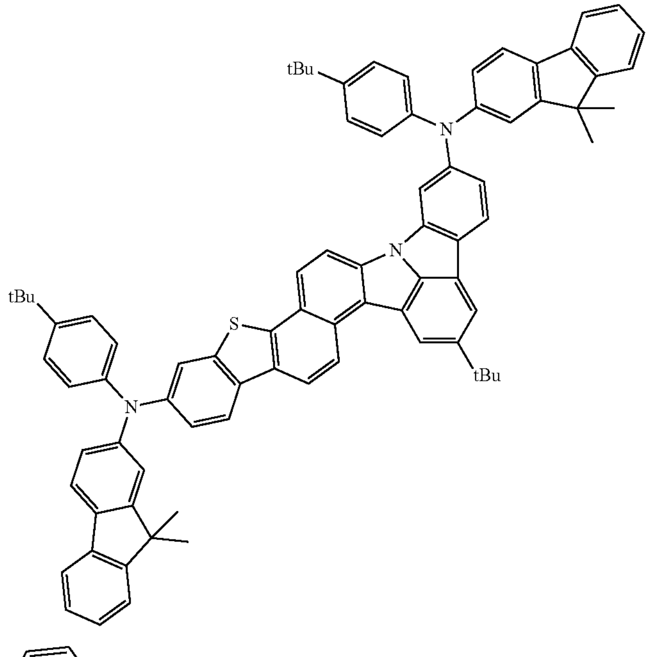
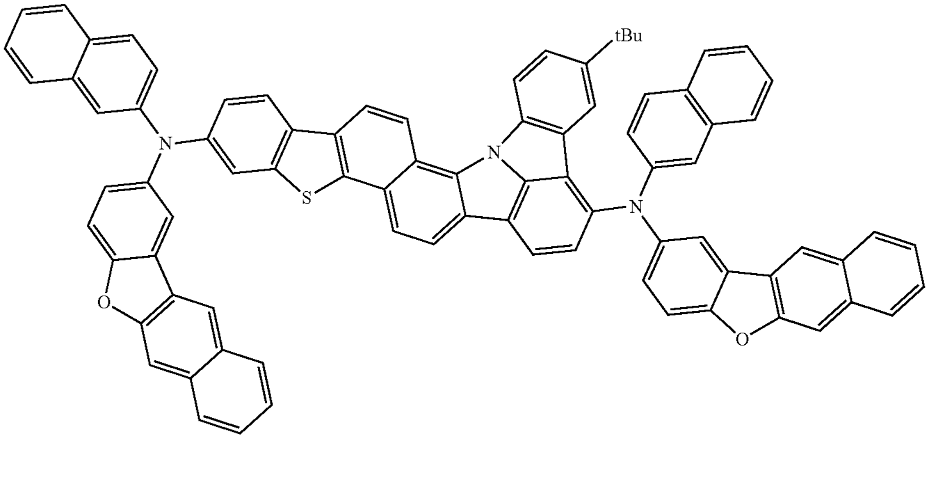

-continued
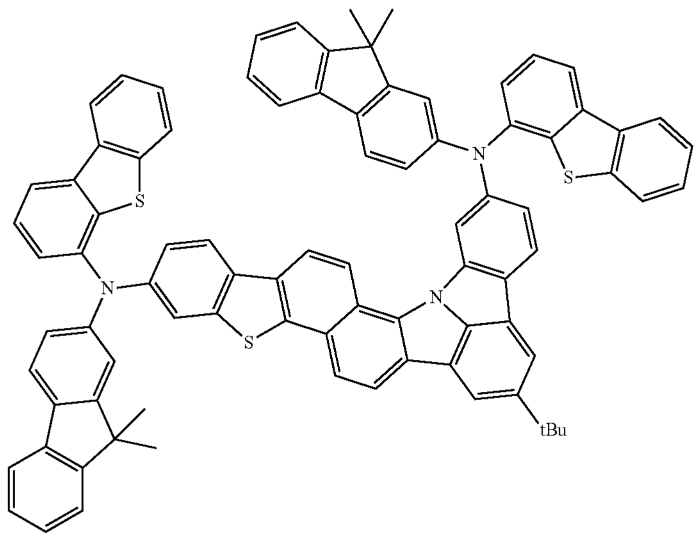
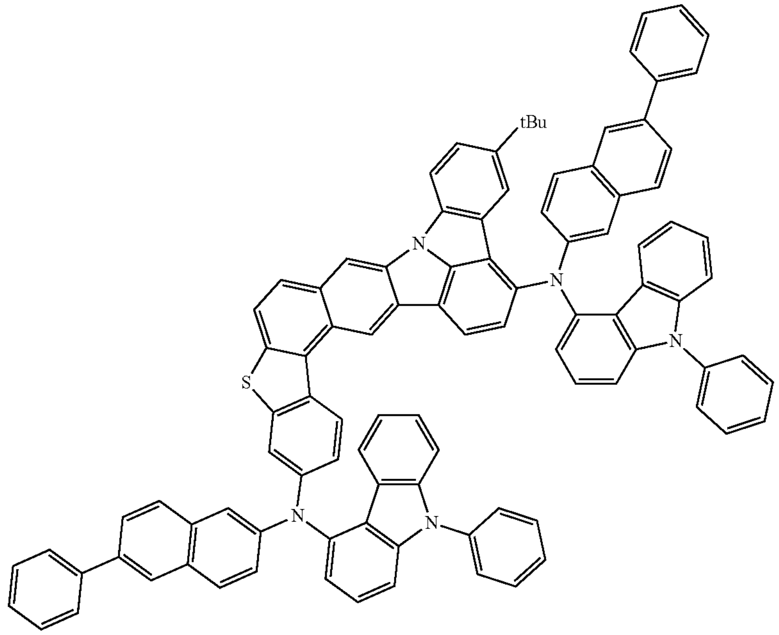

-continued
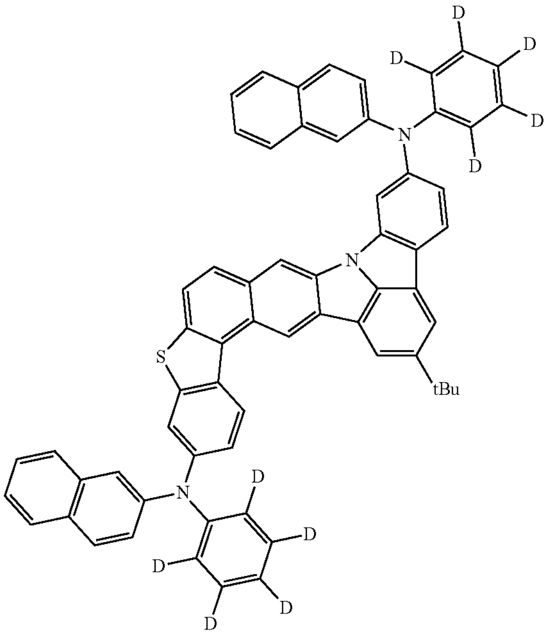
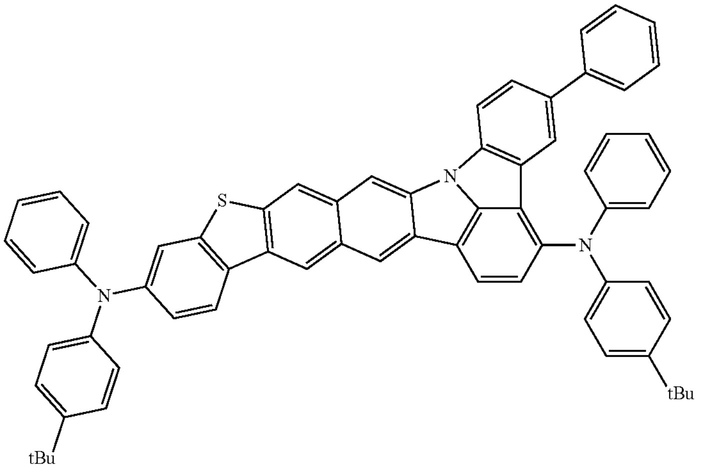
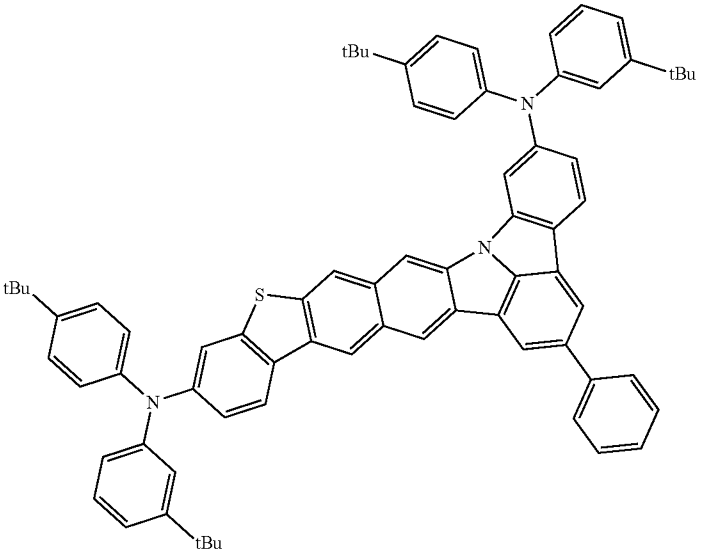

-continued
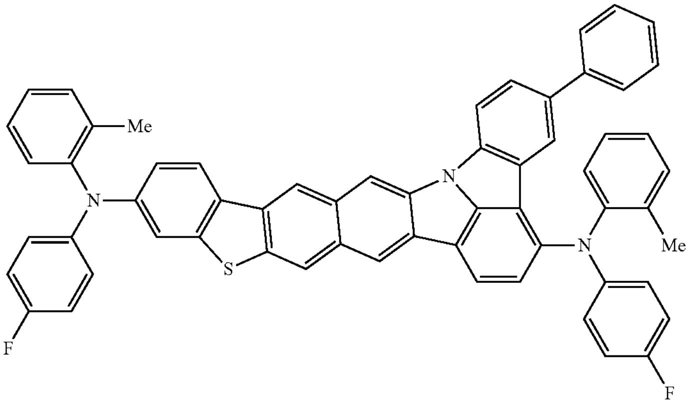
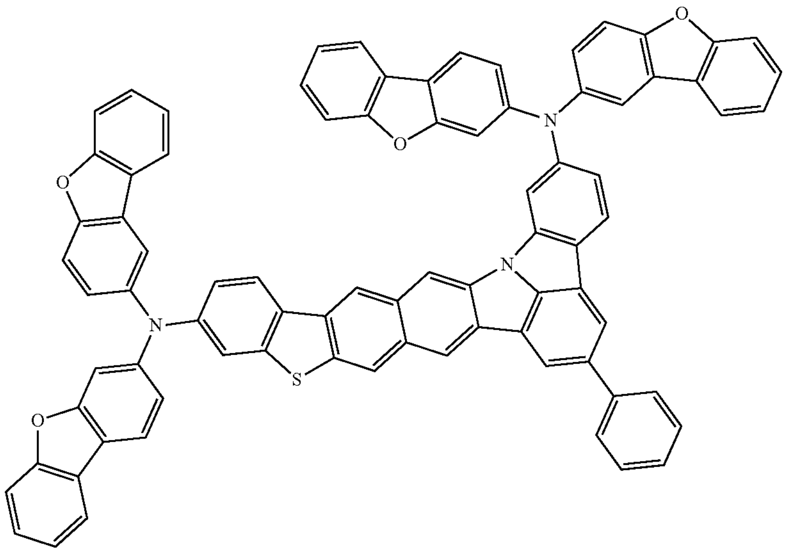
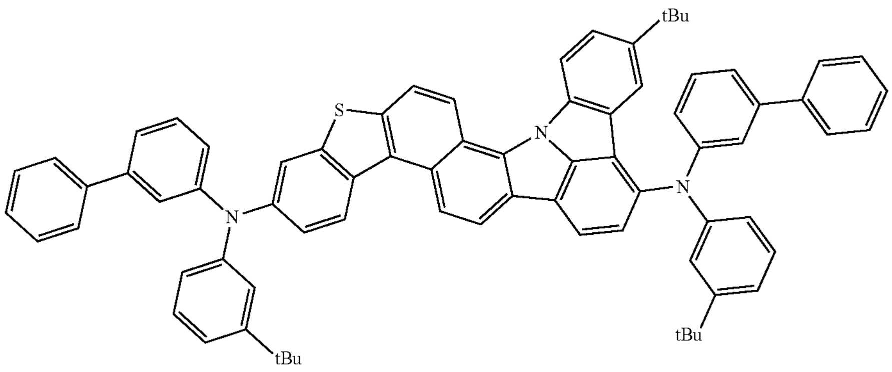

-continued
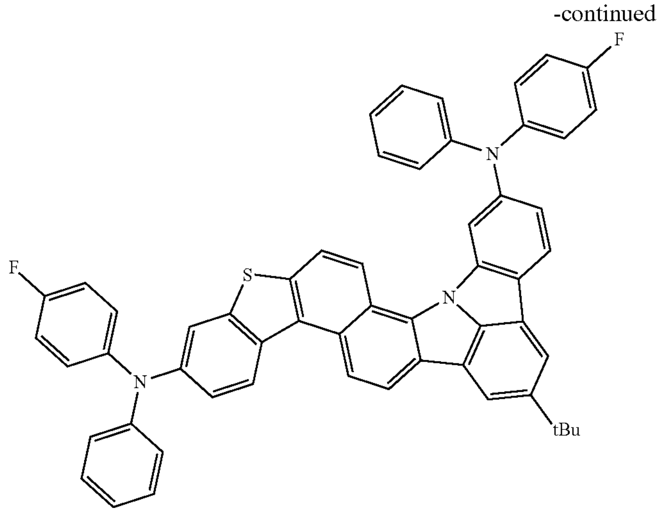
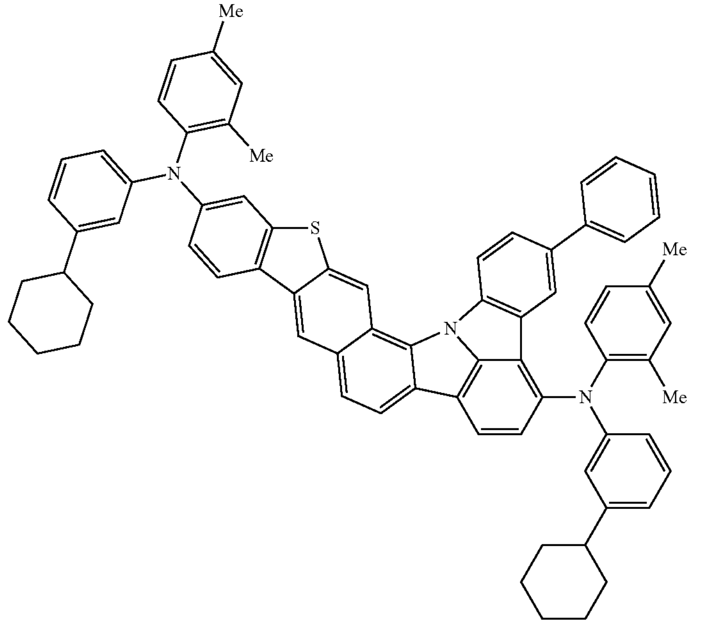
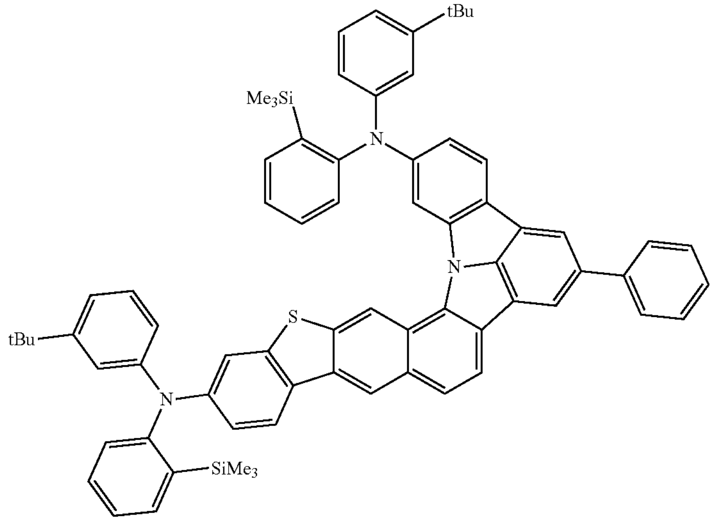

-continued
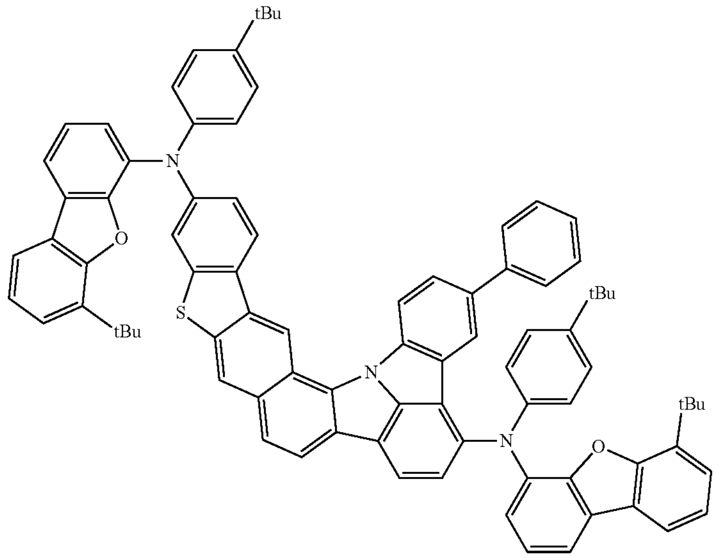
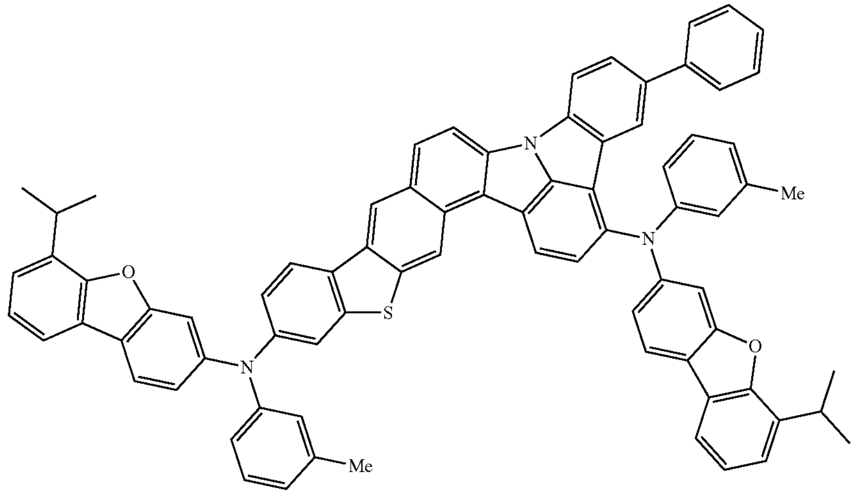
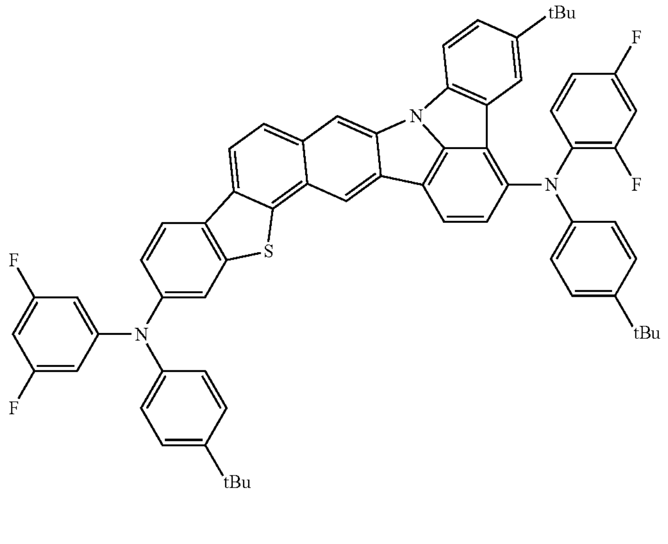

-continued
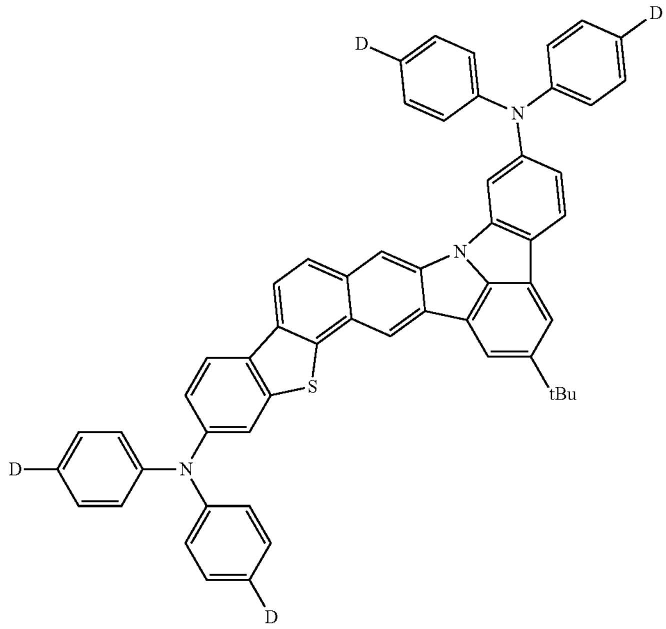
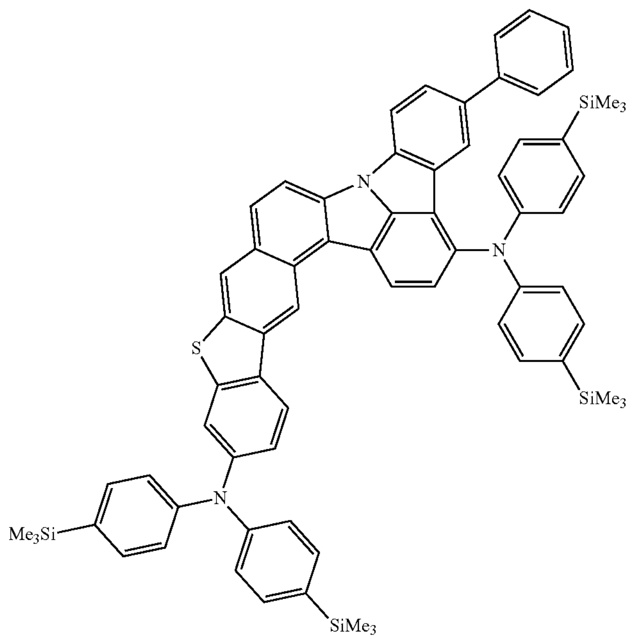

-continued
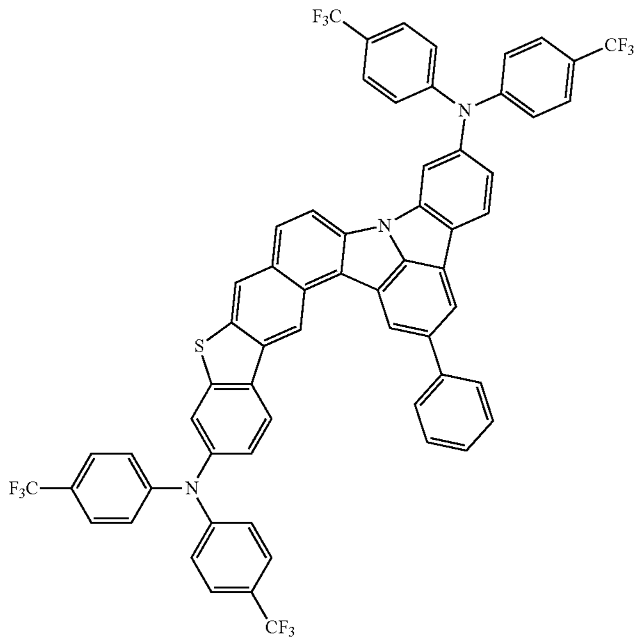
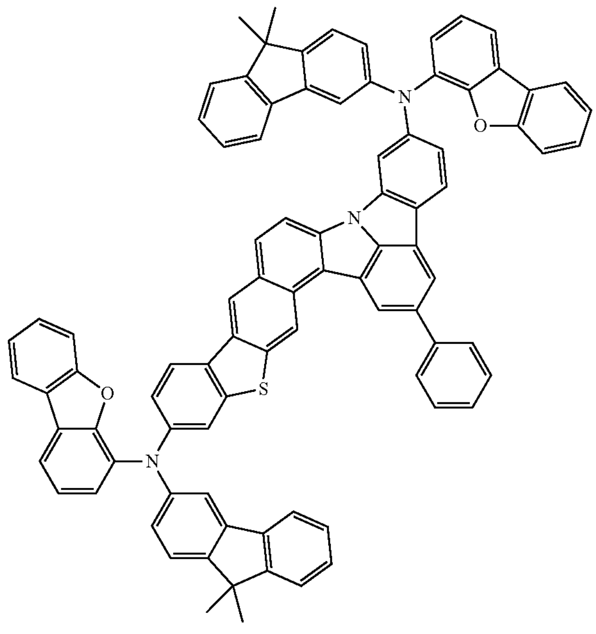

-continued
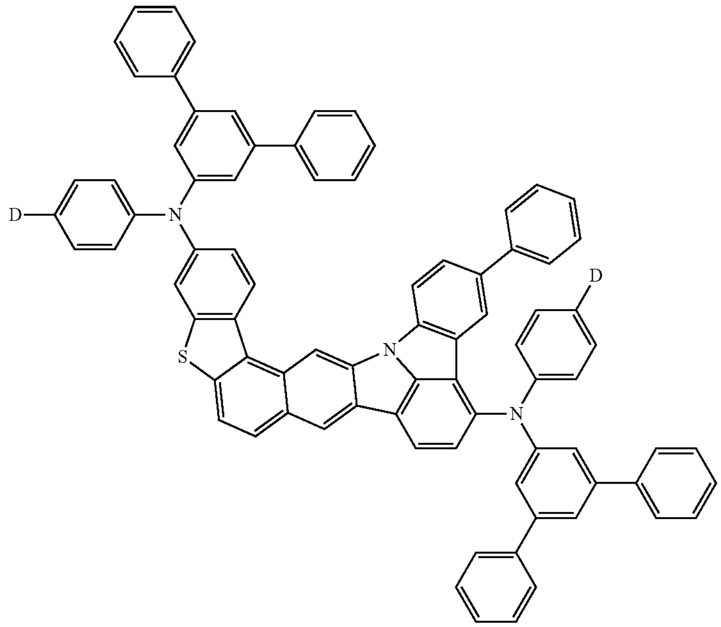
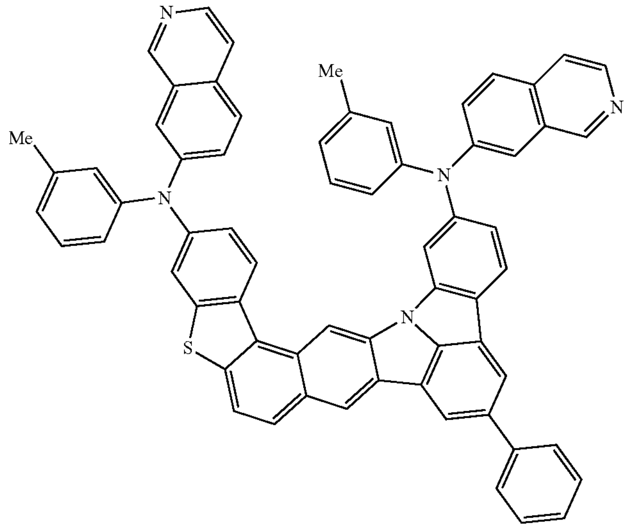
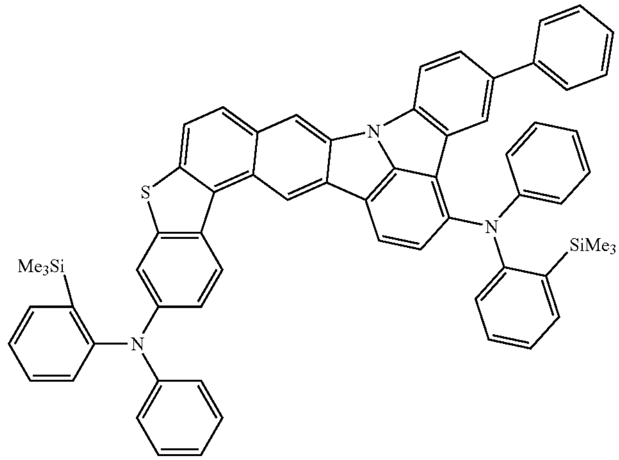

-continued
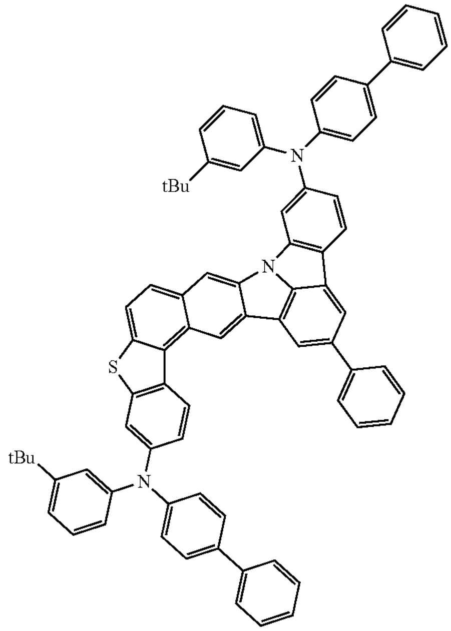
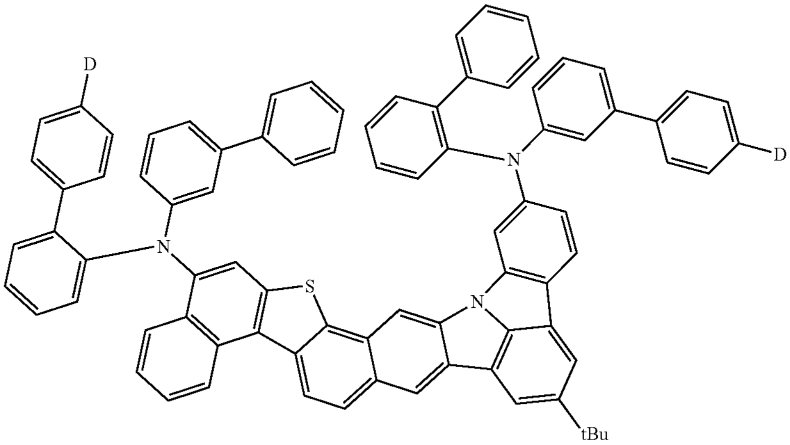
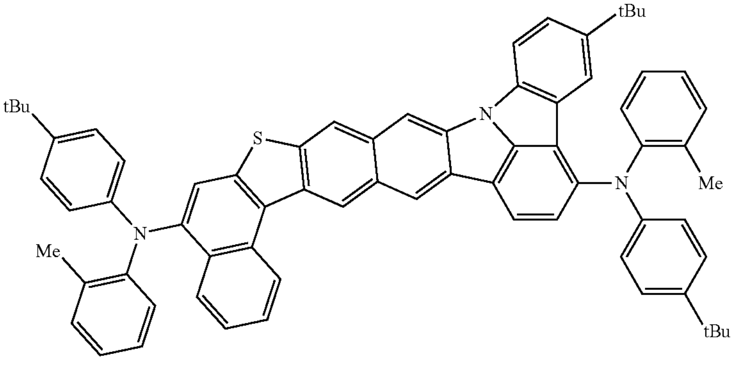

-continued
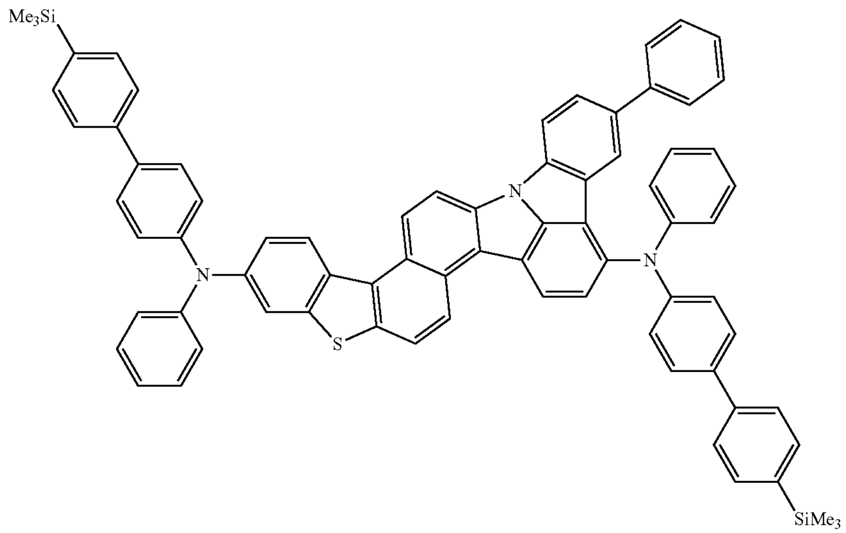
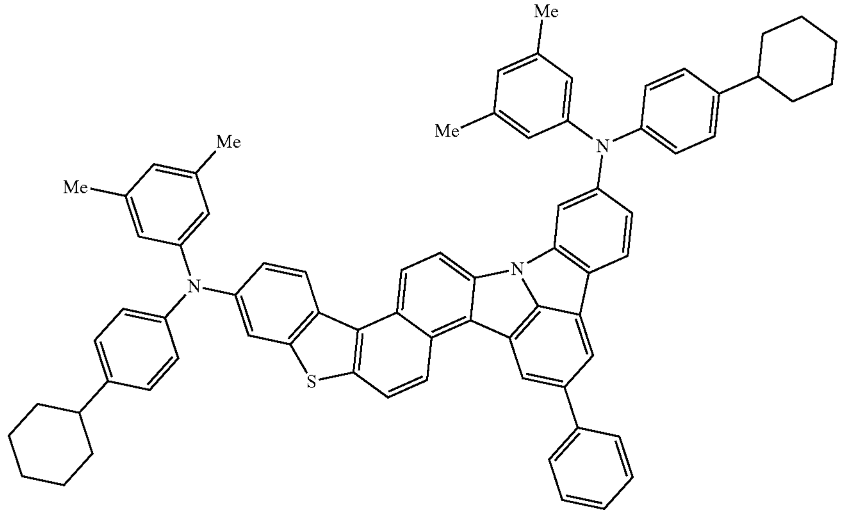
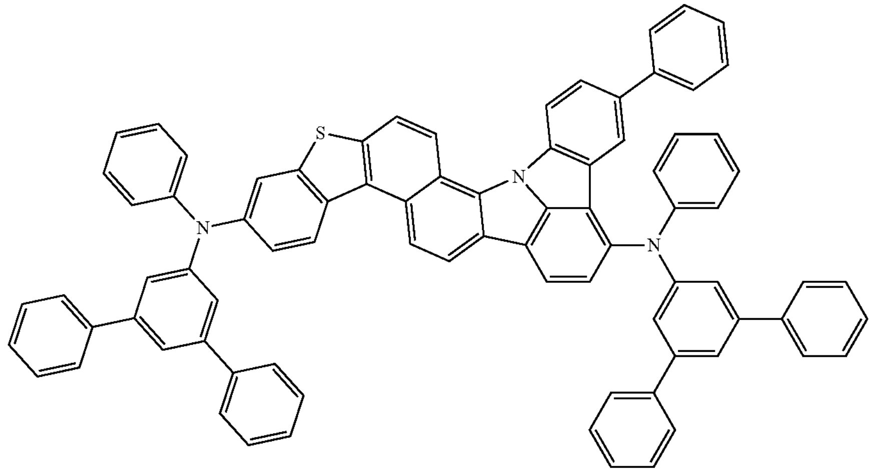

-continued
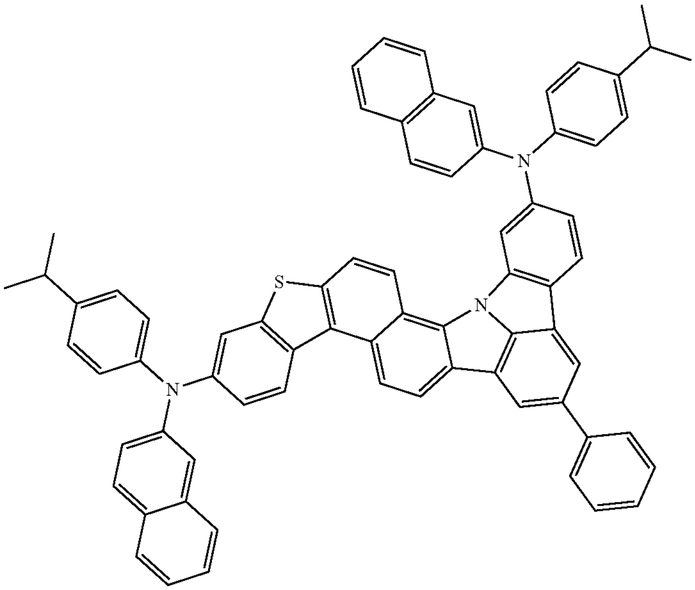
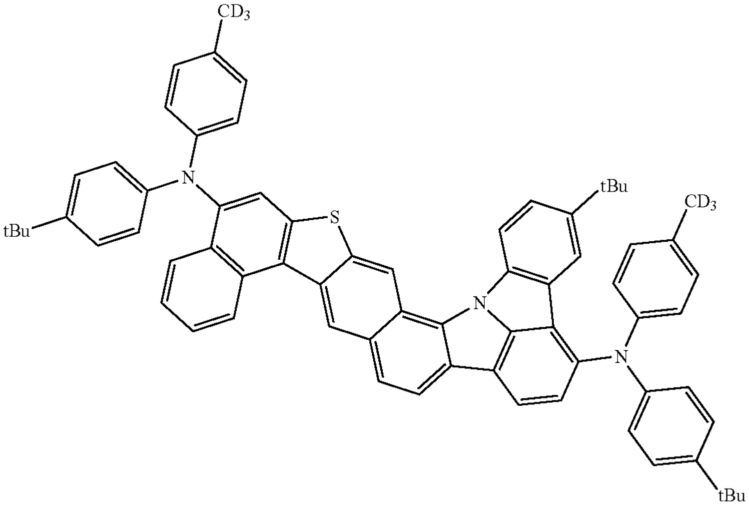
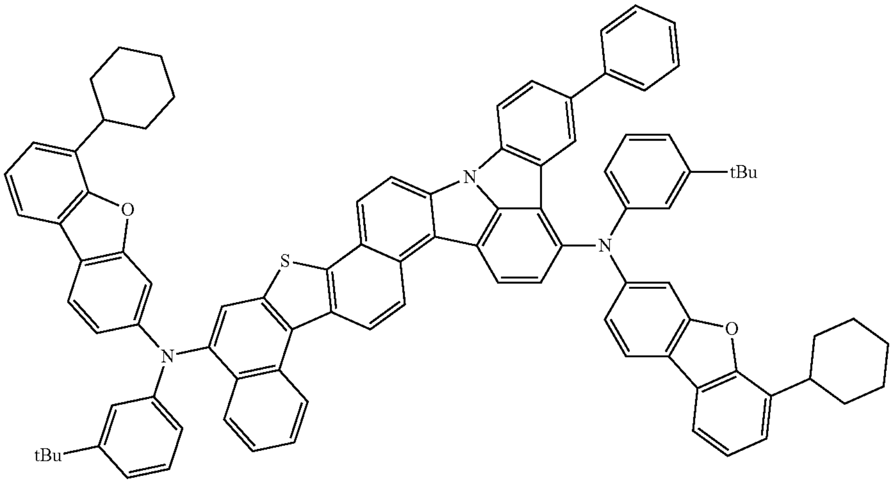

-continued
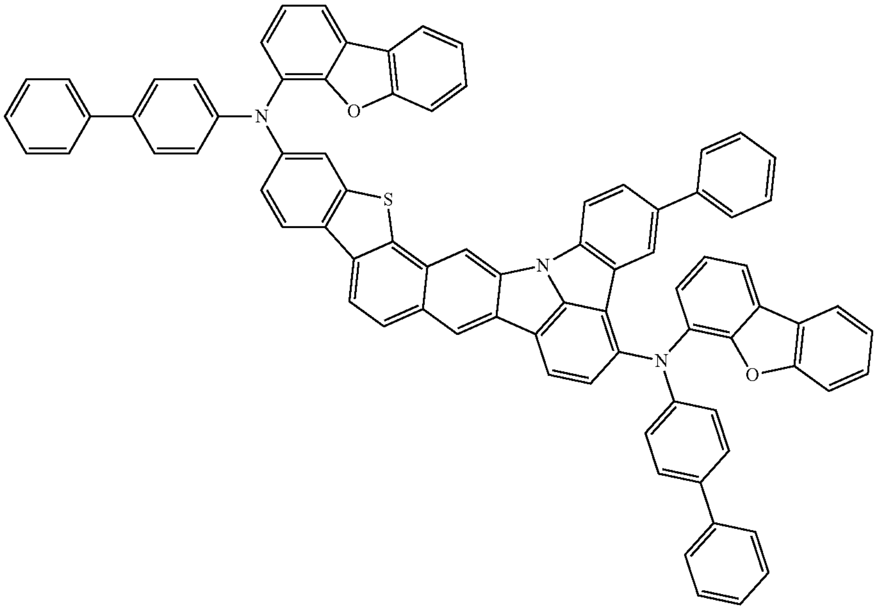
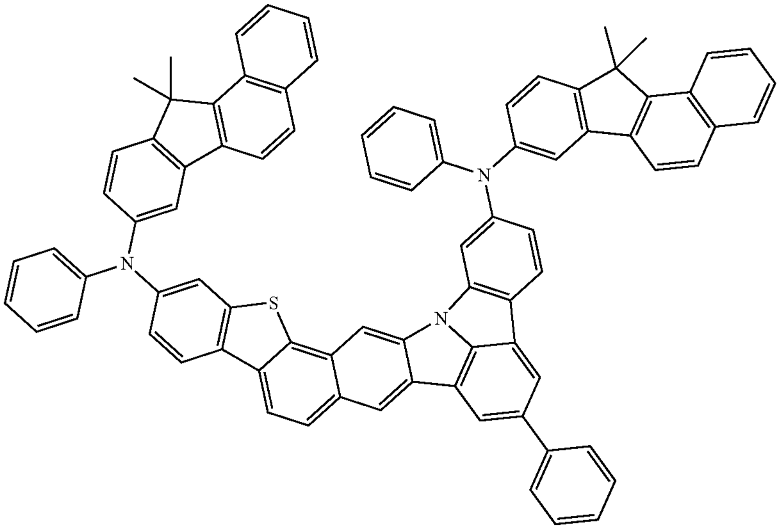
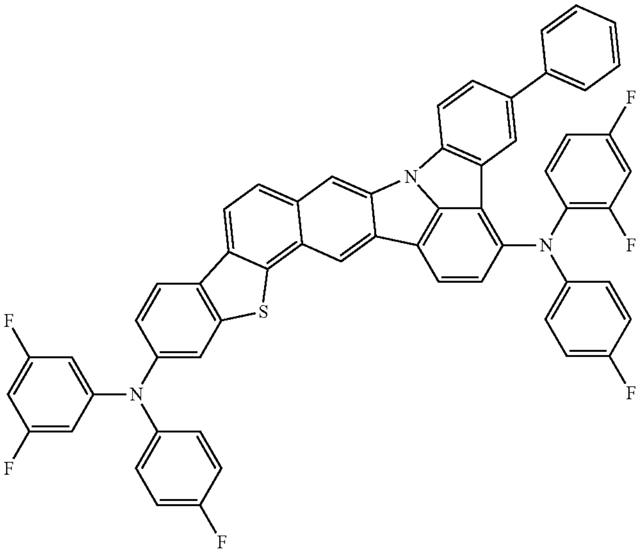

-continued
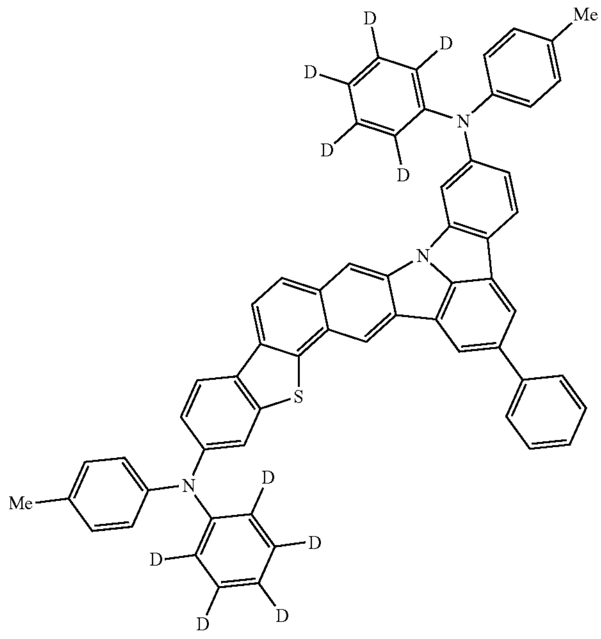
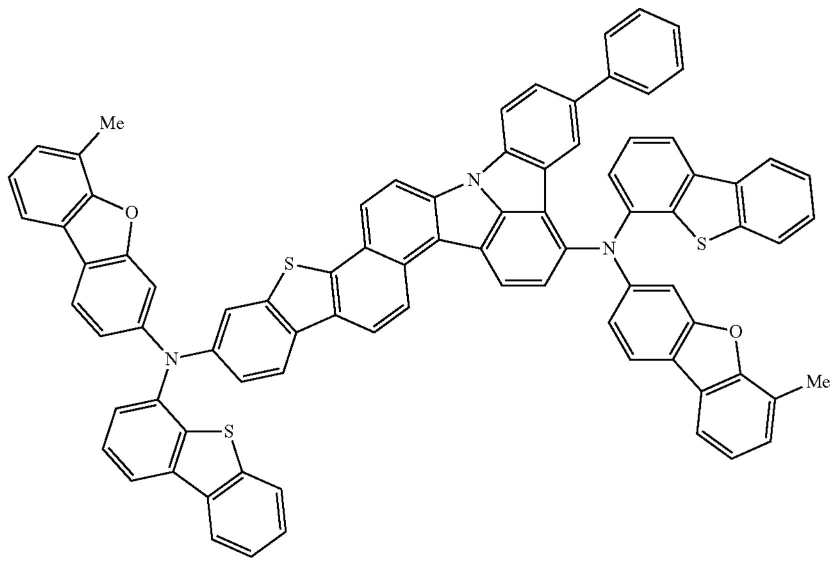

-continued
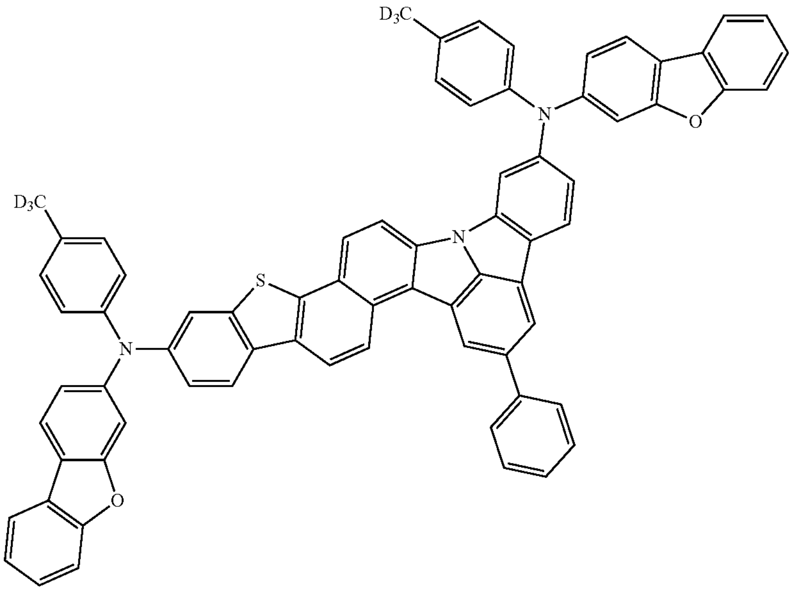
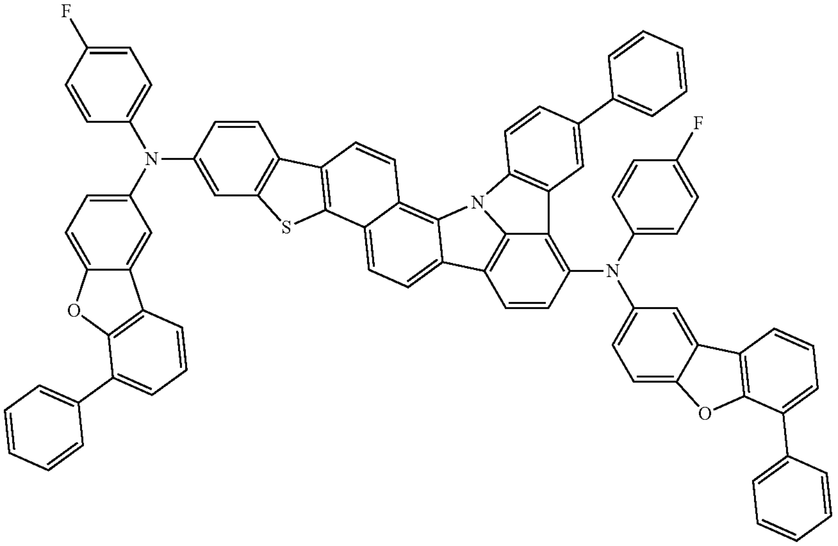
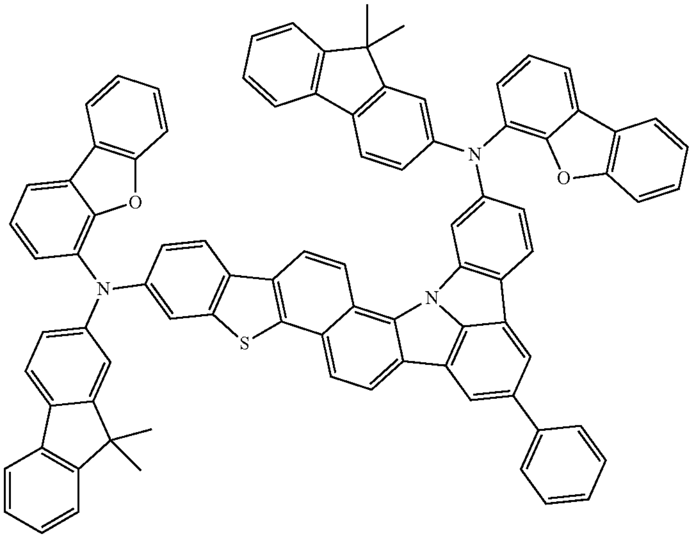
.

In the compounds, tBu means a tert-butyl group, Me means a methyl group, and Ph means a phenyl group.

One embodiment of the present specification provides an organic light emitting device including the compound described above.

In the present specification, a description of a certain member being placed "on" another member includes not only a case of the one member being in contact with the another member but a case of still another member being present between the two members.

In the present specification, a description of a certain part "including" certain constituents means capable of further including other constituents, and does not exclude other constituents unless particularly stated on the contrary.

In the present specification, the "layer" has a meaning compatible with a 'film' mainly used in the art, and means coating covering a target area. The size of the "layer" is not limited, and each "layer" can have the same or a different size. According to one embodiment, the size of the "layer" can be the same as the whole device, can correspond to the size of a specific functional area, or can be as small as a single sub-pixel.

In the present specification, a meaning of a specific A material being included in a B layer includes both i) one or more types of A materials being included in one B layer, and ii) a B layer being formed in one or more layers, and an A material being included in one or more of the B layers that is a multilayer.

In the present specification, a meaning of a specific A material being included in a C layer or a D layer includes both i) being included in one or more layers of one or more C layers, ii) being included in one or more layers of one or more D layers, or iii) being included in each of one or more C layers and one or more D layers.

One embodiment of the present specification provides an organic light emitting device including a first electrode; a second electrode provided opposite to the first electrode; and one or more organic material layers provided between the first electrode and the second electrode, wherein one or more layers of the organic material layers include the heterocyclic compound of Chemical Formula 1.

According to one embodiment of the present specification, the organic material layer includes a light emitting layer, and the light emitting layer includes the heterocyclic compound of Chemical Formula 1.

According to one embodiment of the present specification, the organic material layer includes a light emitting layer, the light emitting layer includes a dopant material, and the dopant material includes the heterocyclic compound of Chemical Formula 1.

The organic light emitting device according to the present specification can include an additional organic material layer in addition to the light emitting layer.

The organic material layer of the organic light emitting device of the present specification can be formed in a single layer structure, but can also be formed in a multilayer structure in which two or more organic material layers are laminated. For example, the organic light emitting device of the present specification can have a structure including a hole injection layer, a hole transfer layer, a light emitting layer, an electron transfer layer, an electron injection layer, an electron blocking layer, a hole blocking layer and the like. However, the structure of the organic light emitting device is not limited thereto, and can include a smaller number of organic layers.

The organic light emitting device according to one embodiment of the present specification includes a light emitting layer, and the light emitting layer includes the heterocyclic compound of Chemical Formula 1 and a compound of the following Chemical Formula 2:

<Chemical Formula 2>

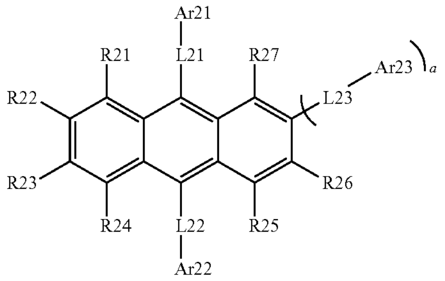

wherein in Chemical Formula 2:

L21 to L23 are the same as or different from each other, and each independently is a direct bond, a substituted or unsubstituted arylene group, or a substituted or unsubstituted heteroarylene group;

R21 to R27 are the same as or different from each other, and each independently is hydrogen, deuterium, a substituted or unsubstituted alkyl group, a substituted or unsubstituted cycloalkyl group, a substituted or unsubstituted silyl group, a substituted or unsubstituted aryl group, or a substituted or unsubstituted heteroaryl group;

Ar21 to Ar23 are the same as or different from each other, and each independently is a substituted or unsubstituted aryl group or a substituted or unsubstituted heteroaryl group; and a is 0 or 1.

According to one embodiment of the present specification, when a is 0, the position of -L23-Ar23 is hydrogen or deuterium.

According to one embodiment of the present specification, L21 to L23 are the same as or different from each other, and each independently is a direct bond, a substituted or unsubstituted monocyclic or polycyclic arylene group having 6 to 30 carbon atoms, or a substituted or unsubstituted monocyclic or polycyclic heteroarylene group having 2 to 30 carbon atoms.

According to one embodiment of the present specification, L21 to L23 are the same as or different from each other, and each independently is a direct bond, a substituted or unsubstituted monocyclic or polycyclic arylene group having 6 to 20 carbon atoms, or a substituted or unsubstituted monocyclic or polycyclic heteroarylene group having 2 to 20 carbon atoms.

According to one embodiment of the present specification, L21 to L23 are the same as or different from each other, and each independently is a direct bond, a monocyclic or polycyclic arylene group having 6 to 20 carbon atoms unsubstituted or substituted with deuterium, or a monocyclic or polycyclic heteroarylene group having 2 to 20 carbon atoms.

According to one embodiment of the present specification, L21 to L23 are the same as or different from each other, and each independently is a direct bond, a phenylene group unsubstituted or substituted with deuterium, a naphthylene group, a divalent thiophene group, or a divalent dibenzothiophene group.

According to one embodiment of the present specification, L21 and L22 are the same as or different from each other, and each independently is a direct bond or a substituted or unsubstituted monocyclic or polycyclic arylene group having 6 to 30 carbon atoms.

According to one embodiment of the present specification, L21 and L22 are the same as or different from each other, and each independently is a direct bond or a substituted or unsubstituted monocyclic or polycyclic arylene group having 6 to 20 carbon atoms.

According to one embodiment of the present specification, L21 and L22 are the same as or different from each other, and each independently is a direct bond or a monocyclic or polycyclic arylene group having 6 to 20 carbon atoms unsubstituted or substituted with deuterium.

According to one embodiment of the present specification, L21 and L22 are the same as or different from each other, and each independently is a direct bond; a phenylene group unsubstituted or substituted with deuterium; or a naphthylene group.

According to one embodiment of the present specification, L23 is a direct bond, a substituted or unsubstituted monocyclic or polycyclic arylene group having 6 to 30 carbon atoms, or a substituted or unsubstituted monocyclic or polycyclic heteroarylene group having 2 to 30 carbon atoms.

According to one embodiment of the present specification, L23 is a direct bond, a substituted or unsubstituted monocyclic or polycyclic arylene group having 6 to 20 carbon atoms, or a substituted or unsubstituted monocyclic or polycyclic heteroarylene group having 2 to 20 carbon atoms.

According to one embodiment of the present specification, L23 is a direct bond, a monocyclic or polycyclic arylene group having 6 to 20 carbon atoms, or a monocyclic or polycyclic heteroarylene group having 2 to 20 carbon atoms.

According to one embodiment of the present specification, L23 is a direct bond, a phenylene group, a naphthylene group, or a divalent thiophene group.

According to one embodiment of the present specification, Ar21 to Ar23 are the same as or different from each other, and each independently is a substituted or unsubstituted monocyclic or polycyclic aryl group having 6 to 30 carbon atoms, or a substituted or unsubstituted monocyclic or polycyclic heteroaryl group having 2 to 30 carbon atoms.

According to one embodiment of the present specification, Ar21 to Ar23 are the same as or different from each other, and each independently is a substituted or unsubstituted monocyclic or polycyclic aryl group having 6 to 20 carbon atoms, or a substituted or unsubstituted monocyclic or polycyclic heteroaryl group having 2 to 20 carbon atoms.

According to one embodiment of the present specification, Ar21 to Ar23 are the same as or different from each other, and each independently is a monocyclic or polycyclic aryl group having 6 to 20 carbon atoms unsubstituted or substituted with deuterium, a cyano group, a halogen group, a linear or branched alkyl group having 1 to 20 carbon atoms, a linear or branched alkylsilyl group having 1 to 20 carbon atoms, or a monocyclic or polycyclic cycloalkyl group having 3 to 20 carbon atoms, or a monocyclic or polycyclic heteroaryl group having 2 to 20 carbon atoms unsubstituted or substituted with deuterium, or a monocyclic or polycyclic aryl group having 6 to 20 carbon atoms.

According to one embodiment of the present specification, Ar21 to Ar23 are the same as or different from each other, and each independently is a phenyl group unsubstituted or substituted with deuterium, a halogen group, a linear or branched alkyl group having 1 to 20 carbon atoms, a linear or branched alkylsilyl group having 1 to 20 carbon atoms, or a monocyclic or polycyclic cycloalkyl group having 3 to 20 carbon atoms; a biphenyl group unsubstituted or substituted with deuterium, a halogen group, or a linear or branched alkylsilyl group having 1 to 20 carbon atoms; a naphthyl group unsubstituted or substituted with deuterium, a cyano group, or a linear or branched alkyl group having 1 to 20 carbon atoms; a phenanthrene group; a benzonaphthofuran group; an indolocarbazole group; a thiophene group unsubstituted or substituted with a monocyclic or polycyclic aryl group having 6 to 20 carbon atoms; a dibenzofuran group unsubstituted or substituted with deuterium, or a monocyclic or polycyclic aryl group having 6 to 20 carbon atoms; a quinoline group; a pyridine group; an isoquinoline group; a dibenzothiophene group; a phenalene group; or an anthracene group.

According to one embodiment of the present specification, Ar21 to Ar23 are the same as or different from each other, and each independently is a phenyl group unsubstituted or substituted with deuterium, F, a methyl group, a cyclohexyl group or a trimethylsilyl group ($Si(CH_3)_3$); a biphenyl group unsubstituted or substituted with deuterium, F or a trimethylsilyl group ($Si(CH_3)_3$); a naphthyl group unsubstituted or substituted with a cyano group or a methyl group; a phenanthrene group; a benzonaphthofuran group; an indolocarbazole group; a thiophene group unsubstituted or substituted with a phenyl group; a dibenzofuran group unsubstituted or substituted with deuterium, a phenyl group or a naphthyl group; a quinoline group; a pyridine group; an isoquinoline group; a dibenzothiophene group; a phenalene group; or an anthracene group.

According to one embodiment of the present specification, Ar21 and Ar22 are the same as or different from each other, and each independently is a phenyl group unsubstituted or substituted with deuterium, F, a methyl group, a cyclohexyl group or a trimethylsilyl group ($Si(CH_3)_3$; a biphenyl group unsubstituted or substituted with deuterium, F or a trimethylsilyl group ($Si(CH_3)_3$); a naphthyl group unsubstituted or substituted with a cyano group or a methyl group; a phenanthrene group; a benzonaphthofuran group; an indolocarbazole group; a thiophene group substituted with a phenyl group; a dibenzofuran group unsubstituted or substituted with deuterium, a phenyl group or a naphthyl group; a quinoline group; a pyridine group; an isoquinoline group; a dibenzothiophene group; a phenalene group; or an anthracene group.

According to one embodiment of the present specification, Ar23 is a substituted or unsubstituted monocyclic or polycyclic aryl group having 6 to 30 carbon atoms; or a substituted or unsubstituted monocyclic or polycyclic heteroaryl group having 2 to 30 carbon atoms.

According to one embodiment of the present specification, Ar23 is a substituted or unsubstituted monocyclic or polycyclic aryl group having 6 to 20 carbon atoms; or a substituted or unsubstituted monocyclic or polycyclic heteroaryl group having 2 to 20 carbon atoms.

According to one embodiment of the present specification, Ar23 is a monocyclic or polycyclic aryl group having 6 to 20 carbon atoms unsubstituted or substituted with deuterium; or a monocyclic or polycyclic heteroaryl group having 2 to 20 carbon atoms.

According to one embodiment of the present specification, Ar23 is a phenyl group unsubstituted or substituted with deuterium; a biphenyl group; a naphthyl group unsubstituted or substituted with deuterium; a phenalene group; a phenanthrene group; an anthracene group; a pyridine group; an isoquinoline group; a dibenzofuran group; or a benzonaphthofuran group.

According to one embodiment of the present specification, Chemical Formula 2 is the following Chemical Formula 2-1 or 2-2:

<Chemical Formula 2-1>

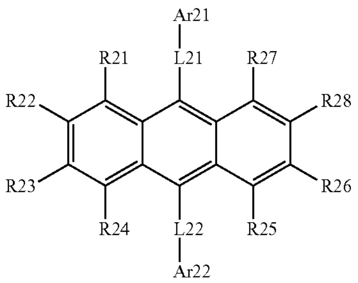

<Chemical Formula 2-2>

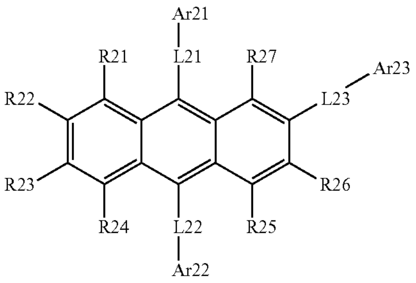

wherein in Chemical Formulae 2-1 and 2-2:

R21 to R27, L21 to L23 and Ar21 to Ar23 have the same definitions as in Chemical Formula 2; and R28 is hydrogen or deuterium.

According to one embodiment of the present specification, R21 to R27 are the same as or different from each other, and each independently is hydrogen or deuterium.

According to one embodiment of the present specification, R21 to R27 are hydrogen.

According to one embodiment of the present specification, R21 to R27 are deuterium.

According to one embodiment of the present specification, R28 is hydrogen.

According to one embodiment of the present specification, R28 is deuterium.

According to one embodiment of the present specification, the compound of Chemical Formula 2 is any one compound selected from among the following compounds:

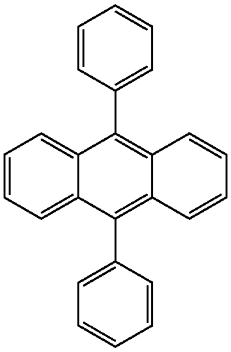

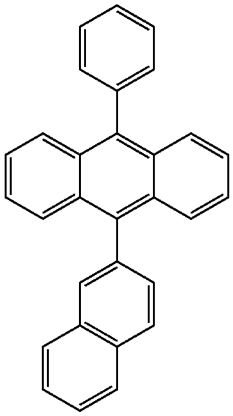

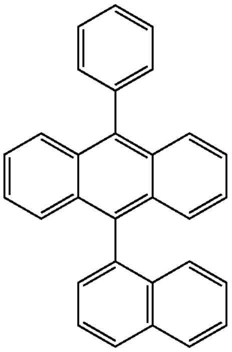

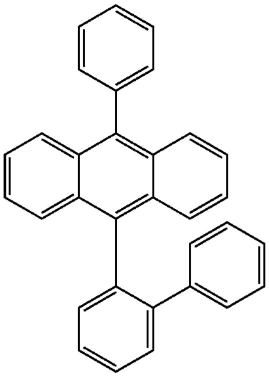

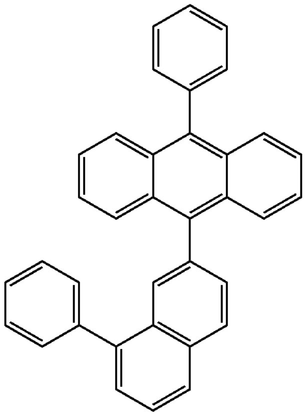

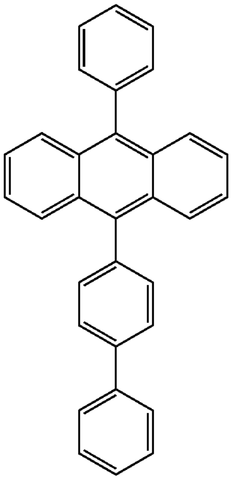

-continued
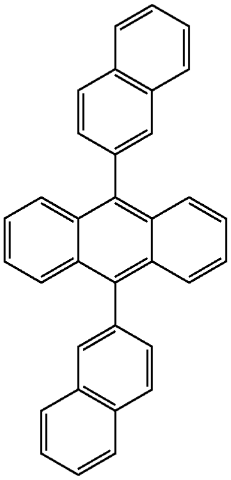
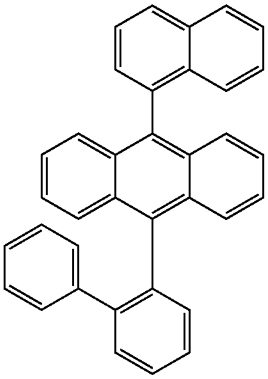
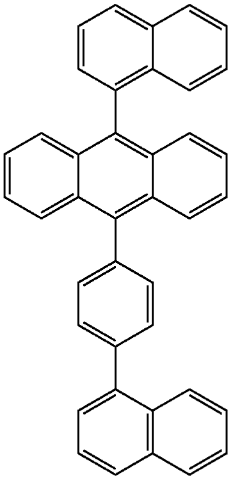
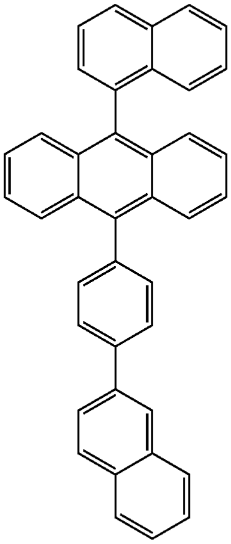
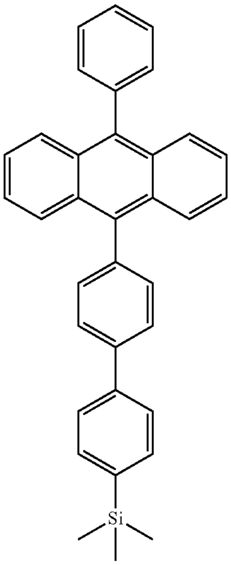
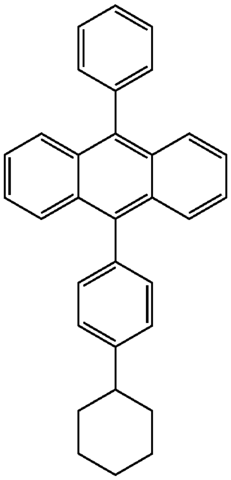
-continued
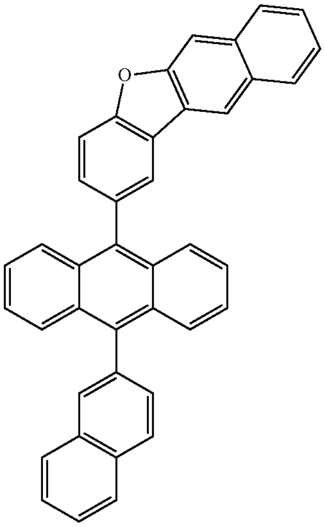
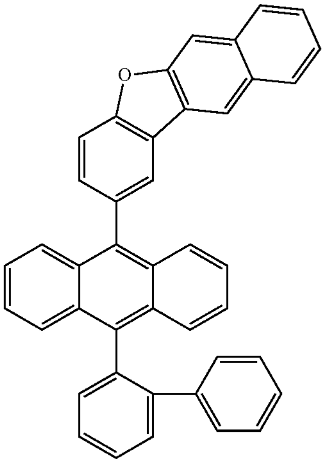
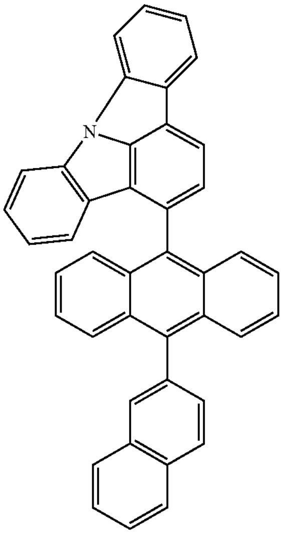

-continued
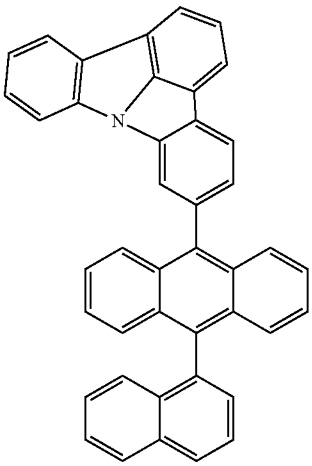
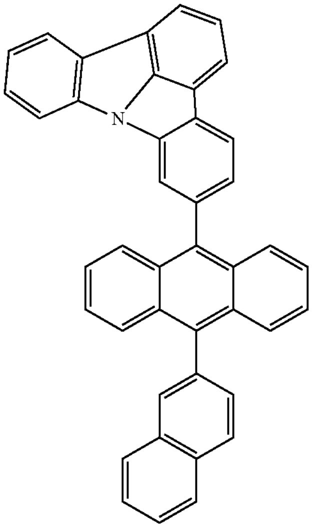
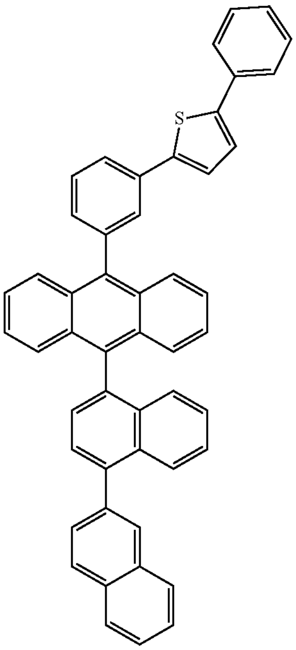
-continued
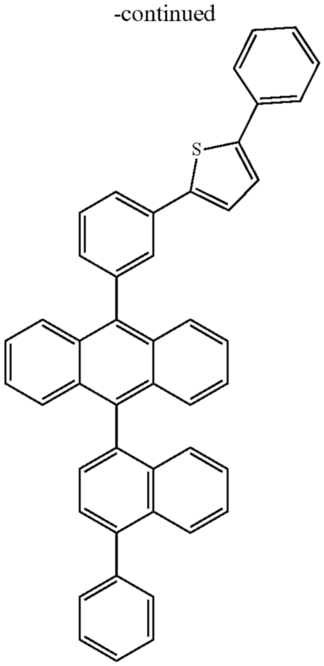
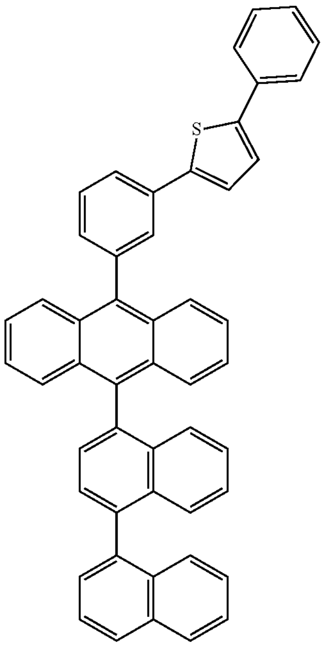

-continued
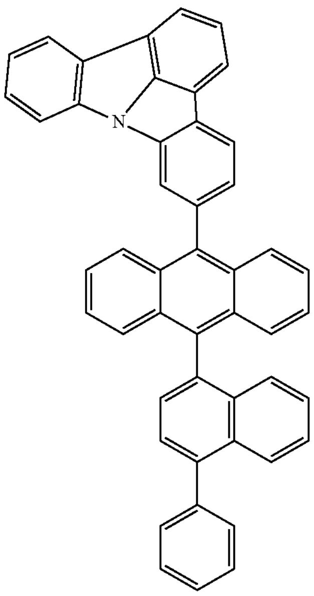
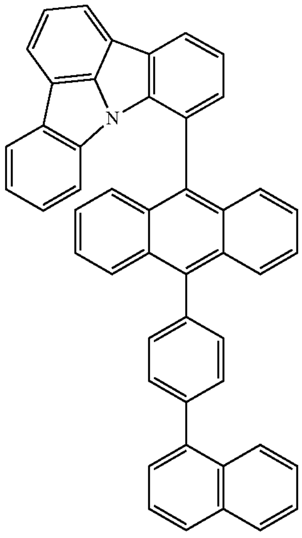
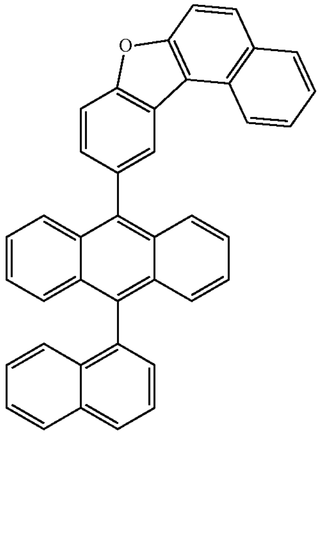
-continued
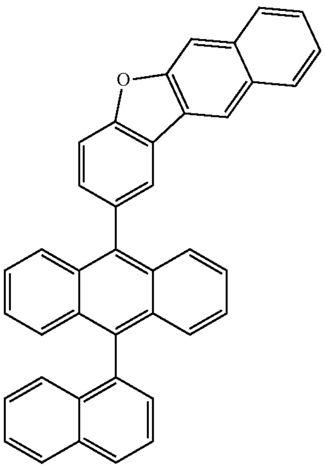
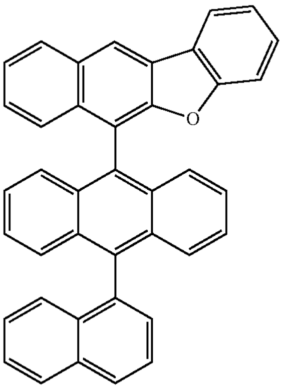
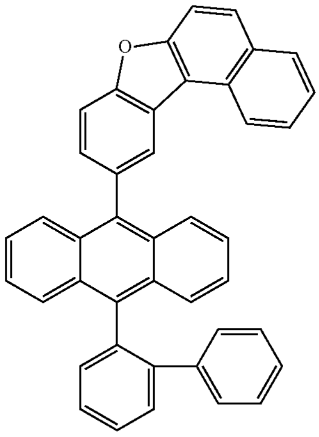

-continued
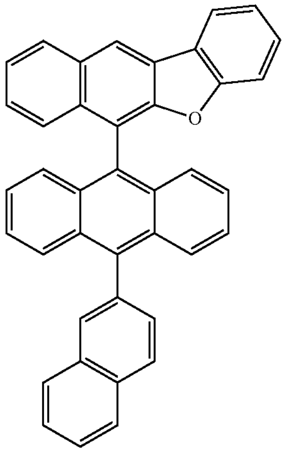
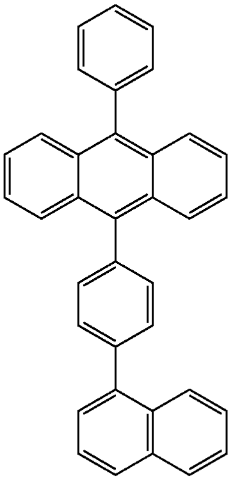
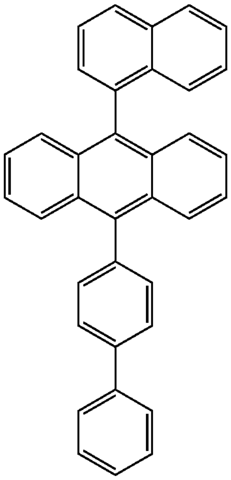
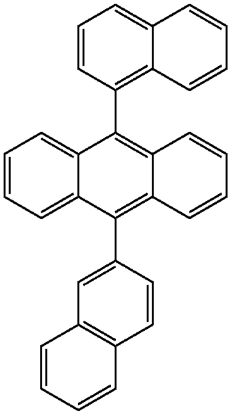
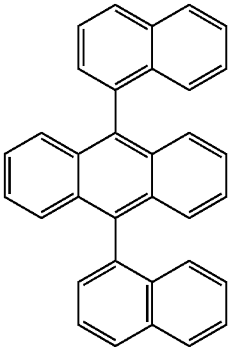
-continued
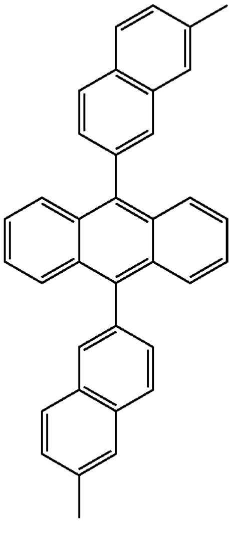
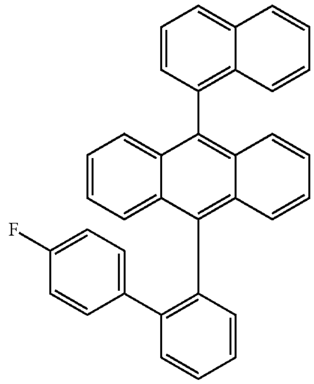
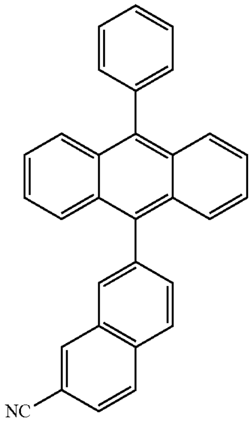
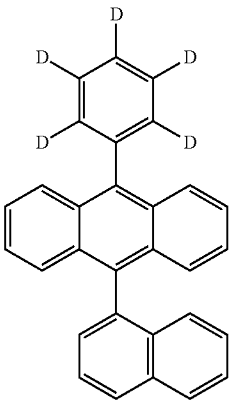
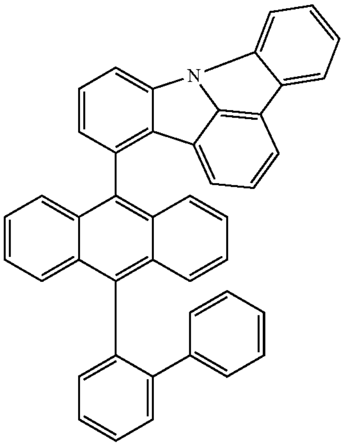

-continued
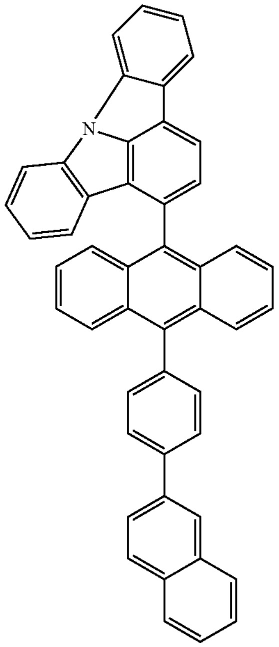
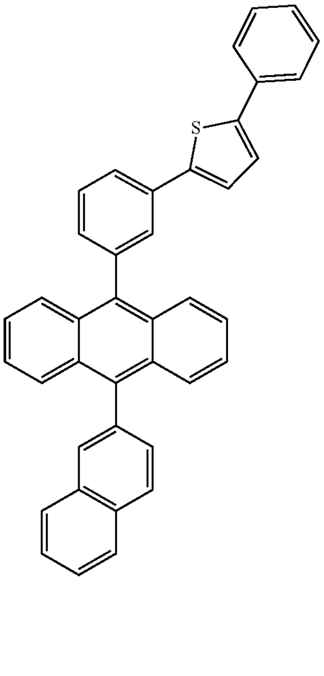
-continued
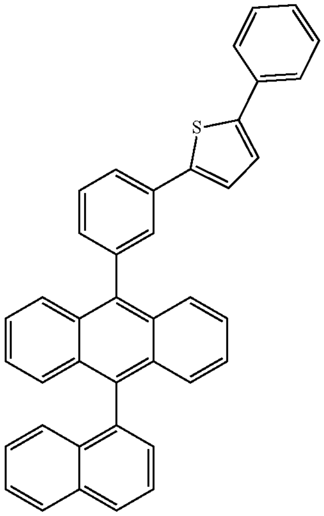
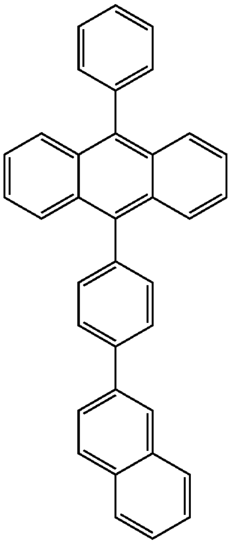
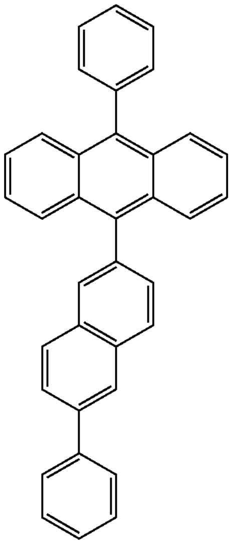
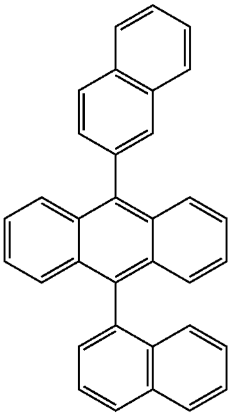
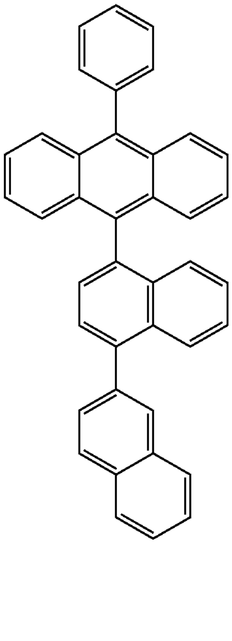
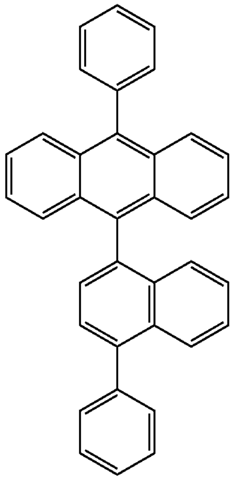

-continued
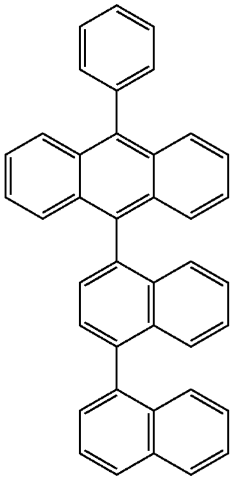
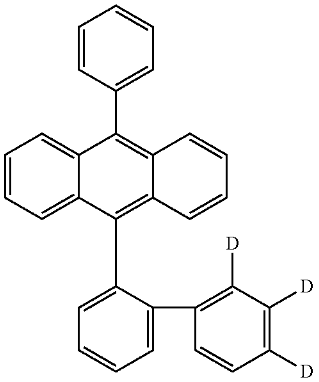
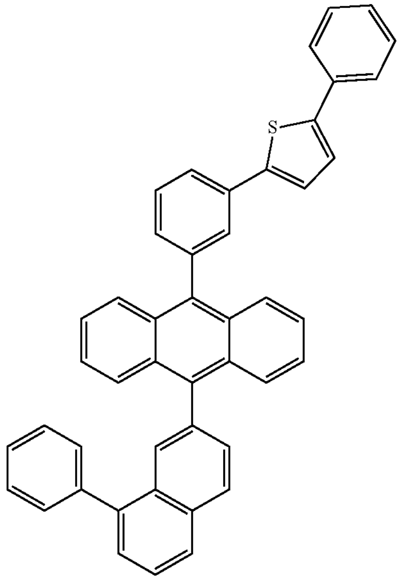
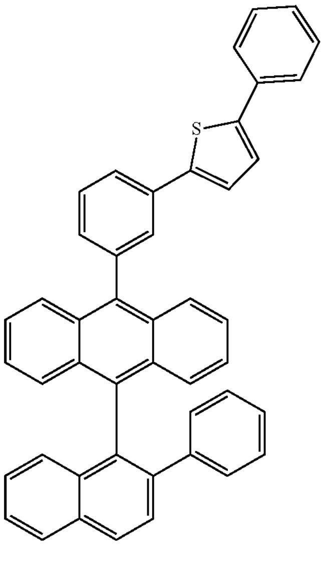
-continued
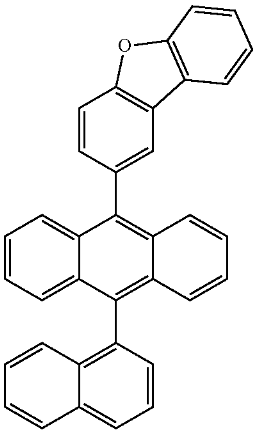
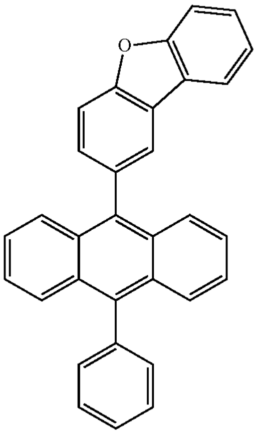
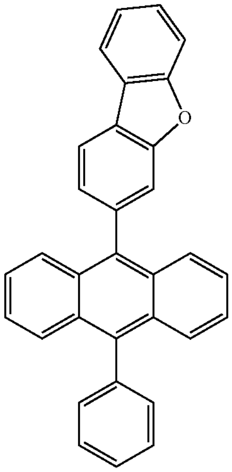
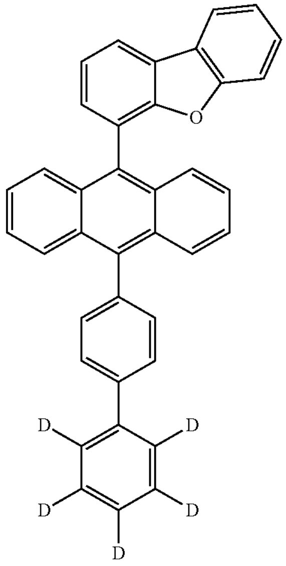
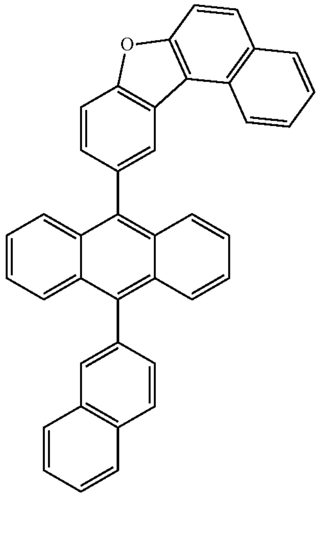

-continued
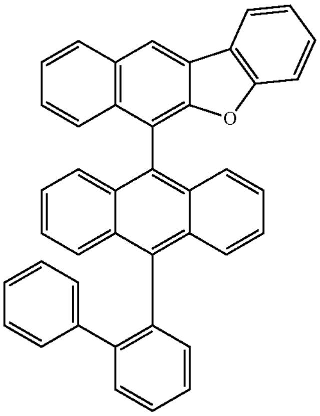
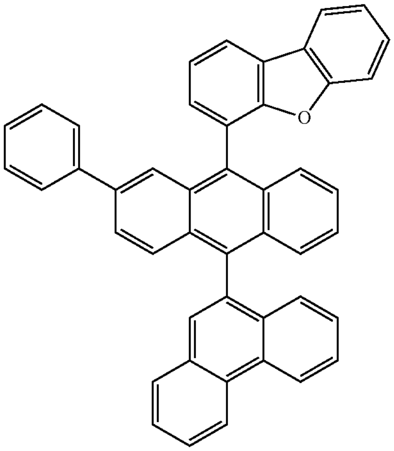
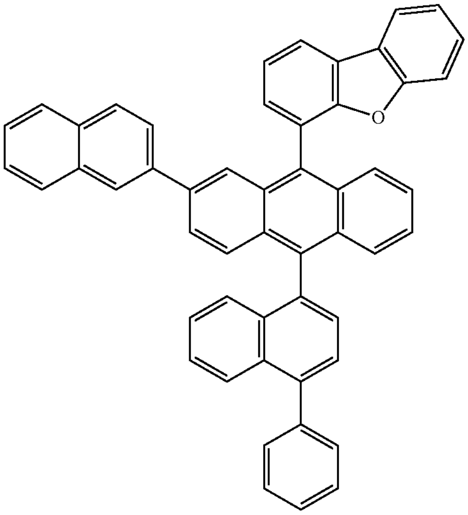
-continued
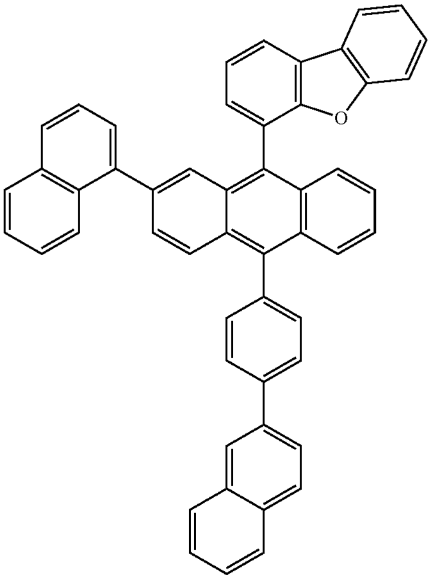
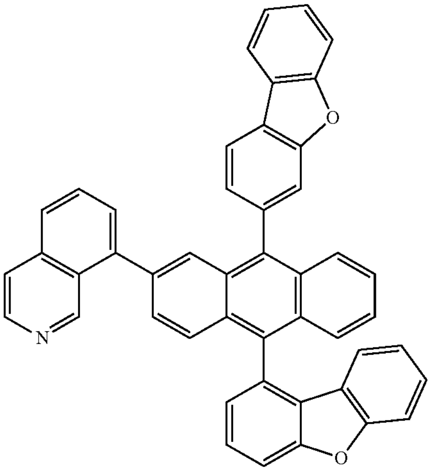
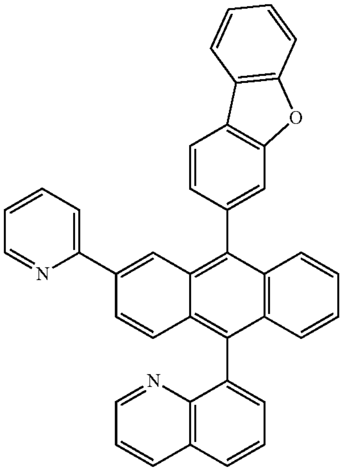

-continued
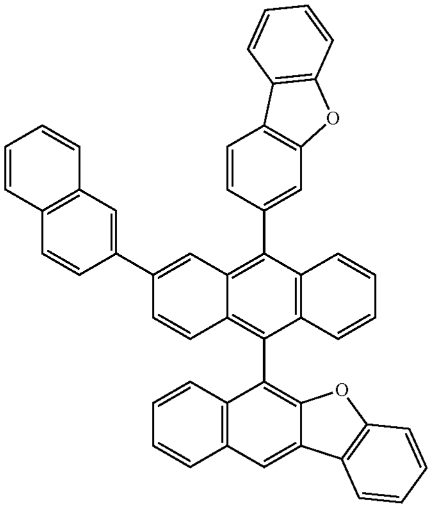
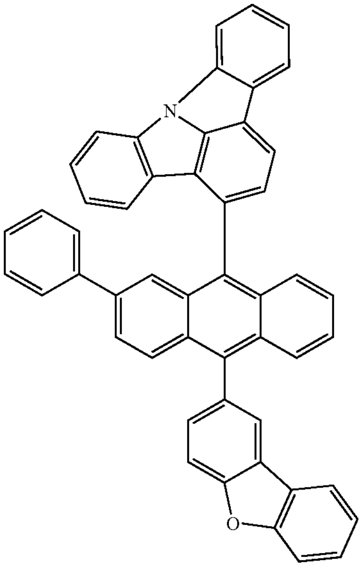
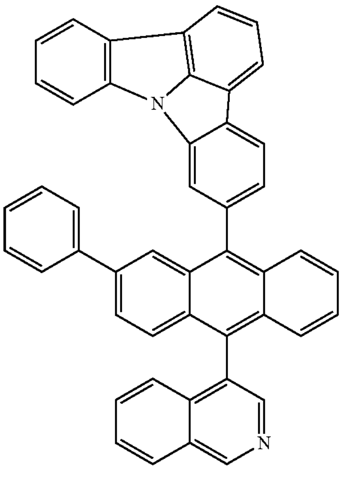
-continued
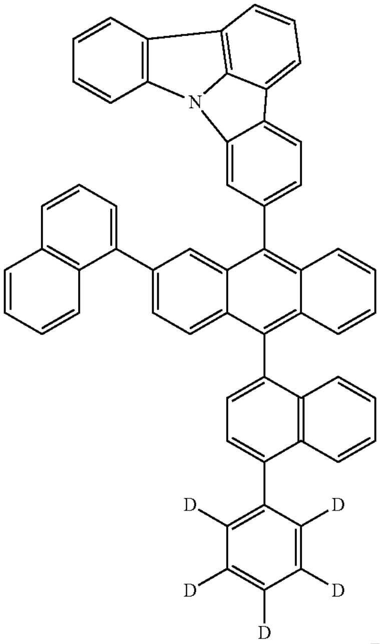
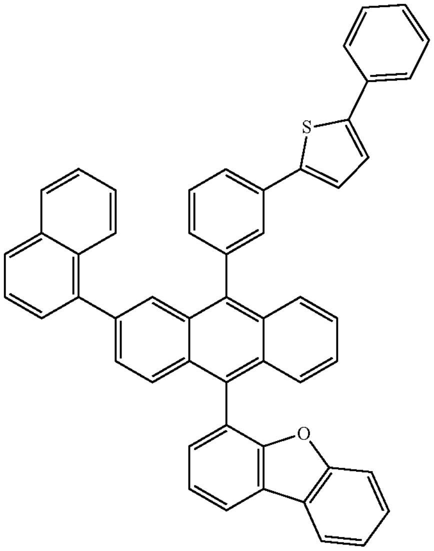
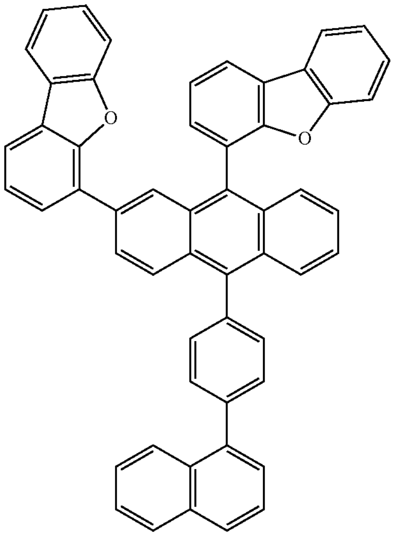

-continued
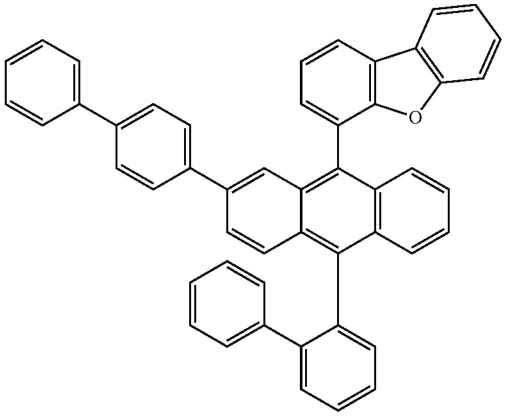
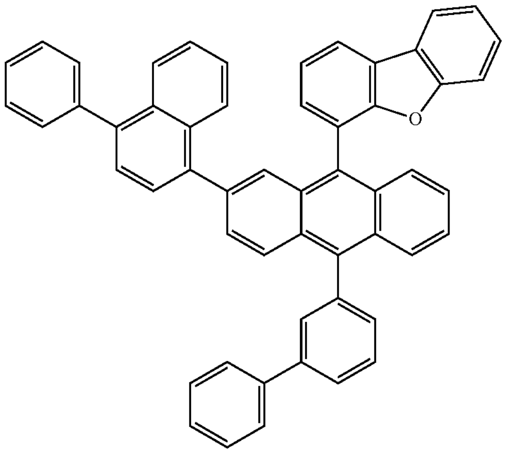
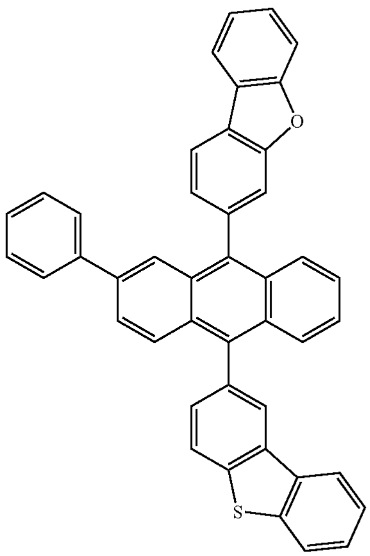
-continued
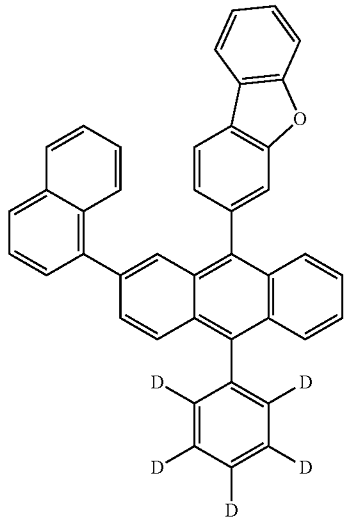
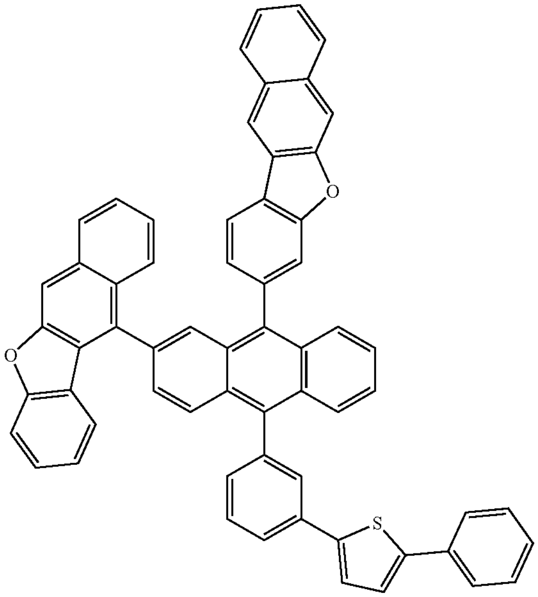
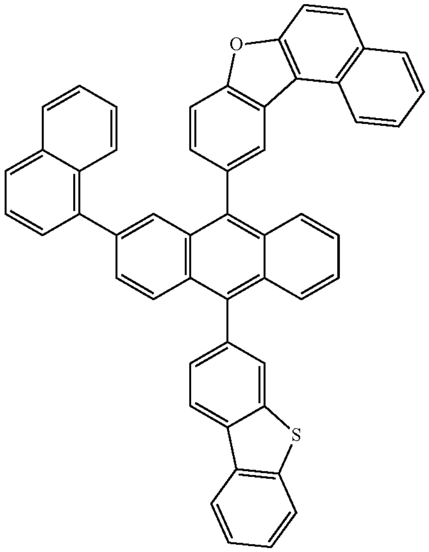

-continued
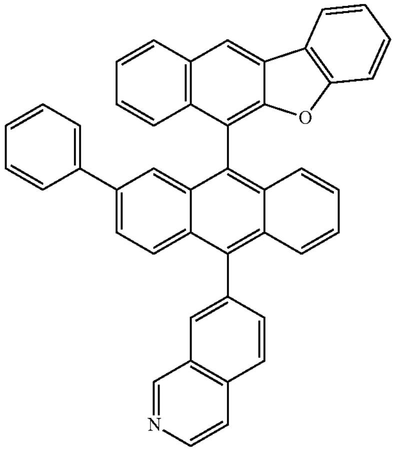
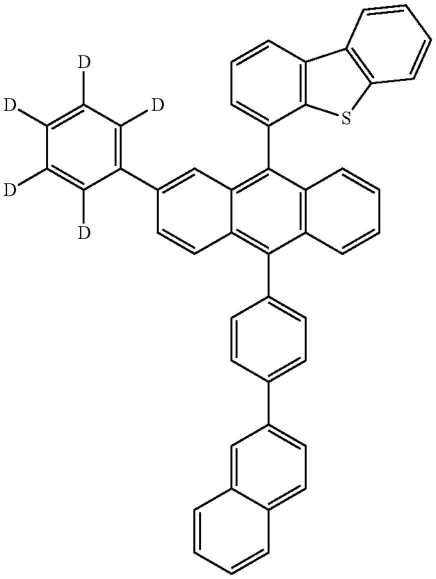
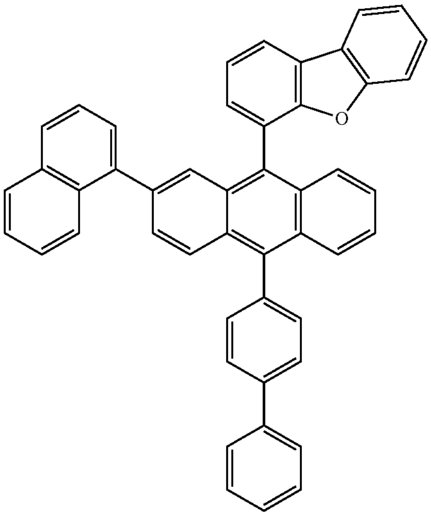
-continued
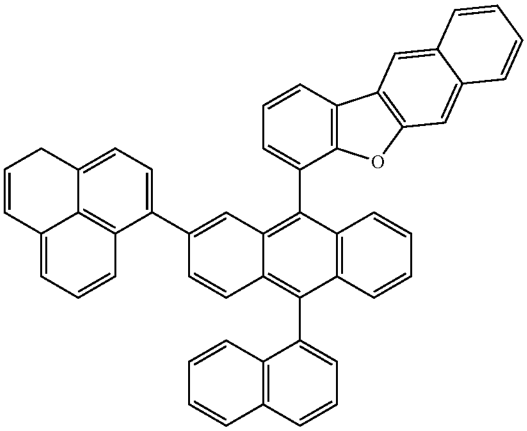
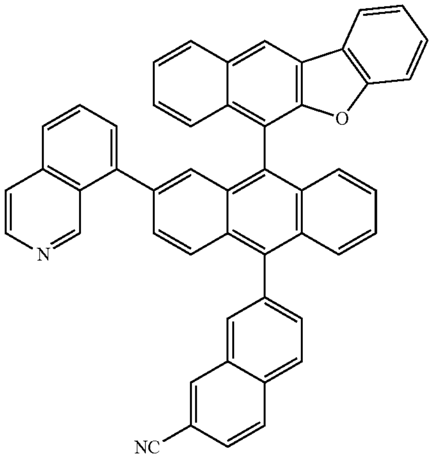
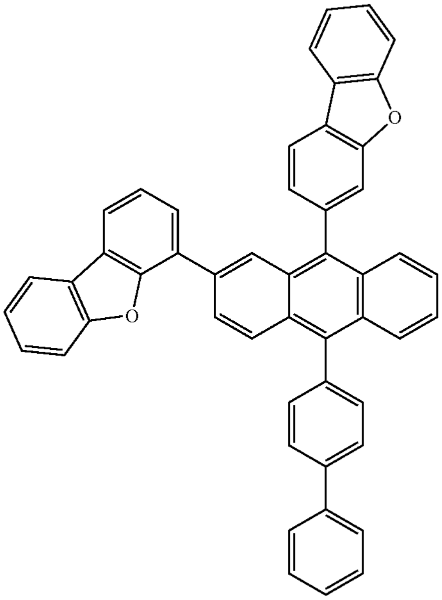

-continued
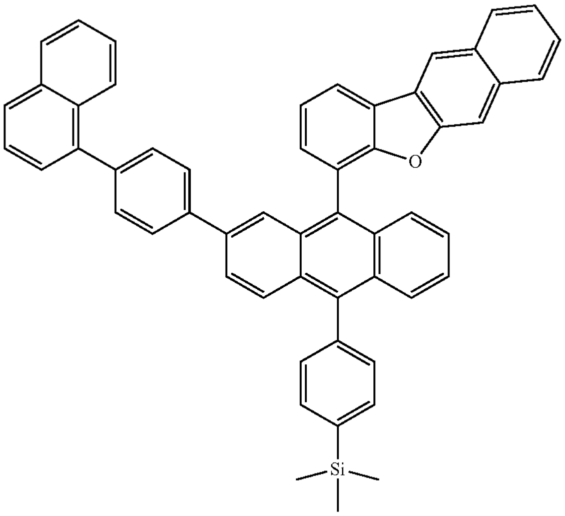
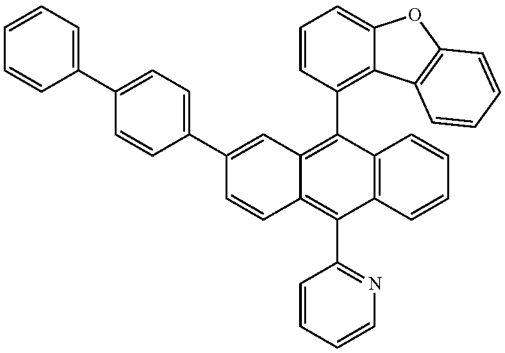
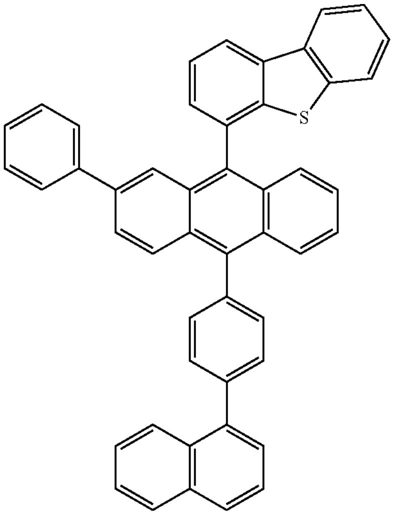
-continued
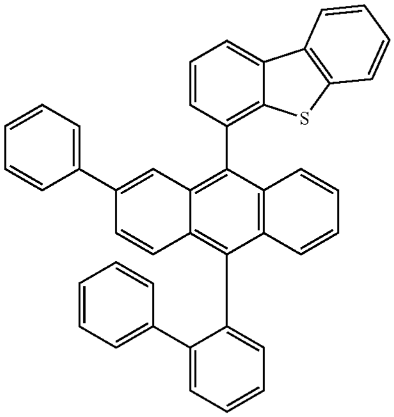
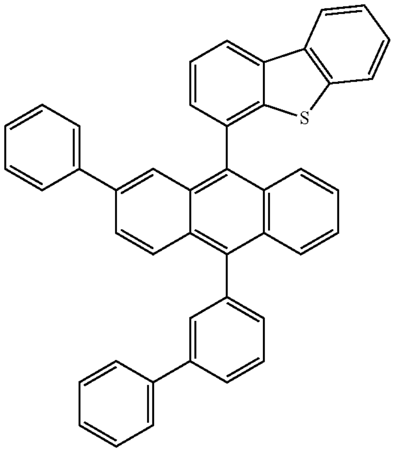
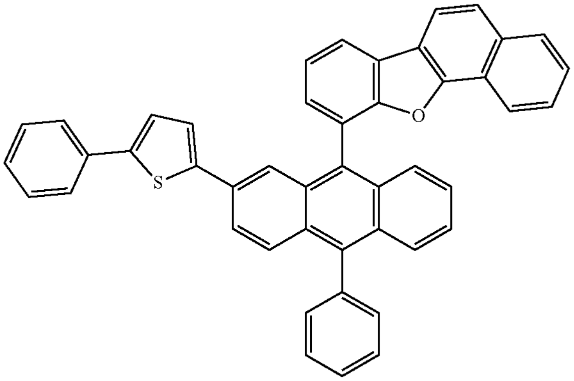

-continued
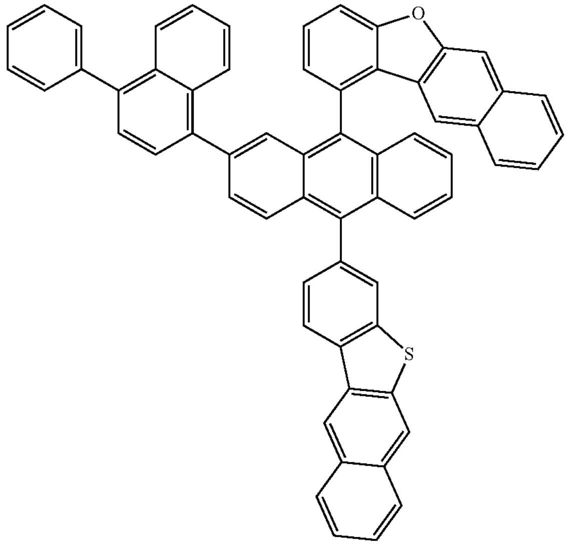
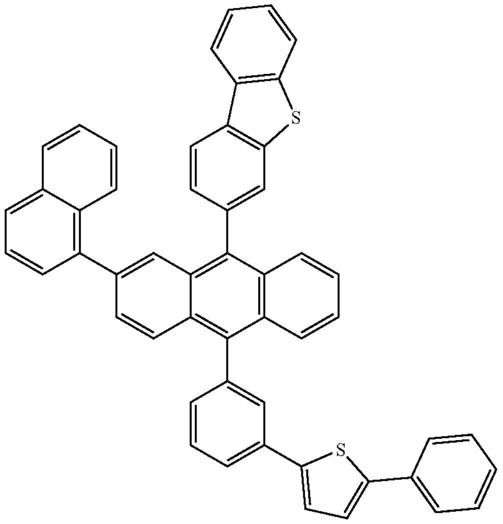
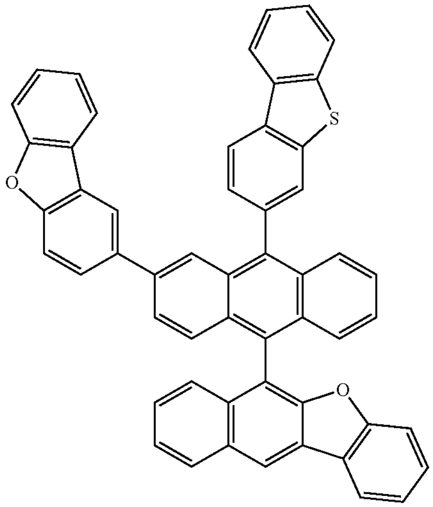
-continued
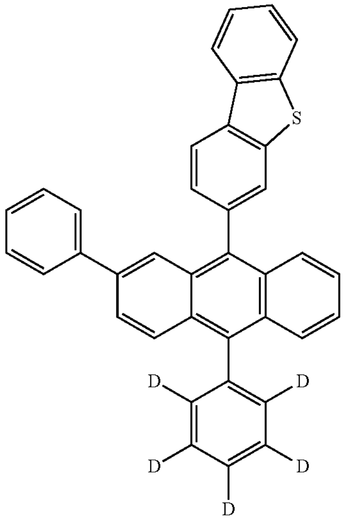
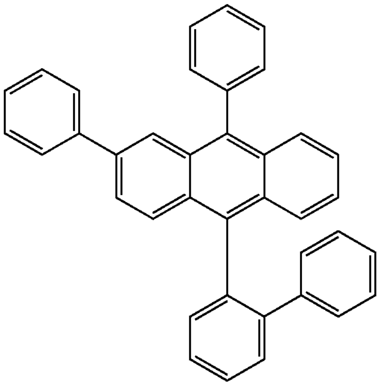
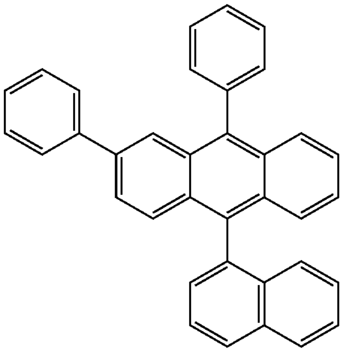
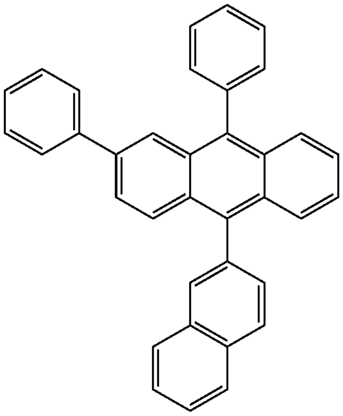

-continued
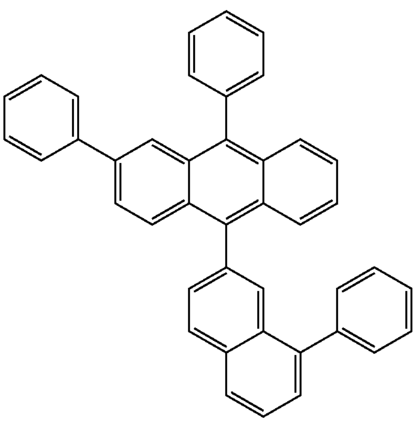
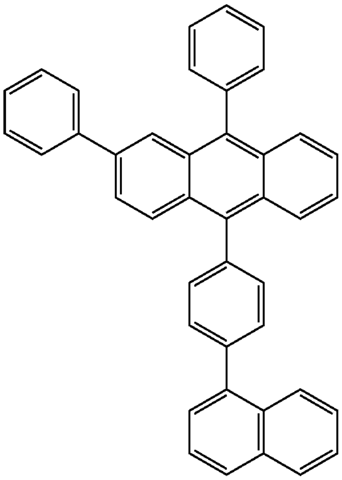
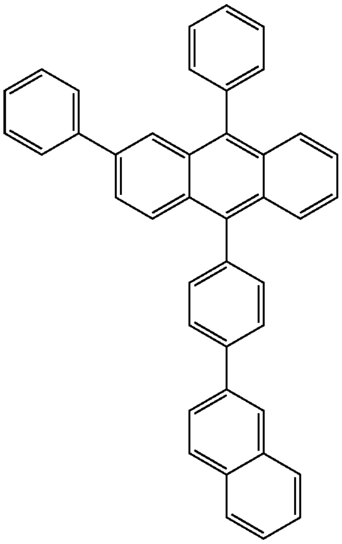
-continued
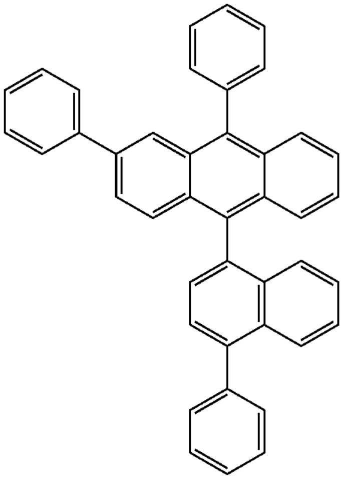
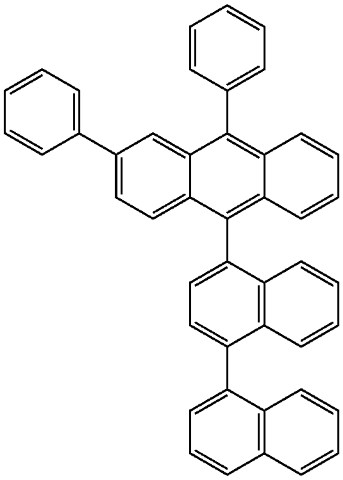
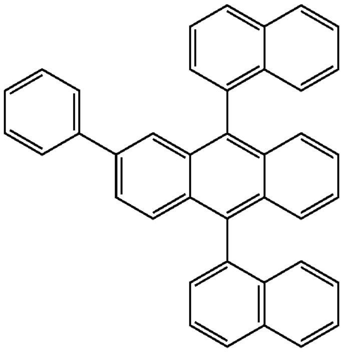
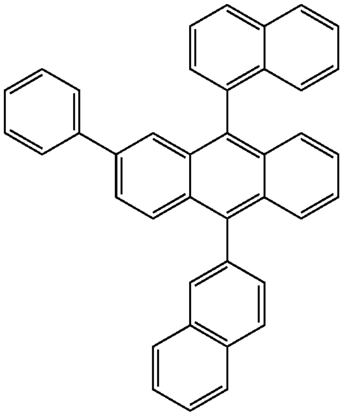

-continued
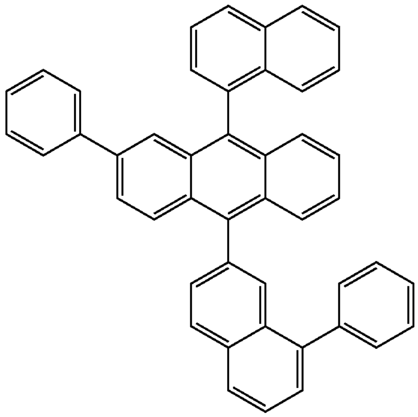
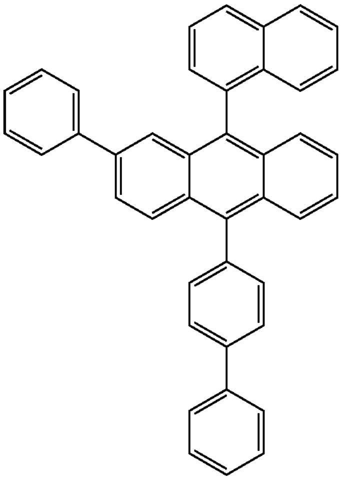
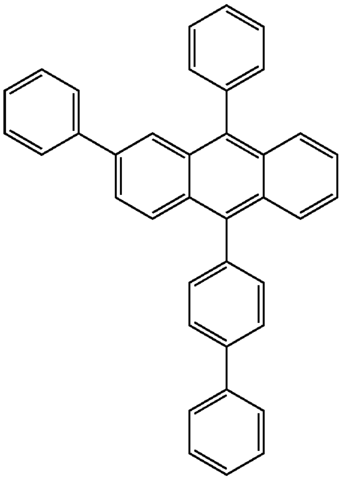
-continued
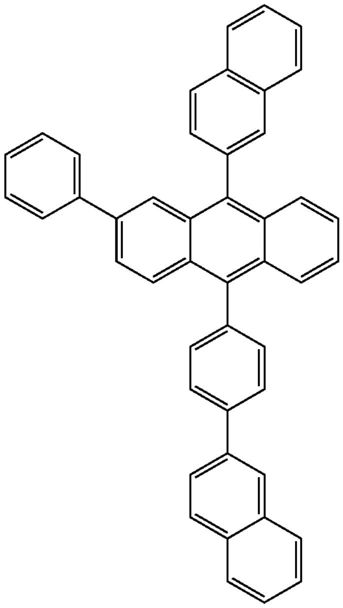
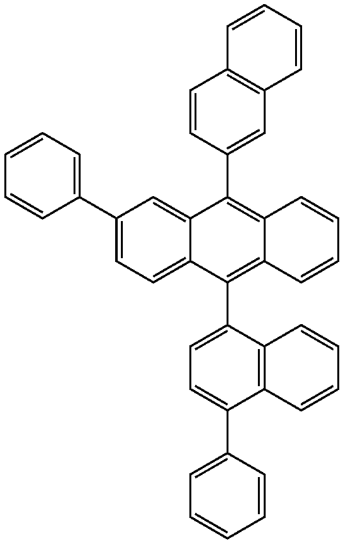
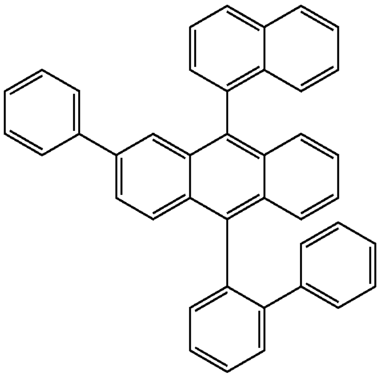

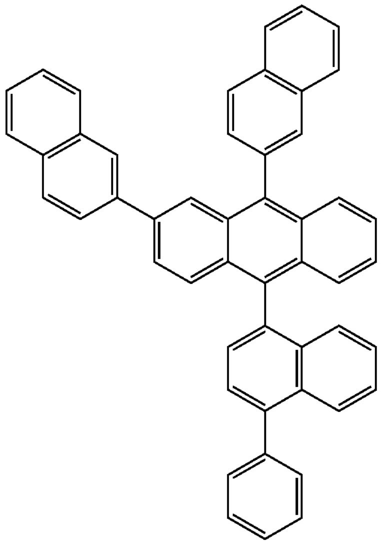
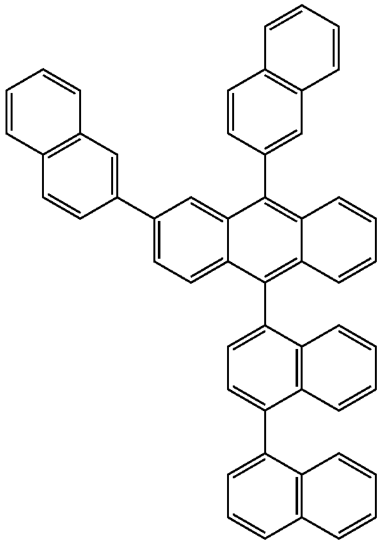
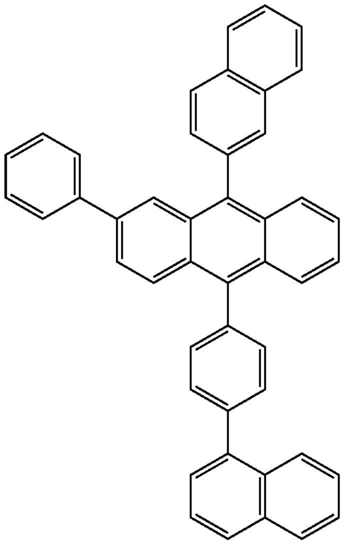
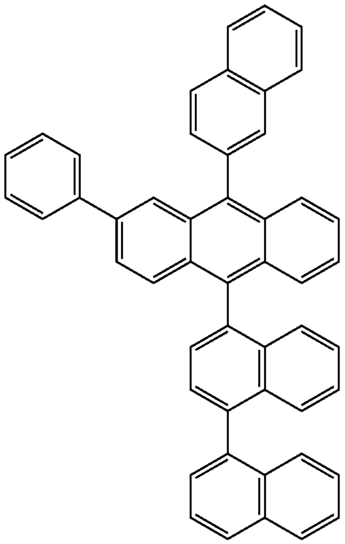
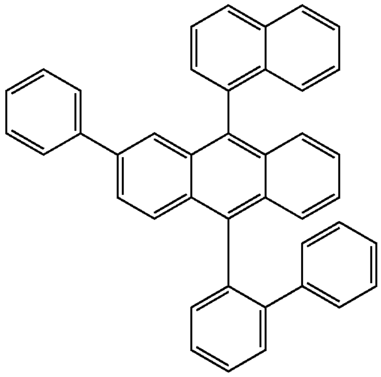
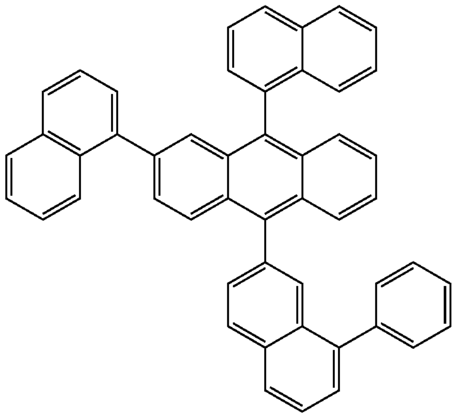

-continued
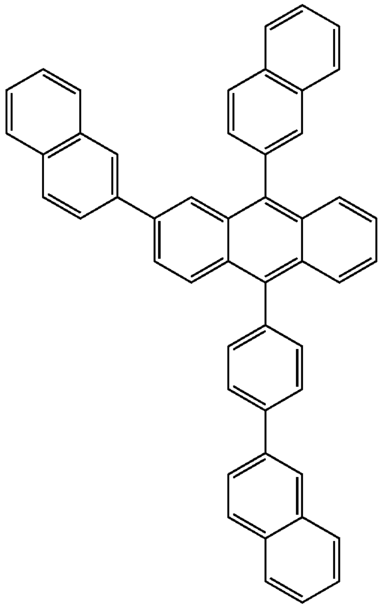
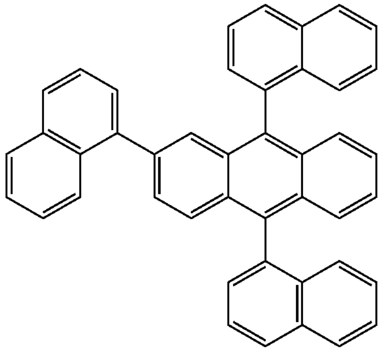
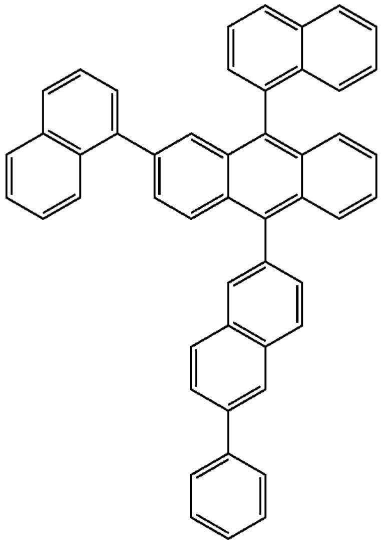
-continued
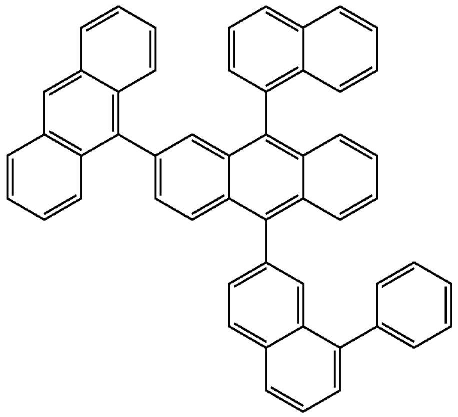
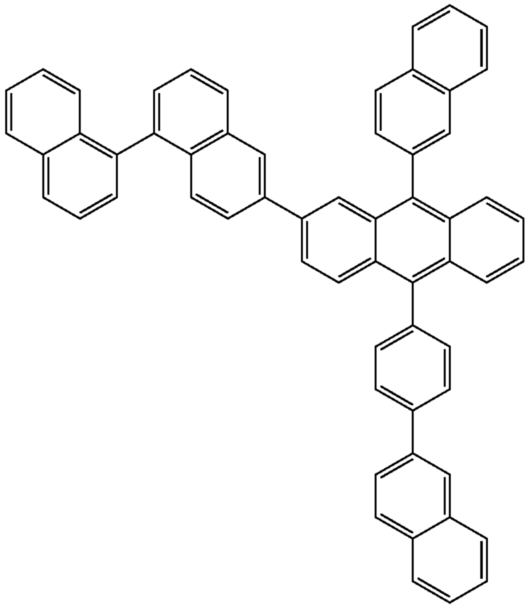
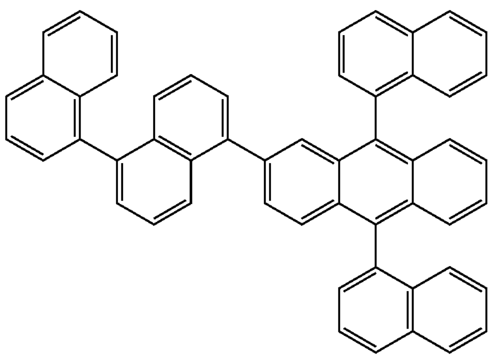

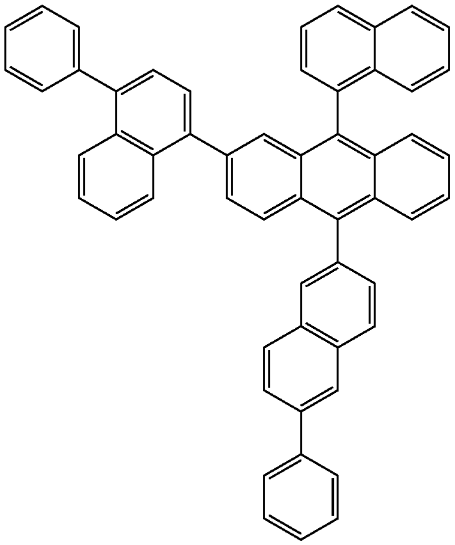
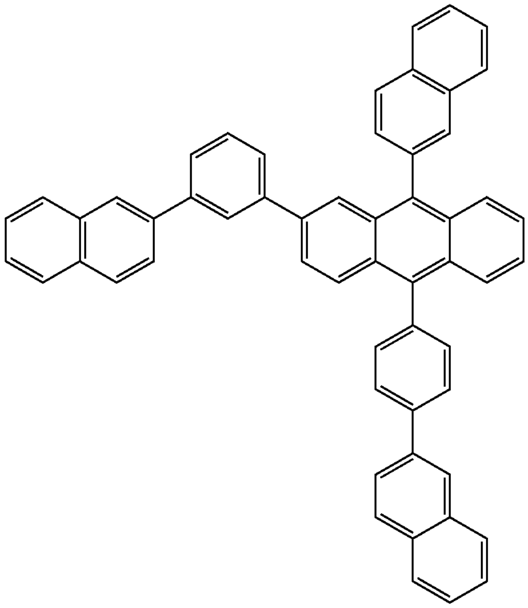
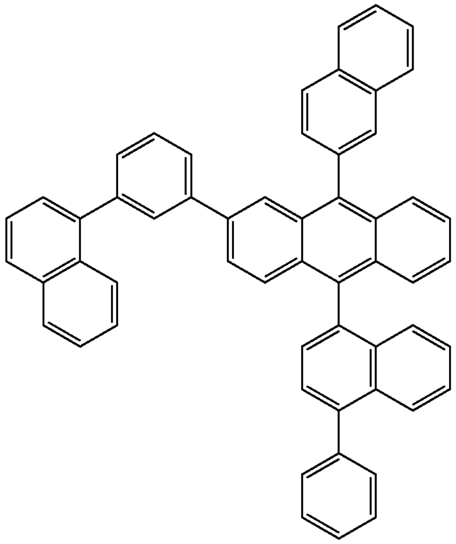
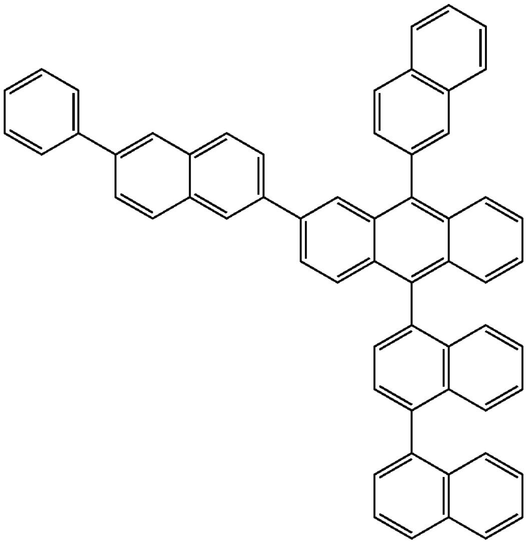
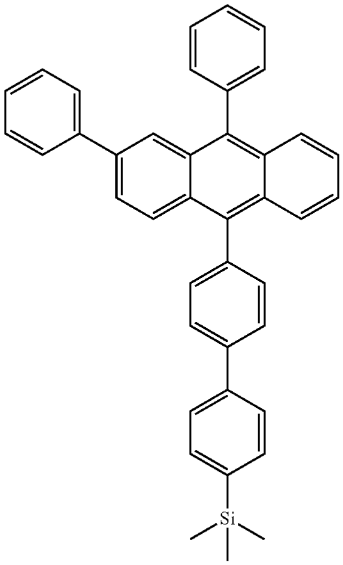
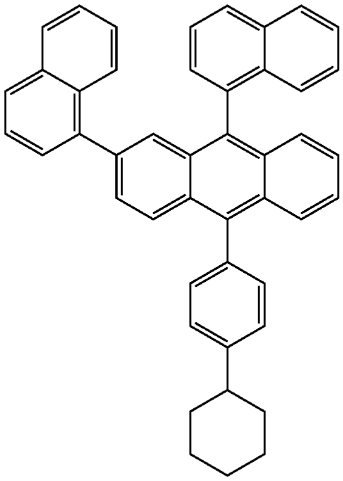

-continued
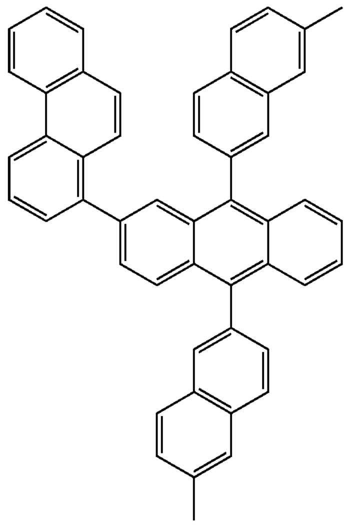
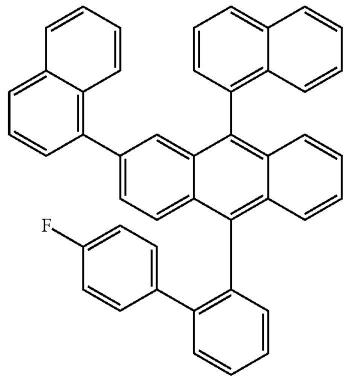
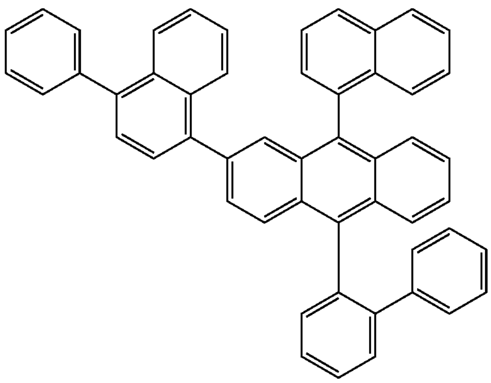
-continued
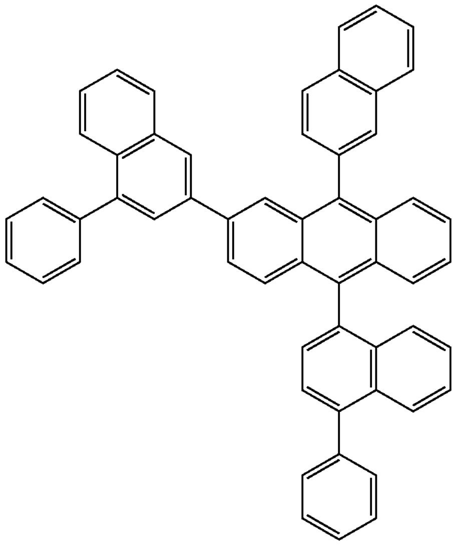
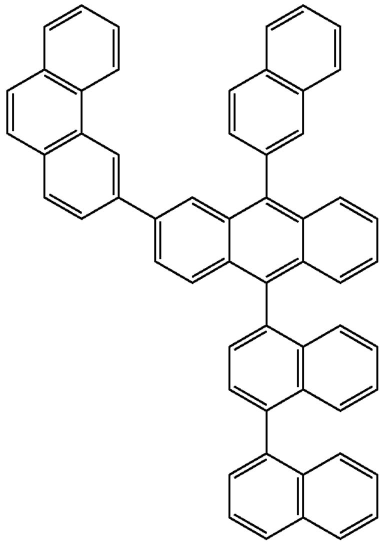
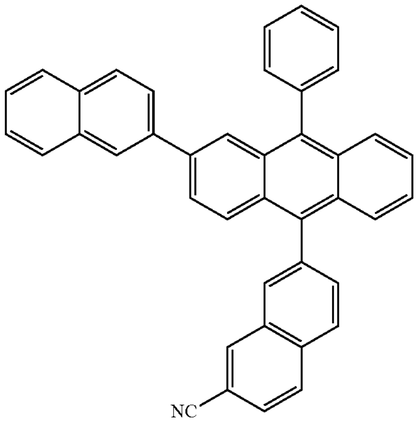

-continued
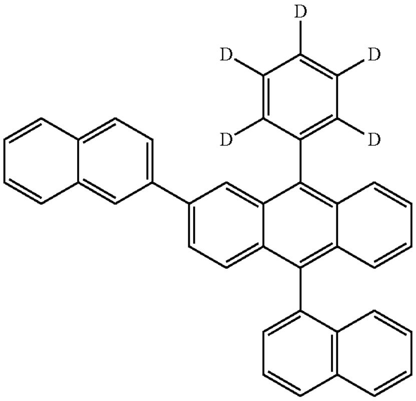
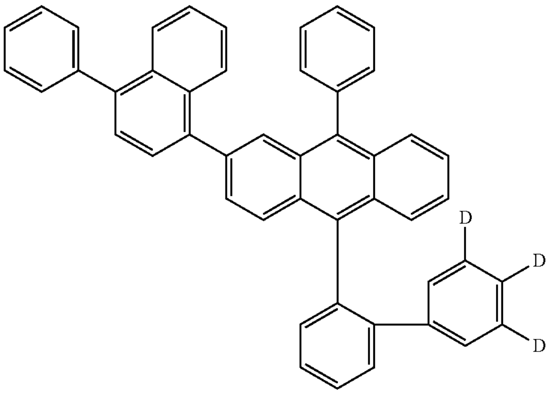
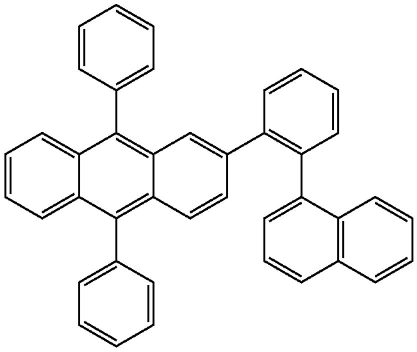
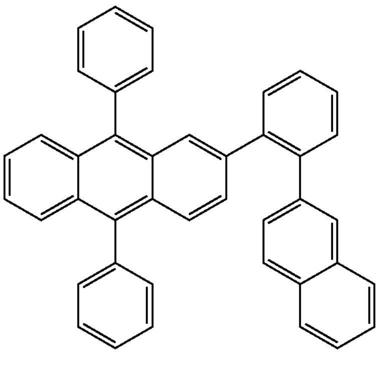
-continued
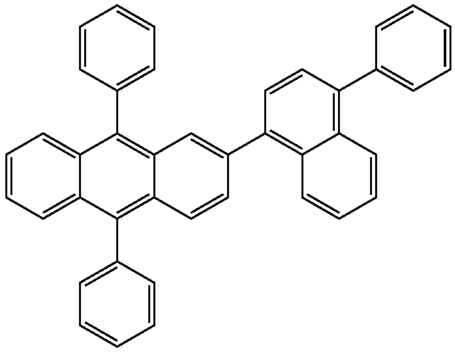
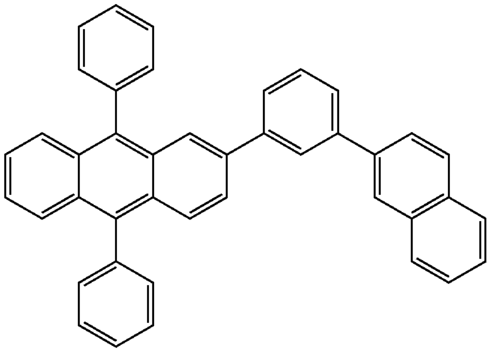
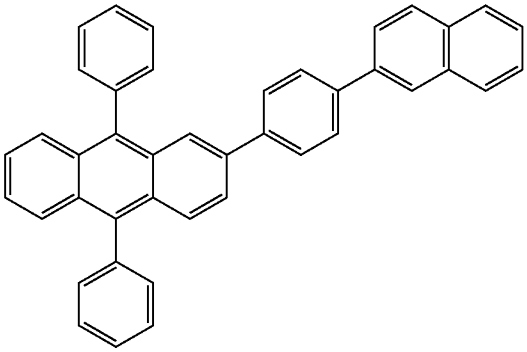
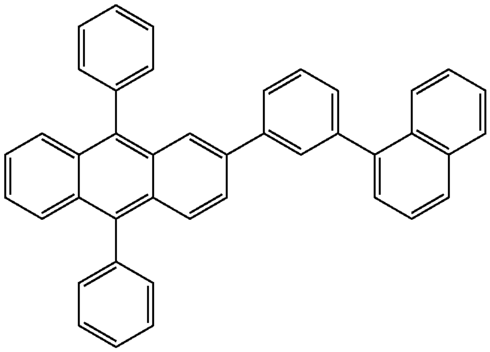

-continued
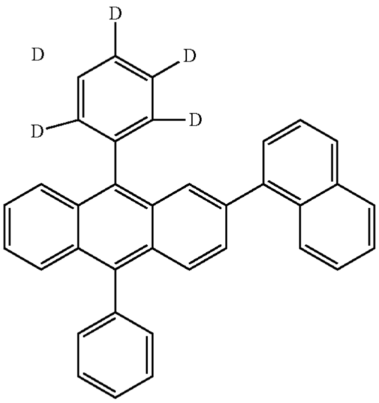
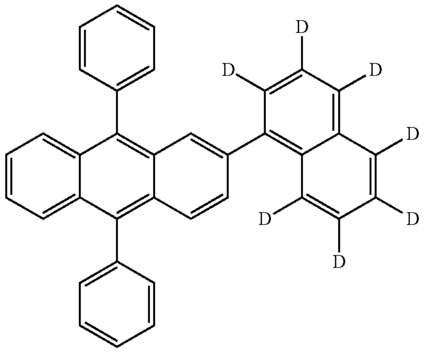
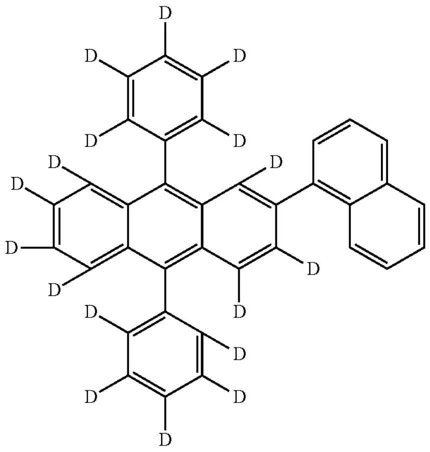
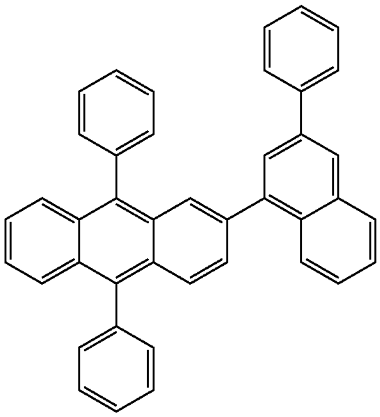
-continued
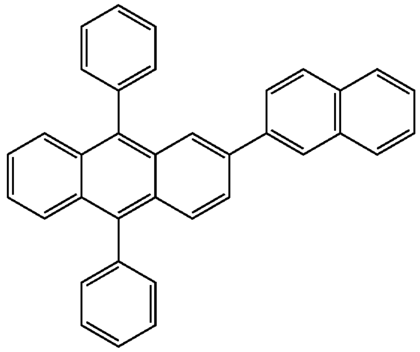
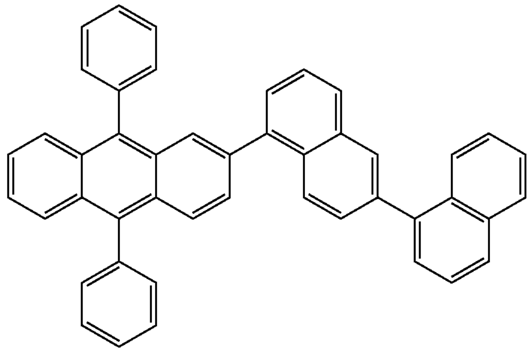
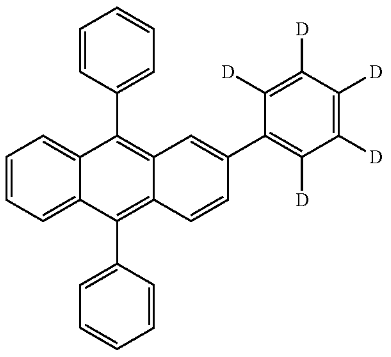
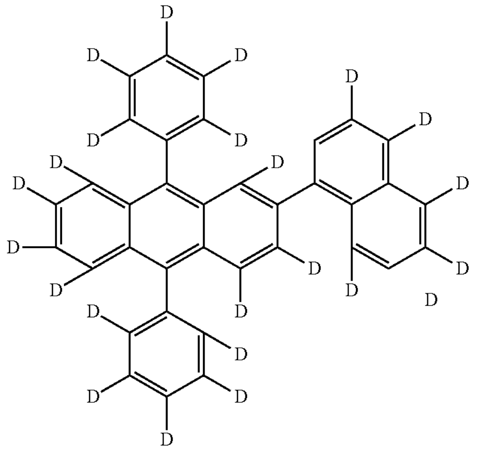

-continued
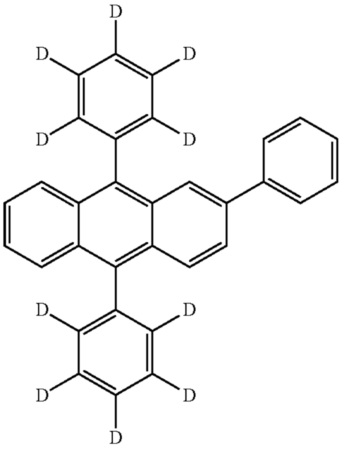
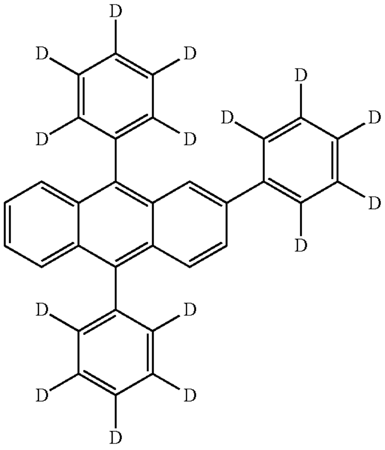
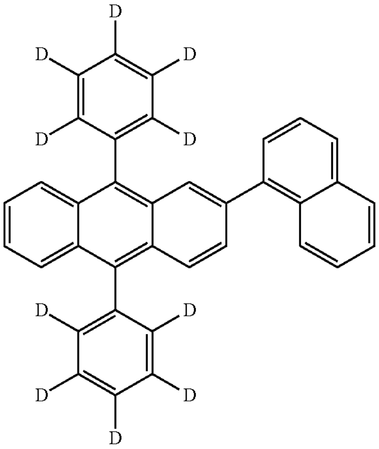
-continued
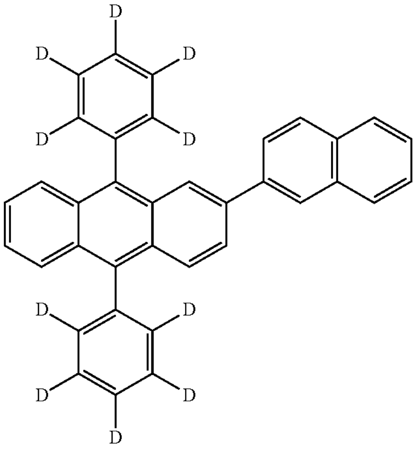
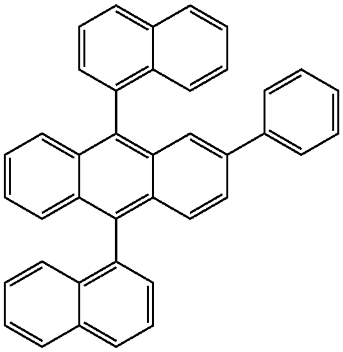
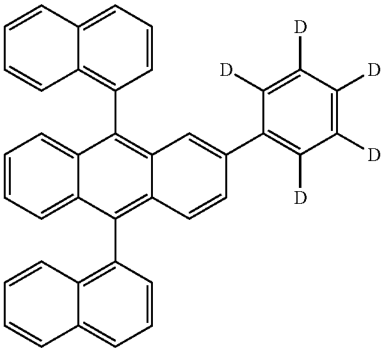
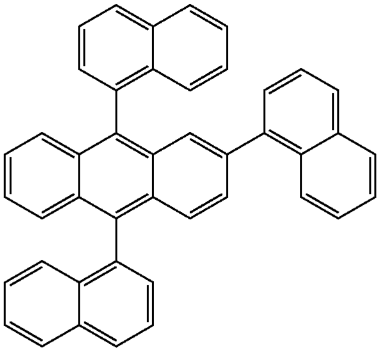

-continued
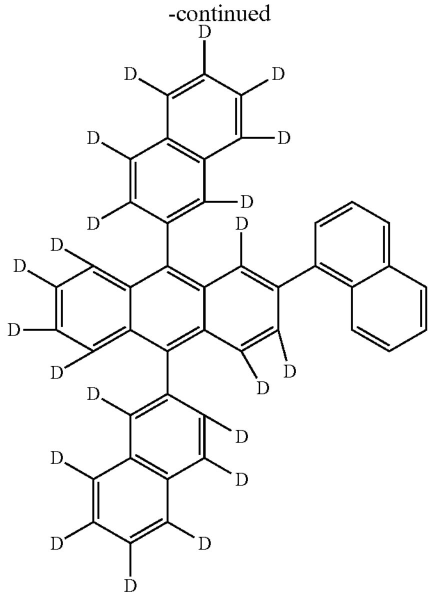
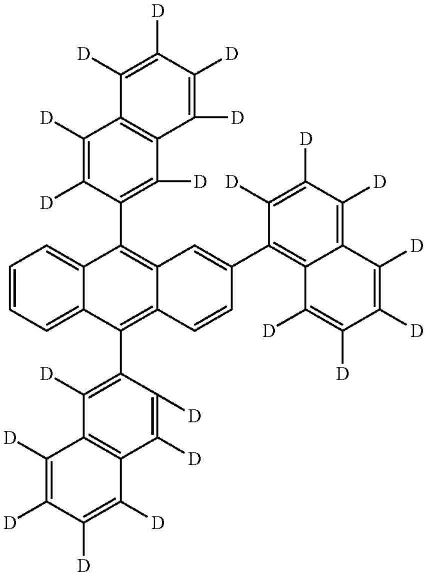
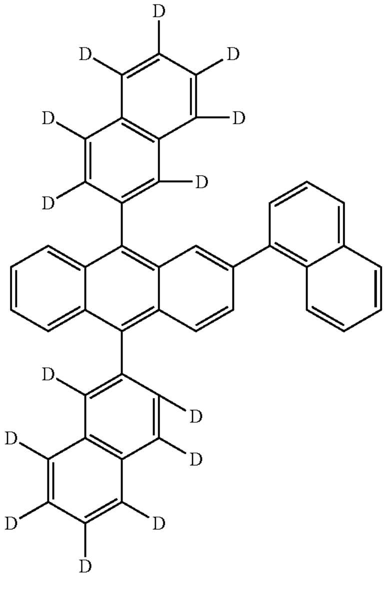
-continued
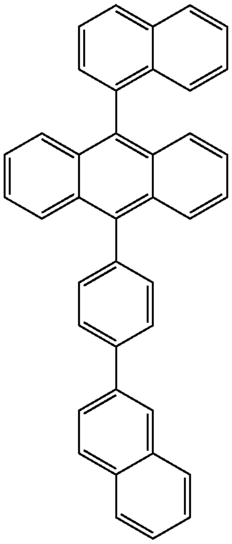
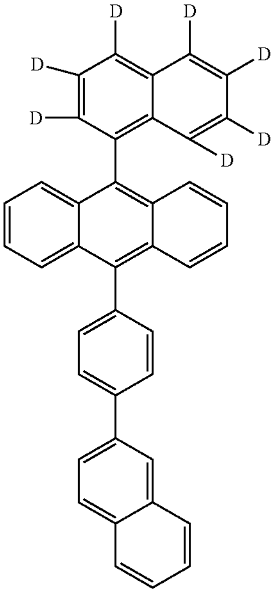
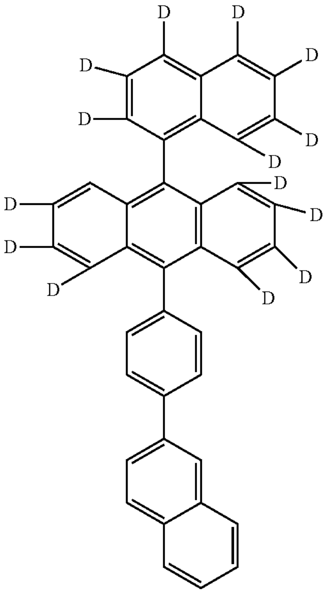
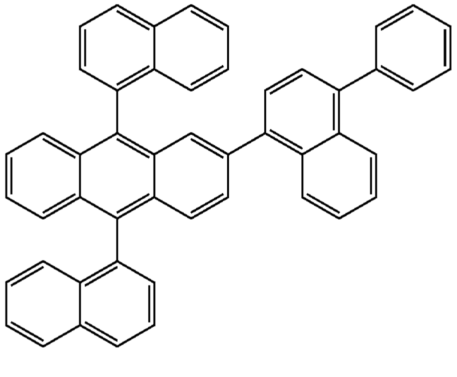

-continued
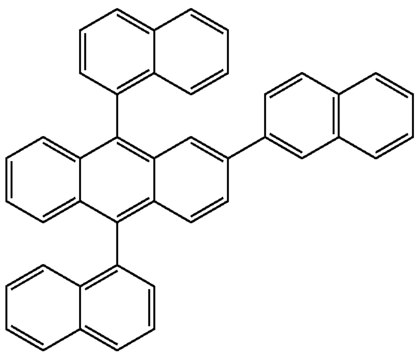
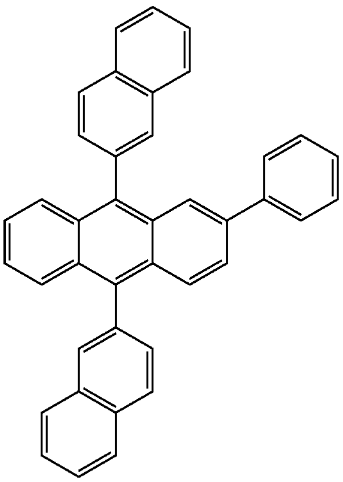
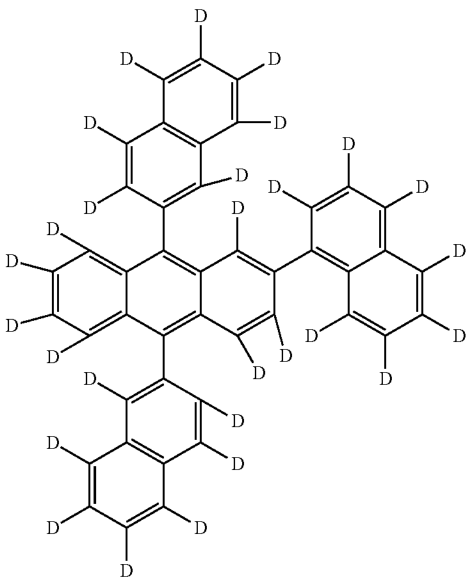
-continued
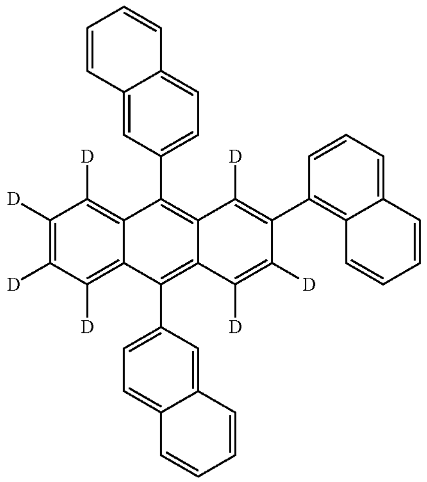
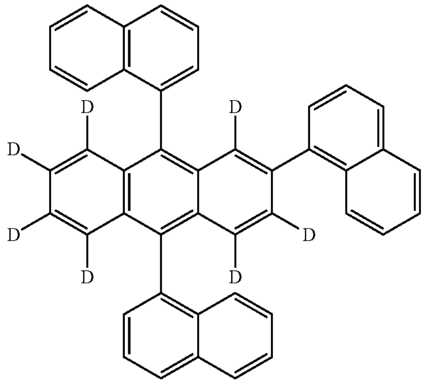
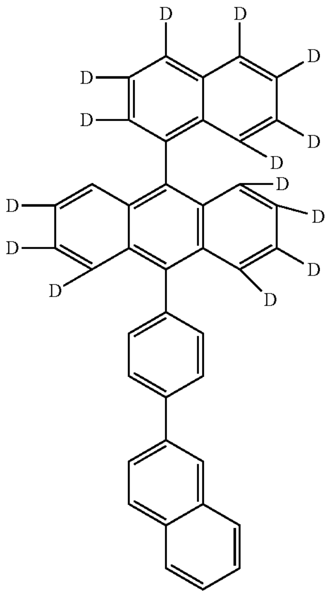

-continued
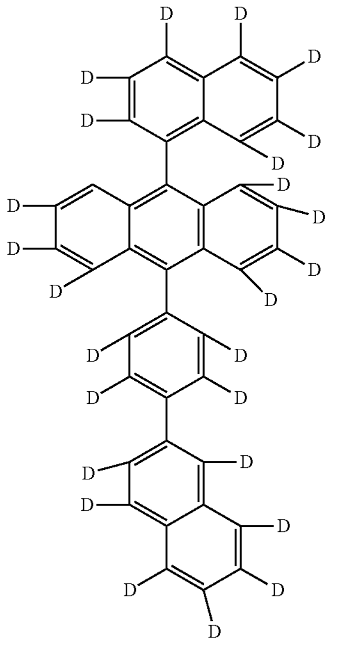
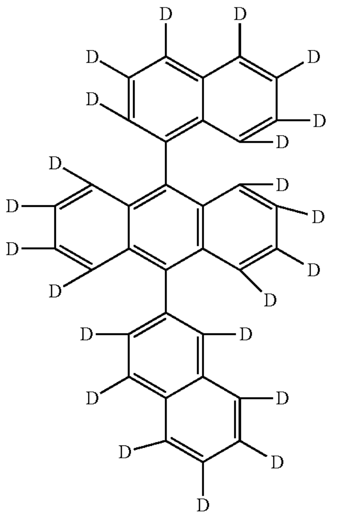
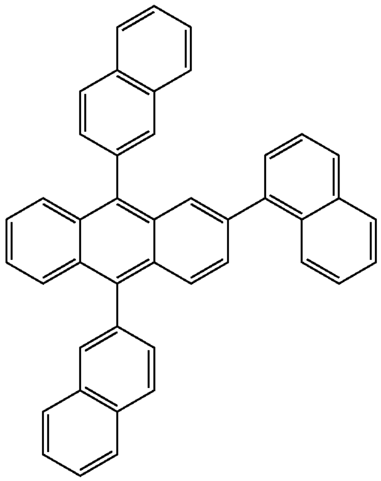
-continued
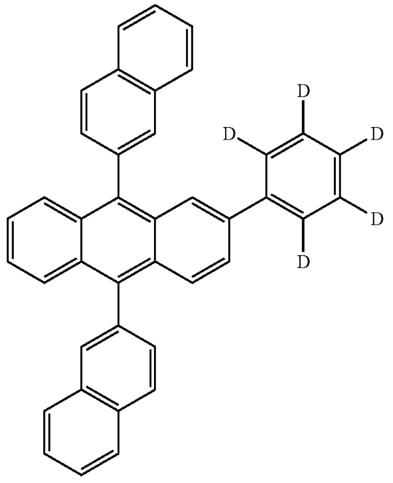
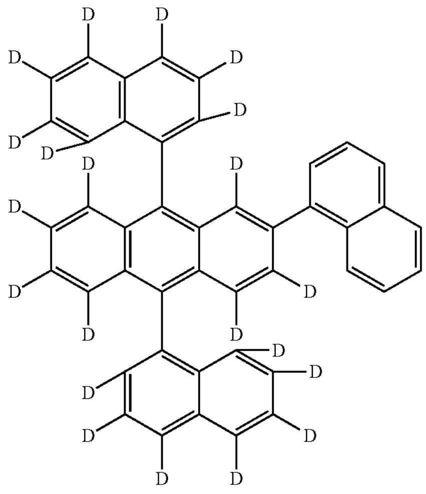
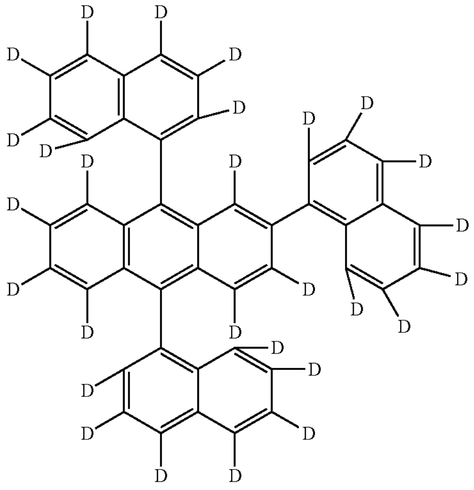

-continued
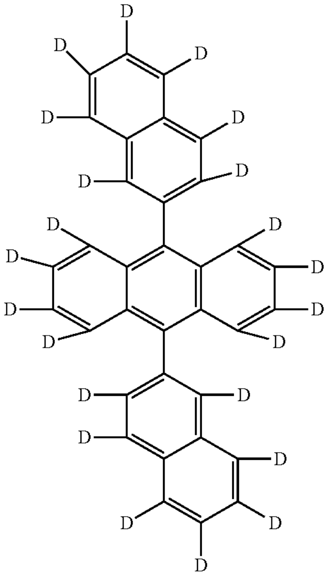
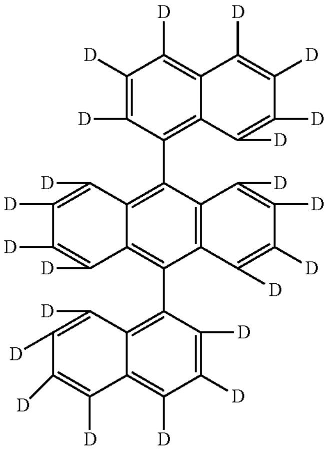
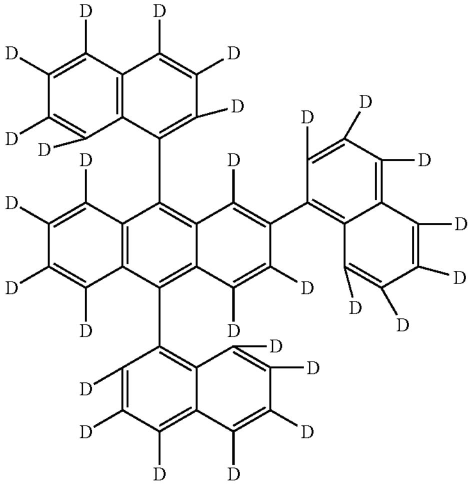
-continued
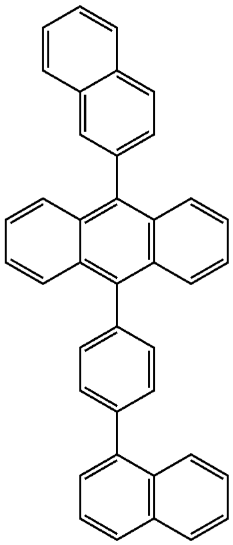
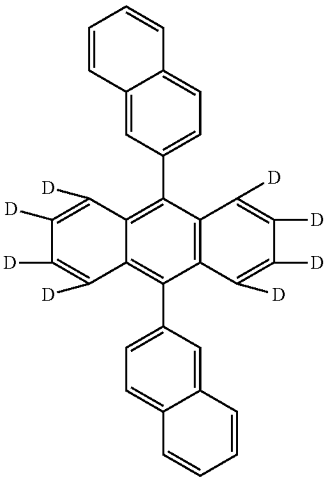
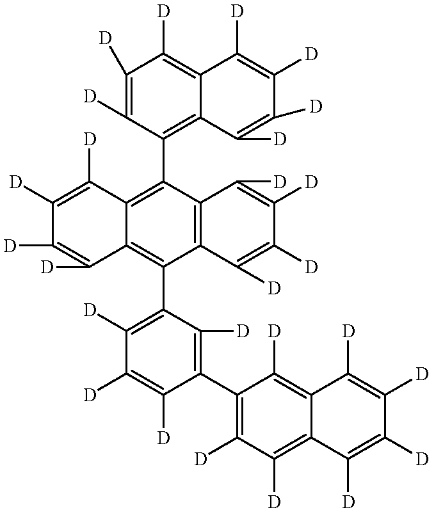
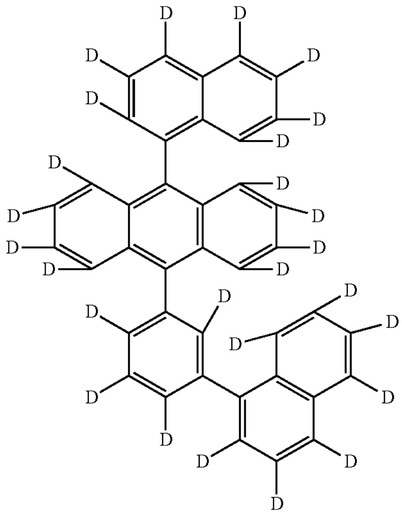

-continued
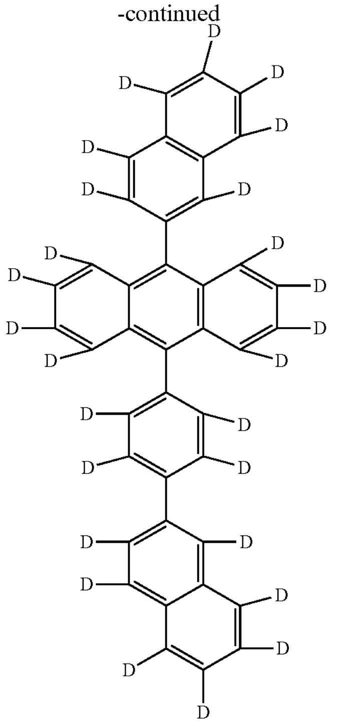
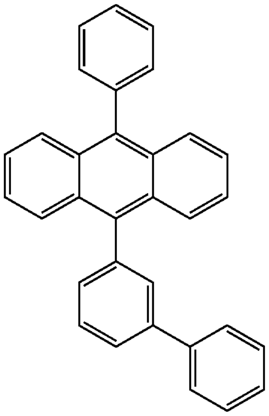
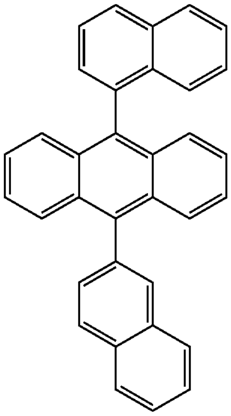
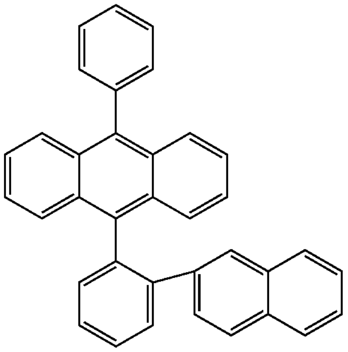
-continued
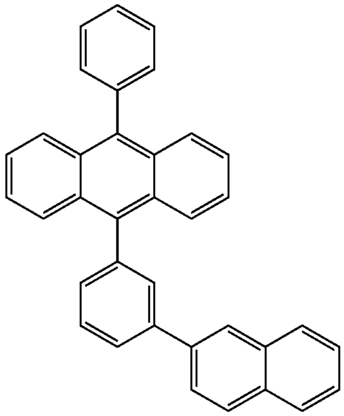
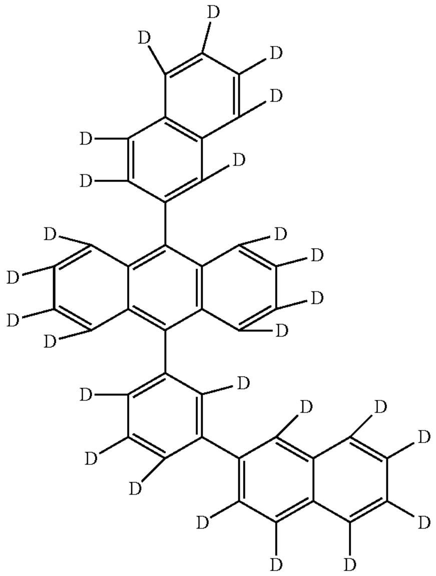
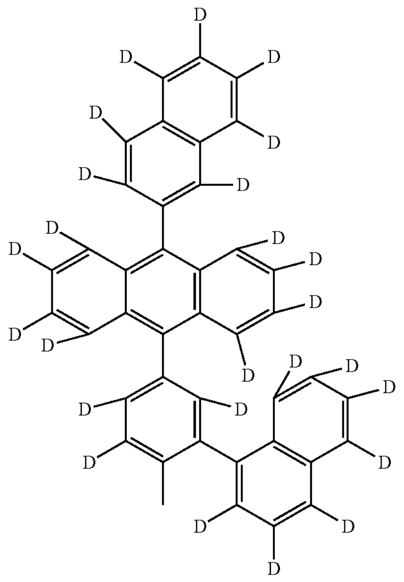

-continued
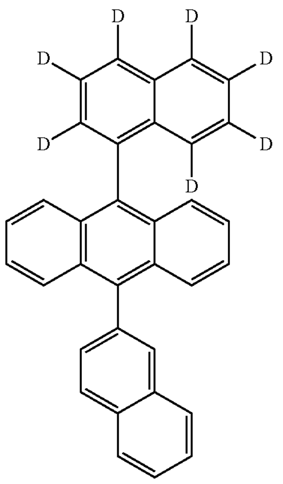
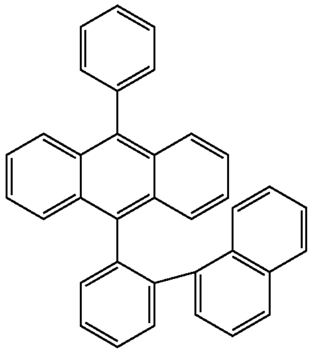
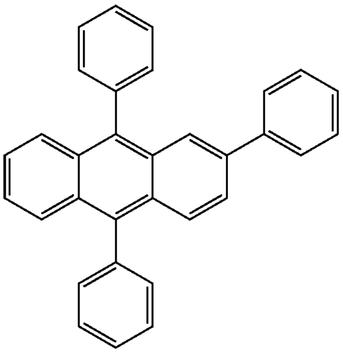
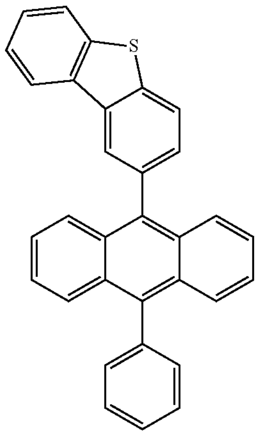
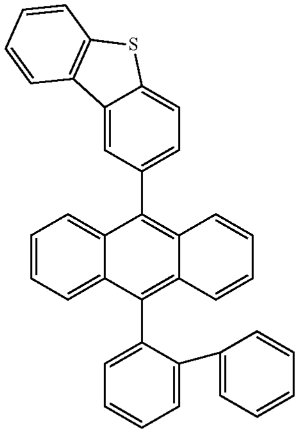
-continued
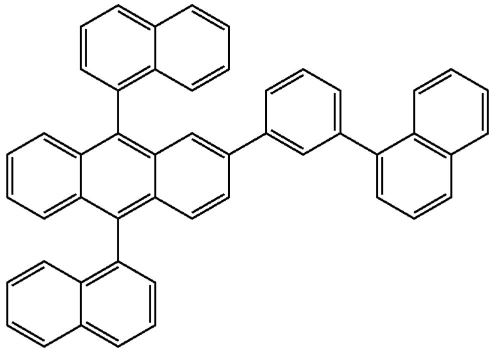
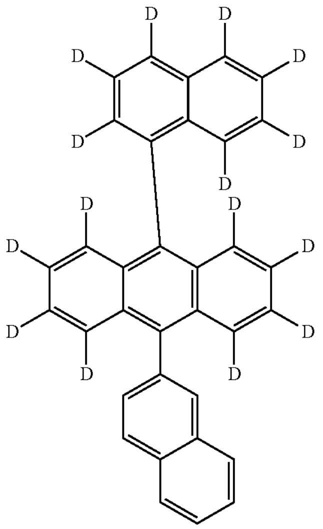
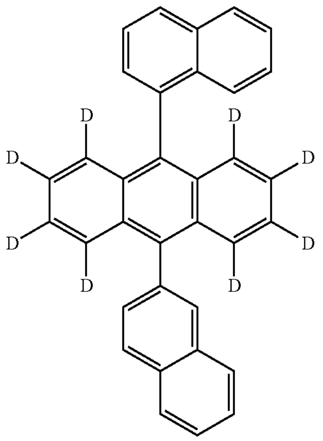

-continued
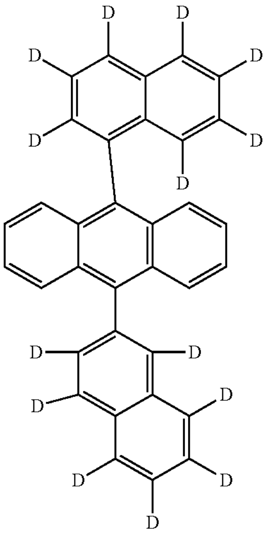
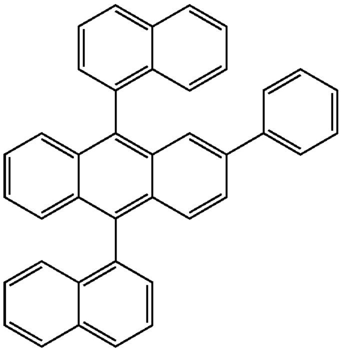
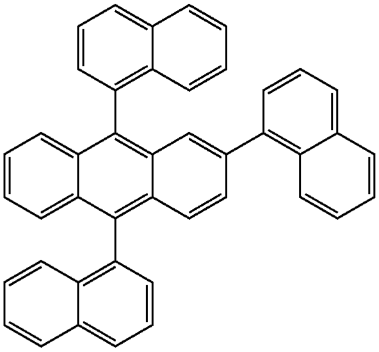
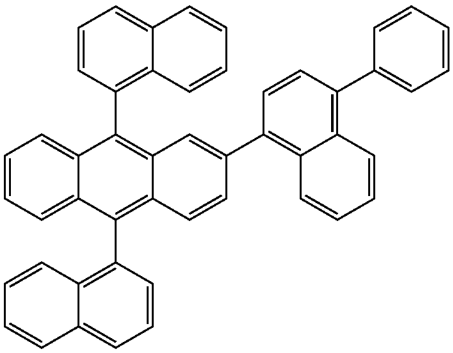
-continued
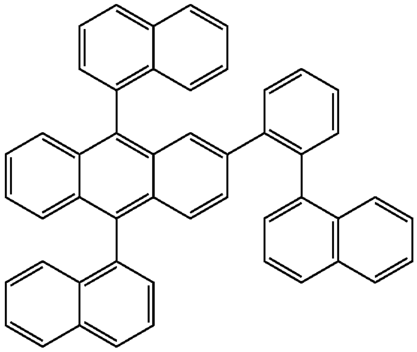
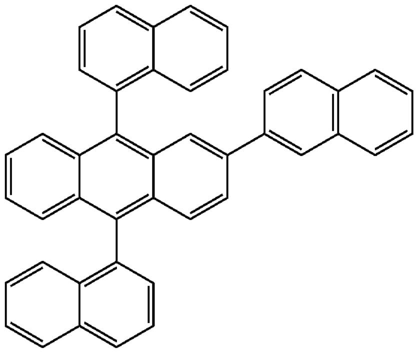
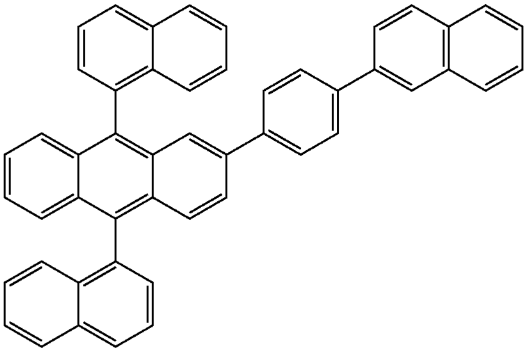
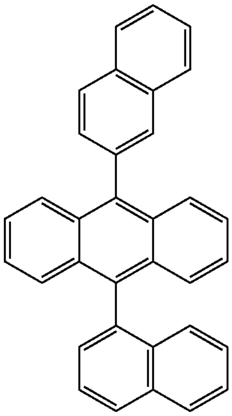
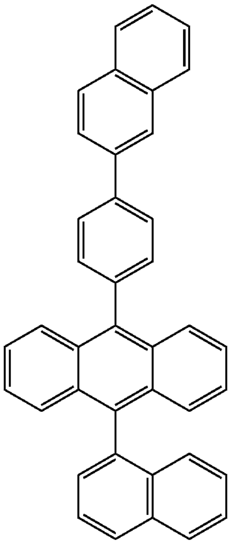

-continued
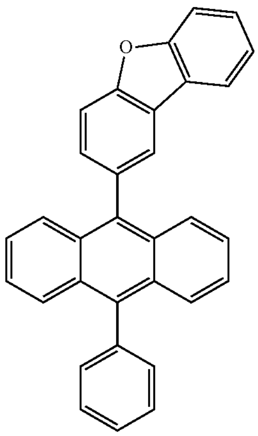
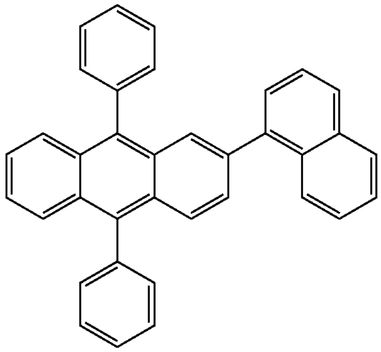
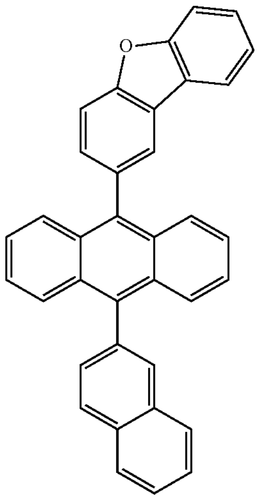
-continued
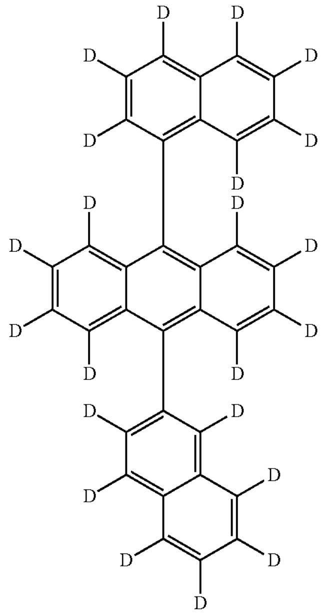
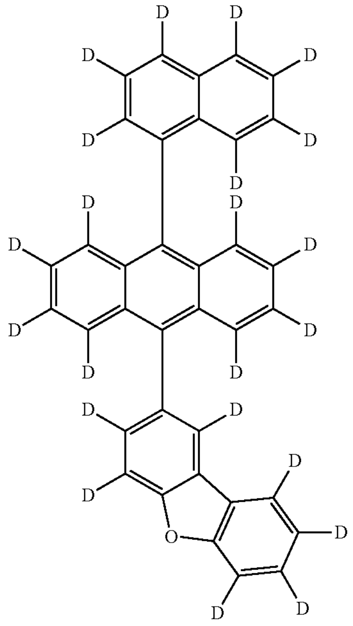

-continued
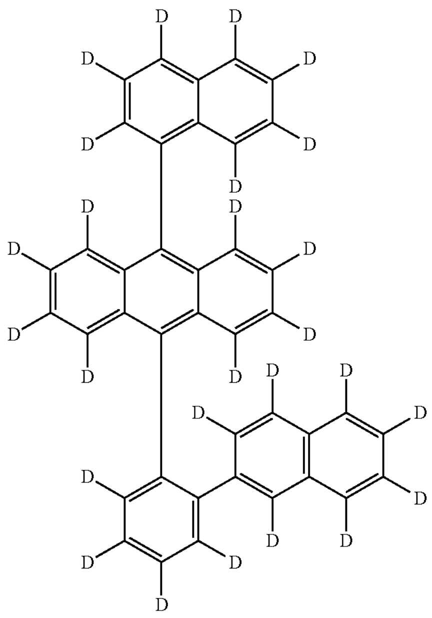
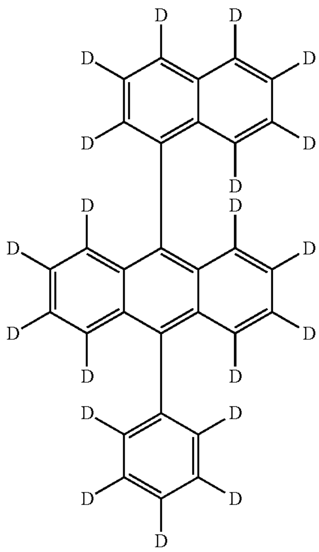
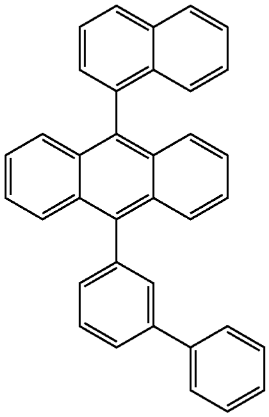
-continued
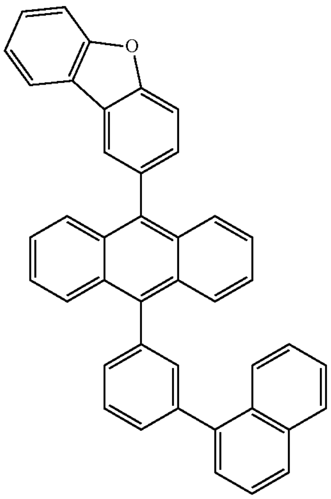
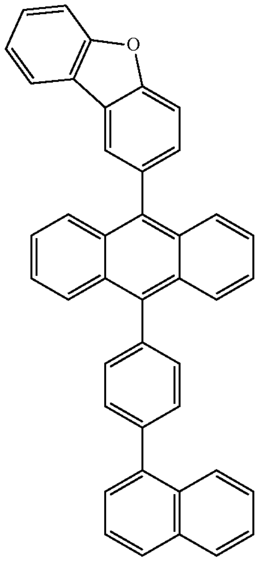
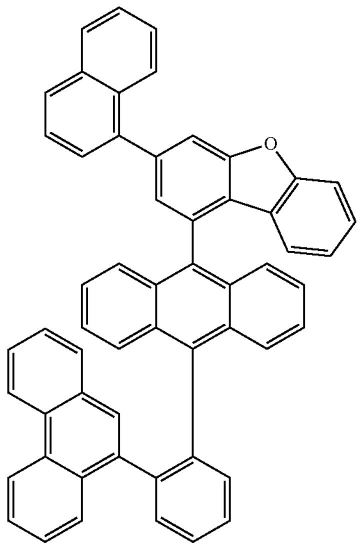

-continued
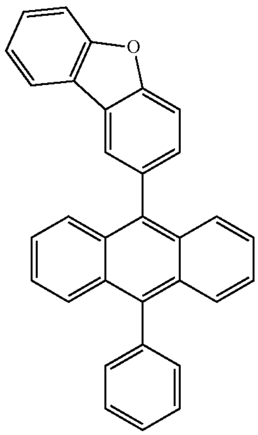
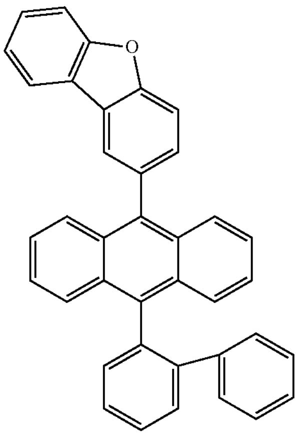
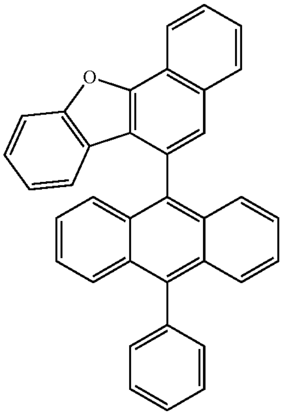
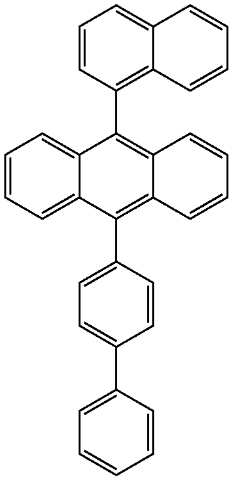
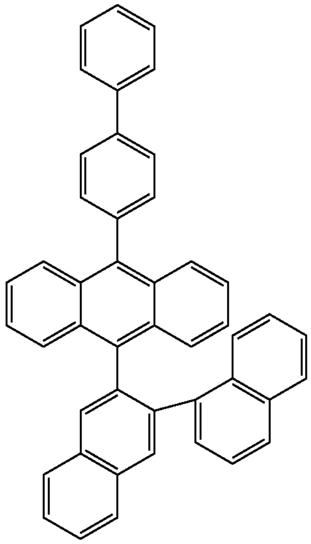
-continued
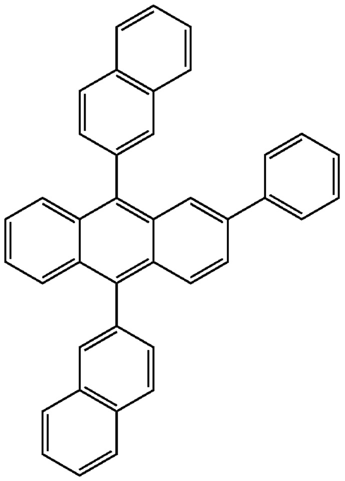
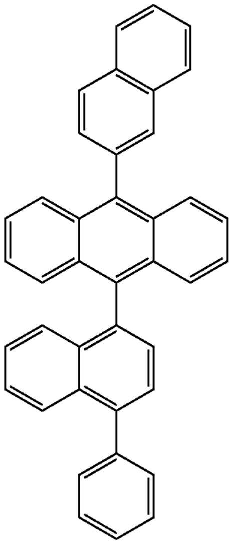
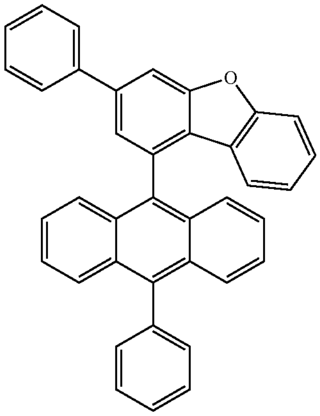
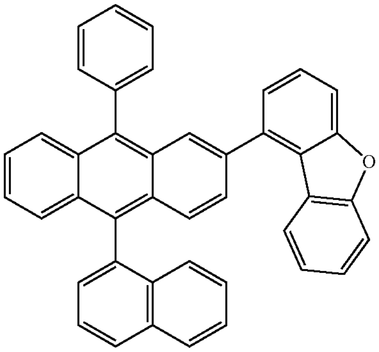

-continued
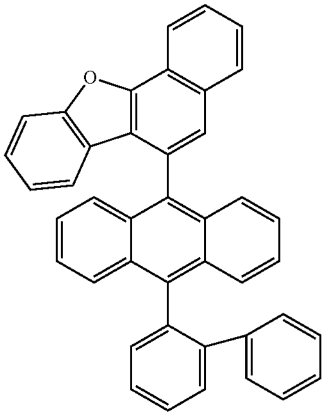
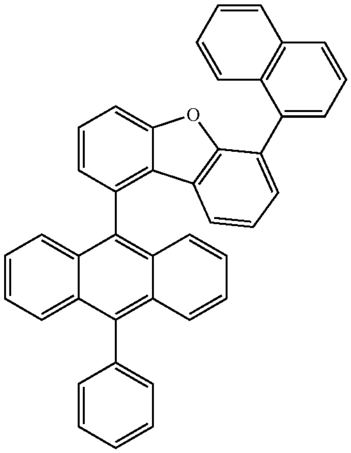
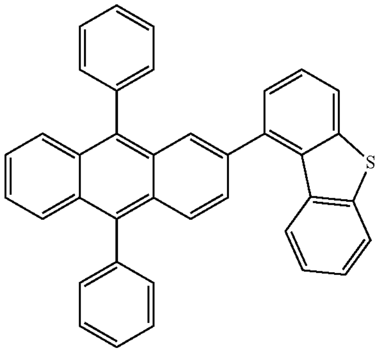
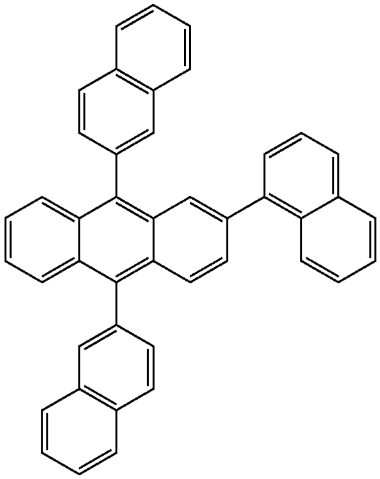
-continued
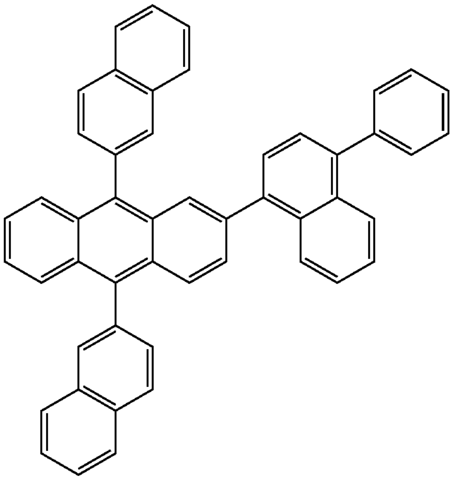
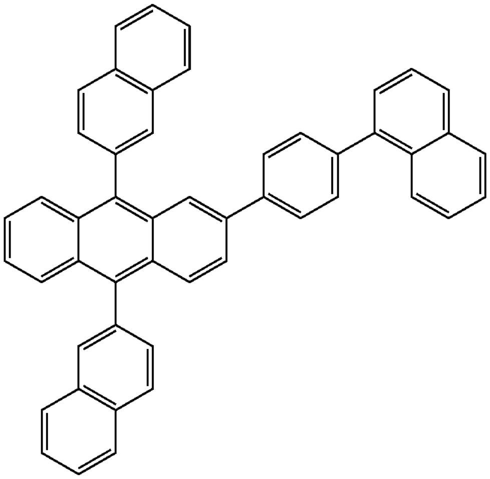
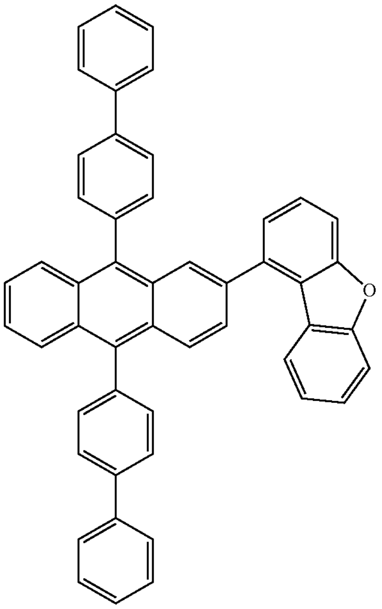

-continued
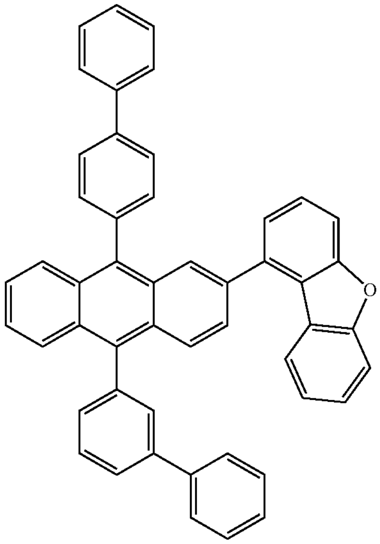
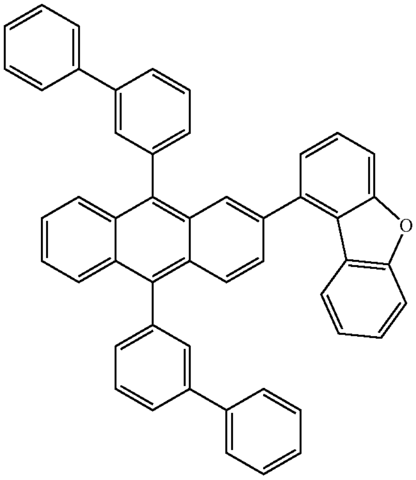
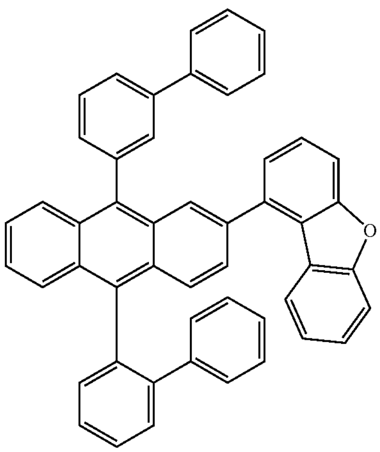
-continued
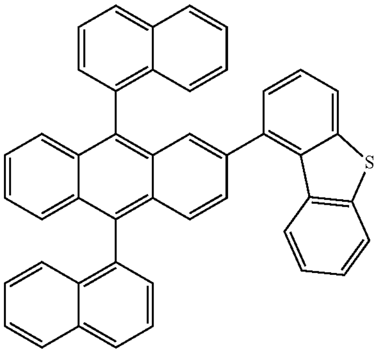
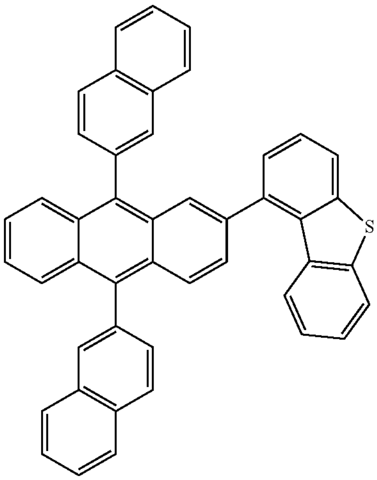
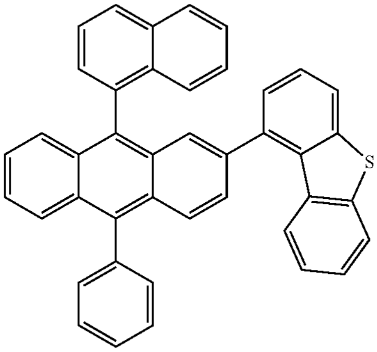
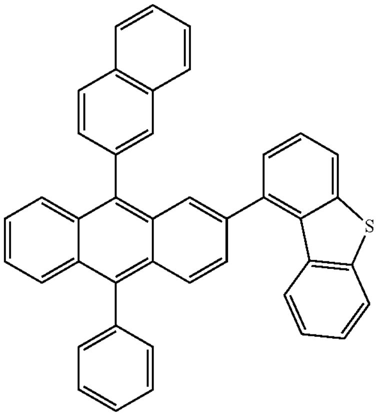

-continued

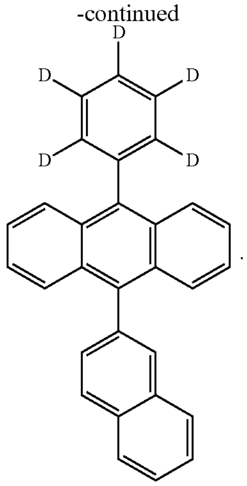

The organic light emitting device according to one embodiment of the present specification includes an organic material layer, the organic material layer includes a light emitting layer, and the light emitting layer includes the heterocyclic compound of Chemical Formula 1 as a dopant of the light emitting layer and includes the compound of Chemical Formula 2 as a host of the light emitting layer.

According to one embodiment of the present specification, a content of the heterocyclic compound of Chemical Formula 1 is from 0.01 parts by weight to 30 parts by weight, from 0.1 parts by weight to 20 parts by weight, or from 0.5 parts by weight to 10 parts by weight based on 100 parts by weight of a weight of the compound of Chemical Formula 2.

According to one embodiment of the present specification, the light emitting layer can further include one host material in addition to the compound of Chemical Formula 2. Herein, the host material further included (mixed host compound) includes fused aromatic ring derivatives, heteroring-containing compounds or the like. Specifically, anthracene derivatives, pyrene derivatives, naphthalene derivatives, pentacene derivatives, phenanthrene compounds, fluoranthene compounds or the like can be included as the fused aromatic ring derivative, and dibenzofuran derivatives, ladder-type furan compounds, pyrimidine derivatives or the like can be included as the heteroring-containing compound, however, the host material further included is not limited thereto.

The compound of Chemical Formula 2 and the mixed host compound have a weight ratio of 95:5 to 5:95, and more preferably 30:70 to 70:30.

According to one embodiment of the present specification, the light emitting layer includes one, two or more types of the compound of Chemical Formula 2.

According to one embodiment of the present specification, the light emitting layer including the heterocyclic compound of Chemical Formula 1 and the compound of Chemical Formula 2 has a blue color.

The organic light emitting device according to one embodiment of the present specification includes two or more light emitting layers, and at least one of the two or more light emitting layers includes the heterocyclic compound of Chemical Formula 1 and the compound of Chemical Formula 2. The light emitting layer including the heterocyclic compound of Chemical Formula 1 and the compound of Chemical Formula 2 has a blue color, and the light emitting layer that does not include the heterocyclic compound of Chemical Formula 1 and the compound of Chemical Formula 2 can include a blue, red or green light emitting compound known in the art.

According to one embodiment of the present specification, the organic material layer includes a hole injection layer or a hole transfer layer.

According to one embodiment of the present specification, the organic material layer includes an electron injection layer or an electron transfer layer.

According to one embodiment of the present specification, the organic material layer includes an electron blocking layer.

According to one embodiment of the present specification, the organic material layer includes a hole blocking layer.

According to one embodiment of the present specification, the organic light emitting device further includes one, two or more layers selected from the group consisting of a hole injection layer, a hole transfer layer, a light emitting layer, an electron transfer layer, an electron injection layer, a hole blocking layer and an electron blocking layer.

According to one embodiment of the present specification, the organic light emitting device includes a first electrode; a second electrode provided opposite to the first electrode; a light emitting layer provided between the first electrode and the second electrode; and two or more organic material layers provided between the light emitting layer and the first electrode, or between the light emitting layer and the second electrode.

According to one embodiment of the present specification, as the two or more organic material layers, two or more can be selected from the group consisting of a light emitting layer, a hole transfer layer, a hole injection layer, a layer carrying out hole transfer and hole injection at the same time, and an electron blocking layer.

In one embodiment of the present specification, the organic light emitting device can include two or more electron transfer layers, but is not limited thereto.

In one embodiment of the present specification, the organic light emitting device can include two or more hole transfer layers, but is not limited thereto.

According to one embodiment of the present specification, the first electrode is an anode or a cathode.

According to one embodiment of the present specification, the second electrode is a cathode or an anode.

According to one embodiment of the present specification, the organic light emitting device can be an organic light emitting device having a structure in which an anode, one or more organic material layers and a cathode are consecutively laminated on a substrate (normal type).

According to one embodiment of the present specification, the organic light emitting device can be an organic light emitting device having a structure in a reverse direction in which a cathode, one or more organic material layers, and an anode are consecutively laminated on a substrate (inverted type).

For example, structures of the organic light emitting device according to one embodiment of the present specification are illustrated in FIG. 1 to FIG. 4. FIG. 1 to FIG. 4 illustrate the organic light emitting device, and the organic light emitting device is not limited thereto.

FIG. 1 illustrates a structure of the organic light emitting device in which an anode (102), a light emitting layer (106) and a cathode (110) are consecutively laminated on a substrate (101). The heterocyclic compound of Chemical Formula 1 is included in the light emitting layer. According to one embodiment of the present specification, the compound of Chemical Formula 2 can be further included in the light emitting layer.

FIG. 2 illustrates a structure of the organic light emitting device in which an anode (102), a hole injection layer (103), a hole transfer layer (104), a light emitting layer (106) and a cathode (110) are consecutively laminated on a substrate (101). According to one embodiment of the present specification, the heterocyclic compound of Chemical Formula 1 is included in the light emitting layer. According to one embodiment of the present specification, the compound of Chemical Formula 2 can be further included in the light emitting layer. According to another embodiment, the heterocyclic compound of Chemical Formula 1 is included in the hole injection layer or the hole transfer layer.

FIG. 3 illustrates a structure of the organic light emitting device in which an anode (102), a hole injection layer (103), a hole transfer layer (104), an electron blocking layer (105), a light emitting layer (106), a hole blocking layer (107), an electron transfer layer (108), an electron injection layer (109) and a cathode (110) are consecutively laminated on a substrate (101). According to one embodiment of the present specification, the heterocyclic compound of Chemical Formula 1 is included in the light emitting layer. According to one embodiment of the present specification, the compound of Chemical Formula 2 can be further included in the light emitting layer. According to another embodiment, the heterocyclic compound of Chemical Formula 1 is included in the hole injection layer, the hole transfer layer, the electron blocking layer, the hole blocking layer, the electron transfer layer or the electron injection layer.

FIG. 4 illustrates a structure of the organic light emitting device in which an anode (102), a hole injection layer (103), a first hole transfer layer (104-1), a second hole transfer layer (104-2), a light emitting layer (106), a first electron transfer layer (108-1), a second electron transfer layer (108-2), an electron injection layer (109) and a cathode (110) are consecutively laminated on a substrate (101). According to one embodiment of the present specification, the heterocyclic compound of Chemical Formula 1 is included in the light emitting layer. According to one embodiment of the present specification, the compound of Chemical Formula 2 can be further included in the light emitting layer. According to another embodiment, the heterocyclic compound of Chemical Formula 1 is included in the hole injection layer, the hole transfer layer, the electron blocking layer, the hole blocking layer, the electron transfer layer or the electron injection layer.

The organic light emitting device of the present specification can be manufactured using materials and methods known in the art, except that the light emitting layer includes the compound, that is, the heterocyclic compound of Chemical Formula 1 and the compound of Chemical Formula 2.

When the organic light emitting device includes a plurality of organic material layers, the organic material layers can be formed with the same materials or different materials.

For example, the organic light emitting device of the present specification can be manufactured by consecutively laminating a first electrode, an organic material layer and a second electrode on a substrate. Herein, the organic light emitting device can be manufactured by forming an anode on a substrate by depositing a metal, a metal oxide having conductivity, or an alloy thereof using a physical vapor deposition (PVD) method such as sputtering or e-beam evaporation, and forming an organic material layer including a hole injection layer, a hole transfer layer, a light emitting layer and an electron transfer layer thereon, and then depositing a material capable of being used as a cathode thereon. In addition to such a method, the organic light emitting device can also be manufactured by consecutively depositing a cathode material, an organic material layer and an anode material on a substrate.

In addition, the heterocyclic compound of Chemical Formula 1 or the compound of Chemical Formula 2 can be formed into an organic material layer using a solution coating method as well as a vacuum deposition method when manufacturing the organic light emitting device. Herein, the solution coating method means spin coating, dip coating, doctor blading, inkjet printing, screen printing, a spray method, roll coating and the like, but is not limited thereto.

In addition to such a method, the organic light emitting device can also be manufactured by consecutively laminating a cathode material, an organic material layer and an anode material on a substrate. However, the manufacturing method is not limited thereto.

As the anode material, materials having large work function are normally preferred so that hole injection to an organic material layer is smooth. Examples thereof include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, but are not limited thereto.

As the cathode material, materials having small work function are normally preferred so that electron injection to an organic material layer is smooth. Examples thereof include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

The organic light emitting device according to the present specification can include an additional light emitting layer in addition to the light emitting layer including the heterocyclic compound of Chemical Formula 1 and/or the compound of Chemical Formula 2. The additional light emitting layer can include a host material and a dopant material. The host material includes fused aromatic ring derivatives, heteroring-containing compounds or the like. Specifically, the fused aromatic ring derivative includes anthracene derivatives, pyrene derivatives, naphthalene derivatives, pentacene derivatives, phenanthrene compounds, fluoranthene compounds and the like, and the heteroring-containing compound includes dibenzofuran derivatives, ladder-type furan compounds, pyrimidine derivatives and the like, however, the material is not limited thereto.

The dopant material includes aromatic amine derivatives, styrylamine compounds, boron complexes, fluoranthene compounds, metal complexes and the like. Specifically, the aromatic amine derivative is a fused aromatic ring derivative having a substituted or unsubstituted arylamine group and includes arylamine group-including pyrene, anthracene, chrysene, periflanthene and the like. In addition, the styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamine group are substituted or unsubstituted. Specifically, styrylamine, styryldiamine, styryltriamine, styryltetramine or the like is included, however, the styrylamine compound is not limited thereto. In addition, the metal complex includes iridium complexes, platinum complexes or the like, but is not limited thereto.

The hole injection layer is a layer receiving holes from an electrode. The hole injection material preferably has, by having an ability to transfer holes, a hole receiving effect from an anode and an excellent hole injection effect for a light emitting layer or a light emitting material. In addition, the hole injection material is preferably a material having an excellent ability to prevent excitons generated in the light emitting layer from moving to an electron injection layer or an electron injection material. In addition, a material having an excellent thin film forming ability is preferred. In addition, the highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials; hexanitrile hexaazatriphenylene-based organic materials; quinacridone-based organic materials; perylene-based organic materials; polythiophene-based conductive polymers such as anthraquinone or polyaniline, and the like, but are not limited thereto.

The hole transfer layer is a layer receiving holes from a hole injection layer and transferring the holes to a light emitting layer. As the hole transfer material, materials having, as a material capable of receiving holes from an anode or a hole injection layer and moving the holes to a light emitting layer, high mobility for the holes are preferred. Specific examples thereof include arylamine-based organic materials, conductive polymers, block copolymers having conjugated parts and non-conjugated parts together, and the like, but are not limited thereto.

The electron transfer layer is a layer receiving electrons from an electron injection layer and transferring the electrons to a light emitting layer. As the electron transfer material, materials capable of favorably receiving electrons from a cathode, moving the electrons to a light emitting layer, and having high mobility for the electrons are preferred. Specific examples thereof include Al complexes of 8-hydroxyquinoline; complexes including $Alq_3$; organic radical compounds; hydroxyflavon-metal complexes, and the like, but are not limited thereto. The electron transfer layer can be used together with any desired cathode material as used in the art. Particularly, the suitable cathode material is a common material having low work function and having an aluminum layer or a silver layer following. Specifically, cesium, barium, calcium, ytterbium, samarium and the like are included, and in each case, an aluminum layer or a silver layer follows.

The electron injection layer is a layer receiving electrons from an electrode. As the electron injection material, materials having an excellent electron transferring ability, having an electron receiving effect from a second electrode, and having an excellent electron injection effect for a light emitting layer or light emitting material are preferred. In addition, materials preventing excitons generated in the light emitting layer from moving to a hole injection layer, and having an excellent thin film forming ability are preferred. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited thereto.

The metal complex compound includes 8-hydroxy-quinolinato lithium, bis(8-hydroxyquinolinato)zinc, bis(8-hydroxyquinolinato)copper, bis(8-hydroxyquinolinato)-manganese, tris(8-hydroxyquinolinato)aluminum, tris(2-methyl-8-hydroxy-quinolinato)aluminum, tris(8-hydroxy-quinolinato)gallium, bis(10-hydroxybenzo[h]quinolinato)-beryllium, bis(10-hydroxy-benzo[h]quinolinato)zinc, bis(2-methyl-8-quinolinato)-chlorogallium, bis(2-methyl-8-quinolinato) (o-cresolato)-gallium, bis(2-methyl-8-quinolinato) (1-naphtholato)aluminum, bis(2-methyl-8-quinolinato) (2-naphtholato)gallium and the like, but is not limited thereto.

The electron blocking layer is a layer capable of enhancing lifetime and efficiency of a device by preventing electrons injected from an electron injection layer from passing through a light emitting layer and entering a hole injection layer. Known material can be used without limit, and the electron blocking layer can be formed between the light emitting layer and the hole injection layer, or between the light emitting layer and a layer carrying out hole injection and hole transfer at the same time.

The hole blocking layer is a layer blocking holes from reaching a light emitting layer, and can be generally formed under the same condition as the electron injection layer. Specific examples thereof can include oxadiazole derivatives, triazole derivatives, phenanthroline derivatives, aluminum complexes and the like, but are not limited thereto.

The organic light emitting device according to the present specification can be a top-emission type, a bottom-emission type or a dual-emission type depending on the materials used.

EXAMPLES

Hereinafter, the present specification will be described in detail with reference to examples, comparative examples and the like. However, the examples and the comparative examples according to the present specification can be modified to various other forms, and the scope of the present specification is not to be construed as being limited to the examples and the comparative examples described below.

Examples and comparative examples of the present specification are provided in order to more fully describe the present specification to those having average knowledge in the art.

Synthesis Example 1. Synthesis of Compound 1

1-1. Synthesis of Intermediate 1

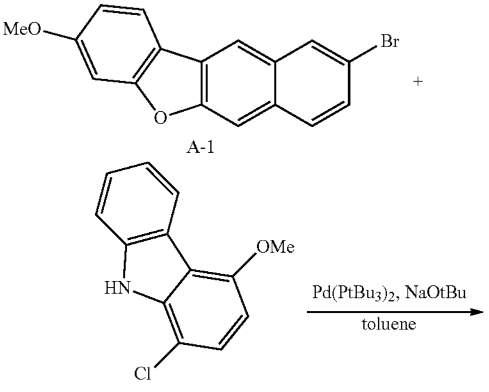

A-1
B-1

-continued

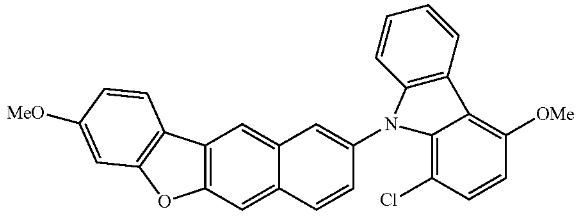

Intermediate 1

After introducing starting material A-1 (10 g), carbazole B-1 (7.2 g), sodium tert-butoxide (4.4 g) and bis(tri(tert-butyl)phosphine)palladium(0) ($Pd(PtBu_3)_2$) (0.3 g) to toluene (250 mL) under the nitrogen atmosphere, the result was heated to 140° C., and stirred for 5 hours. After the reaction was finished, the reaction solution was cooled to room temperature, separated by adding water and aq. $NH_4Cl$ thereto, and then treated with $MgSO_4$ (anhydrous) and filtered. The filtered solution was removed by distillation under vacuum, and then purified by recrystallization to obtain Intermediate 1 (10 g, yield 68%, Mass [M+]=478).

1-2. Synthesis of Intermediate 2

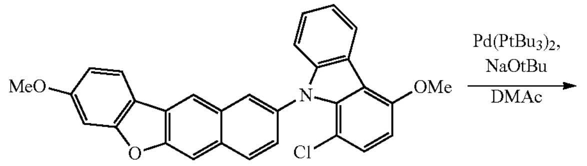

Intermediate 1

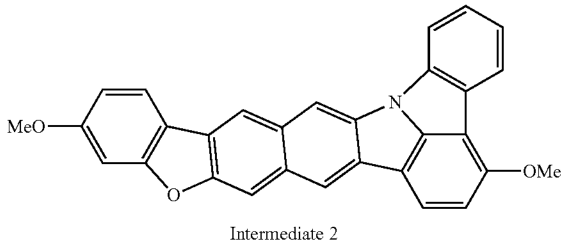

Intermediate 2

After introducing Intermediate 1 (10 g), sodium tert-butoxide (4.0 g) and bis(tri(tert-butyl)phosphine)-palladium (0) ($Pd(PtBu_3)_2$) (0.2 g) to dimethylacetamide (100 mL) under the nitrogen atmosphere, the result was heated to 120° C., and stirred for 10 hours. After the reaction was finished, the reaction solution was cooled to room temperature, separated by adding water and aq. $NH_4Cl$ thereto, and then treated with $MgSO_4$ (anhydrous) and filtered. The filtered solution was removed by distillation under vacuum, and then purified by recrystallization (toluene/hexane) to obtain Intermediate 2 (6.0 g, yield 65%, Mass [M+]=442).

1-3. Synthesis of Intermediate 4

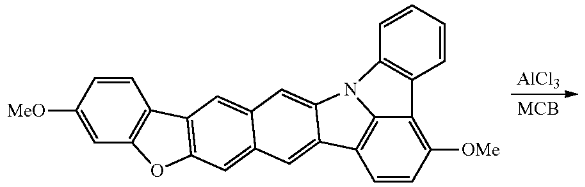

Intermediate 2

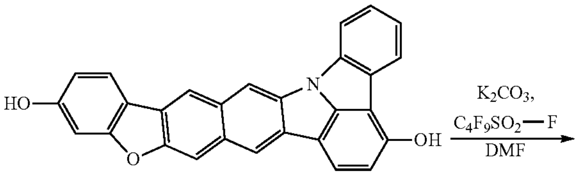

Intermediate 3

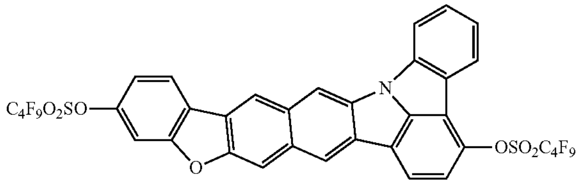

Intermediate 4

After introducing Intermediate 2 (6.0 g) and aluminum chloride (4.5 g) to chlorobenzene (100 mL) under the nitrogen atmosphere, the result was heated to 130° C., and stirred for 8 hours. After the reaction was finished, the reaction solution was cooled to room temperature, separated by adding water and ethyl acetate thereto, and then treated with $MgSO_4$ (anhydrous) and filtered. The filtered solution was removed by distillation under vacuum, and then purified by recrystallization (ethyl acetate/hexane) to obtain Intermediate 3 (4.1 g, yield 73%, Mass [M+]=414).

After introducing dimethylformamide (75 mL) to Intermediate 3 (4.1 g) and potassium carbonate (4.1 g), nonafluorobutanesulfonyl fluoride (3.7 mL) was added dropwise thereto at room temperature, and the result was stirred for 5 hours. After the reaction was finished, the reaction solution was filtered. The filtered solution was separated by adding water and ethyl acetate thereto, and then treated with $MgSO_4$ (anhydrous) and filtered. The filtered solution was removed by distillation under vacuum, and purified by recrystallization (toluene/hexane) to obtain Intermediate 4 (7.6 g, yield 78%, Mass [M+]=978).

1-4. Synthesis of Compound 1

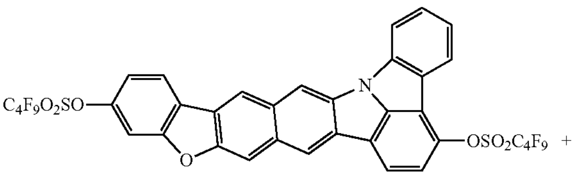

Intermediate 4

-continued

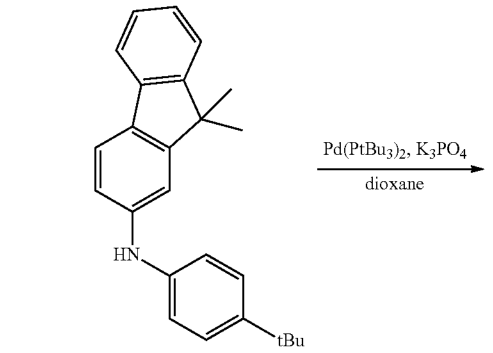

AM-1

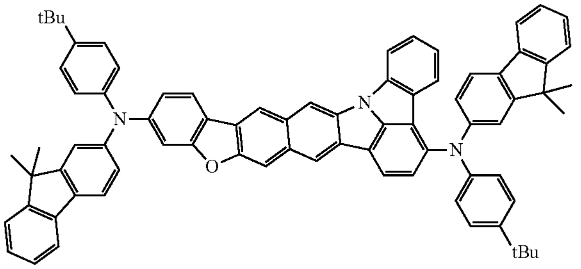

Compound 1

After introducing Intermediate 4 (4.0 g), (4-tert-butylphenyl)-(9,9-dimethyl-9H-fluoren-2-yl)amine (2.8 g), potassium phosphate (2.2 g) and bis(tri(tert-butyl)phosphine) palladium(0) ($Pd(PtBu_3)_2$) (0.04 g) to dioxane (100 mL) under the nitrogen atmosphere, the result was heated to 100° C., and stirred for 28 hours. After the reaction was finished, the reaction solution was cooled to room temperature, separated by adding water and aq. NaCl thereto, and then treated with $MgSO_4$ (anhydrous) and filtered. The filtered solution was removed by distillation under vacuum, and purified by recrystallization (toluene/hexane) to obtain Compound 1 (3.6 g, yield 83%, Mass [M+]=1061).

Synthesis Example 2. Synthesis of Compound 2

2-1. Synthesis of Intermediate 5

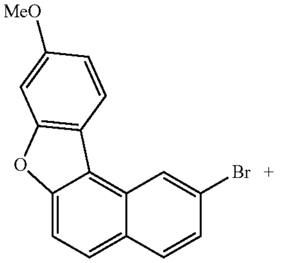

A-2

-continued

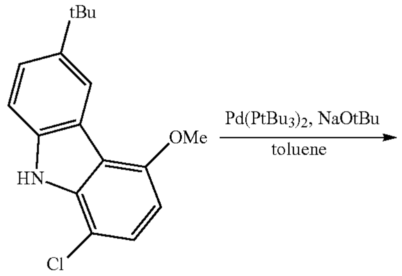

B-2

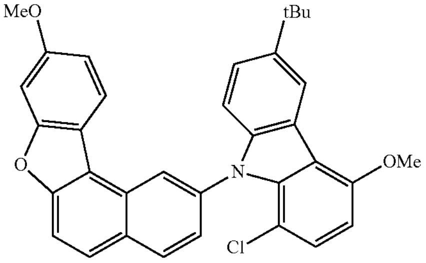

Intermediate 5

Intermediate 5 (6.5 g, yield 79%, Mass [M+]=535) was obtained in the same manner as in Synthesis of Intermediate 1 of Synthesis Example 1, except that A-2 (5.0 g) was used instead of starting material A-1, and B-2 (4.4 g) was used instead of B-1.

2-2. Synthesis of Intermediate 6

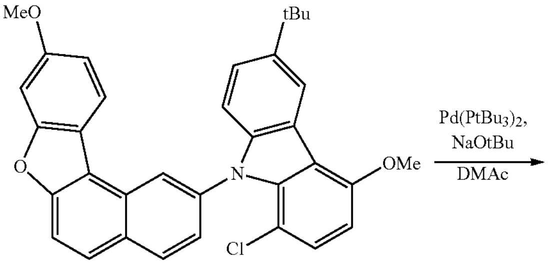

Intermediate 5

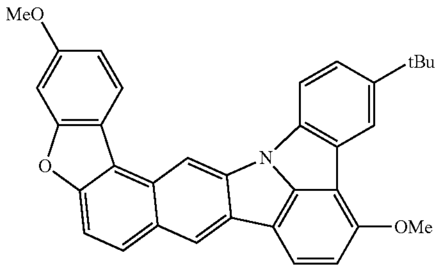

Intermediate 6

Intermediate 6 (4.6 g, yield 75%, Mass [M+]=498) was obtained in the same manner as in Synthesis of Intermediate 2 of Synthesis Example 1, except that Intermediate 5 (10 g) was used instead of Intermediate 1.

2-3. Synthesis of Intermediate 8

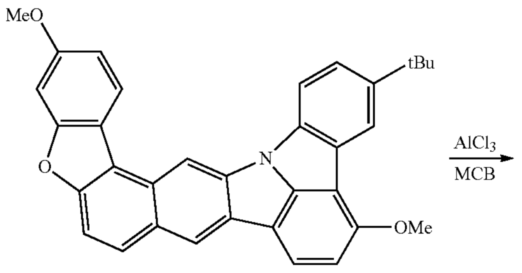

Intermediate 6

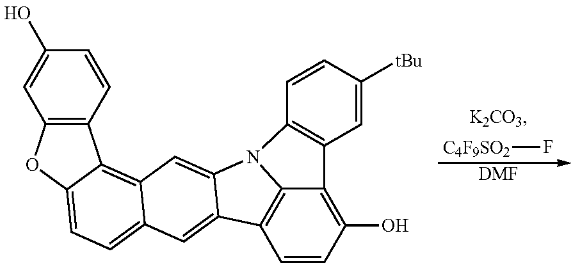

Intermediate 7

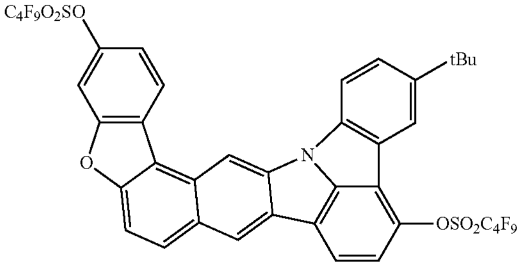

Intermediate 8

Intermediate 7 (3.2 g, yield 74%, Mass [M+]=470) was obtained in the same manner as in Synthesis of Intermediate 3 of Synthesis Example 1, except that Intermediate 6 (4.6 g) was used instead of Intermediate 2.

Intermediate 8 (5.8 g, yield 82%, Mass [M+]=1034) was obtained in the same manner as in Synthesis of Intermediate 4 of Synthesis Example 1, except that Intermediate 7 (3.9 g) was used instead of Intermediate 3.

2-4. Synthesis of Compound 2

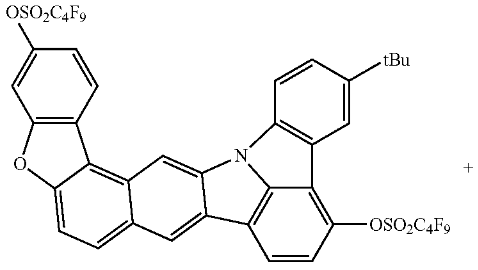

Intermediate 8

-continued

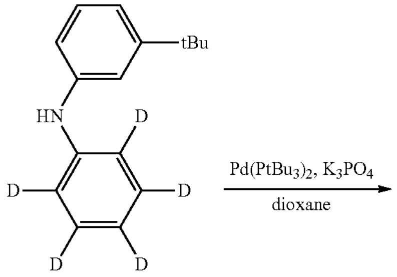

AM-2

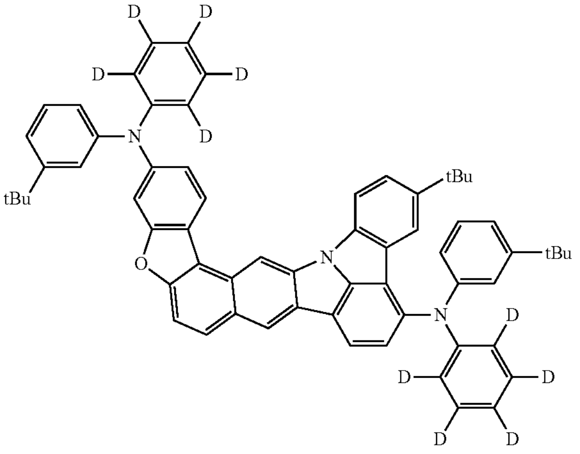

Compound2

Compound 2 (2.2 g, yield 84%, Mass [M+]=895) was obtained in the same manner as in Synthesis of Compound 1 of Synthesis Example 1, except that Intermediate 8 (3.0 g) was used instead of Intermediate 4, and AM-2 (1.3 g) was used instead of AM-1.

Synthesis Example 3. Synthesis of Compound 3

3-1. Synthesis of Intermediate 9

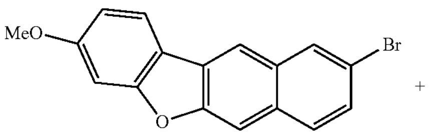

A-1

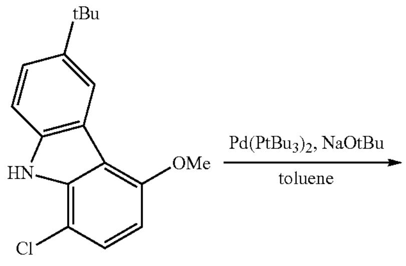

B-2

-continued

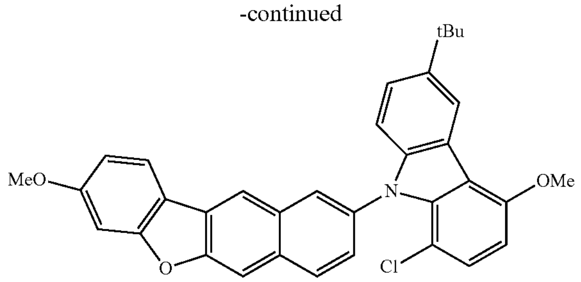

Intermediate 9

Intermediate 9 (6.4 g, yield 78%, Mass [M+]=535) was obtained in the same manner as in Synthesis of Intermediate 1 of Synthesis Example 1, except that B-2 (4.4 g) was used instead of B-1.

3-2. Synthesis of Intermediate 10

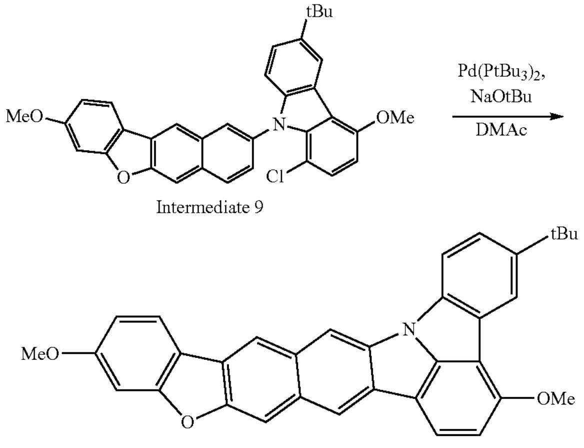

Intermediate 9

Intermediate 10

Intermediate 10 (4.1 g, yield 69%, Mass [M+]=498) was obtained in the same manner as in Synthesis of Intermediate 2 of Synthesis Example 1, except that Intermediate 9 (6.4 g) was used instead of Intermediate 1.

3-3. Synthesis of Intermediate 12

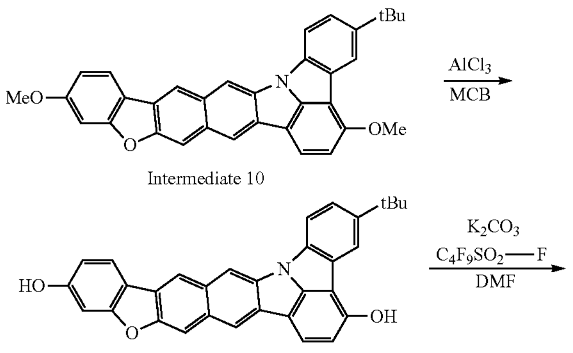

Intermediate 10

Intermediate 11

-continued

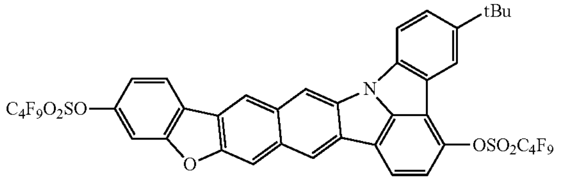

Intermediate 12

Intermediate 11 (3.1 g, yield 80%, Mass [M+]=470) was obtained in the same manner as in Synthesis of Intermediate 3 of Synthesis Example 1, except that Intermediate 10 (4.1 g) was used instead of Intermediate 2.

Intermediate 12 (5.6 g, yield 82%, Mass [M+]=1034) was obtained in the same manner as in Synthesis of Intermediate 4 of Synthesis Example 1, except that Intermediate 11 (3.1 g) was used instead of Intermediate 3.

3-4. Synthesis of Compound 3

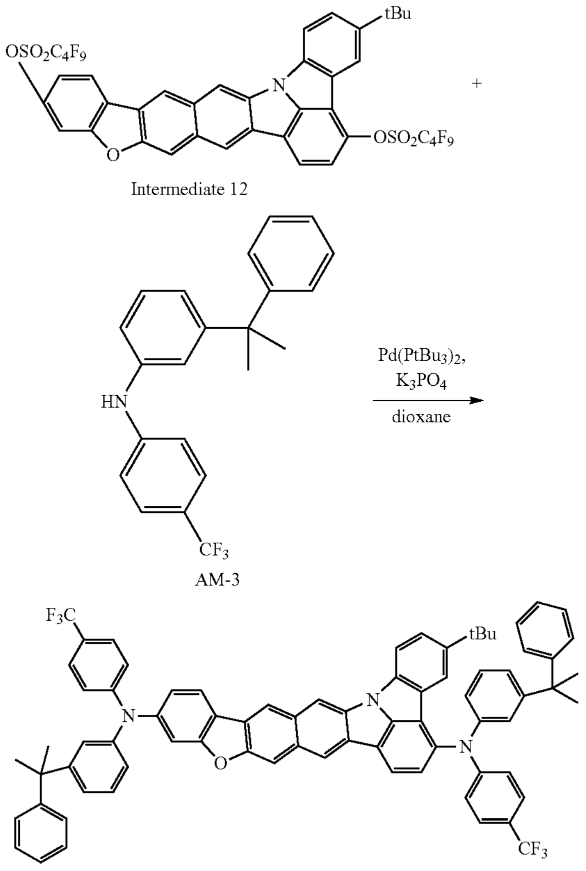

Intermediate 12

AM-3

Compound3

Compound 3 (2.0 g, yield 77%, Mass [M+]=1145) was obtained in the same manner as in Synthesis of Compound 1 of Synthesis Example 1, except that Intermediate 12 (3.0 g) was used instead of Intermediate 4, and AM-3 (2.0 g) was used instead of AM-1.

Synthesis Example 4. Synthesis of Compound 4

4-1. Synthesis of Intermediate 13

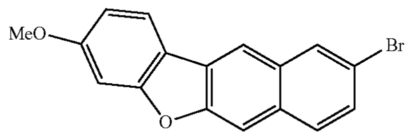

A-1

+

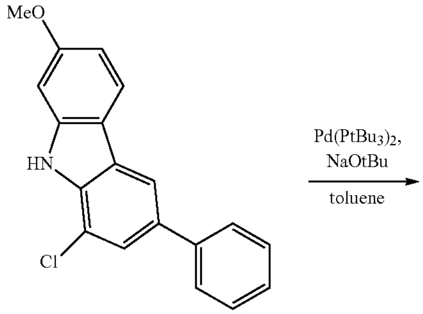

B-5

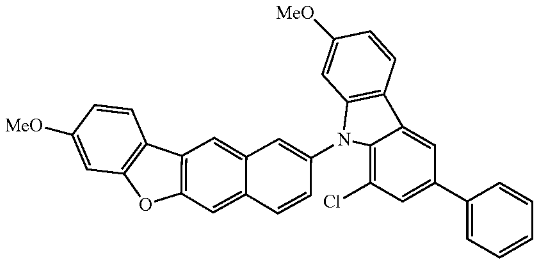

Intermediate 13

Intermediate 13 (7.1 g, yield 84%, Mass [M+]=555) was obtained in the same manner as in Synthesis of Intermediate 1 of Synthesis Example 1, except that B-5 (4.8 g) was used instead of B-1.

4-2. Synthesis of Intermediate 14

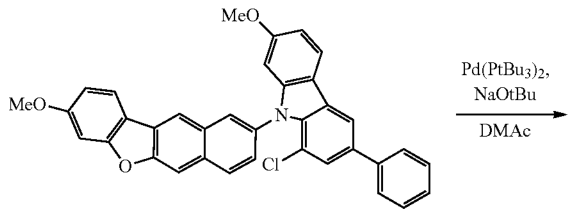

Intermediate 13

-continued

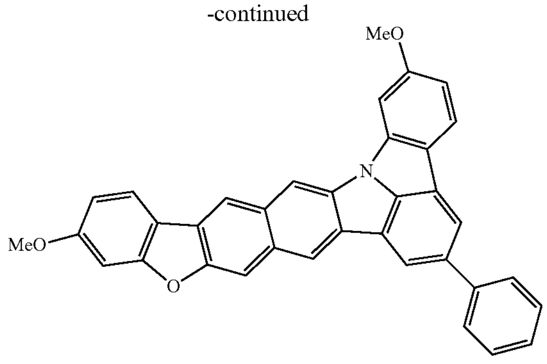

Intermediate 14

Intermediate 14 (4.8 g, yield 72%, Mass [M+]=518) was obtained in the same manner as in Synthesis of Intermediate 2 of Synthesis Example 1, except that Intermediate 13 (7.1 g) was used instead of Intermediate 1.

4-3. Synthesis of Intermediate 16

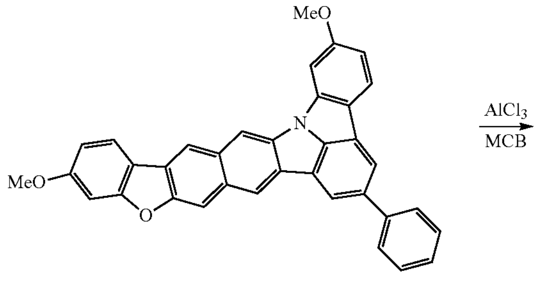

Intermediate 14

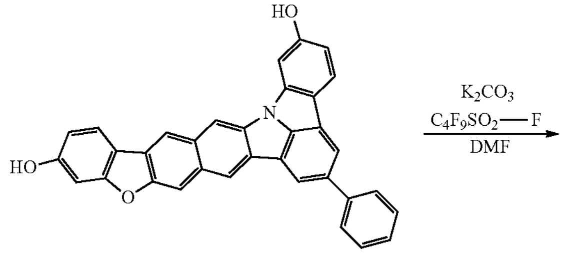

Intermediate 15

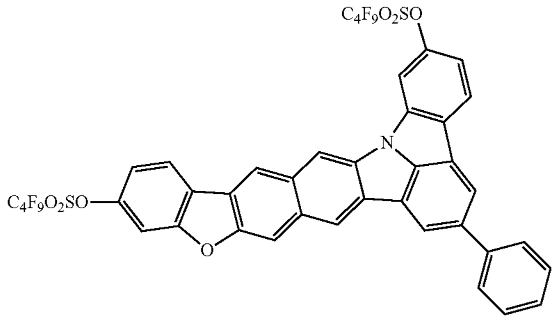

Intermediate 16

Intermediate 15 (3.7 g, yield 81%, Mass [M+]=490) was obtained in the same manner as in Synthesis of Intermediate 3 of Synthesis Example 1, except that Intermediate 14 (4.8 g) was used instead of Intermediate 2.

Intermediate 16 (6.6 g, yield 82%, Mass [M+]=1054) was obtained in the same manner as in Synthesis of Intermediate 4 of Synthesis Example 1, except that Intermediate 15 (3.7 g) was used instead of Intermediate 3.

4-4. Synthesis of Compound 4

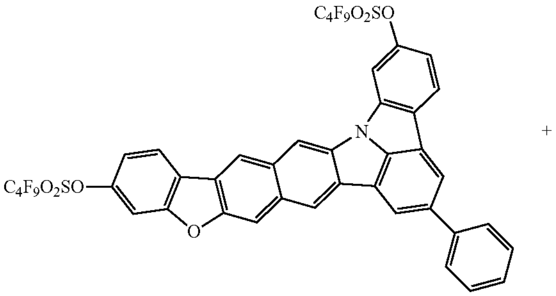

Intermediate 16

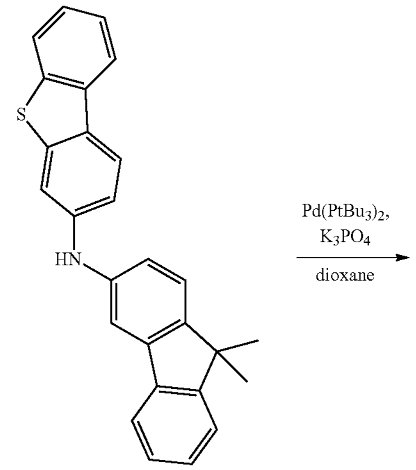

AM-4

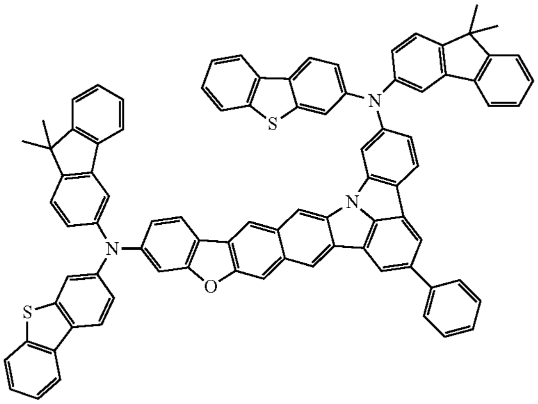

Compound4

Compound 4 (2.4 g, yield 68%, Mass [M+]=1237) was obtained in the same manner as in Synthesis of Compound 1 of Synthesis Example 1, except that Intermediate 16 (3.0 g) was used instead of Intermediate 4, and AM-4 (1.8 g) was used instead of AM-1.

Synthesis Example 5. Synthesis of Compound 5

5-1. Synthesis of Intermediate 17

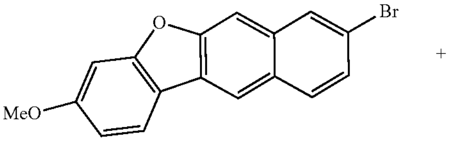

A-3

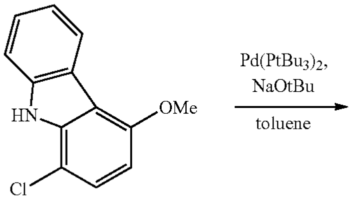

B-1

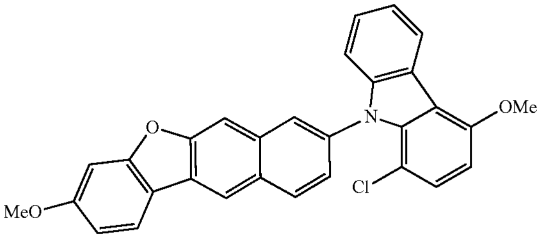

Intermediate 17

Intermediate 17 (3.6 g, yield 78%, Mass [M+]=478) was obtained in the same manner as in Synthesis of Intermediate 1 of Synthesis Example 1, except that A-3 (5.0 g) was used instead of starting material A-1.

5-2. Synthesis of Intermediate 18

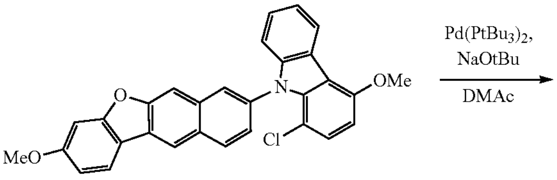

Intermediate 17

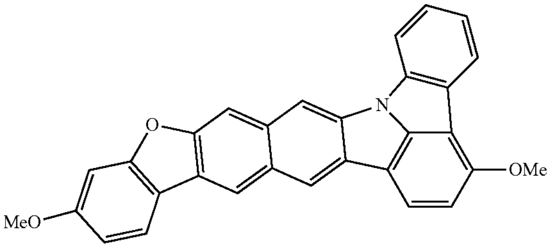

Intermediate 18

Intermediate 18 (3.9 g, yield 74%, Mass [M+]=442) was obtained in the same manner as in Synthesis of Intermediate 2 of Synthesis Example 1, except that Intermediate 17 (5.7

5-3. Synthesis of Intermediate 20

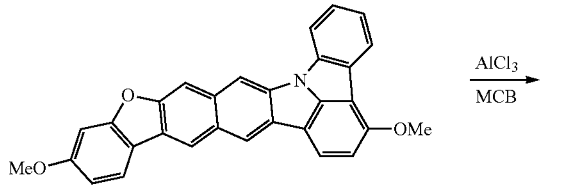

Intermediate 18

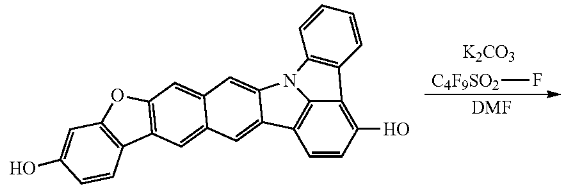

Intermediate 19

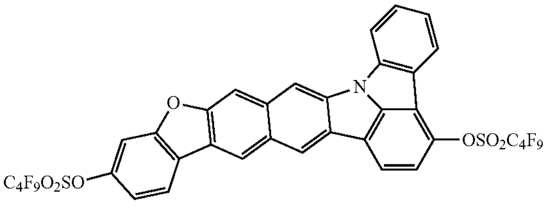

Intermediate 20

Intermediate 19 (2.8 g, yield 77%, Mass [M+]=414) was obtained in the same manner as in Synthesis of Intermediate 3 of Synthesis Example 1, except that Intermediate 18 (3.9 g) was used instead of Intermediate 2.

Intermediate 20 (5.6 g, yield 85%, Mass [M+]=978) was obtained in the same manner as in Synthesis of Intermediate 4 of Synthesis Example 1, except that Intermediate 19 (2.8

5-4. Synthesis of Compound 5

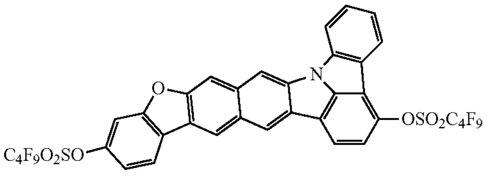

Intermediate 20

+

-continued

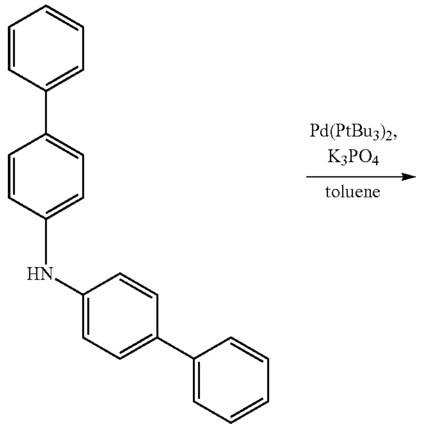

AM-5

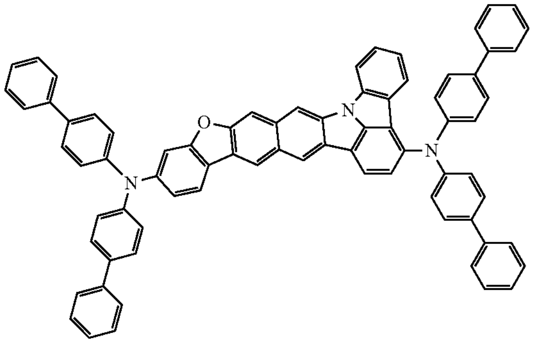

Compound5

Compound 5 (2.4 g, yield 77%, Mass [M+]=1021) was obtained in the same manner as in Synthesis of Compound 1 of Synthesis Example 1, except that Intermediate 20 (3.0 g) was used instead of Intermediate 4, and AM-5 (2.0 g) was used instead of AM-1.

Synthesis Example 6. Synthesis of Compound 6

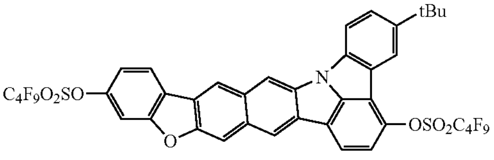

Intermediate 12

+

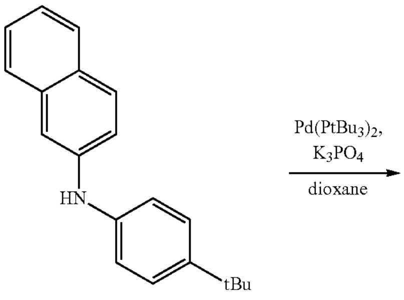

AM-6

-continued

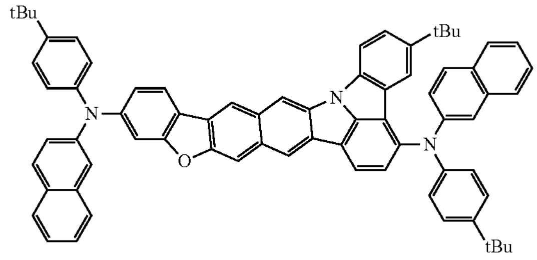

Compound6

Compound 6 (2.3 g, yield 77%, Mass [M+]=985) was obtained in the same manner as in Synthesis of Compound 1 of Synthesis Example 1, except that Intermediate 12 (3.0 g) was used instead of Intermediate 4, and AM-6 (1.6 g) was used instead of AM-1.

Synthesis Example 7. Synthesis of Compound 7

7-1. Synthesis of Intermediate 21

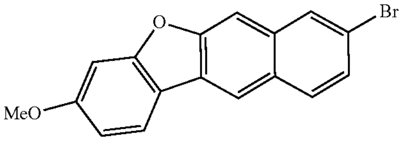

+

A-3

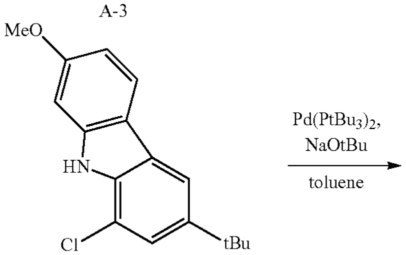

B-3

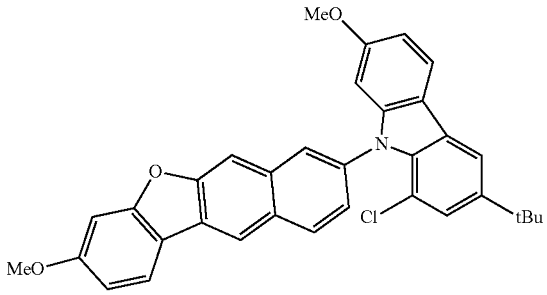

Intermediate 21

Intermediate 21 (6.2 g, yield 76%, Mass [M+]=535) was obtained in the same manner as in Synthesis of Intermediate 1 of Synthesis Example 1, except that A-3 (5.0 g) was used instead of starting material A-1, and B-3 (3.6 g) was used instead of B-1.

7-2. Synthesis of Intermediate 22

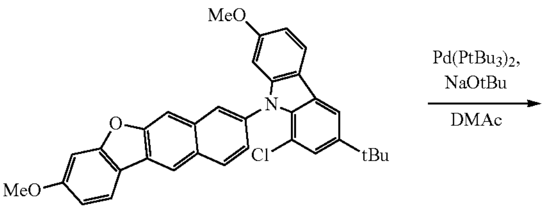

Intermediate 21

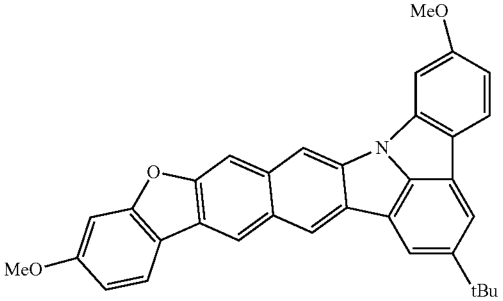

Intermediate 22

Intermediate 22 (3.9 g, yield 68%, Mass [M+]=498) was obtained in the same manner as in Synthesis of Intermediate 2 of Synthesis Example 1, except that Intermediate 21 (6.2 g) was used instead of Intermediate 1.

7-3. Synthesis of Intermediate 24

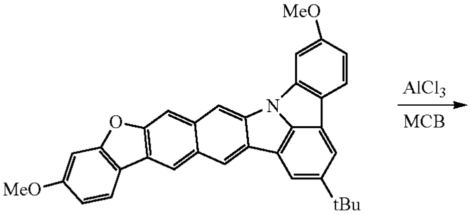

Intermediate 22

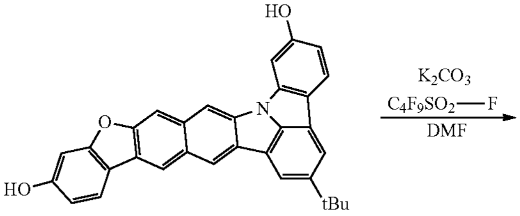

Intermediate 23

-continued

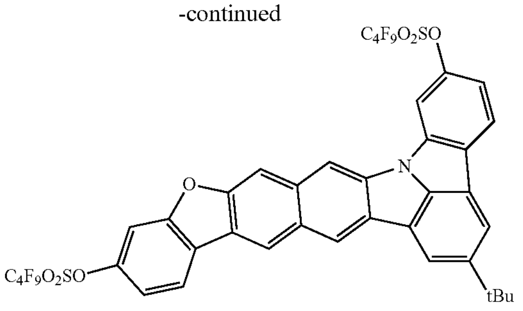

Intermediate 24

Intermediate 23 (3.0 g, yield 79%, Mass [M+]=486) was obtained in the same manner as in Synthesis of Intermediate 3 of Synthesis Example 1, except that Intermediate 22 (3.9 g) was used instead of Intermediate 2.

Intermediate 24 (5.1 g, yield 79%, Mass [M+]=1050) was obtained in the same manner as in Synthesis of Intermediate 4 of Synthesis Example 1, except that Intermediate 23 (3.0 g) was used instead of Intermediate 3.

7-4. Synthesis of Compound 7

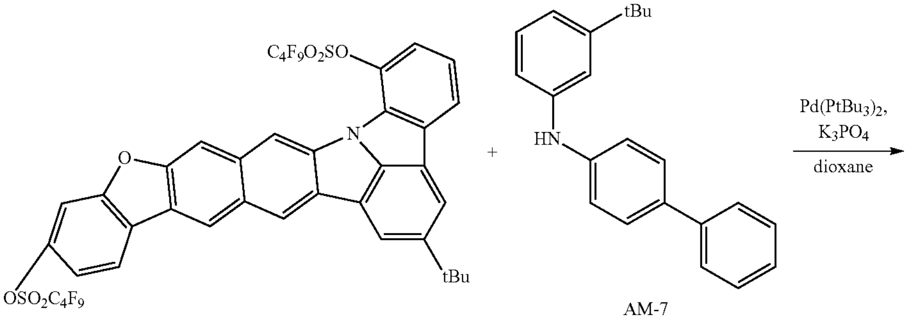

Intermediate 24

AM-7

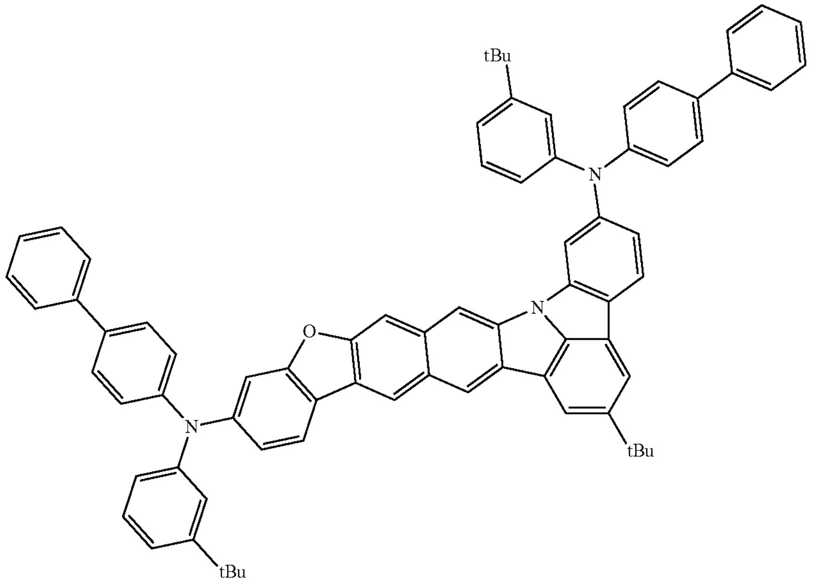

Compound7

Compound 7 (2.4 g, yield 81%, Mass [M+]=1037) was obtained in the same manner as in Synthesis of Compound 1 of Synthesis Example 1, except that Intermediate 24 (3.0 g) was used instead of Intermediate 4, and AM-7 (1.7 g) was used instead of AM-1.

Synthesis Example 8. Synthesis of Compound 8

8-1. Synthesis of Intermediate 25

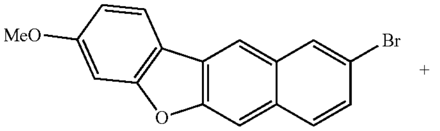

A-1

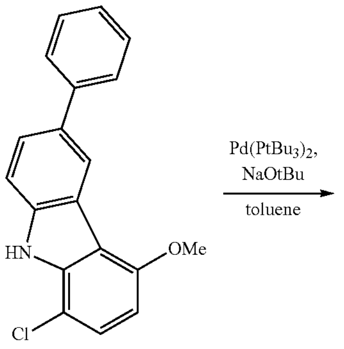

B-4

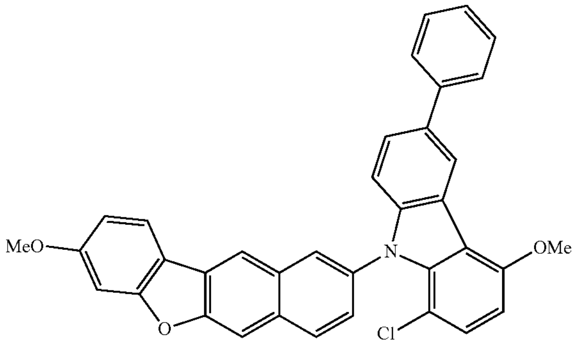

Intermediate 25

Intermediate 25 (6.9 g, yield 81%, Mass [M+]=555) was obtained in the same manner as in Synthesis of Intermediate 1 of Synthesis Example 1, except that B-4 (4.8 g) was used instead of B-1.

8-2. Synthesis of Intermediate 26

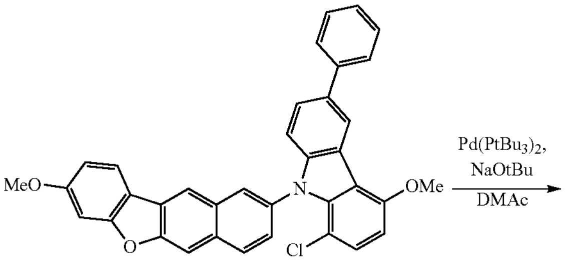

Intermediate 25

-continued

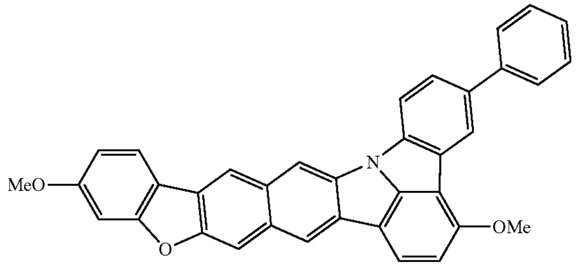

Intermediate 26

Intermediate 26 (4.9 g, yield 76%, Mass [M+]=518) was obtained in the same manner as in Synthesis of Intermediate 2 of Synthesis Example 1, except that Intermediate 25 (6.9 g) was used instead of Intermediate 1.

8-3. Synthesis of Intermediate 28

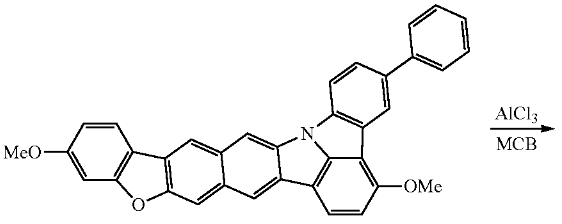

Intermediate 26

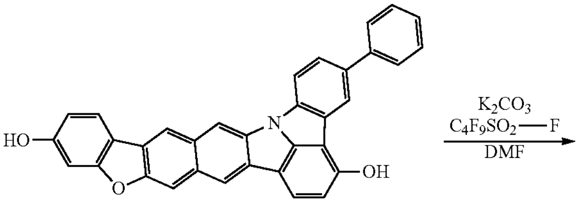

Intermediate 27

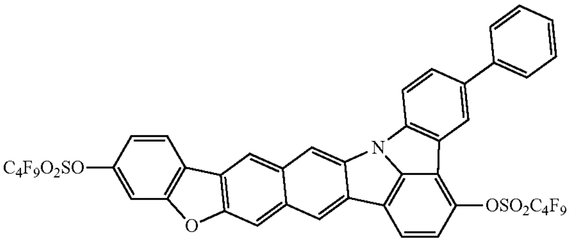

Intermediate 28

Intermediate 27 (3.5 g, yield 76%, Mass [M+]=490) was obtained in the same manner as in Synthesis of Intermediate 3 of Synthesis Example 1, except that Intermediate 26 (4.9 g) was used instead of Intermediate 2.

Intermediate 28 (6.2 g, yield 82%, Mass [M+]=1054) was obtained in the same manner as in Synthesis of Intermediate 4 of Synthesis Example 1, except that Intermediate 27 (3.5 g) was used instead of Intermediate 3.

8-4. Synthesis of Compound 8

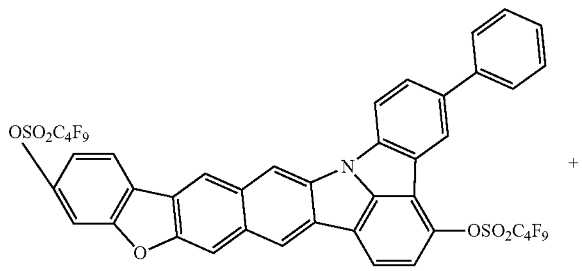

Intermediate 28

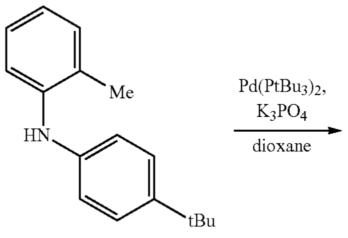

AM-8

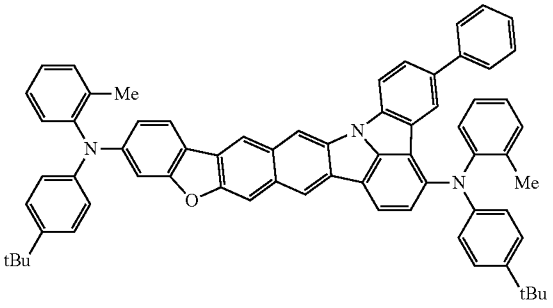

Compound8

Compound 8 (2.6 g, yield 74%, Mass [M+]=933) was obtained in the same manner as in Synthesis of Compound 1 of Synthesis Example 1, except that Intermediate 28 (3.0 g) was used instead of Intermediate 4, and AM-8 (1.4 g) was used instead of AM-1.

Example 9. Synthesis of Compound 9

9-1. Synthesis of Intermediate 29

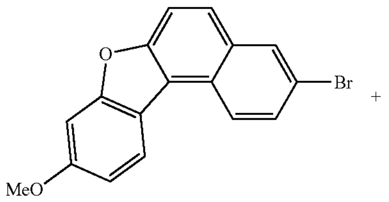

A-4

-continued

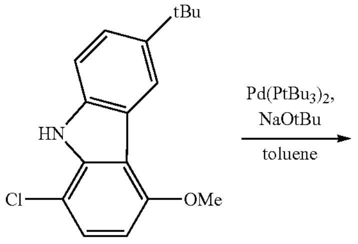

B-2

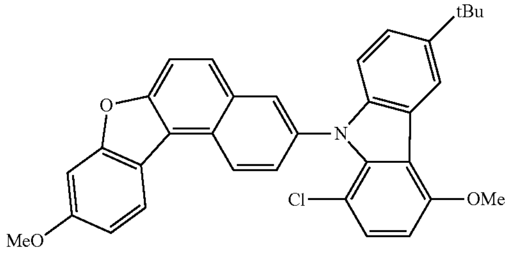

Intermediate 29

Intermediate 29 (6.3 g, yield 77%, Mass [M+]=535) was obtained in the same manner as in Synthesis of Intermediate 1 of Synthesis Example 1, except that A-4 (5.0 g) was used instead of starting material A-1, and B-2 (4.4 g) was used instead of B-1.

9-2. Synthesis of Intermediate 30

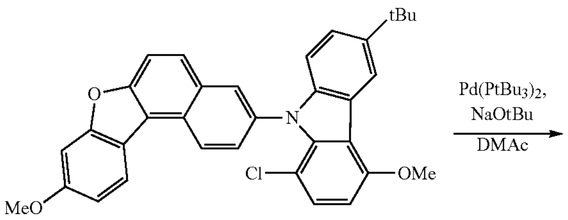

Intermediate 29

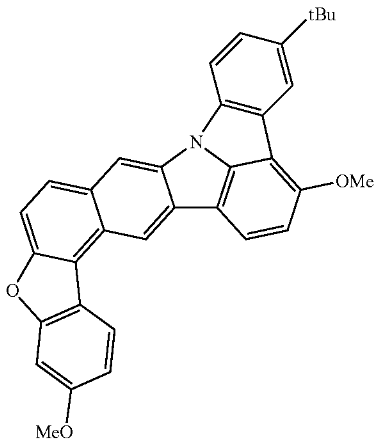

Intermediate 30

Intermediate 30 (3.7 g, yield 63%, Mass [M+]=498) was obtained in the same manner as in Synthesis of Intermediate 2 of Synthesis Example 1, except that Intermediate 29 (6.3

9-3. Synthesis of Intermediate 32

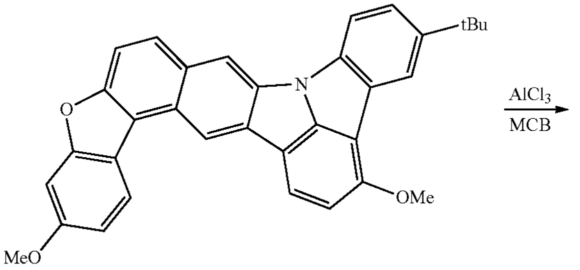

Intermediate 30

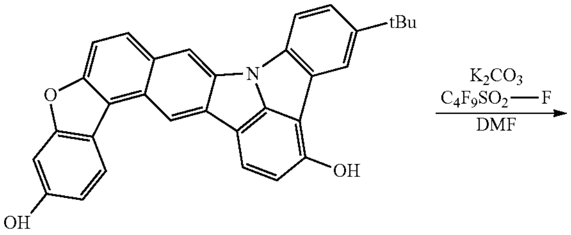

Intermediate 31

-continued

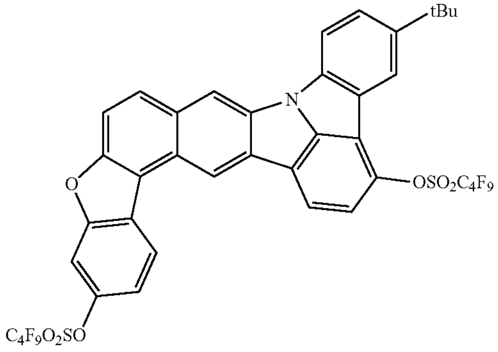

Intermediate 32

Intermediate 31 (2.8 g, yield 78%, Mass [M+]=470) was obtained in the same manner as in Synthesis of Intermediate 3 of Synthesis Example 1, except that Intermediate 30 (3.7 g) was used instead of Intermediate 2.

Intermediate 32 (4.8 g, yield 80%, Mass [M+]=1034) was obtained in the same manner as in Synthesis of Intermediate 4 of Synthesis Example 1, except that Intermediate 31 (2.8 g) was used instead of Intermediate 3.

9-4. Synthesis of Compound 9

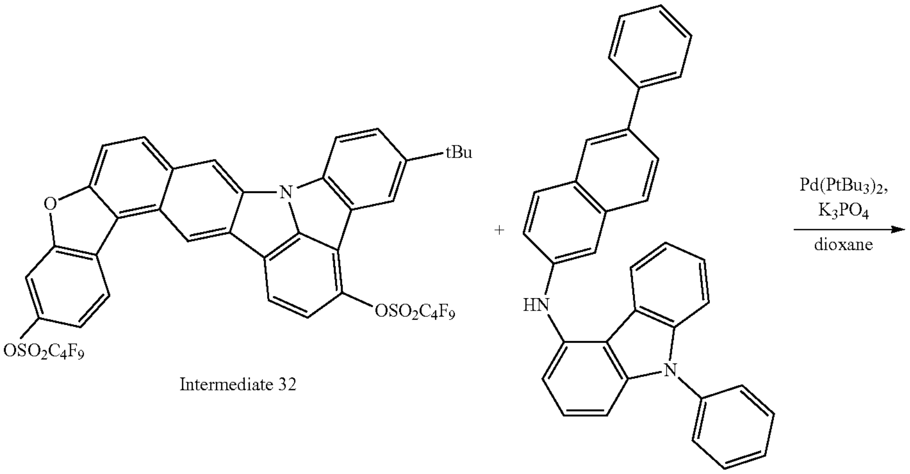

Intermediate 32

AM-9

-continued

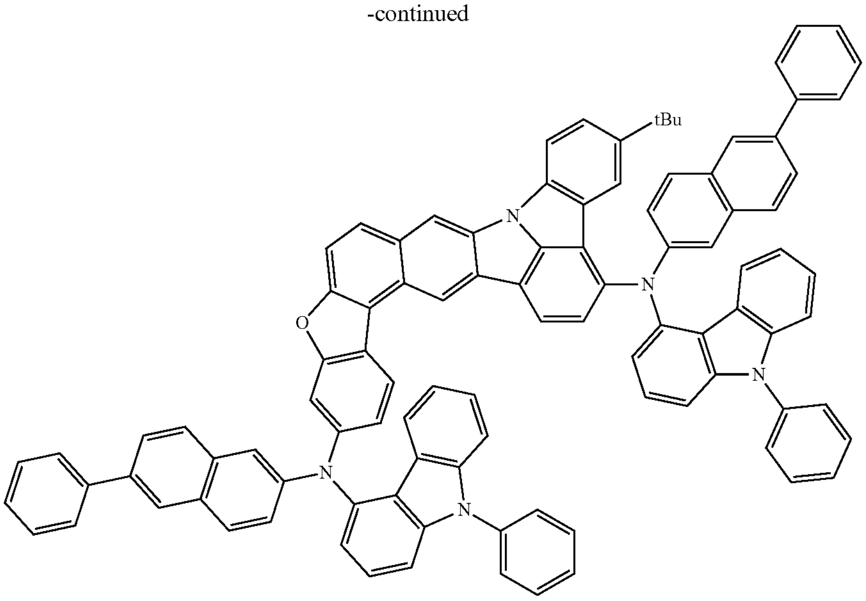

Compound9

Compound 9 (2.7 g, yield 69%, Mass [M+]=1355) was obtained in the same manner as in Synthesis of Compound 1 of Synthesis Example 1, except that Intermediate 32 (3.0 g) was used instead of Intermediate 4, and AM-9 (2.7 g) was used instead of AM-1.

Synthesis Example 10. Synthesis of Compound 10

10-1. Synthesis of Intermediate 33

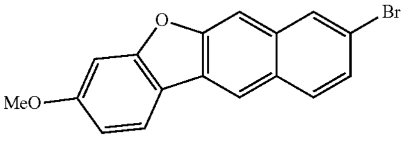

A-3

+

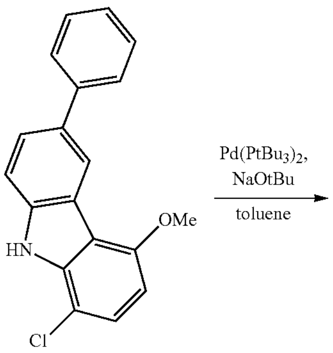

B-4

-continued

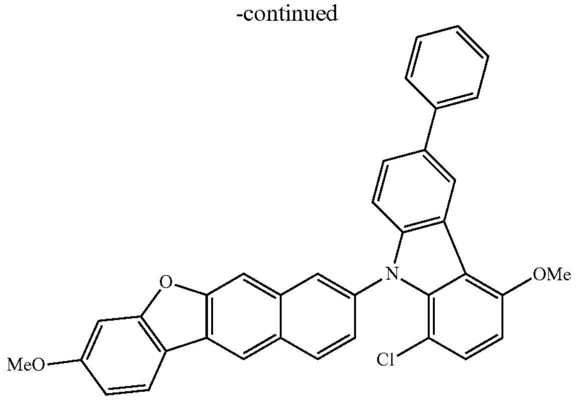

Intermediate 33

Intermediate 33 (6.7 g, yield 79%, Mass [M+]=555) was obtained in the same manner as in Synthesis of Intermediate 1 of Synthesis Example 1, except that A-3 (5.0 g) was used instead of starting material A-1, and B-4 (4.8 g) was used instead of B-1.

10-2. Synthesis of Intermediate 34

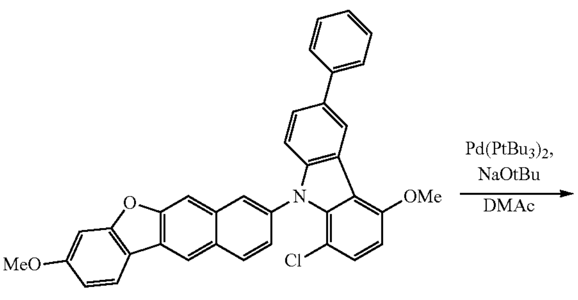

Intermediate 33

-continued

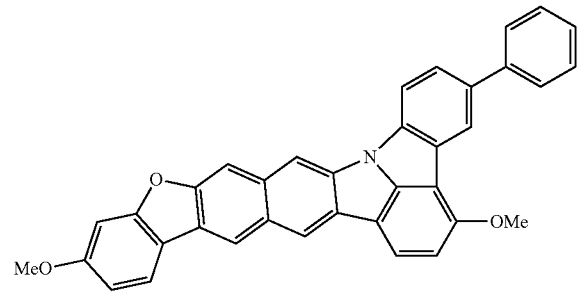

Intermediate 34

Intermediate 34 (4.7 g, yield 75%, Mass [M+]=518) was obtained in the same manner as in Synthesis of Intermediate 2 of Synthesis Example 1, except that Intermediate 33 (6.7 g) was used instead of Intermediate 1.

10-3. Synthesis of Intermediate 36

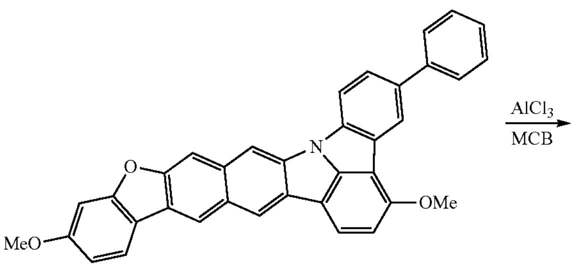

Intermediate 34

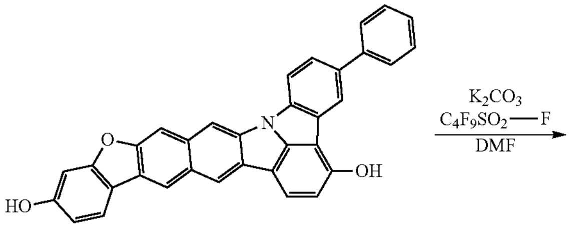

Intermediate 35

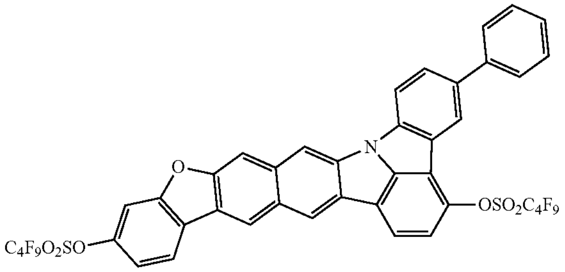

Intermediate 36

Intermediate 35 (3.6 g, yield 81%, Mass [M+]=490) was obtained in the same manner as in Synthesis of Intermediate 3 of Synthesis Example 1, except that Intermediate 34 (4.7 g) was used instead of Intermediate 2.

Intermediate 36 (6.2 g, yield 80%, Mass [M+]=1054) was obtained in the same manner as in Synthesis of Intermediate 4 of Synthesis Example 1, except that Intermediate 35 (3.6

10-4. Synthesis of Compound 10

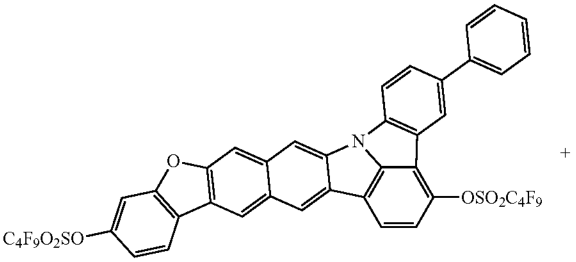

Intermediate 36

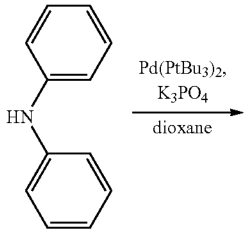

AM-10

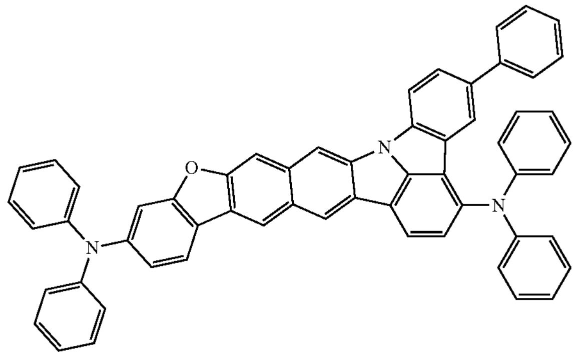

Compound10

Compound 10 (1.8 g, yield 80%, Mass [M+]=792) was obtained in the same manner as in Synthesis of Compound 1 of Synthesis Example 1, except that Intermediate 36 (3.0 g) was used instead of Intermediate 4, and AM-10 (1.0 g) was used instead of AM-1.

Synthesis Example 11. Synthesis of Compound 11

11-1. Synthesis of Intermediate 37

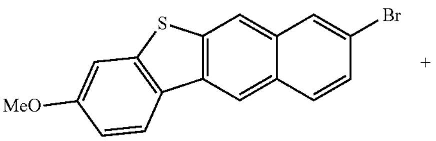

A-5

-continued

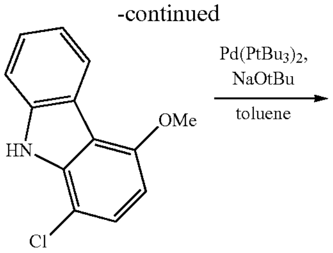

B-1

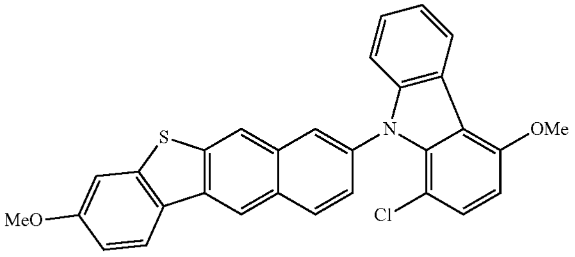

Intermediate 37

Intermediate 37 (6.0 g, yield 83%, Mass [M+]=495) was obtained in the same manner as in Synthesis of Intermediate 1 of Synthesis Example 1, except that A-5 (5.0 g) was used instead of starting material A-1.

11-2. Synthesis of Intermediate 38

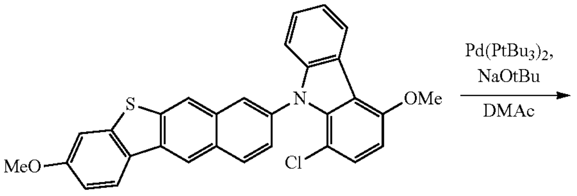

Intermediate 37

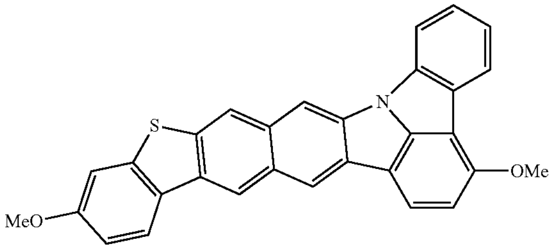

Intermediate 38

Intermediate 38 (3.5 g, yield 63%, Mass [M+]=458) was obtained in the same manner as in Synthesis of Intermediate 2 of Synthesis Example 1, except that Intermediate 37 (6.0 g) was used instead of Intermediate 1.

11-3. Synthesis of Intermediate 40

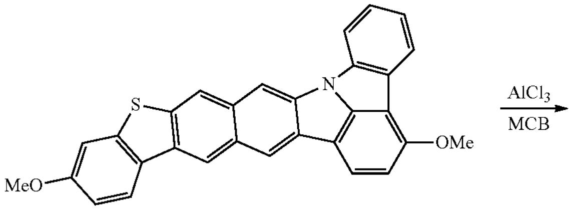

Intermediate 38

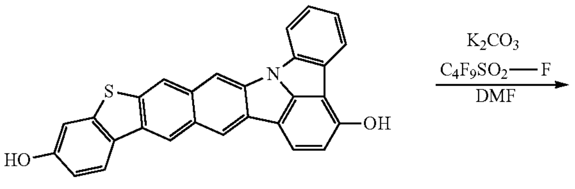

Intermediate 39

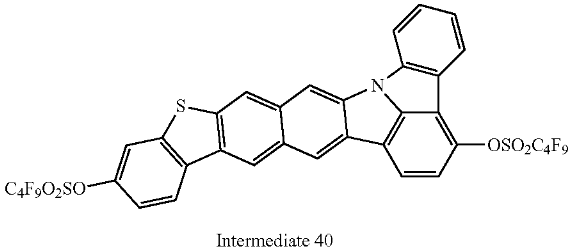

Intermediate 40

Intermediate 39 (2.5 g, yield 76%, Mass [M+]=430) was obtained in the same manner as in Synthesis of Intermediate 3 of Synthesis Example 1, except that Intermediate 38 (3.5 g) was used instead of Intermediate 2.

Intermediate 40 (4.1 g, yield 71%, Mass [M+]=994) was obtained in the same manner as in Synthesis of Intermediate 4 of Synthesis Example 1, except that Intermediate 39 (2.5

11-4. Synthesis of Compound 11
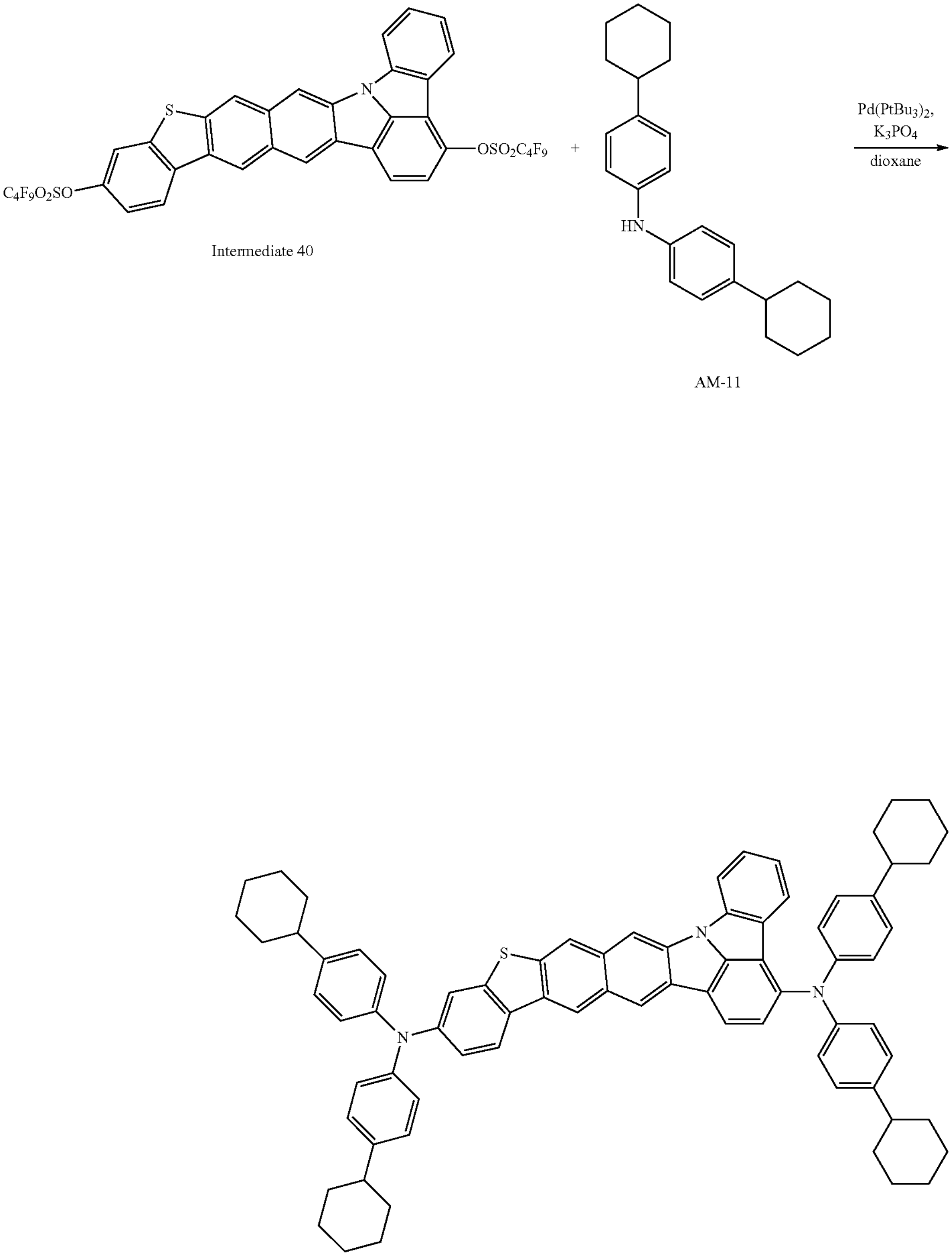
Intermediate 40
AM-11
Compound11
Compound 11 (2.3 g, yield 72%, Mass [M+]=1061) was obtained in the same manner as in Synthesis of Compound 1 of Synthesis Example 1, except that Intermediate 40 (3.0 g) was used instead of Intermediate 4, and AM-11 (2.0 g) was used instead of AM-1.

Synthesis Example 12. Synthesis of Compound 12

12-1. Synthesis of Intermediate 41

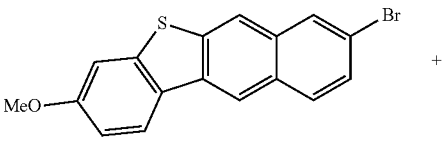

A-5

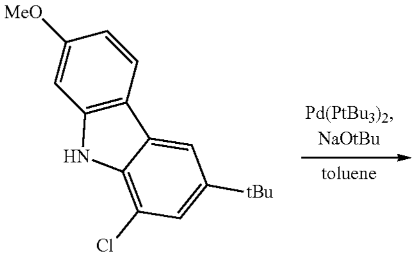

B-3

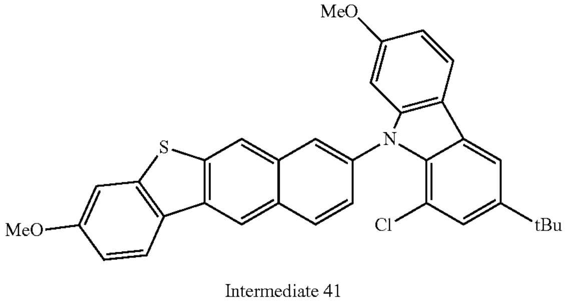

Intermediate 41

Intermediate 41 (6.2 g, yield 77%, Mass [M+]=551) was obtained in the same manner as in Synthesis of Intermediate 1 of Synthesis Example 1, except that A-5 (5.0 g) was used instead of starting material A-1, and B-3 (4.2 g) was used instead of B-1.

12-2. Synthesis of Intermediate 42

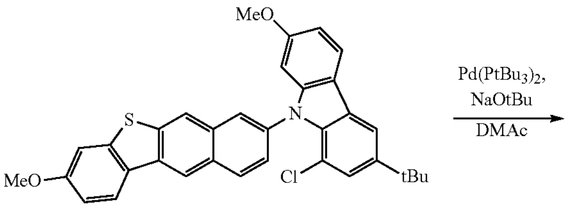

Intermediate 41

-continued

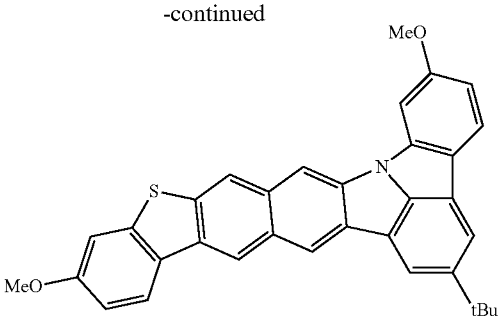

Intermediate 42

Intermediate 42 (3.9 g, yield 67%, Mass [M+]=514) was obtained in the same manner as in Synthesis of Intermediate 2 of Synthesis Example 1, except that Intermediate 41 (6.2 g) was used instead of Intermediate 1.

12-3. Synthesis of Intermediate 44

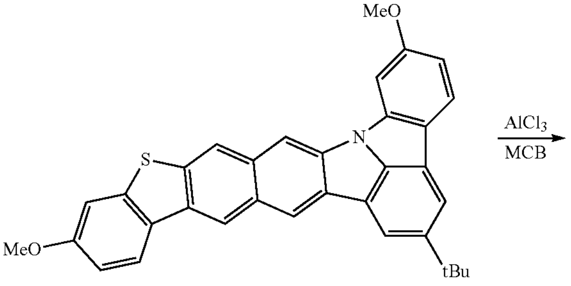

Intermediate 42

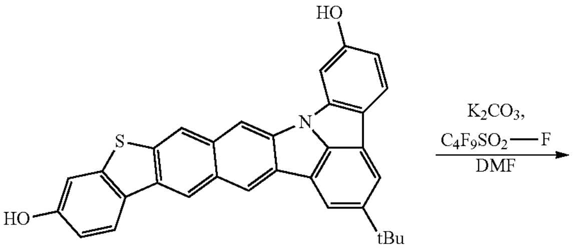

Intermediate 43

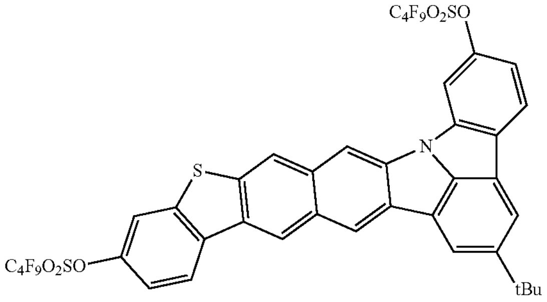

Intermediate 44

Intermediate 43 (2.7 g, yield 73%, Mass [M+]=486) was obtained in the same manner as in Synthesis of Intermediate 3 of Synthesis Example 1, except that Intermediate 42 (3.9 g) was used instead of Intermediate 2.

Intermediate 44 (4.2 g, yield 72%, Mass [M+]=1050) was obtained in the same manner as in Synthesis of Intermediate 4 of Synthesis Example 1, except that Intermediate 43 (2.7 g) was used instead of Intermediate 3.

12-4. Synthesis of Compound 12

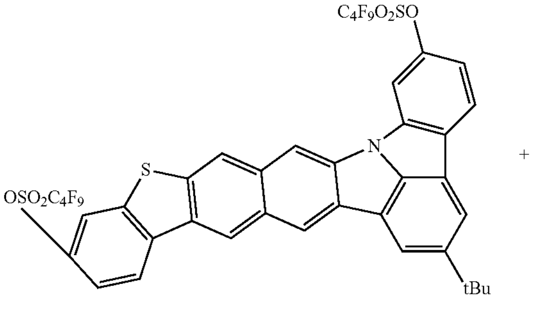

Intermediate 44

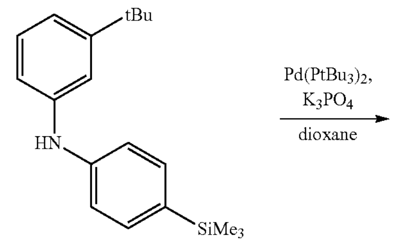

AM-12

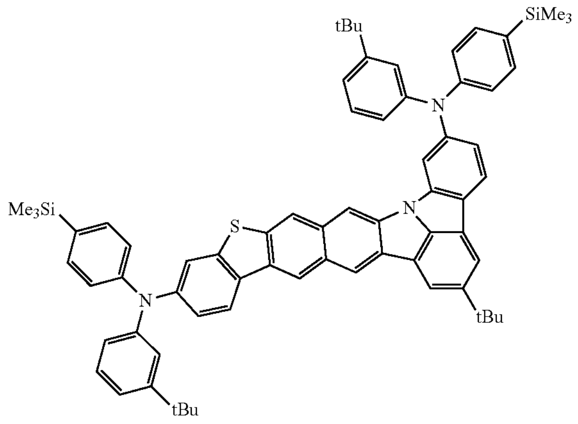

Compound12

Compound 12 (2.4 g, yield 80%, Mass [M+]=1045) was obtained in the same manner as in Synthesis of Compound 1 of Synthesis Example 1, except that Intermediate 44 (3.0 g) was used instead of Intermediate 4, and AM-12 (1.7 g) was used instead of AM-1.

Synthesis Example 13. Synthesis of Compound 13

13-1. Synthesis of Intermediate 45

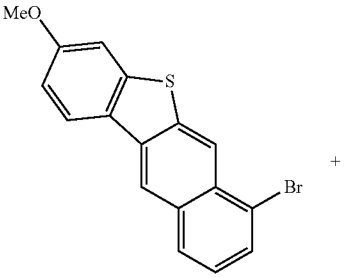

A-6

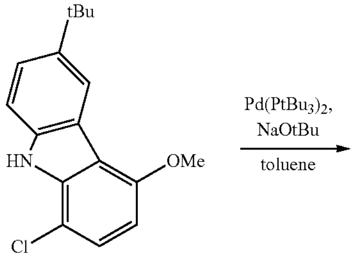

B-2

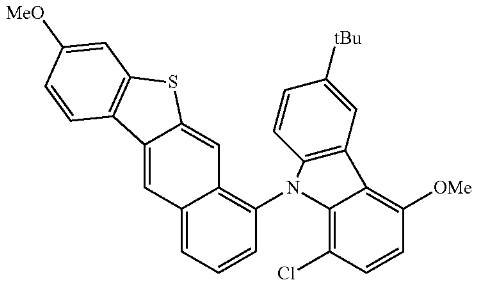

Intermediate 45

Intermediate 45 (5.8 g, yield 72%, Mass [M+]=551) was obtained in the same manner as in Synthesis of Intermediate 1 of Synthesis Example 1, except that A-6 (5.0 g) was used instead of starting material A-1, and B-2 (4.2 g) was used instead of B-1.

13-2. Synthesis of Intermediate 46

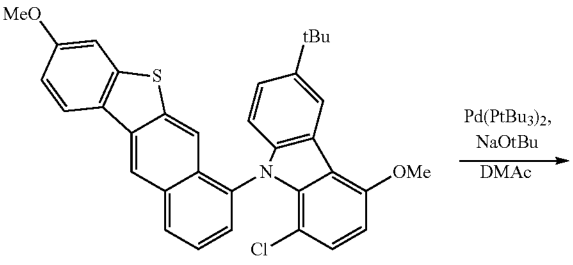

Intermediate 45

-continued

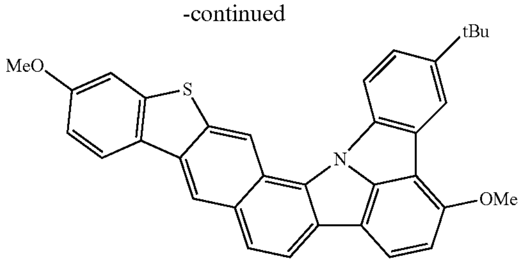

Intermediate 46

Intermediate 46 (3.4 g, yield 63%, Mass [M+]=514) was obtained in the same manner as in Synthesis of Intermediate 2 of Synthesis Example 1, except that Intermediate 45 (5.8

13-3. Synthesis of Intermediate 48

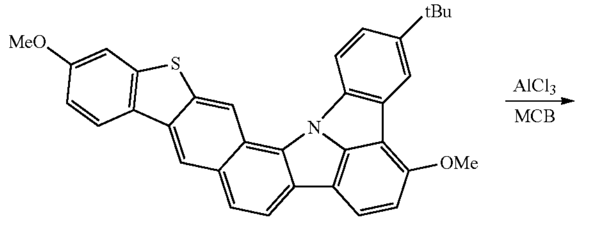

Intermediate 46

-continued

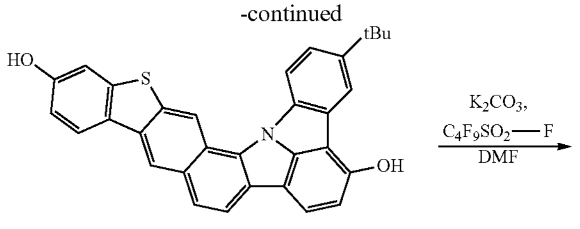

Intermediate 47

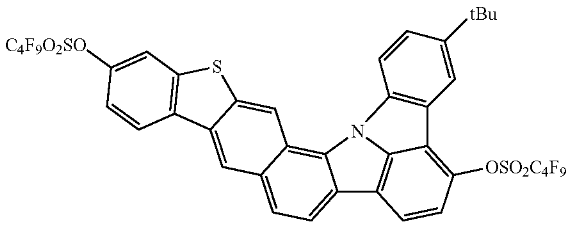

Intermediate 48

Intermediate 47 (2.4 g, yield 75%, Mass [M+]=486) was obtained in the same manner as in Synthesis of Intermediate 3 of Synthesis Example 1, except that Intermediate 46 (3.4 g) was used instead of Intermediate 2.

Intermediate 48 (4.0 g, yield 77%, Mass [M+]=1050) was obtained in the same manner as in Synthesis of Intermediate 4 of Synthesis Example 1, except that Intermediate 47 (2.4

13-4. Synthesis of Compound 13

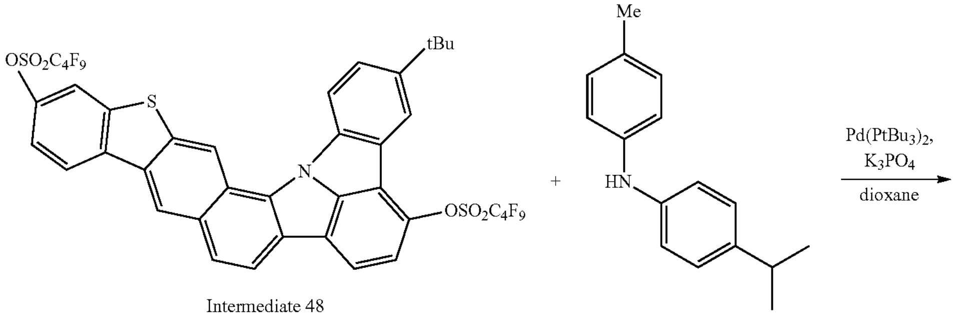

Intermediate 48

AM-13

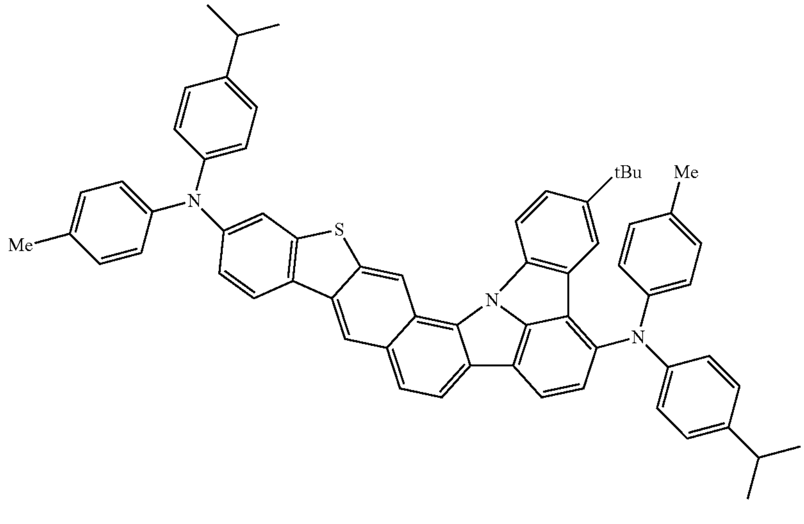

Compound13

Compound 13 (2.0 g, yield 82%, Mass [M+]=901) was obtained in the same manner as in Synthesis of Compound 1 of Synthesis Example 1, except that Intermediate 48 (3.0 g) was used instead of Intermediate 4, and AM-13 (1.3 g) was used instead of AM-1.

Synthesis Example 14. Synthesis of Compound 14

14-1. Synthesis of Intermediate 49

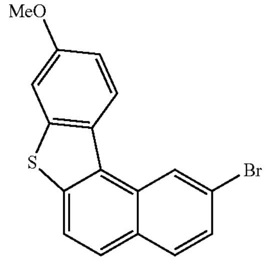

+

A-7

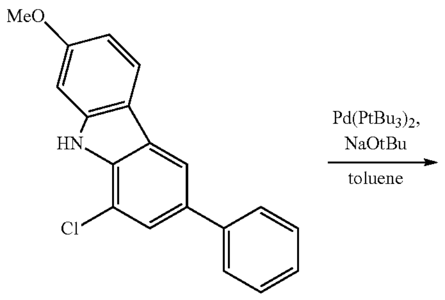

B-5

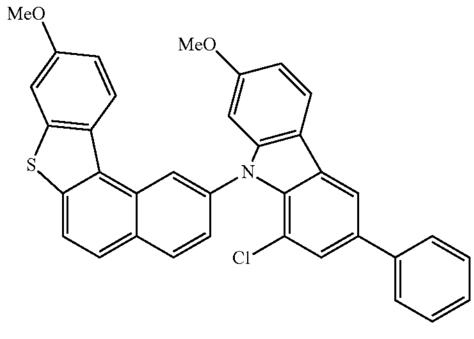

Intermediate 49

Intermediate 49 (6.1 g, yield 73%, Mass [M+]=571) was obtained in the same manner as in Synthesis of Intermediate 1 of Synthesis Example 1, except that A-7 (5.0 g) was used instead of starting material A-1, and B-5 (4.5 g) was used instead of B-1.

14-2. Synthesis of Intermediate 50

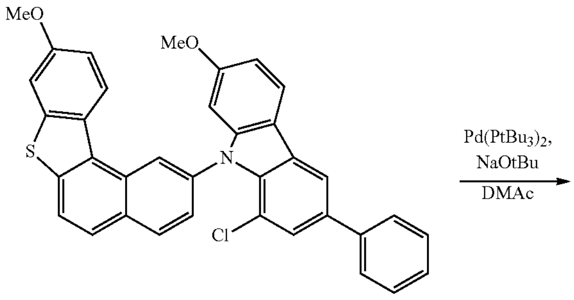

Intermediate 49

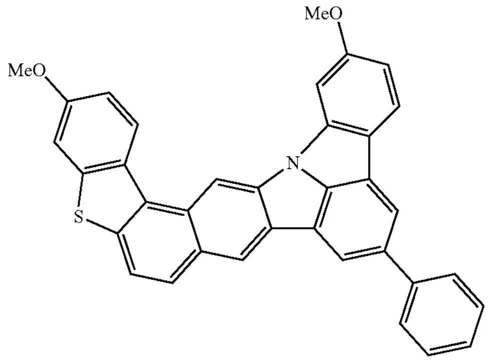

Intermediate 50

Intermediate 50 (3.7 g, yield 65%, Mass [M+]=534) was obtained in the same manner as in Synthesis of Intermediate 2 of Synthesis Example 1, except that Intermediate 49 (6.1

14-3. Synthesis of Intermediate 52

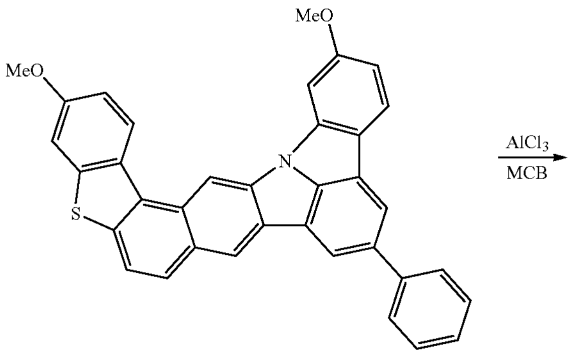

Intermediate 50

-continued

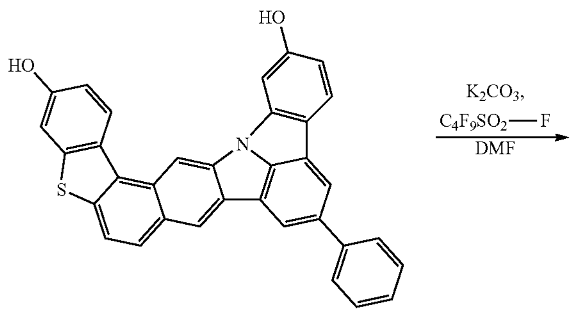

Intermediate 51

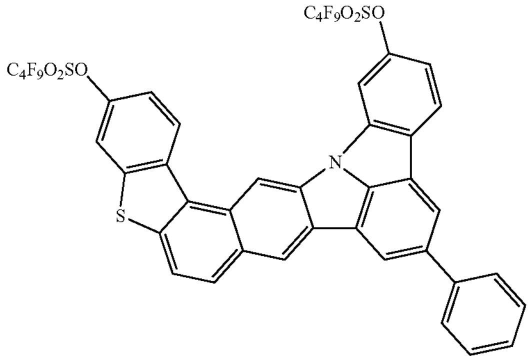

Intermediate 52

Intermediate 51 (2.6 g, yield 74%, Mass [M+]=506) was obtained in the same manner as in Synthesis of Intermediate 3 of Synthesis Example 1, except that Intermediate 50 (3.7 g) was used instead of Intermediate 2.

Intermediate 52 (3.9 g, yield 71%, Mass [M+]=1070) was obtained in the same manner as in Synthesis of Intermediate 4 of Synthesis Example 1, except that Intermediate 51 (2.6 g) was used instead of Intermediate 3.

14-4. Synthesis of Compound 14

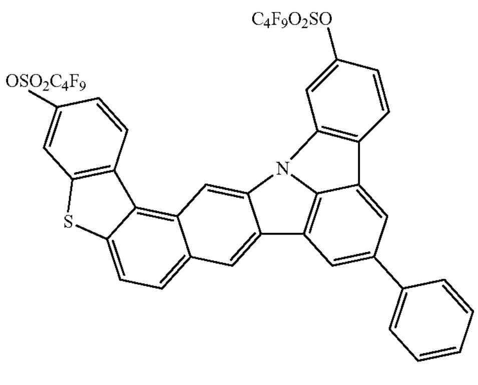

Intermediate 52

+

-continued

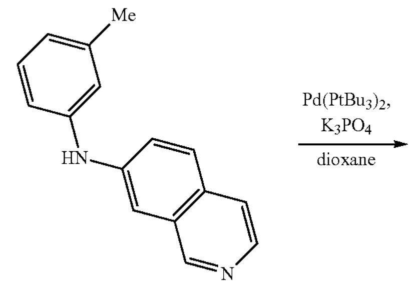

AM-14

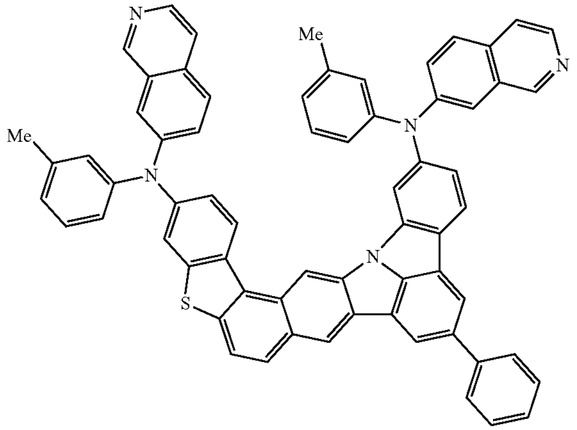

Compound14

Compound 14 (2.1 g, yield 80%, Mass [M+]=938) was obtained in the same manner as in Synthesis of Compound 1 of Synthesis Example 1, except that Intermediate 52 (3.0 g) was used instead of Intermediate 4, and AM-14 (1.3 g) was used instead of AM-1.

Synthesis Example 15. Synthesis of Compound 15

15-1. Synthesis of Intermediate 53

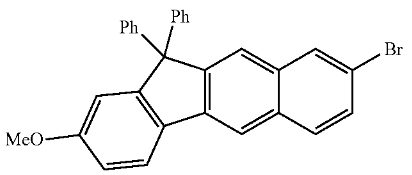

A-8

+

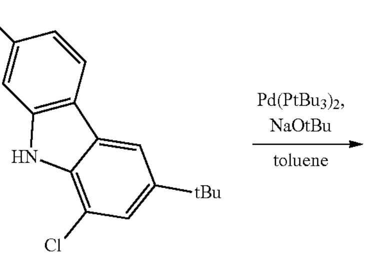

B-3

-continued

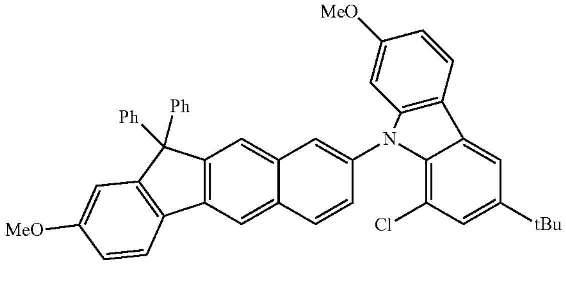

Intermediate 53

Intermediate 53 (5.7 g, yield 80%, Mass [M+]=685) was obtained in the same manner as in Synthesis of Intermediate 1 of Synthesis Example 1, except that A-8 (5.0 g) was used instead of starting material A-1, and B-3 (3.0 g) was used instead of B-1.

15-2. Synthesis of Intermediate 54

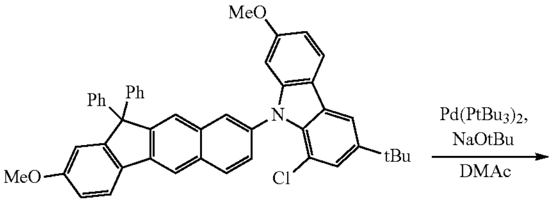

Intermediate 53

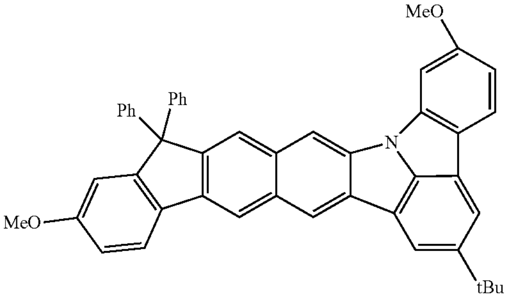

Intermediate 54

Intermediate 54 (3.7 g, yield 69%, Mass [M+]=648) was obtained in the same manner as in Synthesis of Intermediate 2 of Synthesis Example 1, except that Intermediate 53 (5.7 g) was used instead of Intermediate 1.

15-3. Synthesis of Intermediate 56

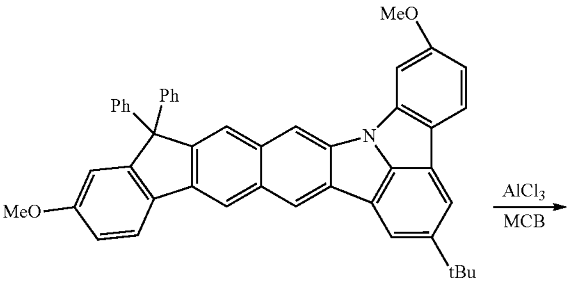

Intermediate 54

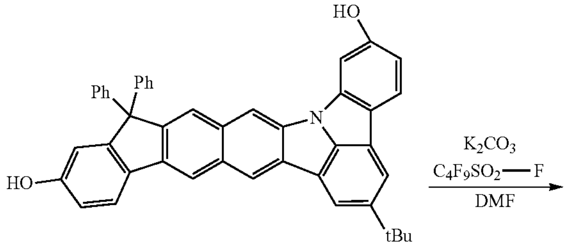

Intermediate 55

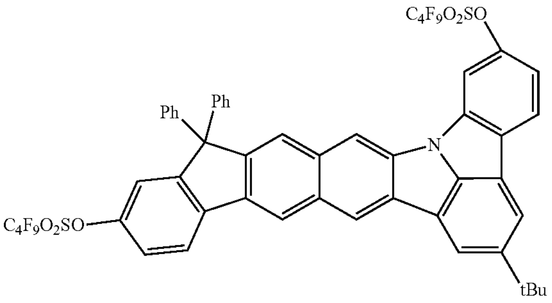

Intermediate 56

Intermediate 55 (2.5 g, yield 71%, Mass [M+]=620) was obtained in the same manner as in Synthesis of Intermediate 3 of Synthesis Example 1, except that Intermediate 54 (3.7 g) was used instead of Intermediate 2.

Intermediate 56 (3.6 g, yield 75%, Mass [M+]=1184) was obtained in the same manner as in Synthesis of Intermediate 4 of Synthesis Example 1, except that Intermediate 55 (2.5

15-4. Synthesis of Compound 15

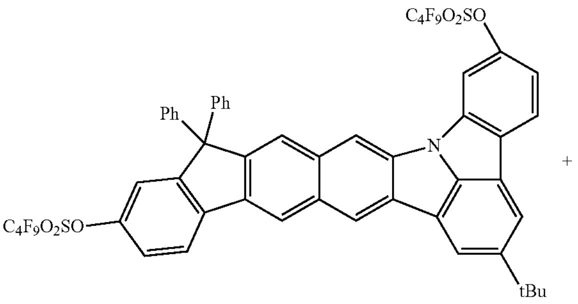

Intermediate 56

-continued

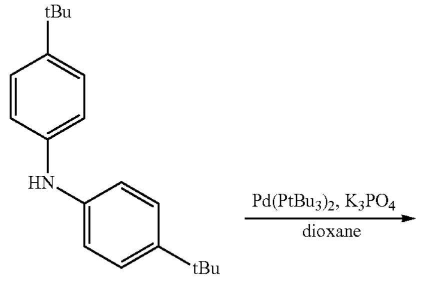

AM-15

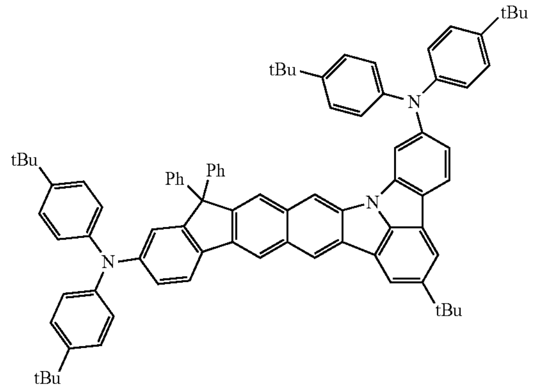

Compound 16

Compound 15 (2.3 g, yield 79%, Mass [M+]=1147) was obtained in the same manner as in Synthesis of Compound 1 of Synthesis Example 1, except that Intermediate 56 (3.0 g) was used instead of Intermediate 4, and AM-15 (1.4 g) was used instead of AM-1.

Synthesis Example 16. Synthesis of Compound 16

16-1. Synthesis of Intermediate 57

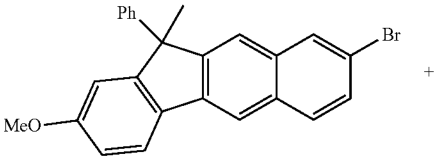

A-9

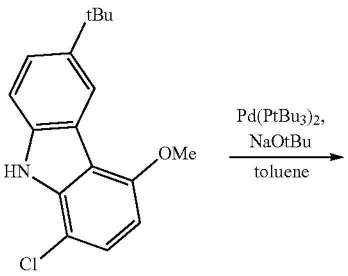

B-2

-continued

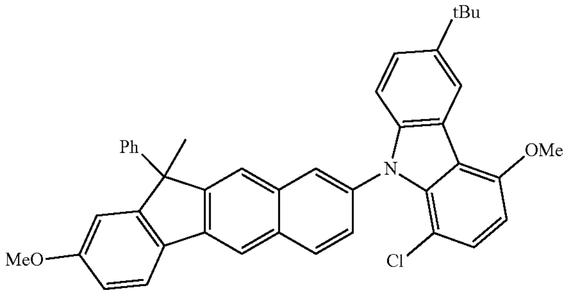

Intermediate 57

Intermediate 57 (5.3 g, yield 71%, Mass [M+]=623) was obtained in the same manner as in Synthesis of Intermediate 1 of Synthesis Example 1, except that A-9 (5.0 g) was used instead of starting material A-1, and B-2 (3.5 g) was used instead of B-1.

16-2. Synthesis of Intermediate 58

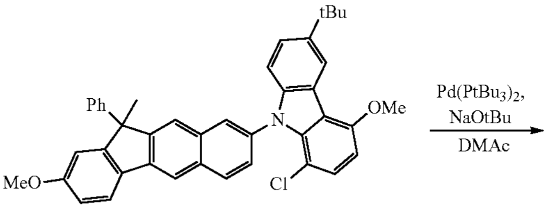

Intermediate 57

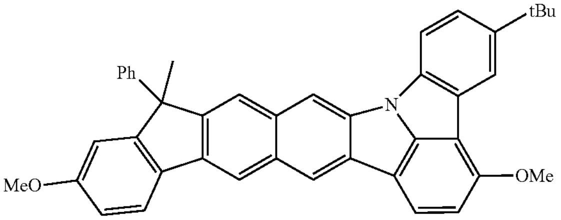

Intermediate 58

Intermediate 58 (3.0 g, yield 60%, Mass [M+]=586) was obtained in the same manner as in Synthesis of Intermediate 2 of Synthesis Example 1, except that Intermediate 57 (5.3 g) was used instead of Intermediate 1.

16-3. Synthesis of Intermediate 60

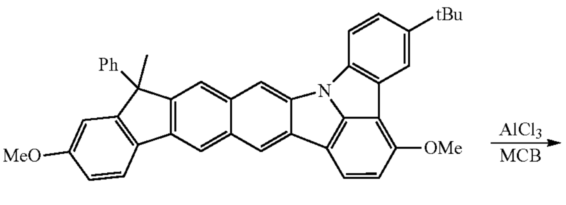

Intermediate 58

-continued

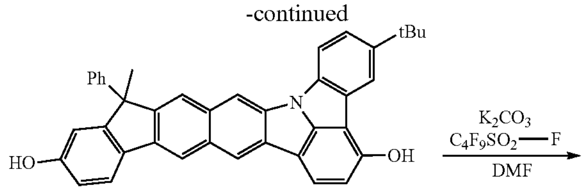

Intermediate 59

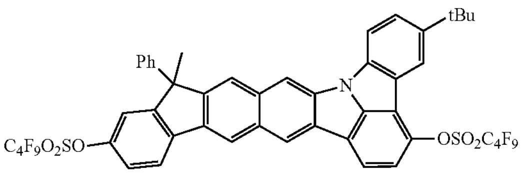

Intermediate 60

Intermediate 59 (2.2 g, yield 77%, Mass [M+]=558) was obtained in the same manner as in Synthesis of Intermediate 3 of Synthesis Example 1, except that Intermediate 58 (3.0 g) was used instead of Intermediate 2.

Intermediate 60 (3.4 g, yield 77%, Mass [M+]=1122) was obtained in the same manner as in Synthesis of Intermediate 4 of Synthesis Example 1, except that Intermediate 59 (2.2

16-4. Synthesis of Compound 16

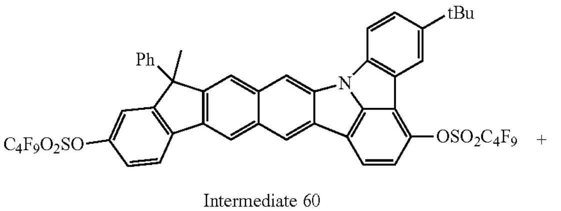

Intermediate 60

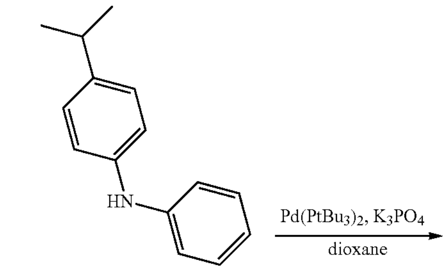

AM-16

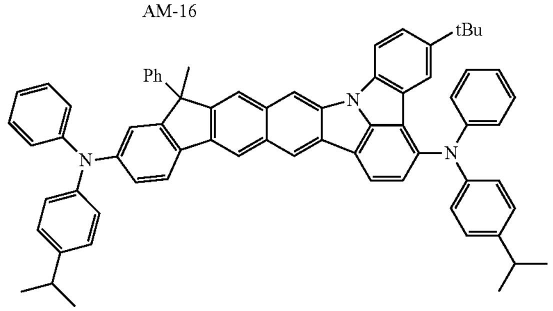

Compound 16

Compound 16 (1.9 g, yield 75%, Mass [M+]=945) was obtained in the same manner as in Synthesis of Compound 1 of Synthesis Example 1, except that Intermediate 60 (3.0 g) was used instead of Intermediate 4, and AM-16 (1.1 g) was used instead of AM-1.

Synthesis Example 17. Synthesis of Compound 17

17-1. Synthesis of Intermediate 61

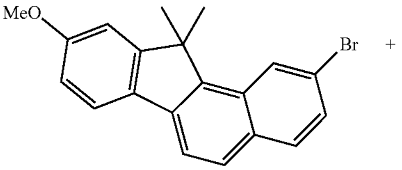

A-10

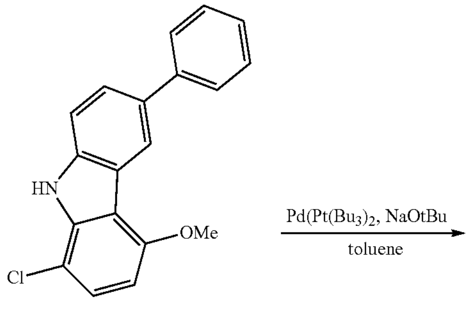

B-4

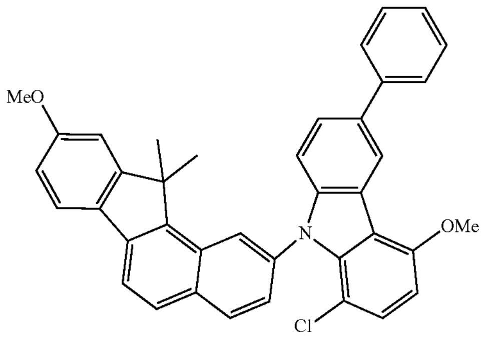

Intermediate 61

Intermediate 61 (6.0 g, yield 73%, Mass [M+]=581) was obtained in the same manner as in Synthesis of Intermediate 1 of Synthesis Example 1, except that A-10 (5.0 g) was used instead of starting material A-1, and B-4 (4.4 g) was used instead of B-1.

17-2. Synthesis of Intermediate 62

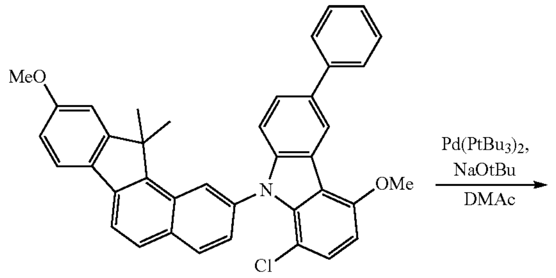

Intermediate 61

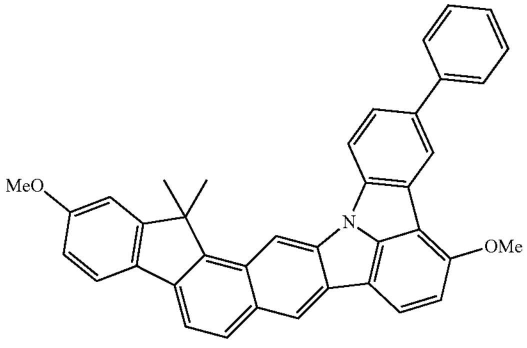

Intermediate 62

Intermediate 62 (3.2 g, yield 57%, Mass [M+]=544) was obtained in the same manner as in Synthesis of Intermediate 2 of Synthesis Example 1, except that Intermediate 61 (6.0 g) was used instead of Intermediate 1.

17-3. Synthesis of Intermediate 64

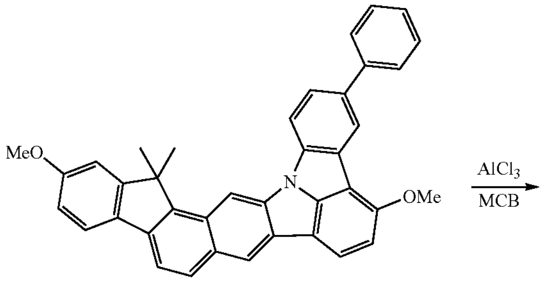

Intermediate 62

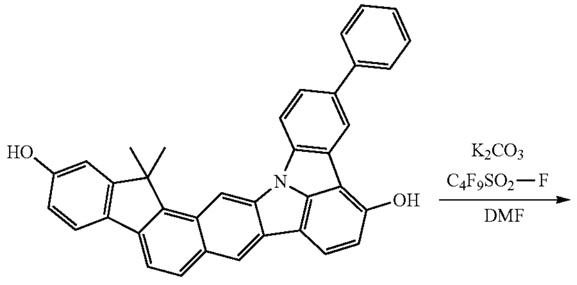

Intermediate 63

-continued

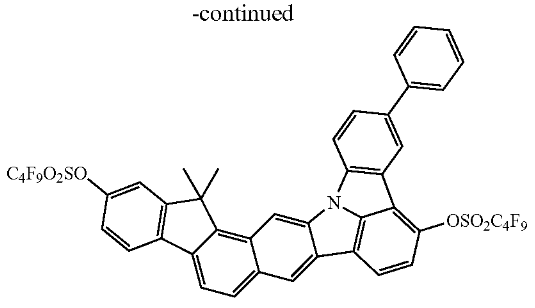

Intermediate 64

Intermediate 63 (2.3 g, yield 76%, Mass [M+]=516) was obtained in the same manner as in Synthesis of Intermediate 3 of Synthesis Example 1, except that Intermediate 62 (3.2 g) was used instead of Intermediate 2.

Intermediate 64 (3.5 g, yield 73%, Mass [M+]=1080) was obtained in the same manner as in Synthesis of Intermediate 4 of Synthesis Example 1, except that Intermediate 63 (2.3 g) was used instead of Intermediate 3.

17-4. Synthesis of Compound 17

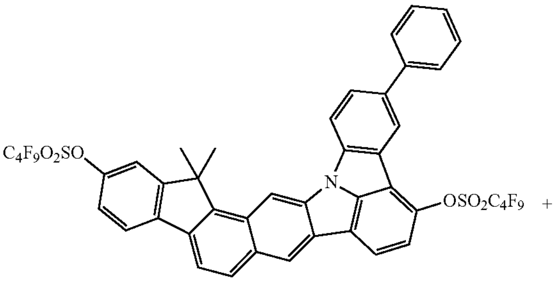

Intermediate 64

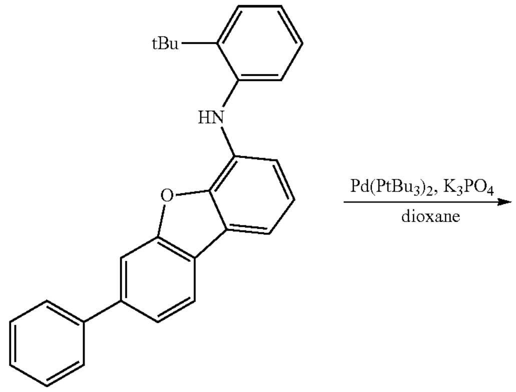

AM-17

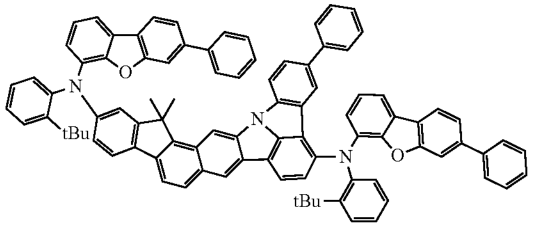

Compound 17

Compound 17 (2.3 g, yield 66%, Mass [M+]=1263) was obtained in the same manner as in Synthesis of Compound 1 of Synthesis Example 1, except that Intermediate 64 (3.0 g) was used instead of Intermediate 4, and AM-17 (2.2 g) was used instead of AM-1.

Synthesis Example 18. Synthesis of Compound 18

18-1. Synthesis of Intermediate 65

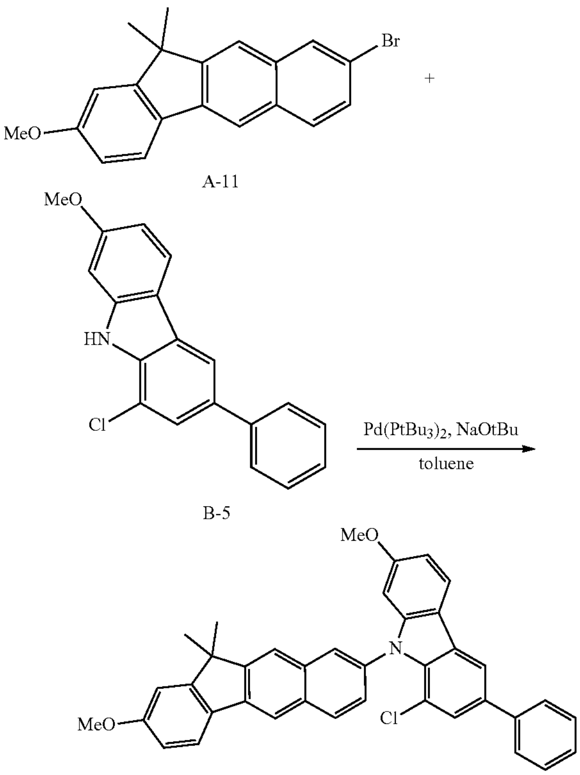

A-11

B-5

Intermediate 65

Intermediate 65 (6.1 g, yield 74%, Mass [M+]=581) was obtained in the same manner as in Synthesis of Intermediate 1 of Synthesis Example 1, except that A-11 (5.0 g) was used instead of starting material A-1, and B-5 (4.4 g) was used instead of B-1.

18-2. Synthesis of Intermediate 66

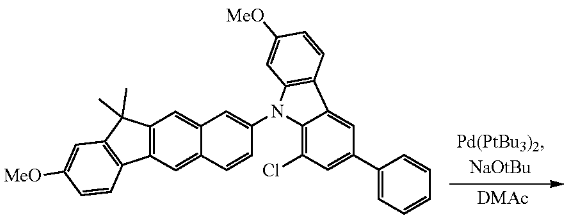

Intermediate 65

-continued

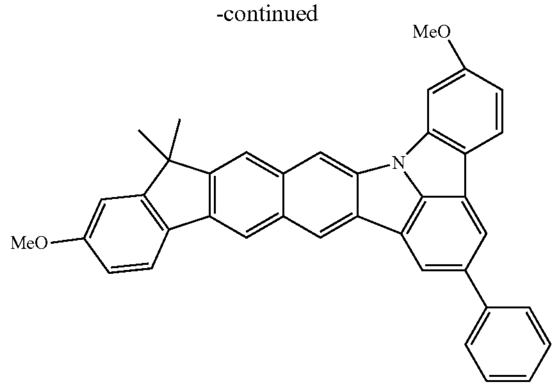

Intermediate 66

Intermediate 66 (3.4 g, yield 60%, Mass [M+]=544) was obtained in the same manner as in Synthesis of Intermediate 2 of Synthesis Example 1, except that Intermediate 65 (6.1

18-3. Synthesis of Intermediate 68

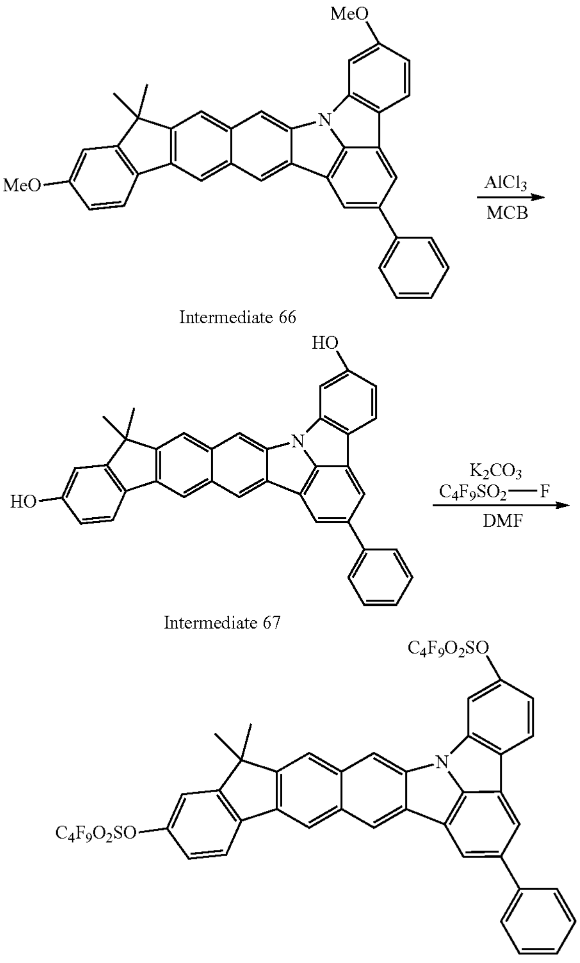

Intermediate 66

Intermediate 67

Intermediate 68

Intermediate 67 (2.4 g, yield 73%, Mass [M+]=516) was obtained in the same manner as in Synthesis of Intermediate 3 of Synthesis Example 1, except that Intermediate 66 (3.4 g) was used instead of Intermediate 2.

Intermediate 68 (3.5 g, yield 70%, Mass [M+]=1079) was obtained in the same manner as in Synthesis of Intermediate 4 of Synthesis Example 1, except that Intermediate 67 (2.4

18-4. Synthesis of Compound 18

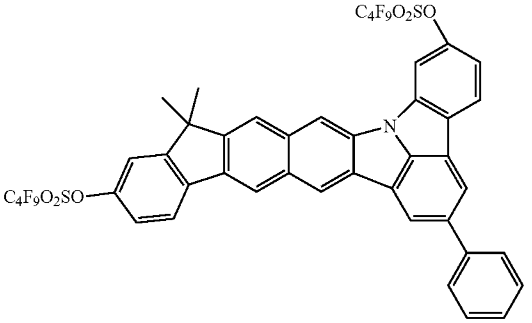

Intermediate 68

+

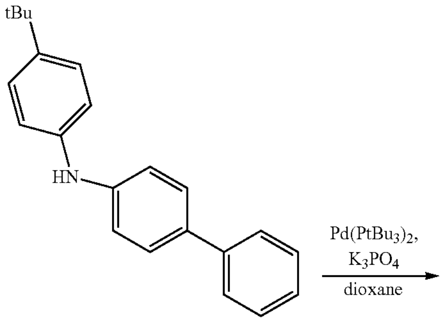

AM-18

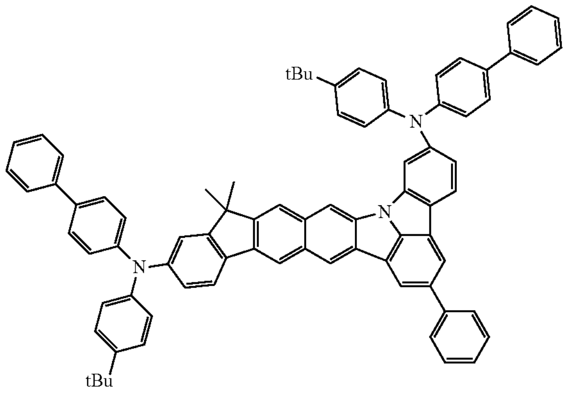

Compound 18

Compound 18 (2.2 g, yield 73%, Mass [M+]=1080) was obtained in the same manner as in Synthesis of Compound 1 of Synthesis Example 1, except that Intermediate 68 (3.0 g) was used instead of Intermediate 4, and AM-18 (1.7 g) was used instead of AM-1.

Synthesis Example 19. Synthesis of Compound 19

19-1. Synthesis of Intermediate 69

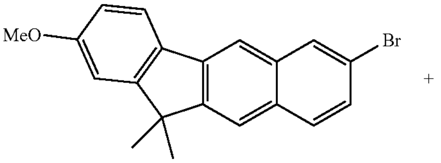

A-12

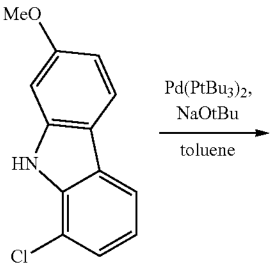

B-6

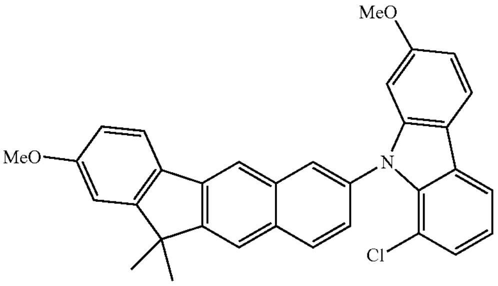

Intermediate 69

Intermediate 69 (5.7 g, yield 80%, Mass [M+]=505) was obtained in the same manner as in Synthesis of Intermediate 1 of Synthesis Example 1, except that A-12 (5.0 g) was used instead of starting material A-1, and B-6 (3.3 g) was used instead of B-1.

19-2. Synthesis of Intermediate 70

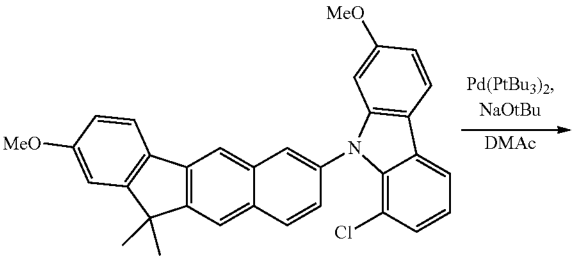

Intermediate 69

-continued

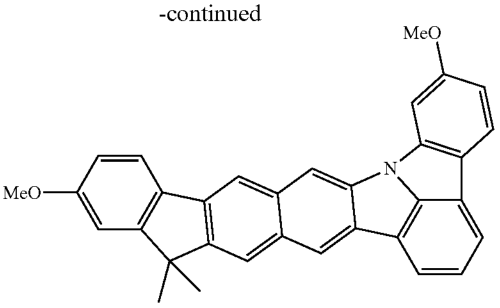

Intermediate 70

Intermediate 70 (3.6 g, yield 68%, Mass [M+]=468) was obtained in the same manner as in Synthesis of Intermediate 2 of Synthesis Example 1, except that Intermediate 69 (5.7 g) was used instead of Intermediate 1.

19-3. Synthesis of Intermediate 72

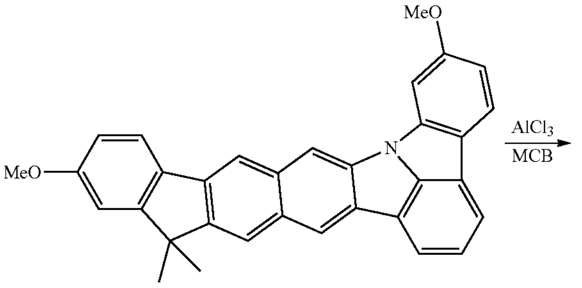

Intermediate 70

-continued

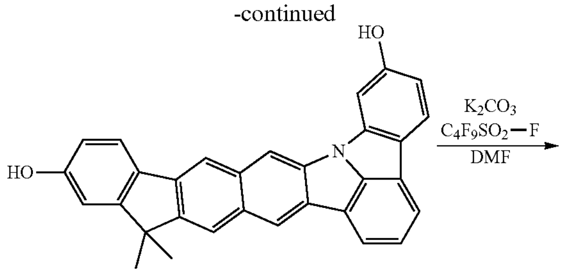

Intermediate 71

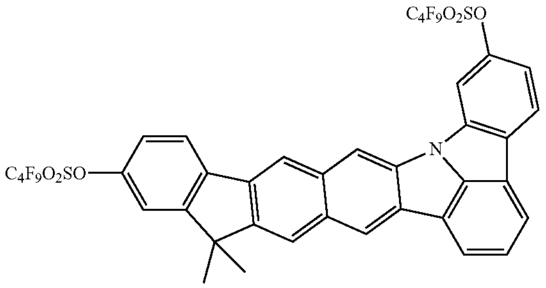

Intermediate 72

Intermediate 71 (2.7 g, yield 77%, Mass [M+]=456) was obtained in the same manner as in Synthesis of Intermediate 3 of Synthesis Example 1, except that Intermediate 70 (3.6 g) was used instead of Intermediate 2.

Intermediate 72 (4.2 g, yield 69%, Mass [M+]=1020) was obtained in the same manner as in Synthesis of Intermediate 4 of Synthesis Example 1, except that Intermediate 71 (2.7 g) was used instead of Intermediate 3.

19-4. Synthesis of Compound 19

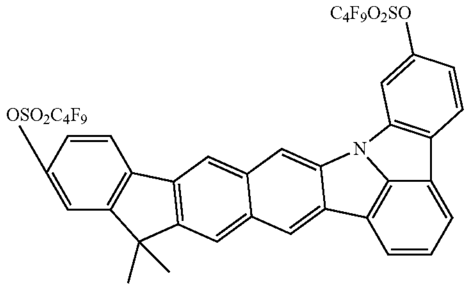

Intermediate 72

+

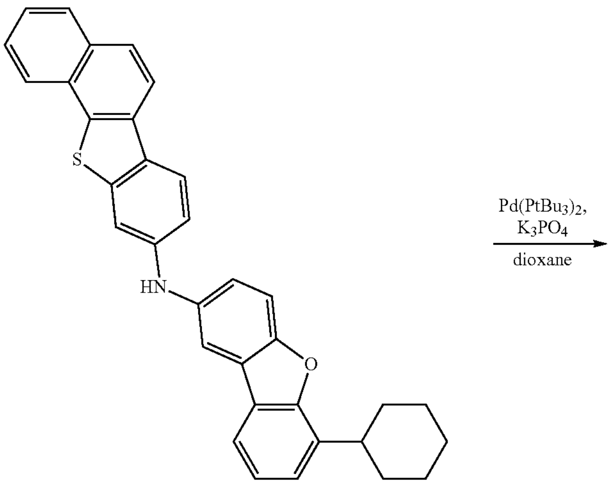

AM-19

-continued

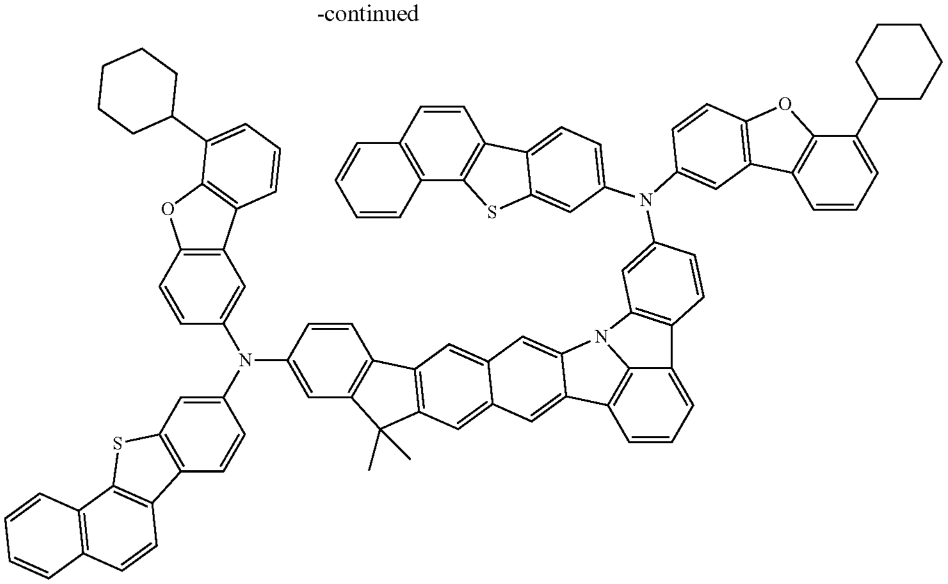

Compound19

Compound 19 (3.1 g, yield 75%, Mass [M+]=1399) was obtained in the same manner as in Synthesis of Compound 1 of Synthesis Example 1, except that Intermediate 72 (3.0 g) was used instead of Intermediate 4, and AM-19 (2.9 g) was used instead of AM-1.

Synthesis Example 20. Synthesis of Compound 20

20-1. Synthesis of Intermediate 73

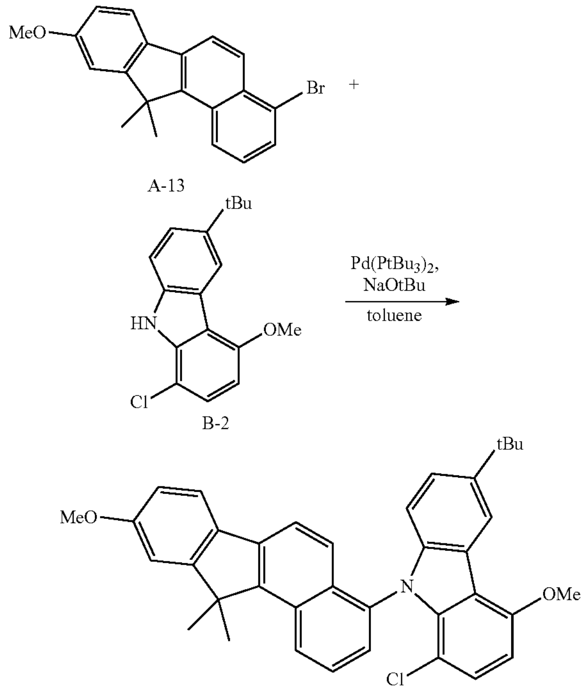

A-13

B-2

Intermediate 73

Intermediate 73 (5.6 g, yield 71%, Mass [M+]=561) was obtained in the same manner as in Synthesis of Intermediate 1 of Synthesis Example 1, except that A-13 (5.0 g) was used instead of starting material A-1, and B-2 (4.1 g) was used instead of B-1.

20-2. Synthesis of Intermediate 74

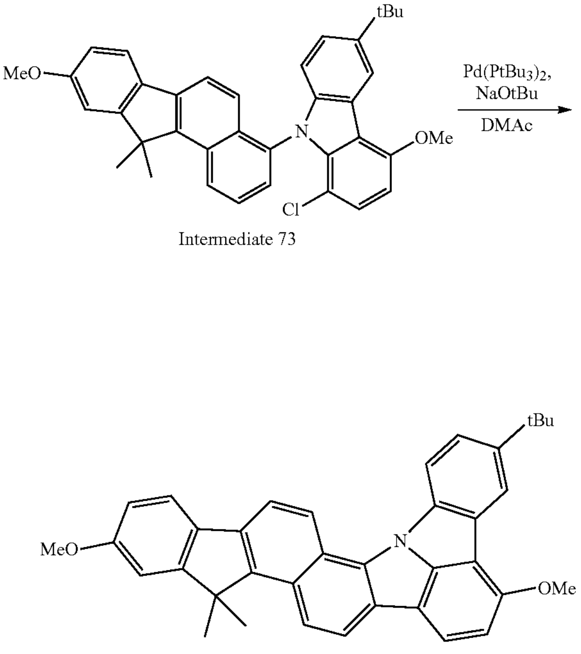

Intermediate 73

Intermediate 74

Intermediate 74 (3.5 g, yield 67%, Mass [M+]=523) was obtained in the same manner as in Synthesis of Intermediate 2 of Synthesis Example 1, except that Intermediate 73 (5.6

20-3. Synthesis of Intermediate 76

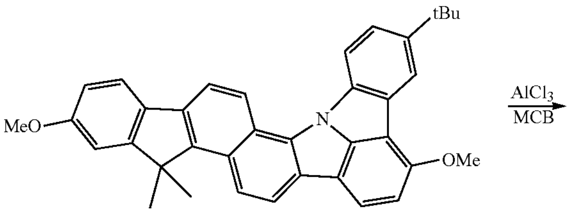

Intermediate 74

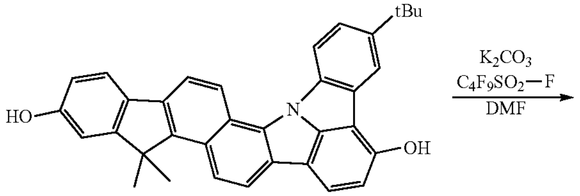

Intermediate 75

-continued

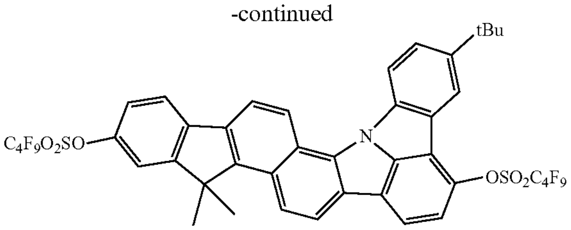

Intermediate 76

Intermediate 75 (2.5 g, yield 75%, Mass [M+]=496) was obtained in the same manner as in Synthesis of Intermediate 3 of Synthesis Example 1, except that Intermediate 74 (3.5 g) was used instead of Intermediate 2.

Intermediate 76 (4.0 g, yield 75%, Mass [M+]=1060) was obtained in the same manner as in Synthesis of Intermediate 4 of Synthesis Example 1, except that Intermediate 75 (2.5 g) was used instead of Intermediate 3.

20-4. Synthesis of Compound 20

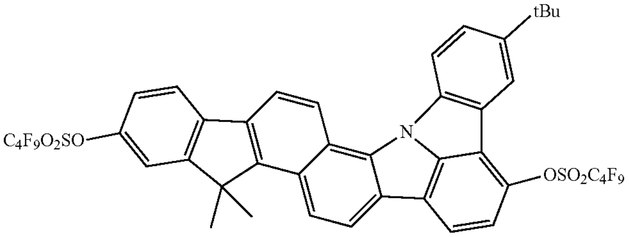

Intermediate 76

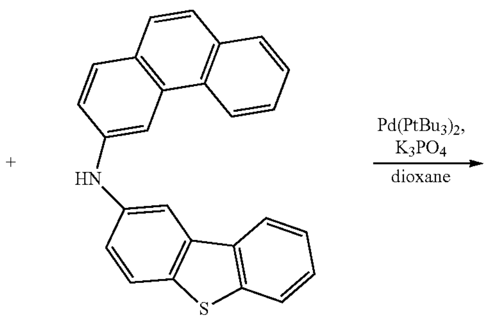

AM-20

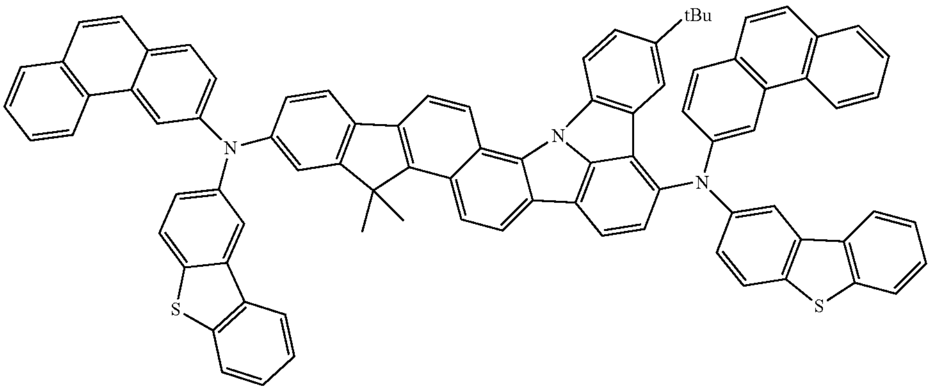

Compound20

Compound 20 (2.5 g, yield 73%, Mass [M+]=1211) was obtained in the same manner as in Synthesis of Compound 1 of Synthesis Example 1, except that Intermediate 76 (3.0 g) was used instead of Intermediate 4, and AM-20 (2.1 g) was used instead of AM-1.

Synthesis Example 21. Synthesis of Compound 21

21-1. Synthesis of Intermediate 77

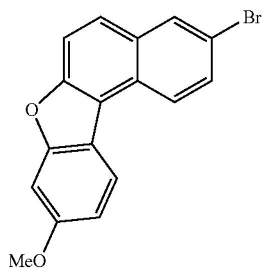

A-4

+

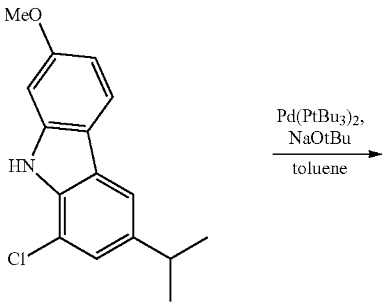

B-7

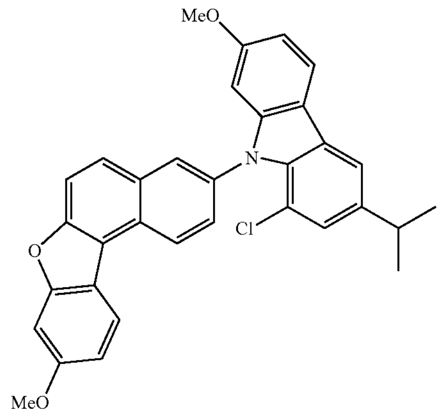

Intermediate 77

Intermediate 77 (6.2 g, yield 78%, Mass [M+]=521) was obtained in the same manner as in Synthesis of Intermediate 1 of Synthesis Example 1, except that A-4 (5.0 g) was used instead of starting material A-1, and B-7 (4.2 g) was used instead of B-1.

21-2. Synthesis of Intermediate 78

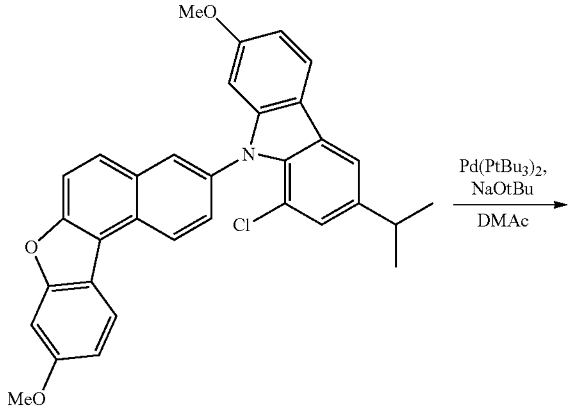

Intermediate 77

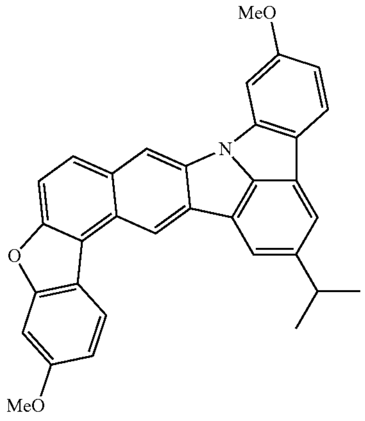

Intermediate 78

Intermediate 78 (3.3 g, yield 57%, Mass [M+]=484) was obtained in the same manner as in Synthesis of Intermediate 2 of Synthesis Example 1, except that Intermediate 77 (6.2 g) was used instead of Intermediate 1.

21-3. Synthesis of Intermediate 80

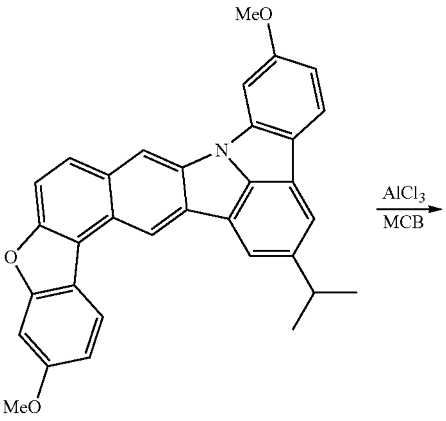

Intermediate 78

-continued

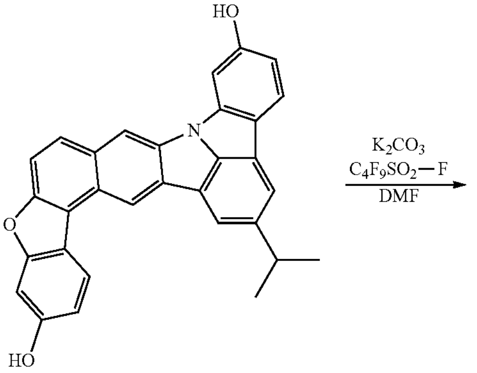

Intermediate 79

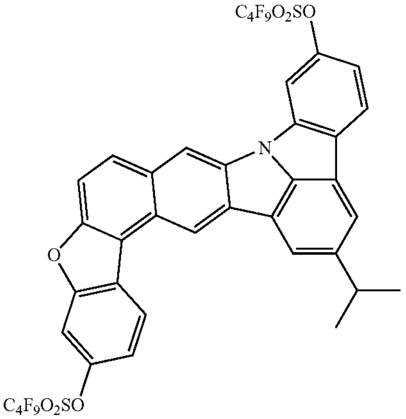

Intermediate 80

Intermediate 79 (2.4 g, yield 77%, Mass [M+]=456) was obtained in the same manner as in Synthesis of Intermediate 3 of Synthesis Example 1, except that Intermediate 78 (3.3 g) was used instead of Intermediate 2.

Intermediate 80 (3.9 g, yield 73%, Mass [M+]=1020) was obtained in the same manner as in Synthesis of Intermediate 4 of Synthesis Example 1, except that Intermediate 79 (2.4

21-4. Synthesis of Compound 21

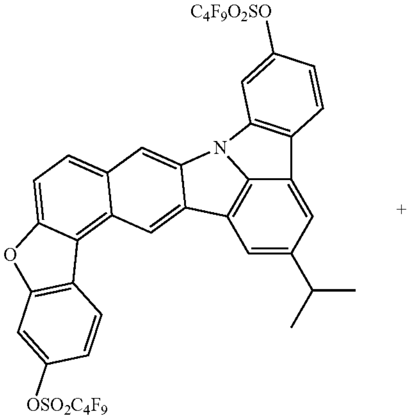

Intermediate 80

-continued

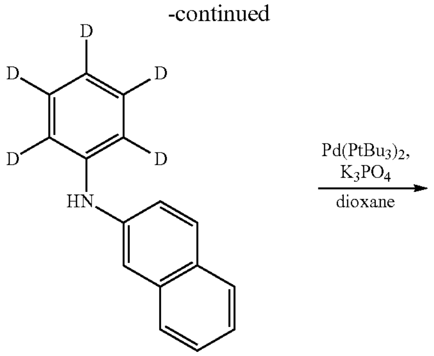

AM-21

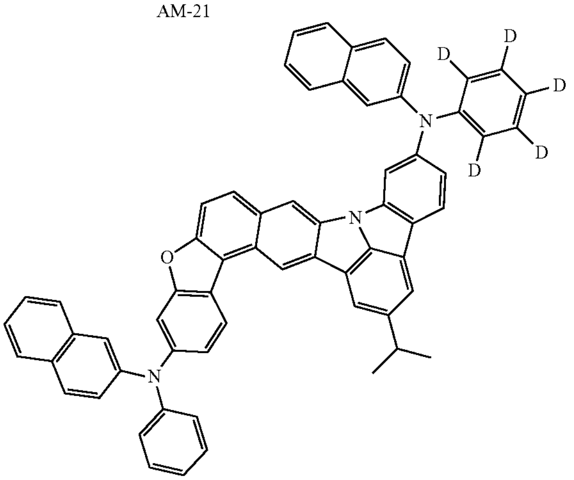

Compound21

Compound 21 (2.1 g, yield 82%, Mass [M+]=869) was obtained in the same manner as in Synthesis of Compound 1 of Synthesis Example 1, except that Intermediate 80 (3.0 g) was used instead of Intermediate 4, and AM-21 (1.3 g) was used instead of AM-1.

Synthesis Example 22. Synthesis of Compound 22

22-1. Synthesis of Intermediate 81

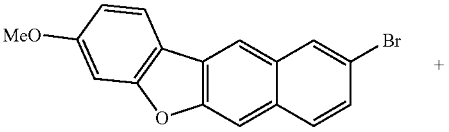

A-1

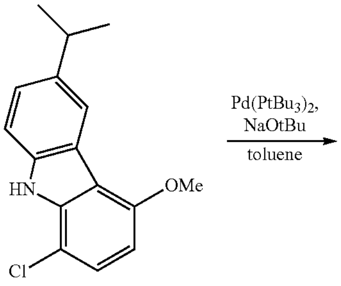

B-8

-continued

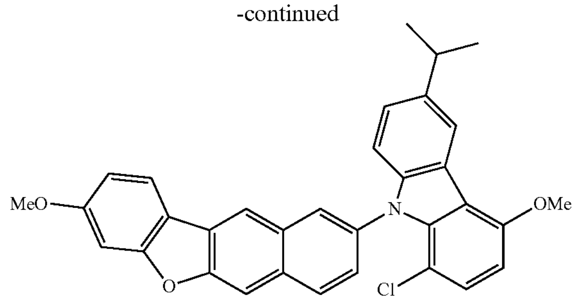

Intermediate 81

Intermediate 81 (5.8 g, yield 73%, Mass [M+]=521) was obtained in the same manner as in Synthesis of Intermediate 1 of Synthesis Example 1, except that B-8 (4.2 g) was used instead of B-1.

22-2. Synthesis of Intermediate 82

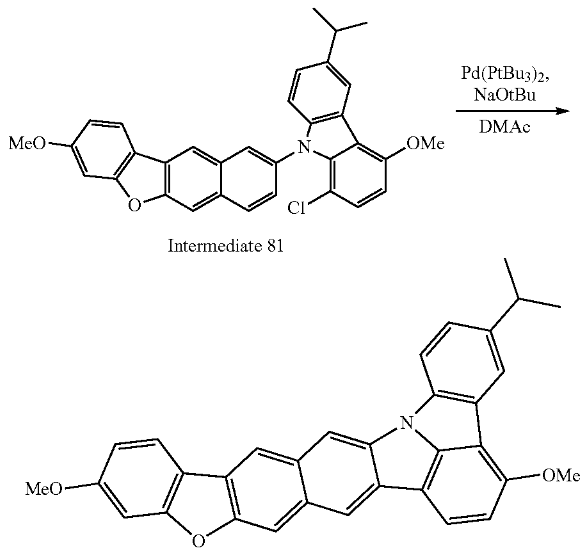

Intermediate 81

Intermediate 82

Intermediate 82 (3.5 g, yield 65%, Mass [M+]=484) was obtained in the same manner as in Synthesis of Intermediate 2 of Synthesis Example 1, except that Intermediate 81 (5.8

22-3. Synthesis of Intermediate 84

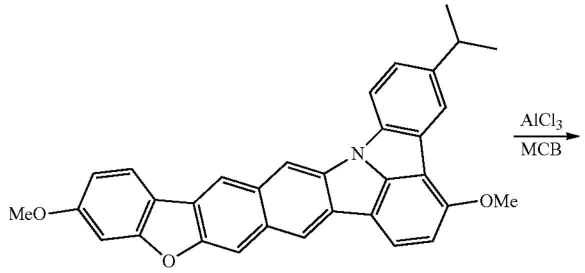

Intermediate 82

-continued

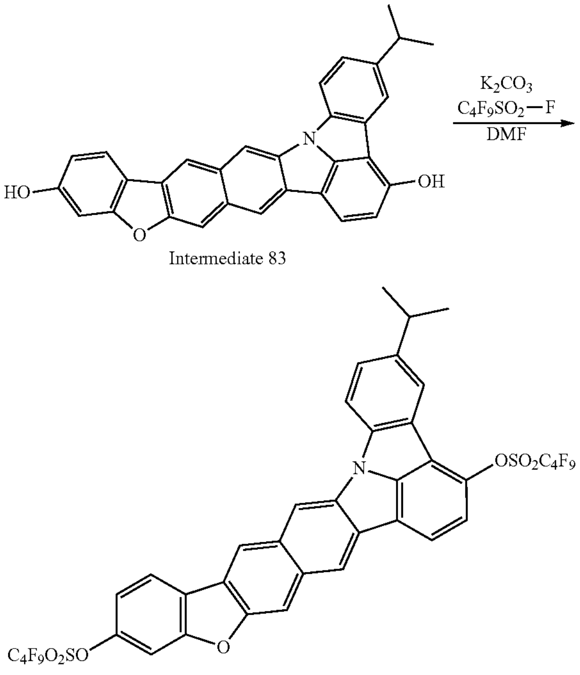

Intermediate 83

Intermediate 84

Intermediate 83 (2.5 g, yield 76%, Mass [M+]=456) was obtained in the same manner as in Synthesis of Intermediate 3 of Synthesis Example 1, except that Intermediate 82 (3.5 g) was used instead of Intermediate 2.

Intermediate 84 (4.0 g, yield 71%, Mass [M+]=1020) was obtained in the same manner as in Synthesis of Intermediate 4 of Synthesis Example 1, except that Intermediate 83 (2.5

22-4. Synthesis of Compound 22

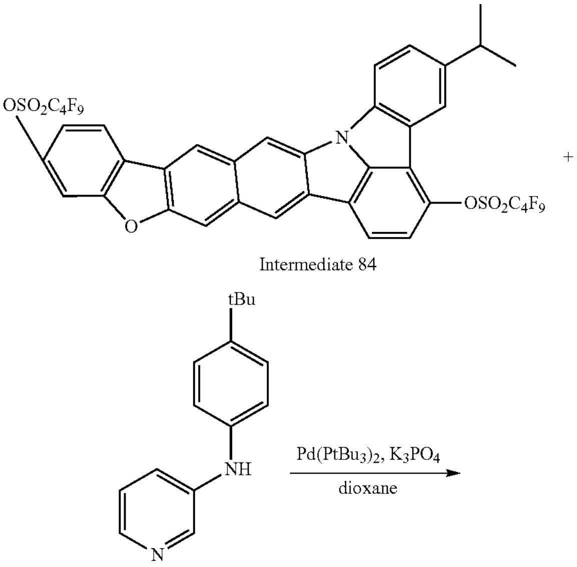

Intermediate 84

AM-22

-continued

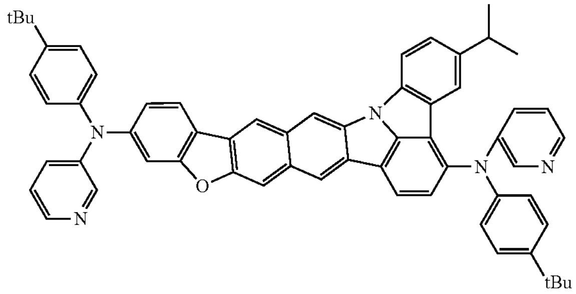

Compound 22

Compound 22 (2.0 g, yield 78%, Mass [M+]=873) was obtained in the same manner as in Synthesis of Compound 1 of Synthesis Example 1, except that Intermediate 84 (3.0 g) was used instead of Intermediate 4, and AM-22 (1.3 g) was used instead of AM-1.

Synthesis Example 23. Synthesis of Compound 23

23-1. Synthesis of Intermediate 85

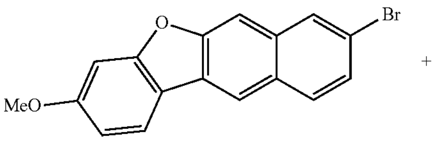

A-3

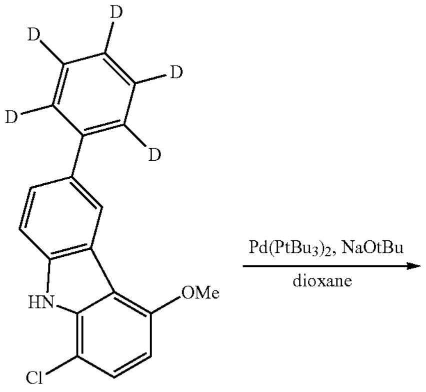

B-9

-continued

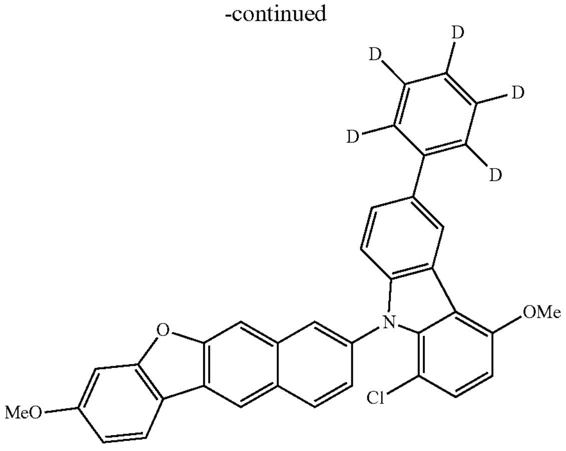

Intermediate 85

Intermediate 85 (6.1 g, yield 71%, Mass [M+]=560) was obtained in the same manner as in Synthesis of Intermediate 1 of Synthesis Example 1, except that A-3 (5.0 g) was used instead of starting material A-1, and B-9 (4.8 g) was used instead of B-1.

23-2. Synthesis of Intermediate 86

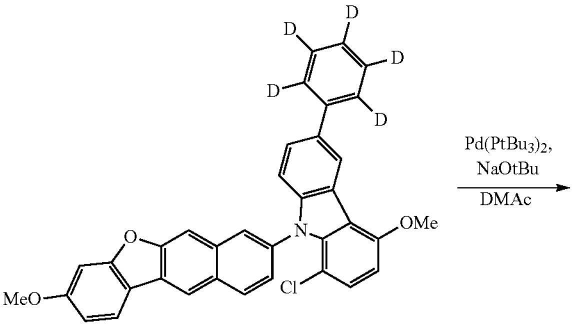

Intermediate 85

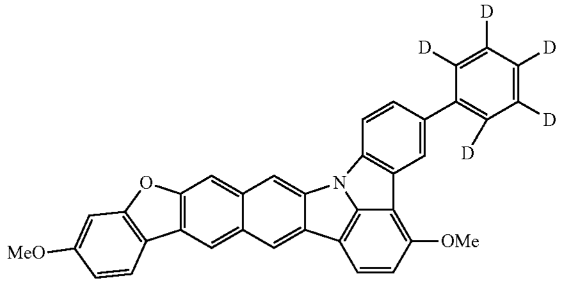

Intermediate 86

Intermediate 86 (3.5 g, yield 61%, Mass [M+]=523) was obtained in the same manner as in Synthesis of Intermediate 2 of Synthesis Example 1, except that Intermediate 85 (6.1 g) was used instead of Intermediate 1.

23-3. Synthesis of Intermediate 88

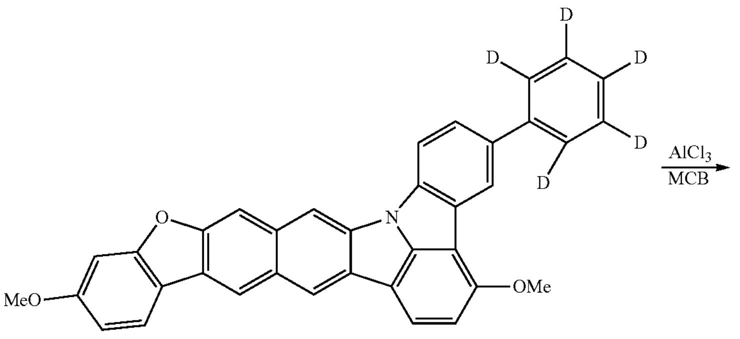

Intermediate 86

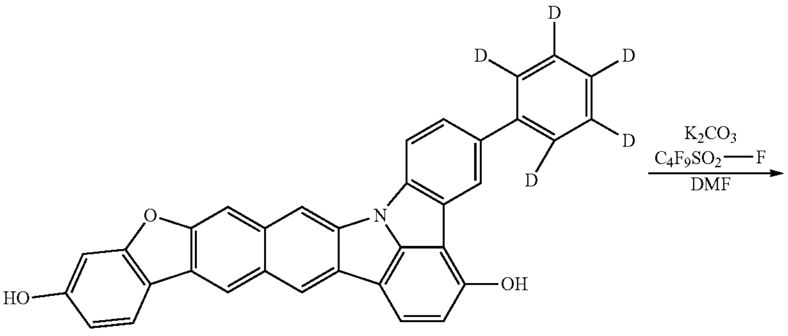

Intermediate 87

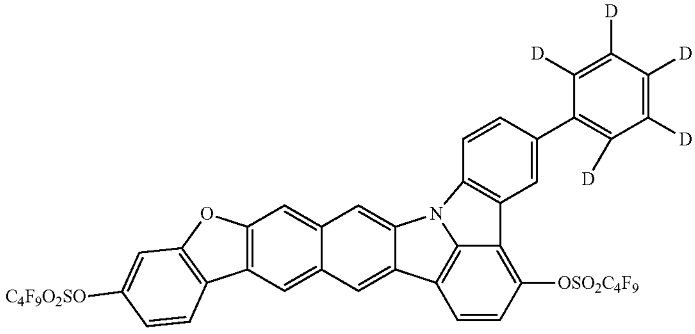

Intermediate 88

Intermediate 87 (2.4 g, yield 72%, Mass [M+]=495) was obtained in the same manner as in Synthesis of Intermediate 3 of Synthesis Example 1, except that Intermediate 86 (3.5 g) was used instead of Intermediate 2.

Intermediate 88 (3.8 g, yield 73%, Mass [M+]=1075) was obtained in the same manner as in Synthesis of Intermediate 4 of Synthesis Example 1, except that Intermediate 87 (2.4 g) was used instead of Intermediate 3.

23-4. Synthesis of Compound 23
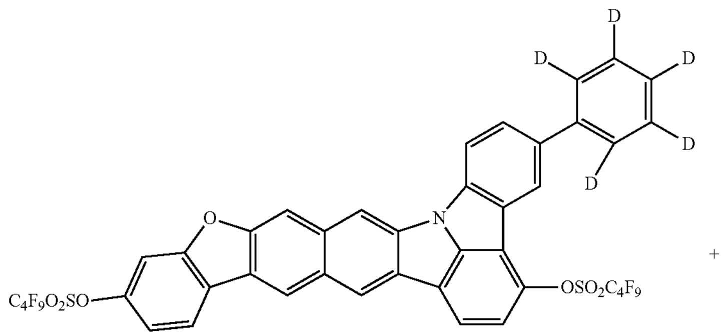
Intermediate 88
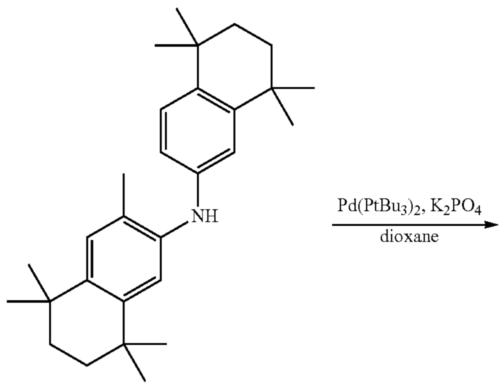
AM-23
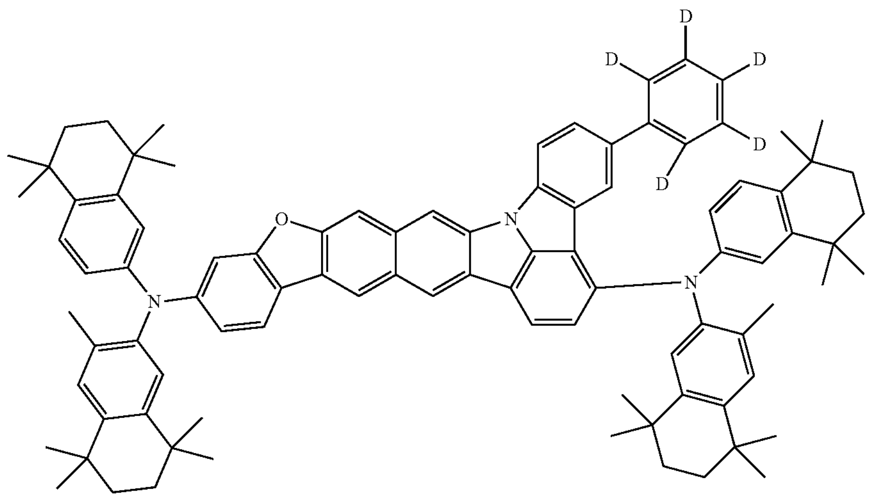
Compound 23
Compound 23 (2.4 g, yield 68%, Mass [M+]=1266) was obtained in the same manner as in Synthesis of Compound 1 of Synthesis Example 1, except that Intermediate 88 (3.0 g) was used instead of Intermediate 4, and AM-23 (2.2 g) was used instead of AM-1.

Synthesis Example 24. Synthesis of Compound 24
24-1. Synthesis of Intermediate 89
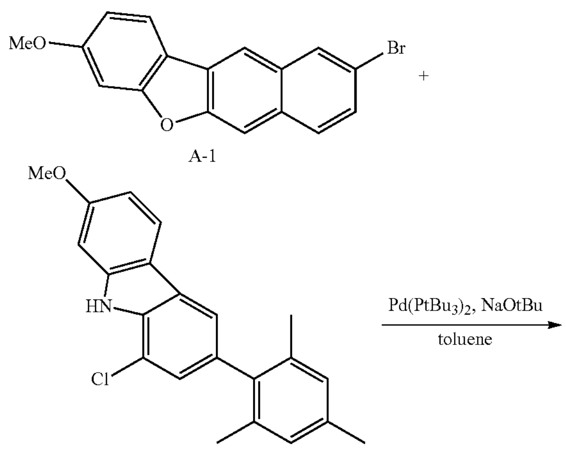
A-1
B-10
-continued
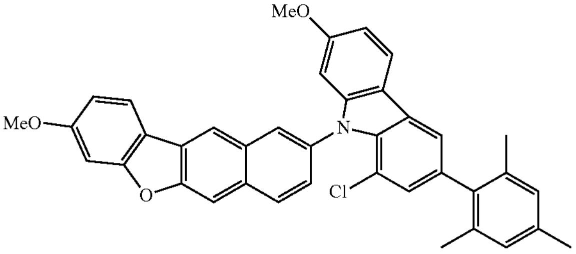
Intermediate 89
Intermediate 89 (7.1 g, yield 77%, Mass [M+]=597) was obtained in the same manner as in Synthesis of Intermediate 1 of Synthesis Example 1, except that B-10 (4.8 g) was used instead of B-1.
24-2. Synthesis of Intermediate 90
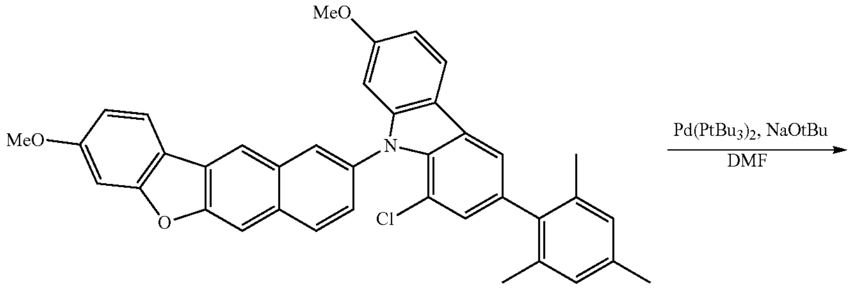
Intermediate 89
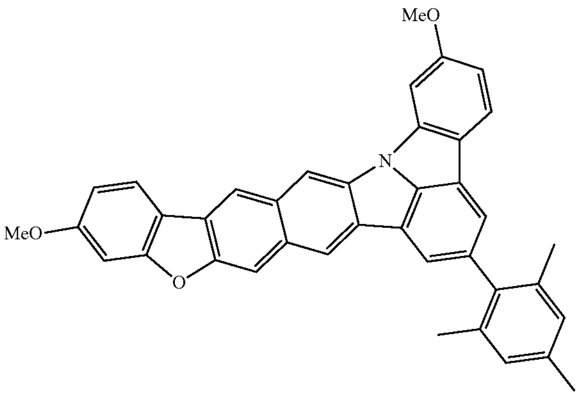
Intermediate 90

Intermediate 90 (4.1 g, yield 62%, Mass [M+]=560) was obtained in the same manner as in Synthesis of Intermediate 2 of Synthesis Example 1, except that Intermediate 89 (7.1

24-3. Synthesis of Intermediate 92

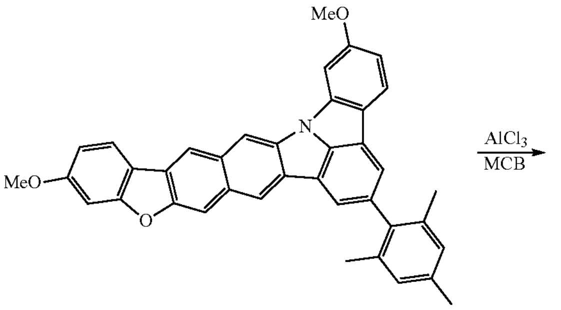

Intermediate 90

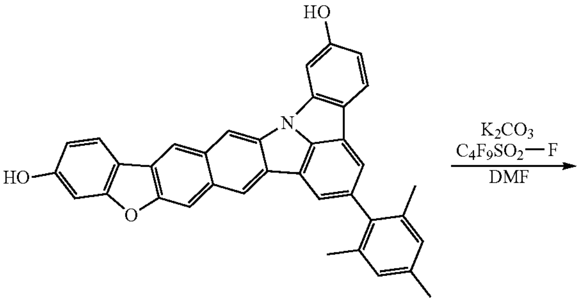

Intermediate 91

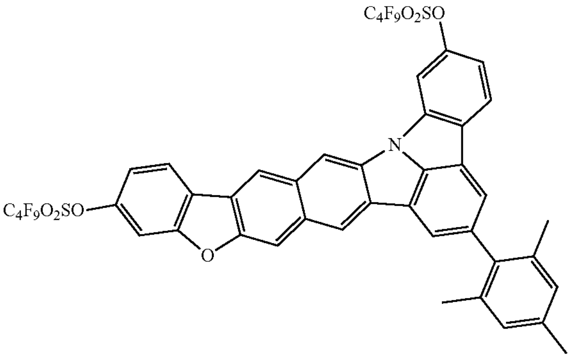

Intermediate 92

Intermediate 91 (2.9 g, yield 74%, Mass [M+]=532) was obtained in the same manner as in Synthesis of Intermediate 3 of Synthesis Example 1, except that Intermediate 90 (4.1 g) was used instead of Intermediate 2.

Intermediate 92 (4.0 g, yield 67%, Mass [M+]=1096) was obtained in the same manner as in Synthesis of Intermediate 4 of Synthesis Example 1, except that Intermediate 91 (2.9 g) was used instead of Intermediate 3.

24-4. Synthesis of Compound 24

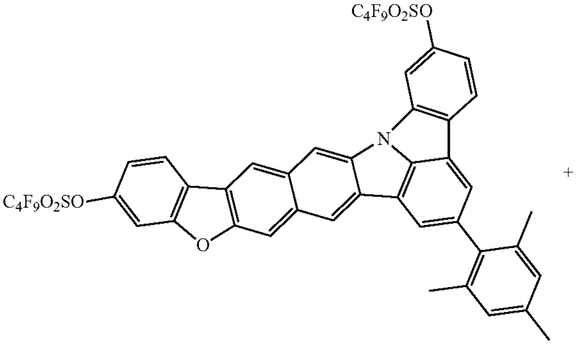

Intermediate 92

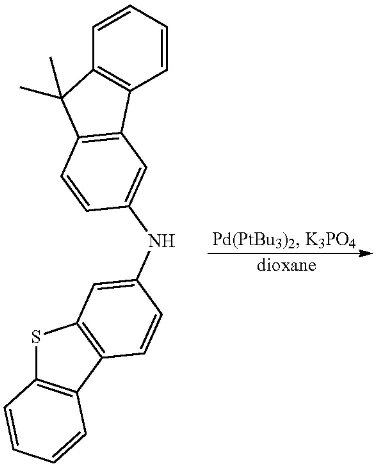

AM-4

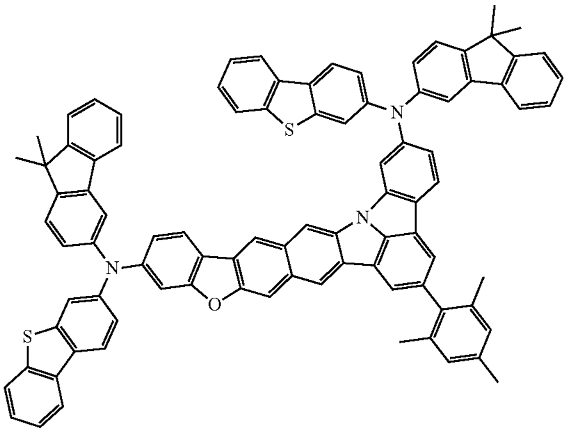

Compound 24

Compound 24 (3.2 g, yield 69%, Mass [M+]=1279) was obtained in the same manner as in Synthesis of Compound 1 of Synthesis Example 1, except that Intermediate 92 (4.0 g) was used instead of Intermediate 4, and AM-4 (2.9 g) was used instead of AM-1.

Synthesis Example 25. Synthesis of Compound 25

25-1. Synthesis of Intermediate 93

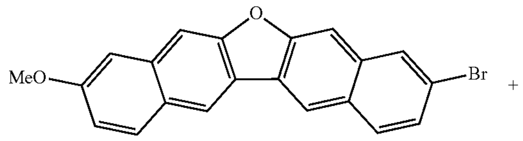

A-14

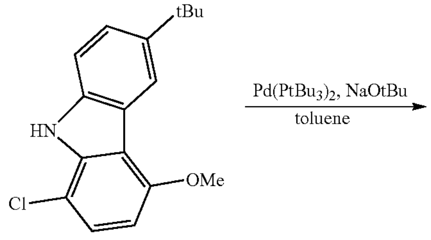

B-2

-continued

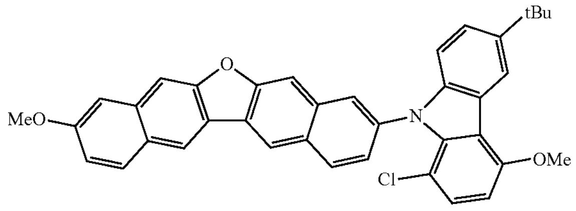

Intermediate 93

Intermediate 93 (6.0 g, yield 78%, Mass [M+]=585) was obtained in the same manner as in Synthesis of Intermediate 1 of Synthesis Example 1, except that A-14 (5.0 g) was used instead of starting material A-1, and B-2 (3.9 g) was used instead of B-1.

25-2. Synthesis of Intermediate 94

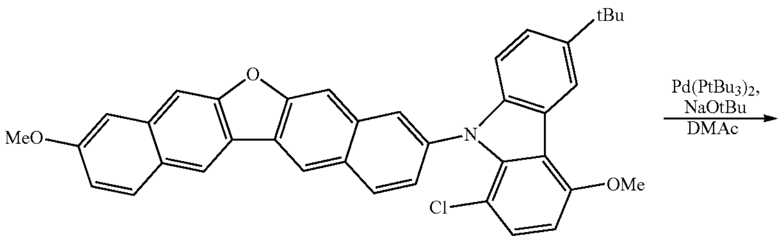

Intermediate 93

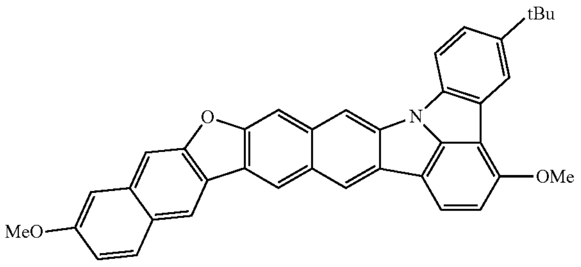

Intermediate 94

Intermediate 94 (3.5 g, yield 62%, Mass [M+]=548) was obtained in the same manner as in Synthesis of Intermediate 2 of Synthesis Example 1, except that Intermediate 93 (6.0

25-3. Synthesis of Intermediate 96

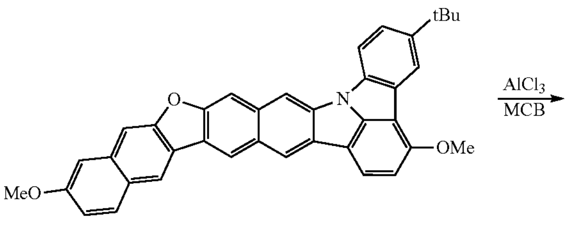

Intermediate 94

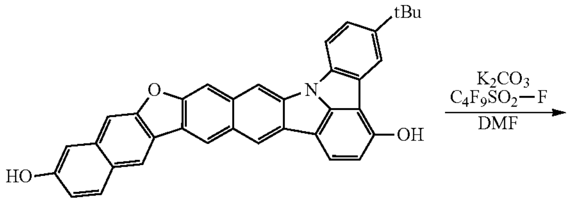

Intermediate 95

-continued

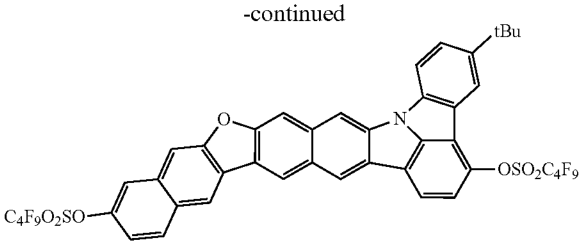

Intermediate 96

Intermediate 95 (2.5 g, yield 75%, Mass [M+]=520) was obtained in the same manner as in Synthesis of Intermediate 3 of Synthesis Example 1, except that Intermediate 94 (3.5 g) was used instead of Intermediate 2.

Intermediate 96 (3.8 g, yield 73%, Mass [M+]=1084) was obtained in the same manner as in Synthesis of Intermediate 4 of Synthesis Example 1, except that Intermediate 95 (2.5

25-4. Synthesis of Compound 25

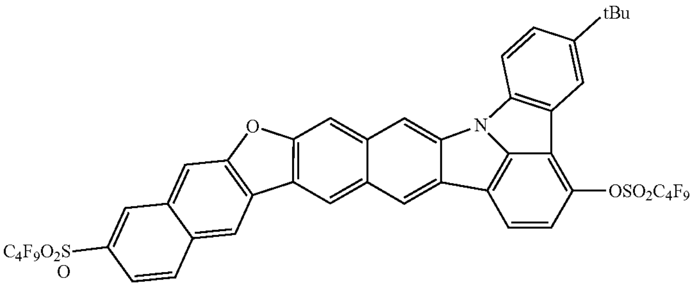

Intermediate 96

+

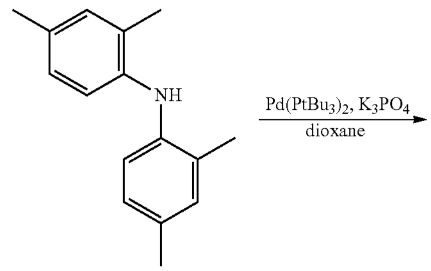

AM-24

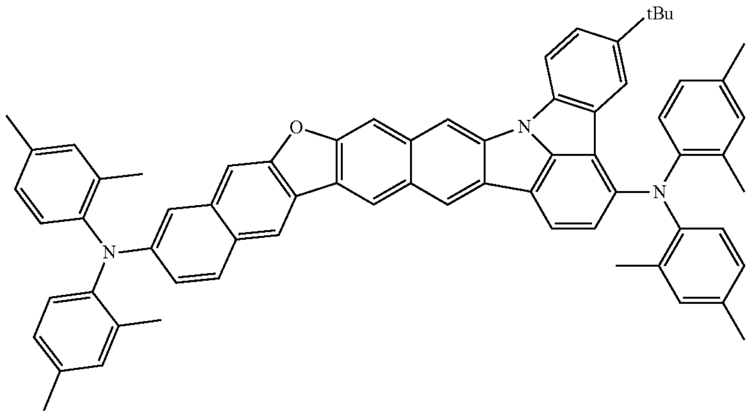

Compound 25

Compound 25 (2.5 g, yield 76%, Mass [M+]=935) was obtained in the same manner as in Synthesis of Compound 1 of Synthesis Example 1, except that Intermediate 96 (3.8 g) was used instead of Intermediate 4, and AM-24 (1.6 g) was used instead of AM-1.

Synthesis Example 26. Synthesis of Compound 26

26-1. Synthesis of Intermediate 97

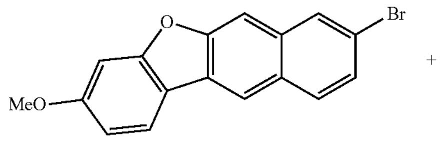

A-3

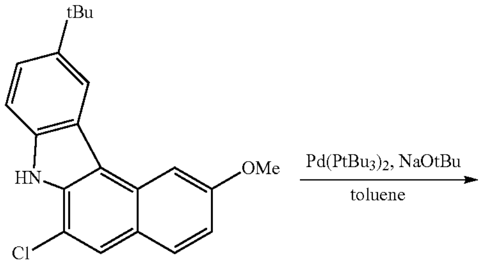

B-11

-continued

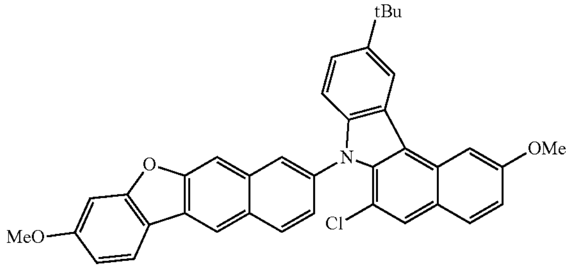

Intermediate 97

Intermediate 97 (7.0 g, yield 78%, Mass [M+]=585) was obtained in the same manner as in Synthesis of Intermediate 1 of Synthesis Example 1, except that A-3 (5.0 g) was used instead of starting material A-1, and B-11 (5.2 g) was used instead of B-1.

26-2. Synthesis of Intermediate 98

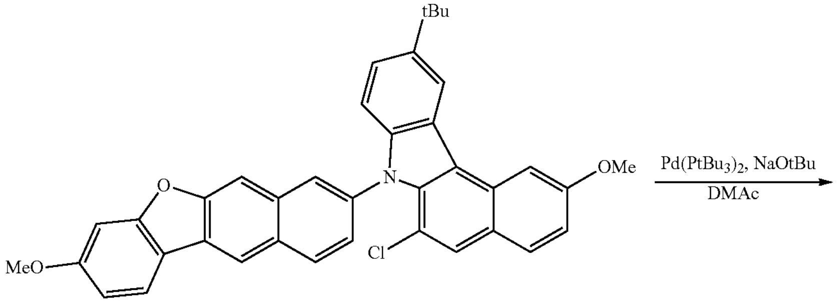

Intermediate 97

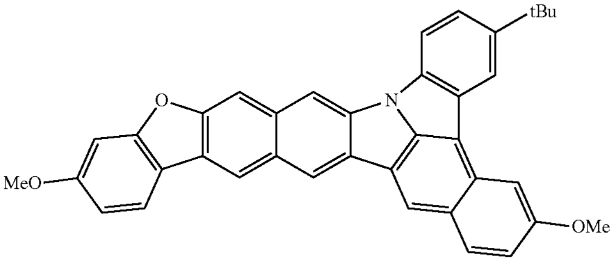

Intermediate 98

Intermediate 98 (4.0 g, yield 61%, Mass [M+]=548) was obtained in the same manner as in Synthesis of Intermediate 2 of Synthesis Example 1, except that Intermediate 97 (7.0 g) was used instead of Intermediate 1.

26-3. Synthesis of Intermediate 100

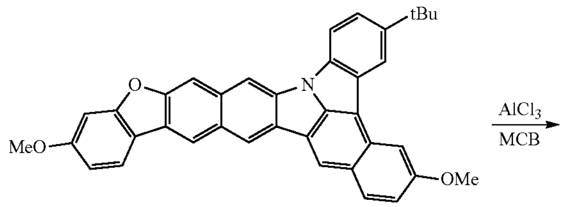

Intermediate 98

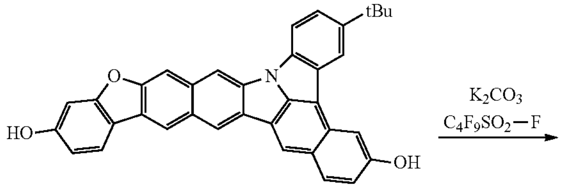

Intermediate 99

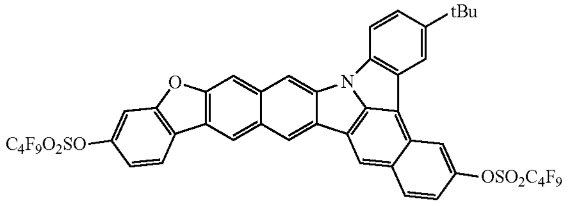

Intermediate 100

Intermediate 99 (2.8 g, yield 74%, Mass [M+]=520) was obtained in the same manner as in Synthesis of Intermediate 3 of Synthesis Example 1, except that Intermediate 98 (4.0 g) was used instead of Intermediate 2.

Intermediate 100 (4.2 g, yield 72%, Mass [M+]=1084) was obtained in the same manner as in Synthesis of Intermediate 4 of Synthesis Example 1, except that Intermediate 99 (2.8 g) was used instead of Intermediate 3.

26-4. Synthesis of Compound 26

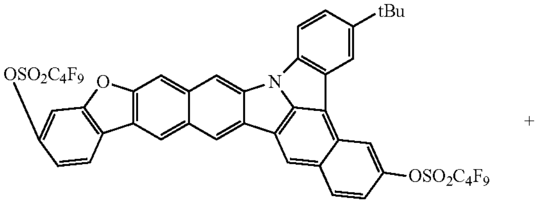

Intermediate 100

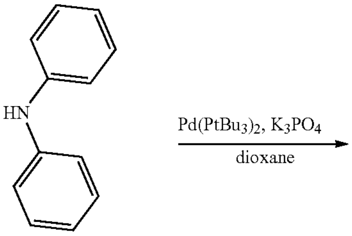

AM-10

-continued

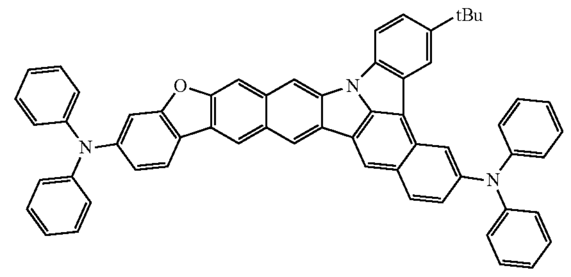

Compound26

Compound 26 (2.4 g, yield 75%, Mass [M+]=823) was obtained in the same manner as in Synthesis of Compound 1 of Synthesis Example 1, except that Intermediate 100 (4.2 g) was used instead of Intermediate 4, and AM-10 (1.3 g) was used instead of AM-1.

Synthesis Example 27. Synthesis of Compound 27

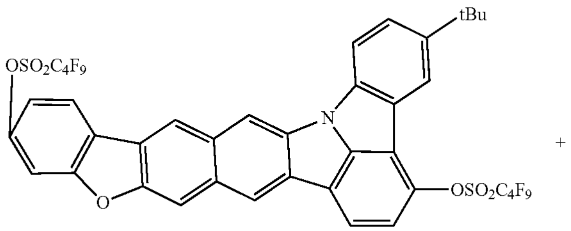

Intermediate 12

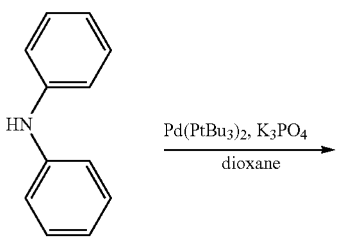

AM-10

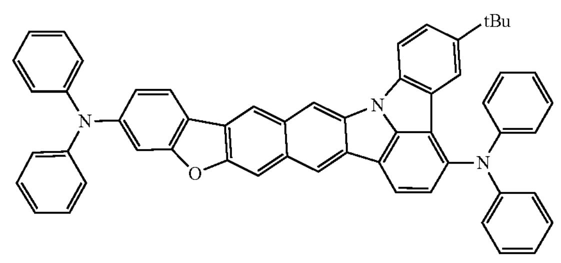

Compound27

Compound 27 (1.7 g, yield 76%, Mass [M+]=772) was obtained in the same manner as in Synthesis of Compound 1 of Synthesis Example 1, except that Intermediate 12 (3.0 g) was used instead of Intermediate 4, and AM-10 (1.0 g) was used instead of AM-1.

Synthesis Example 28. Synthesis of Compound 28

28-1. Synthesis of Intermediate 101

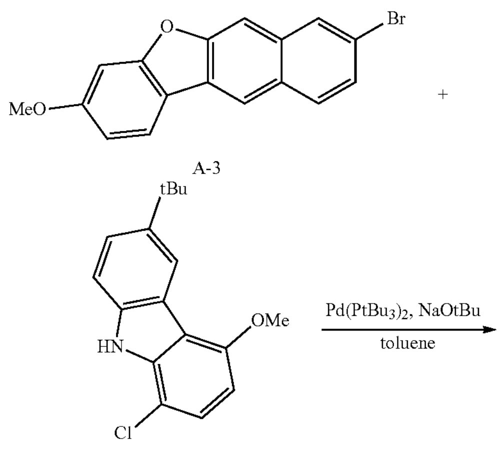

A-3

B-2

-continued

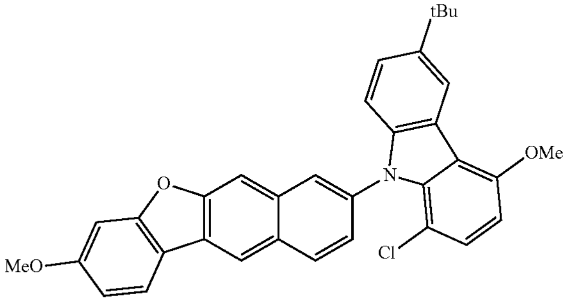

Intermediate 101

Intermediate 101 (6.6 g, yield 81%, Mass [M+]=535) was obtained in the same manner as in Synthesis of Intermediate 1 of Synthesis Example 1, except that A-3 (5.0 g) was used instead of starting material A-1, and B-2 (4.4 g) was used instead of B-1.

28-2. Synthesis of Intermediate 102

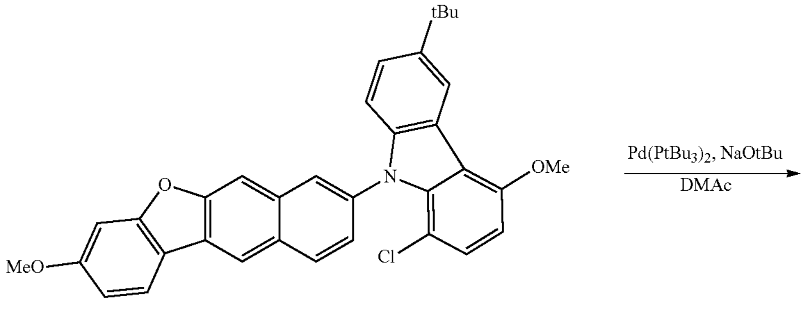

Intermediate 101

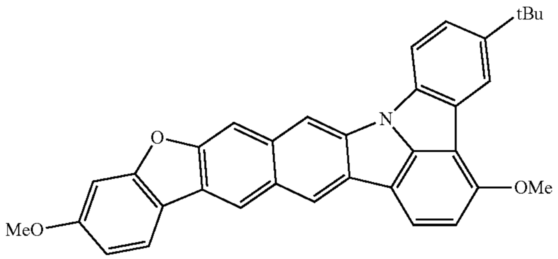

Intermediate 102

Intermediate 102 (4.6 g, yield 75%, Mass [M+]=498) was obtained in the same manner as in Synthesis of Intermediate 2 of Synthesis Example 1, except that Intermediate 101 (6.6

28-3. Synthesis of Intermediate 104

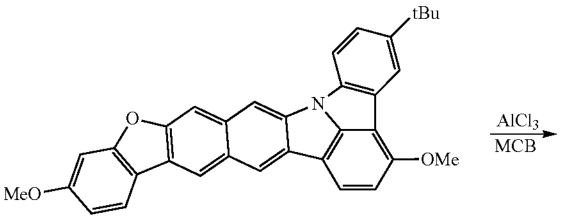

Intermediate 102

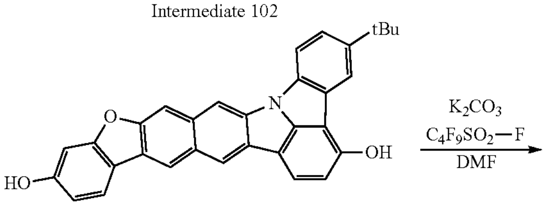

Intermediate 103

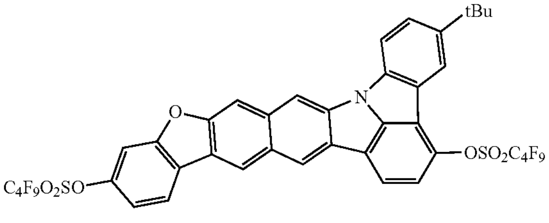

Intermediate 104

Intermediate 103 (3.2 g, yield 74%, Mass [M+]=470) was obtained in the same manner as in Synthesis of Intermediate 3 of Synthesis Example 1, except that Intermediate 102 (4.6 g) was used instead of Intermediate 2.

Intermediate 104 (5.0 g, yield 71%, Mass [M+]=1034) was obtained in the same manner as in Synthesis of Intermediate 4 of Synthesis Example 1, except that Intermediate 103 (3.2 g) was used instead of Intermediate 3.

28-4. Synthesis of Compound 28

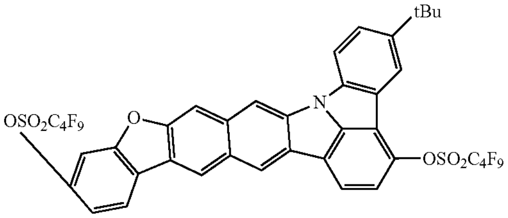

+

Intermediate 104

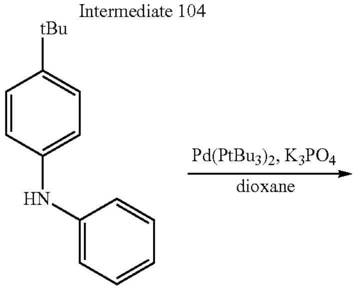

AM-25

-continued

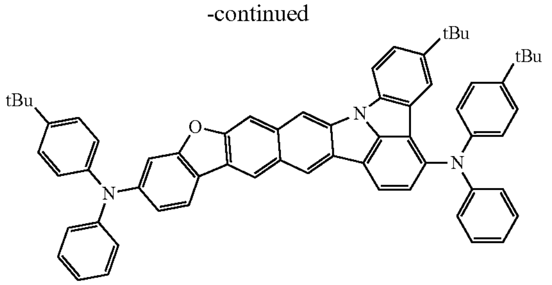

Compound28

Compound 28 (2.0 g, yield 78%, Mass [M+]=885) was obtained in the same manner as in Synthesis of Compound 1 of Synthesis Example 1, except that Intermediate 104 (3.0 g) was used instead of Intermediate 4, and AM-25 (1.3 g) was used instead of AM-1.

Synthesis Example 29. Synthesis of Compound 29

29-1. Synthesis of Intermediate 105

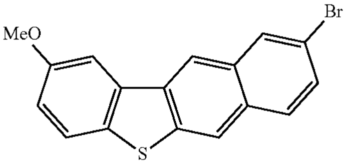

+

A-15

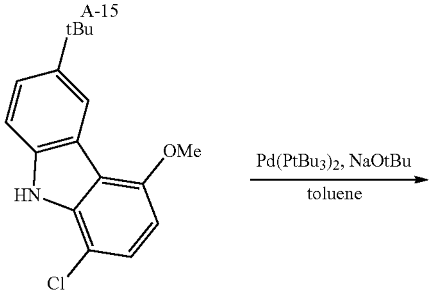

B-2

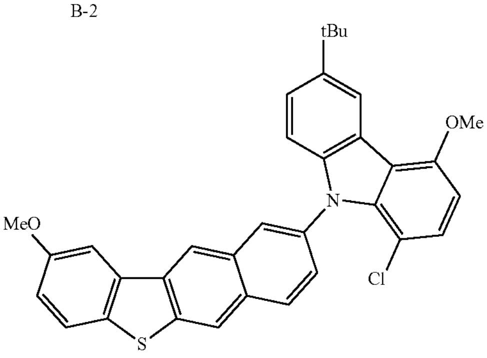

Intermediate 105

Intermediate 105 (6.1 g, yield 76%, Mass [M+]=551) was obtained in the same manner as in Synthesis of Intermediate 1 of Synthesis Example 1, except that A-15 (5.0 g) was used instead of starting material A-1, and B-2 (4.2 g) was used instead of B-1.

29-2. Synthesis of Intermediate 106

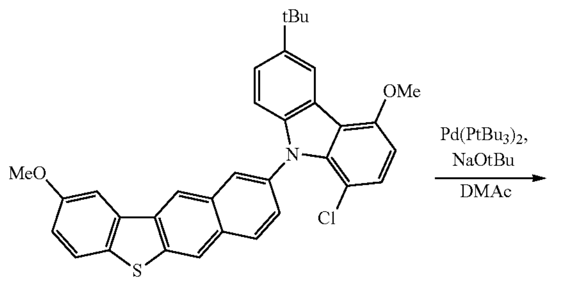

Intermediate 105

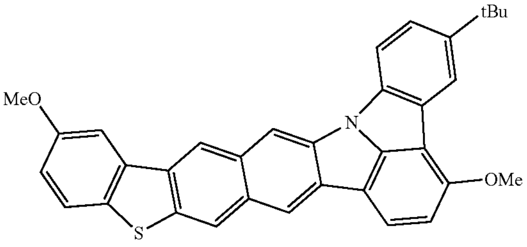

Intermediate 106

Intermediate 106 (3.8 g, yield 67%, Mass [M+]=514) was obtained in the same manner as in Synthesis of Intermediate 2 of Synthesis Example 1, except that Intermediate 105 (6.1 g) was used instead of Intermediate 1.

29-3. Synthesis of Intermediate 108

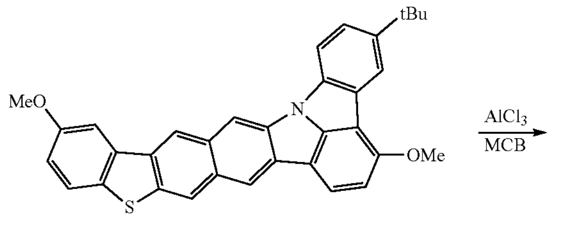

Intermediate 106

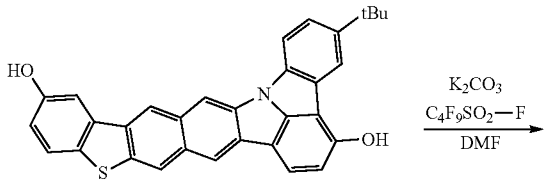

Intermediate 107

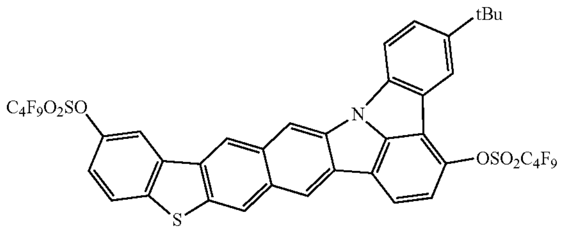

Intermediate 108

Intermediate 107 (2.6 g, yield 72%, Mass [M+]=486) was obtained in the same manner as in Synthesis of Intermediate 3 of Synthesis Example 1, except that Intermediate 106 (3.8 g) was used instead of Intermediate 2.

Intermediate 108 (4.0 g, yield 71%, Mass [M+]=1050) was obtained in the same manner as in Synthesis of Intermediate 4 of Synthesis Example 1, except that Intermediate 107 (2.6 g) was used instead of Intermediate 3.

29-4. Synthesis of Compound 29

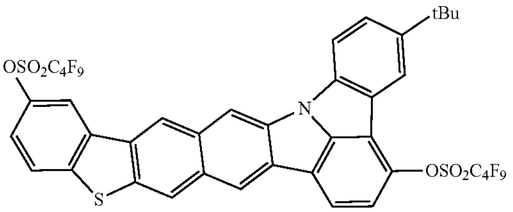

Intermediate 108

+

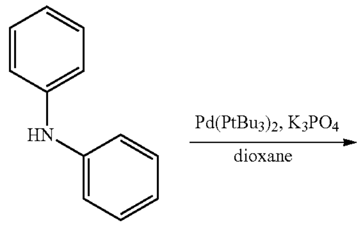

AM-10

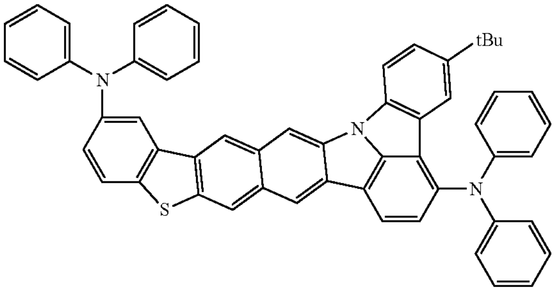

Compound29

Compound 29 (1.6 g, yield 71%, Mass [M+]=789) was obtained in the same manner as in Synthesis of Compound 1 of Synthesis Example 1, except that Intermediate 108 (3.0 g) was used instead of Intermediate 4, and AM-10 (1.0 g) was used instead of AM-1.

Synthesis Example 30. Synthesis of Compound 30

30-1. Synthesis of Intermediate 109

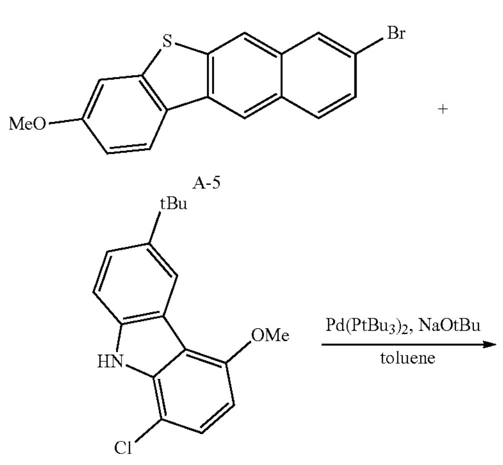

A-5

B-2

-continued

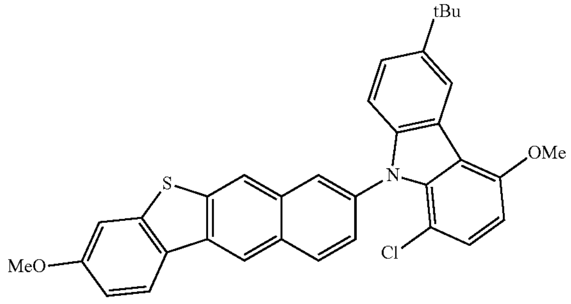

Intermediate 109

Intermediate 109 (6.0 g, yield 75%, Mass [M+]=551) was obtained in the same manner as in Synthesis of Intermediate 1 of Synthesis Example 1, except that A-5 (5.0 g) was used instead of starting material A-1, and B-2 (4.2 g) was used instead of B-1.

30-2. Synthesis of Intermediate 110

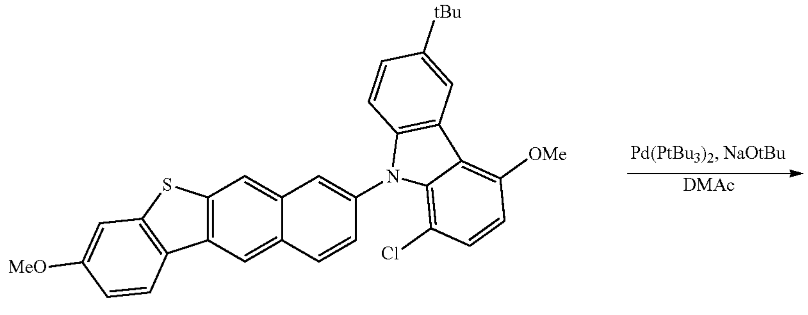

Intermediate 109

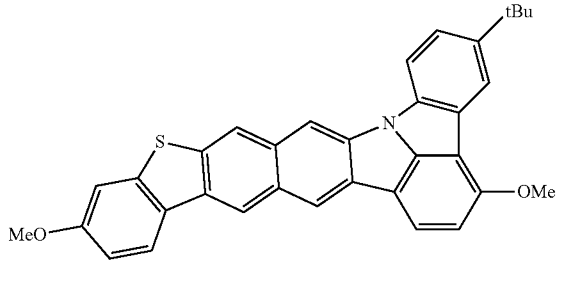

Intermediate 110

Intermediate 110 (3.8 g, yield 68%, Mass [M+]=514) was obtained in the same manner as in Synthesis of Intermediate 2 of Synthesis Example 1, except that Intermediate 109 (6.0 g) was used instead of Intermediate 1.

30-3. Synthesis of Intermediate 112

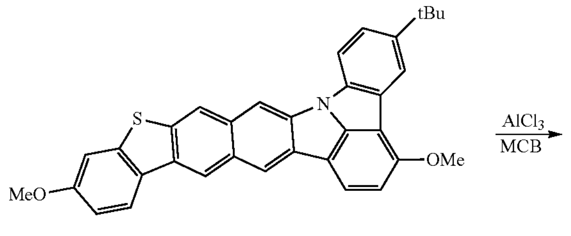

Intermediate 110

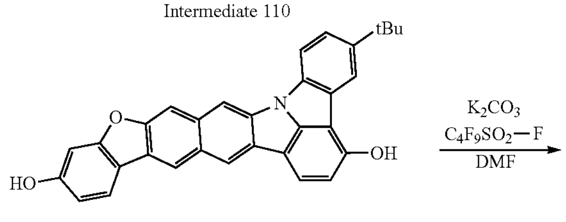

Intermediate 111

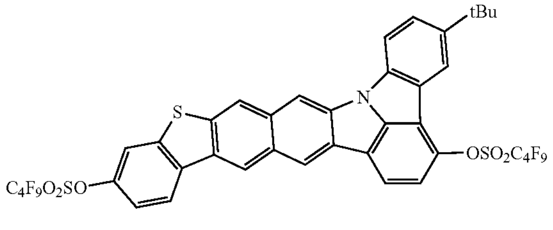

Intermediate 112

Intermediate 111 (2.6 g, yield 72%, Mass [M+]=486) was obtained in the same manner as in Synthesis of Intermediate 3 of Synthesis Example 1, except that Intermediate 110 (3.8 g) was used instead of Intermediate 2.

Intermediate 112 (4.0 g, yield 71%, Mass [M+]=1050) was obtained in the same manner as in Synthesis of Intermediate 4 of Synthesis Example 1, except that Intermediate 111 (2.6 g) was used instead of Intermediate 3.

30-4. Synthesis of Compound 30

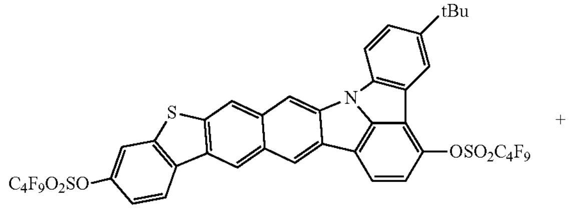

Intermediate 112

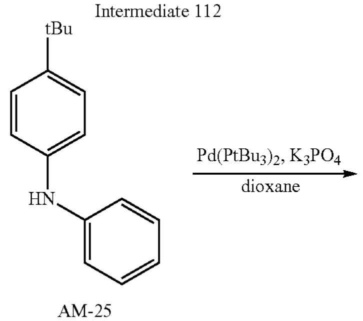

AM-25

-continued

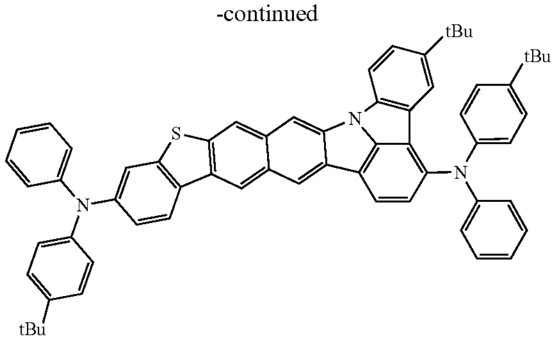

Compound30

Compound 30 (2.0 g, yield 77%, Mass [M+]=901) was obtained in the same manner as in Synthesis of Compound 1 of Synthesis Example 1, except that Intermediate 112 (3.0 g) was used instead of Intermediate 4, and AM-25 (1.3 g) was used instead of AM-1.

Manufacture of Organic Light Emitting Device

Example 1

A glass substrate on which indium tin oxide (ITO) was coated as a thin film to a thickness of 1,500 Å was placed in distilled water containing dissolved detergent and ultrasonically cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonically cleaned with solvents of isopropyl alcohol, acetone and methanol, then dried, and then transferred to a plasma cleaner. The substrate was cleaned for 5 minutes using oxygen plasma, and then transferred to a vacuum deposition apparatus.

On the transparent ITO electrode prepared as above, the following Compound HAT was thermal vacuum deposited to a thickness of 50 Å to form a hole injection layer. On the hole injection layer, a first hole transfer layer having a thickness of 1200 Å was formed by vacuum depositing the following Compound HT-A, and subsequently, a second hole transfer layer having a thickness of 110 Å was formed by vacuum depositing Compound HT-B. On the second hole transfer layer, a light emitting layer having a thickness of 200 Å was formed by vacuum depositing Compound BH-A as a light emitting host and the following Compound 1 as a dopant in a weight ratio of 97:3.

On the light emitting layer, the following Compound ET-A and Compound LiQ were vacuum deposited to a thickness of 200 Å in a weight ratio of 1:1 to form a first electron transfer layer. A second electron transfer layer was formed on the first electron transfer layer by vacuum depositing [LiF] to a thickness of 100 Å. Aluminum was deposited on the second electron transfer layer to a thickness of 1000 Å to form a cathode.

In the above-described process, the deposition rates of the organic materials were maintained at 1.0 Å/sec, the deposition rates of the lithium fluoride and the aluminum of the cathode were maintained at 0.3 Å/sec and 2.0 Å/sec to 5.0 Å/sec, respectively, and the degree of vacuum during the deposition was maintained at $5\times10^{-8}$ torr to $1\times10^{-7}$ to manufacture an organic light emitting device.

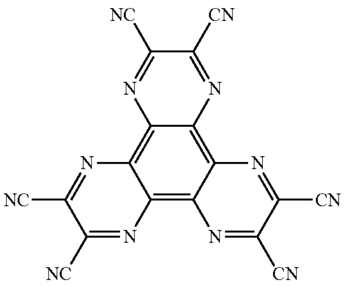
HAT
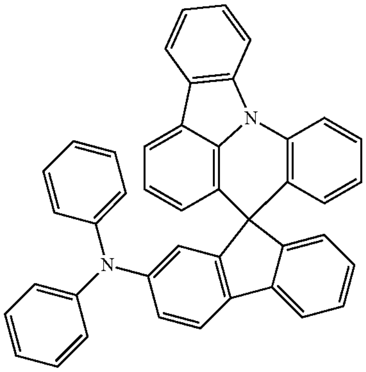
HT-A
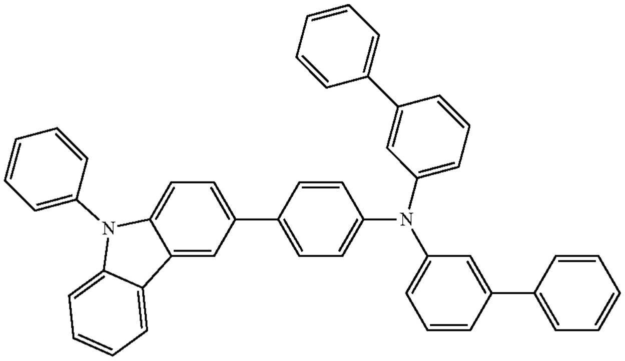
HT-B
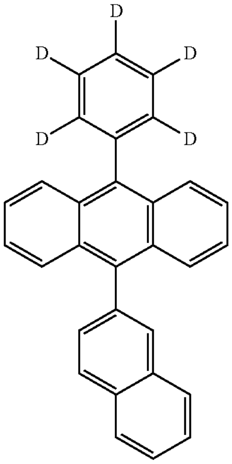
BH-A
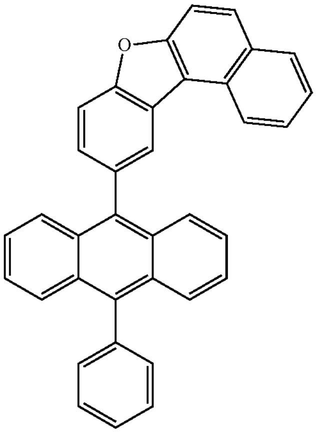
BH-B
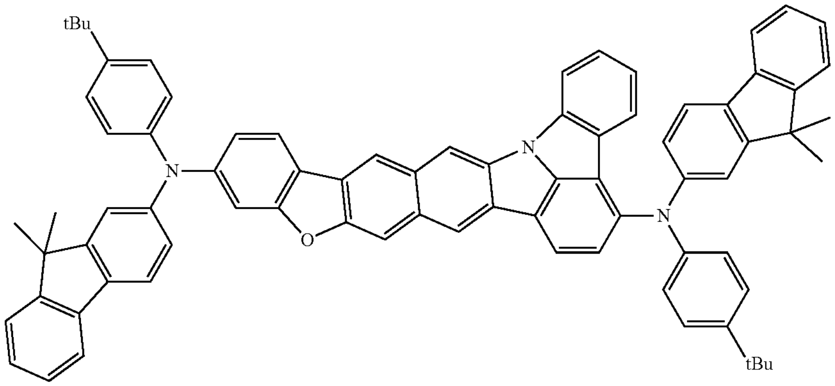
Compound 1

-continued

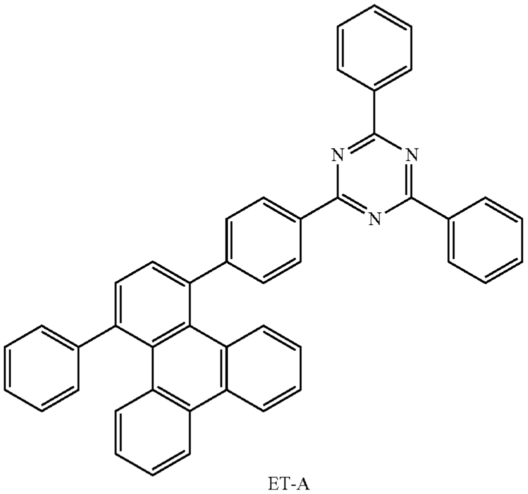

ET-A

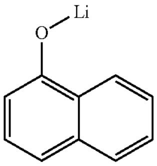

Liq

Examples 2 to 21 and Comparative Examples 1 to 3

Organic light emitting devices were manufactured in the same manner as in Example 1 except that compounds described in the following Table 1 were used instead of Compound 1 as the dopant of the light emitting layer.

Examples 22 to 30 and Comparative Examples 4 and 5

Organic light emitting devices were manufactured in the same manner as in Example 1 except that compounds described in the following Table 1 were used instead of Compound 1 as the dopant of the light emitting layer, and BH-B was used instead of BH-A as the host of the light emitting layer.

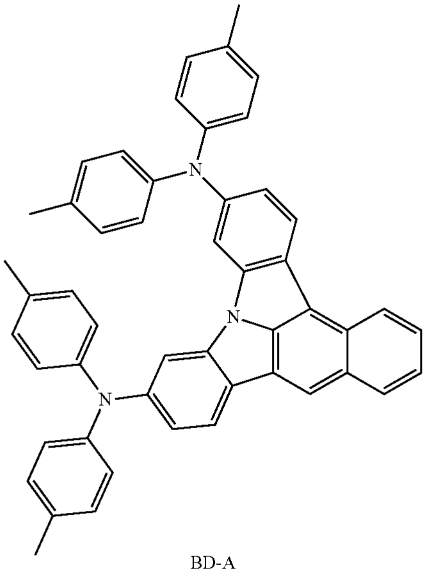

BD-A

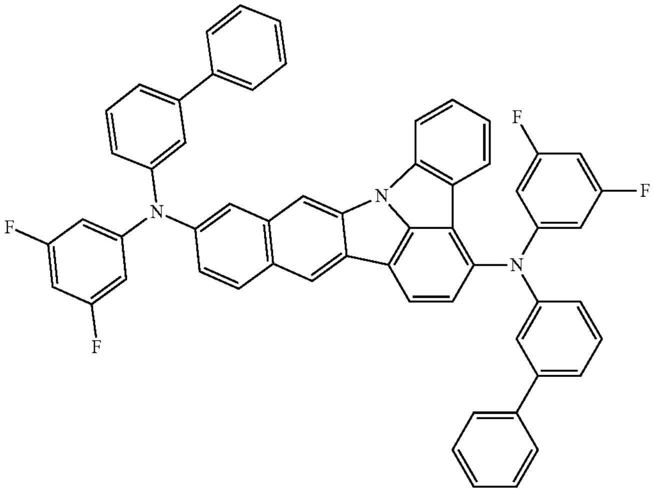

BD-B

-continued

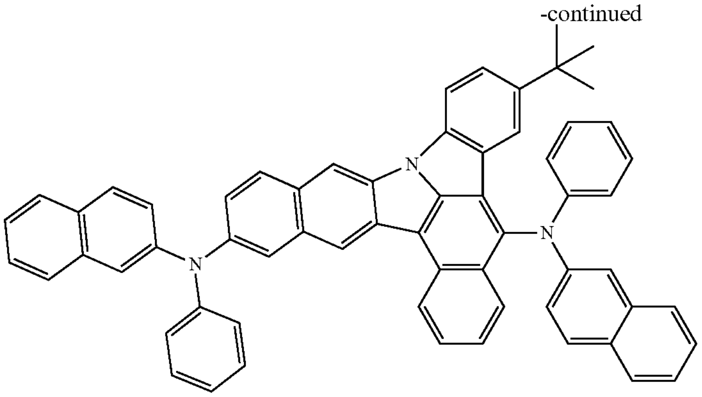

BD-C

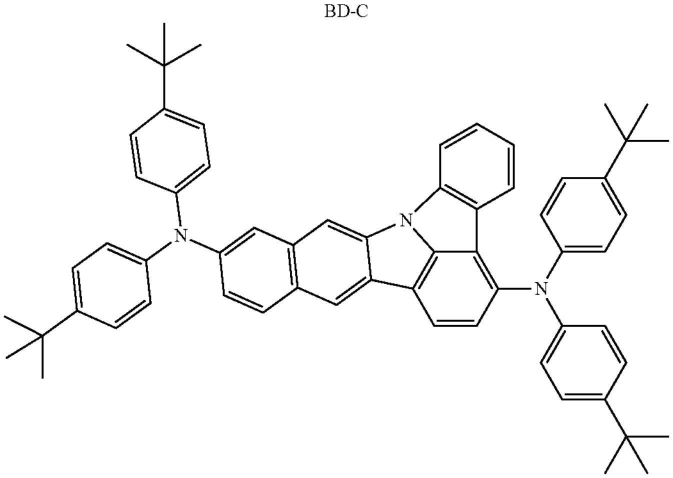

BD-D

For each of the organic light emitting devices of Examples 1 to 30 and Comparative Examples 1 to 5, voltage and efficiency when applying current density of 10 mA/cm$^2$ and a lifetime ($T_{97}$) when applying current density of 20 mA/cm$^2$ were measured, and the results are shown in the following Table 1. Herein, $T_{97}$ represents time taken for luminance to decrease to 97% when employing initial luminance at current density of 20 mA/cm$^2$ as 100%.

TABLE 1

| | Host | Dopant | Light Emission Efficiency (Cd/A) | Lifetime, $T_{97}$ (h) |
|---|---|---|---|---|
| Example 1 | BH-A | Compound 1 | 5.98 | 71 |
| Example 2 | BH-A | Compound 2 | 6.14 | 76 |
| Example 3 | BH-A | Compound 3 | 6.29 | 73 |
| Example 4 | BH-A | Compound 5 | 6.03 | 72 |
| Example 5 | BH-A | Compound 6 | 6.40 | 72 |
| Example 6 | BH-A | Compound 8 | 6.29 | 73 |
| Example 7 | BH-A | Compound 9 | 6.14 | 70 |
| Example 8 | BH-A | Compound 10 | 6.24 | 73 |
| Example 9 | BH-A | Compound 11 | 6.08 | 74 |
| Example 10 | BH-A | Compound 13 | 6.24 | 73 |
| Example 11 | BH-A | Compound 16 | 6.19 | 70 |
| Example 12 | BH-A | Compound 17 | 6.29 | 71 |
| Example 13 | BH-A | Compound 20 | 6.14 | 69 |
| Example 14 | BH-A | Compound 22 | 6.34 | 69 |
| Example 15 | BH-A | Compound23 | 6.29 | 75 |
| Example 16 | BH-A | Compound 25 | 6.03 | 70 |
| Example 17 | BH-A | Compound 26 | 6.23 | 72 |
| Example 18 | BH-A | Compound 27 | 6.34 | 74 |
| Example 19 | BH-A | Compound 28 | 6.24 | 73 |
| Example 20 | BH-A | Compound 29 | 6.29 | 72 |

TABLE 1-continued

| | Host | Dopant | Light Emission Efficiency (Cd/A) | Lifetime, $T_{97}$ (h) |
|---|---|---|---|---|
| Example 21 | BH-A | Compound 30 | 6.18 | 72 |
| Comparative Example 1 | BH-A | BD-B | 5.30 | 57 |
| Comparative Example 2 | BH-A | BD-C | 5.00 | 58 |
| Comparative Example 3 | BH-A | BD-D | 3.90 | 55 |
| Example 22 | BH-B | Compound 4 | 6.19 | 70 |
| Example 23 | BH-B | Compound 7 | 5.93 | 73 |
| Example 24 | BH-B | Compound 12 | 5.98 | 71 |
| Example 25 | BH-B | Compound 14 | 6.08 | 69 |
| Example 26 | BH-B | Compound 15 | 6.03 | 73 |
| Example 27 | BH-B | Compound 18 | 5.93 | 70 |
| Example 28 | BH-B | Compound 19 | 5.77 | 70 |
| Example 29 | BH-B | Compound 21 | 6.14 | 73 |
| Example 30 | BH-B | Compound 24 | 6.19 | 69 |
| Comparative Example 4 | BH-B | BD-A | 5.20 | 60 |
| Comparative Example 5 | BH-B | BD-D | 4.10 | 55 |

In Table 1, it was seen that Examples 1 to 30 using Chemical Formula 1 according to one embodiment of the present specification as a dopant of a light emitting layer of an organic light emitting device had superior light emission efficiency and lifetime compared to Comparative Examples 1 to 5 using compounds in which a and b of Chemical Formula 1 are a benzene ring or a naphthalene ring as a dopant of a light emitting layer of an organic light emitting device.

This is due to the fact that, by a of Chemical Formula 1 including a substituted or unsubstituted tetracyclic or higher aromatic or heteroaromatic ring, an overlap of HOMO and LUMO orbitals increases, which increases oscillator strength, and as a result, efficiency and lifetime of the organic light emitting device including Chemical Formula 1 of the present specification are superior.

The invention claimed is:

1. A heterocyclic compound of Chemical Formula 1:

<Chemical Formula 1>

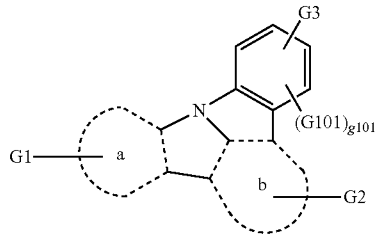

wherein in Chemical Formula 1:

a is the following Chemical Formula a-1, and b is a benzene ring or a naphthalene ring;

any two of G1 to G3 are a group of the following Chemical Formula A and the two Chemical Formula A are the same as each other, and the remaining group of G1 to G3 that is not the following Chemical Formula A, and G101, are the same as or different from each other, and each independently is hydrogen, deuterium, a halogen group, a cyano group, a nitro group, a substituted or unsubstituted silyl group, a substituted or unsubstituted boron group, a substituted or unsubstituted alkyl group, a substituted or unsubstituted alkoxy group, a substituted or unsubstituted cycloalkyl group, a substituted or unsubstituted aryl group, or a substituted or unsubstituted heteroaryl group;

g101 is an integer of 1 to 3; and when g101 is 2 or greater, the two or more G101s are the same as or different from each other, <Chemical Formula A>

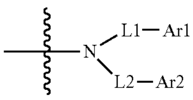

wherein in Chemical Formula A:

L1 and L2 are the same as or different from each other, and each independently is a direct bond, a substituted or unsubstituted arylene group, or a substituted or unsubstituted heteroarylene group;

Ar1 and Ar2 are the same as or different from each other, and each independently is hydrogen, deuterium, a halogen group, a cyano group, a nitro group, a substituted or unsubstituted silyl group, a substituted or unsubstituted boron group, a substituted or unsubstituted alkyl group, a substituted or unsubstituted alkoxy group, a substituted or unsubstituted cycloalkyl group, a substituted or unsubstituted aryl group, a substituted or unsubstituted fused ring group of aromatic hydrocarbon ring and aliphatic hydrocarbon ring, or a substituted or unsubstituted heteroaryl group, or bond to each other to form a substituted or unsubstituted heteroring; and

means a site bonding to Chemical Formula 1;

<Chemical Formula a-1>

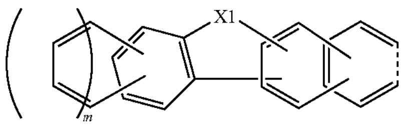

wherein Chemical Formula a-1:

X1 is O, S or CRR';

m is 0 or 1;

R and R' are the same as or different from each other, and each independently a substituted or unsubstituted alkyl group; or a substituted or unsubstituted aryl group, or bond to each other to form a substituted or unsubstituted ring; and is a site bonding to Chemical Formula 1.

2. The heterocyclic compound of claim 1, wherein Chemical Formula 1 is any one of the following Chemical Formulae 1-1 to 1-3:

<Chemical Formula 1-1>

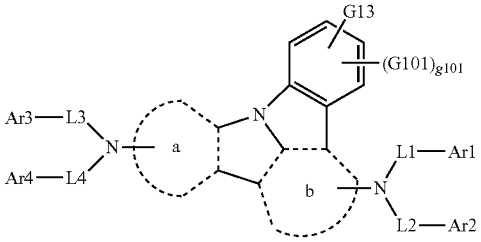

<Chemical Formula 1-2>

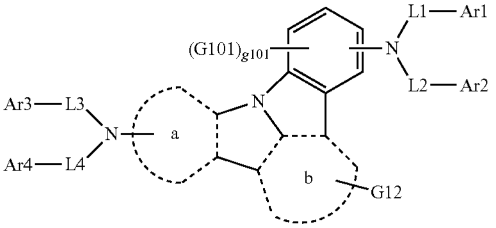

-continued

<Chemical Formula 1-3>

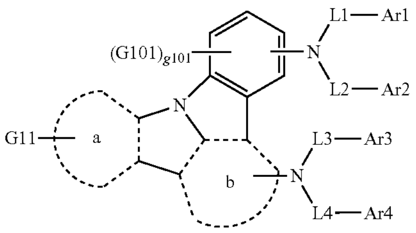

wherein in Chemical Formulae 1-1 to 1-3:

a, b, G101 and g101 have the same definitions as in Chemical Formula 1;

L1, L2, Ar1 and Ar2 have the same definitions as in Chemical Formula A;

G11 to G13 are the same as or different from each other, and each independently is hydrogen, deuterium, a halogen group, a cyano group, a nitro group, a substituted or unsubstituted silyl group, a substituted or unsubstituted boron group, a substituted or unsubstituted alkyl group, a substituted or unsubstituted alkoxy group, a substituted or unsubstituted cycloalkyl group, a substituted or unsubstituted aryl group, or a substituted or unsubstituted heteroaryl group;

L3 and L4 are the same as or different from each other, and each independently is a direct bond, a substituted or unsubstituted arylene group, or a substituted or unsubstituted heteroarylene group; and Ar3 and Ar4 are the same as or different from each other, and each independently is hydrogen, deuterium, a halogen group, a cyano group, a nitro group, a substituted or unsubstituted silyl group, a substituted or unsubstituted boron group, a substituted or unsubstituted alkyl group, a substituted or unsubstituted alkoxy group, a substituted or unsubstituted cycloalkyl group, a substituted or unsubstituted aryl group, a substituted or unsubstituted fused ring group of aromatic hydrocarbon ring and aliphatic hydrocarbon ring, or a substituted or unsubstituted heteroaryl group, or bond to each other to form a substituted or unsubstituted heteroring, and Ar3 is the same as Ar1, and Ar4 is the same as Ar2.

3. The heterocyclic compound claim 1, wherein Chemical Formula 1 is any one of the following Chemical Formulae 1-5 to 1-10:

<Chemical Formula 1-5>

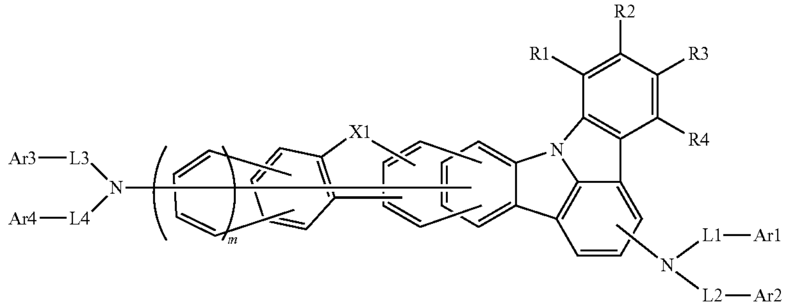

<Chemical Formula 1-6>

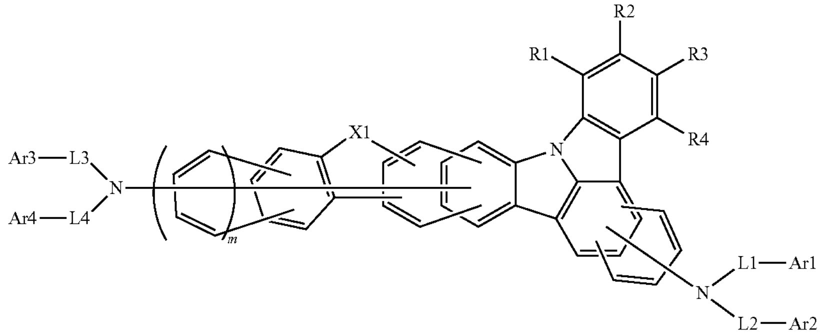

<Chemical Formula 1-7>

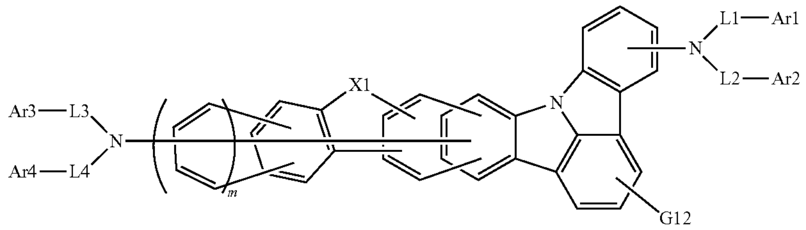

-continued

<Chemical Formula 1-8>

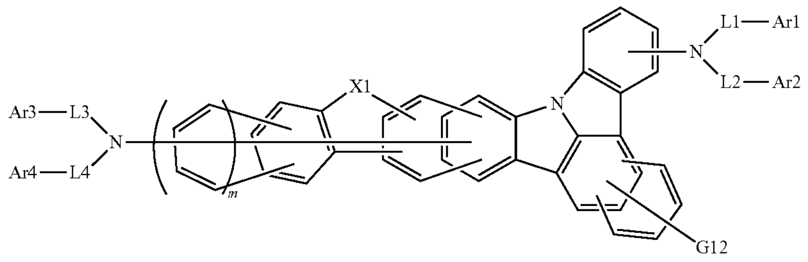

<Chemical Formula 1-9>

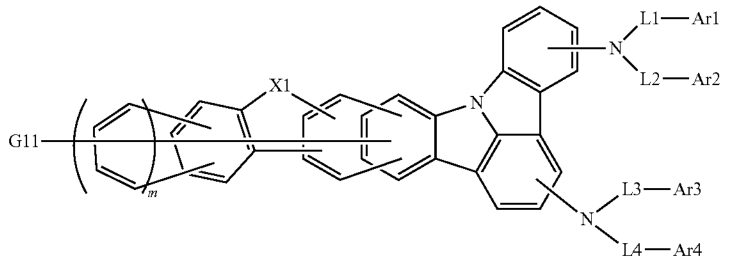

<Chemical Formula 1-10>

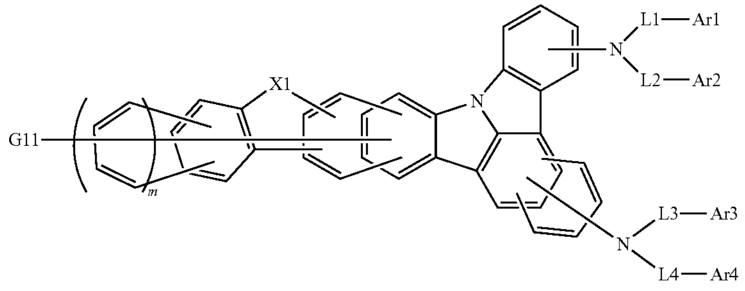

wherein in Chemical Formulae 1-5 to 1-10:

L1, L2, Ar1 and Ar2 have the same definitions as in Chemical Formula A;

R1 to R4, G11 and G12 are the same as or different from each other, and each independently is hydrogen, deuterium, a halogen group; a cyano group, a nitro group, a substituted or unsubstituted silyl group, a substituted or unsubstituted boron group, a substituted or unsubstituted alkyl group, a substituted or unsubstituted alkoxy group, a substituted or unsubstituted cycloalkyl group, a substituted or unsubstituted aryl group, or a substituted or unsubstituted heteroaryl group;

L3 and L4 are the same as or different from each other, and each independently is a direct bond, a substituted or unsubstituted arylene group, or a substituted or unsubstituted heteroarylene group;

Ar3 and Ar4 are the same as or different from each other, and each independently is hydrogen, deuterium, a halogen group, a cyano group, a nitro group, a substituted or unsubstituted silyl group, a substituted or unsubstituted boron group, a substituted or unsubstituted alkyl group, a substituted or unsubstituted alkoxy group, a substituted or unsubstituted cycloalkyl group, a substituted or unsubstituted aryl group, a substituted or unsubstituted fused ring group of aromatic hydrocarbon ring and aliphatic hydrocarbon ring, or a substituted or unsubstituted heteroaryl group, or bond to each other to form a substituted or unsubstituted heteroring;

Ar3 is the same as Ar1, and Ar4 is the same as Ar2;

X1 is O, S or CRR';

m is 0 or 1; and

R and R' are the same as or different from each other, and each independently is a substituted or unsubstituted alkyl group or a substituted or unsubstituted aryl group, or bond to each other to form a substituted or unsubstituted ring.

4. The heterocyclic compound of claim 1, wherein the remaining group of G1 to G3 that is not Chemical Formula A, and G101, are the same as or different from each other, and each independently is hydrogen, deuterium, a linear or branched alkyl group having 1 to 30 carbon atoms, or a monocyclic or polycyclic aryl group having 6 to 30 carbon atoms unsubstituted or substituted with deuterium, or a linear or branched alkyl group having 1 to 30 carbon atoms.

5. The heterocyclic compound of claim 1, wherein L1 and L2 are the same as or different from each other, and each independently is a direct bond, a monocyclic or polycyclic arylene group having 6 to 30 carbon atoms, or a monocyclic or polycyclic heteroarylene group having 2 to 30 carbon atoms.

6. The heterocyclic compound of claim 1, wherein Ar1 and Ar2 are the same as or different from each other, and each independently is hydrogen; deuterium; a cyano group; a halogen group; a linear or branched alkyl group having 1 to 30 carbon atoms unsubstituted or substituted with deuterium, or a monocyclic or polycyclic aryl group having 6 to 30 carbon atoms; a linear or branched alkylsilyl group having 1 to 30 carbon atoms; a linear or branched haloalkyl group having 1 to 30 carbon atoms; a linear or branched alkoxy group having 1 to 30 carbon atoms; a monocyclic or polycyclic cycloalkyl group having 3 to 30 carbon atoms; a monocyclic or polycyclic aryl group having 6 to 30 carbon atoms unsubstituted or substituted with deuterium, a halogen group, a linear or branched alkyl group having 1 to 30 carbon atoms unsubstituted or substituted with deuterium, or a linear or branched haloalkyl group having 1 to 30 carbon atoms; a fused ring group of monocyclic or polycyclic aromatic hydrocarbon ring having 6 to 30 carbon atoms and monocyclic or polycyclic aliphatic hydrocarbon ring having 3 to 30 carbon atoms unsubstituted or substituted with a linear or branched alkyl group having 1 to 30 carbon atoms; or a monocyclic or polycyclic heteroaryl group having 2 to 30 carbon atoms.

7. The heterocyclic compound of claim 1, wherein Chemical Formula 1 is any one compound selected from among the following compounds:

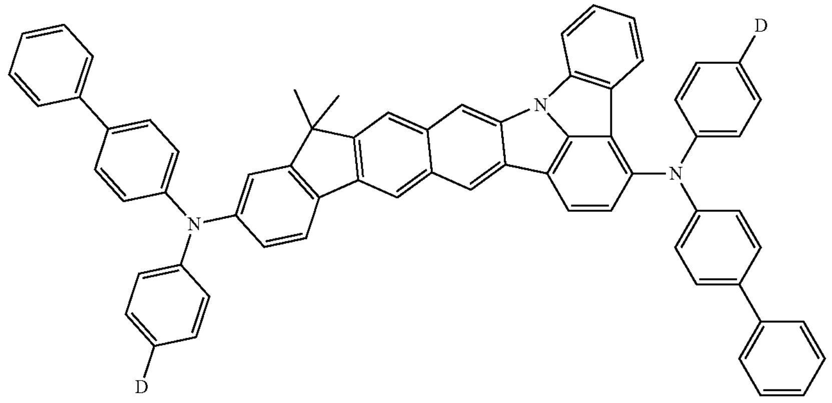

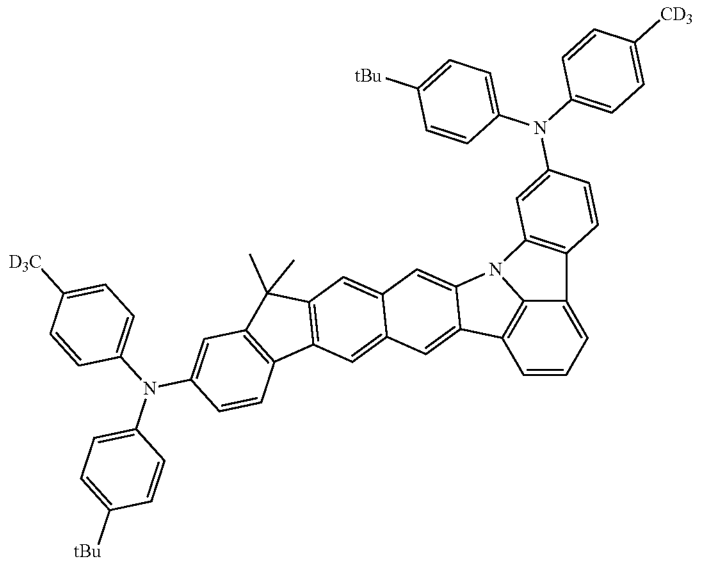

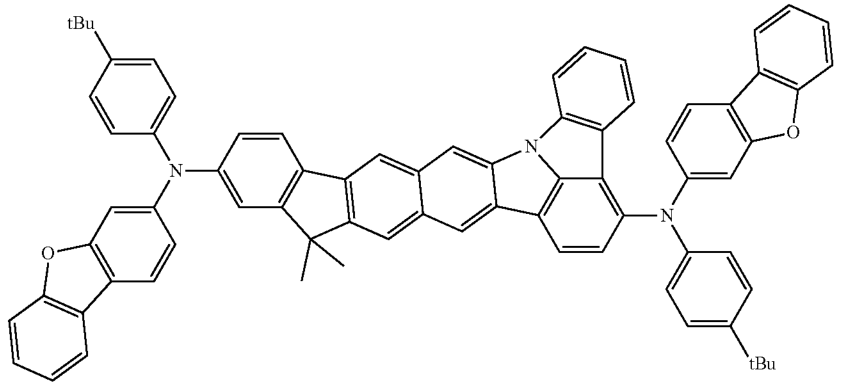

-continued
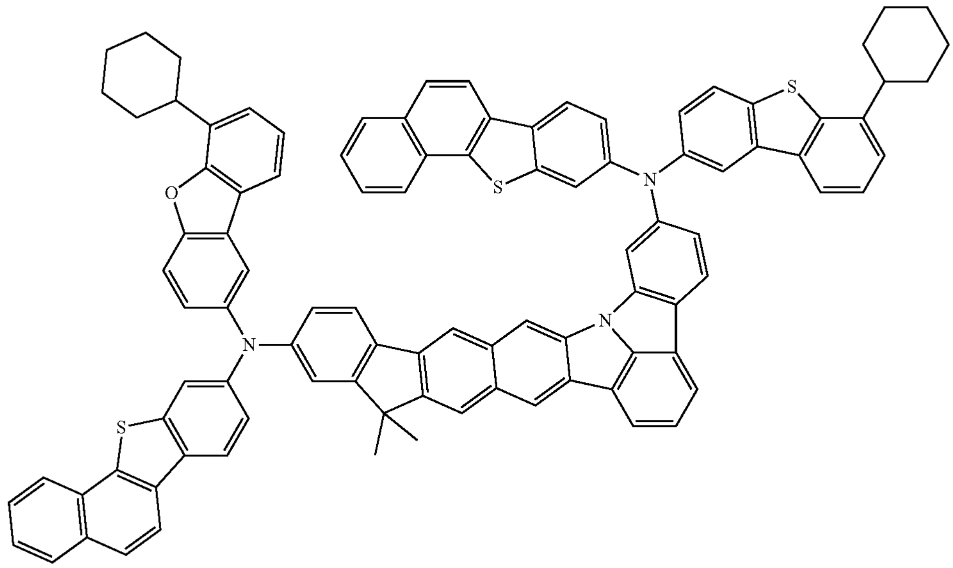
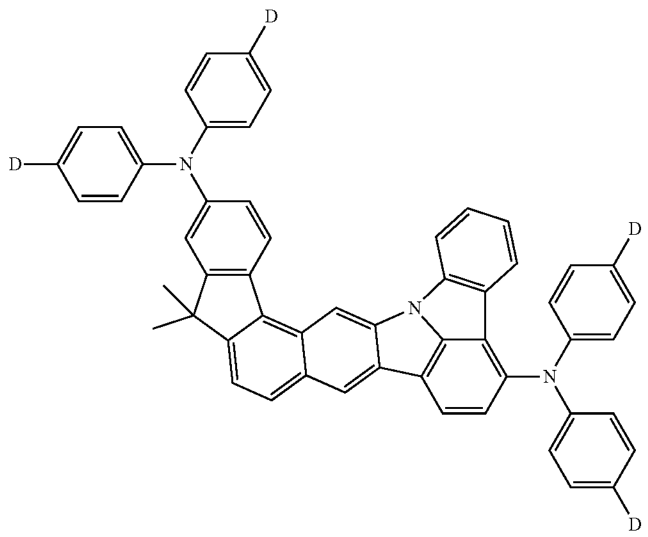
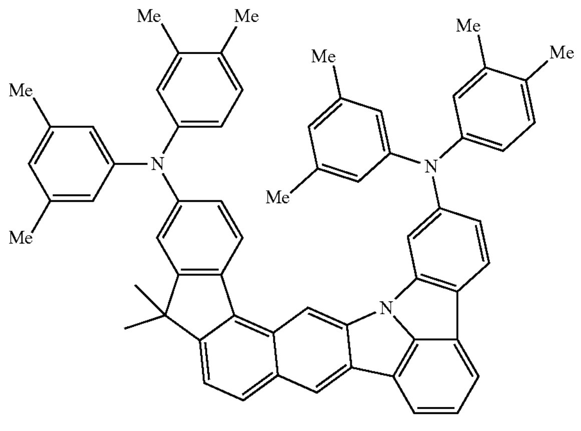

-continued
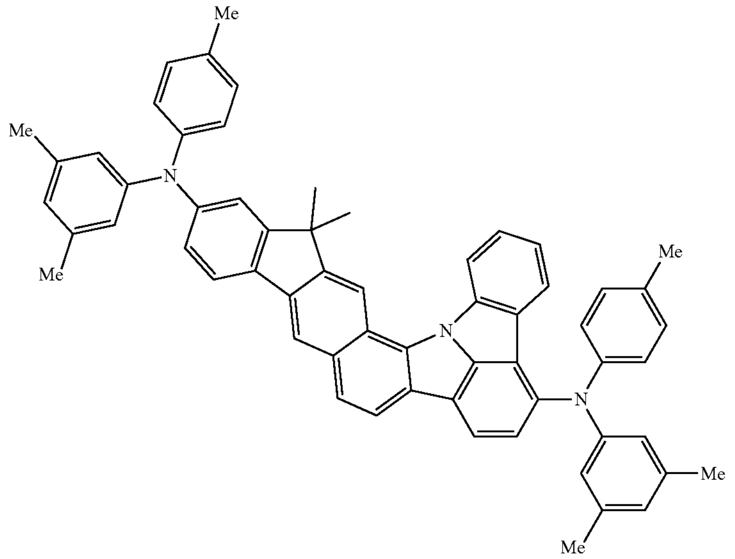
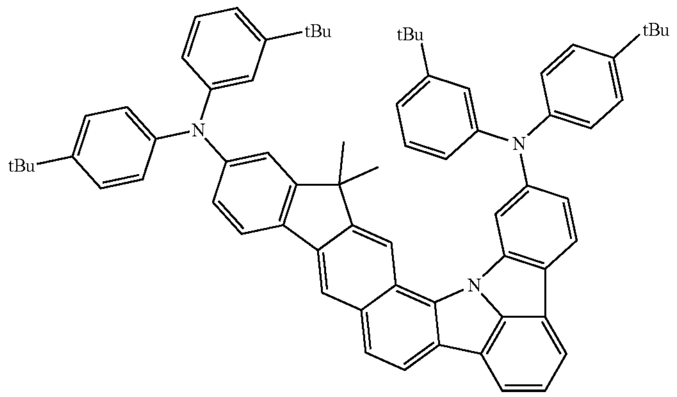
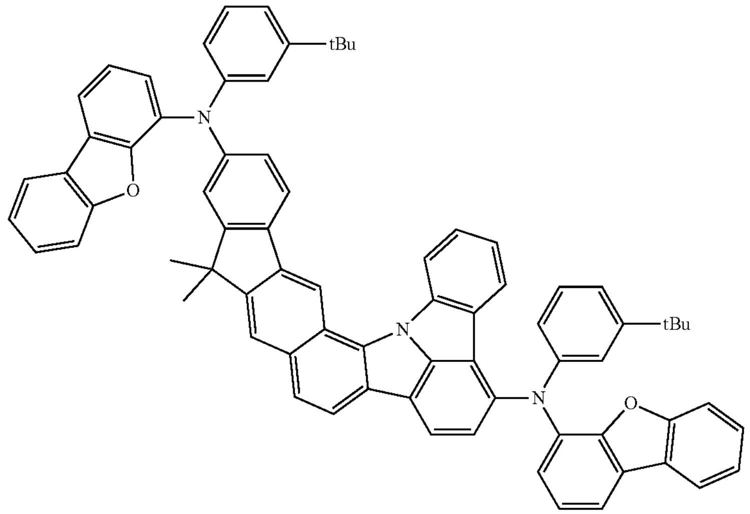

-continued
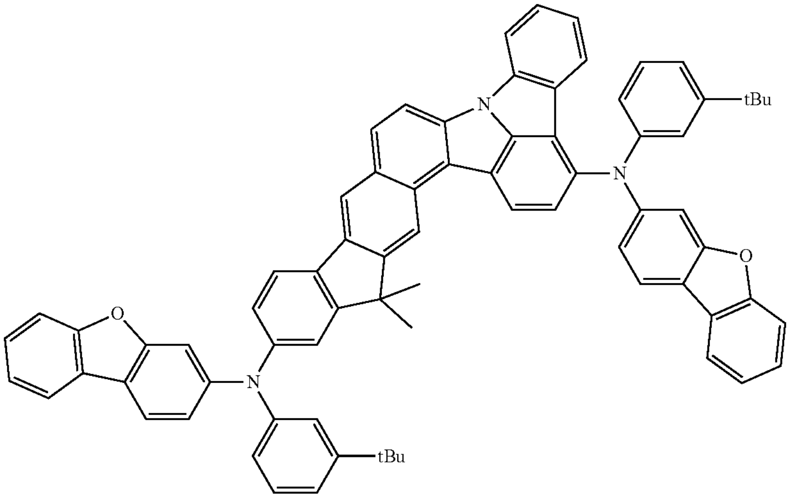
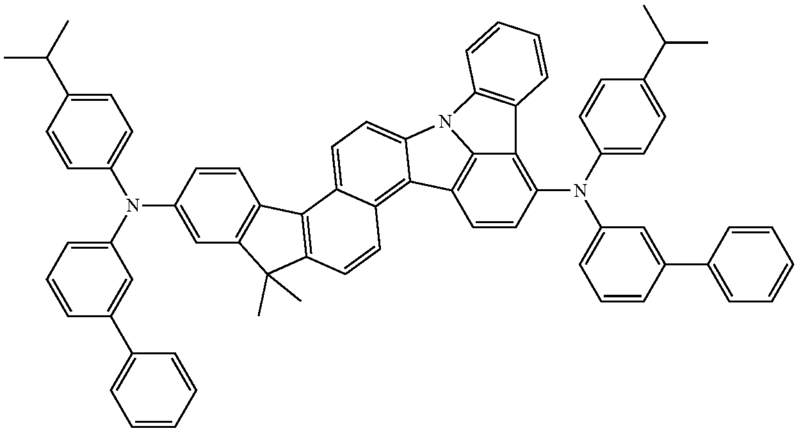
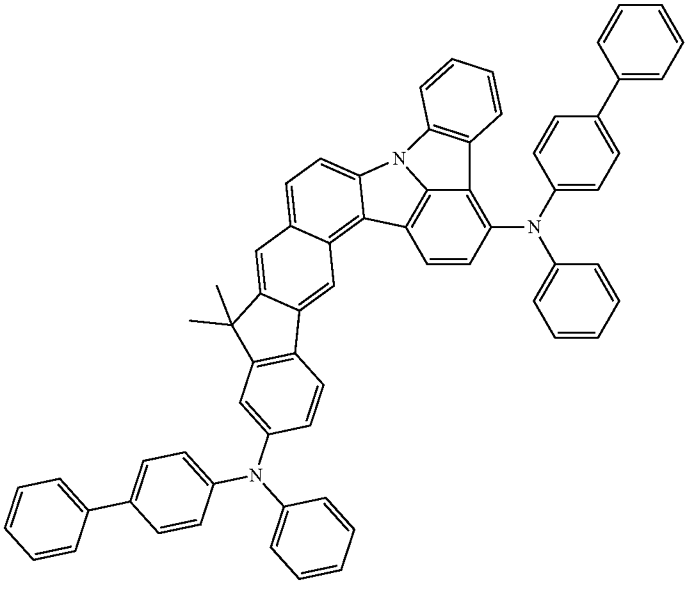

-continued
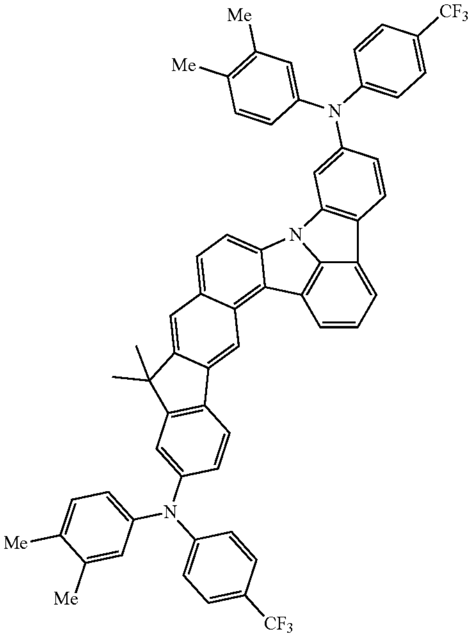
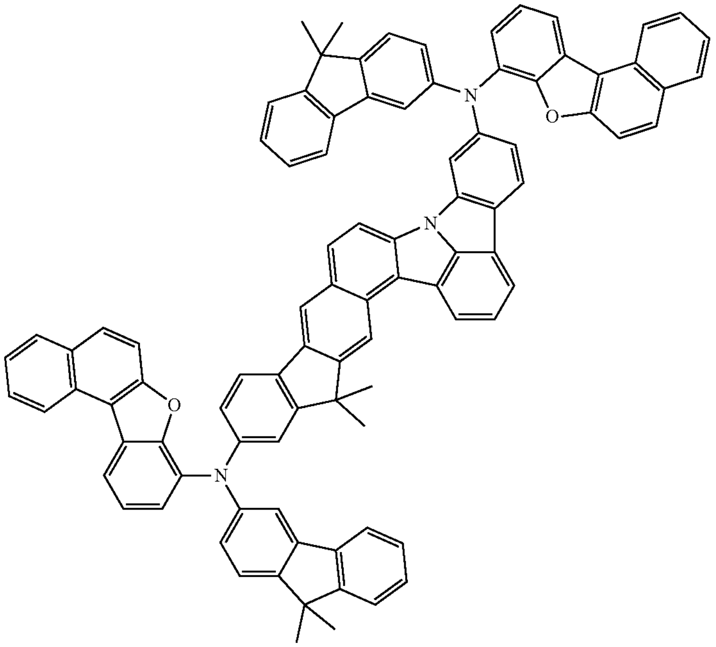
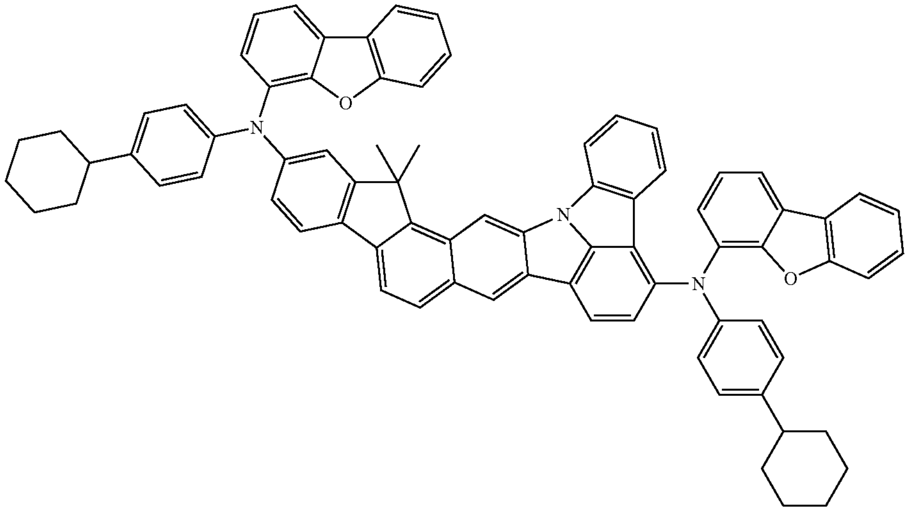
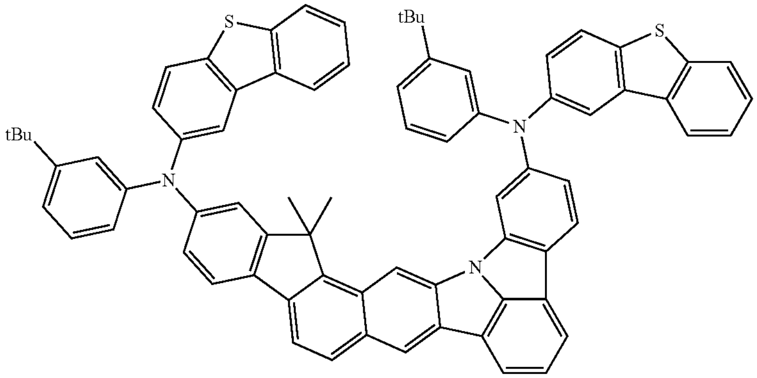

-continued
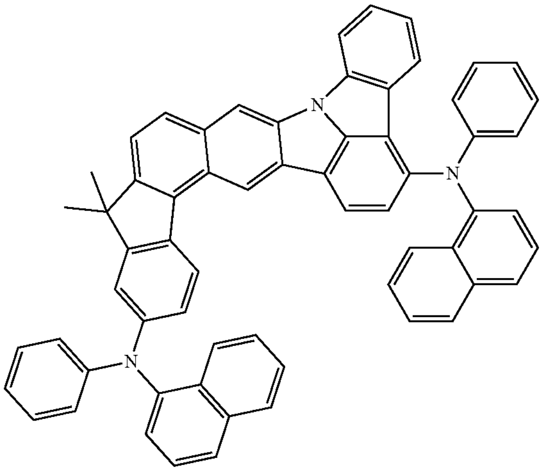
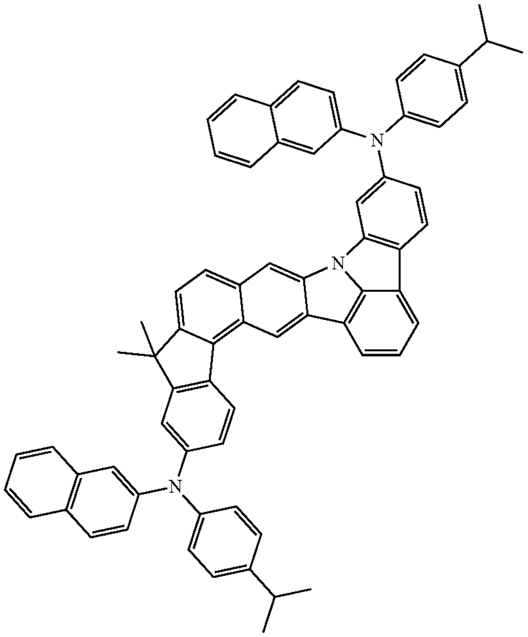
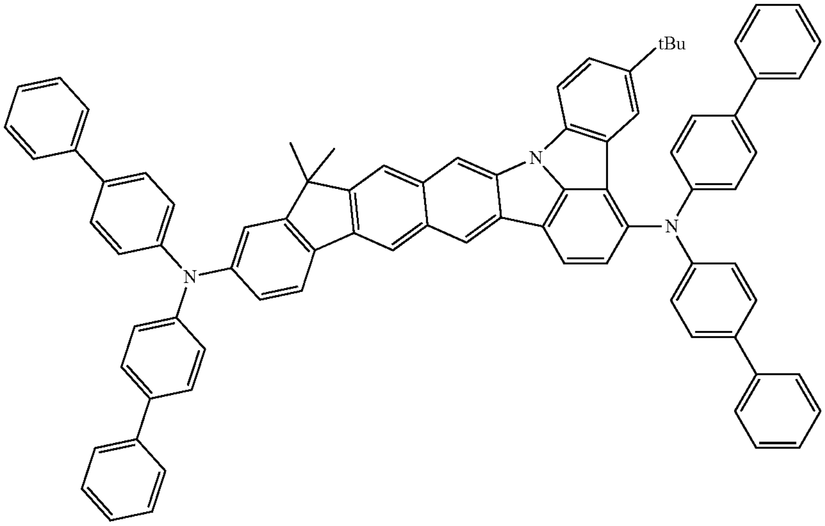

-continued
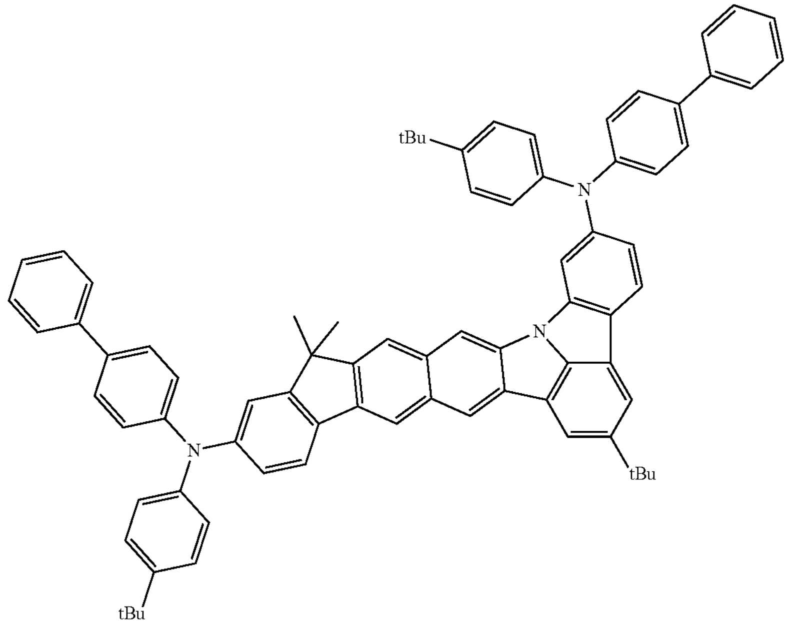
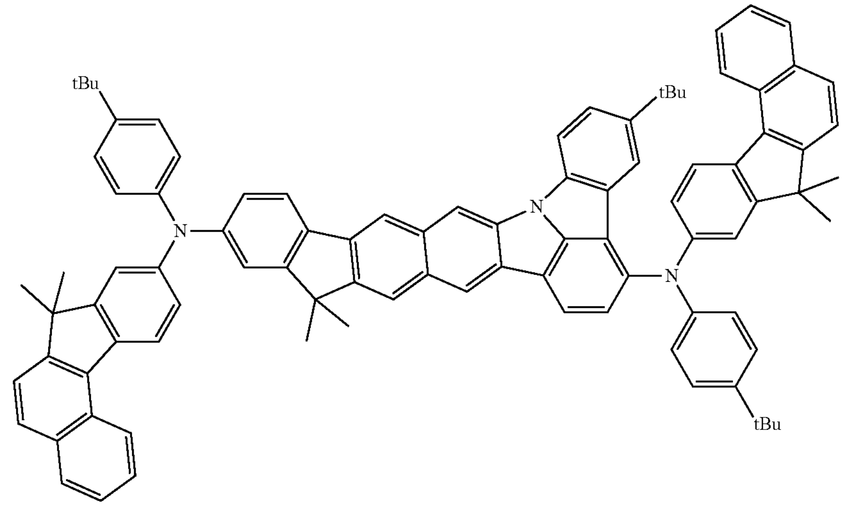
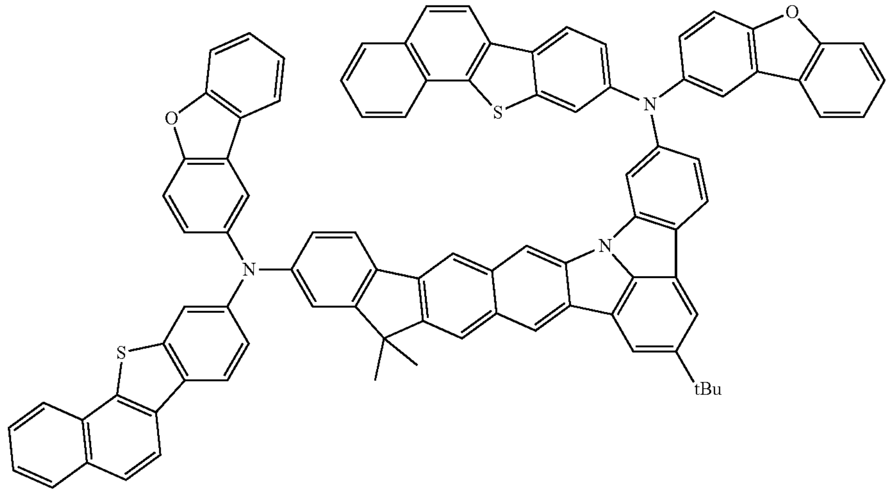

-continued
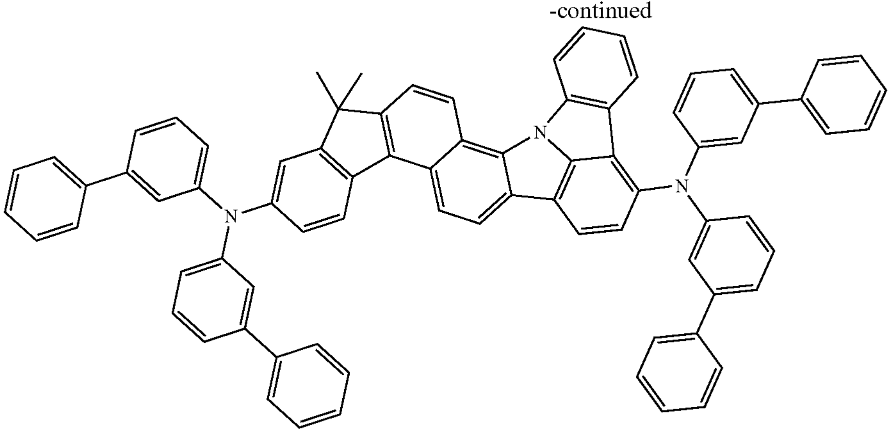
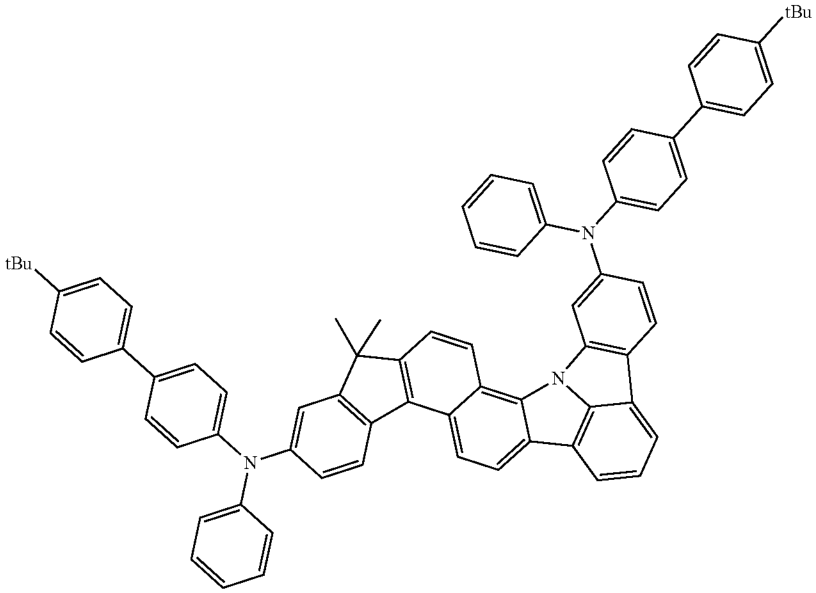
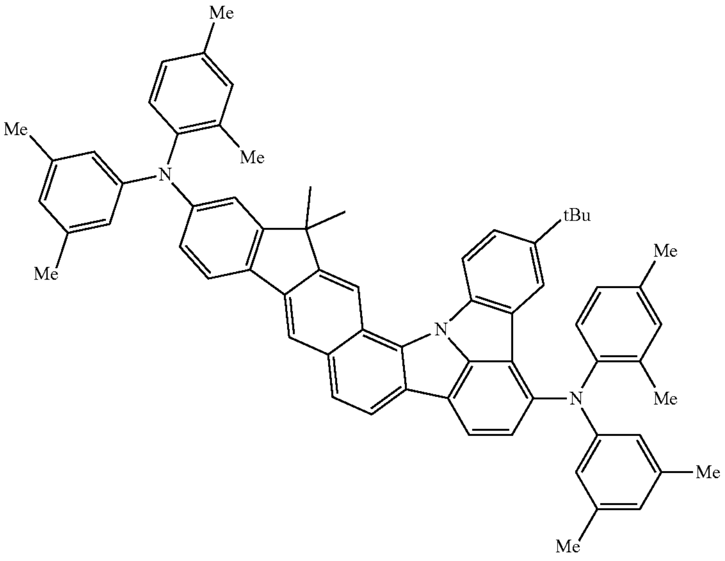

-continued
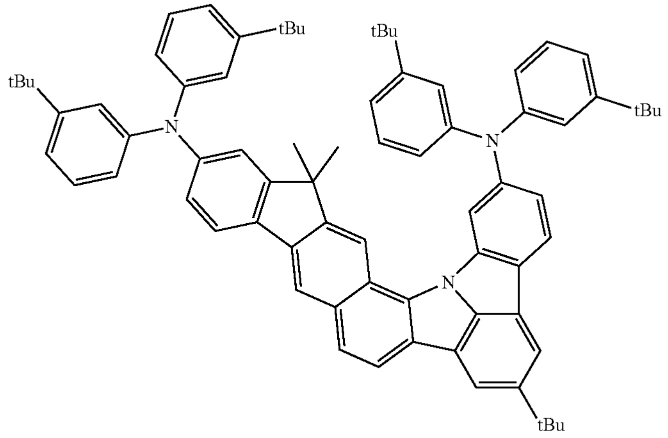
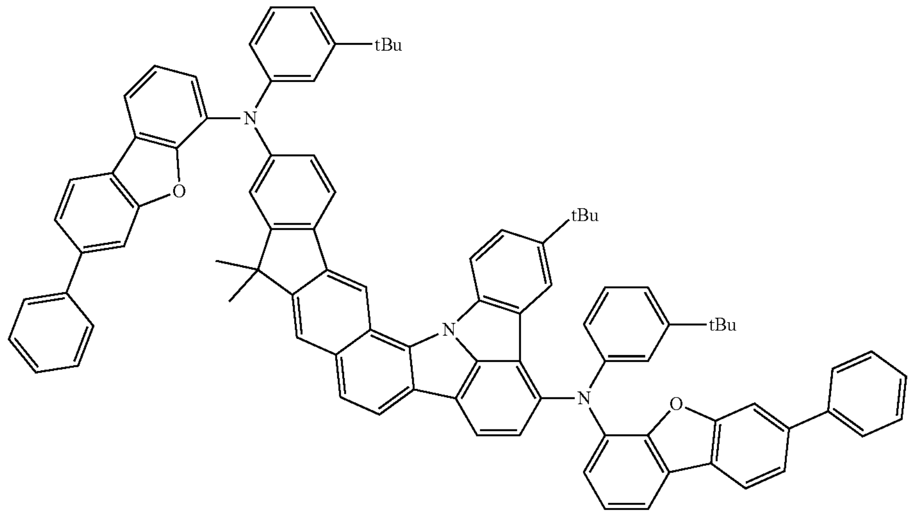
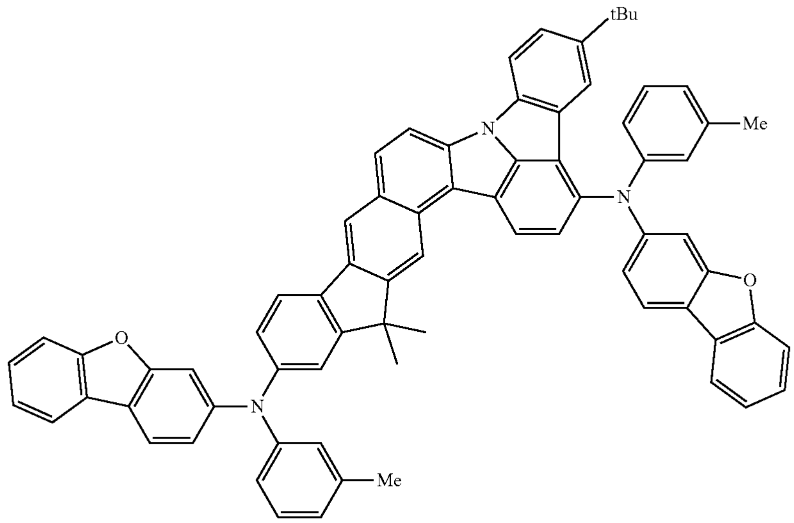

-continued
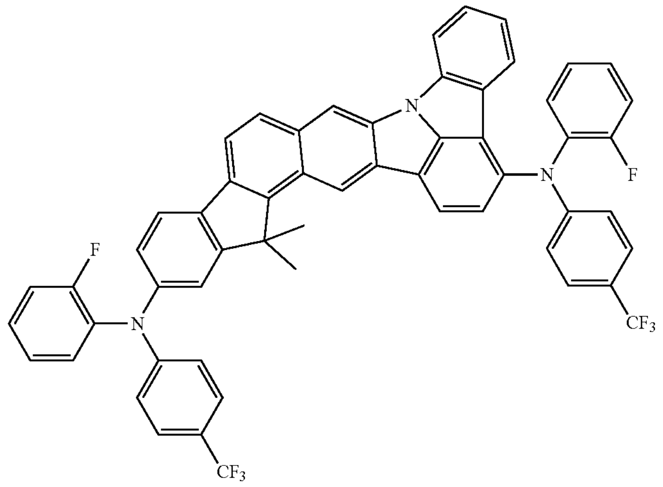
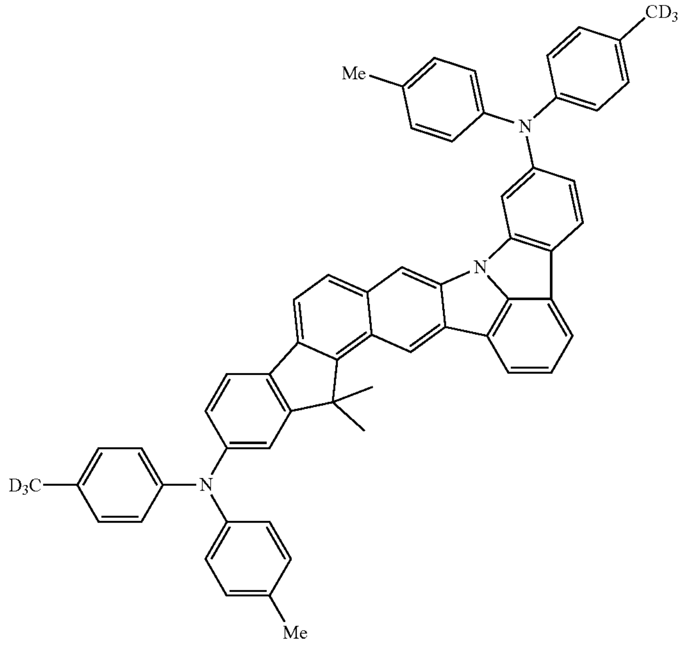

-continued
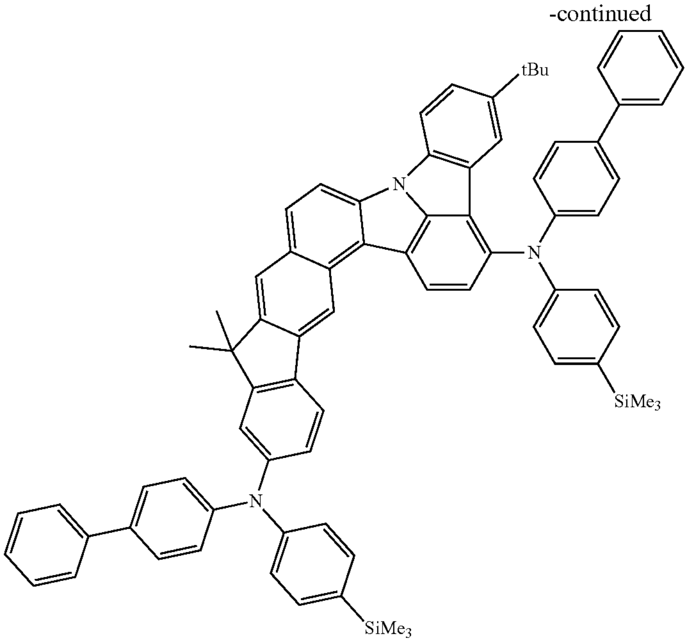
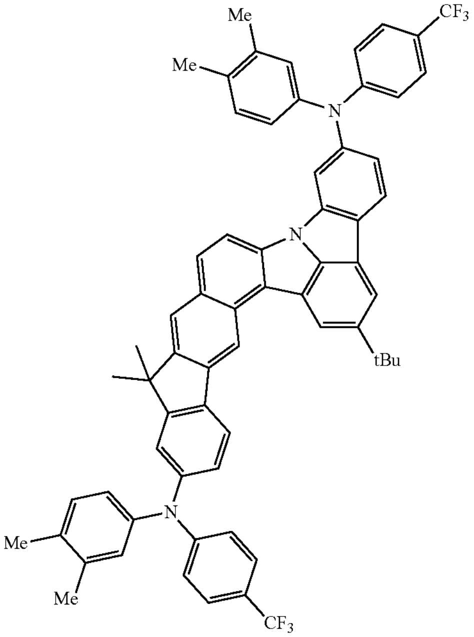
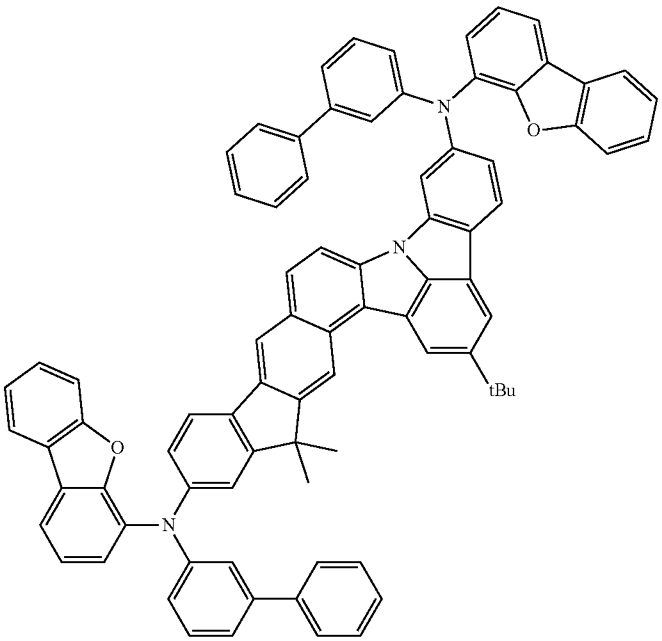

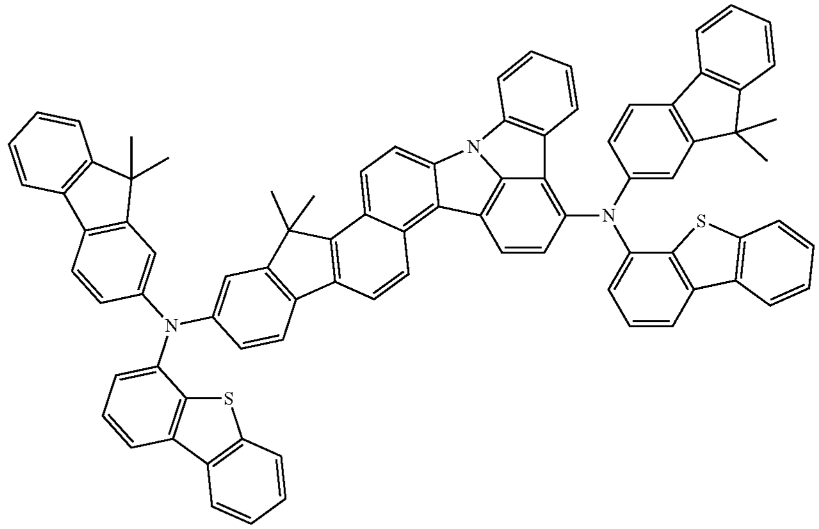
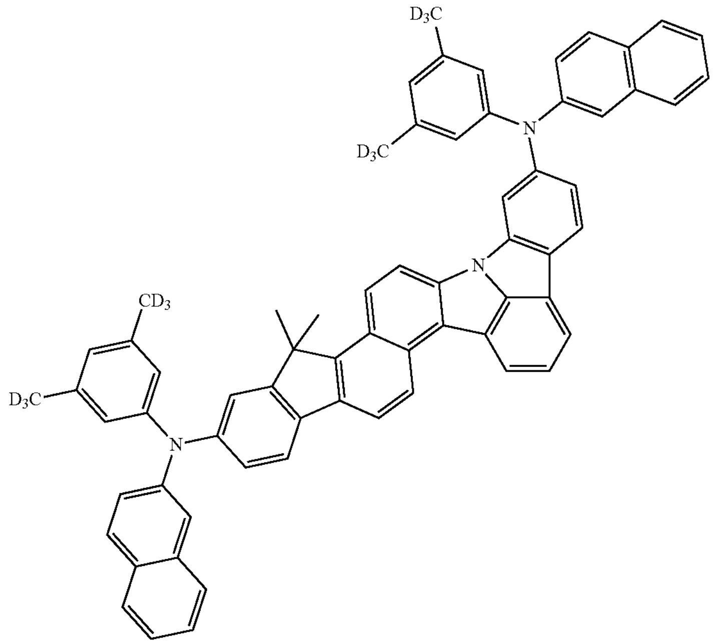
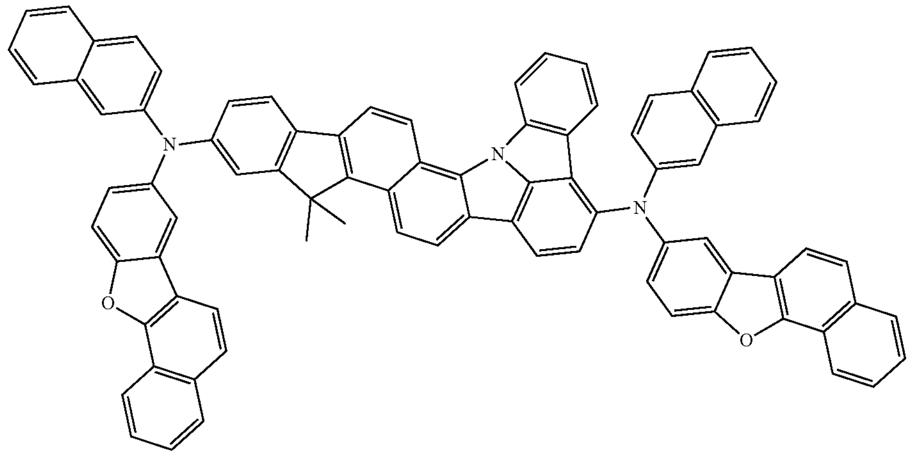

-continued
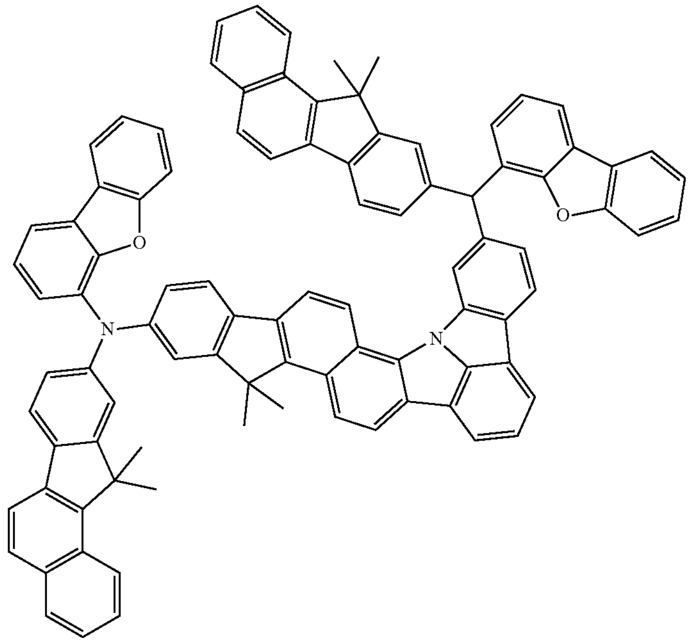
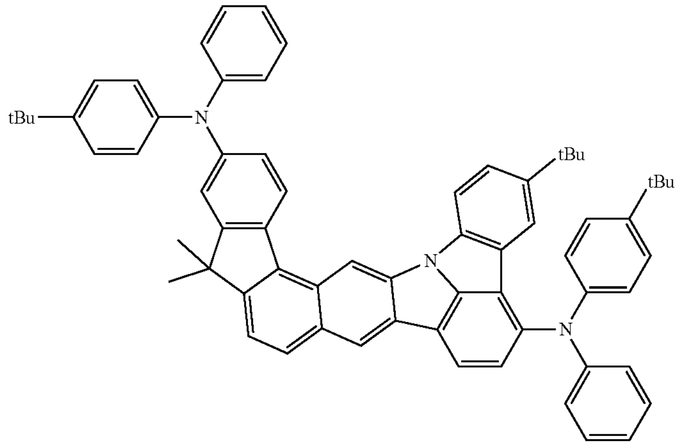
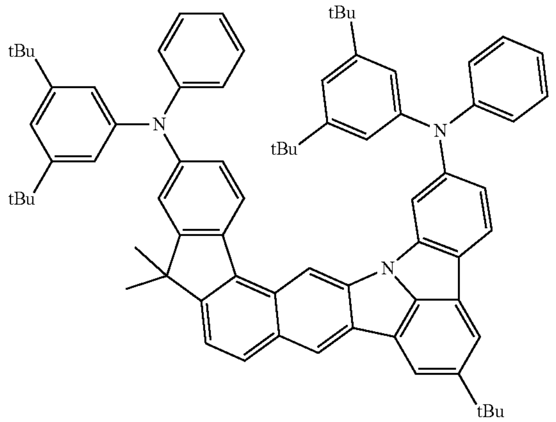

-continued
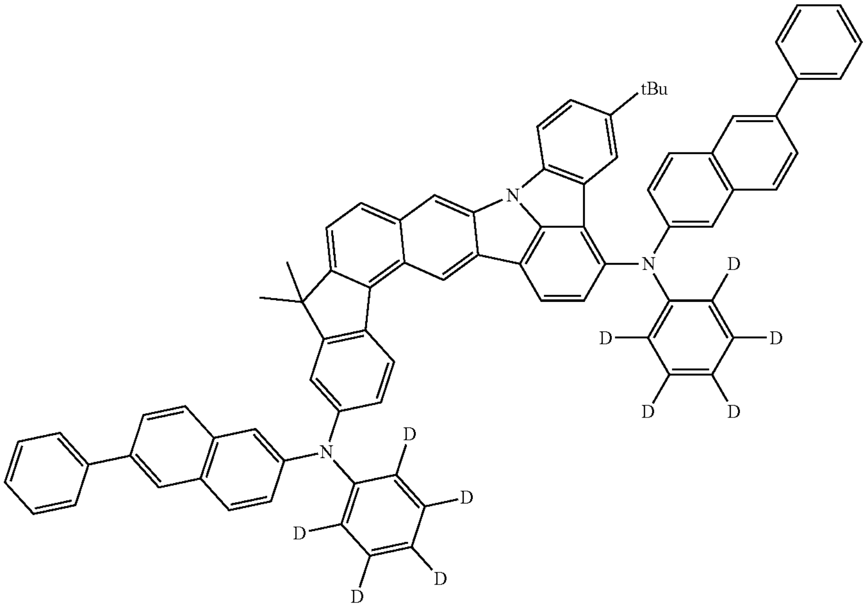
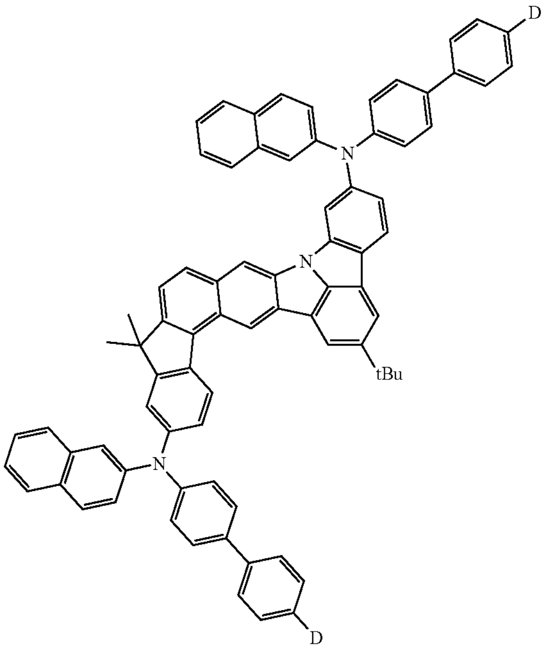

-continued
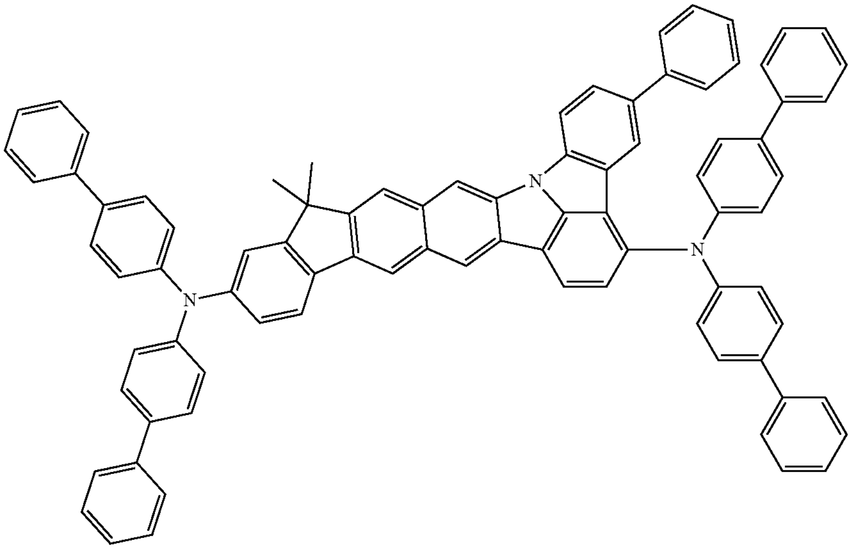
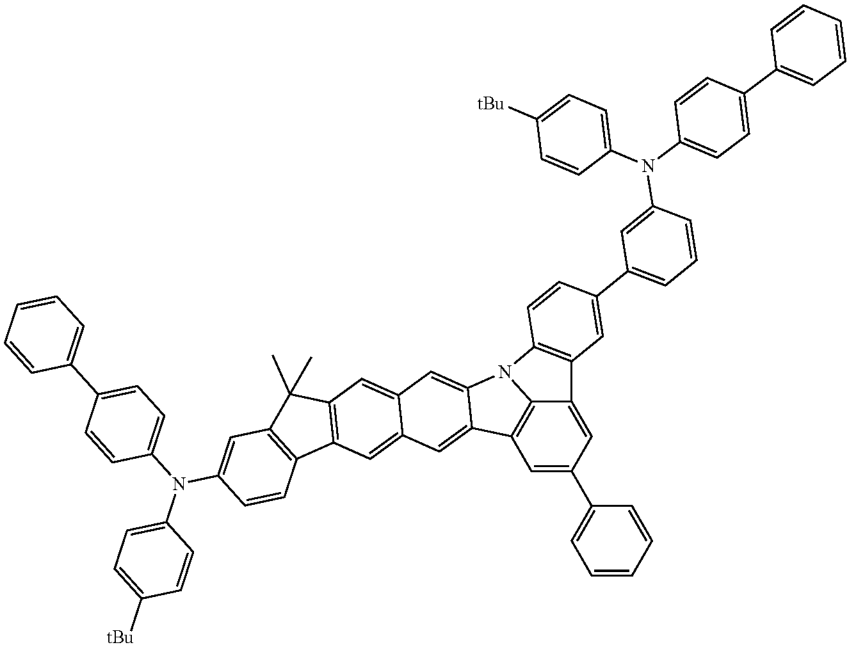
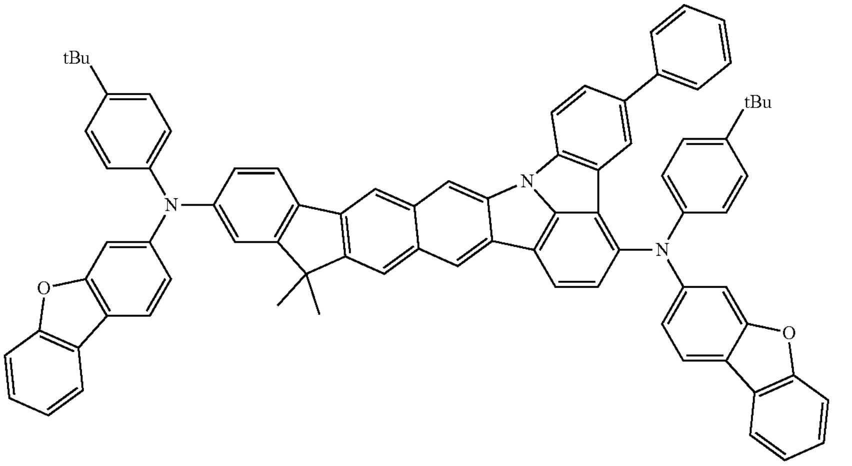

-continued
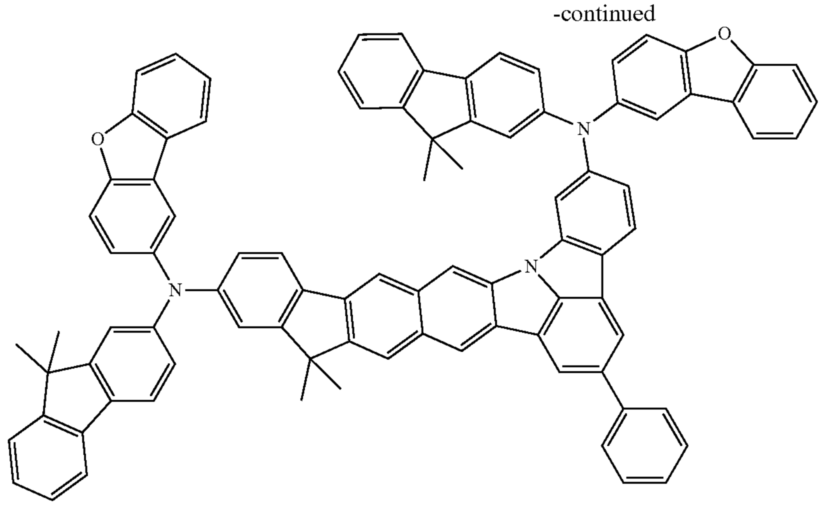
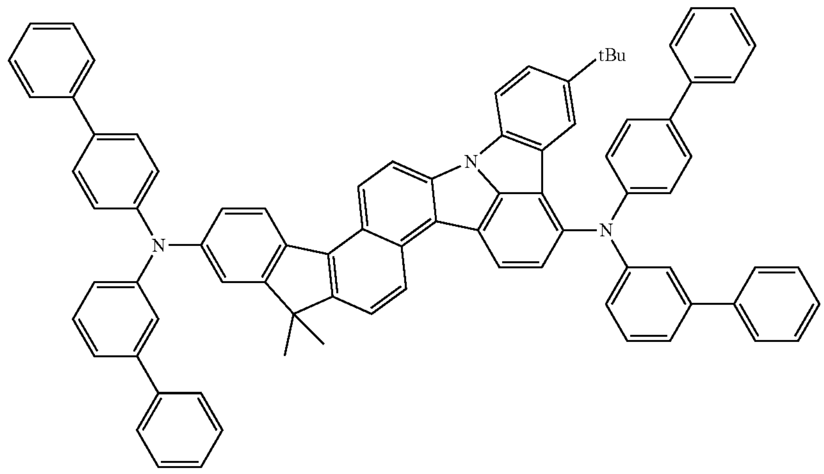
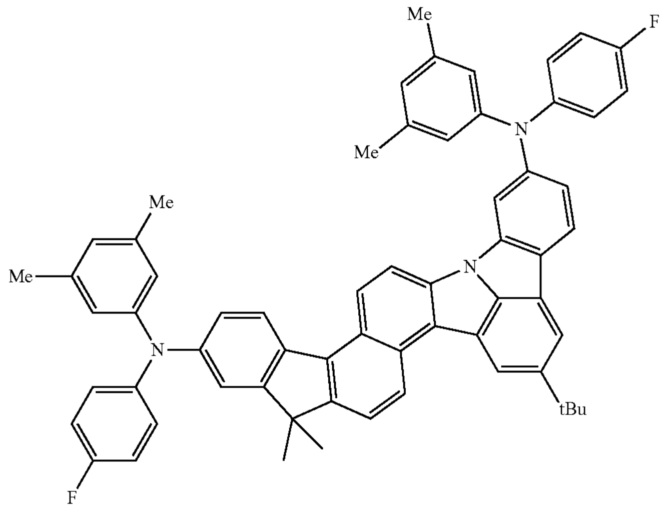

-continued
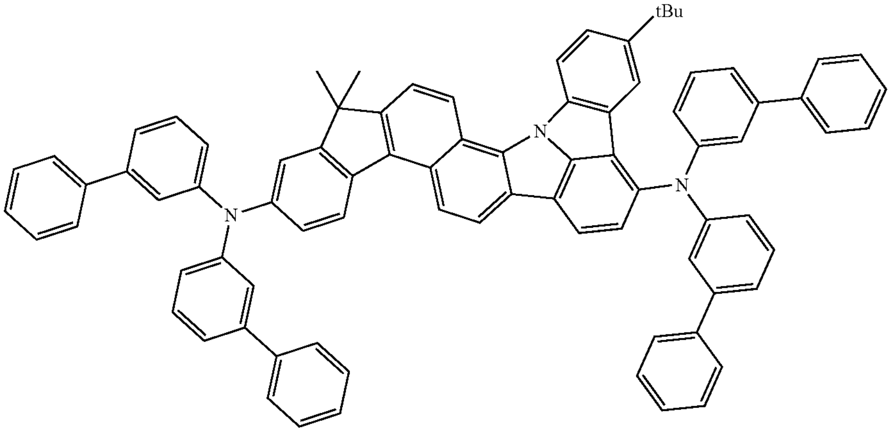
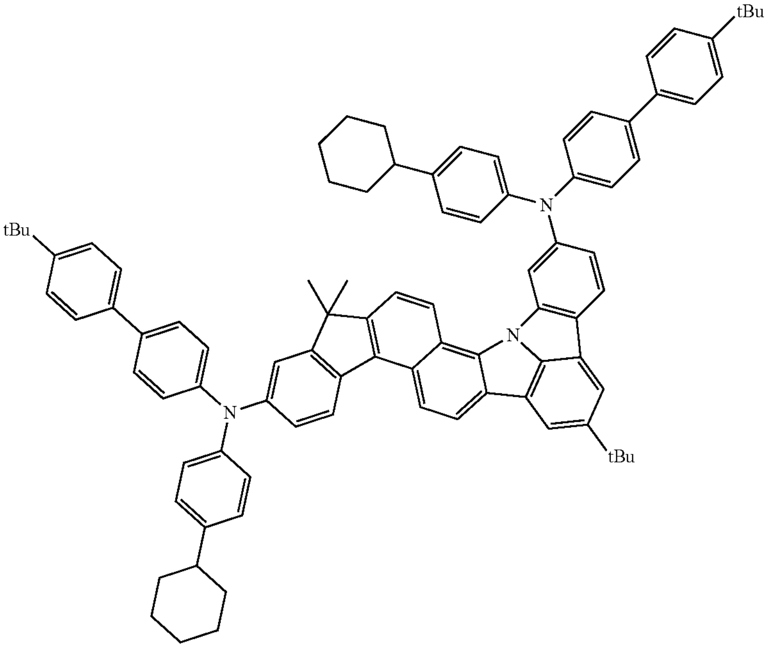
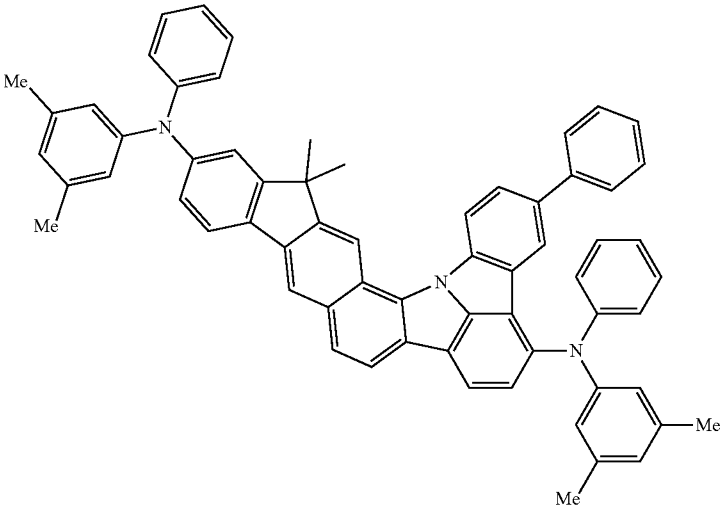

-continued
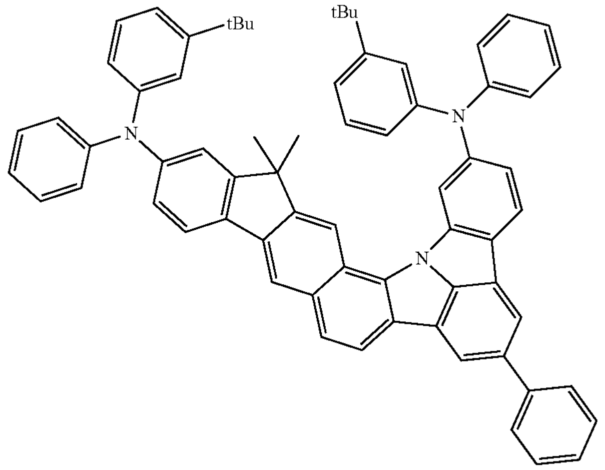
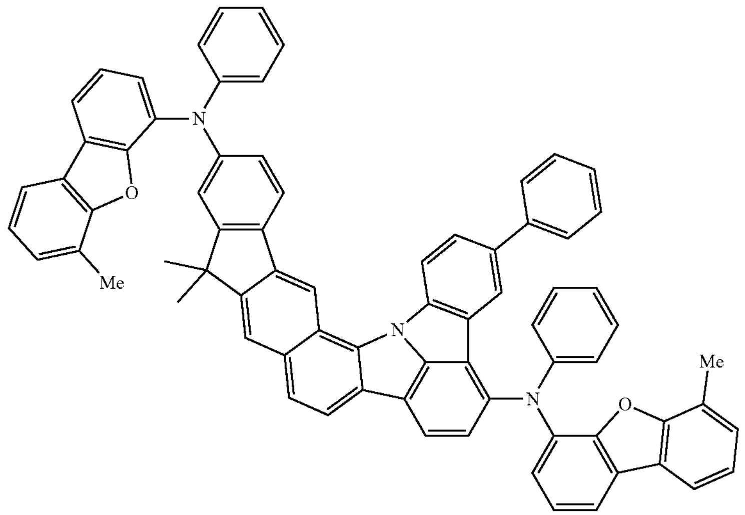
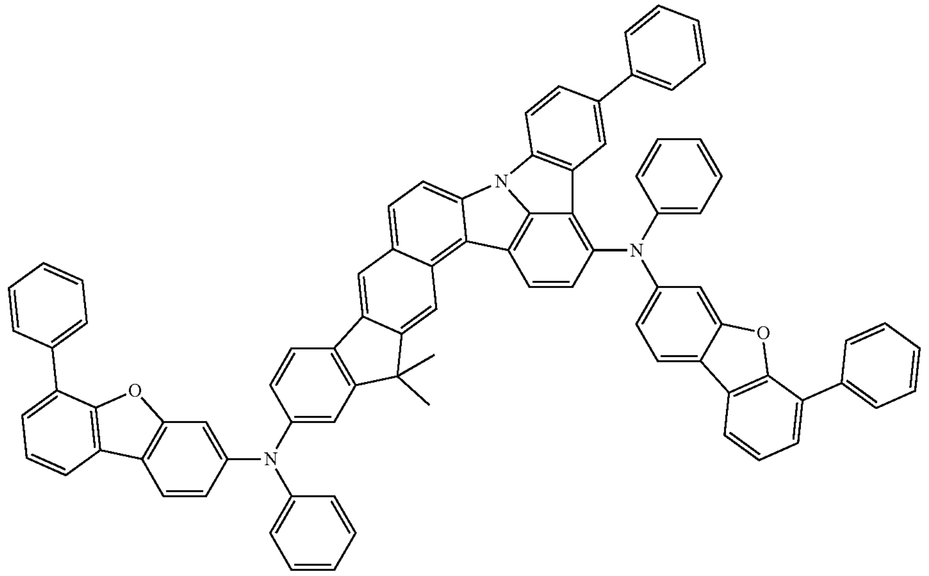

-continued
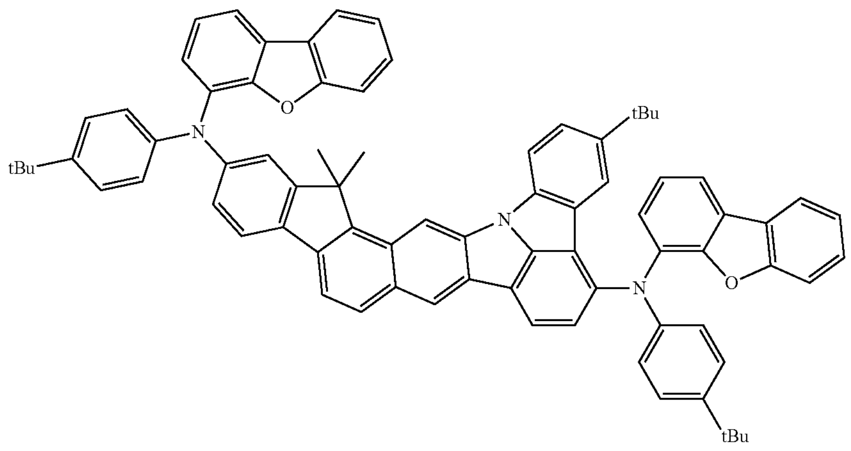
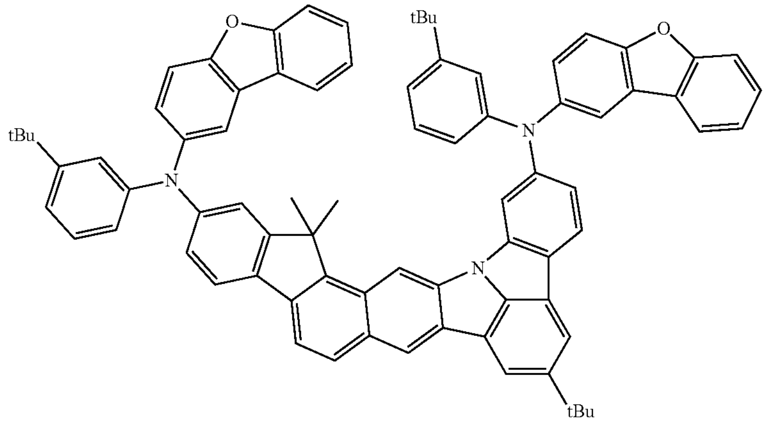
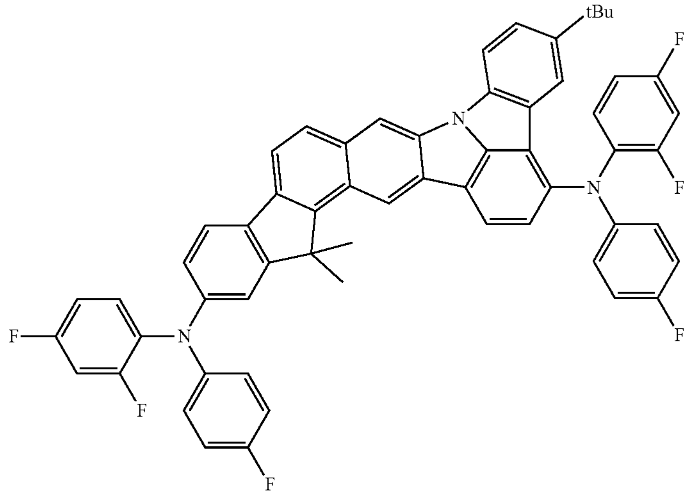

-continued
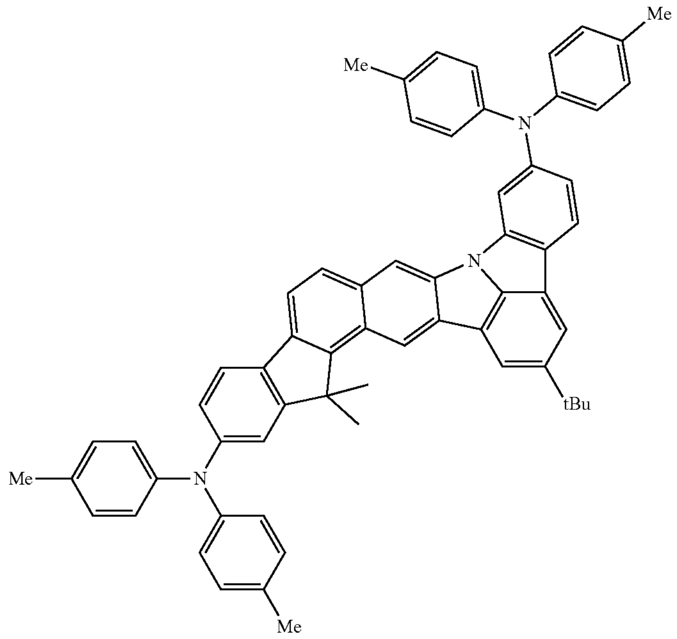
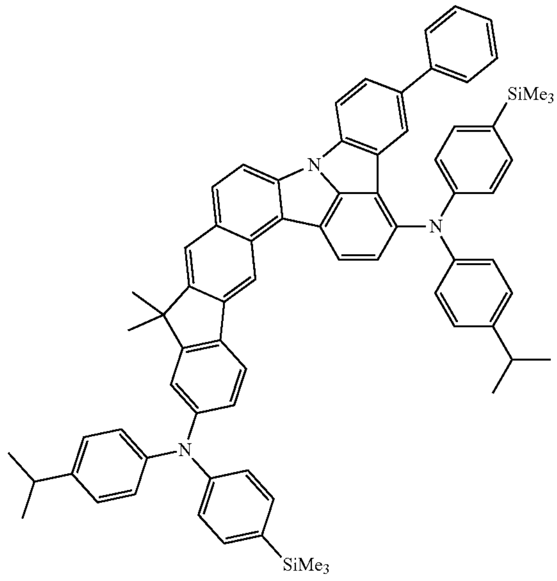
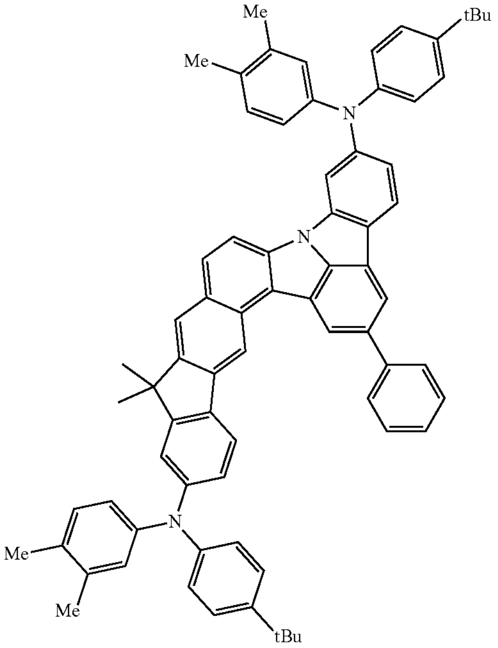

-continued
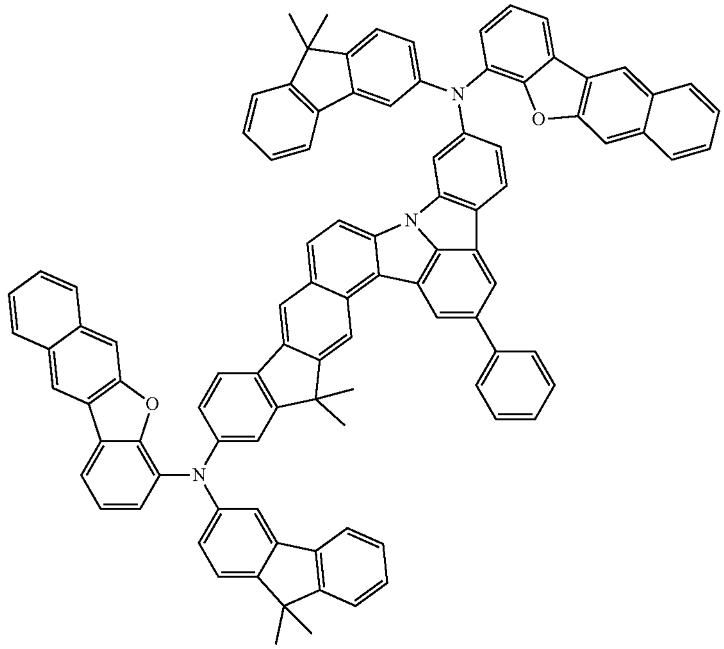
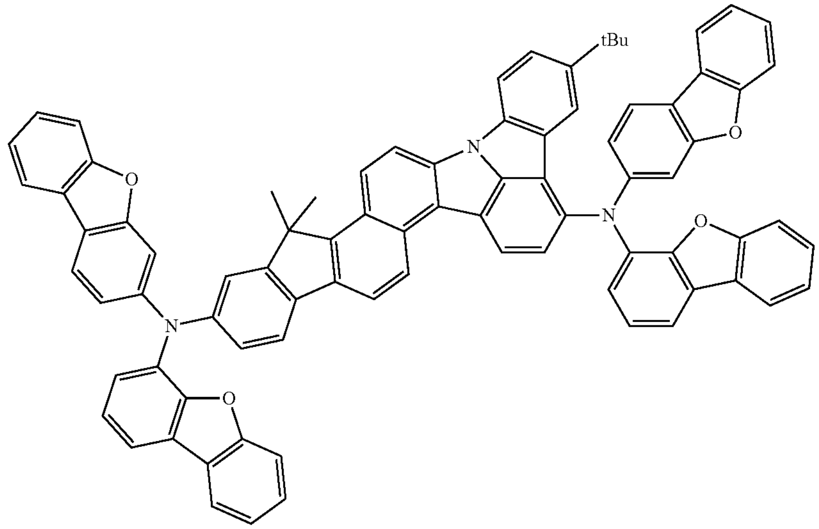

-continued
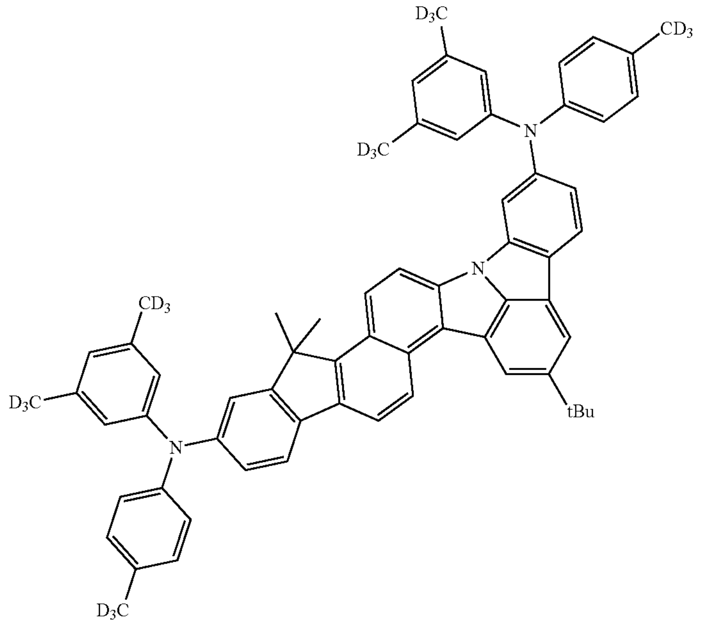
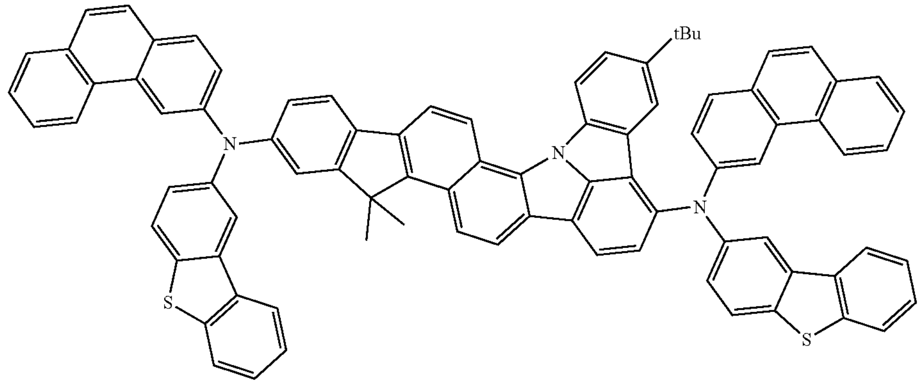
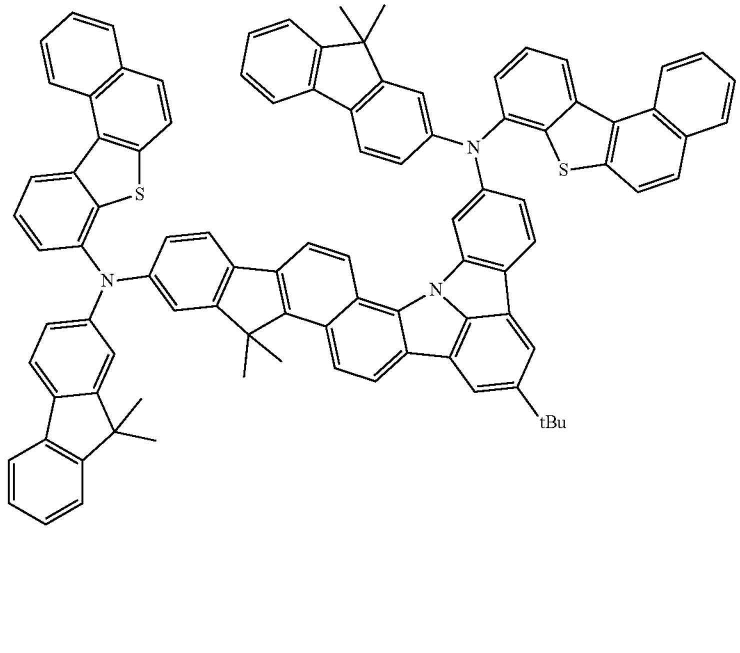

-continued
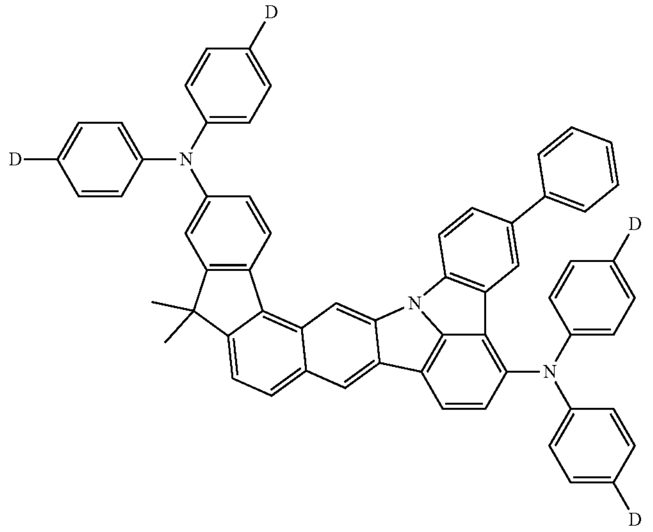
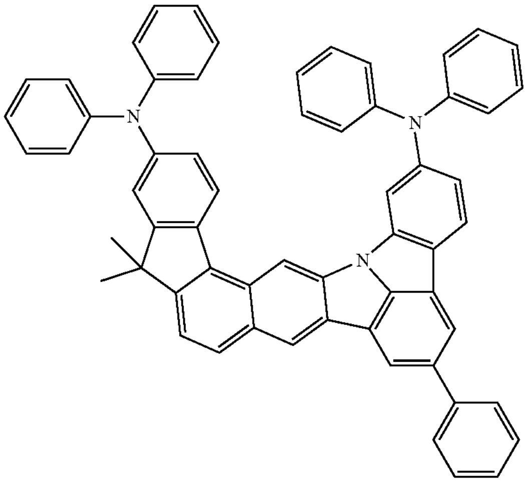
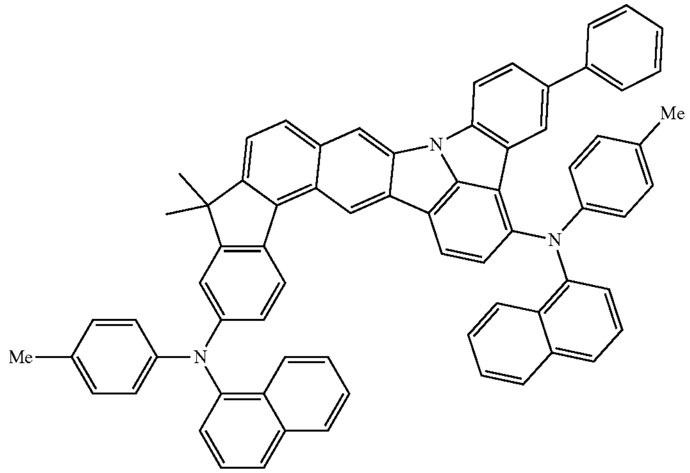
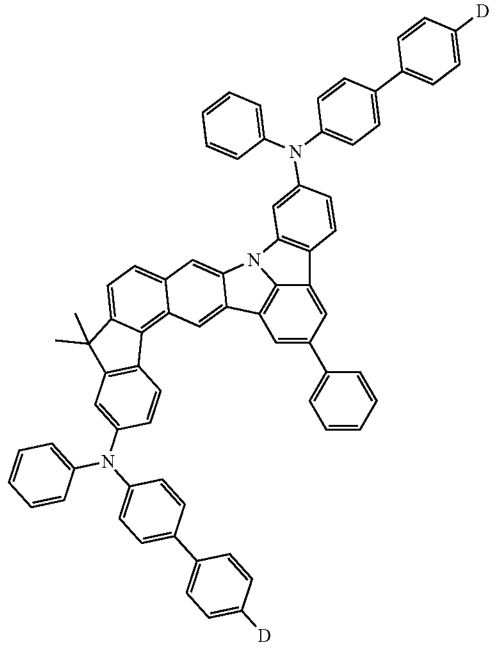
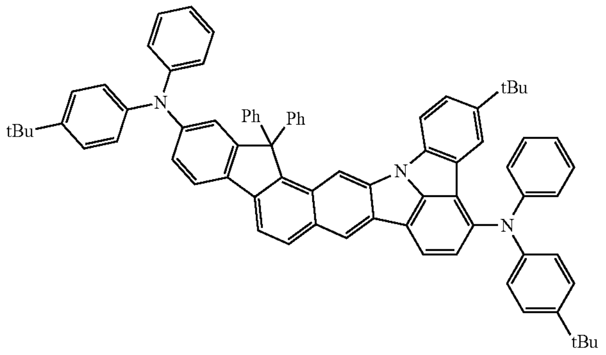

-continued
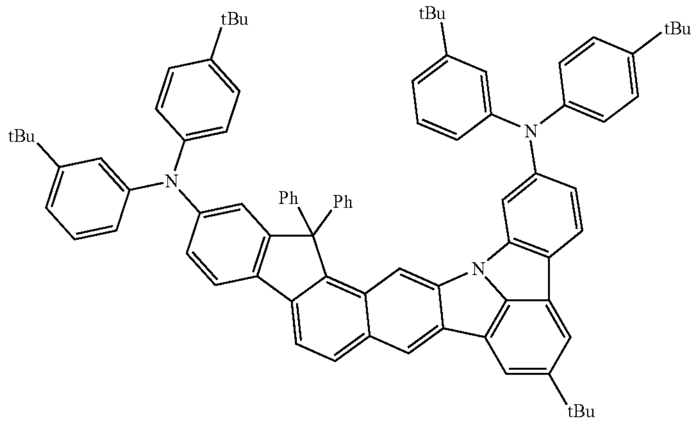
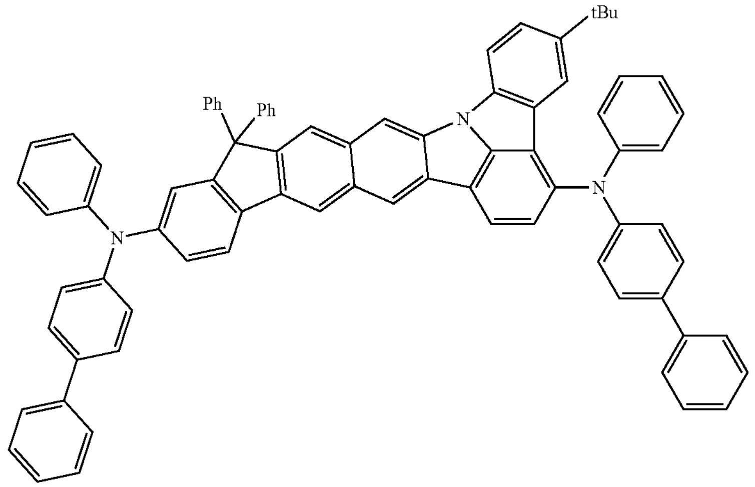
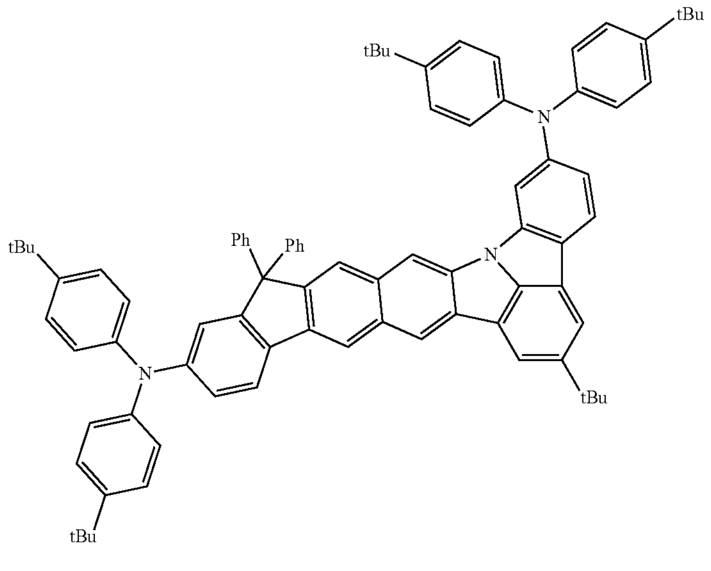

-continued
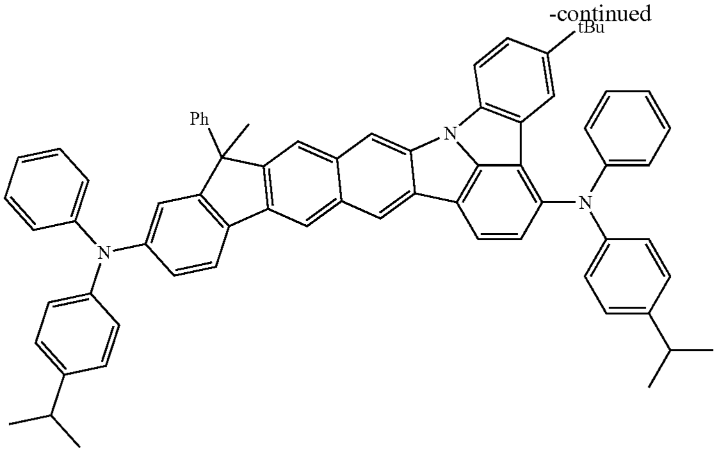
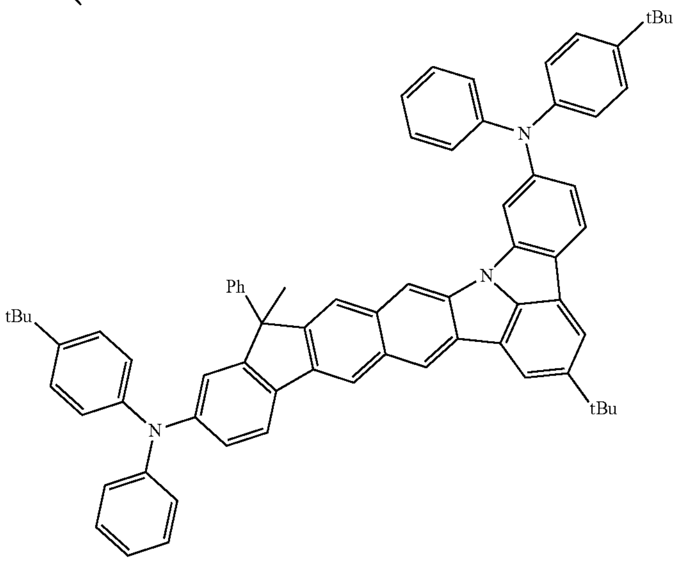
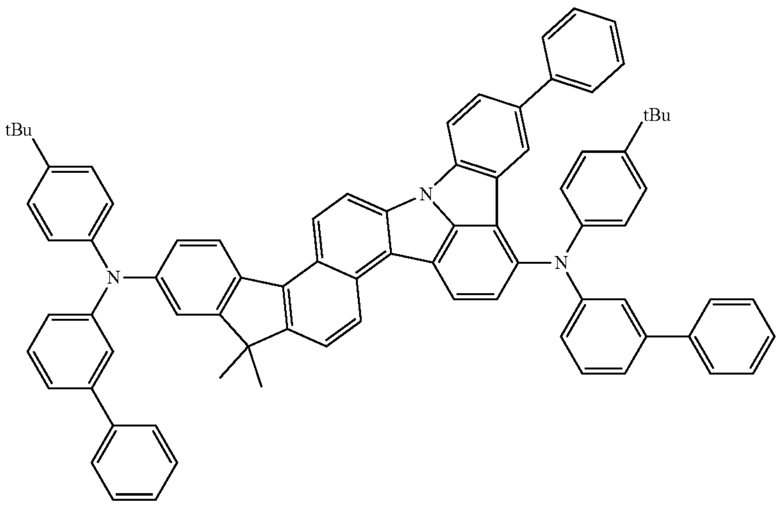

-continued
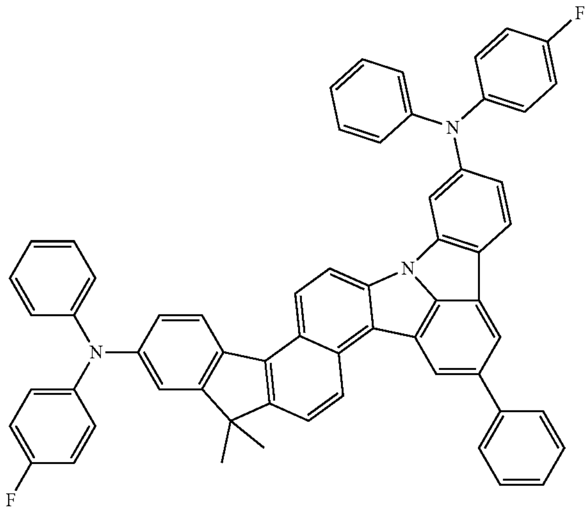
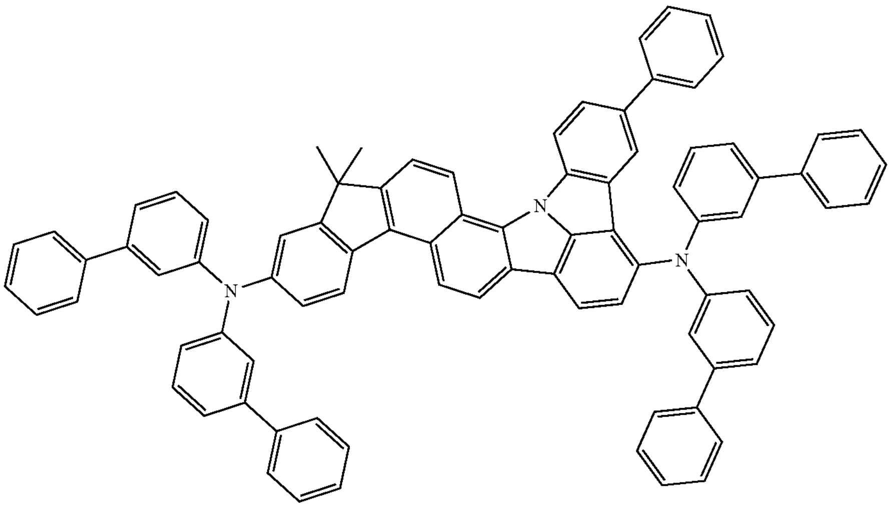
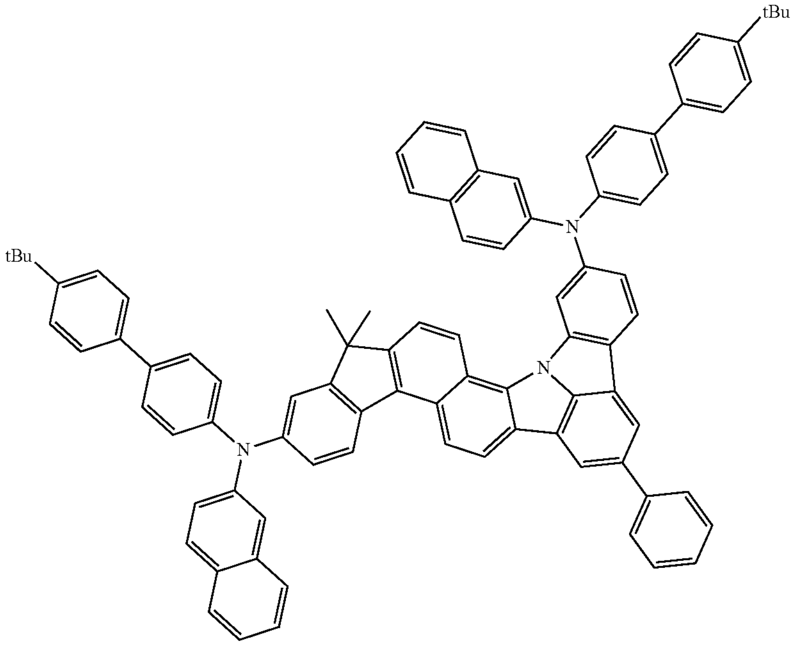

-continued
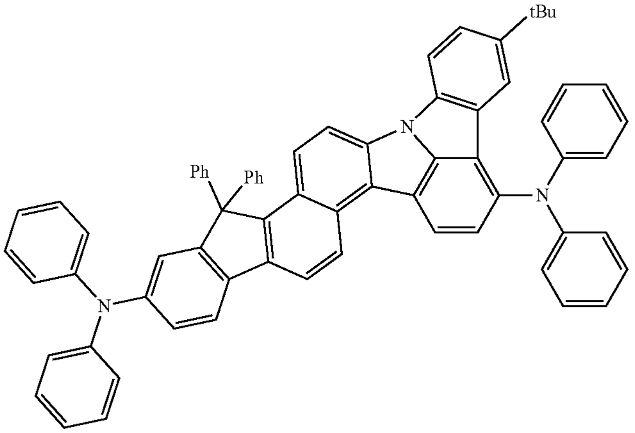
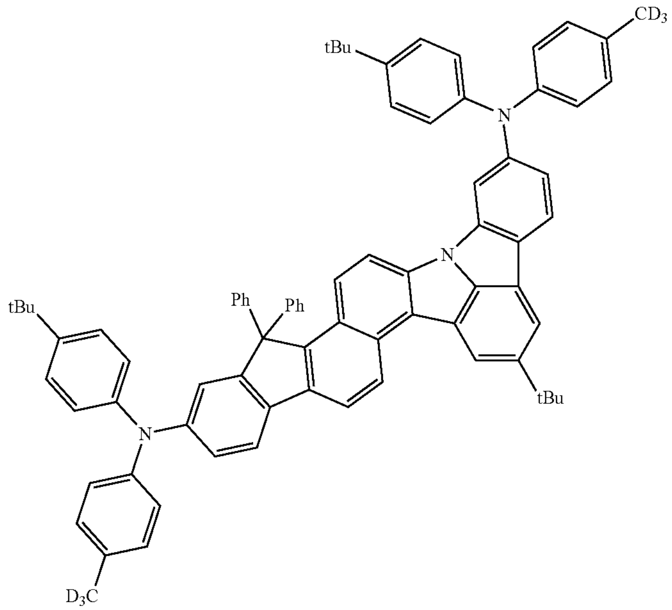
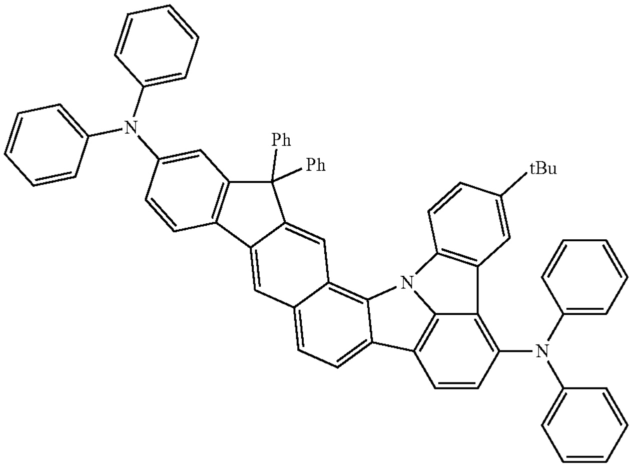

-continued
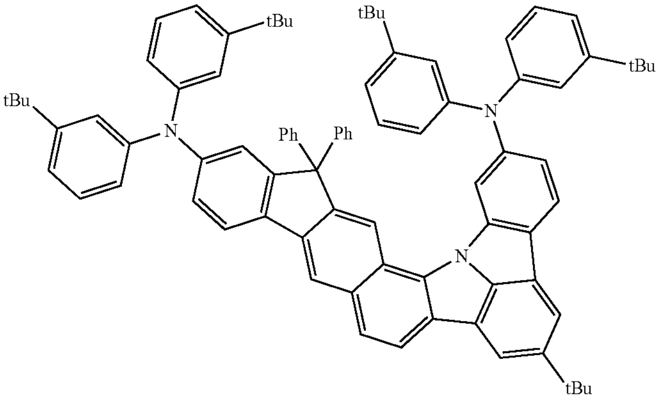
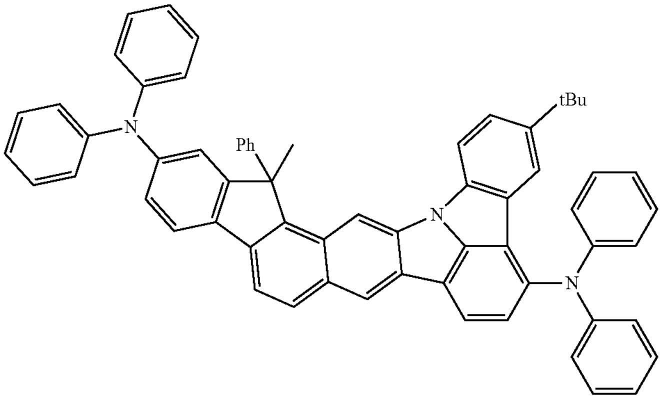
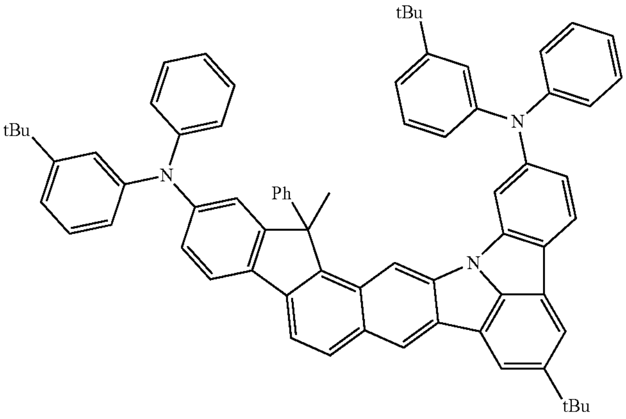
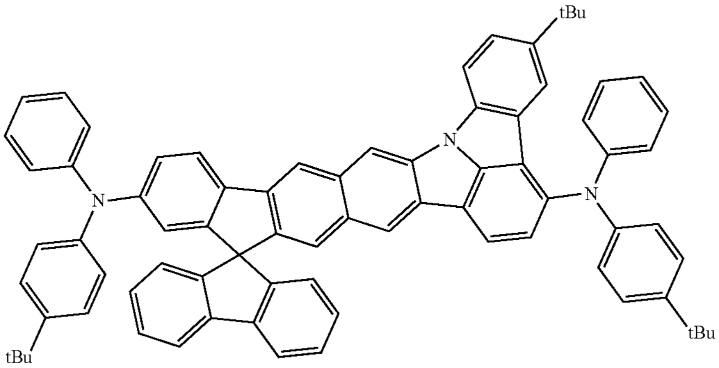

-continued
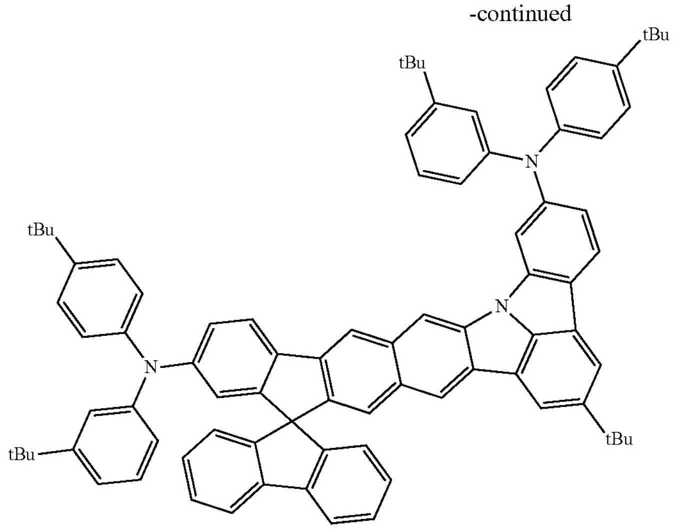
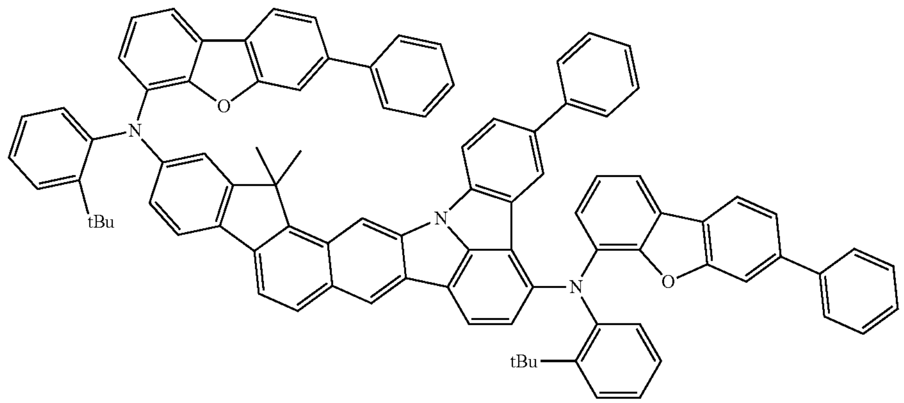
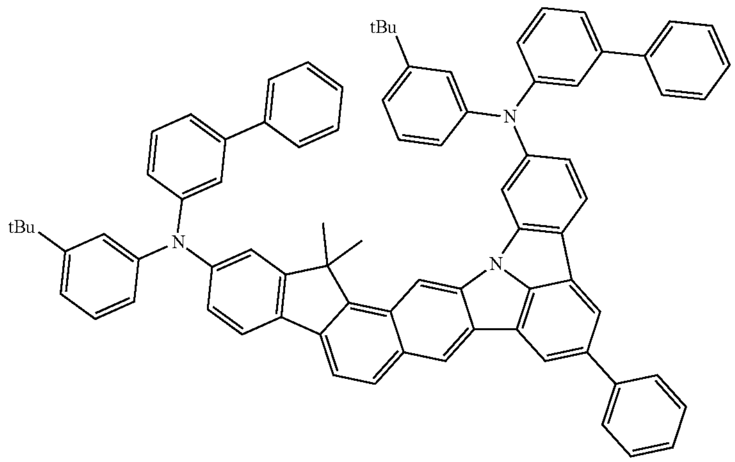

-continued
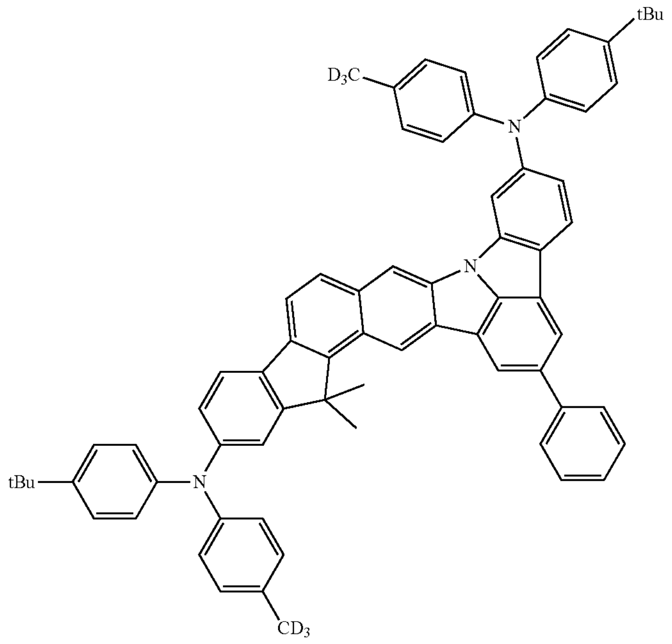
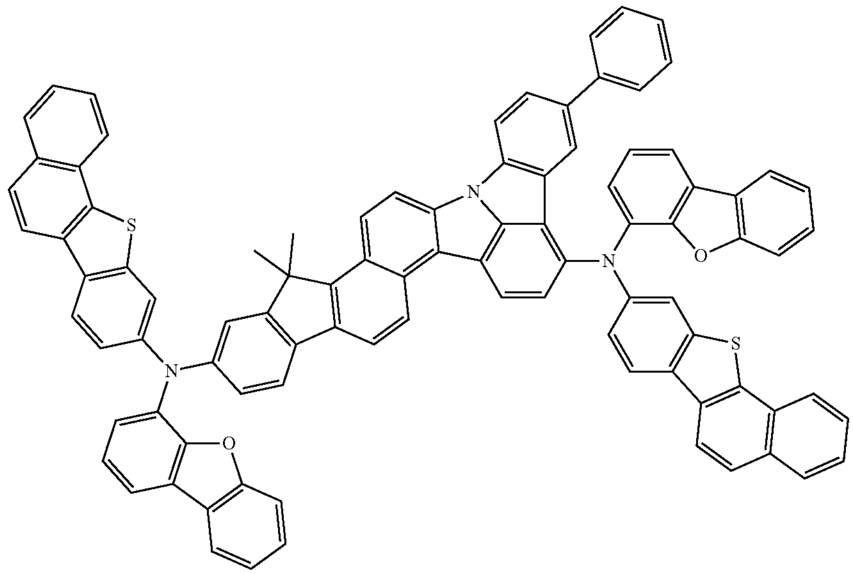

-continued
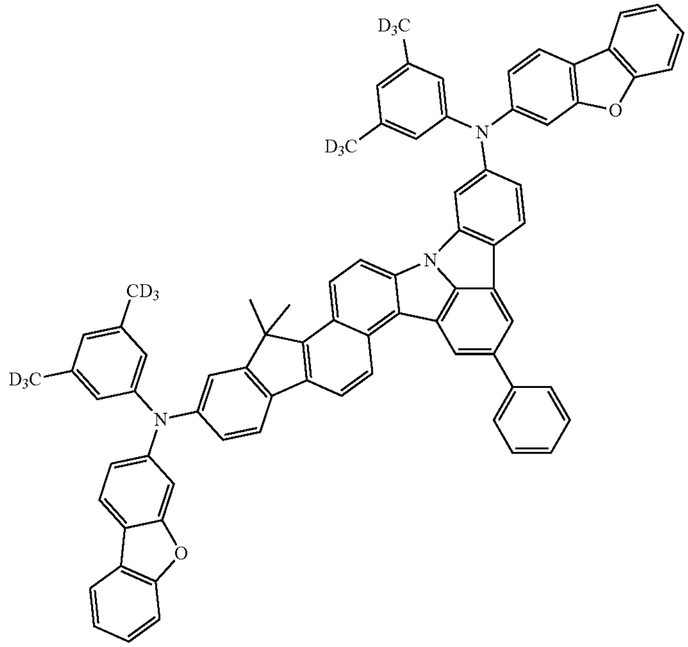
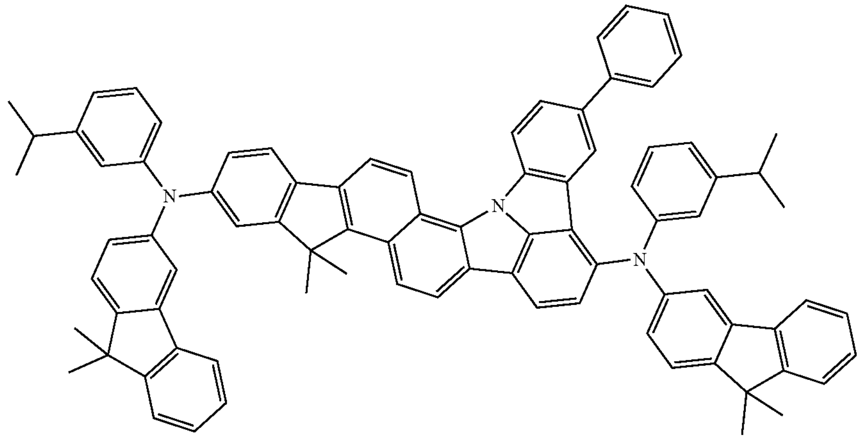
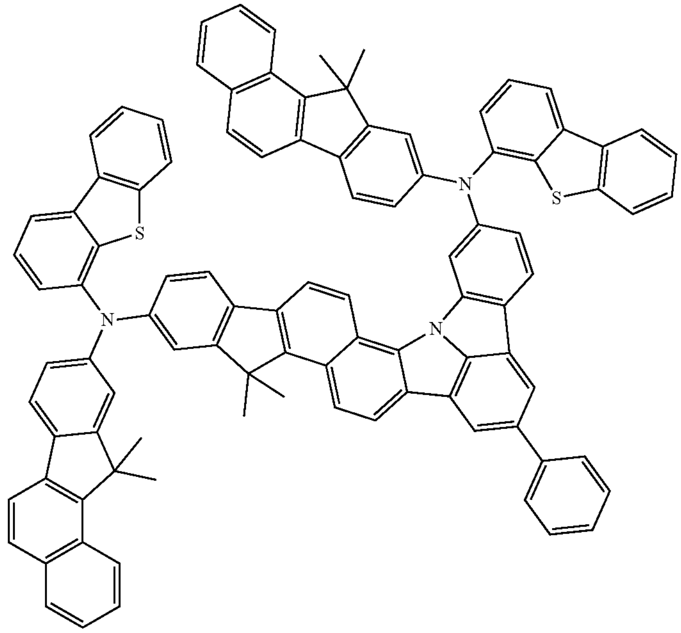

-continued
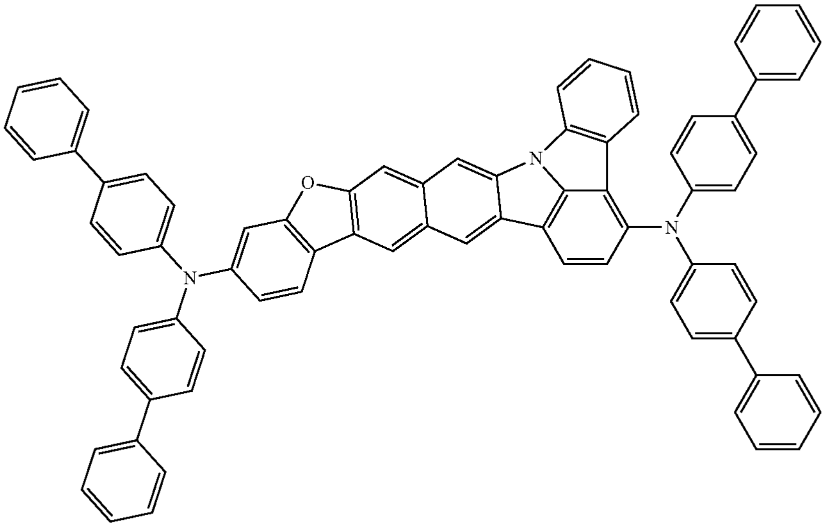
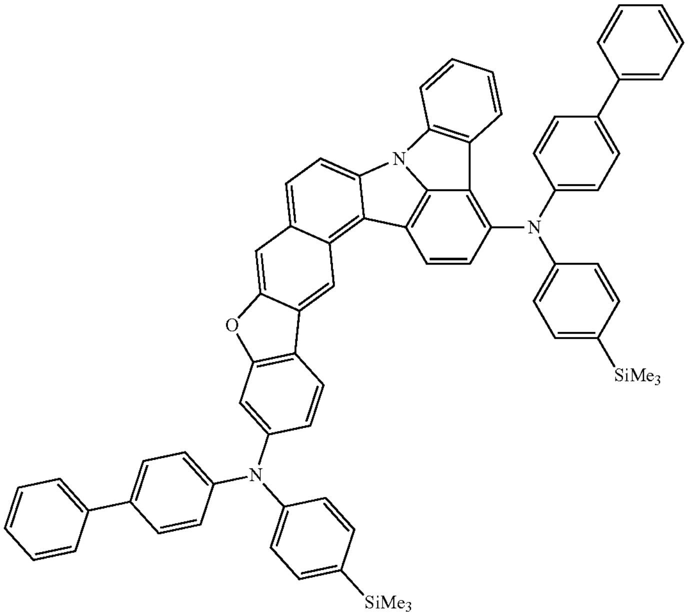

-continued
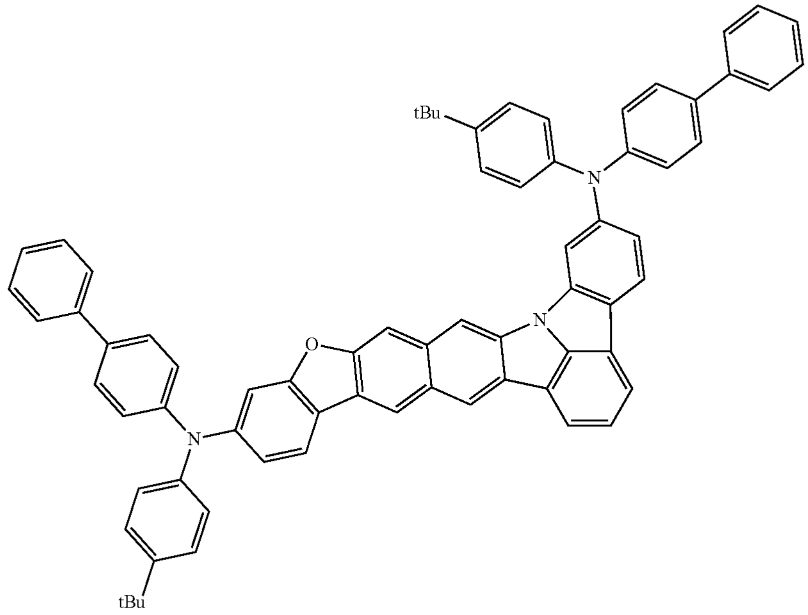
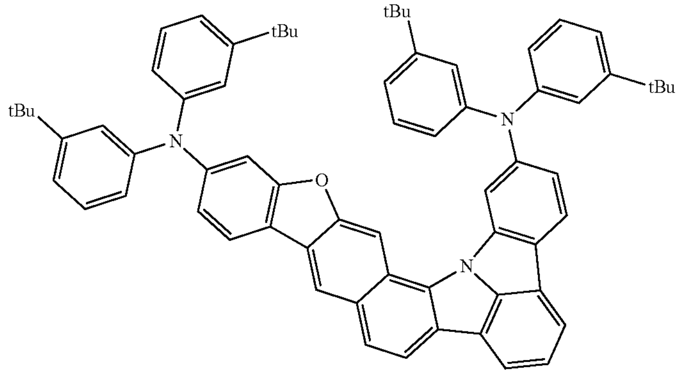
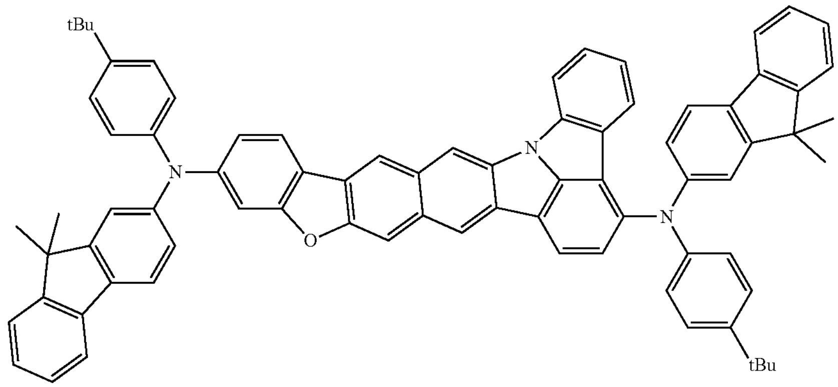

-continued
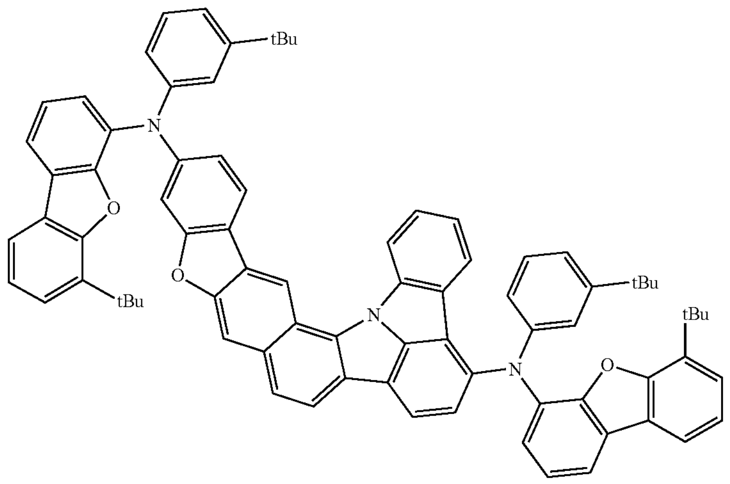
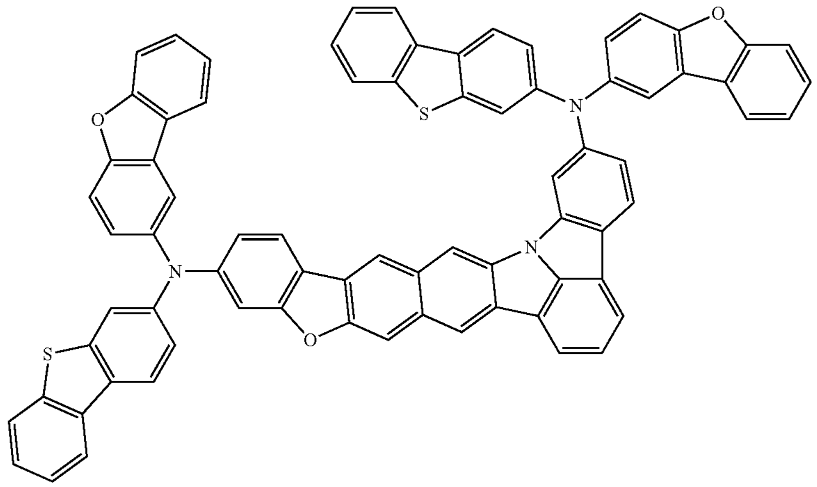
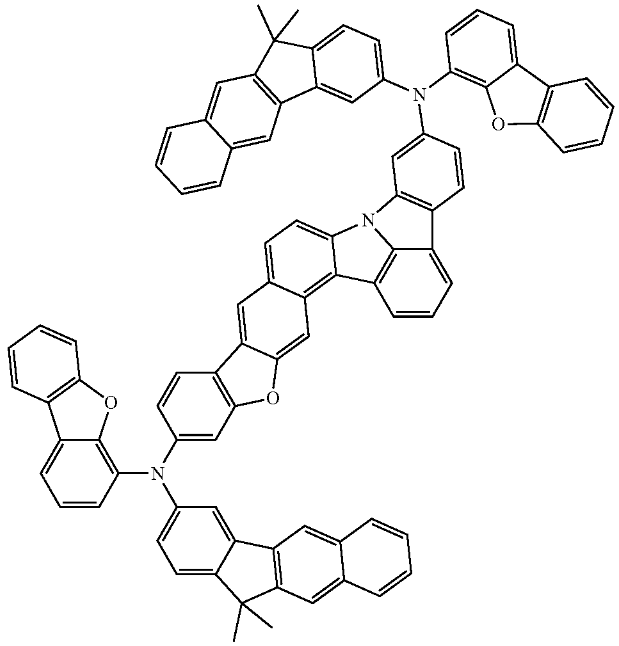

-continued
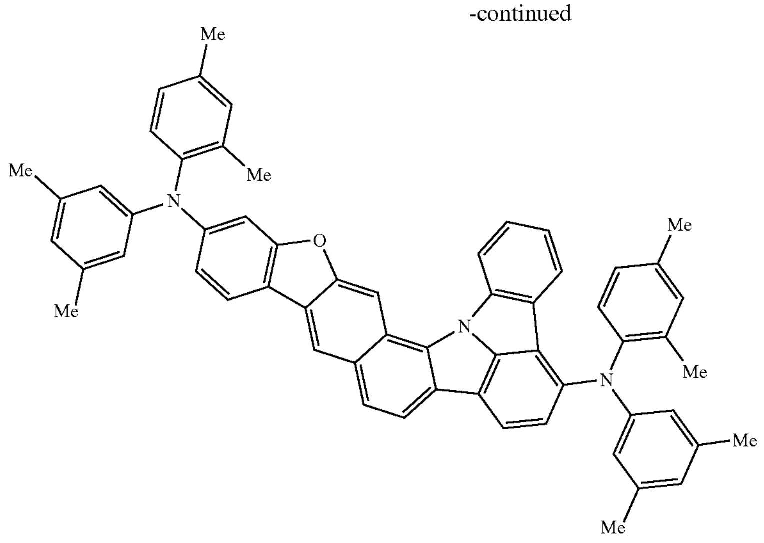
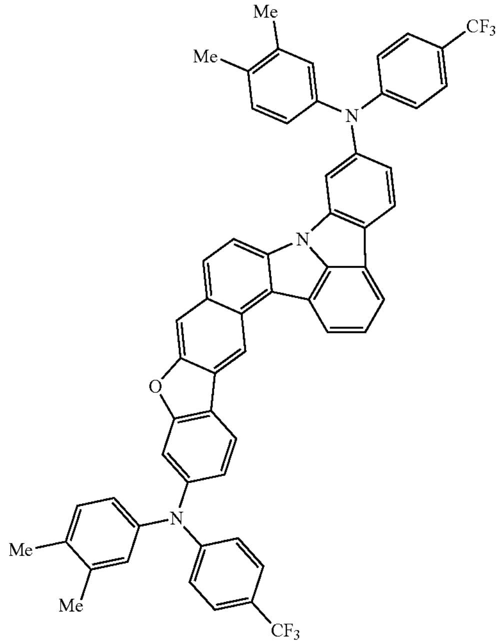
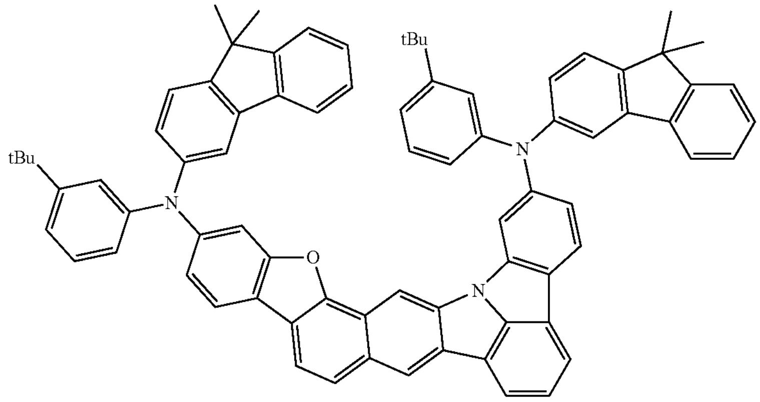

-continued
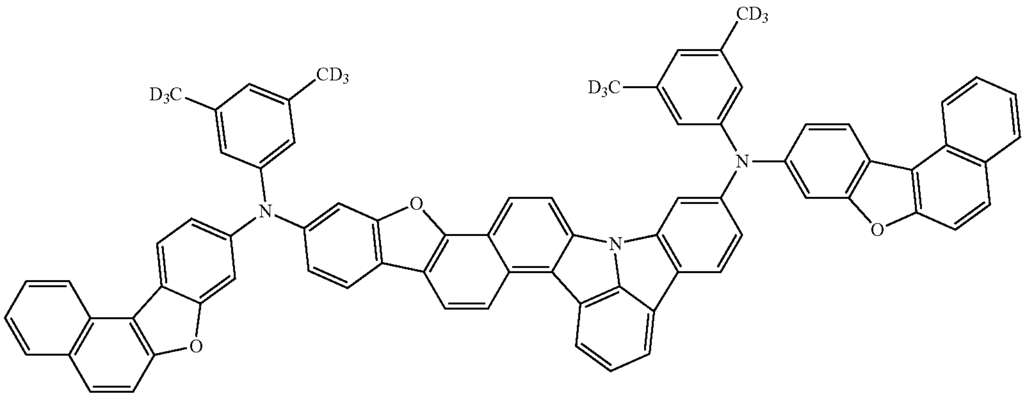
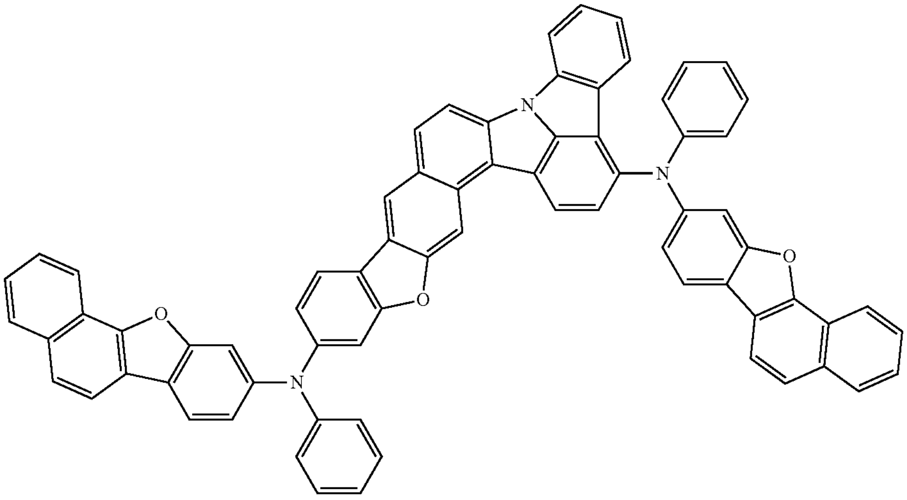
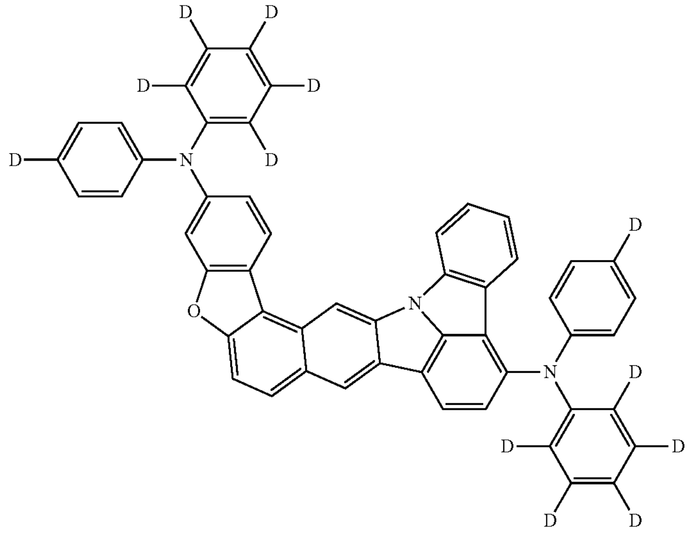

-continued
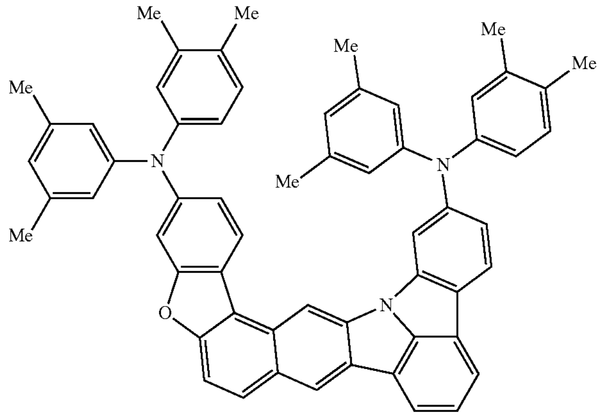
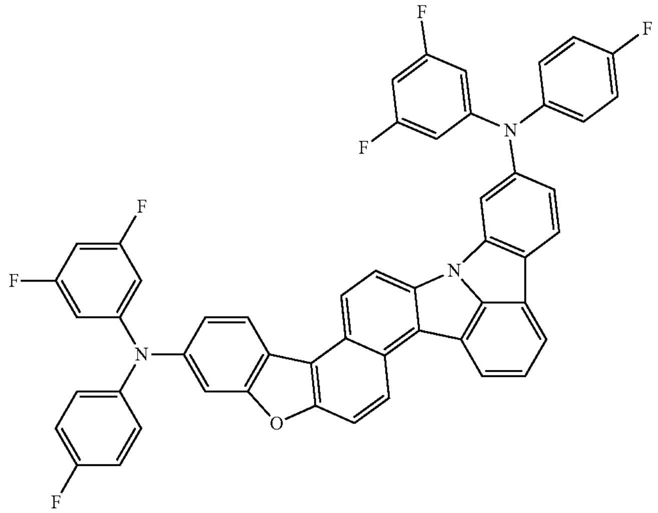
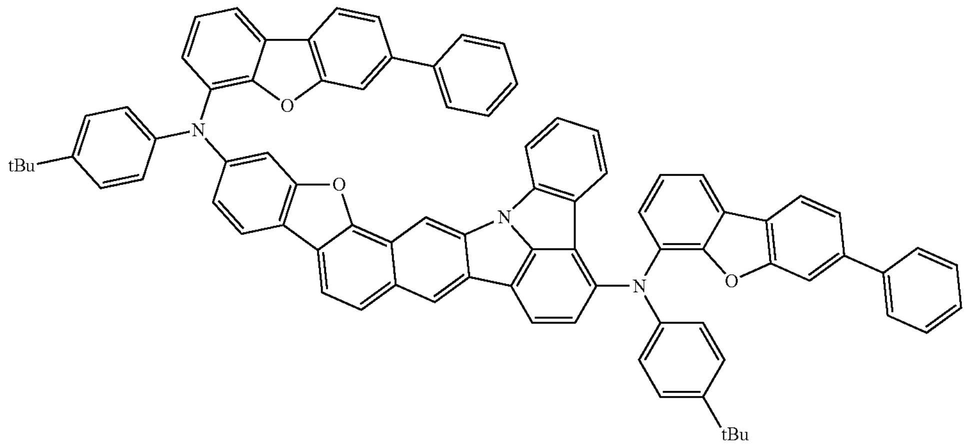

-continued
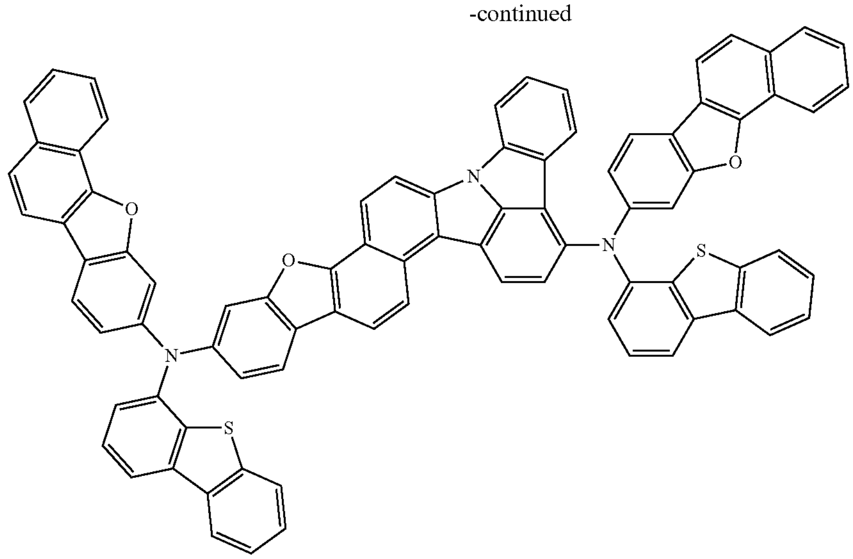
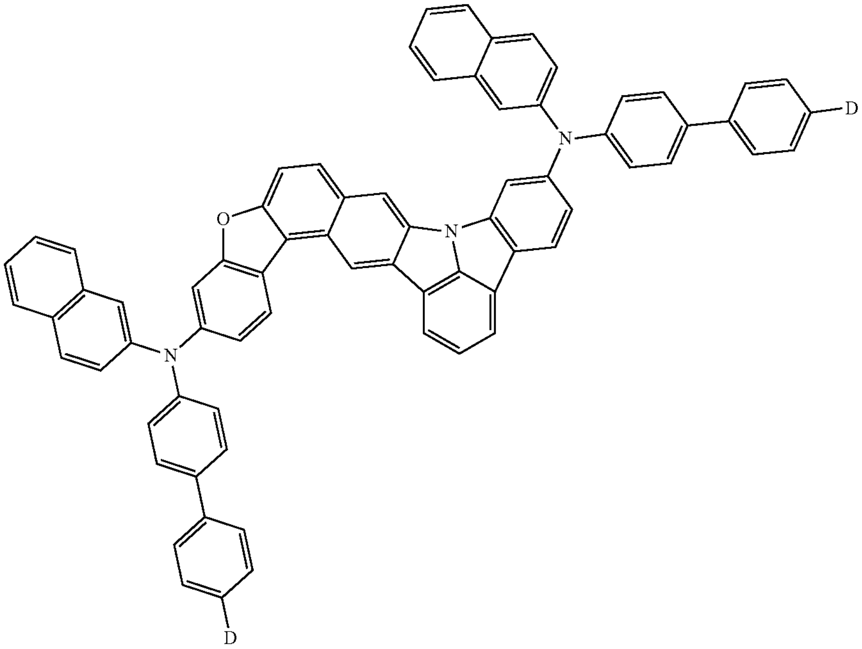

-continued
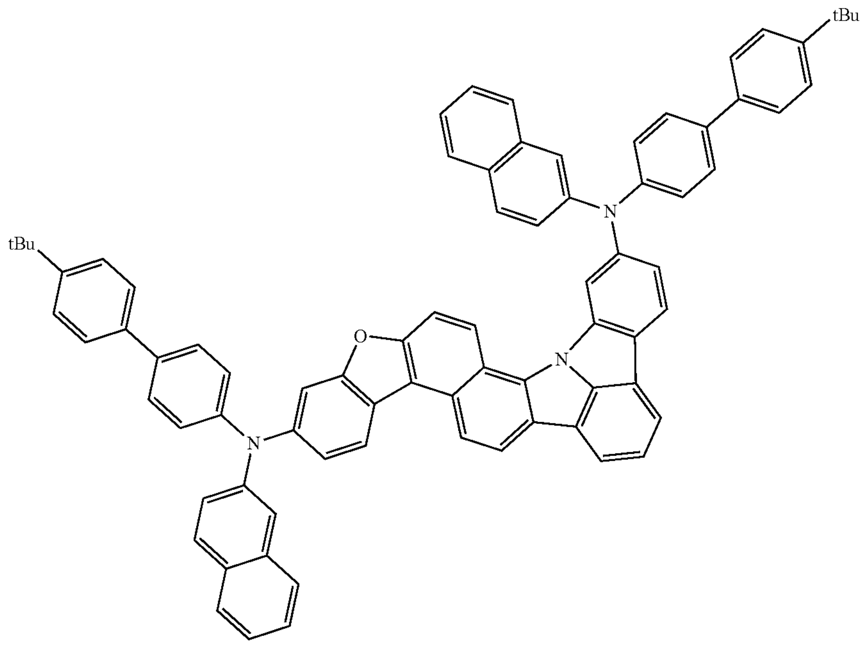
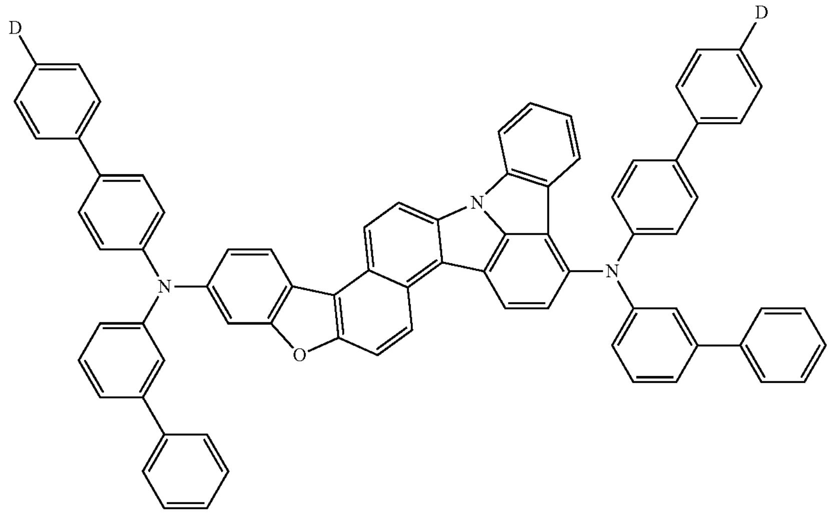

-continued
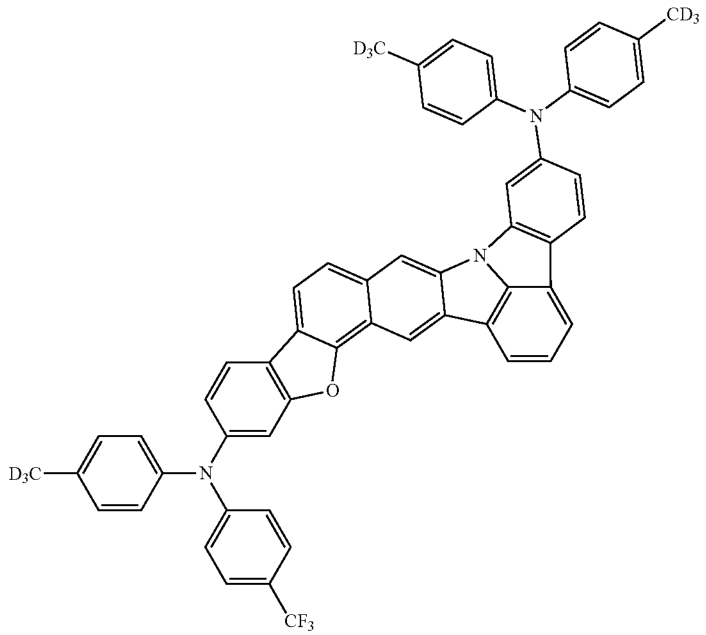
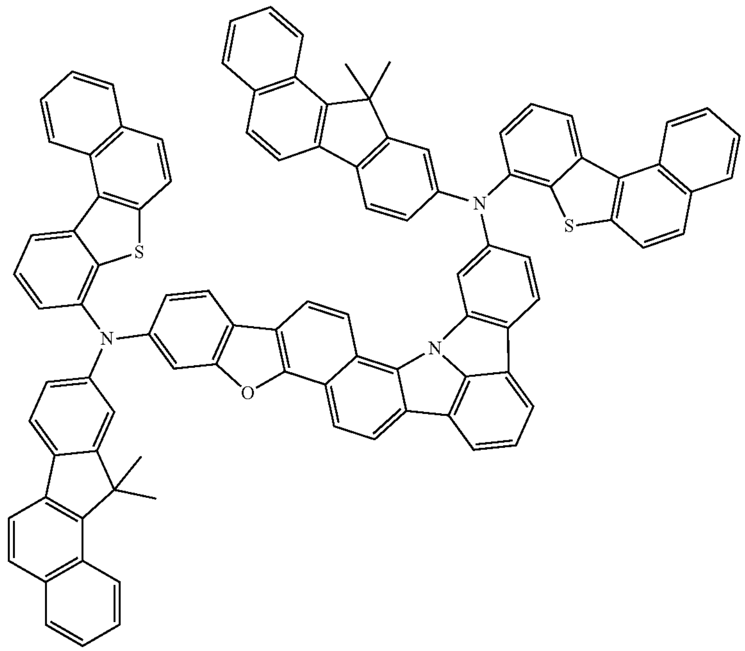

-continued
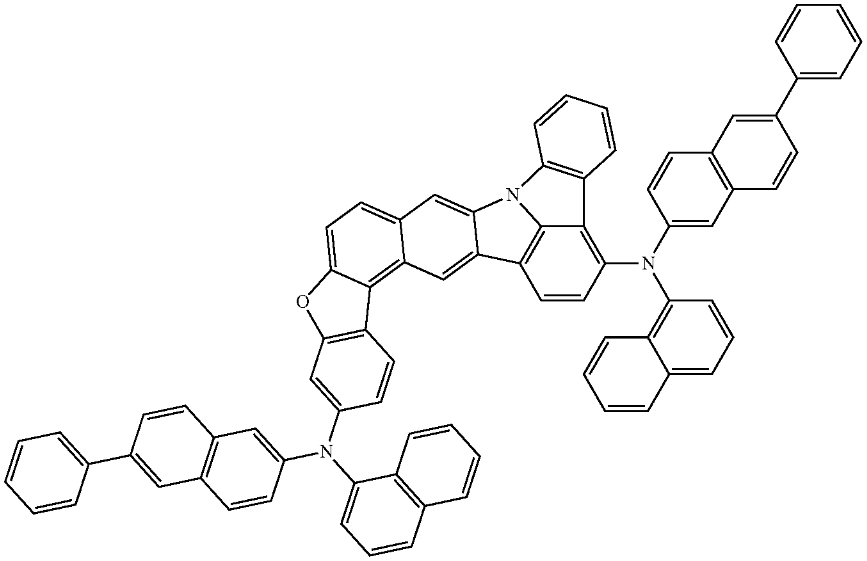
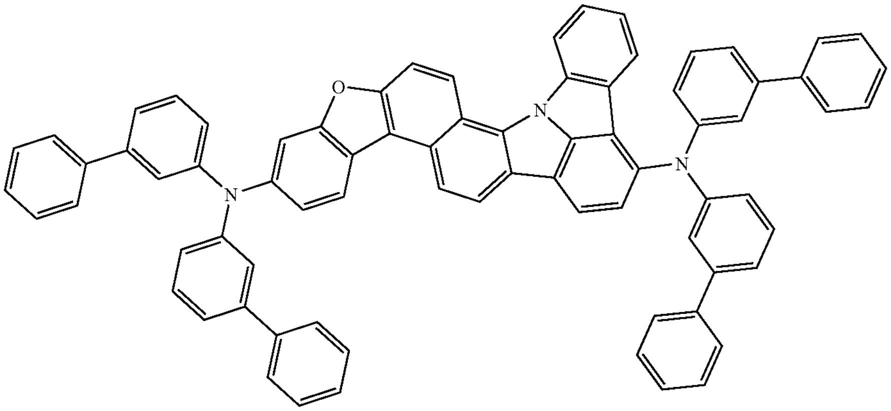
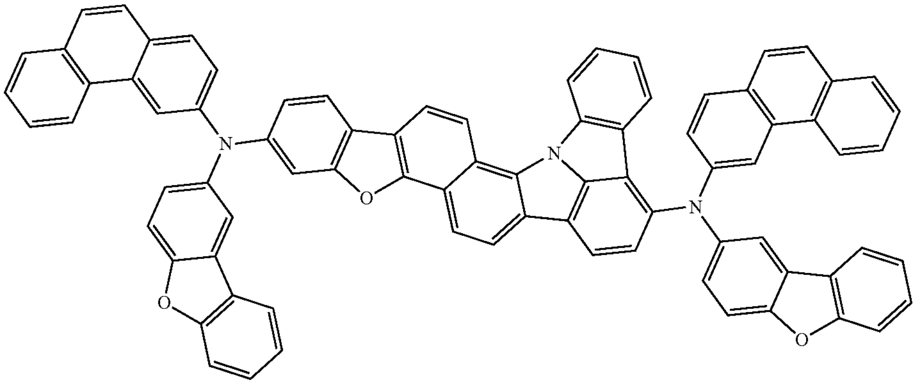

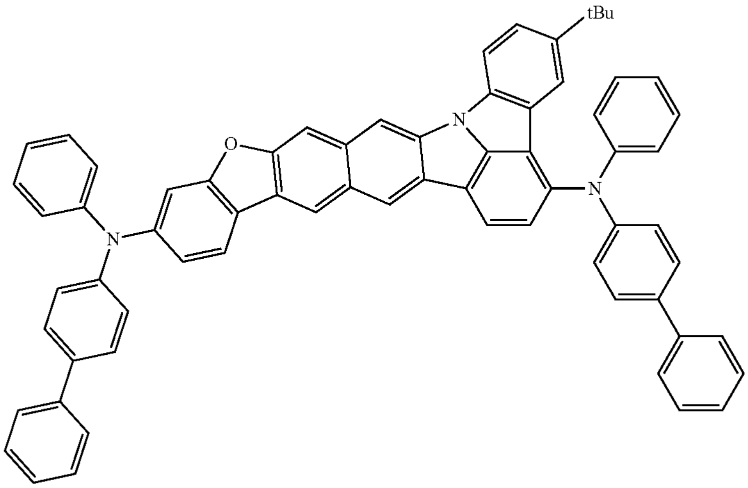
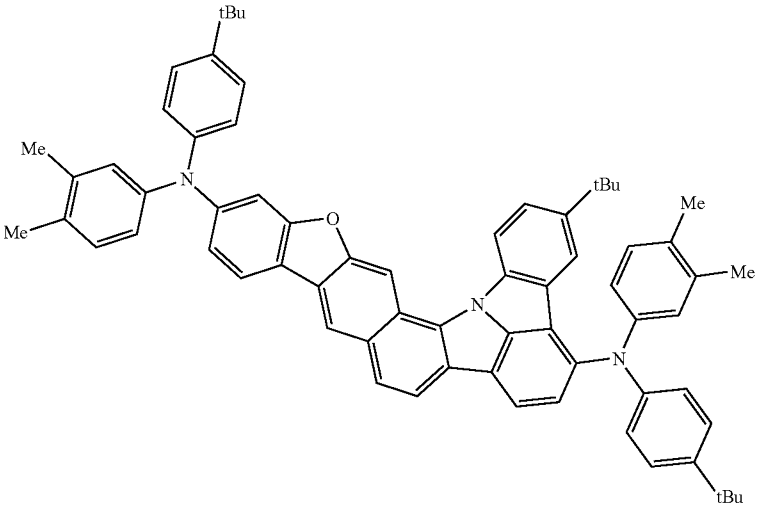
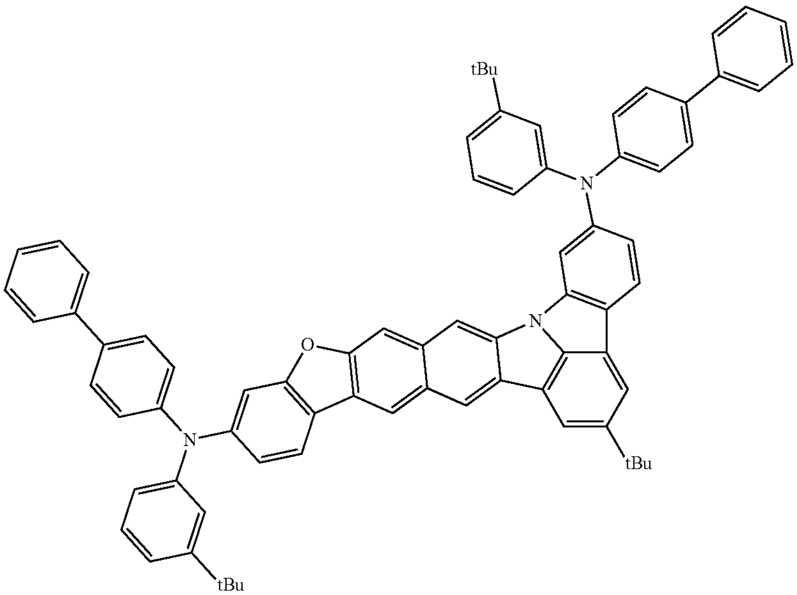

-continued
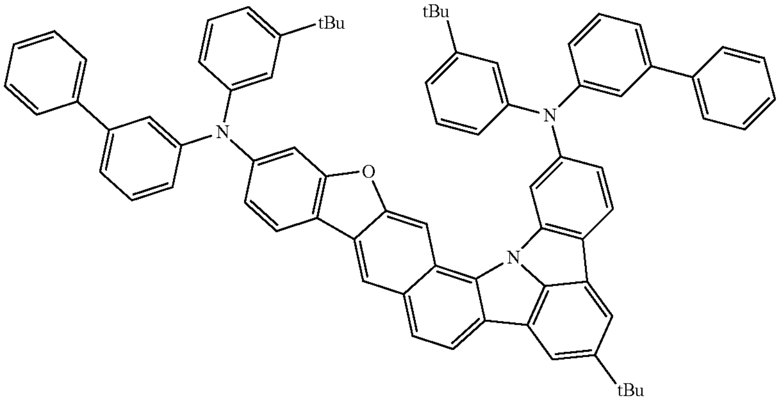
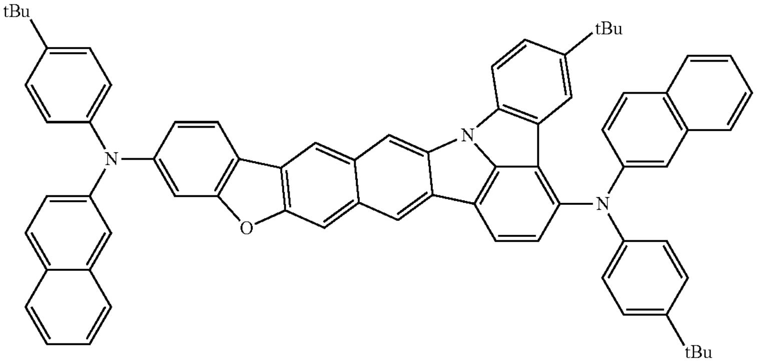
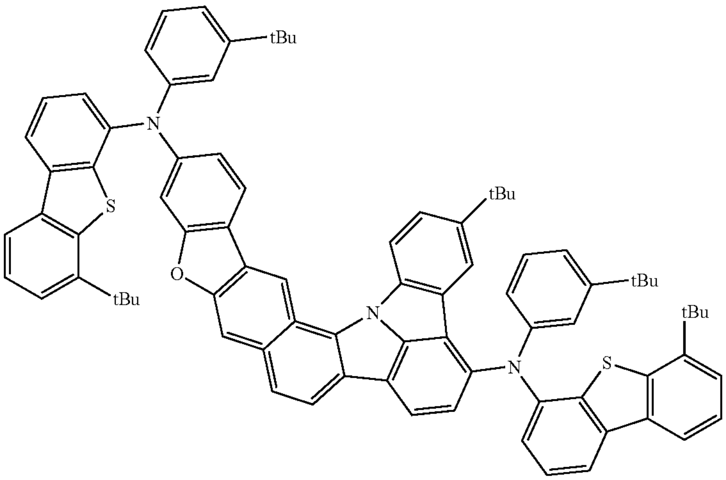
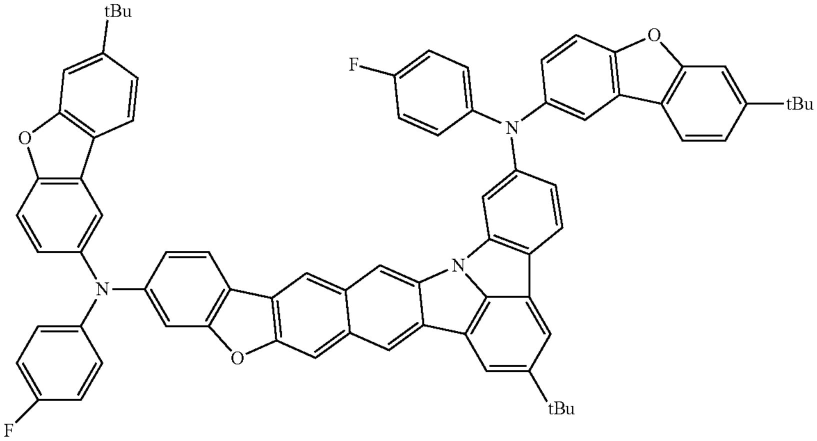

-continued
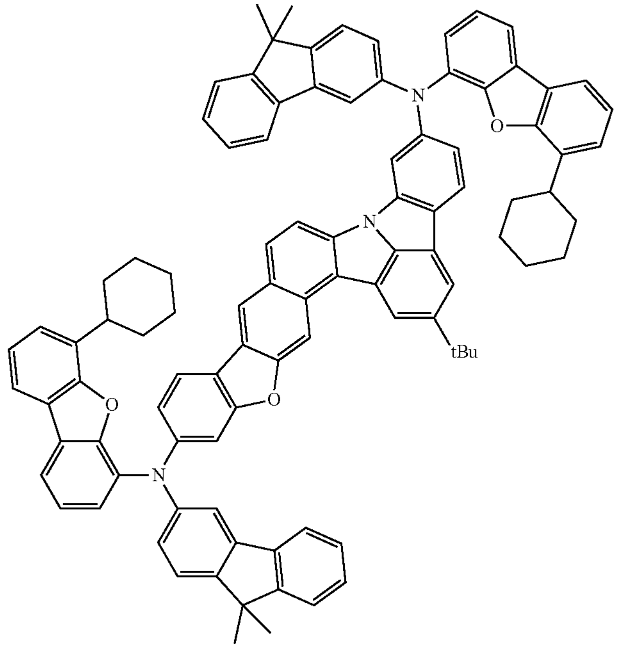
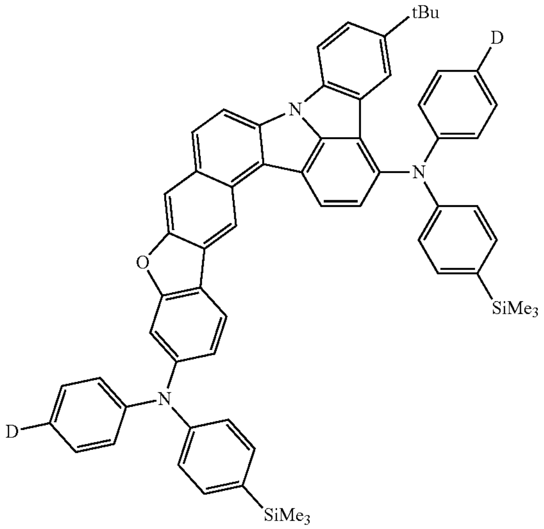
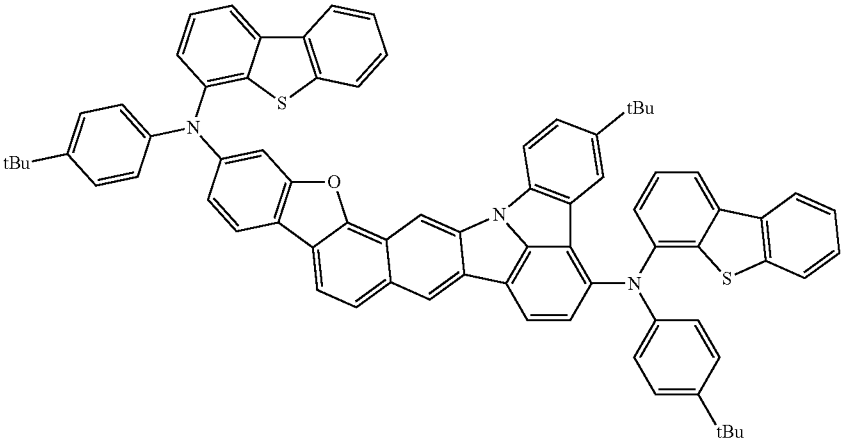

-continued
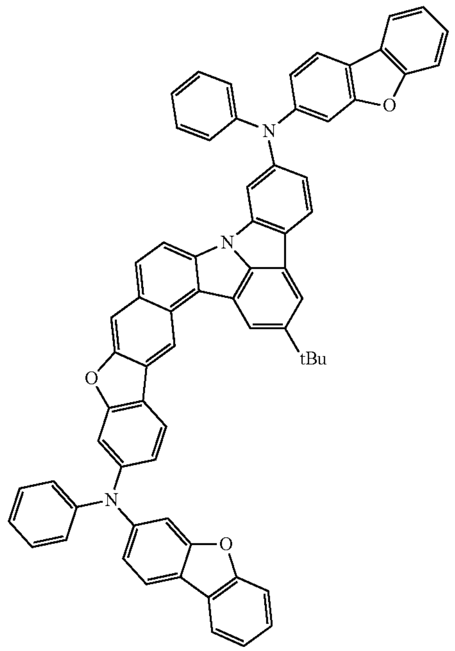
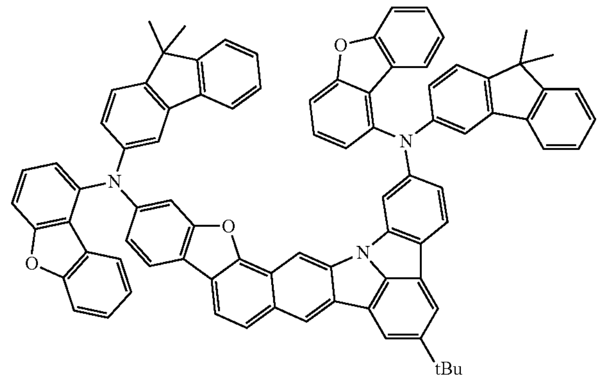
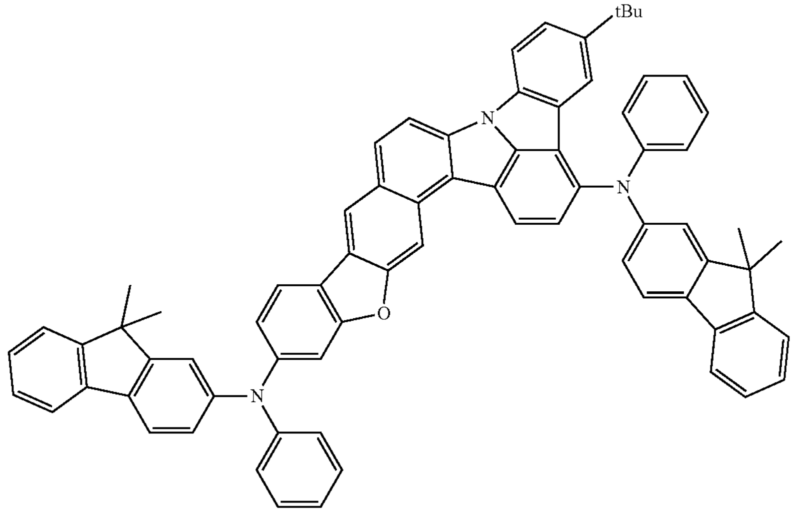
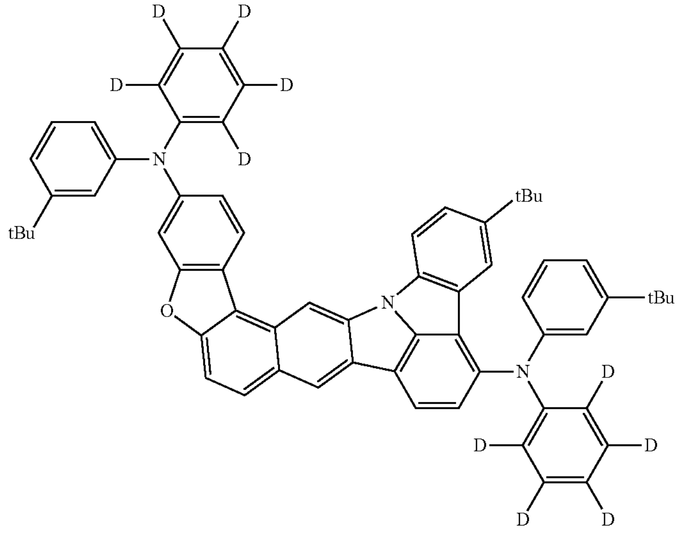

-continued
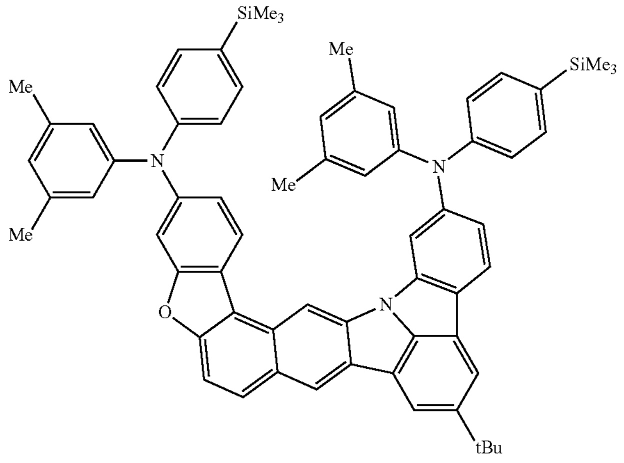
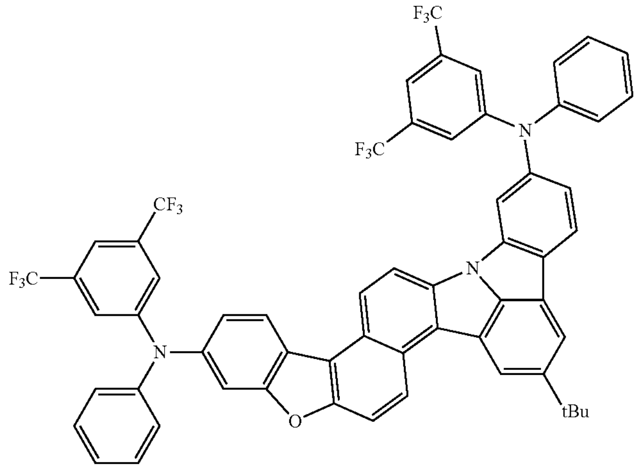
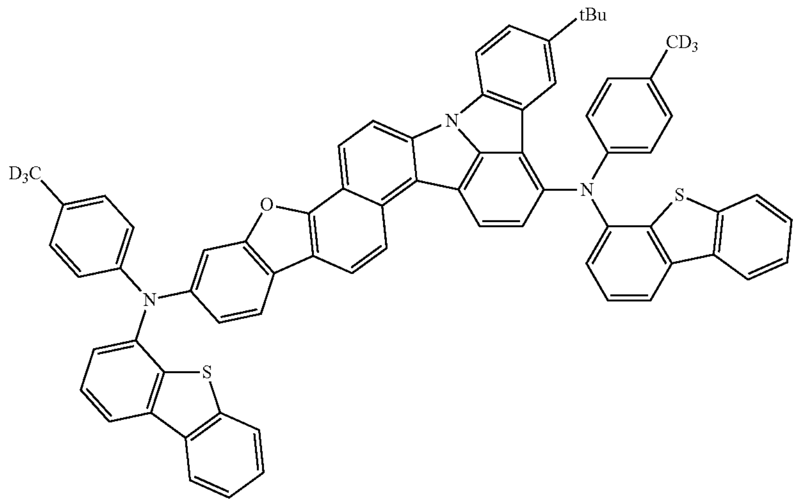

-continued
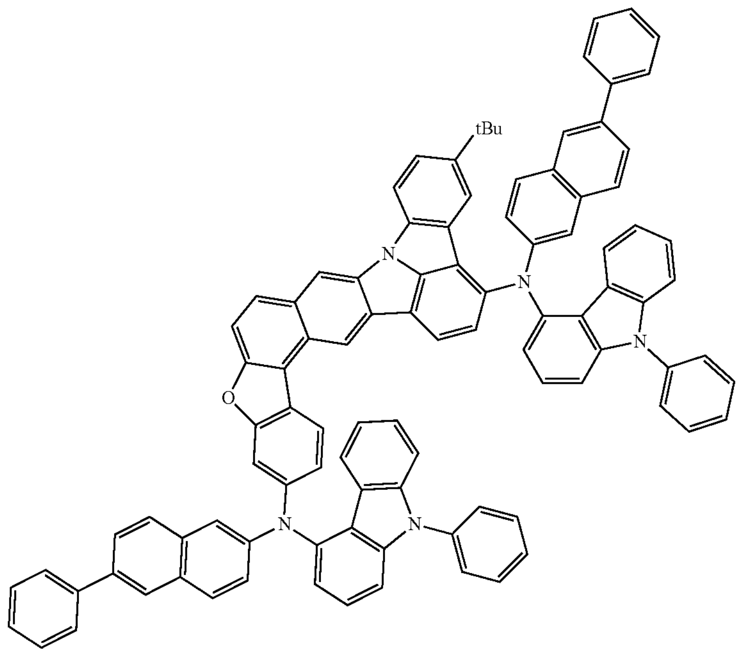
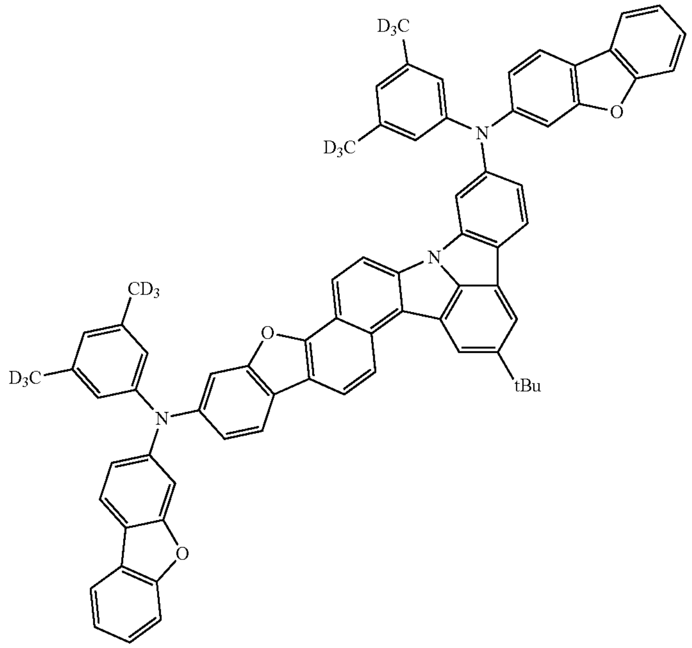

-continued
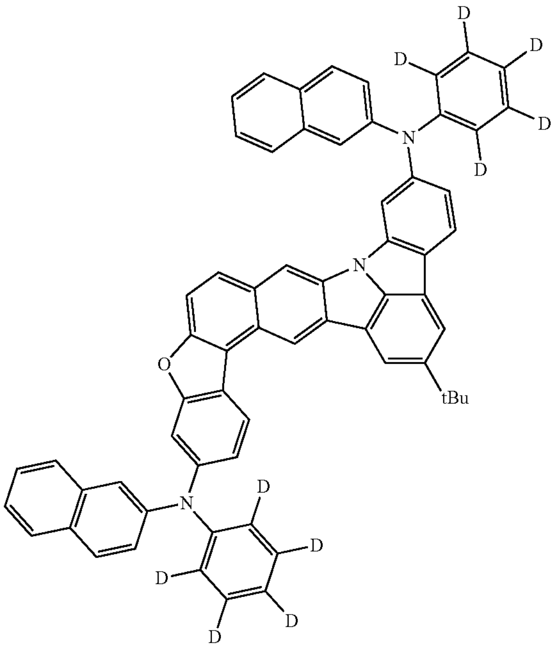
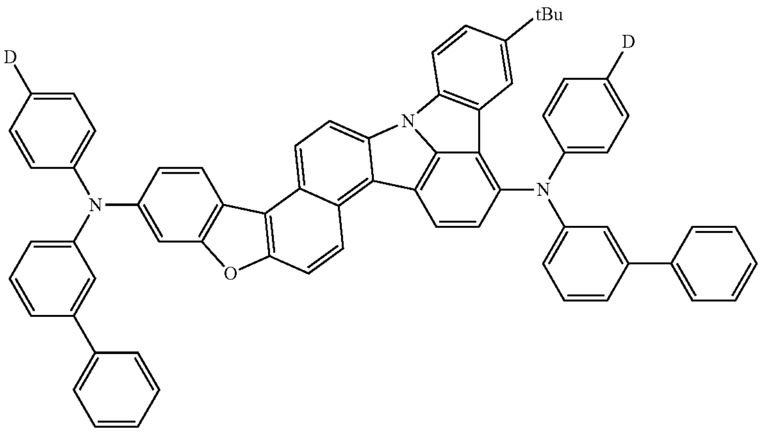
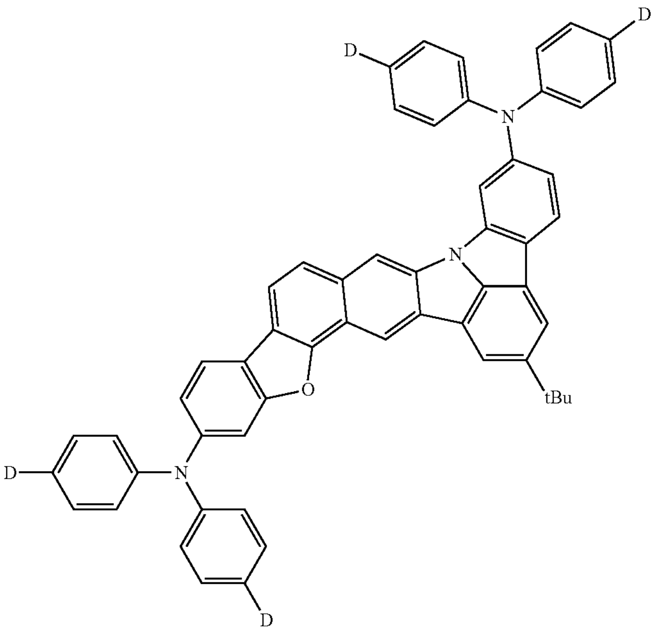

-continued
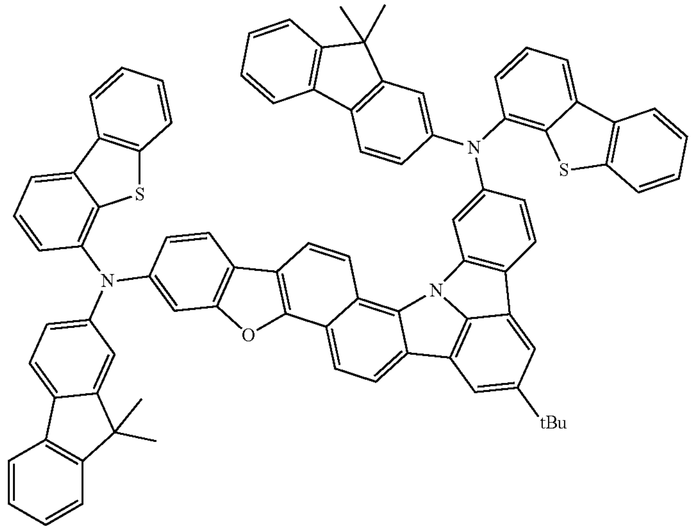
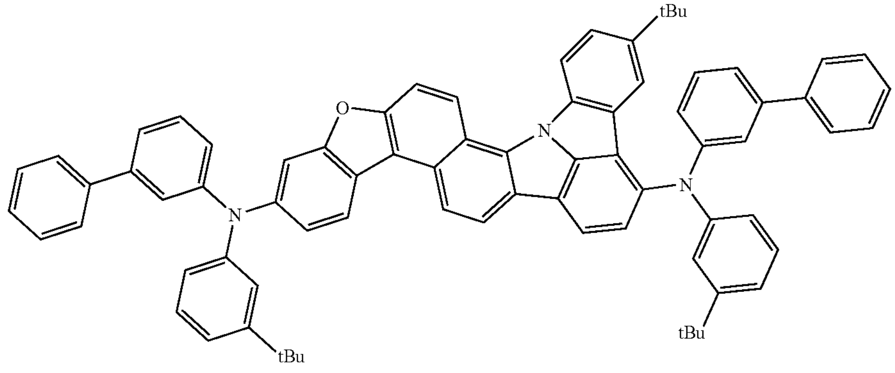
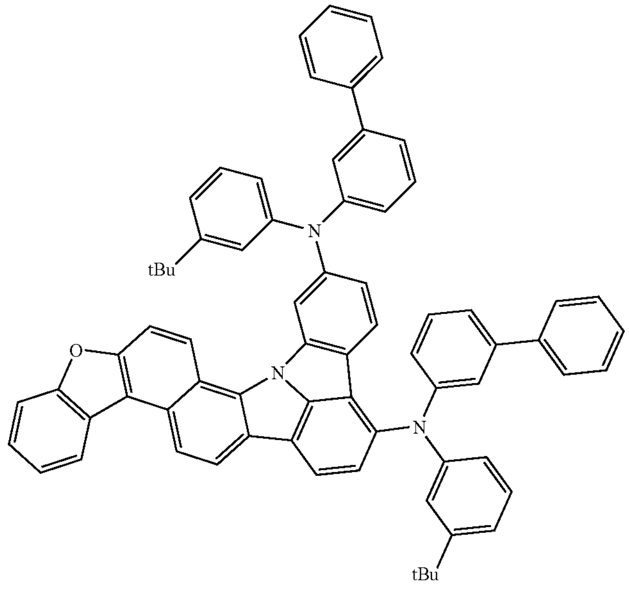

-continued
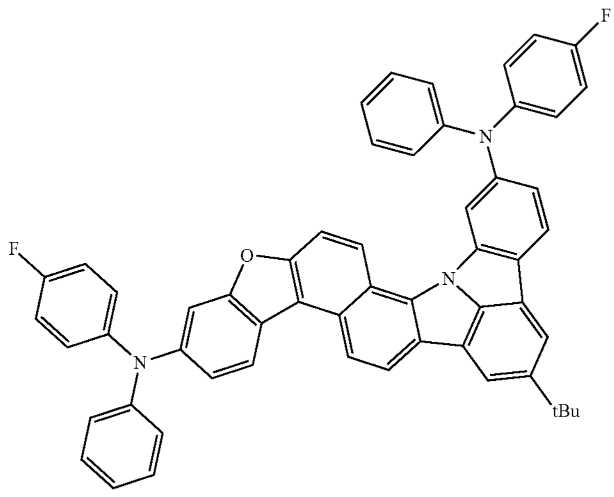
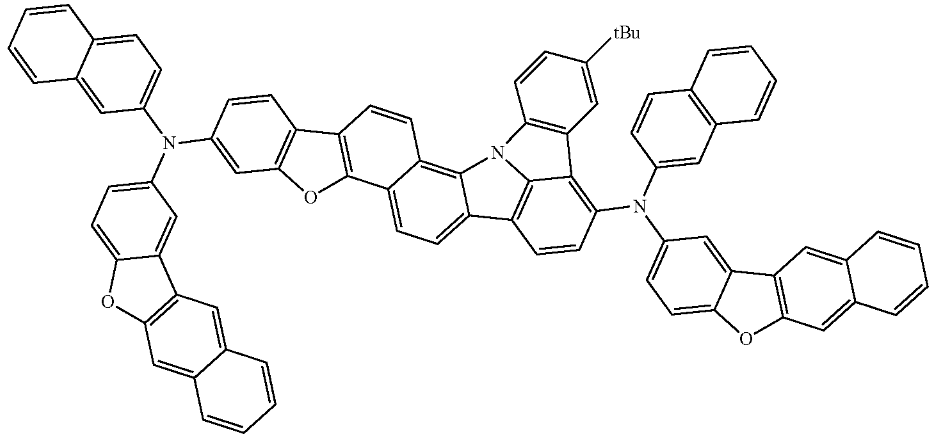
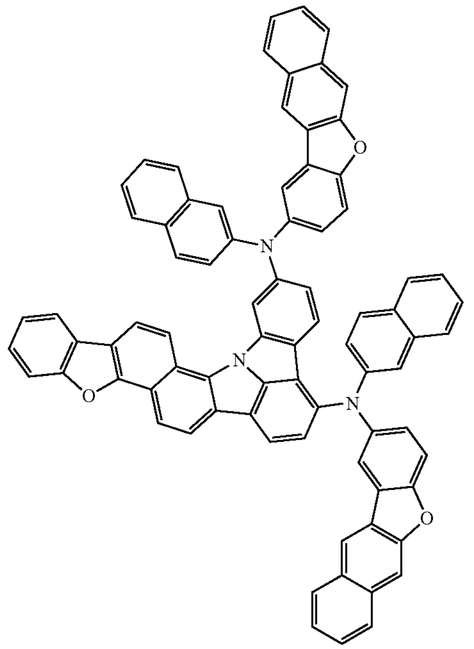
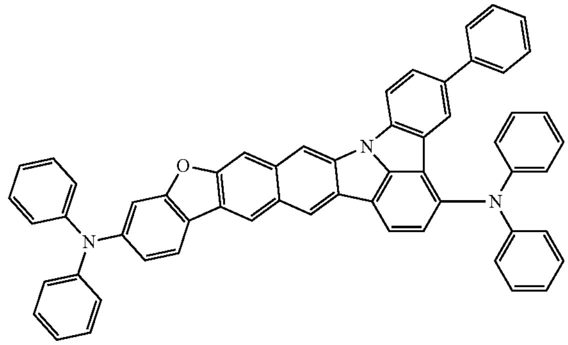

-continued
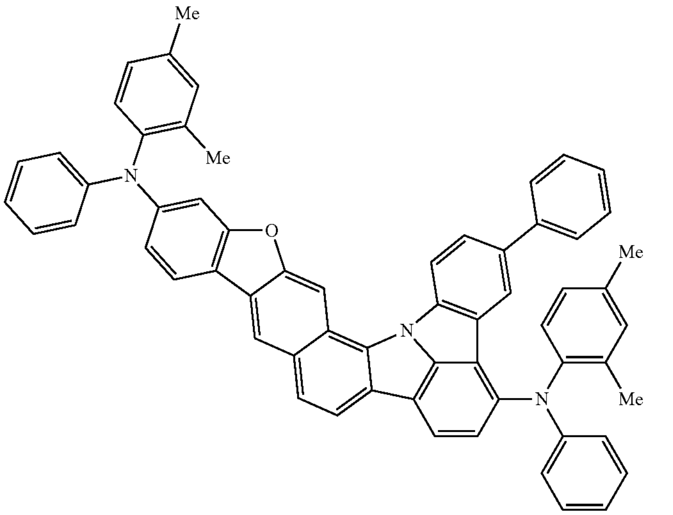
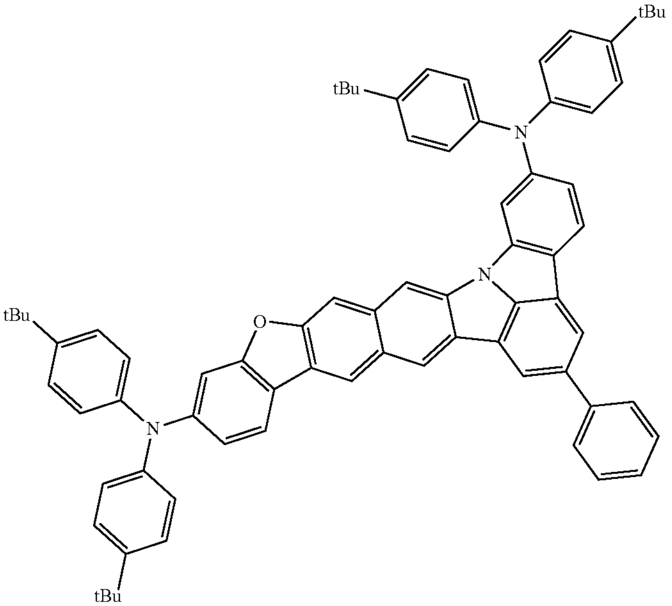
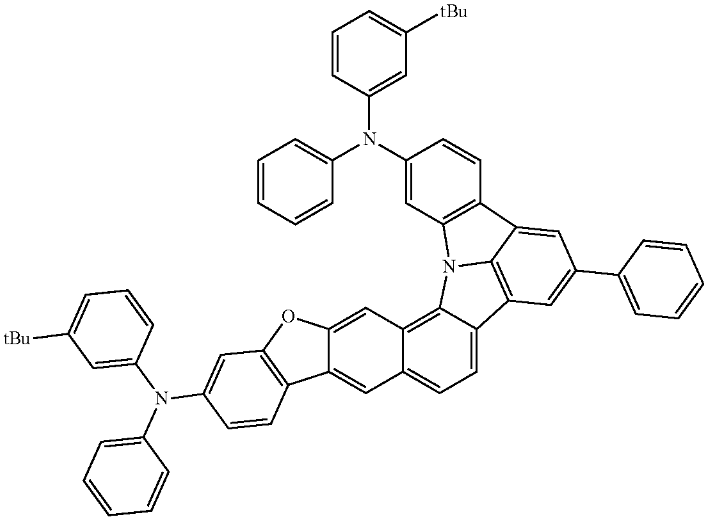

-continued
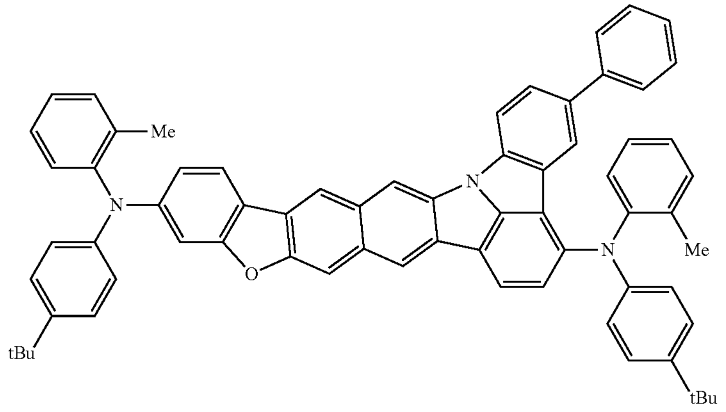
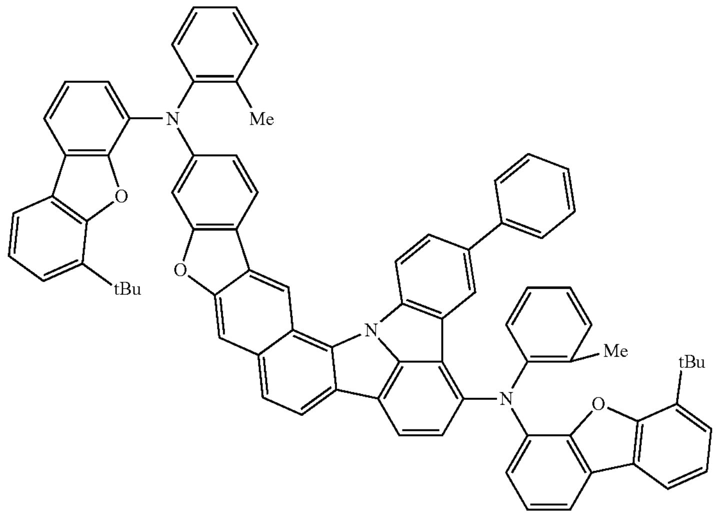
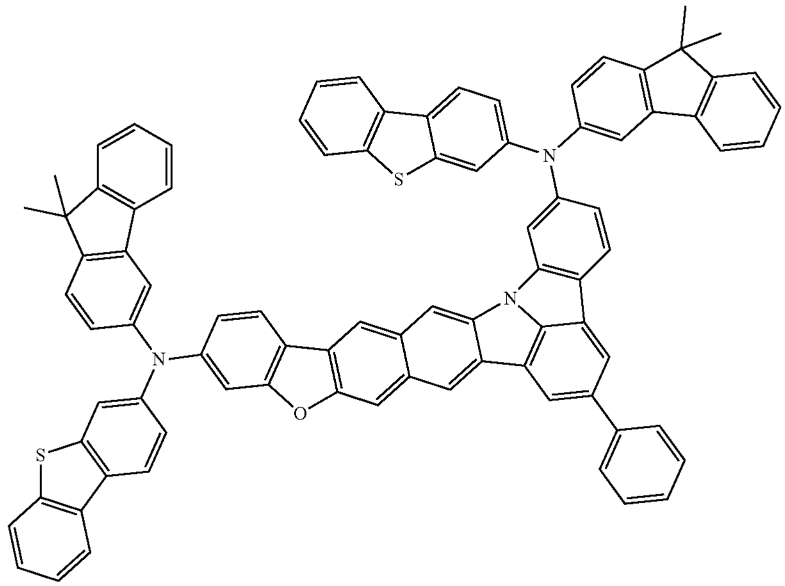

-continued
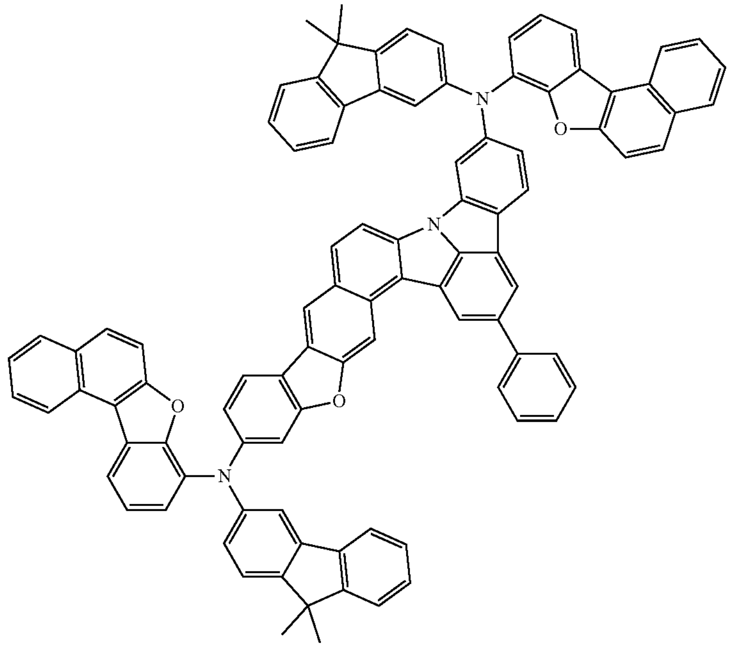
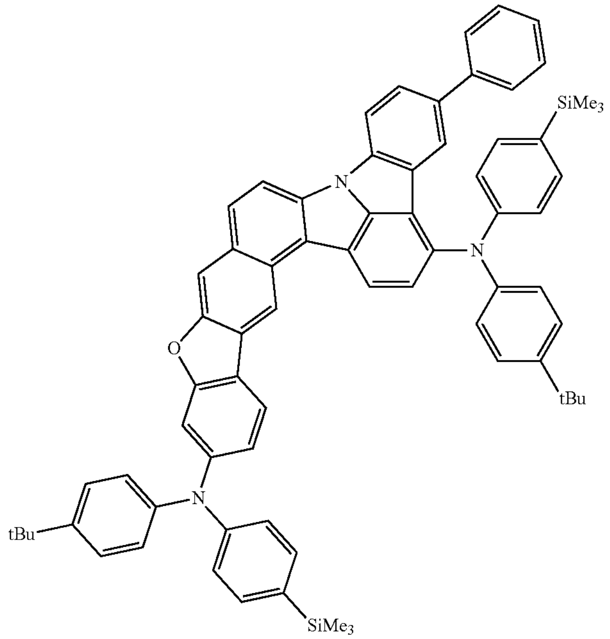

-continued
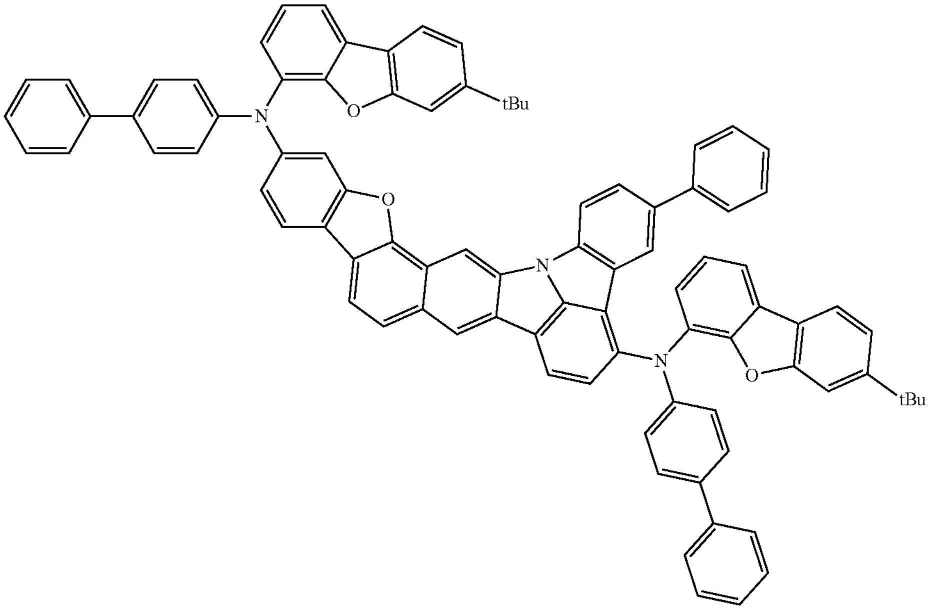
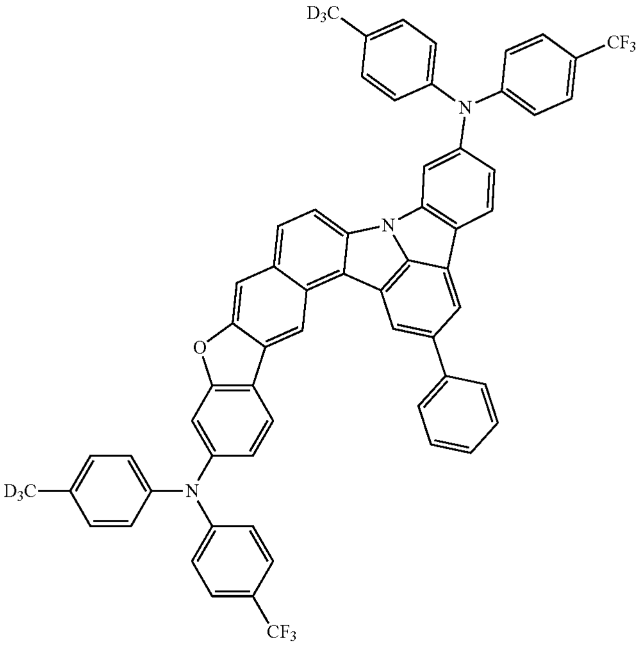

-continued
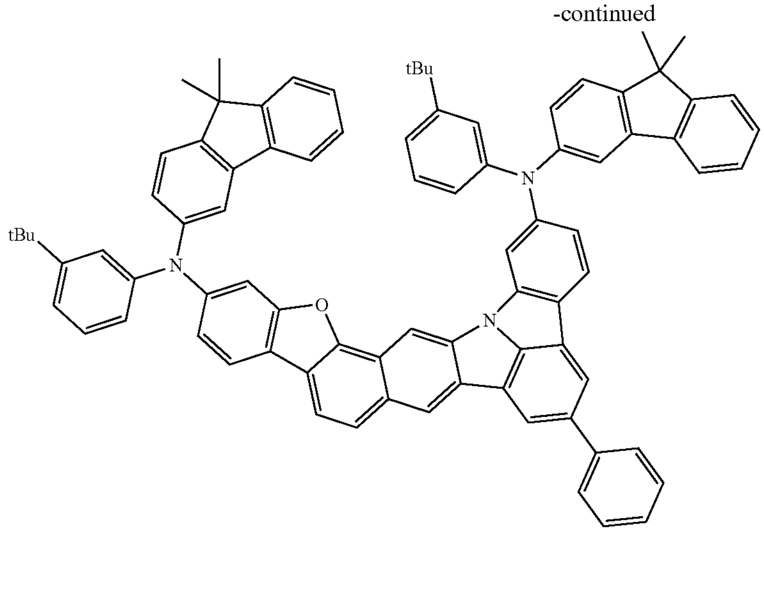
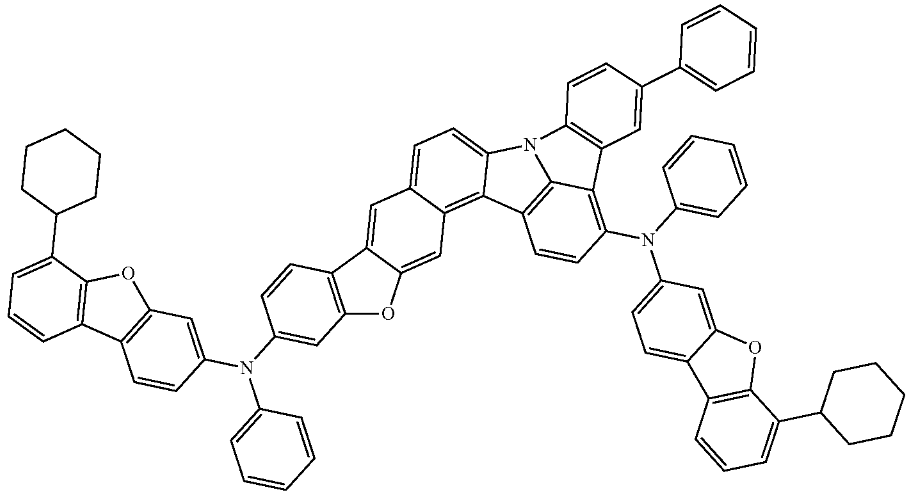
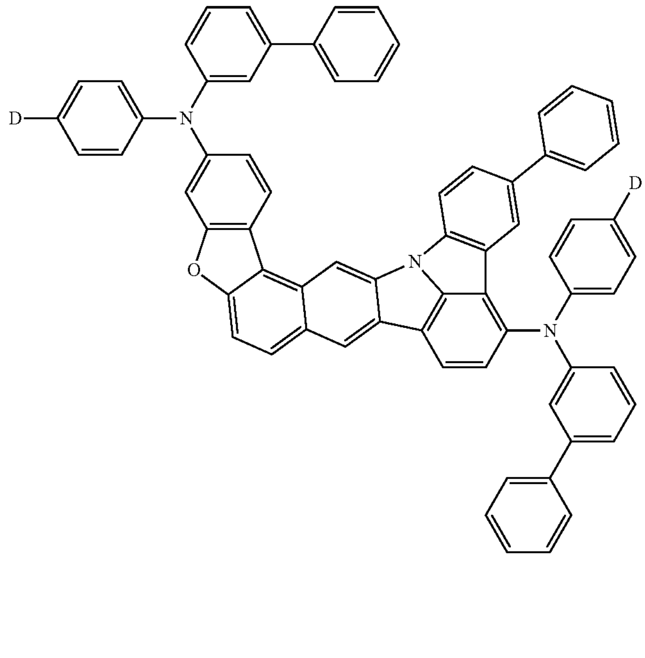

-continued
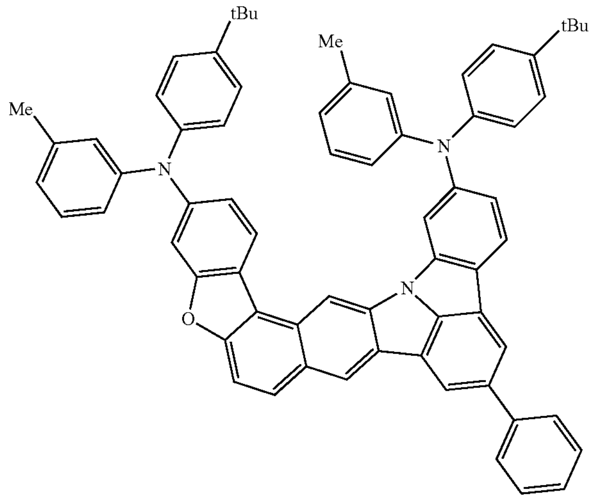
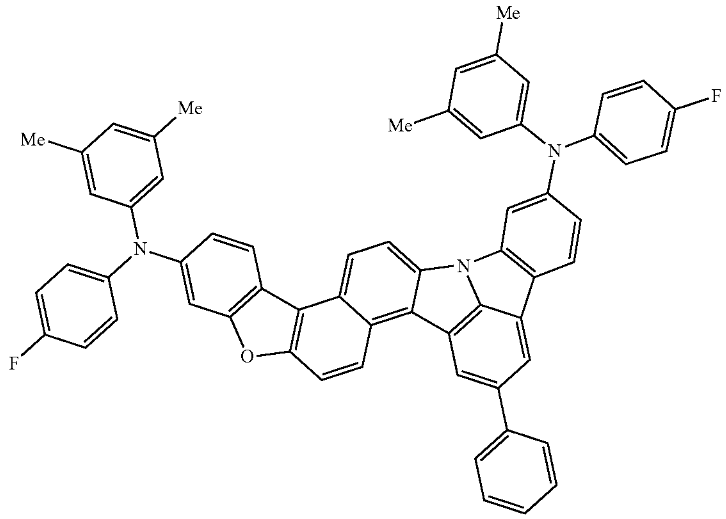
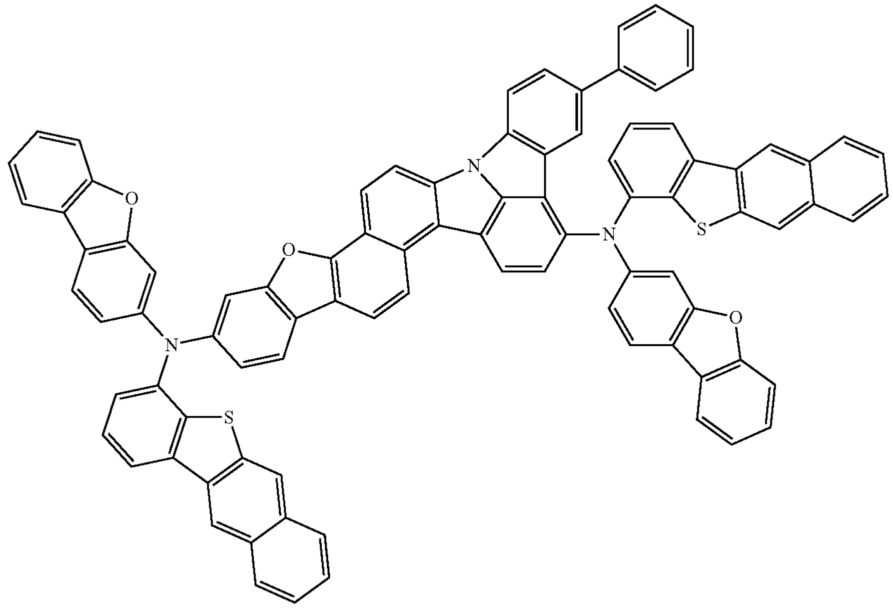

-continued
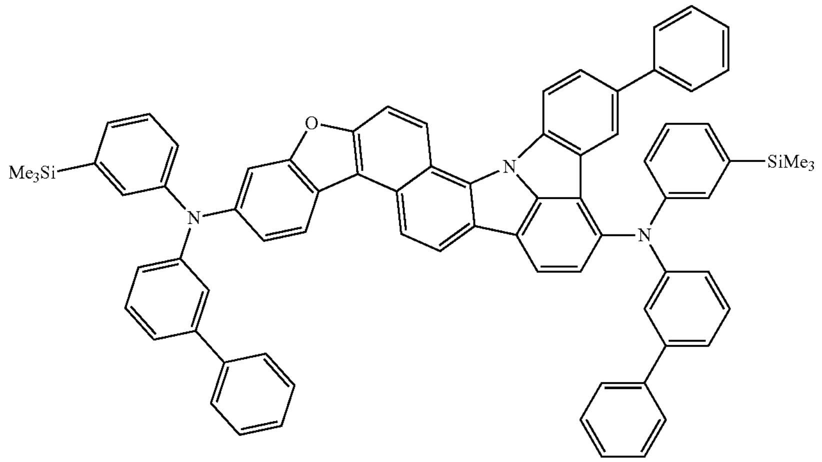
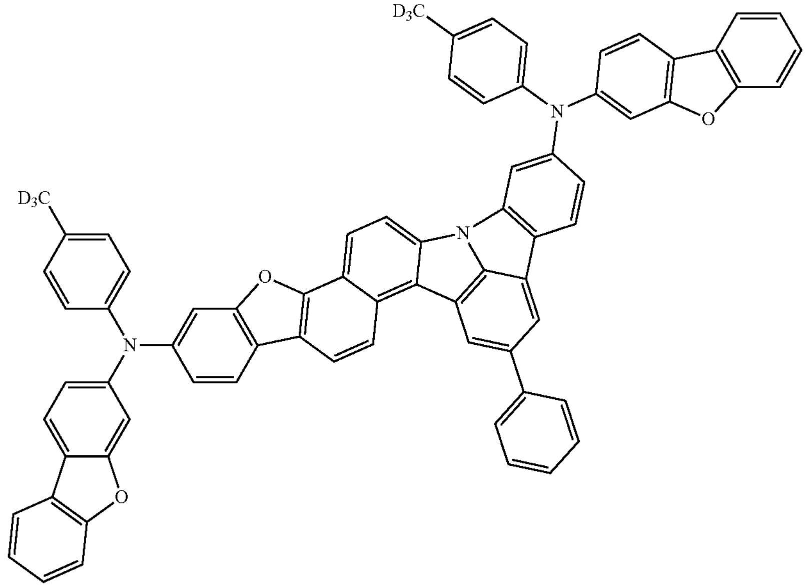
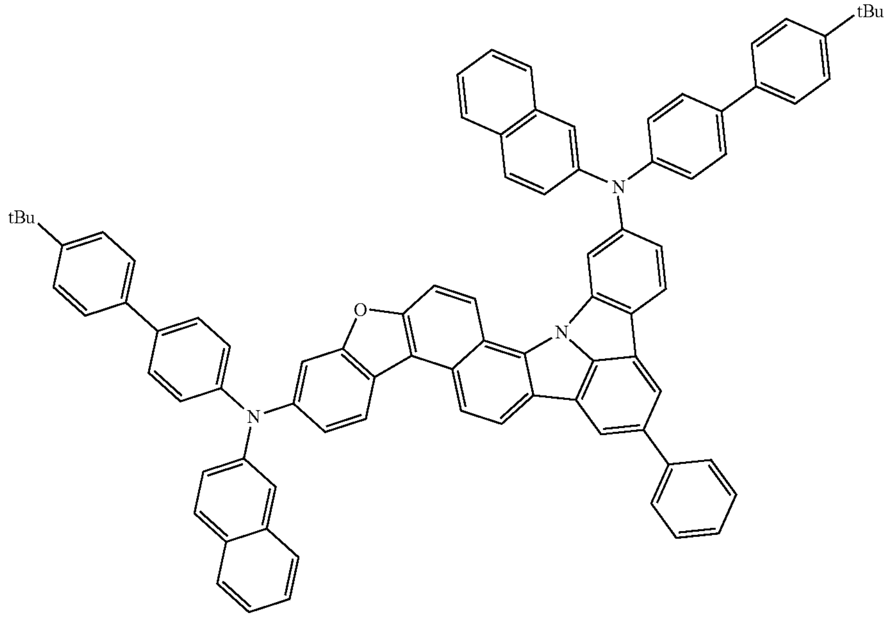

-continued
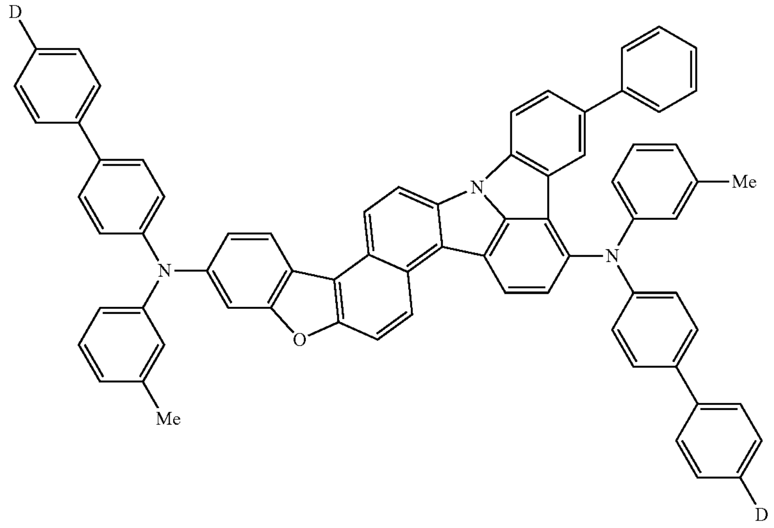
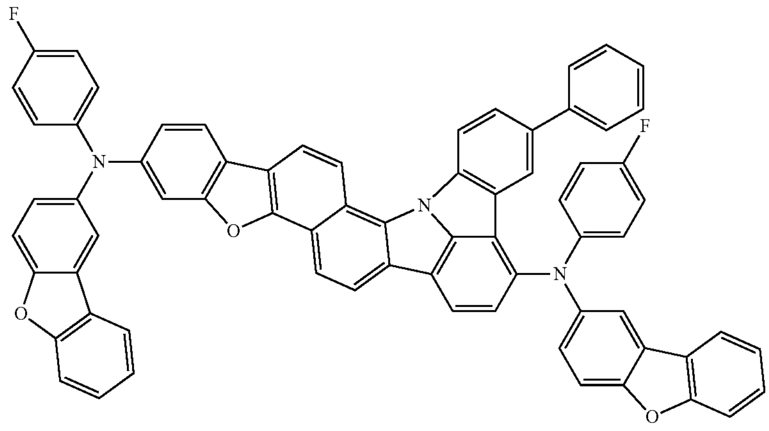
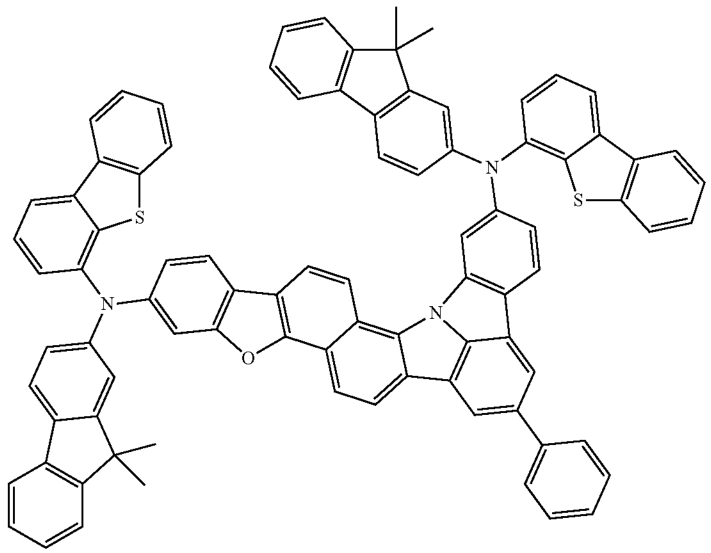

-continued
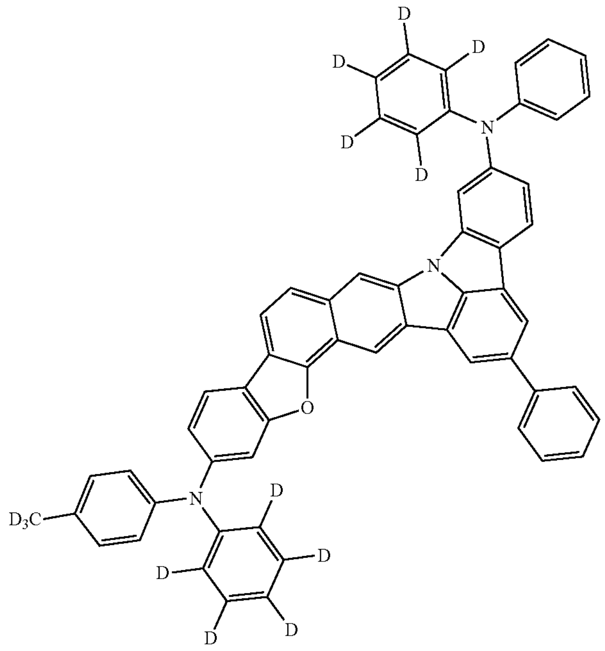
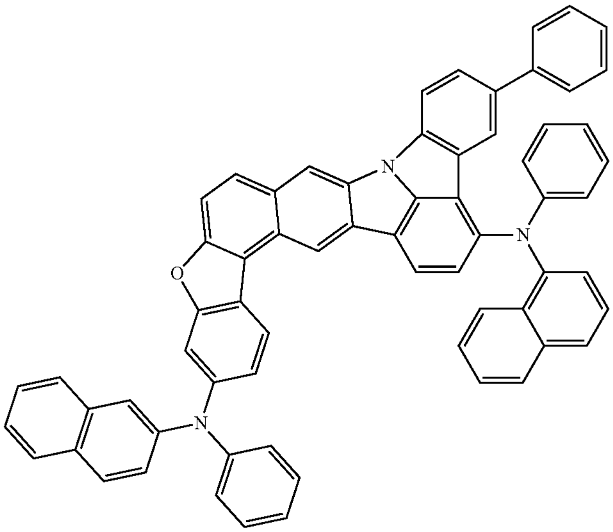
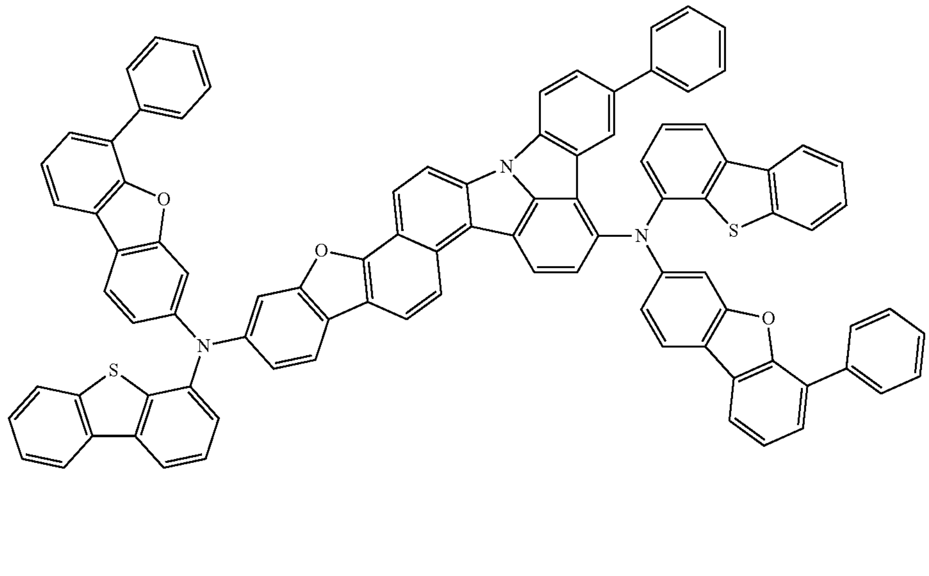

-continued
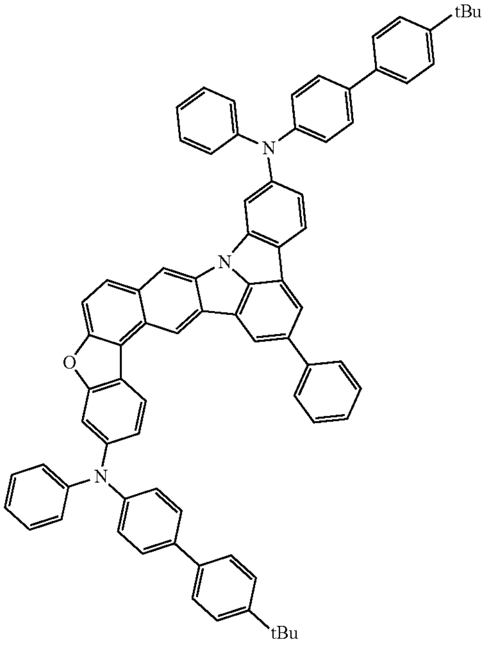
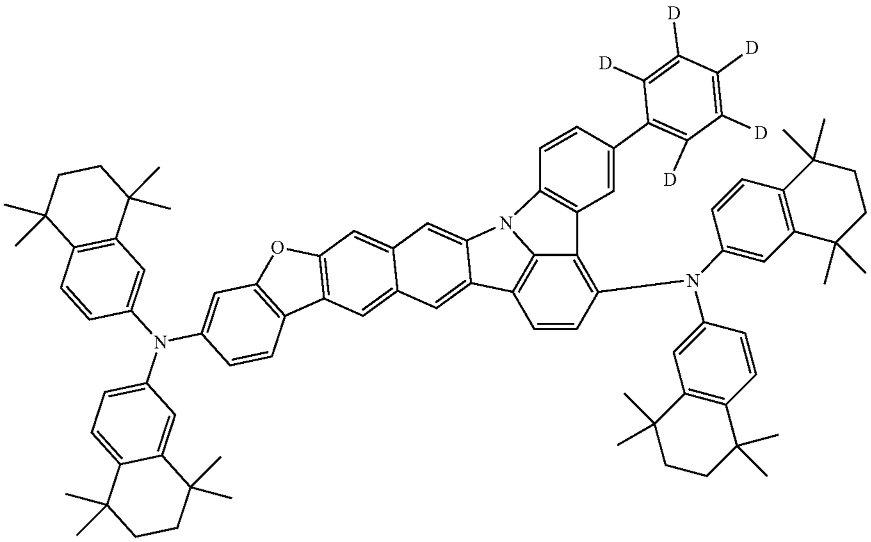

-continued
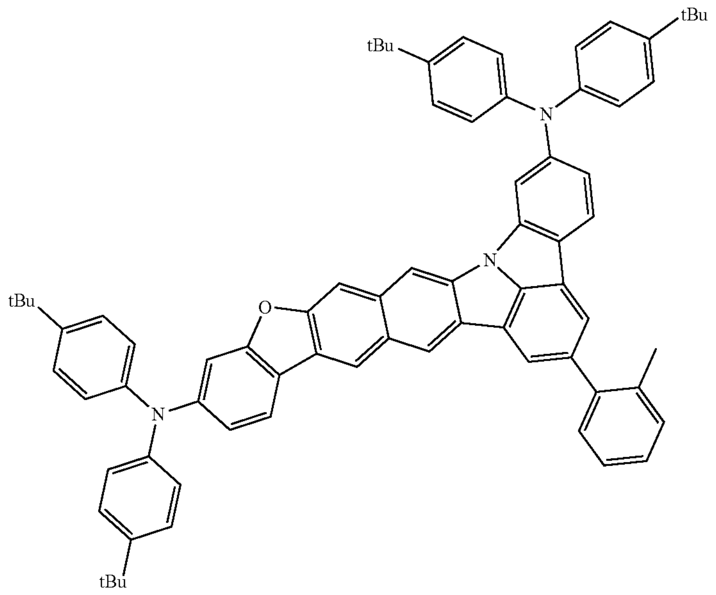
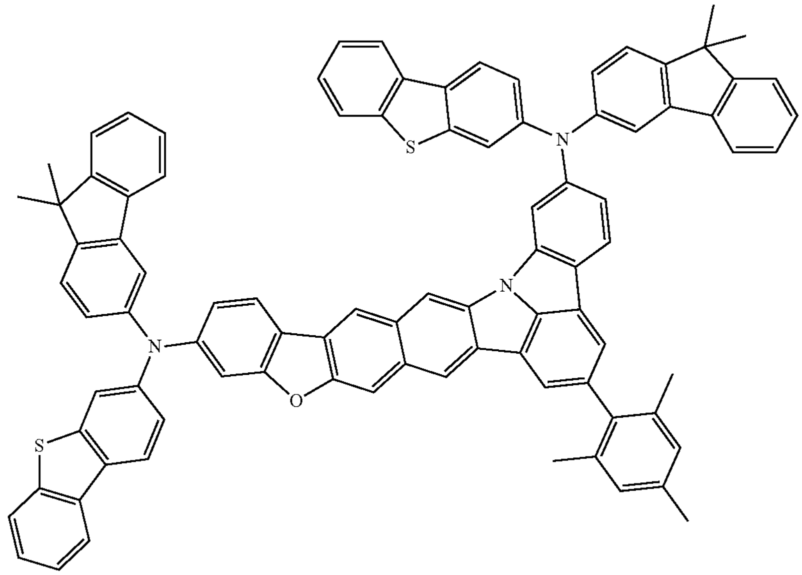
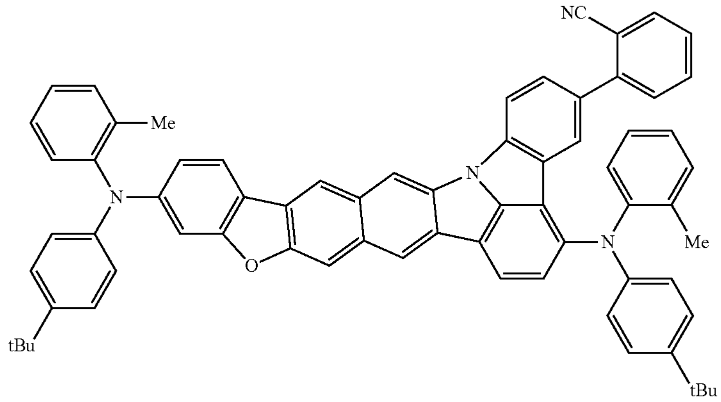

-continued
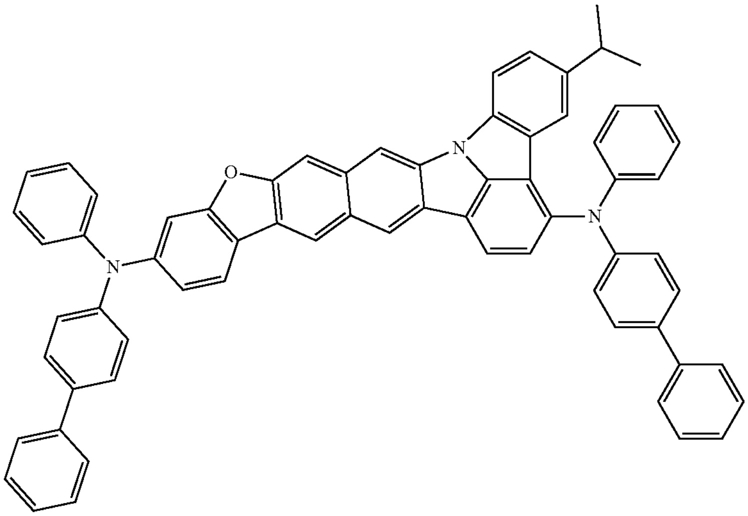
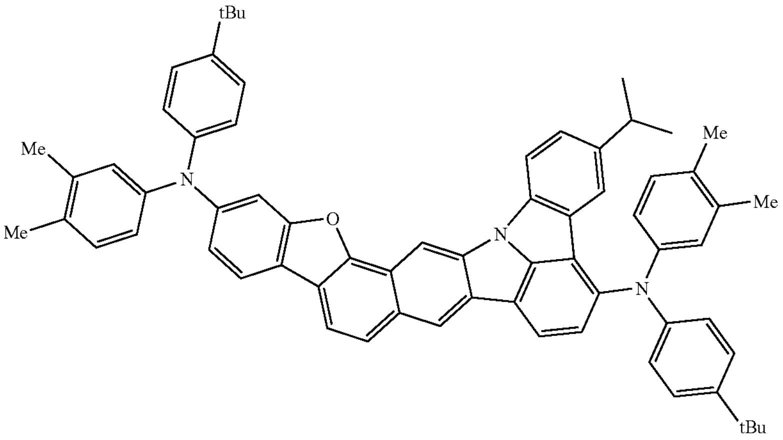
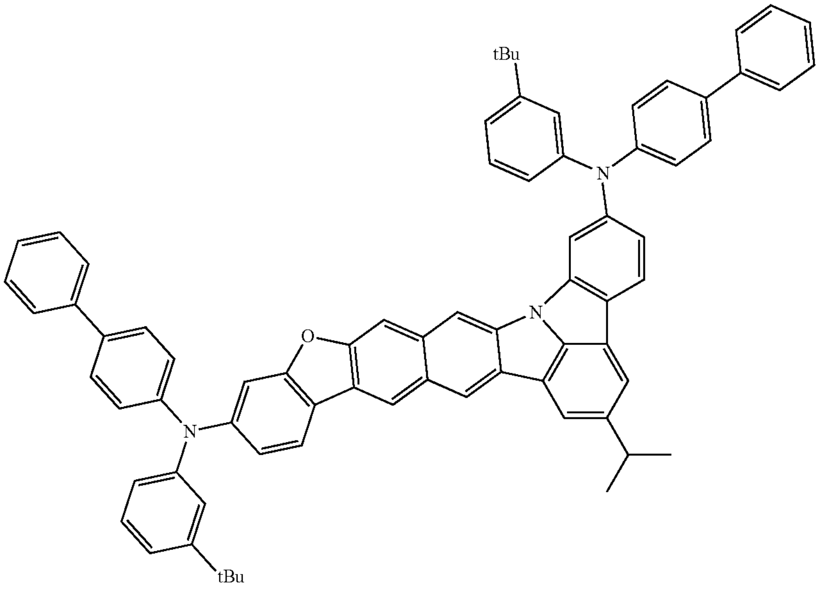

-continued
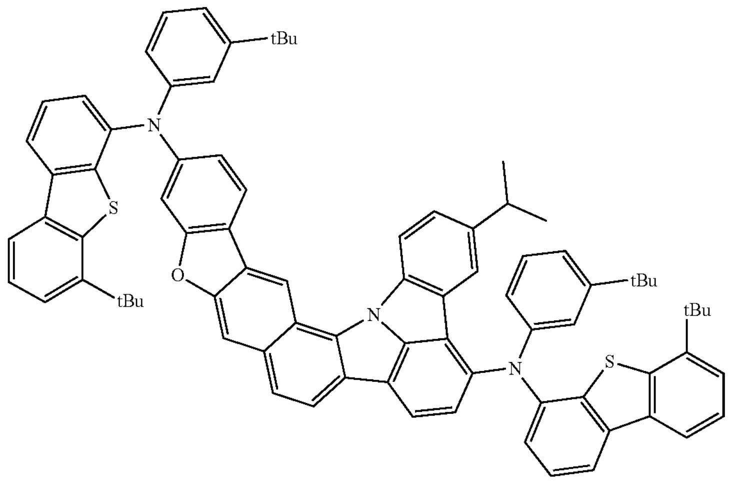
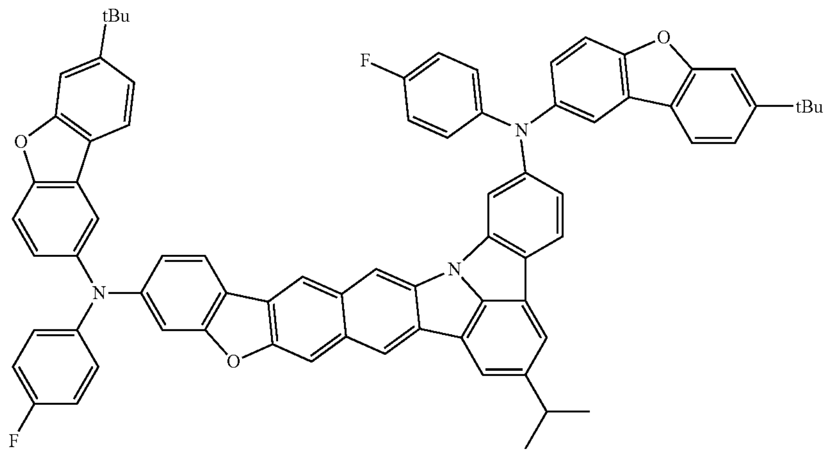
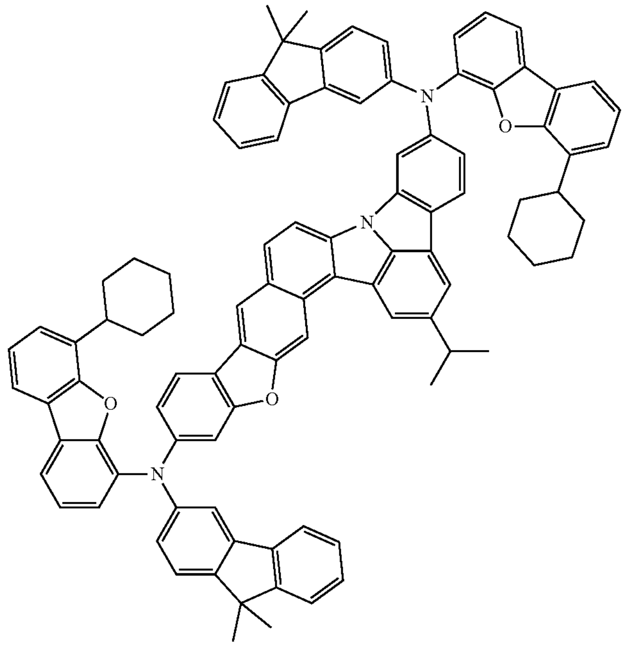

-continued
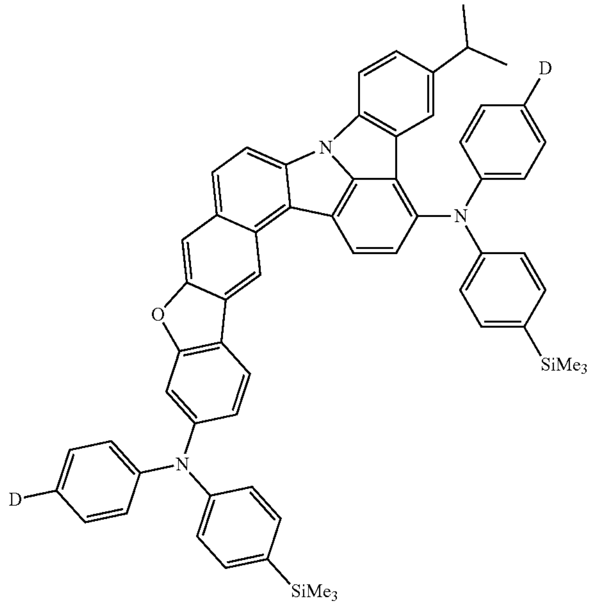
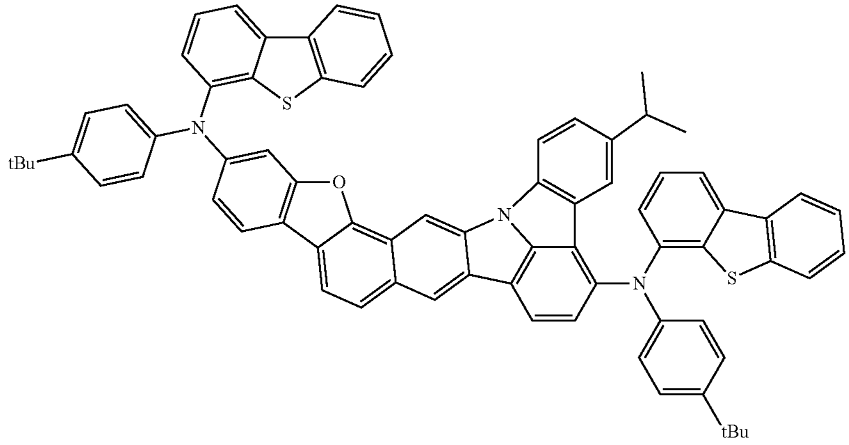
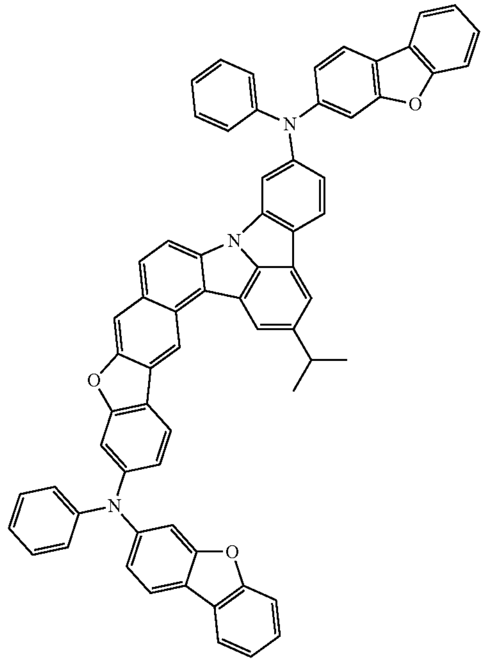

-continued
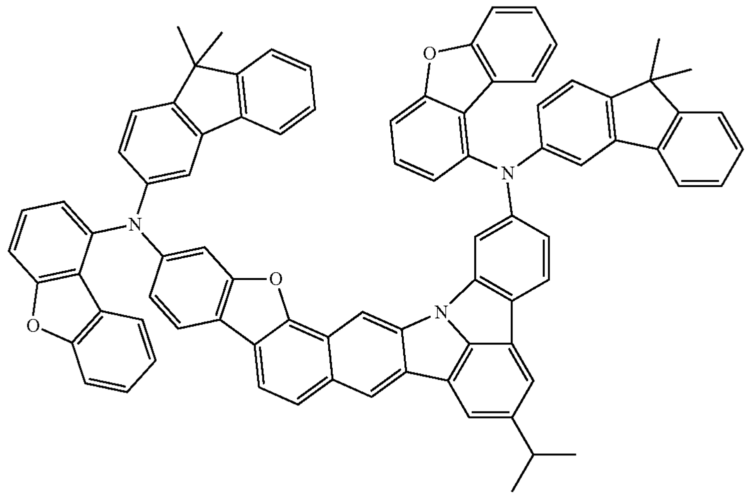
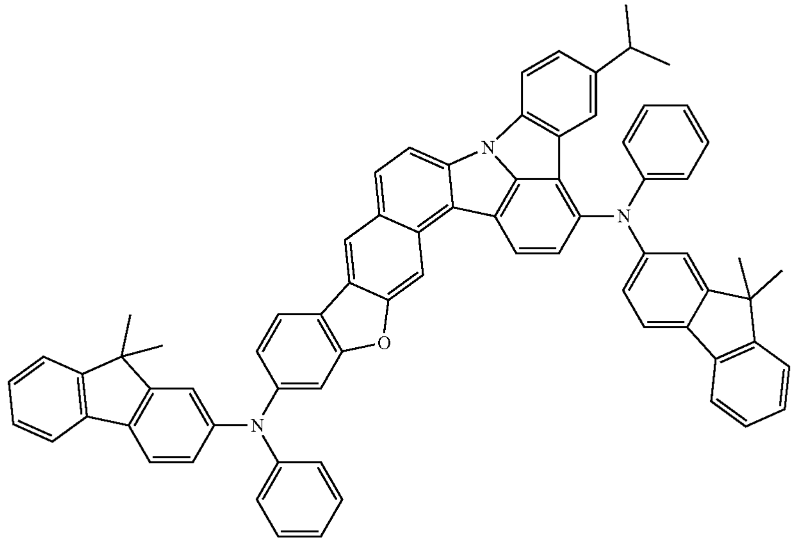
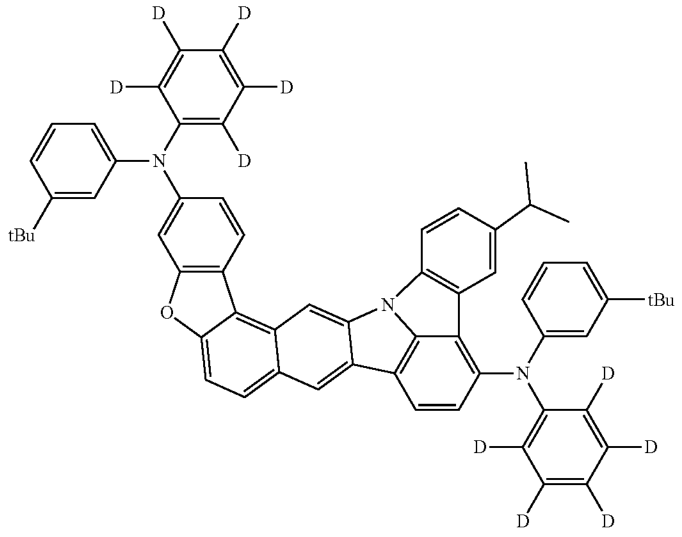

-continued
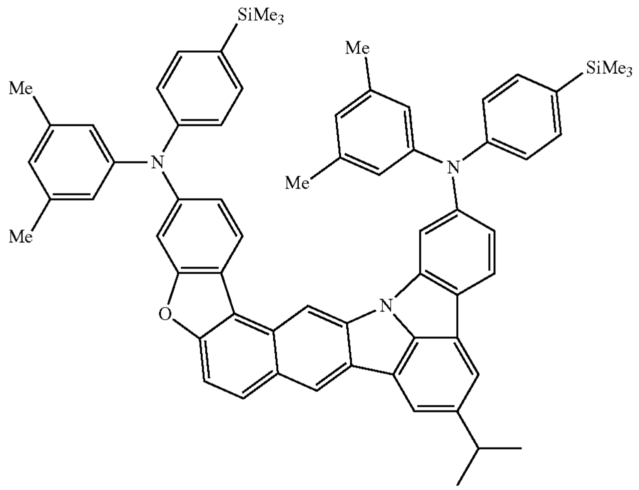
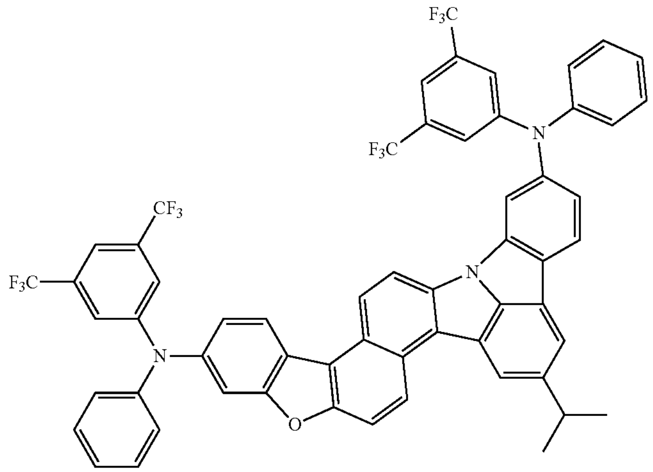
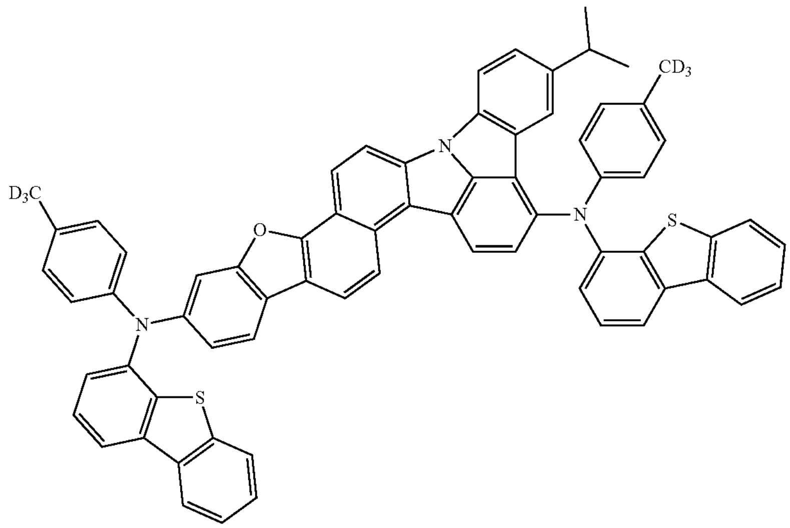

-continued
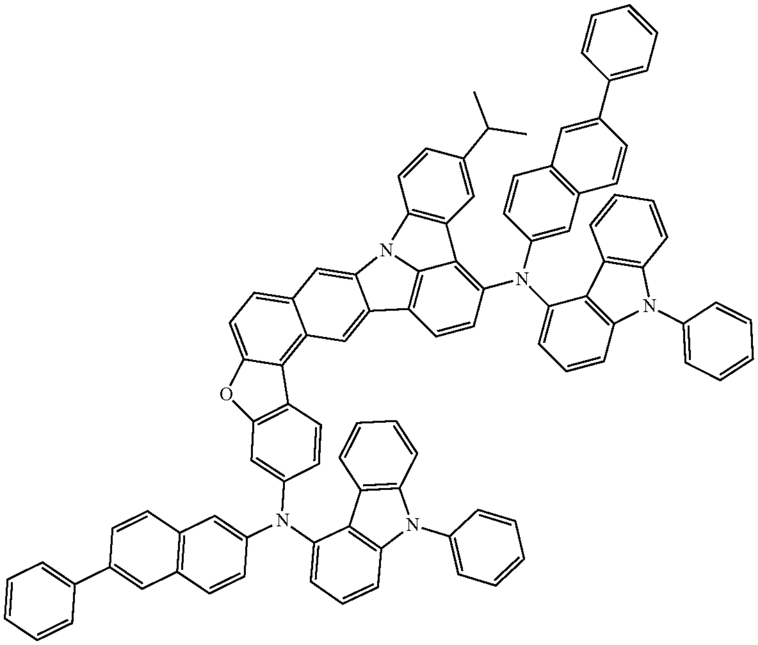
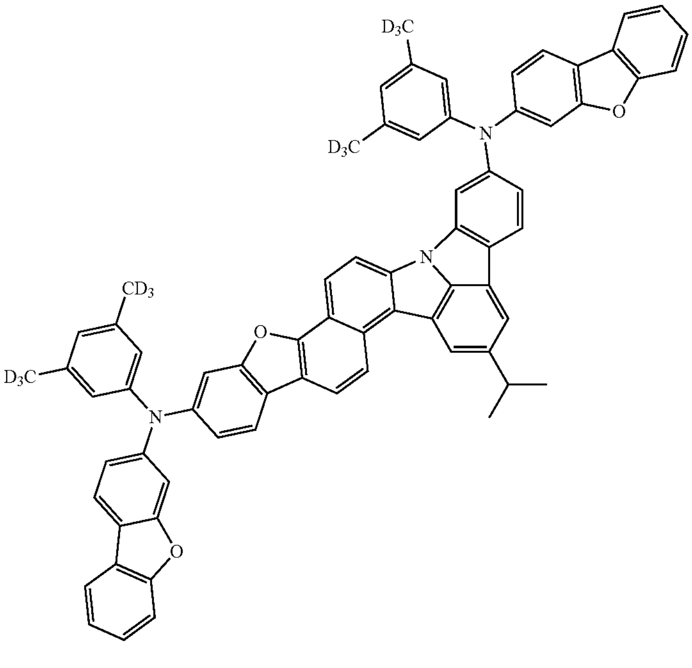

-continued
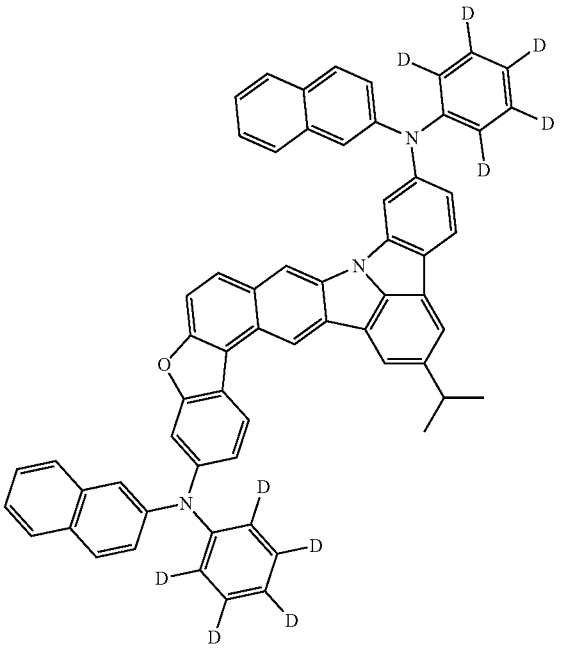
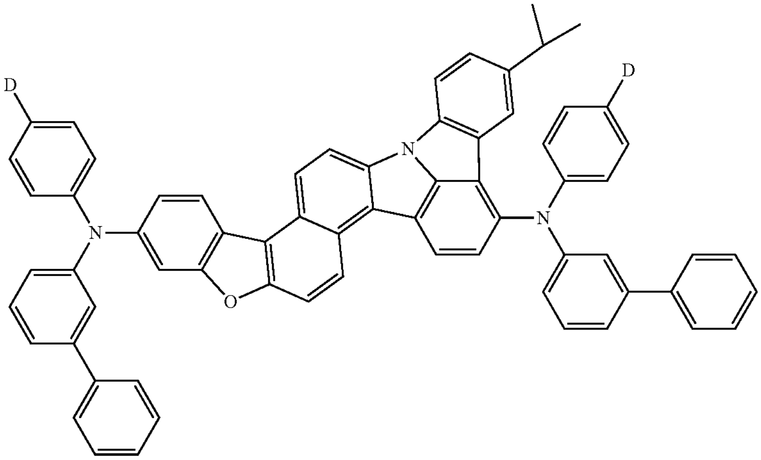
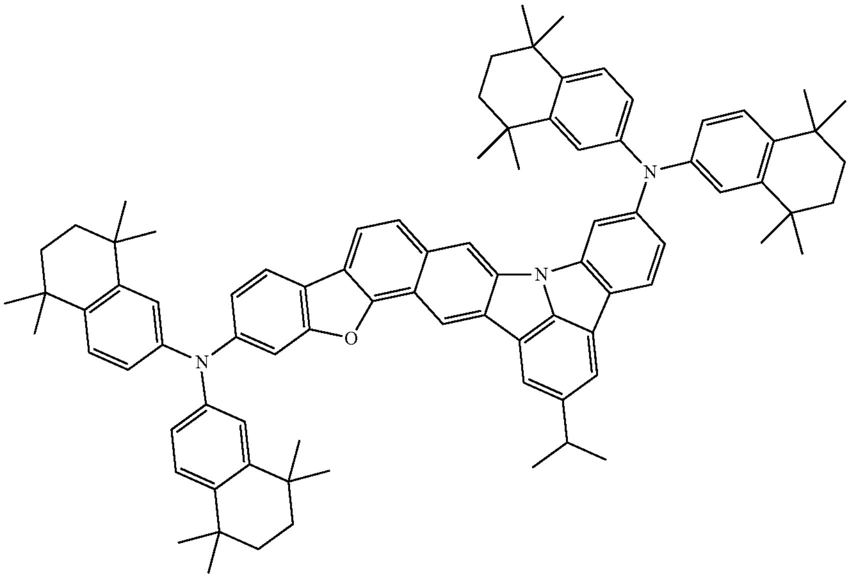

-continued
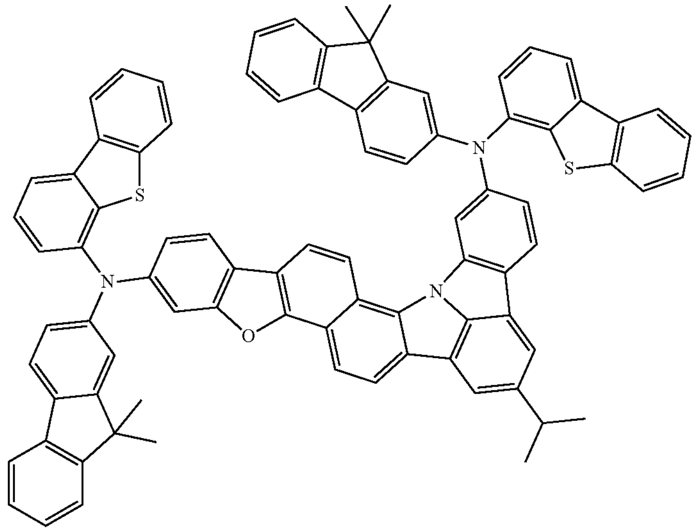
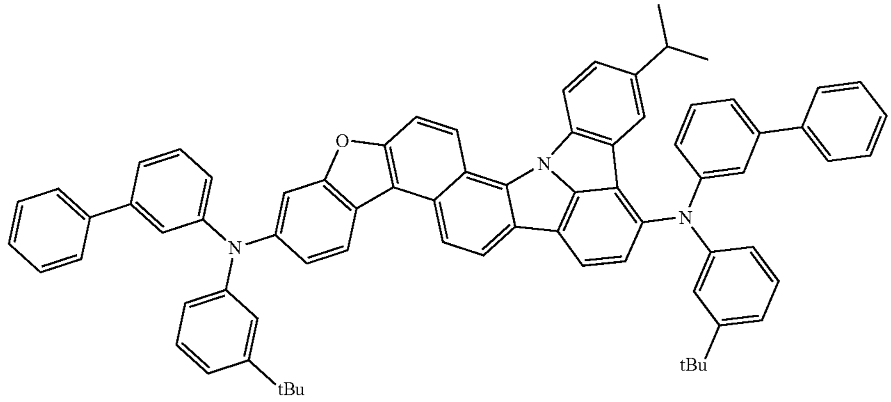
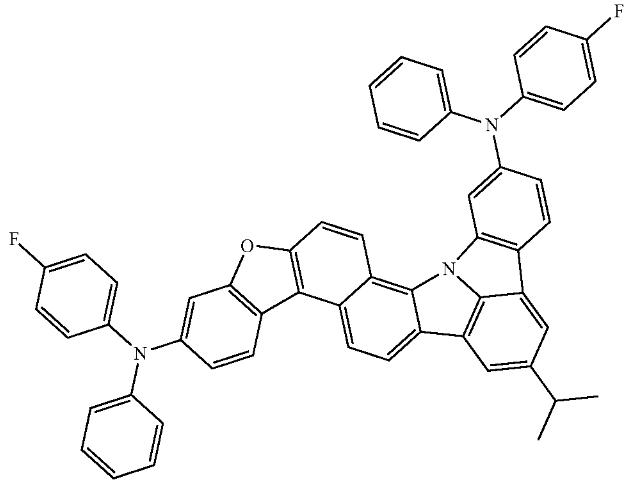

-continued
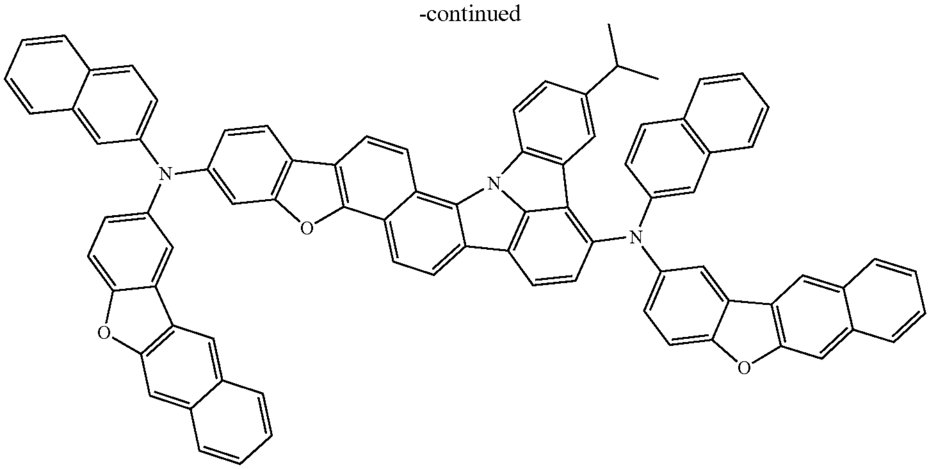
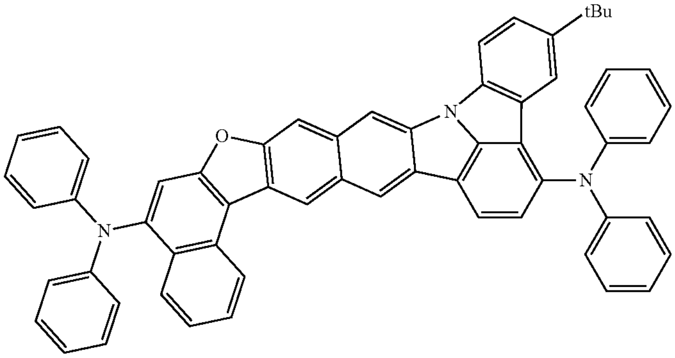
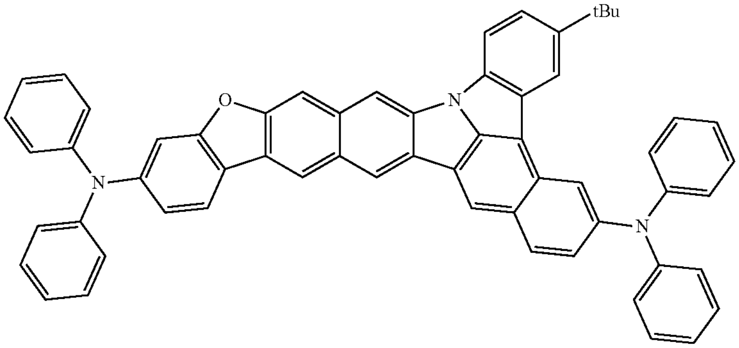

-continued
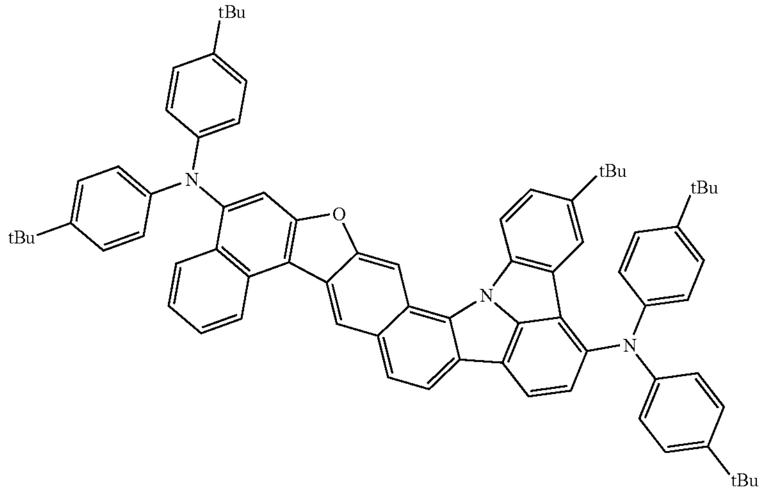
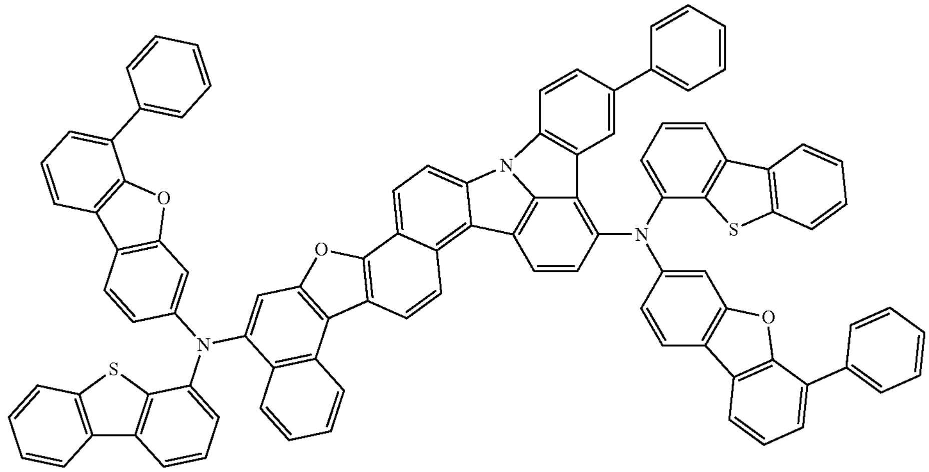
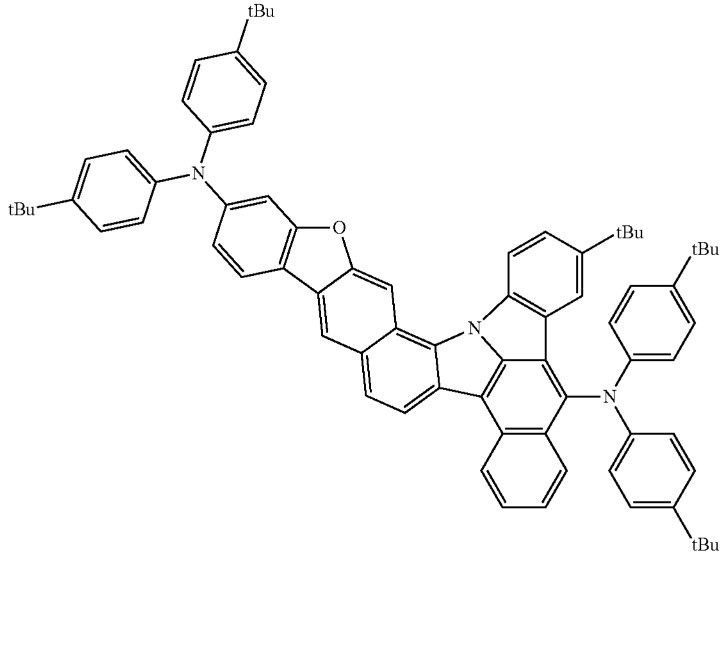

-continued
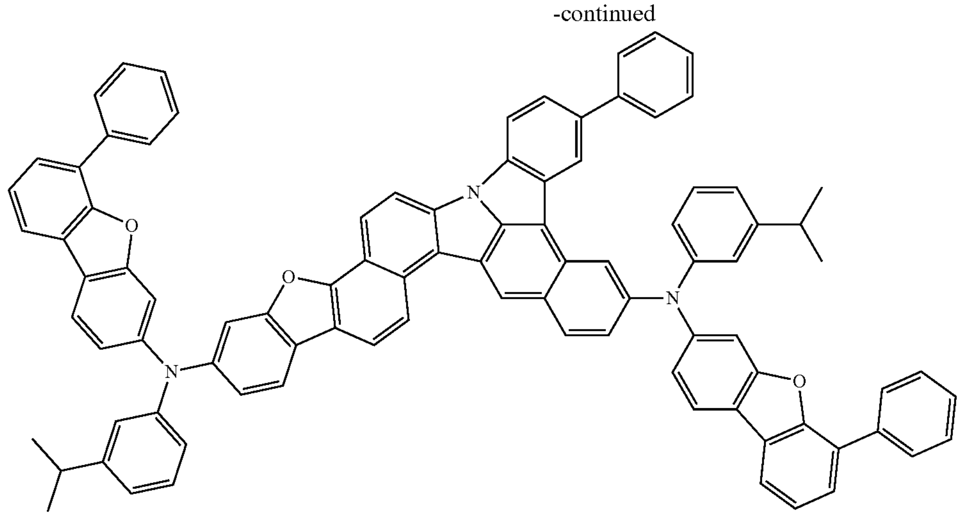
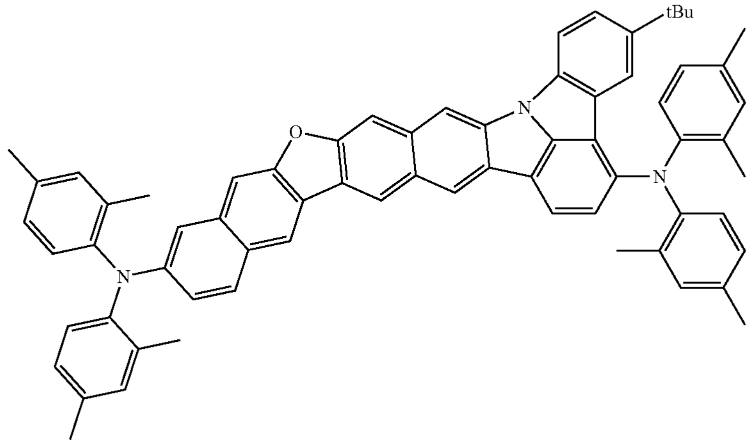
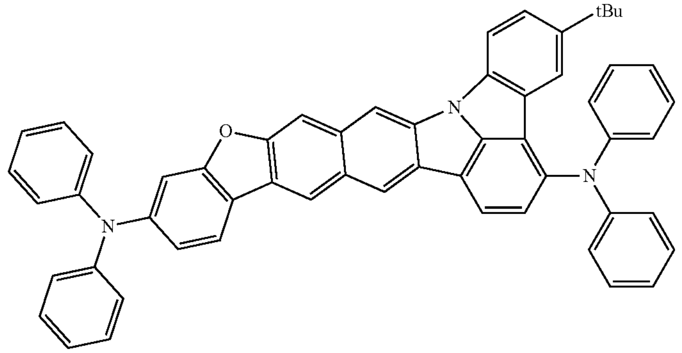
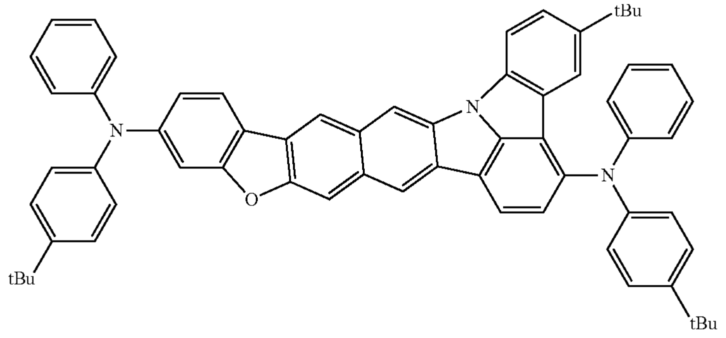

-continued
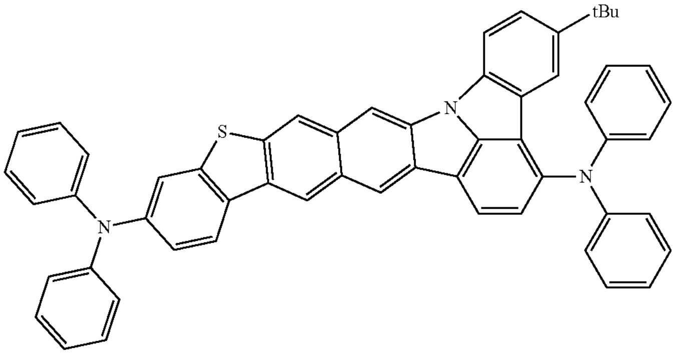
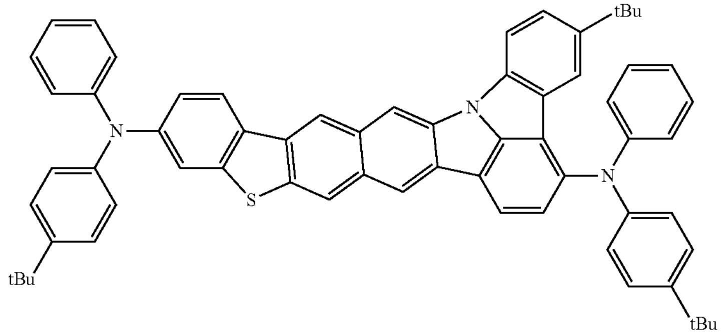
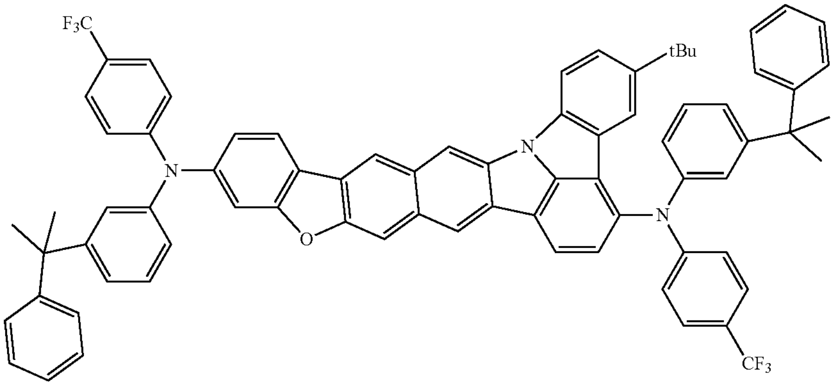
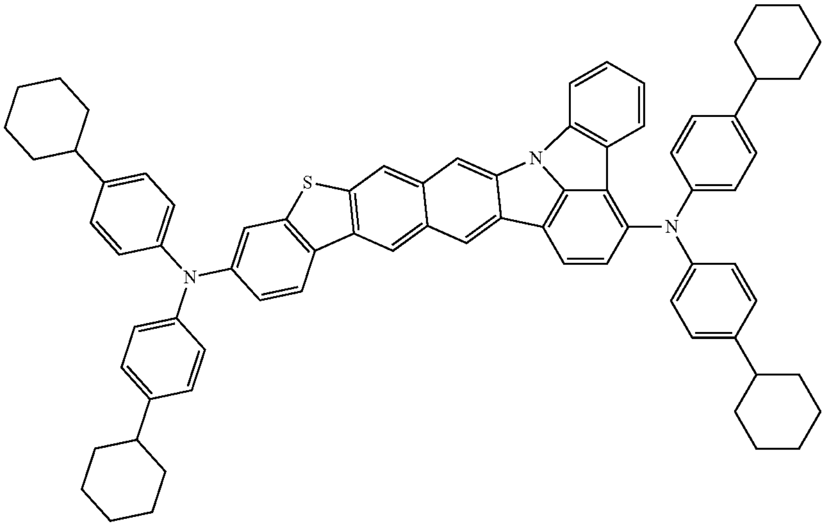

-continued
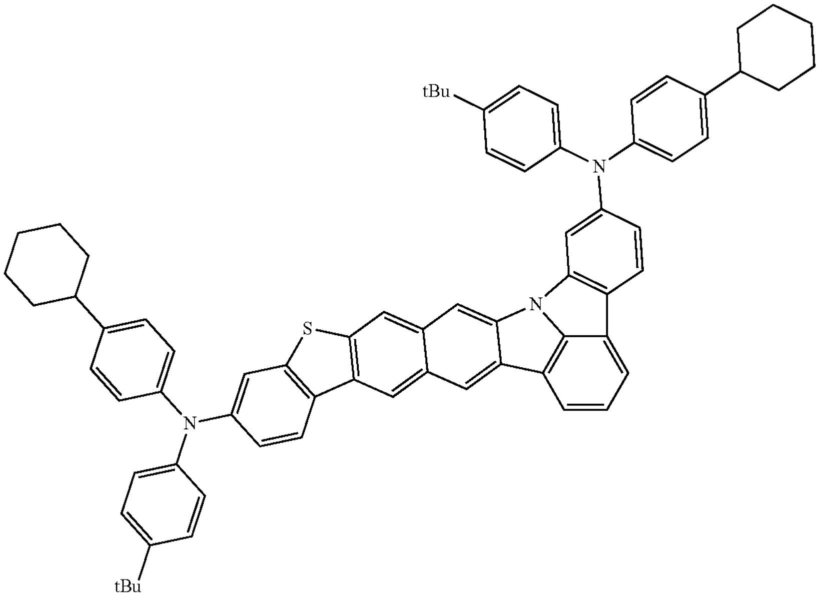
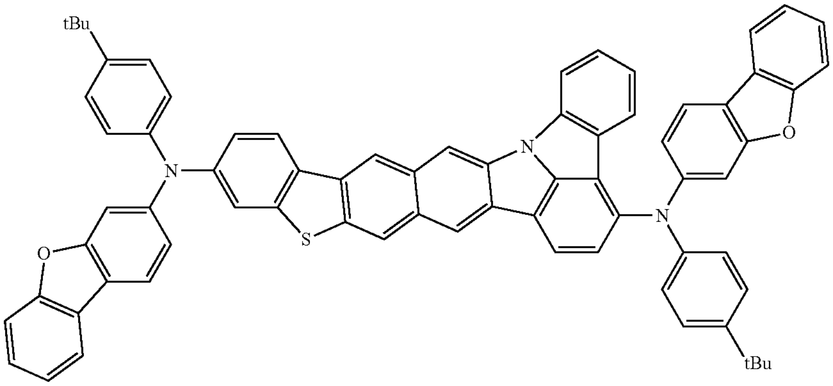
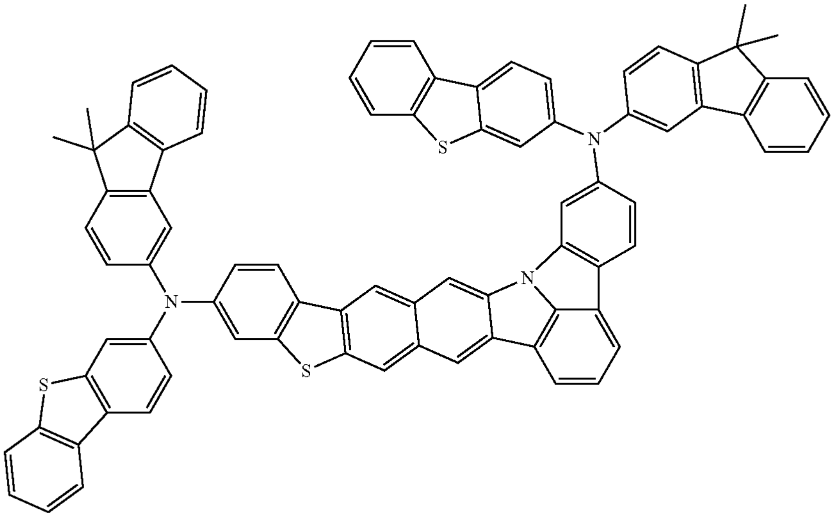

-continued
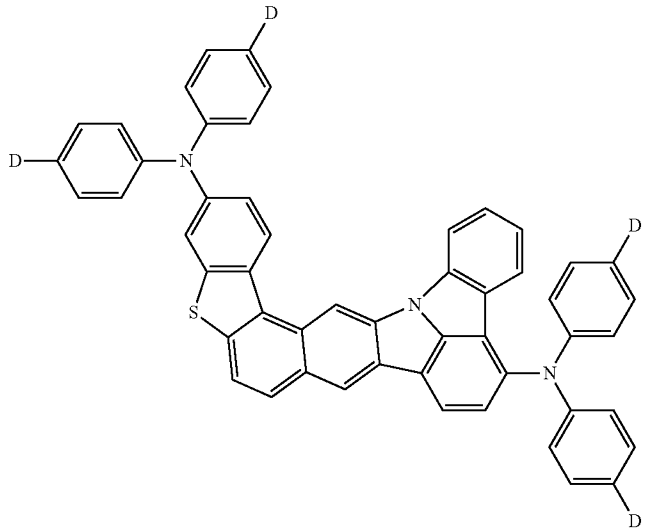
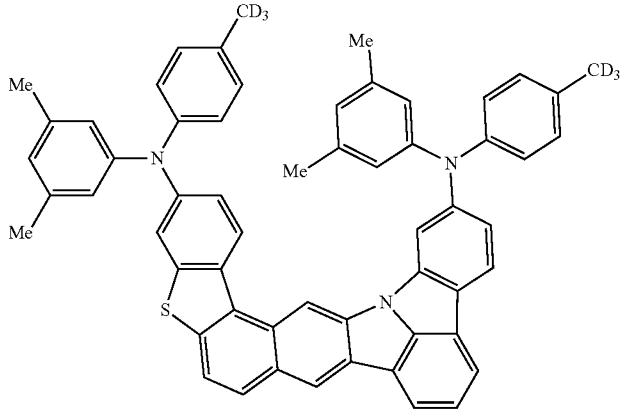
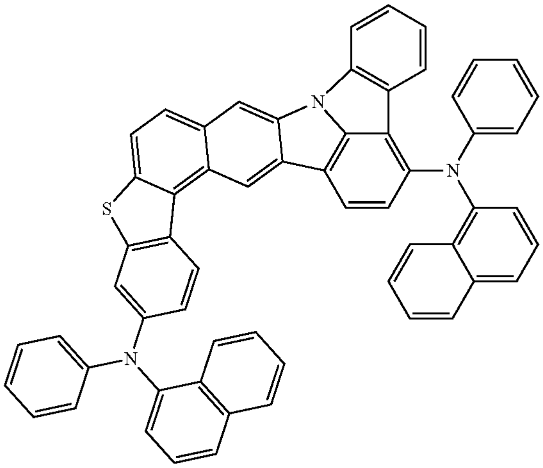
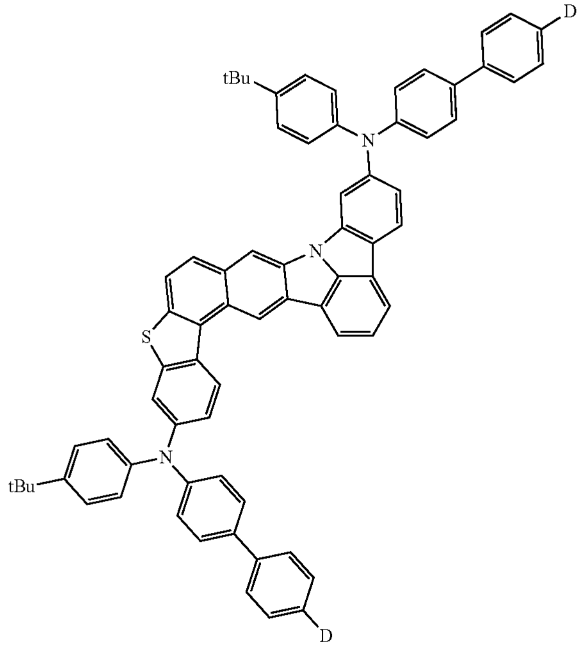

-continued
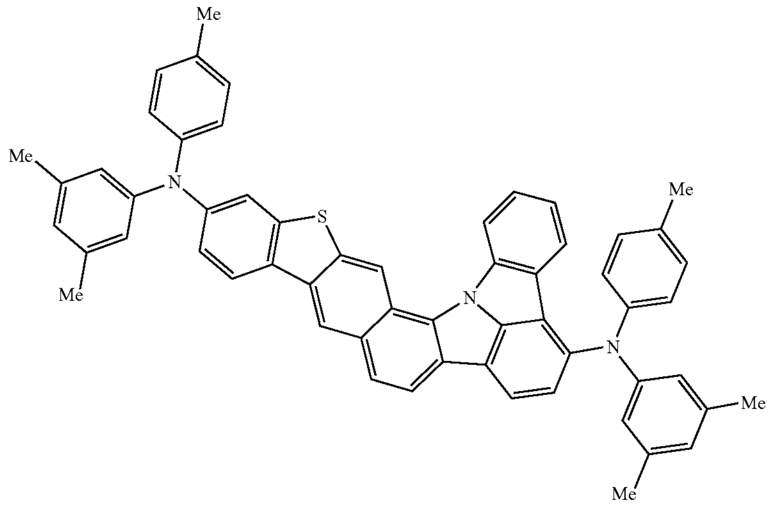
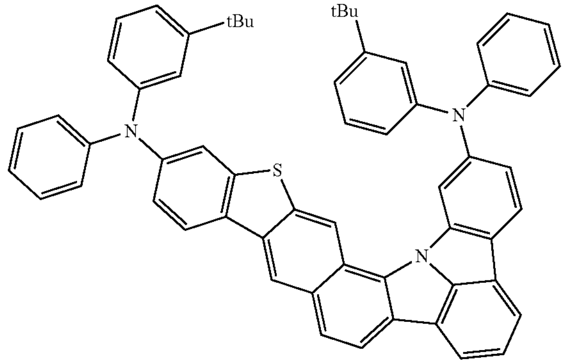
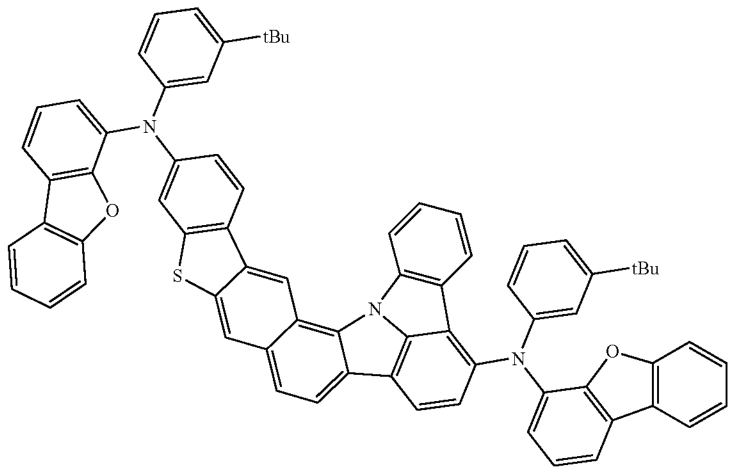

-continued
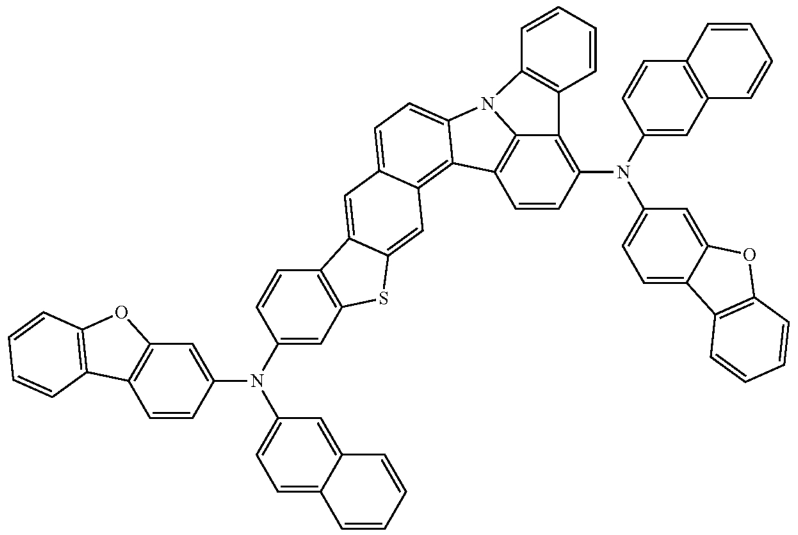
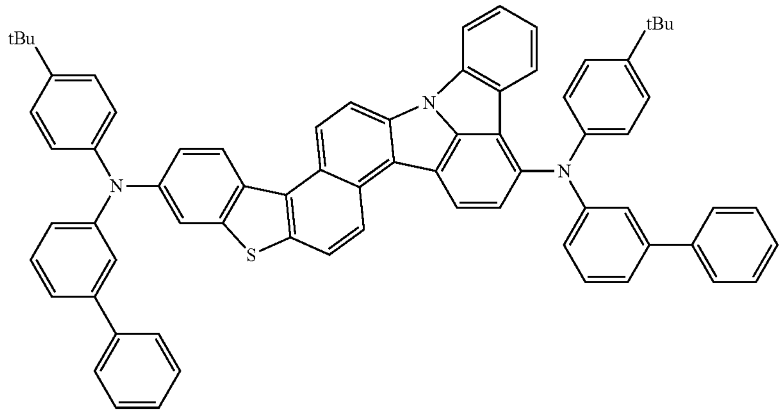
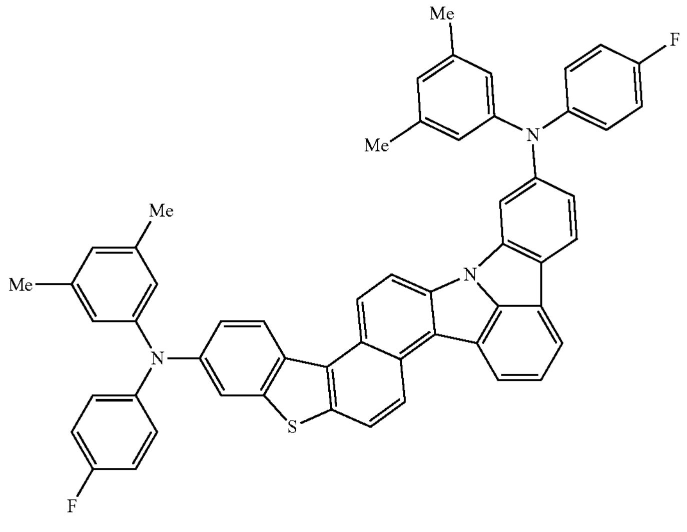

-continued
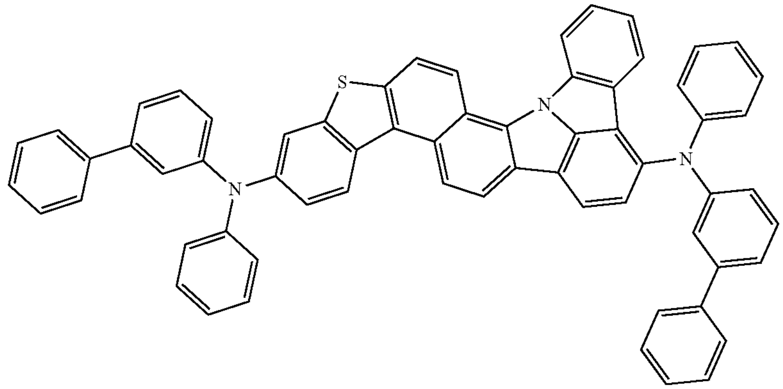
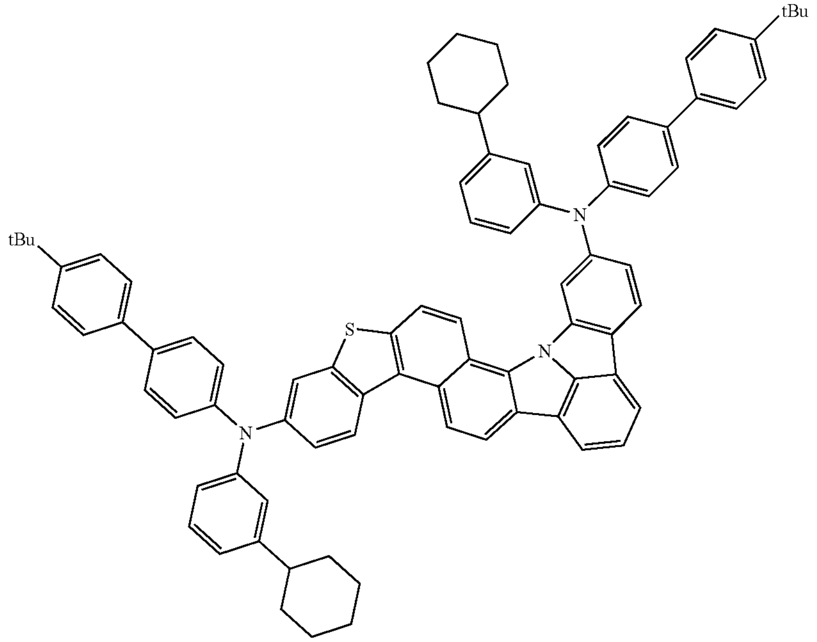
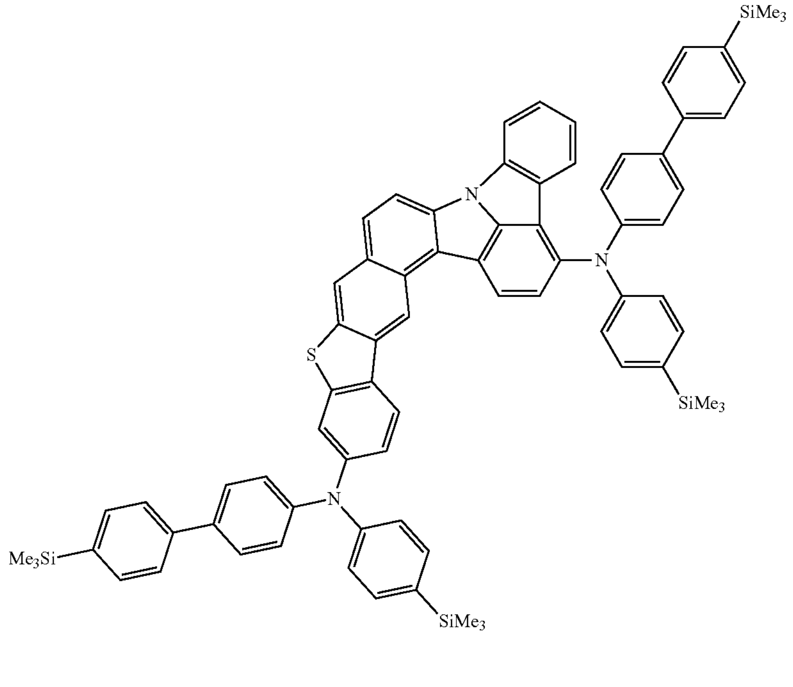

-continued
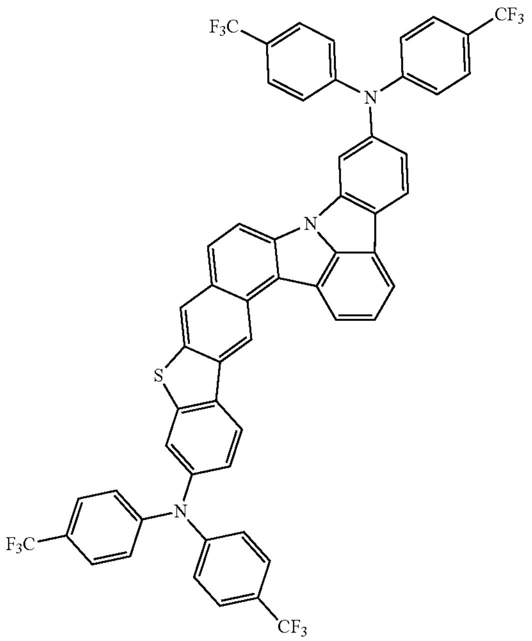
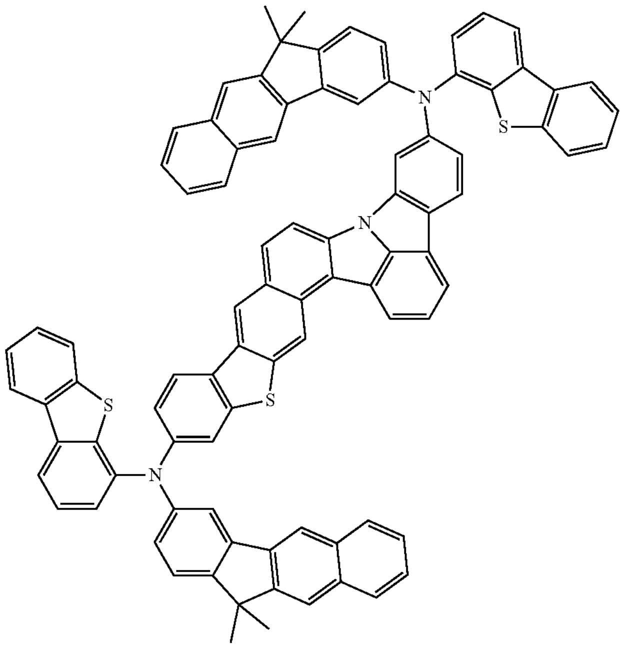
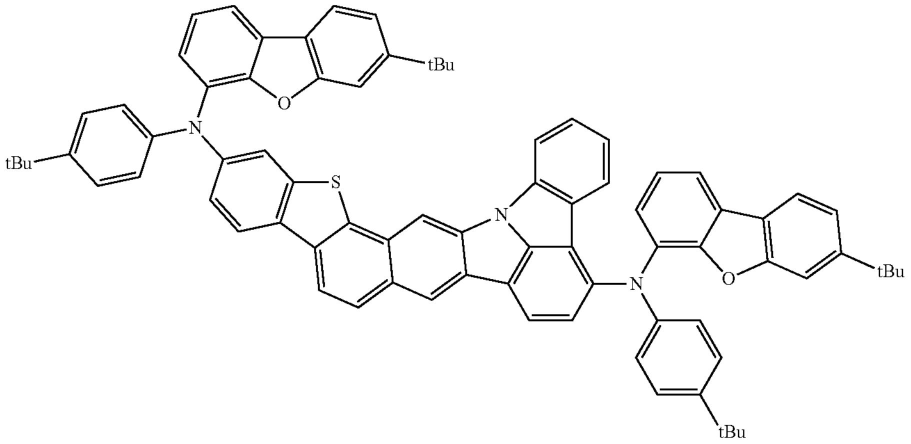
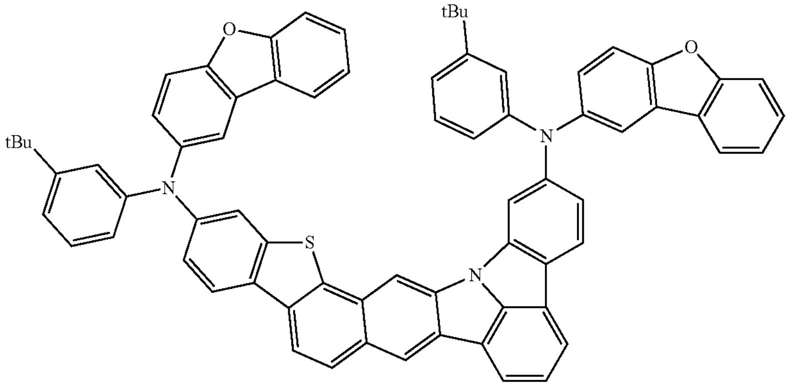

-continued
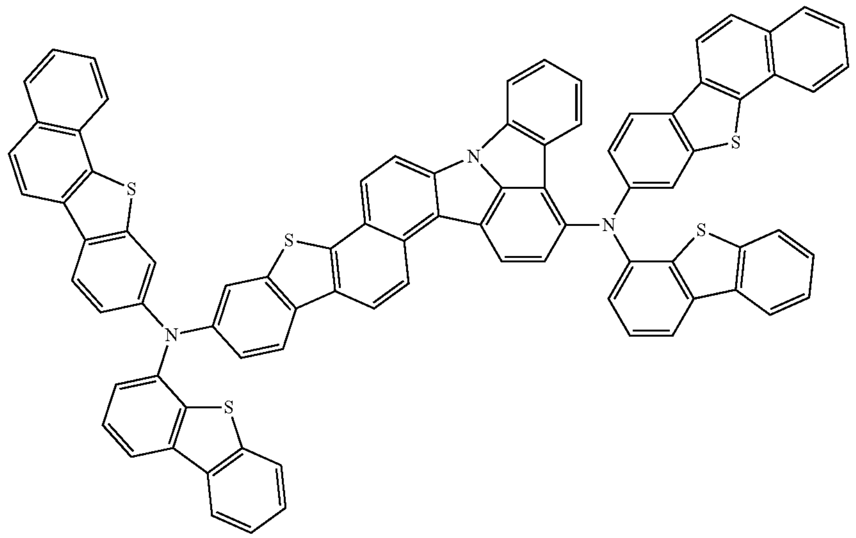
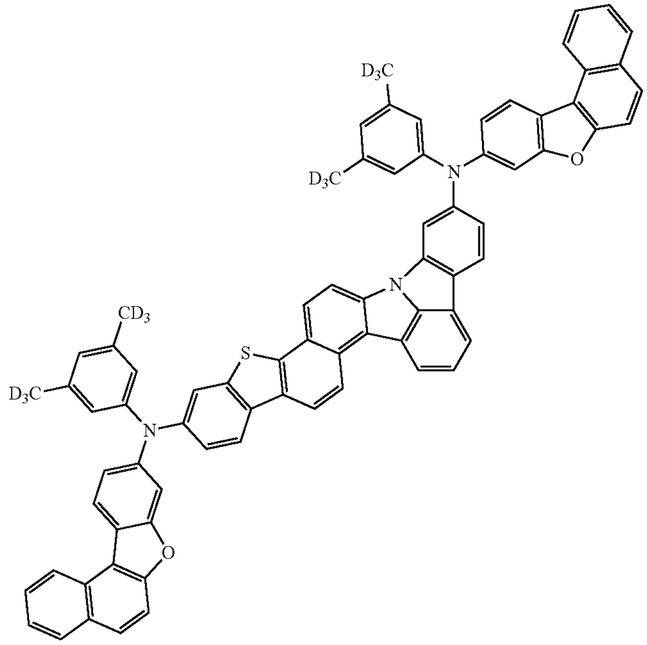
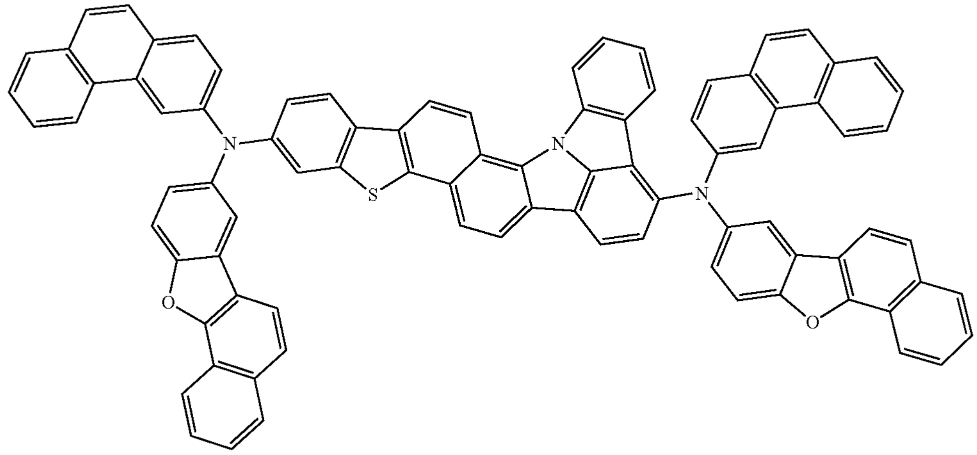

-continued
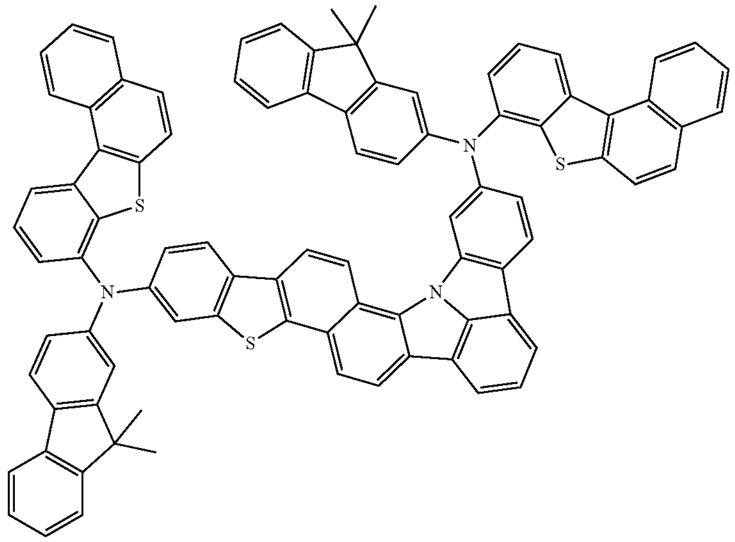
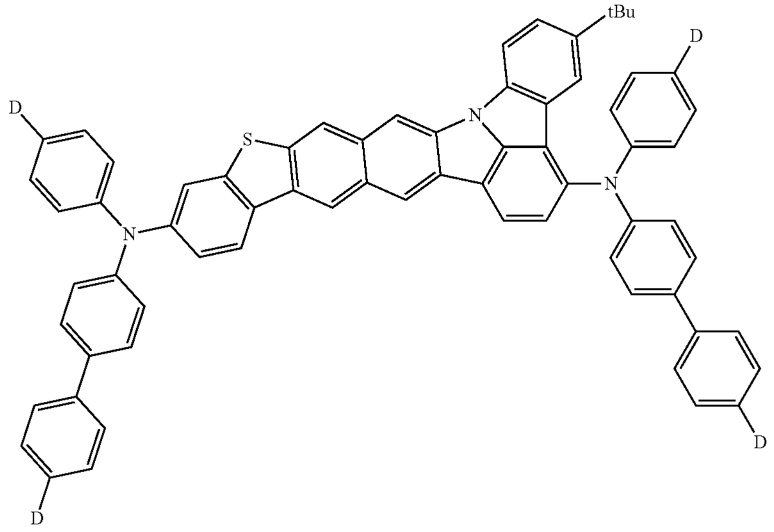
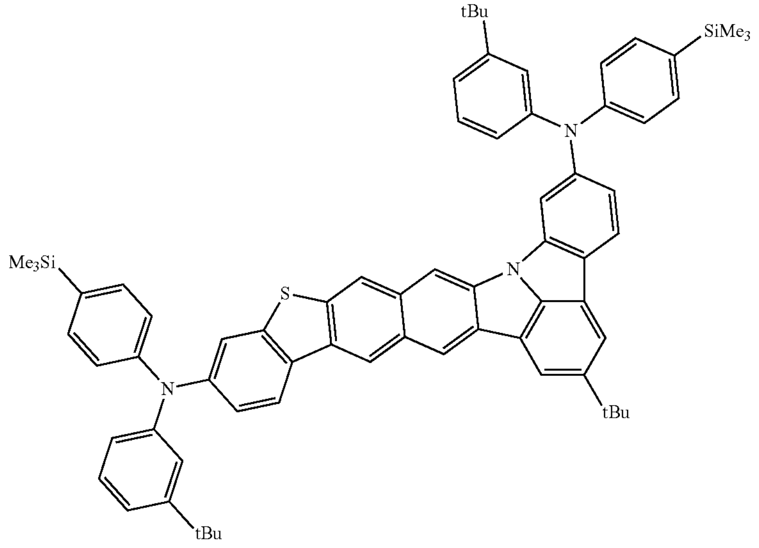

-continued
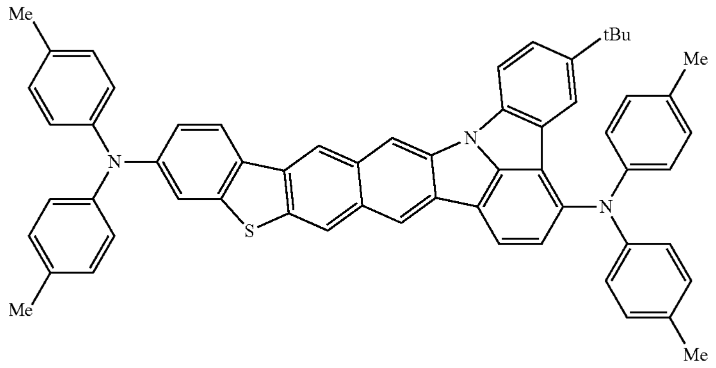
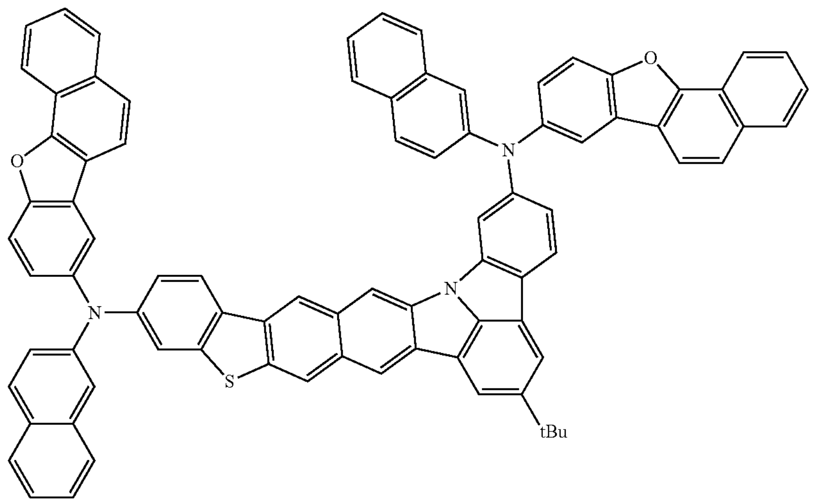
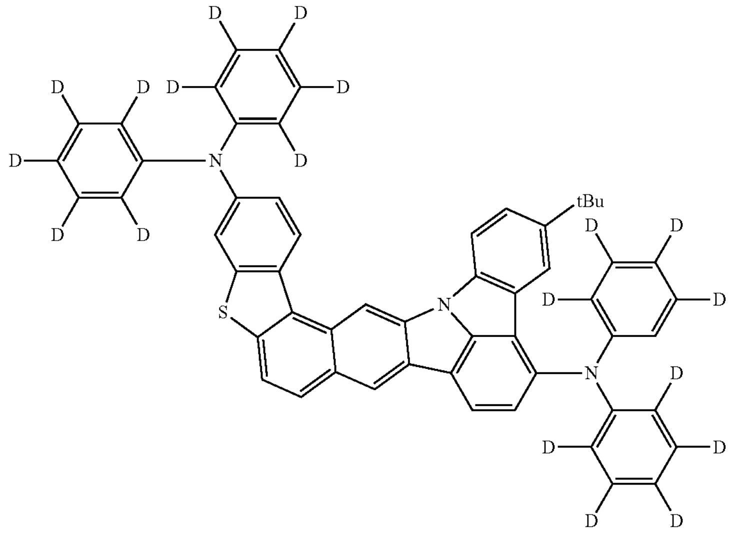

-continued
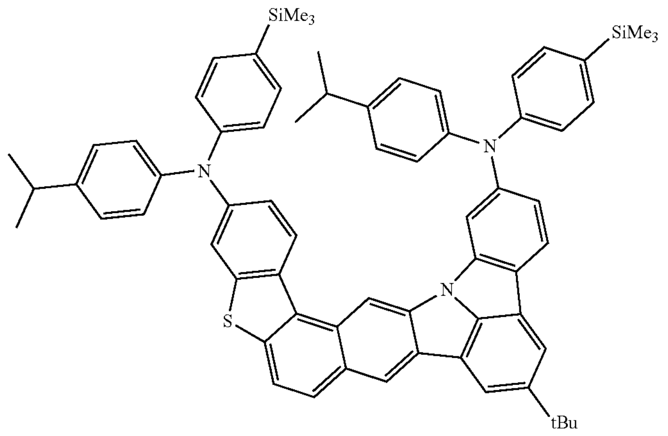
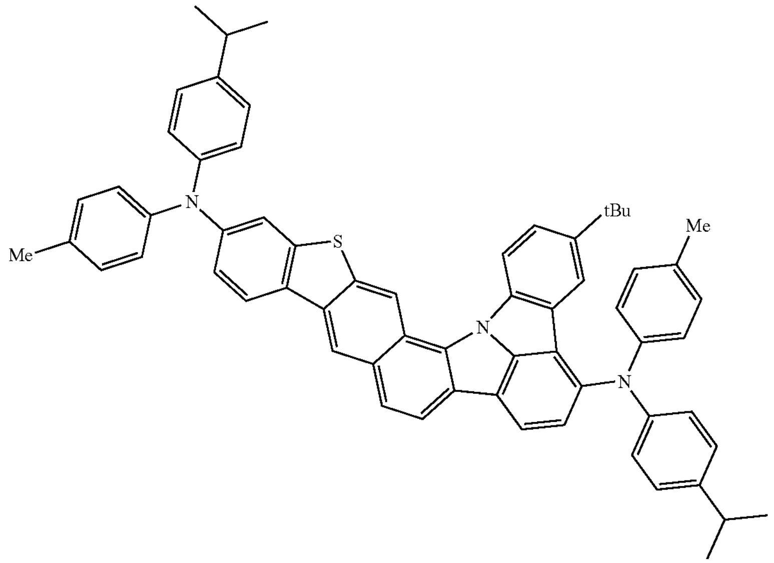
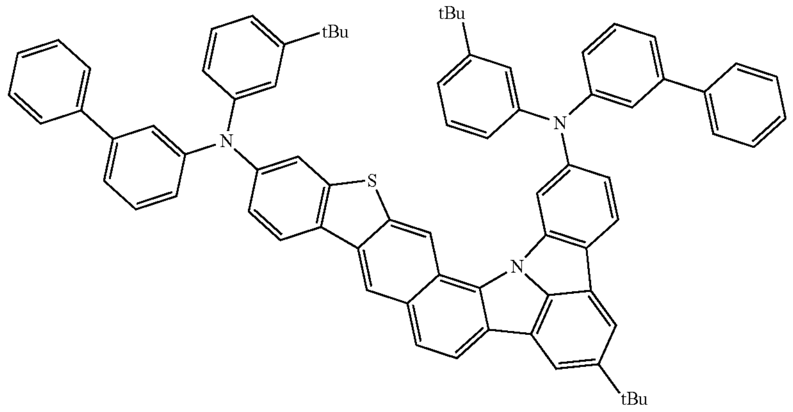

-continued
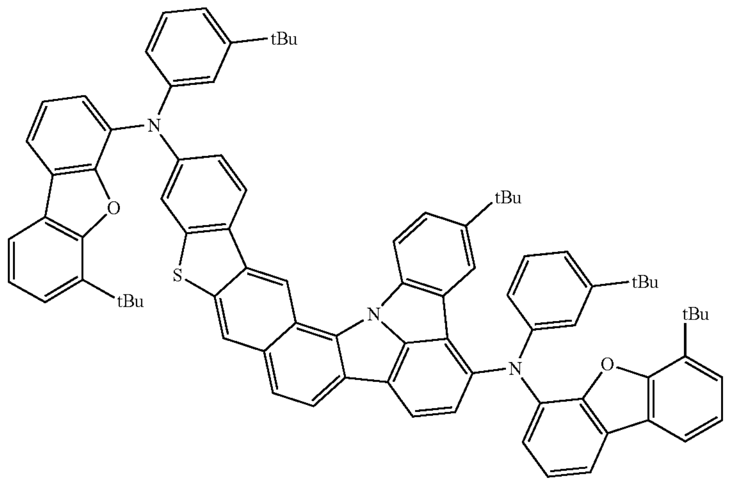
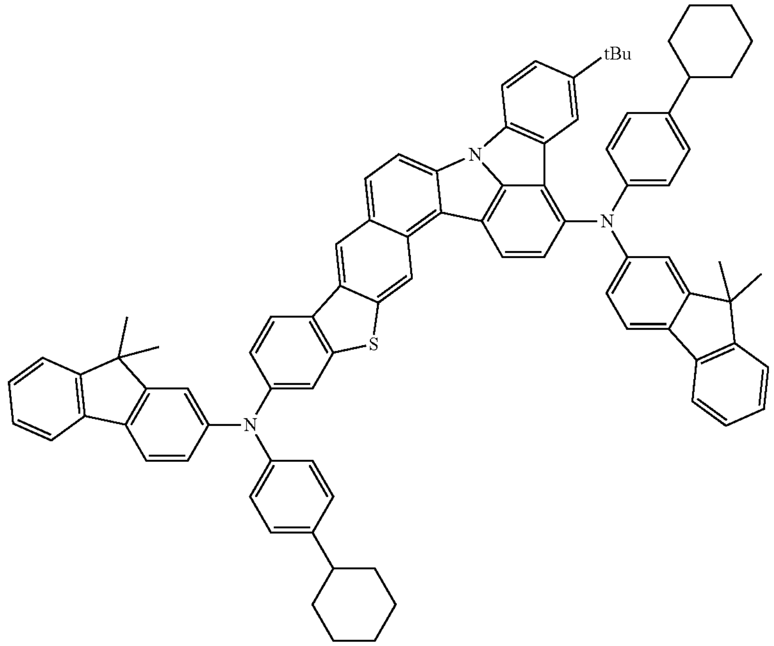
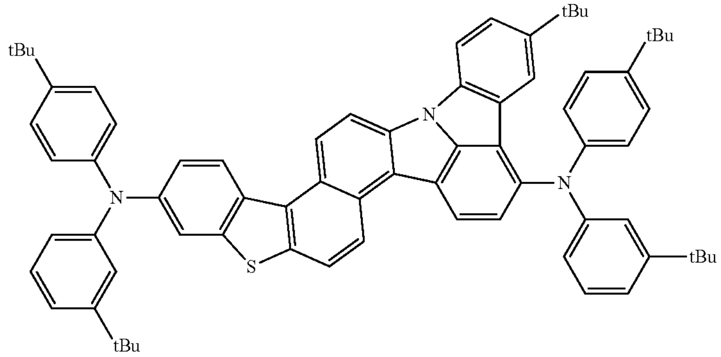

-continued
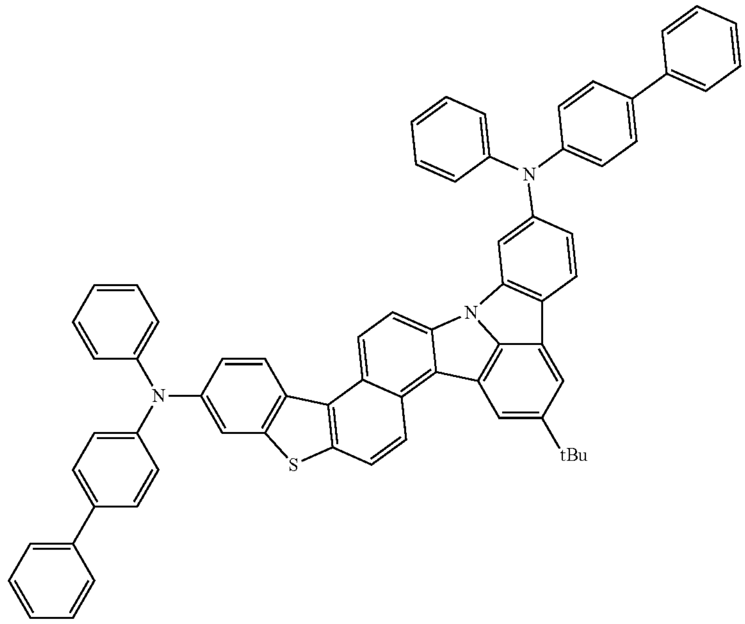
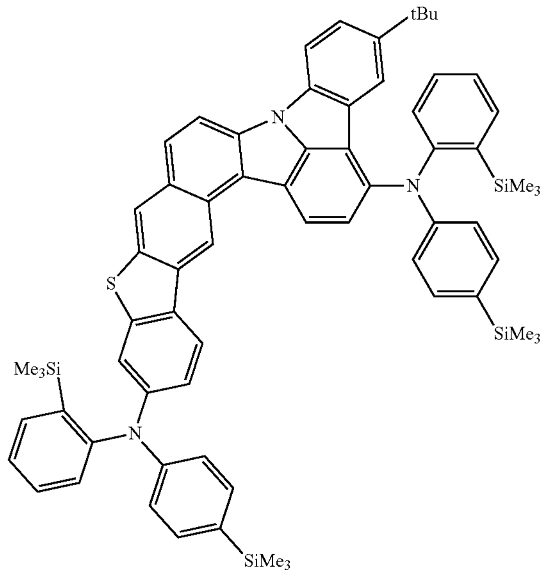

-continued
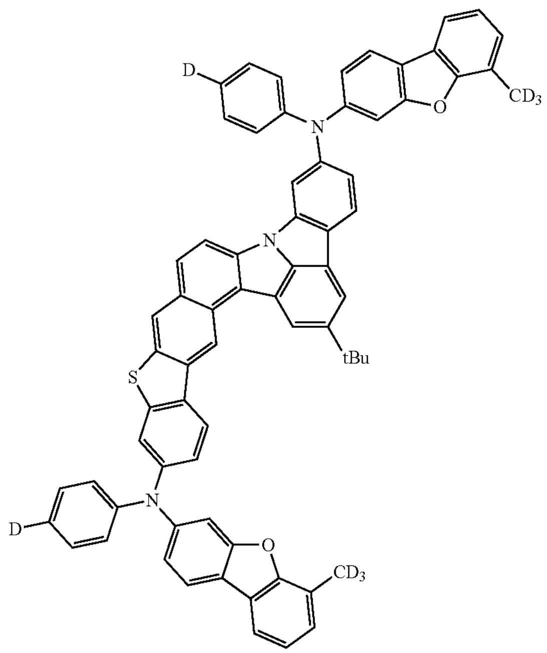
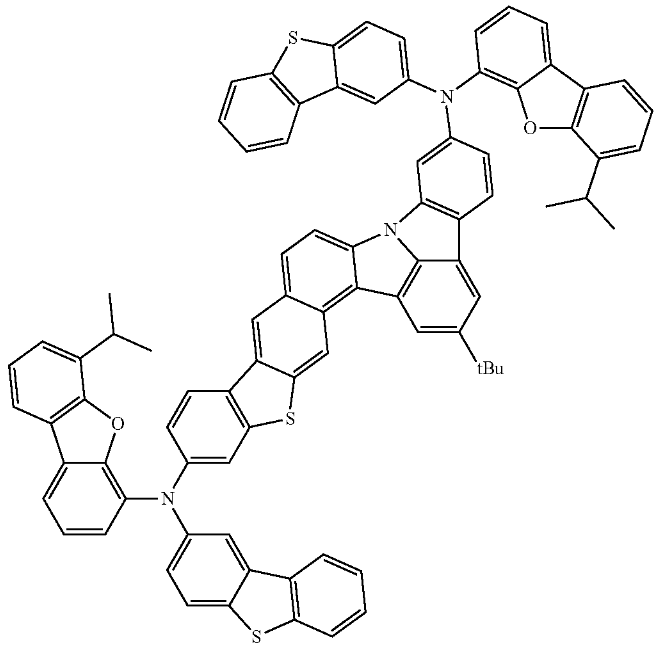

-continued
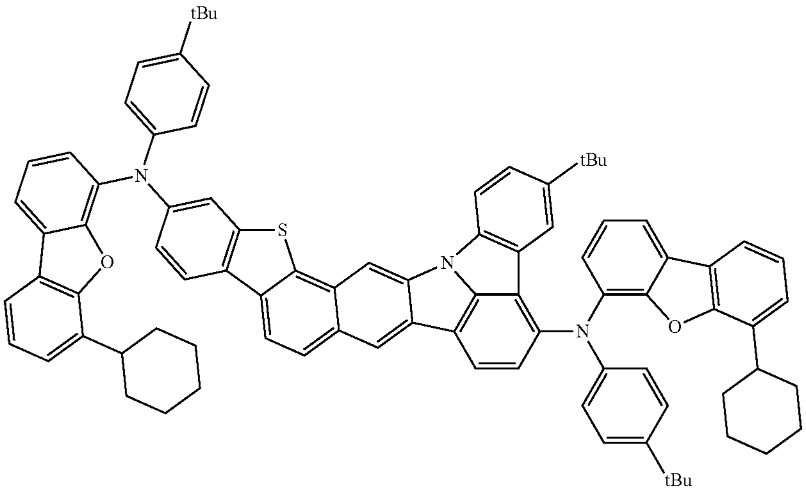
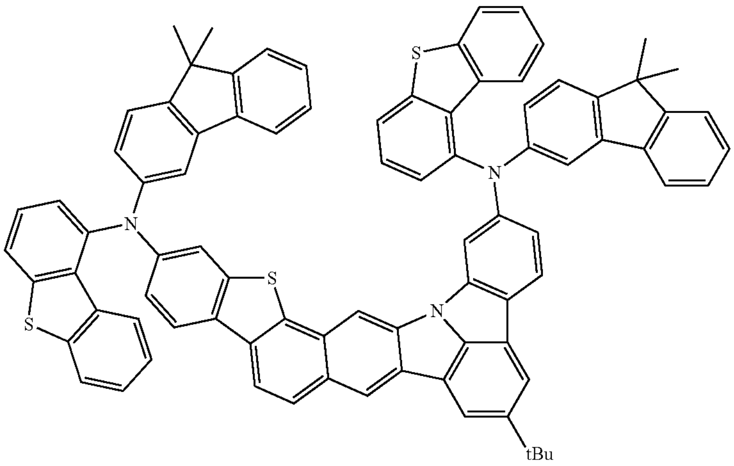
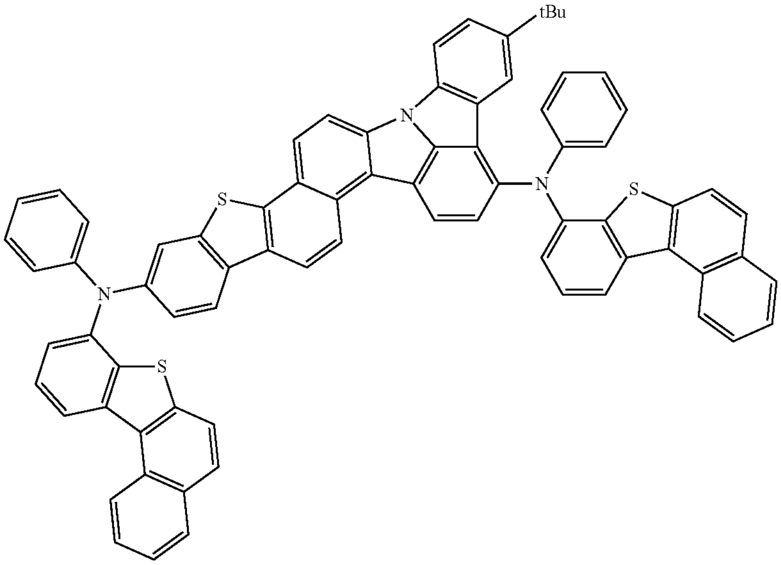

-continued
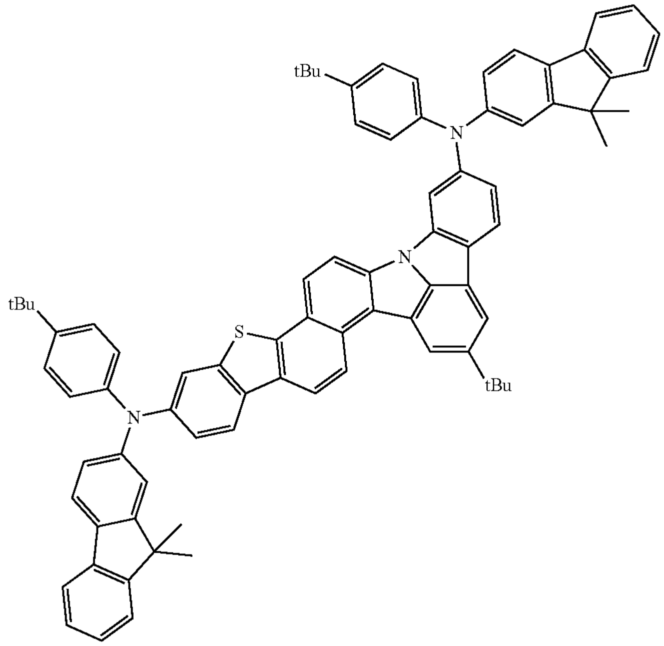
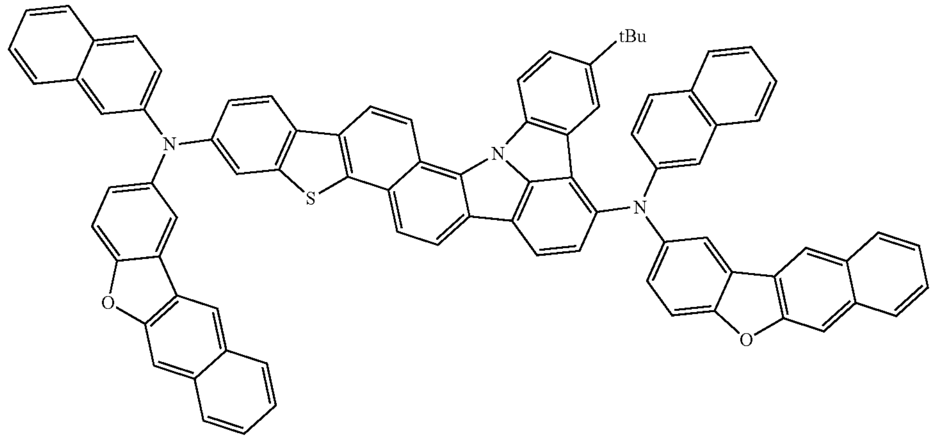
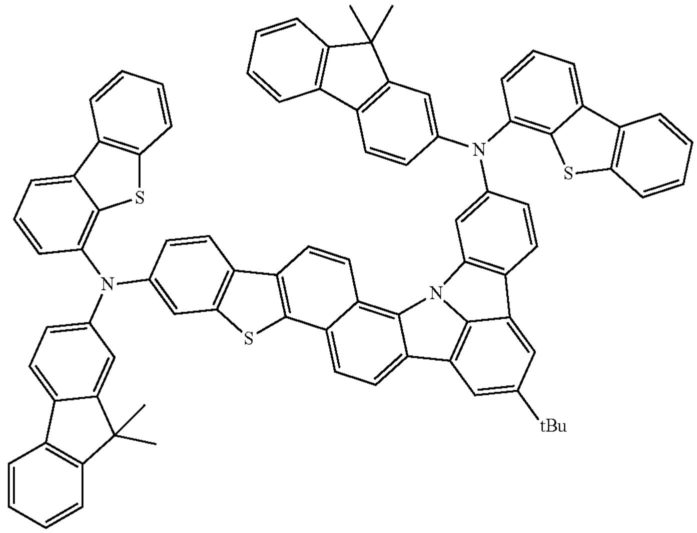

-continued
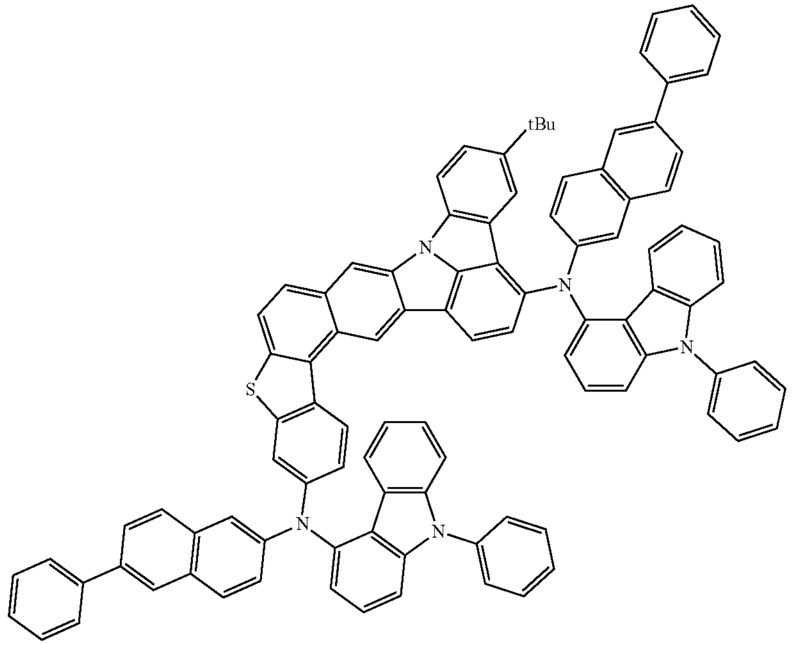
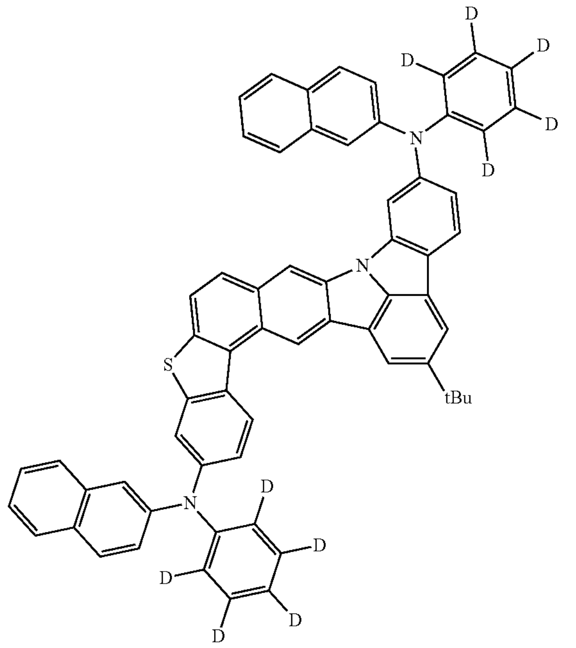

-continued
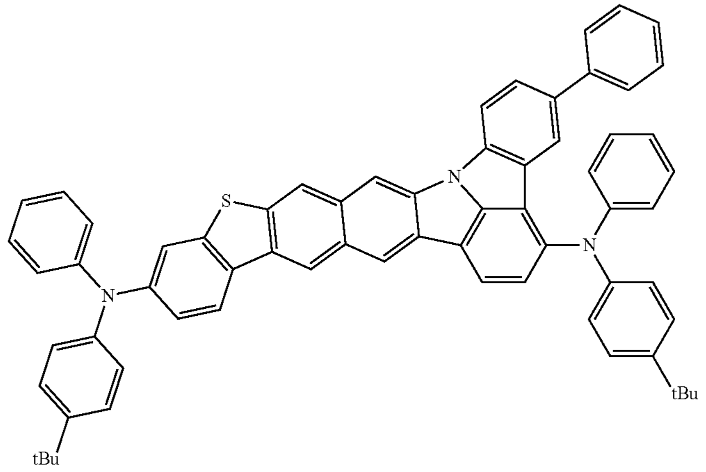
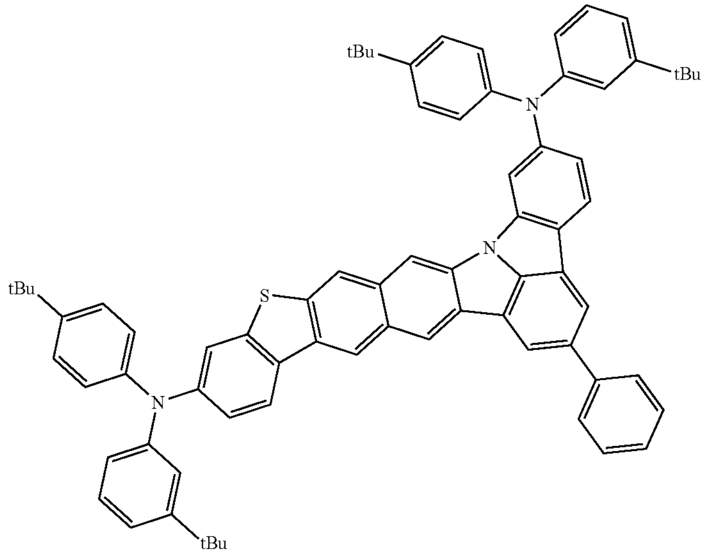
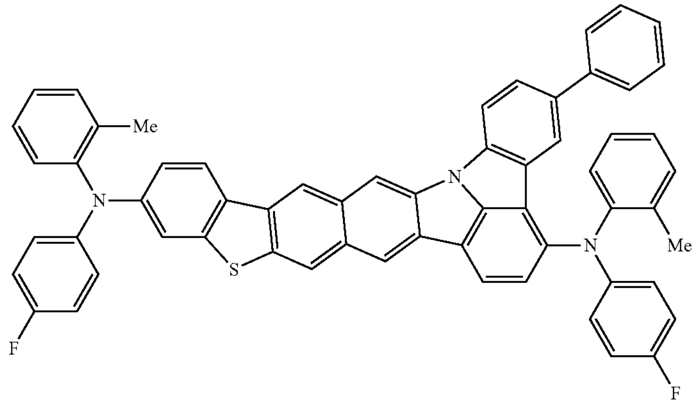

-continued
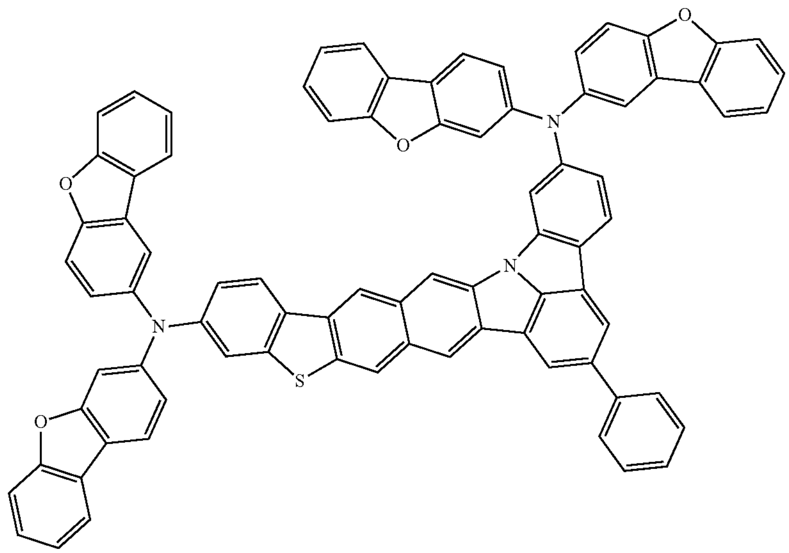
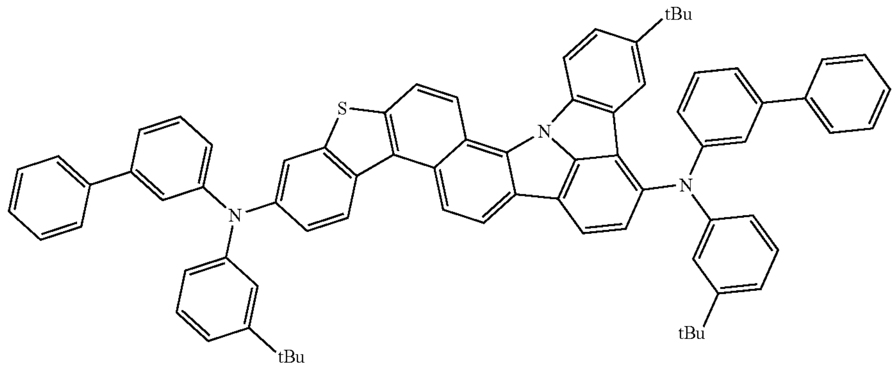
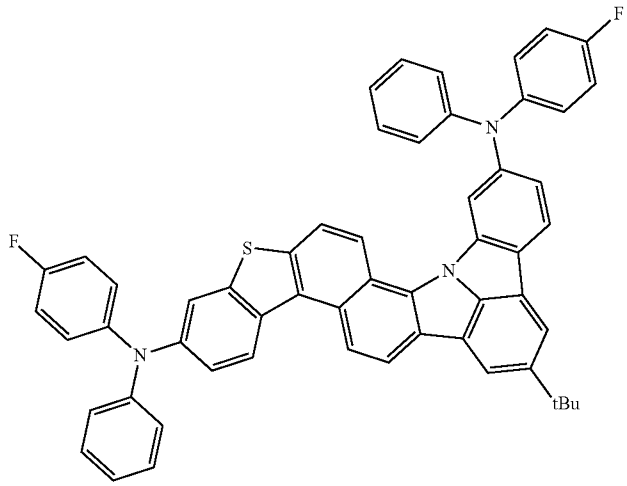

-continued
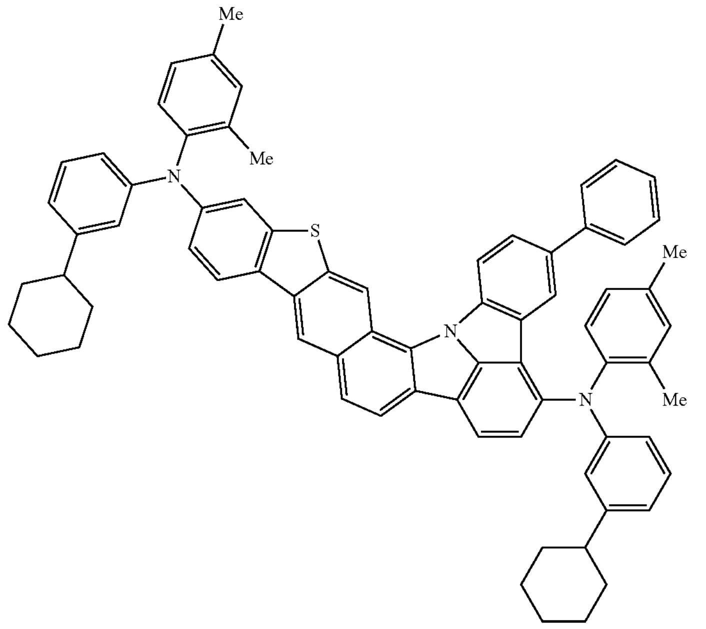
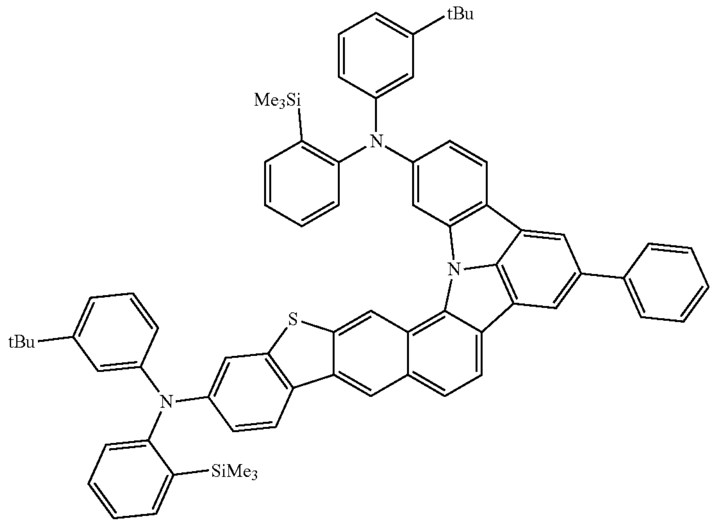
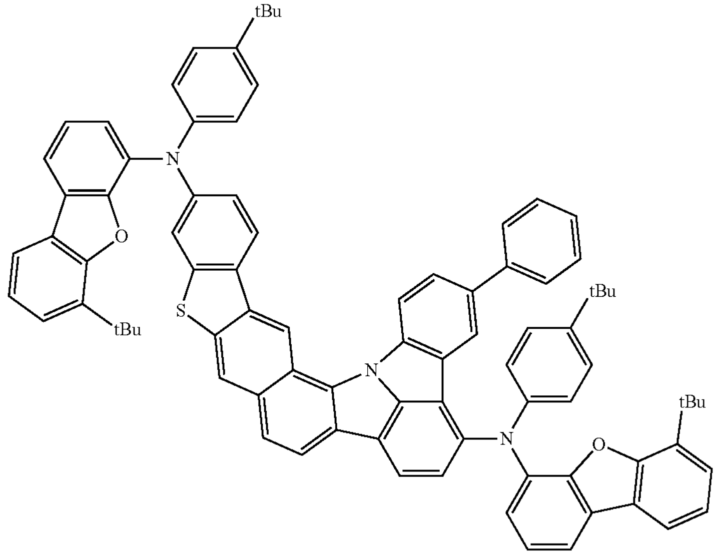

-continued
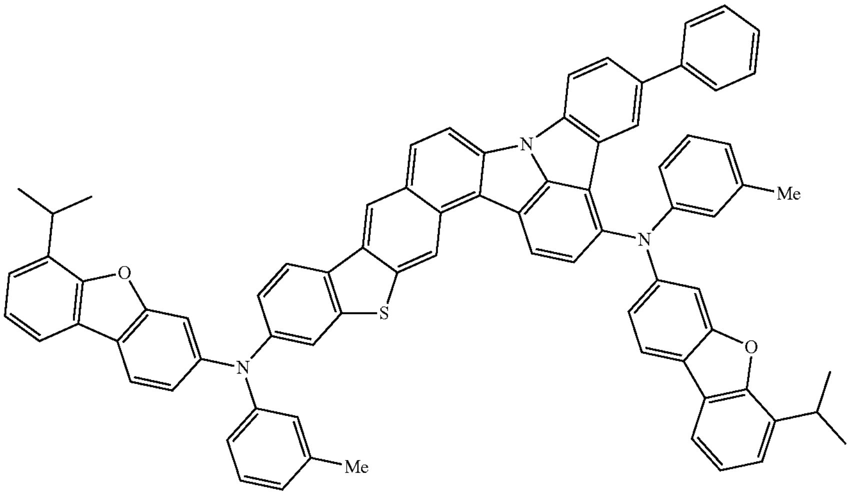 [SMILES: Cc1cccc(N(c2ccc3c(c2)oc2c(C(C)C)cccc23)c2ccc3c(c2)sc2cc4c(ccc5c4c4ccc(N(c6cccc(C)c6)c6ccc7c(c6)oc6c(C(C)C)cccc67)c6c7cc(-c8ccccc8)ccc7n5c46)cc23)c1]
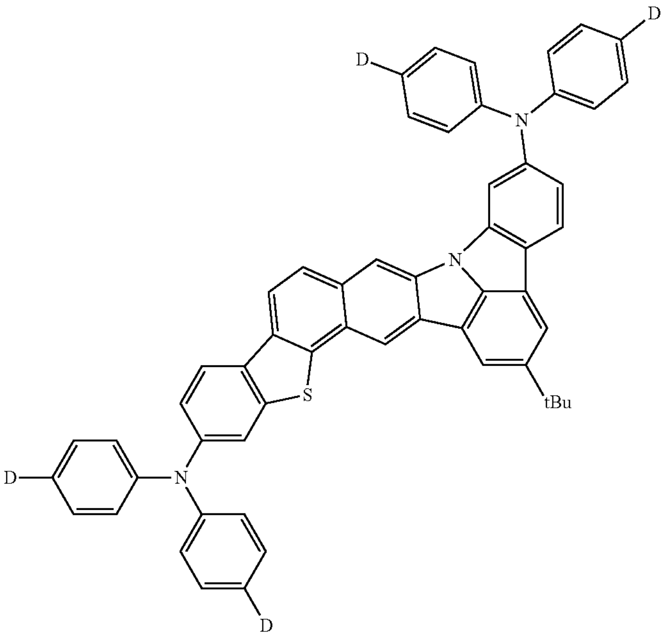

-continued
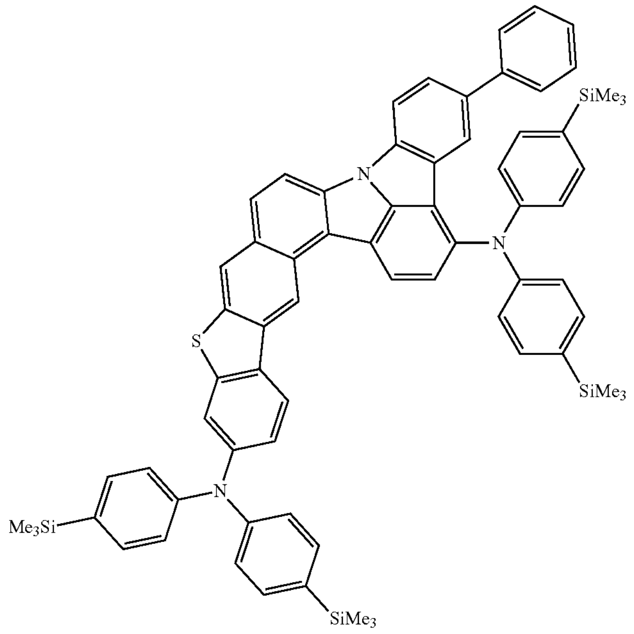
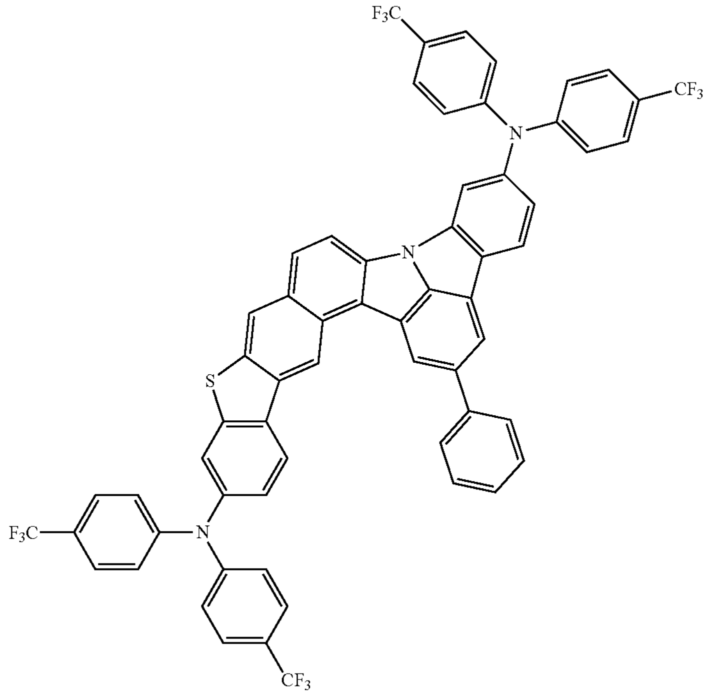

-continued
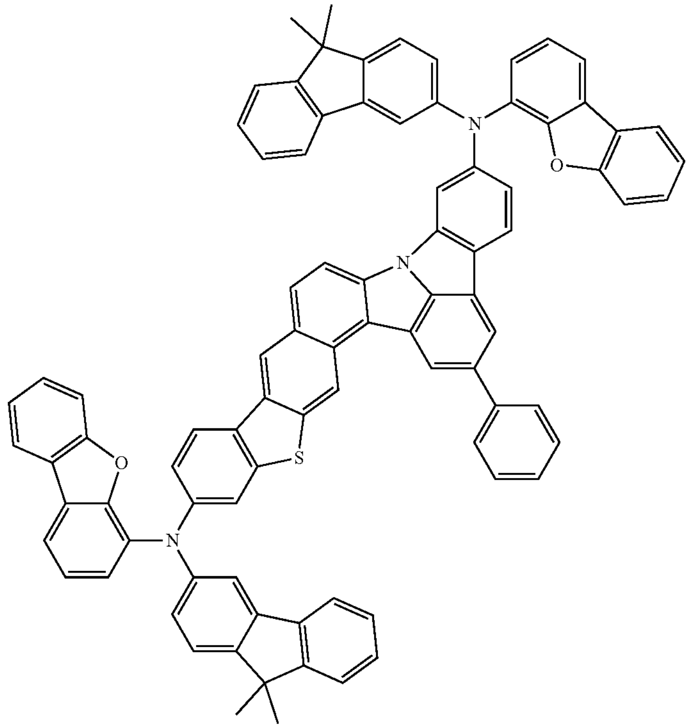
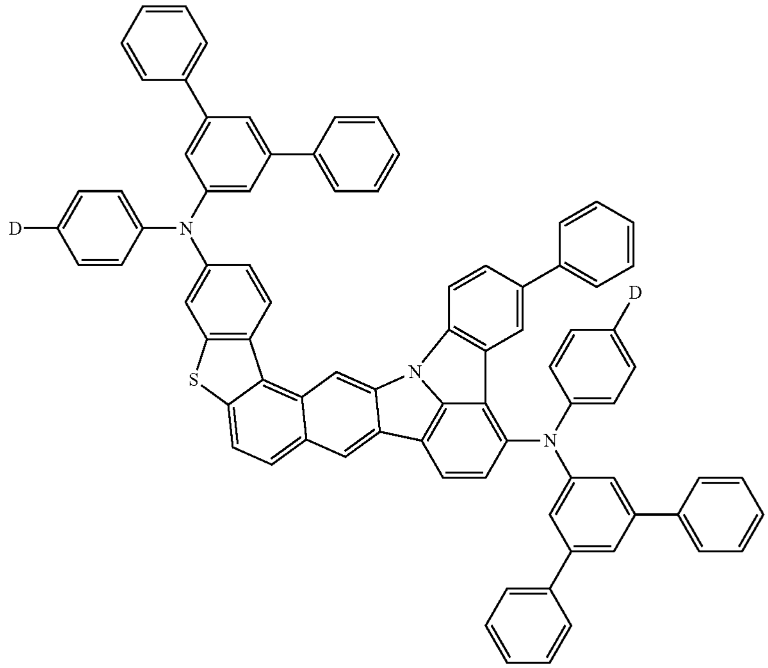

-continued
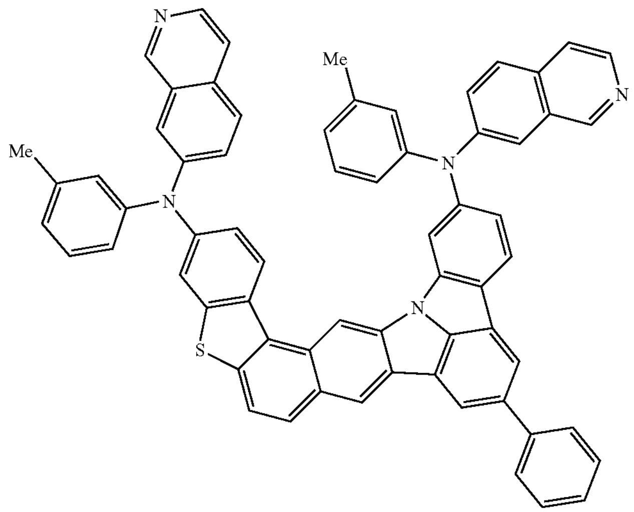
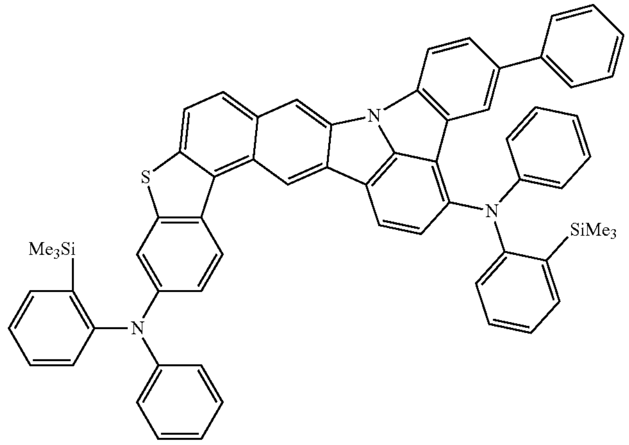

-continued
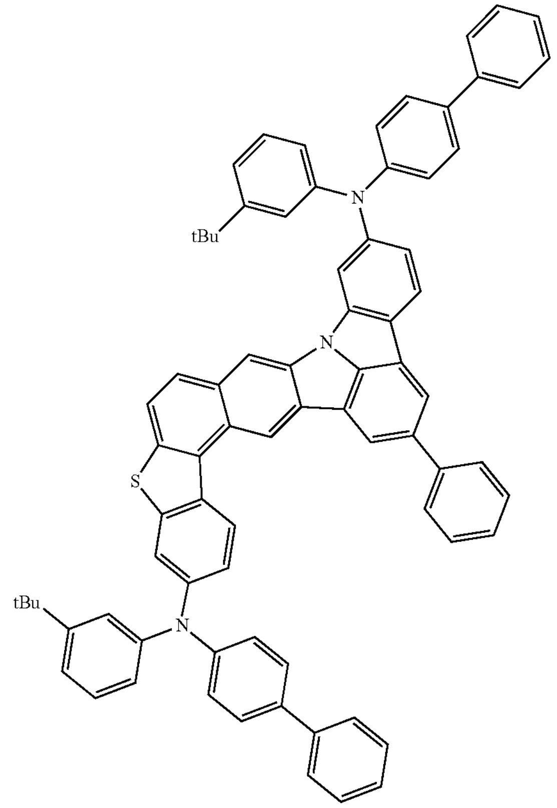
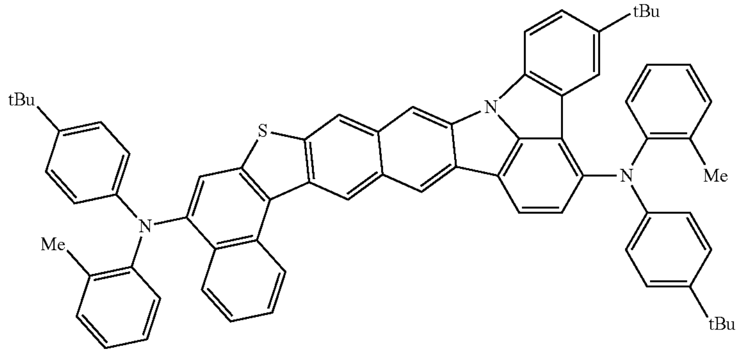
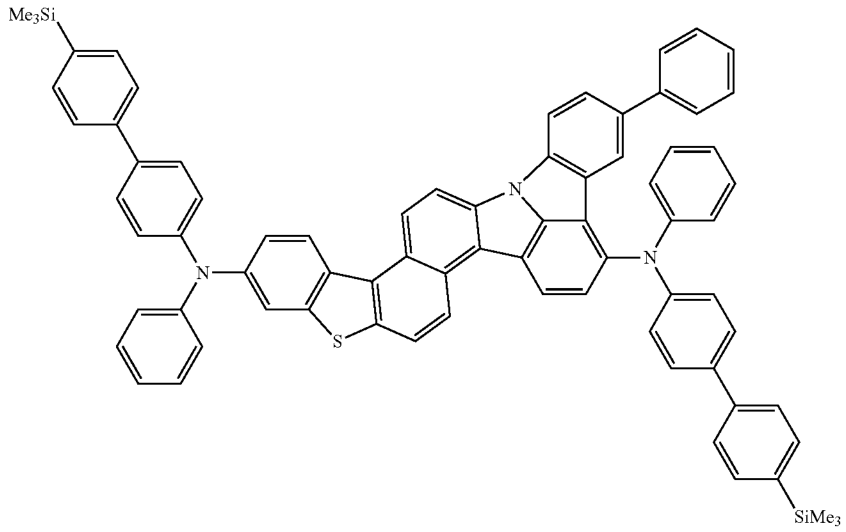

-continued
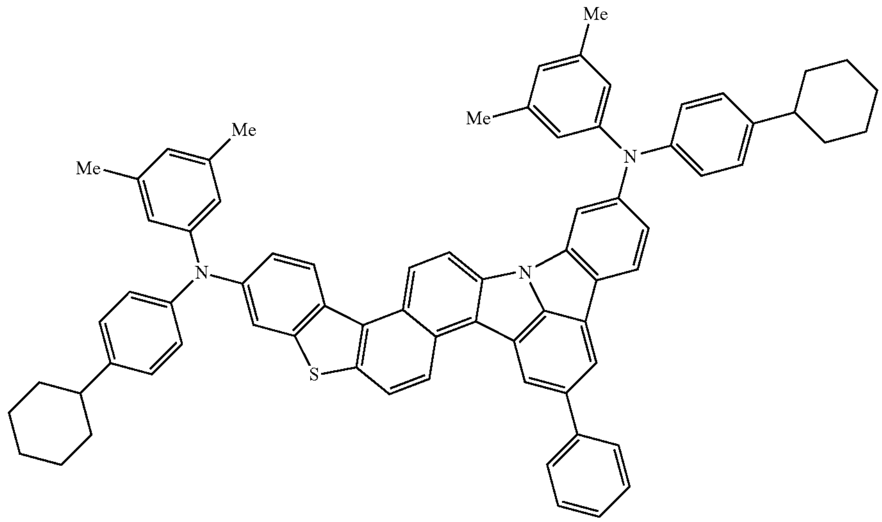
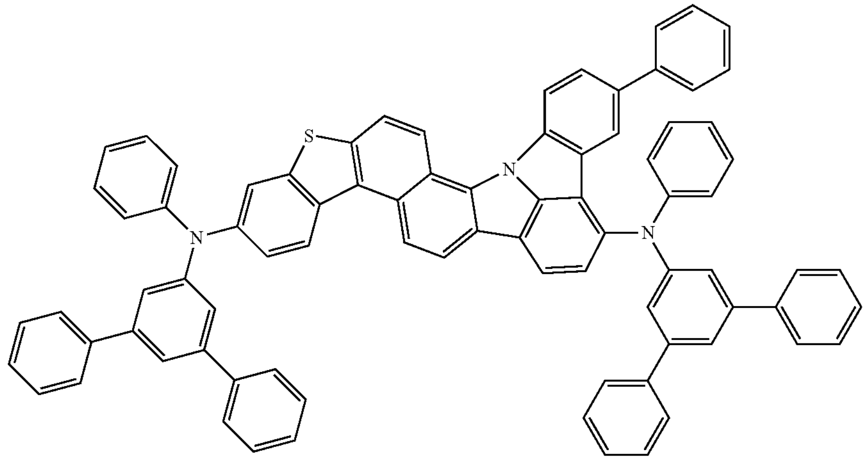
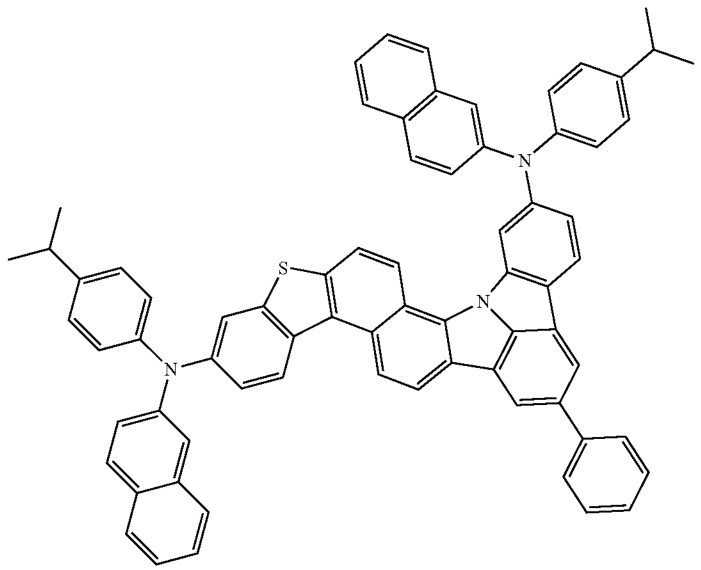

-continued
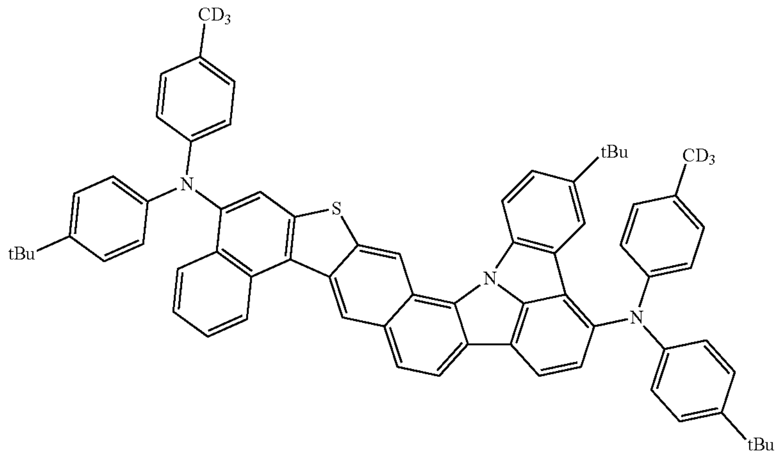
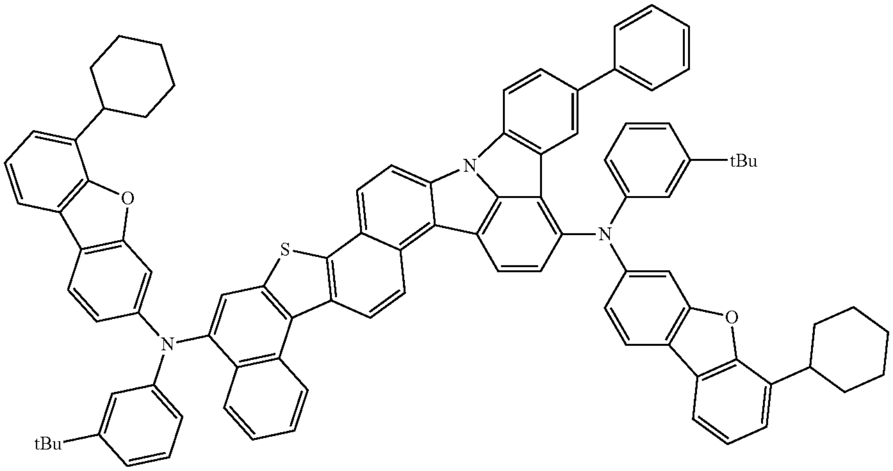
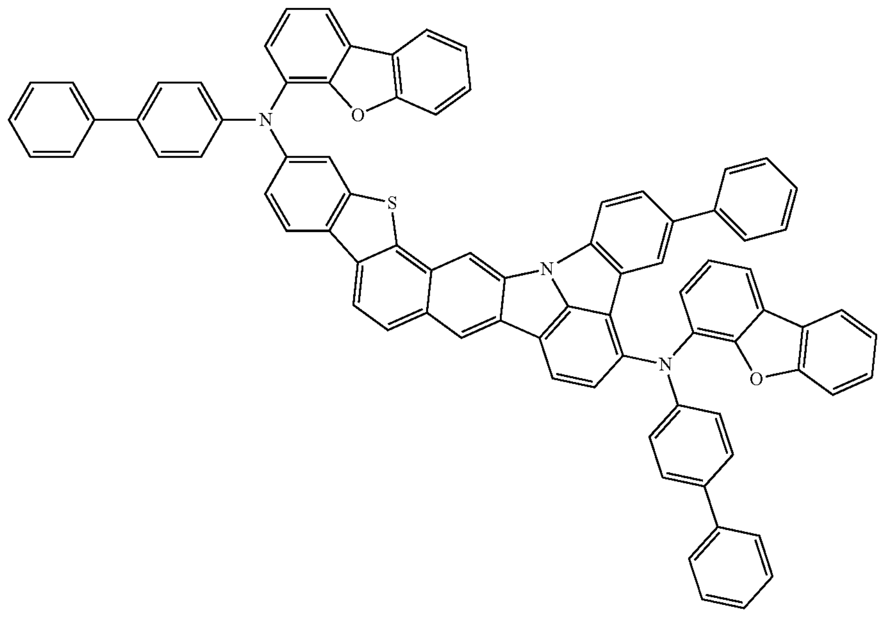

-continued
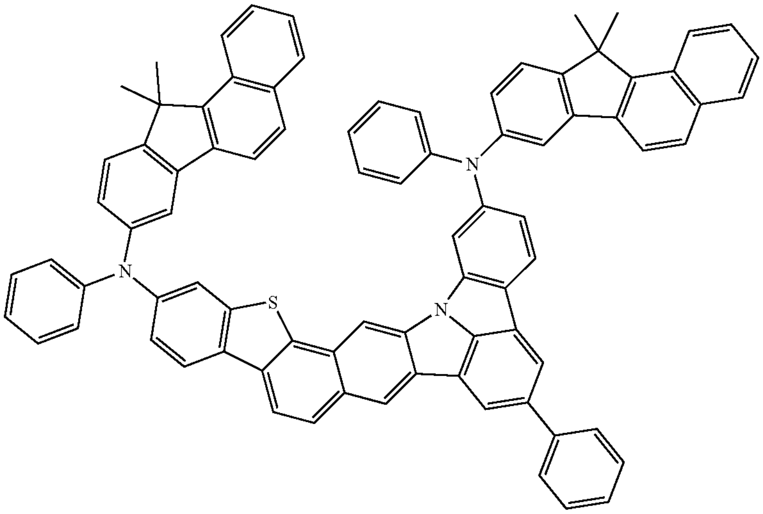
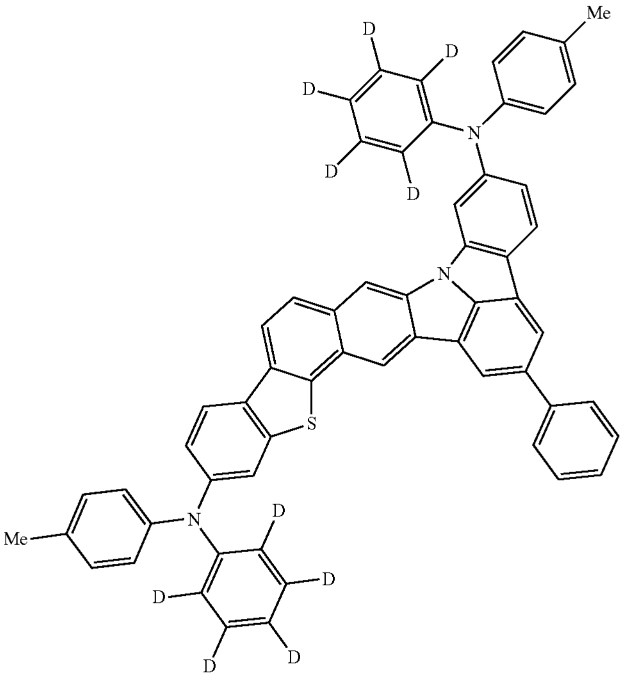

-continued
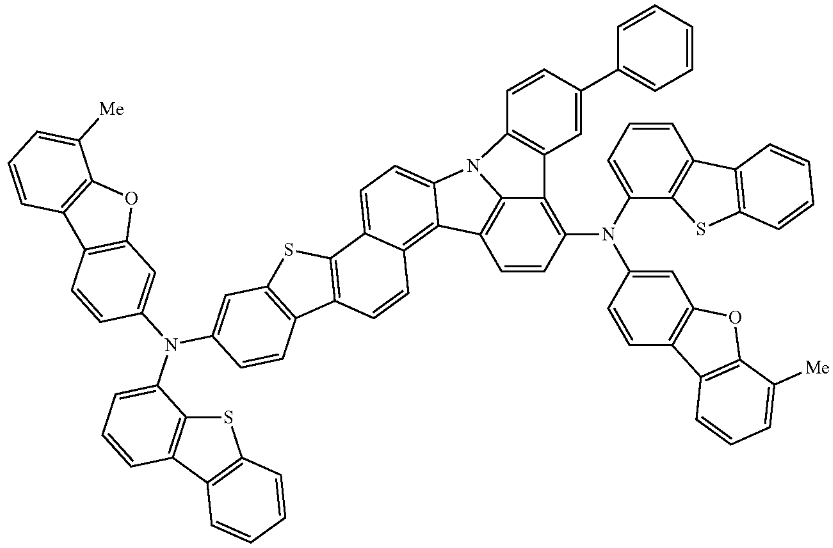
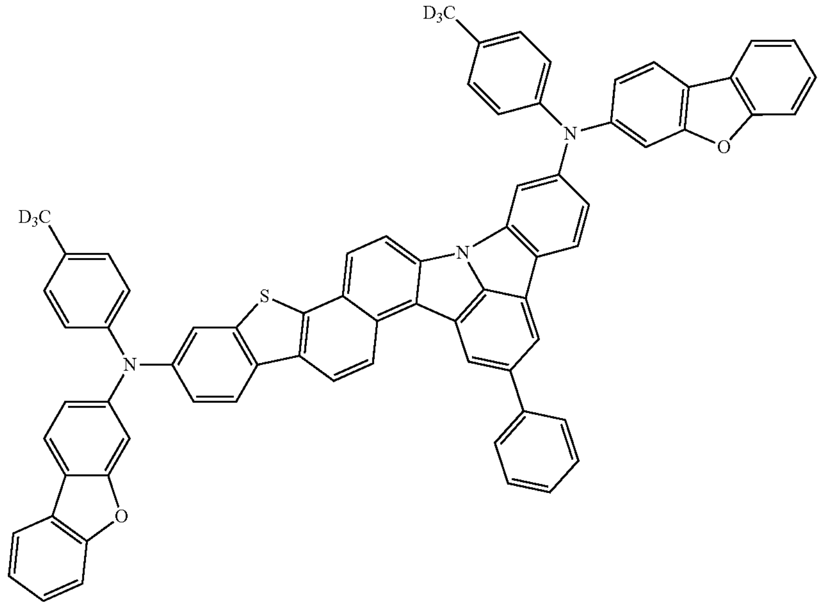
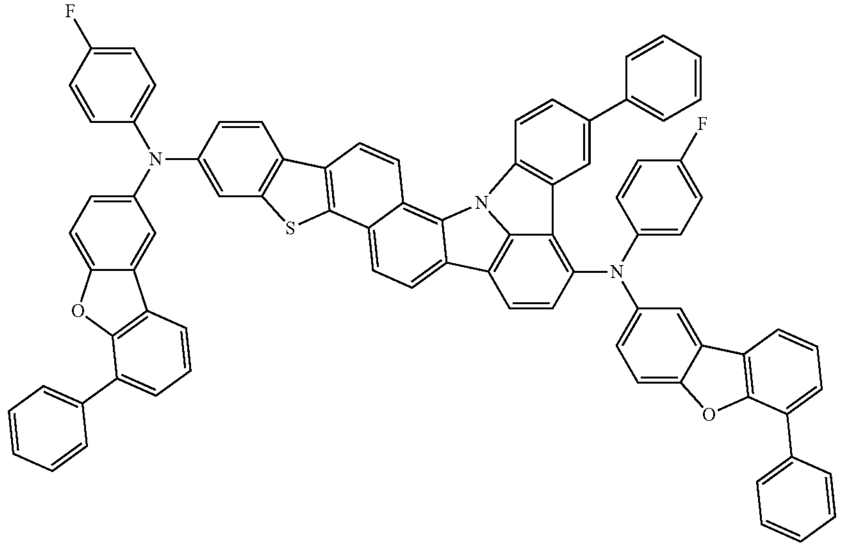

-continued

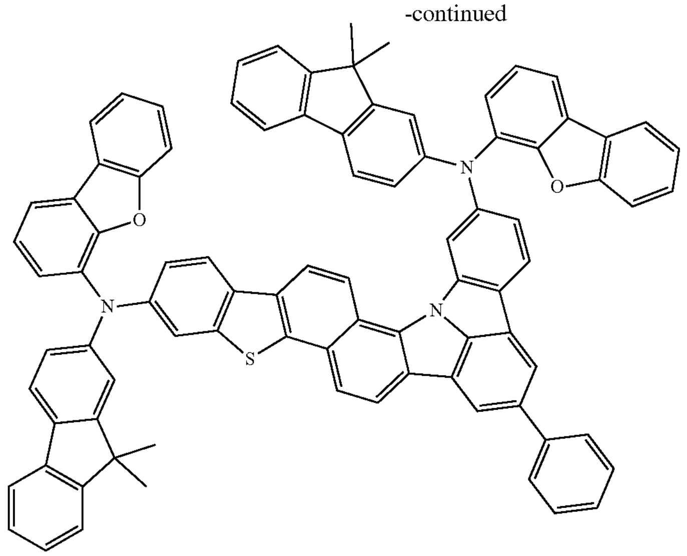

wherein in the compounds:

tBu means a tert-butyl group, Me means a methyl group, and Ph means a phenyl group.

8. An organic light emitting device comprising:

a first electrode;

a second electrode provided opposite to the first electrode; and one or more organic material layers provided between the first electrode and the second electrode, wherein one or more layers of the organic material layers include the heterocyclic compound of claim 1.

9. The organic light emitting device of claim 8, wherein the organic material layer includes a light emitting layer, and the light emitting layer includes the heterocyclic compound.

10. The organic light emitting device of claim 8, wherein the organic material layer includes a light emitting layer, the light emitting layer includes a dopant material, and the dopant material is the heterocyclic compound.

11. The organic light emitting device of claim 8, wherein the organic material layer includes a light emitting layer, and the light emitting layer includes the heterocyclic compound and a compound of Chemical Formula 2:

<Chemical Formula 2>

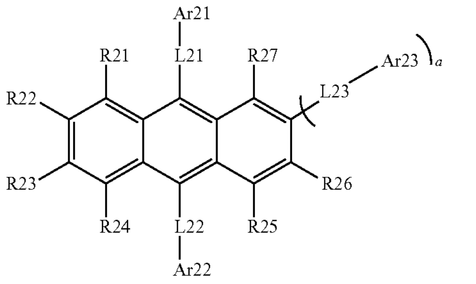

wherein in Chemical Formula 2:

L21 to L23 are the same as or different from each other, and each independently is a direct bond, a substituted or unsubstituted arylene group, or a substituted or unsubstituted heteroarylene group;

R21 to R27 are the same as or different from each other, and each independently is hydrogen, deuterium, a substituted or unsubstituted alkyl group, a substituted or unsubstituted cycloalkyl group, a substituted or unsubstituted silyl group, a substituted or unsubstituted aryl group, or a substituted or unsubstituted heteroaryl group;

Ar21 to Ar23 are the same as or different from each other, and each independently is a substituted or unsubstituted aryl group or a substituted or unsubstituted heteroaryl group; and a is 0 or 1.

12. The organic light emitting device of claim 8, wherein the organic material layer includes a hole injection layer or a hole transfer layer, and the hole injection layer or the hole transfer layer includes the heterocyclic compound.

13. The organic light emitting device of claim 8, wherein the organic material layer includes an electron injection layer or an electron transfer layer, and the electron injection layer or the electron transfer layer includes the heterocyclic compound.

14. The organic light emitting device of claim 8, wherein the organic material layer further includes one, two or more layers selected from the group consisting of a light emitting layer, a hole injection layer, a hole transfer layer, an electron injection layer, an electron transfer layer, an electron blocking layer and a hole blocking layer.

* * * * *